(12) United States Patent
Hennessy et al.

(10) Patent No.: US 10,206,394 B2
(45) Date of Patent: Feb. 19, 2019

(54) HERBICIDAL COMPOUNDS

(71) Applicant: Syngenta Participations AG, Basel (CH)

(72) Inventors: Alan Joseph Hennessy, Bracknell (GB); Shuji Hachisu, Bracknell (GB); Jeffrey Steven Wailes, Bracknell (GB); Nigel James Willetts, Bracknell (GB); Ian Stuart Cloudsdale, Chapel Hill, NC (US); Janice Black, Bracknell (GB); Emma Briggs, Bracknell (GB); Suzanna Jane Dale, Bracknell (GB)

(73) Assignee: SYNGENTA PARTICIPATIONS AG, Basel (CH)

( * ) Notice: Subject to any disclaimer, the term of this patent is extended or adjusted under 35 U.S.C. 154(b) by 22 days.

(21) Appl. No.: 15/520,233

(22) PCT Filed: Oct. 13, 2015

(86) PCT No.: PCT/EP2015/073707
§ 371 (c)(1),
(2) Date: Apr. 19, 2017

(87) PCT Pub. No.: WO2016/062587
PCT Pub. Date: Apr. 28, 2016

(65) Prior Publication Data
US 2017/0311596 A1    Nov. 2, 2017

(30) Foreign Application Priority Data
Oct. 20, 2014 (GB) .................................. 1418567.2

(51) Int. Cl.
| A01N 37/18 | (2006.01) |
| A01N 43/60 | (2006.01) |
| A01N 43/16 | (2006.01) |
| A01N 43/40 | (2006.01) |
| C07D 213/40 | (2006.01) |
| A01N 43/78 | (2006.01) |
| A01N 37/34 | (2006.01) |
| A01N 43/54 | (2006.01) |

(Continued)

(52) U.S. Cl.
CPC ............ *A01N 37/18* (2013.01); *A01N 37/34* (2013.01); *A01N 43/08* (2013.01); *A01N 43/10* (2013.01); *A01N 43/16* (2013.01); *A01N 43/40* (2013.01); *A01N 43/54* (2013.01); *A01N 43/56* (2013.01); *A01N 43/58* (2013.01); *A01N 43/60* (2013.01); *A01N 43/78* (2013.01); *A01N 43/80* (2013.01); *A01N 43/84* (2013.01); *C07D 213/40* (2013.01); *C07D 213/50* (2013.01); *C07D 213/61* (2013.01); *C07D 231/16* (2013.01); *C07D 239/30* (2013.01); *C07D 277/24* (2013.01); *C07D 277/28* (2013.01); *C07D 277/56* (2013.01); *C07D 277/64* (2013.01); *C07D 295/185* (2013.01); *C07D 305/08* (2013.01); *C07D 307/52* (2013.01); *C07D 309/04* (2013.01); *C07D 309/14* (2013.01); *C07D 331/04* (2013.01); *C07D 333/20* (2013.01); *C07D 333/28* (2013.01); *C07D 401/12* (2013.01); *C07D 409/12* (2013.01); *C07D 417/12* (2013.01)

(58) Field of Classification Search
None
See application file for complete search history.

(56) References Cited

U.S. PATENT DOCUMENTS 9,808,003 B2 * 11/2017 Avery ..................... A01N 43/52
2017/0320863 A1 * 11/2017 Hachisu ................. A01N 35/06

FOREIGN PATENT DOCUMENTS

WO      2010/000773 A1    1/2010

OTHER PUBLICATIONS

International Search Report in Application No. PCT/EP2015/073707 dated Jan. 28, 2016.
Wang et al., "Bicyclic Guanidine-Catalyzed Direct Asymmetric Allylic Addition of N-Aryl Alkylidene-Syccinimides", Chemistry A European Journal, vol. 16, No. 42, Nov. 8, 2010.

*Primary Examiner* — Mina Haghighatian
*Assistant Examiner* — Erin E Hirt

(57) ABSTRACT

The present invention relates to a compound of formula (I) wherein $R^1$, $R^2$, $R^3$, $R^4$, $R^5$, $R^6$, $R^7$, $R^8$, $R^9$, $R^{10}$, $R^{11}$ and G are as defined herein; and wherein the compound of formula (I) is optionally present as an agrochemically acceptable salt thereof. These compounds are suitable for use as herbicides. The invention therefore also relates to a method of controlling weeds, especially grassy monocotyledonous weeds, in crops of useful plants, comprising applying a compound of formula (I), or a herbicidal composition comprising such a compound, to the plants or to the locus thereof.

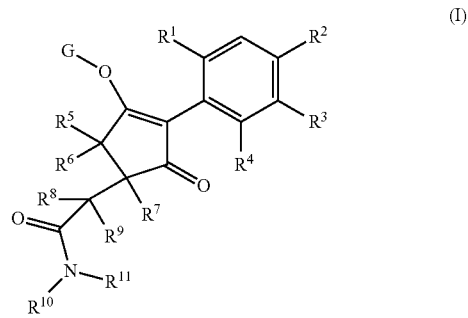

16 Claims, No Drawings

(51) Int. Cl.
*A01N 43/56* (2006.01)
*C07D 309/04* (2006.01)
*C07D 309/14* (2006.01)
*C07D 231/16* (2006.01)
*C07D 331/04* (2006.01)
*C07D 333/20* (2006.01)
*C07D 333/28* (2006.01)
*C07D 401/12* (2006.01)
*C07D 239/30* (2006.01)
*C07D 409/12* (2006.01)
*C07D 417/12* (2006.01)
*C07D 277/24* (2006.01)
*C07D 277/28* (2006.01)
*C07D 277/56* (2006.01)
*C07D 277/64* (2006.01)
*C07D 295/185* (2006.01)
*C07D 213/50* (2006.01)
*C07D 213/61* (2006.01)
*C07D 305/08* (2006.01)
*C07D 307/52* (2006.01)
*A01N 43/08* (2006.01)
*A01N 43/10* (2006.01)
*A01N 43/58* (2006.01)
*A01N 43/80* (2006.01)
*A01N 43/84* (2006.01)

\* cited by examiner

HERBICIDAL COMPOUNDS

RELATED APPLICATION INFORMATION

This application is a 371 of International Application No. PCT/EP2015/073707 filed 13 Oct. 2015 which claims priority to GB Application No. 1418567.2, filed 20 Oct. 2015, the contents of which are incorporated herein by reference herein.

The present invention relates to novel, herbicidally active cyclopentanedione compounds, specifically 2-(substituted-phenyl)-cyclopentane-1,3-dione compounds, and derivatives thereof (e.g. enol ketone tautomer derivatives thereof), to processes for their preparation, to herbicidal compositions comprising those compounds, and to their use in controlling weeds such as grassy monocotyledonous weeds, especially in crops of useful plants, or in inhibiting undesired plant growth.

U.S. Pat. No. 4,338,122 discloses 2-aryl-1,3-cyclopentanedione compounds exhibiting acaricidal and herbicidal activity. WO 96/01798 discloses 2-aryl-cyclopentane-1,3-dione derivatives and their use as pesticides and herbicides. WO 96/03366 discloses fused 2-(2,4,6-trimethylphenyl)cyclopentane-1,3-dione derivatives and their use as pesticides and herbicides.

WO 99/43649A1 discloses inter alia (4-aryl-phenyl)-substituted or (4-heteroaryl-phenyl)-substituted cyclic keto-enols, including several types of cyclic diones and derivatives thereof. WO 99/48869 A1 discloses inter alia (3-aryl-phenyl)-substituted or (3-heteroaryl-phenyl)-substituted cyclic keto-enols, including several types of cyclic diones and derivatives thereof.

WO01/17972A2 discloses (4-methyl-phenyl)-substituted (such as 4-methyl-2,6-diethyl-phenyl-substituted) heterocycles (e.g. heterocyclic diones) or cyclopentane-1,3-dione derivatives, suitable for use as herbicides. WO 01/74770 discloses $C_2$-phenyl-substituted cyclic ketoenols and their use as pesticides and herbicides.

WO 03/013249A1 discloses selective herbicidal compositions comprising (a) a (substituted-phenyl)-substituted cyclic ketoenol and (b) a compound which improves crop plant compatibility, in particular cloquintocet-mexyl or mefenpyr-diethyl. In WO 03/013249 A1, the cyclic ketoenol (whose tautomer is a cyclic dione) can for example be a 2-(substituted-phenyl)-cyclopentane-1,3-dione, or a derivative (e.g. ester or carbonate derivative) thereof.

WO 2007/068427A2 discloses a composition comprising (a) a (substituted-phenyl)-substituted cyclic ketoenol as a herbicide, and (b) an ammonium and/or phosphonium salt to boost activity. In WO 2007/068427 A2, the cyclic ketoenol (whose tautomer is a cyclic dione) can for example be a 2-(substituted-phenyl)-cyclopentane-1,3-dione or a derivative (e.g. ester or carbonate derivative) thereof.

WO 2009/019005A2 discloses fused bicyclic and oxygen-bridged cyclopentanedione derivatives, specifically 10-oxatricyclo-[5.2.1.0$^{2,6}$]decane-3,5-diones and derivatives, which are substituted by substituted-phenyl and which have herbicidal activity.

WO 2010/000773A1 discloses 5-(heterocyclylalkyl)-3-hydroxy-2-phenyl-cyclopent-2-enones and certain derivatives thereof as herbicides.

WO 2010/069834A1 discloses cyclopentane-1,3-diones having both heteroarylmethyl- and 2-(substituted-phenyl)-substituents on the cyclopentane ring, and derivatives thereof containing latentiating groups; these compounds are disclosed as having herbicidal properties.

WO 2011/007146A1 discloses certain 2-(substituted-phenyl)-cyclopentane-1,3-dione derivatives having herbicidal and/or plant-growth-inhibiting properties, in which at the 4-position of the cyclopentane-1,3-dione there is a substituent A-CHR$^4$— in which A is unsubstituted or substituted $C_3$-$C_7$cycloalkyl or A is optionally substituted phenyl.

Other cyclopentane-1,3-dione compounds substituted by substituted-phenyl and having herbicidal activity are described in WO 2010/089210A1 and WO 2010/102848A1.

WO 2010/102758A2 discloses (haloalkylmethoxy-)-phenyl-substituted cyclic keto-enols as pest control agents and/or as herbicides.

WO 2013/079672A1 discloses that certain substituted spiroheterocyclic pyrrolidine dione compounds, having an alkynyl-phenyl- headgroup, have herbicidal properties.

WO 2013/079708A1 discloses cyclopentane-1,3-dione compounds and derivatives (e.g. fused and/or spirocyclic bicyclic derivatives) thereof, which are substituted at the 2-position of the cyclopentane-1,3-dione by a phenyl which itself is substituted at the 4-position by (specifically) either prop-1-ynyl or chloroethynyl and at the 2-position by (specifically) either methyl or chlorine, and derivatives of the enol ketone tautomer of such cyclopentanediones, which have herbicidal activity and/or plant-growth-inhibiting properties, especially in the control of grassy monocotyledonous weeds and/or when used post-emergence.

2-(Substituted-phenyl)-cyclopentane-1,3-dione compounds, and derivatives of the enol ketone tautomer of such cyclopentane-1,3-diones, which have an alkynyl-methyl- or similar substituent on the cyclopentane-1,3-dione, and which have herbicidal activity and/or plant-growth-inhibiting properties, especially in the control of grassy monocotyledonous weeds and/or when used post-emergence, have now been found, which are encompassed by the present invention.

Thus, according to the present invention there is provided a compound of formula (I):

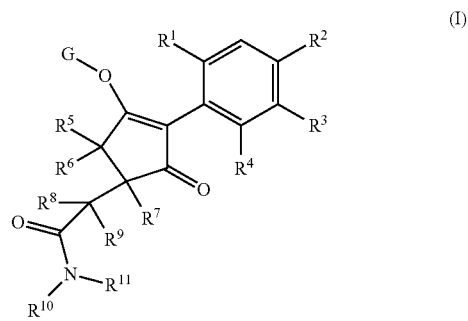

wherein:
R$^1$ is selected from the group consisting of methyl, ethyl, n-propyl, cyclopropyl, trifluoromethyl, vinyl, ethynyl, fluorine, chlorine, bromine, methoxy, difluoromethoxy and trifluoromethoxy; and
either (a): R$^2$ is R$^{2A}$ and R$^3$ is R$^{3A}$;
or (b): R$^2$ is R$^{2B}$ and R$^3$ is R$^{3B}$;
wherein:
R$^{2A}$ is selected from the group consisting of hydrogen, methyl, ethyl, n-propyl, isopropyl, cyclopropyl, $C_1$-$C_2$fluoroalkyl, vinyl, prop-1-enyl, prop-1-ynyl, —C≡C—R$^{2AA}$, halogen and ($C_1$-$C_2$fluoroalkyl)-methoxy-; wherein R$^{2AA}$ is selected from the group consisting of hydrogen, chlorine, fluorine, trifluoromethyl, ethyl and cyclopropyl;

or $R^{2A}$ is phenyl optionally substituted by 1, 2 or 3 substituents independently selected from the group consisting of halogen, $C_1$-$C_2$alkyl, $C_1$-$C_2$fluoroalkyl, methoxymethyl, vinyl, ethynyl, $C_1$-$C_3$alkoxy, $C_1$-$C_2$fluoroalkoxy, —S(O)$_p$methyl, cyano or nitro, provided that either one or none (i.e. no more than one) of these optional substituents are methoxymethyl, vinyl, ethynyl, —S(O)$_p$methyl or nitro;

or $R^{2A}$ is a monocyclic heteroaryl optionally substituted by 1, 2 or 3 substituents independently selected from the group consisting of halogen, $C_1$-$C_2$alkyl, $C_1$-$C_2$fluoroalkyl, methoxymethyl, vinyl, ethynyl, $C_1$-$C_3$alkoxy, $C_1$-$C_2$fluoroalkoxy, —S(O)$_p$methyl, cyano and nitro, provided that either one or none (i.e. no more than one) of these optional substituents are methoxymethyl, vinyl, ethynyl, —S(O)$_p$methyl or nitro;

$R^{3A}$ is selected from the group consisting of hydrogen, methyl, fluorine and chlorine;

and wherein $R^{2B}$ is hydrogen, methyl or fluorine; and either $R^{3B}$ is phenyl optionally substituted by 1, 2 or 3 substituents independently selected from the group consisting of halogen, $C_1$-$C_2$alkyl, $C_1$-$C_2$fluoroalkyl, methoxymethyl, vinyl, ethynyl, $C_1$-$C_2$alkoxy, $C_1$-$C_2$fluoroalkoxy, —S(O)$_p$methyl, cyano and nitro, provided that either one or none (i.e. no more than one) of these optional substituents are methoxymethyl, vinyl, ethynyl, —S(O)$_p$methyl or nitro; or $R^{3B}$ is a monocyclic heteroaryl optionally substituted by 1, 2 or 3 substituents independently selected from the group consisting of halogen, $C_1$-$C_2$alkyl, $C_1$-$C_2$fluoroalkyl, methoxymethyl, vinyl, ethynyl, $C_1$-$C_2$alkoxy, $C_1$-$C_2$fluoroalkoxy, —S(O)$_p$methyl, cyano and nitro, provided that either one or none (i.e. no more than one) of these optional substituents are methoxymethyl, vinyl, ethynyl, —S(O)$_p$methyl or nitro;

$R^4$ is selected from the group consisting of hydrogen, methyl, ethyl, n-propyl, cyclopropyl, trifluoromethyl, vinyl, ethynyl, fluorine, chlorine, bromine, $C_1$-$C_3$alkoxy, $C_1$-$C_2$fluoroalkoxy, $C_1$-$C_2$alkoxy-$C_1$-$C_3$alkoxy-, or $C_1$fluoroalkoxy-$C_1$-$C_3$alkoxy-;

$R^5$, $R^6$ and $R^7$ are independently selected from the group consisting of hydrogen, $C_1$-$C_6$alkyl, $C_2$-$C_3$ alkenyl, $C_2$-$C_3$alkynyl, $C_1$-$C_2$haloalkyl and $C_1$-$C_2$alkoxy$C_1$-$C_2$alkyl;

$R^8$ and $R^9$ are independently selected from the group consisting of hydrogen, fluorine and $C_1$-$C_3$alkyl;

$R^{10}$ is selected from the group consisting of hydrogen, $C_1$-$C_6$alkyl, $C_3$-$C_8$cycloalkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkylcyano, $C_1$-$C_6$alkoxy$C_1$-$C_6$-alkyl-, $C_1$-$C_6$alkoxy-$C_2$-$C_6$-alkenyl-, $C_1$-$C_6$alkoxy-$C_2$-$C_6$-alkynyl-, $C_1$-$C_6$alkenyloxy$C_1$-$C_6$-alkyl-, $C_1$-$C_6$alkoxy-$C_2$-$C_3$-alkoxy-$C_2$-$C_3$-alkyl-, $C_1$-$C_6$alkylcarbonyl- and $C_1$-$C_6$alkylcarbonyl$C_1$-$C_6$-alkyl-;

$R^{11}$ is selected from the group consisting of hydrogen, $C_1$-$C_6$alkyl, $C_3$-$C_8$cycloalkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkylcyano, $C_1$-$C_6$alkoxy$C_1$-$C_6$-alkyl-, $C_1$-$C_6$alkoxy-$C_2$-$C_6$-alkenyl-, $C_1$-$C_6$alkoxy-$C_2$-$C_6$-alkynyl-, $C_1$-$C_6$alkenyloxy$C_1$-$C_6$-alkyl-, $C_1$-$C_6$alkoxy-$C_2$-$C_3$-alkoxy-$C_2$-$C_3$-alkyl-, $C_1$-$C_6$alkylcarbonyl-, $C_1$-$C_6$alkylcarbonyl$C_1$-$C_6$-alkyl-; or $R^{11}$ is —(CR'R'')$_n$—$X^1$—$R^{13}$ wherein $X^1$ is a bond, —(CH=CH)— or —(C=O)— and wherein R' and R'' are independently selected from hydrogen and methyl or together from a $C_2$-$C_3$ alkylene chain); or $R^{10}$ and $R^{11}$ together form a four to six membered heterocycle, the heterocycle comprising one or more heteroatoms selected from the group consisting of oxygen, nitrogen and sulphur; the heterocycle being optionally substituted by one or more independent $R^{12}$;

$R^{12}$ is selected from the group consisting of halogen, $C_1$-$C_6$alkyl, $C_1$-$C_6$haloalkyl, $C_1$-$C_6$haloalkoxy, $C_1$-$C_6$alkoxy-, nitro, —(CO)OR$^{14}$, cyano, phenyl, pyridyl;

$R^{13}$ is a three- to ten-membered mono- or bicyclic ring system, which may be aromatic, saturated or partially saturated and can contain from 1 to 4 heteroatoms each independently selected from the group consisting of nitrogen, oxygen and sulphur the ring system being optionally substituted by one or more $R^{12}$ substituents;

$R^{14}$ is H or $C_1$-$C_6$ alkyl;

n=0, 1, 2, 3 or 4;

p=0, 1 or 2; and

G is hydrogen; an agriculturally acceptable metal, or an agriculturally acceptable sulfonium or ammonium group; or G is —C($X^a$)—$R^a$, —C($X^b$)—$X^c$—$R^b$, —C($X^d$)—N($R^c$)—$R^d$, —SO$_2$—$R^g$, —P($X^e$)($R^f$)—$R^g$, —CH$_2$—$X^f$—$R^h$; or phenyl-CH$_2$— or phenyl-CH($C_1$-$C_2$alkyl)- (in each of which the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or heteroaryl-CH$_2$— or heteroaryl-CH($C_1$-$C_2$alkyl)- (in each of which the heteroaryl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or phenyl-C(O)—CH$_2$— (wherein the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro); or $C_1$-$C_6$alkoxy-C(O)—CH$_2$—, $C_1$-$C_6$alkyl-C(O)—CH$_2$—, $C_1$-$C_6$alkoxy-C(O)—CH=CH—, $C_2$-$C_7$alken-1-yl-CH$_2$—, $C_2$-$C_7$alken-1-yl-CH($C_1$-$C_2$alkyl)-, $C_2$-$C_4$fluoroalken-1-yl-CH$_2$—, $C_2$-$C_7$alkyn-1-yl-CH$_2$—, or $C_2$-$C_7$alkyn-1-yl-CH($C_1$-$C_2$alkyl)-;

wherein $X^a$, $X^b$, $X^c$, $X^d$, $X^e$ and $X^f$ are independently of each other oxygen or sulfur; and wherein $R^a$ is H, $C_1$-$C_{21}$alkyl, $C_2$-$C_{21}$alkenyl, $C_2$-$C_{18}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_6$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_6$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl$C_1$-$C_5$alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkyl-thio, $C_1$-$C_3$alkylsulfinyl, $C_1$-$C_3$alkylsulfonyl, halogen, cyano, or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or by nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino or $C_3$-$C_7$cycloalkoxy;

or $R^c$ and $R^d$, together with the nitrogen to which they are bonded, to form an unsubstituted 4, 5, 6 or 7 (e.g. 5 or 6) membered ring, optionally containing one heteroatom selected from O or S; and $R^g$ is $C_1$-$C_{10}$alkyl, $C_2$-$C_{10}$alkenyl, $C_2$-$C_{10}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$alkoxy, $C_1$-$C_{10}$fluoroalkoxy, $C_1$-$C_5$alkylamino or di($C_1$-$C_4$alkyl)amino;

$R^f$ and $R^g$ are are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$fluoroalkoxy, $C_1$-$C_5$alkylamino or di($C_1$-$C_4$alkyl)amino; or benzyloxy or phenoxy, wherein the benzyl and phenyl groups are in turn optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$) alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), phenoxy($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), heteroaryloxy($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; $C_1$-$C_6$alkyl-C(O)—; or phenyl-C(O)— wherein the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine, bromine, cyano or nitro;

wherein "heteroaryl" means an aromatic ring system containing at least one ring heteroatom and consisting either of a single ring or of two fused rings;

and wherein the compound of formula (I) is optionally present as an agrochemically acceptable salt thereof.

In the substituent definitions of the compounds of the formula I, each alkyl moiety either alone or as part of a larger group (such as alkoxy, alkylthio, alkoxycarbonyl, alkylcarbonyl, alkylaminocarbonyl, or dialkylaminocarbonyl, et al.) can be straight-chained or branched. Typically, the alkyl is, for example, methyl, ethyl, n-propyl, isopropyl, n-butyl, sec-butyl, isobutyl, tert-butyl, n-pentyl, neopentyl, or n-hexyl. The alkyl groups can e.g. be $C_1$-$C_6$alkyl groups (except where already defined more narrowly), but are preferably $C_1$-$C_4$alkyl or $C_1$-$C_3$alkyl groups (except where already defined more narrowly), and, more preferably, are $C_1$-$C_2$alkyl groups such as methyl.

Alkenyl and alkynyl moieties can be in the form of straight or branched chains, and the alkenyl moieties, where appropriate, can be of either the (E)- or (Z)-configuration. The alkenyl or alkynyl are typically $C_2$-$C_3$alkenyl or $C_2$-$C_3$alkynyl such as vinyl, allyl, ethynyl, propargyl or prop-1-ynyl. Alkenyl and alkynyl moieties can contain one or more double and/or triple bonds in any combination; but preferably contain only one double bond (for alkenyl) or only one triple bond (for alkynyl).

Halogen is fluorine, chlorine, bromine or iodine. Preferred halogens are fluorine, chlorine or bromine. More preferably, in various aspects and/or embodiments of the invention, halogen is fluorine or chlorine.

Fluoroalkyl groups are alkyl groups which are substituted with one or more (e.g. 1, 2, 3, 4 or 5; in particular 1, 2 or 3; e.g. 1 or 2) fluorine atoms. Fluoroalkyl is typically $C_1$-$C_3$fluoroalkyl or $C_1$-$C_2$fluoroalkyl (preferably $C_1$fluoroalkyl), such as $CF_3$, $CHF_2$, $CH_2F$, $CH_3CHF$—, $CF_3CH_2$—, $CHF_2CH_2$—, $CH_2FCH_2$—, $CHF_2CF_2$— or $(CH_3)_2CF$—. Fluoroalkoxy is typically $C_1$-$C_3$fluoroalkoxy or $C_1$-$C_2$fluoroalkoxy (preferably $C_1$fluoroalkoxy), such as $CF_3O$, $CHF_2O$, $CH_2FO$, $CH_3CHFO$—, $CF_3CH_2O$—, $CHF_2CH_2O$— or $CH_2FCH_2O$—.

In the context of the present specification the term "aryl" means phenyl or naphthyl. A preferred aryl group is phenyl.

The term "heteroaryl" as used herein means an aromatic ring system containing at least one ring heteroatom and consisting either of a single ring or of two fused rings. Preferably, single rings will contain 1, 2 or 3 ring heteroatoms and bicyclic systems 1, 2, 3 or 4 ring heteroatoms which will preferably be selected from nitrogen, oxygen and sulfur. Typically, a "heteroaryl" is furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl or indolizinyl; optionally present, where chemically possible, as an agrochemically acceptable salt thereof.

The term "heterocyclyl" as used herein, except where explicitly stated otherwise, means a 4, 5, 6 or 7 (in particular 5, 6 or 7) membered monocyclic organic ring or a 8, 9, 10 or 11 (in particular 8, 9 or 10) membered fused bicyclic organic ring system, which is fully saturated, and which has one or two (preferably one) ring heteroatoms independently selected from oxygen, sulfur and nitrogen. Where the heterocyclyl has two ring heteroatoms, preferably, the two ring heteroatoms are separated by at least two ring carbon atoms. Preferably, the heterocyclyl is attached at a ring carbon atom within the heterocyclyl. In particular, the heterocyclyl can be tetrahydrofuranyl, tetrahydropyranyl, tetrahydrothiophenyl, 1,4-dioxanyl, 1,4-dithianyl, morpholinyl, thiomorpholinyl, pyrrolidinyl, piperidinyl or piperazinyl; more particularly tetrahydrofuranyl (e.g. tetrahydrofuran-2-yl or particularly tetrahydrofuran-3-yl), tetrahydropyranyl (e.g. tetrahydropyran-2-yl, tetrahydropyran-3-yl or particularly tetrahydropyran-4-yl), morpholinyl, pyrrolidinyl (e.g. pyrrolidin-2-yl or particularly pyrrolidin-3-yl), piperidinyl (e.g. piperidin-2-yl, piperidin-3-yl or particularly piperidin-4-yl) or piperazinyl. In a particular embodiment, the heterocyclyl, when optionally substituted, is optionally substituted by 1 or 2 (e.g. 1) ring-carbon substituents independently being $C_1$-$C_3$alkyl (e.g. $C_1$-$C_2$alkyl), $C_1$-$C_2$fluoroalkyl or oxo (=O), and/or is optionally substituted by one $C_1$-$C_3$alkyl (e.g. $C_1$-$C_2$alkyl), $C_1$-$C_2$fluoroalkyl or $C_1$-$C_3$alkoxy (e.g. $C_1$-$C_2$alkyl or $C_1$-$C_2$fluoroalkyl) substituent on a ring nitrogen if present, and/or is optionally substituted by one or two oxo (=O) substituents on a ring sulfur if present.

Preferably, a cycloalkyl is cyclopropyl, cyclobutyl, cyclopentyl or cyclohexyl. (Cycloalkyl)alkyl is preferably (cycloalkyl)methyl such as ($C_3$-$C_6$cycloalkyl)methyl in particular cyclopropylmethyl. Preferably, cycloalkenyl is cyclopentenyl or cyclohexenyl.

The invention relates also to the agriculturally acceptable salts which the compounds of formula I are able to form with transition metal, alkali metal and alkaline earth metal bases, amines, quaternary ammonium bases or tertiary sulfonium bases.

Among the transition metal, alkali metal and alkaline earth metal salt formers, special mention should be made of the hydroxides of copper, iron, lithium, sodium, potassium, magnesium and calcium, and preferably the hydroxides, bicarbonates and carbonates of sodium and potassium.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkyl-amines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-isopropylamine, di-n-butylamine, di-n-amylamine, di-isoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, tri-isopropylamine, tri-n-butylamine, tri-isobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and di-isopropylamine.

Preferred quaternary ammonium bases suitable for salt formation correspond, for example, to the formula [N($R_a$ $R_b$ $R_c$ $R_d$)]OH, wherein $R_a$, $R_b$, $R_c$ and $R_d$ are each independently of the others hydrogen, $C_1$-$C_4$alkyl. Further suitable tetraalkylammonium bases with other anions can be obtained, for example, by anion exchange reactions.

Preferred tertiary sulfonium bases suitable for salt formation correspond, for example, to the formula [S$R_e$$R_f$$R_g$]OH, wherein $R_e$, $R_f$ and $R_g$ are each independently of the others $C_1$-$C_4$ alkyl. Trimethylsulfonium hydroxide is especially preferred. Suitable sulfonium bases may be obtained from the reaction of thioethers, in particular dialkylsulfides, with alkylhalides, followed by conversion to a suitable base, for example a hydroxide, by anion exchange reactions.

It should be understood that in those compounds of formula I, where G is a metal, ammonium or sulfonium as mentioned above and as such represents a cation, the corresponding negative charge is largely delocalised across the O—C=C—C=O unit.

The compounds of formula I according to the invention also include hydrates which may be formed during the salt formation.

The latentiating groups (i.e. leaving or removeable groups) within G (for example, without limitation, the latentiating groups where G is —C($X^a$)—$R^a$ or —C($X^b$)—$X^c$—$R^b$, et al.) are generally selected to allow their removal, typically by one or a combination of biochemical, chemical or physical processes, to afford the corresponding compound of formula (I) where G is H, before, during or following (preferably during or following) application of the compound of formula (I) to the treated area (e.g. field) or to plants. Examples of these processes include enzymatic cleavage or other in/on-plant cleavage (e.g. cleavage of ester and/or carbonate moieties), chemical hydrolysis, and/or photolysis. Some compounds bearing such groups G occasionally offer certain advantages or different technical properties, such as improved and/or more consistent and/or different penetration of the cuticula of the plants treated, increased and/or different tolerance of certain crops, improved and/or different compatibility or stability in formulated mixtures containing other herbicides, herbicide safeners, plant growth regulators, fungicides or insecticides, or reduced and/or different leaching properties in soils.

The preferred (including more preferred, most preferred, et al.), suitable and/or particular values of the substituents in, or other features of, the compound of formula (I), in particular (and without limitation): G, $R^1$, $R^2$, $R^{2A}$, $R^{2AA}$, $R^{2B}$, $R^3$, $R^{3A}$, $R^{3B}$, $R^4$, $R^{4A}$, $R^{4B}$, $R^{4C}$, $R^5$, $R^6$, $R^7$, $R^8$, $R^9$, $R^{10}$, $R^{11}$, $R^{11B}$, $R^{12}$, $R^{12A}$, $R^{12AA}$, $R^{12B}$, $R^{13}$, $R^{13A}$, $R^{13AA}$, $R^{13B}$, $R^{14}$, $R^{14A}$, $R^{14B}$, $R^{15}$, $R^{16}$, $R^a$, $R^b$, $R^c$, $R^d$, $R^e$, $R^f$, $R^g$, $R^h$, $X^a$, $X^b$, $X^c$, $X^d$, $X^e$, and/or $X^f$; are set out below (and/or generally herein), and can be either taken alone or taken together with one or more of any other preferred (including more preferred, most preferred, et al.), suitable and/or particular values of the substituents in, or other features of, the compound of formula (I), in any and all possible combination(s) thereof.

Preferably, e.g. in all aspects and/or embodiments of the invention, G is hydrogen; an agriculturally acceptable metal (e.g. an agriculturally acceptable alkali metal or alkaline earth metal), or an agriculturally acceptable sulfonium or ammonium group; or G is —C($X^a$)—$R^a$ or —C($X^b$)—$X^c$—$R^b$, wherein $X^a$, $R^a$, $X^b$, $X^c$ and $R^b$ are as defined herein. More preferably, G is hydrogen, or an agriculturally acceptable alkali metal (e.g. lithium, sodium or potassium) or an agriculturally acceptable alkaline earth metal (e.g. calcium or magnesium), or —C($X^a$)—$R^a$ or —C($X^b$)—$X^c$—$R^b$.

In a particular embodiment, G is a group —C($X^a$)—$R^a$ or —C($X^b$)—$X^c$—$R^b$, wherein $X^a$, $R^a$, $X^b$, $X^c$ and $R^b$ are as defined herein.

Preferably, $X^a$, $X^b$, $X^c$, $X^d$, $X^e$ and/or $X^f$ are oxygen; and/or $X^c$ sulfur. More preferably, $X^a$, $X^b$, $X^c$, $X^d$, $X^e$ and $X^f$ are oxygen; and/or $X^c$ is sulfur.

Preferably, $R^a$ is $C_1$-$C_{10}$alkyl (e.g. $C_1$-$C_6$alkyl), $C_2$-$C_6$alkenyl (e.g. $C_2$-$C_4$alkenyl), $C_2$-$C_6$alkynyl (e.g. $C_2$-$C_4$alkynyl), $C_3$-$C_6$cycloalkyl, $C_3$-$C_6$cycloalkyl-methyl-, $C_1$-$C_4$alkoxy$C_1$-$C_4$alkyl, phenyl-methyl- (in which the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano); phenyl or phenyl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; or monocyclic heteroaryl or monocyclic heteroaryl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano.

More preferably, $R^a$ is $C_1$-$C_{10}$alkyl (e.g. $C_1$-$C_6$alkyl), $C_2$-$C_6$alkenyl (e.g. $C_2$-$C_4$alkenyl), $C_2$-$C_6$alkynyl (e.g. $C_2$-$C_4$alkynyl), $C_3$-$C_6$cycloalkyl, or $C_1$-$C_4$alkoxy$C_1$-$C_4$alkyl.

Preferably, $R^b$ is $C_1$-$C_{10}$alkyl (e.g. $C_1$-$C_6$alkyl), $C_2$-$C_5$alkenyl-$CH_2$— (e.g. $C_2$-$C_3$alkenyl-$CH_2$—), $C_2$-$C_4$alkenyl-CH(Me)- (e.g. $C_2$-$C_3$alkenyl-CH(Me)-), $C_2$-$C_5$alkynyl-$CH_2$— (e.g. $C_2$-$C_3$alkynyl-$CH_2$—), $C_2$-$C_4$alkynyl-CH(Me)- (e.g. $C_2$-$C_3$alkynyl-CH(Me)-), $C_3$-$C_6$cycloalkyl, $C_3$-$C_6$cycloalkyl-methyl-, $C_1$-$C_4$alkoxy$C_1$-$C_4$alkyl, phenyl-methyl- (in which the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano); phenyl or phenyl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; or monocyclic heteroaryl or monocyclic heteroaryl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano.

More preferably, $R^b$ is $C_1$-$C_{10}$alkyl (e.g. $C_1$-$C_6$alkyl), $C_2$-$C_5$alkenyl-$CH_2$— (e.g. $C_2$-$C_3$alkenyl-$CH_2$—), $C_2$-$C_4$alkenyl-CH(Me)- (e.g. $C_2$-$C_3$alkenyl-CH(Me)-), $C_2$-$C_5$alkynyl-$CH_2$— (e.g. $C_2$-$C_3$alkynyl-$CH_2$—), $C_2$-$C_4$alkynyl-CH(Me)- (e.g. $C_2$-$C_3$alkynyl-CH(Me)-), $C_3$-$C_6$cycloalkyl, or $C_1$-$C_4$alkoxy$C_1$-$C_4$alkyl.

Preferably, $X^a$, $X^b$ and $X^c$ are oxygen (and/or $X^c$ is sulfur); and $R^a$ is $C_1$-$C_{10}$alkyl (e.g. $C_1$-$C_6$alkyl), $C_2$-$C_6$alkenyl (e.g. $C_2$-$C_4$alkenyl), $C_2$-$C_6$alkynyl (e.g. $C_2$-$C_4$alkynyl), $C_3$-$C_6$cycloalkyl, $C_3$-$C_6$cycloalkyl-methyl-, $C_1$-$C_4$alkoxy$C_1$-$C_4$alkyl, phenyl-methyl- (in which the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano); phenyl or phenyl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; or monocyclic heteroaryl or monocyclic heteroaryl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; and $R^b$ is $C_1$-$C_{10}$alkyl (e.g. $C_1$-$C_6$alkyl), $C_2$-$C_5$alkenyl-$CH_2$— (e.g. $C_2$-$C_3$alkenyl-$CH_2$—), $C_2$-$C_4$alkenyl-CH(Me)- (e.g. $C_2$-$C_3$alkenyl-CH(Me)-), $C_2$-$C_5$alkynyl-$CH_2$— (e.g. $C_2$-$C_3$alkynyl-$CH_2$—), $C_2$-$C_4$alkynyl-CH(Me)- (e.g. $C_2$-$C_3$alkynyl-CH(Me)-), $C_3$-$C_6$cycloalkyl, $C_3$-$C_6$cycloalkyl-methyl-, $C_1$-$C_4$alkoxy$C_1$-$C_4$alkyl, phenyl-methyl- (in which the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano); phenyl or phenyl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; or monocyclic heteroaryl or monocyclic heteroaryl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano.

In a particularly preferable embodiment, G is hydrogen, —C($X^a$)—$R^a$ or —C($X^b$)—$X^c$—$R^b$.

In another preferable embodiment, G is hydrogen, or an agriculturally acceptable alkali metal or alkaline earth metal, or an agriculturally acceptable sulfonium or ammonium group. In a particular embodiment, G is hydrogen, or an agriculturally acceptable alkali metal (e.g. lithium, sodium or potassium) or an agriculturally acceptable alkaline earth metal (e.g. calcium or magnesium).

Most preferably, G is hydrogen.

In a preferred embodiment of the present invention, $R^1$ is selected from the group consisting of methyl, ethyl, cyclopropyl, ethynyl, fluorine, chlorine, bromine, methoxy, difluoromethoxy and trifluoromethoxy. In a more preferred embodiment of the present invention, $R^1$ is selected from the group consisting of methyl, ethyl, ethynyl, fluorine, chlorine, bromine, methoxy, difluoromethoxy and trifluoromethoxy. In an even more preferred embodiment, $R^1$ is selected from the group consisting of methyl, fluorine, chlorine, bromine, difluoromethoxy and trifluoromethoxy. Still more preferably, $R^1$ is selected from the group consisting of methyl, fluorine and chlorine. More preferably, $R^1$ is methyl or chlorine, most preferably methyl.

In the context of the present invention, either (a): $R^2$ is $R^{2A}$ and $R^3$ is $R^{3A}$; or (b): $R^2$ is $R^{2B}$ and $R^3$ is $R^{3B}$.

Most preferably, e.g. in all aspects and/or embodiments of the invention, $R^2$ is $R^{2A}$ and $R^3$ is $R^{3A}$.

Preferably, e.g. in all aspects and/or embodiments of the invention, $R^{3A}$ is hydrogen or methyl.

Most preferably, e.g. in all aspects and/or embodiments of the invention, $R^{3A}$ is hydrogen.

When $R^{2A}$ is halogen, then preferably it is chlorine or bromine.

When $R^{2A}$ is ($C_1$-$C_2$fluoroalkyl)-methoxy-, then preferably it is $C_1$fluoroalkyl-methoxy-, such as $CF_3CH_2O$ or $CHF_2CH_2O$.

$R^{2A}$ can be —C≡C—$R^{2AA}$. Preferably, $R^{2AA}$ is hydrogen, fluorine or trifluoromethyl. More preferably, $R^{2AA}$ is hydrogen.

Preferably, e.g. in all aspects and/or embodiments of the invention, $R^{2A}$ is selected from the group consisting of methyl, ethynyl and prop-1-ynyl; or $R^{2A}$ is phenyl optionally substituted by 1, 2 or 3 (preferably 1 or 2) substituents independently being halogen (in particular fluorine, chlorine or bromine, more particularly fluorine or chlorine), $C_1$-$C_2$alkyl, $C_1$-$C_2$fluoroalkyl, $C_1$-$C_2$alkoxy, $C_1$-$C_2$fluoroalkoxy, cyano or nitro, provided that either one or none (i.e. no more than one) of these optional substituents are $C_1$-$C_2$alkyl, $C_1$-$C_2$alkoxy or nitro; or $R^{2A}$ is monocyclic 6-membered or 5-membered heteroaryl (e.g. pyridin-2-yl, pyridin-3-yl, pyrimidin-2-yl, pyrimidin-5-yl, pyridazin-3-yl, or pyrazol-1-yl) optionally substituted by 1, 2 or 3 (preferably 1 or 2) substituents independently being halogen (in particular fluorine, chlorine or bromine, more particularly fluorine or chlorine), $C_1$-$C_2$alkyl, $C_1$-$C_2$fluoroalkyl, $C_1$-$C_2$alkoxy, $C_1$-$C_2$fluoroalkoxy, cyano or nitro, provided that either one or none (i.e. no more than one) of these optional substituents are $C_1$-$C_2$alkyl, $C_1$-$C_2$alkoxy or nitro.

Preferably, e.g. in all aspects and/or embodiments of the invention, when $R^{2A}$ is optionally substituted phenyl, then $R^{2A}$ is of sub-formula (2Aa):

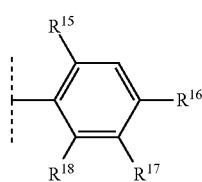

(2Aa)

in which:
$R^{15}$ is selected from the group consisting of hydrogen, $C_1$-$C_2$alkyl (preferably methyl), fluorine and chlorine, in particular hydrogen;
$R^{16}$ is selected from the group consisting of hydrogen, halogen (especially fluorine or chlorine), $C_1$-$C_2$alkyl, $C_1$-$C_2$fluoroalkyl, $C_1$-$C_2$alkoxy, $C_1$-$C_2$fluoroalkoxy, cyano and nitro;
$R^{17}$ is selected from the group consisting of hydrogen, halogen (especially fluorine or chlorine), $C_1$-$C_2$alkyl, $C_1$-$C_2$fluoroalkyl, $C_1$-$C_2$alkoxy, $C_1$-$C_2$fluoroalkoxy, cyano and nitro; and
$R^{18}$ is selected from the group consisting of hydrogen, halogen (especially fluorine or chlorine), $C_1$-$C_2$alkyl, $C_1$-$C_2$fluoroalkyl, $C_1$-$C_2$alkoxy, $C_1$-$C_2$fluoroalkoxy, cyano and nitro.

In an especially preferred embodiment,
$R^{15}$ is hydrogen;
$R^{16}$ is fluorine, chlorine, bromine, $C_1$fluoroalkyl, $C_1$fluoroalkoxy, or cyano;
$R^{17}$ is hydrogen, fluorine or chlorine; and
$R^{18}$ is hydrogen, fluorine, chlorine, bromine, or $C_1$fluoroalkyl.

Preferably, e.g. in all aspects and/or embodiments of the invention, when $R^{2A}$ is optionally substituted monocyclic heteroaryl (e.g. monocyclic 6-membered or 5-membered heteroaryl, in particular pyridin-2-yl, pyridin-3-yl, pyrimidin-2-yl, pyrimidin-5-yl, pyridazin-3-yl, or pyrazol-1-yl), then $R^{2A}$ is selected from the group consisting of ($R^{2Ab}$), ($R^{2Ac}$), ($R^{2Ad}$), ($R^{2Ae}$), ($R^{2Af}$), $R^{2Ag}$, $R^{Ah}$, $R^{2Ai}$ and $R^{2Aj}$:

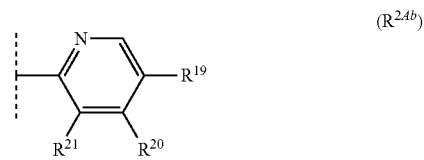

($R^{2Ab}$)

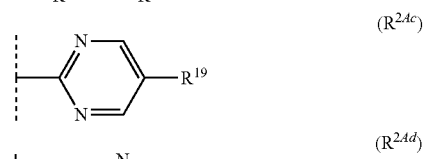

($R^{2Ac}$)

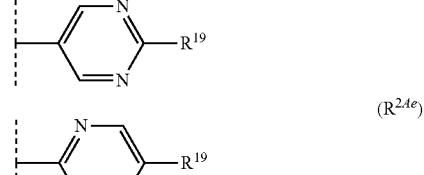

($R^{2Ad}$)

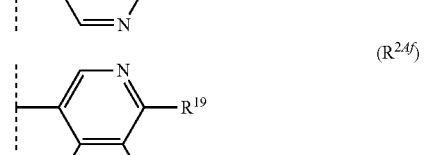

($R^{2Ae}$)

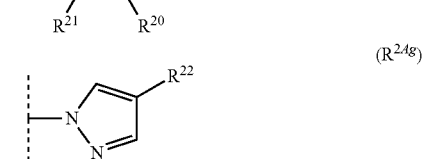

($R^{2Af}$)

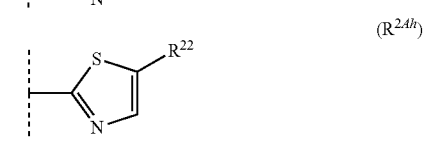

($R^{2Ag}$)

($R^{2Ah}$)

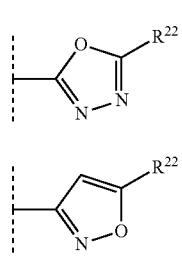

wherein:

$R^{19}$ is selected from the group consisting of halogen (in particular fluorine, chlorine or bromine, more particularly fluorine or chlorine), $C_1$-$C_2$alkyl, $C_1$-$C_2$fluoroalkyl, $C_1$-$C_2$alkoxy, $C_1$-$C_2$fluoroalkoxy, cyano and nitro;

$R^{20}$ is selected from the group consisting of hydrogen, halogen (in particular fluorine, chlorine or bromine, more particularly fluorine or chlorine), $C_1$-$C_2$alkyl, $C_1$-$C_2$fluoroalkyl, $C_1$-$C_2$alkoxy, $C_1$-$C_2$fluoroalkoxy, cyano and nitro; and $R^{21}$ is selected from the group consisting of hydrogen, halogen (in particular fluorine, chlorine or bromine, more particularly fluorine or chlorine), $C_1$-$C_2$alkyl, $C_1$-$C_2$fluoroalkyl, $C_1$-$C_2$alkoxy, $C_1$-$C_2$fluoroalkoxy, cyano and nitro;

provided that either one or none (i.e. no more than one) of $R^{19}$, $R^{20}$ and $R^{21}$ are $C_1$-$C_2$alkyl, $C_1$-$C_2$alkoxy or nitro; and $R^{22}$ is selected from the group consisting of hydrogen, halogen (in particular fluorine, chlorine or bromine, more particularly fluorine or chlorine), methyl, $C_1$fluoroalkyl (e.g. trifluoromethyl), $C_1$fluoroalkoxy (e.g. difluoromethoxy or trifluoromethoxy) and cyano.

Preferably, $R^{19}$ is selected from the group consisting of halogen (in particular fluorine, chlorine or bromine), $C_1$fluoroalkyl (e.g. trifluoromethyl), $C_1$fluoroalkoxy (e.g. difluoromethoxy or trifluoromethoxy) and cyano. More preferably, $R^{19}$ is halogen; even more preferably fluorine, chlorine or bromine. Most preferably, $R^{19}$ is fluorine or chlorine; in particular chlorine.

Preferably, $R^{20}$ is selected from the group consisting of hydrogen, fluorine and chlorine; more preferably hydrogen or fluorine. Most preferably, $R^{20}$ is hydrogen.

Preferably, $R^{21}$ is selected from the group consisting of hydrogen, halogen (in particular fluorine, chlorine or bromine, more particularly fluorine or chlorine) and $C_1$fluoroalkyl (e.g. trifluoromethyl). More preferably, $R^{21}$ is hydrogen or halogen; even more preferably hydrogen, fluorine, chlorine or bromine. Most preferably, $R^{21}$ is hydrogen, fluorine or chlorine; in particular hydrogen or fluorine.

Preferably, $R^{22}$ is selected from the group consisting of hydrogen, fluorine, chlorine, methyl, $C_1$fluoroalkyl (e.g. trifluoromethyl) and $C_1$fluoroalkoxy (e.g. difluoromethoxy or trifluoromethoxy). Most preferably $R^{22}$ is fluorine or chlorine, in particular chlorine.

In a particularly preferred embodiment of the present invention, $R^{24}$ is optionally substituted monocyclic heteroaryl of sub-formula ($2^{Ab}$), wherein $R^{19}$ is fluorine or chlorine, $R^{20}$ is hydrogen and $R^{21}$ is fluorine.

In another preferred embodiment of the present invention, $R^4$ is selected from the group consisting of hydrogen, methyl, fluorine, chlorine, methoxy, ethoxy, $C_1$fluoroalkyl-methoxy- (in particular trifluoromethyl-methoxy- or difluoromethyl-methoxy-), or MeO—$CH_2$—$CH_2$—O—. Still more preferably, e.g. in all aspects and/or embodiments of the invention, $R^4$ is methyl, chlorine or methoxy.

In a particularly preferred embodiment of the present invention, is a compound of Formula (I) wherein (i) $R^1$ is methyl, $R^3$ is hydrogen and $R^4$ is methyl; (ii) $R^1$ is methyl, $R^3$ is hydrogen and $R^4$ is vinyl; (iii) $R^1$ is methyl, $R^3$ is hydrogen and $R^4$ is ethynyl; (iv) $R^1$ is methyl, $R^3$ is hydrogen and $R^4$ is hydrogen; (v) $R^1$ is ethyl, $R^3$ is hydrogen and $R^4$ is hydrogen; or (vi) $R^1$ is methoxy-, $R^3$ is hydrogen and $R^4$ is hydrogen.

In a particularly preferred embodiment of the present invention, is a compound of Formula (I) wherein $R^1$ is methyl or ethyl, preferably methyl, $R^2$ is methyl or prop-1-ynyl, $R^3$ is hydrogen and $R^4$ is methyl.

In a particularly preferred embodiment of the present invention, is a compound of Formula (I) wherein $R^1$ is methyl or ethyl, preferably methyl, $R^2$ is methyl or prop-1-ynyl, $R^3$ is hydrogen and $R^4$ is vinyl.

In a particularly preferred embodiment of the present invention, is a compound of Formula (I) wherein $R^1$ is methyl or ethyl, preferably methyl, $R^2$ is methyl or prop-1-ynyl, $R^3$ is hydrogen and $R^4$ is ethynyl.

In a particularly preferred embodiment of the present invention, is a compound of Formula (I) wherein $R^1$ is methyl or ethyl, preferably methyl, $R^2$ is $R^{24b}$ (wherein $R^{19}$ is fluorine or chlorine, $R^{20}$ is hydrogen and $R^{21}$ is fluorine), $R^3$ is hydrogen and $R^4$ is methyl.

In a particularly preferred embodiment of the present invention, is a compound of Formula (I) wherein $R^1$ is methyl or ethyl, preferably methyl, $R^2$ is $R^{24b}$ (wherein $R^{19}$ is fluorine or chlorine, $R^{20}$ is hydrogen and $R^{21}$ is fluorine), $R^3$ is hydrogen and $R^4$ is vinyl.

In a particularly preferred embodiment of the present invention, is a compound of Formula (I) wherein $R^1$ is methyl or ethyl, preferably methyl, $R^2$ is $R^{24b}$ (wherein $R^{19}$ is fluorine or chlorine, $R^{20}$ is hydrogen and $R^{21}$ is fluorine), $R^3$ is hydrogen and $R^4$ is ethynyl.

In another preferred embodiment of the present invention, $R^5$, $R^6$, $R^7$, $R^8$ and $R^9$ are hydrogen.

In another preferred embodiment of the present invention, $R^{10}$ is hydrogen or $C_1$-$C_6$alkyl (e.g methyl, ethyl), more preferably hydrogen.

In another preferred embodiment of the present invention, $R^{11}$ is selected from the group consisting of $C_1$-$C_6$alkyl, $C_2$-$C_6$alkenyl, $C_2$-$C_6$alkynyl, $C_1$-$C_6$alkoxy$C_1$-$C_6$-alkyl- and $C_1$-$C_6$alkoxy-$C_2$-$C_3$-alkoxy-$C_2$-$C_3$-alkyl-.

In another preferred embodiment of the present invention, $R^{11}$ is —$(CH_2)_n$—$X^2$—$R^{13}$ wherein $R^{13}$ is selected from the group consisting of $R^{13a}$ to $R^{13o}$

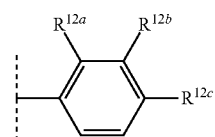

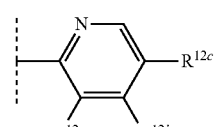

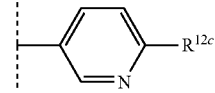

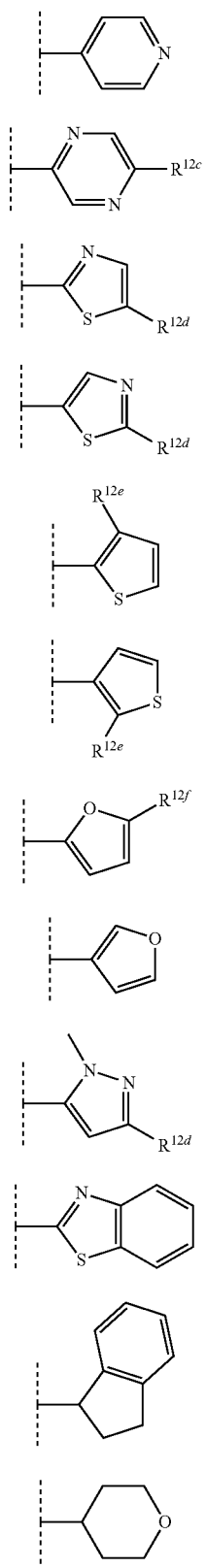

wherein
R$^{12a}$ is selected from the group consisting of hydrogen, C$_1$-C$_4$alkyl (especially methyl), C$_1$-C$_4$haloalkyl, halogen (especially chlorine or fluorine), C$_1$-C$_4$alkoxy (especially methoxy), cyano and nitro;

R$^{12b}$ is selected from the group consisting of hydrogen, C$_1$-C$_4$alkyl (especially methyl), halogen (especially chlorine or fluorine), C$_1$-C$_4$alkoxy, nitro and phenyl;

R$^{12c}$ is selected from the group consisting of hydrogen, C$_1$-C$_4$alkyl (especially methyl), halogen (especially chlorine or fluorine), C$_1$-C$_4$alkoxy, C$_1$-C$_4$haloalkyl (especially CF$_3$) and C$_1$-C$_4$haloalkoxy- (especially —OCH$_3$);

R$^{12d}$ is hydrogen or halogen (especially chlorine);

R$^{12e}$ is selected from the group consisting of hydrogen, halogen (especially bromine) and C$_1$-C$_2$alkyl (especially methyl); and R$^{12f}$ is hydrogen or C$_1$-C$_2$alkyl (especially methyl).

In a particularly preferred embodiment, R$^{11}$ is —(CH$_2$)$_n$—R$^{13}$ wherein n is 1, and R$^{13}$ is R$^{13a}$.

In another embodiment of the present invention, R$^{10}$ and R$^{11}$ together form a four to six membered heterocycle, the heterocycle comprising one or more heteroatoms selected from the group consisting of oxygen, nitrogen and sulphur; the heterocycle being optionally substituted by one or more independent R$^{12}$.

Preferably, n=0, 1 or 2.

In another embodiment of the present invention, the compound of Formula (I) is a compound of formula (Ia):

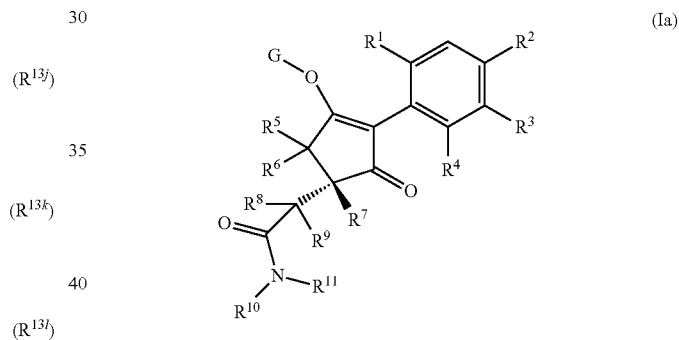

wherein R$^1$, R$^2$, R$^3$, R$^4$, R$^5$, R$^6$, R$^7$, R$^8$, R$^9$, R$^{10}$, R$^{11}$ and G are as defined in any of claims 1 to 14.

Preferably, 40% or more (in particular 45% or more) by molarity of the compound of formula (Ia) has the indicated stereochemistry at the ring-carbon atom bonded to R$^7$ and —CR$^8$R$^9$—(CO)NR$^{10}$R$^{11}$. For example, this broadest definition of formula (Ia) includes compounds which are substantially racemic at the ring-carbon atom bonded to R$^7$ and —CR$^8$R$^9$—(CO)NR$^{10}$R$^{11}$, and also includes compounds enriched with isomer(s) having the stereochemistry indicated at the ring-carbon atom bonded to R$^7$ and —CR$^8$R$^9$—(CO)NR$^{10}$R$^{11}$.

More preferably, more than 50% (still more preferably more than 70% or more than 80%, most preferably more than 90% or more than 95%) by molarity of the compound of formula (Ia) has the indicated stereochemistry at the ring-carbon atom bonded to R$^7$ and —CR$^8$R$^9$—(CO)NR$^{10}$R$^{11}$. This more preferred definition of formula (Ia) includes compounds enriched with isomer(s) having the stereochemistry indicated at the ring-carbon atom bonded to R$^7$ and —CR$^8$R$^9$—(CO)NR$^{10}$R$^{11}$.

Depending on the nature of the substituents G, R$^1$, R$^2$, R$^3$, R$^4$, R$^5$, R$^6$, R$^7$, R$^8$, R$^9$, and R$^{10}$, compounds of formula (I) may exist in different isomeric or tautomeric forms.

For example, when G is hydrogen, compounds of formula (I) may exist in different tautomeric forms. This invention covers all such isomers and/or tautomers and/or mixtures thereof in all proportions. These isomers and/or tautomers are within the scope of the claimed compounds of formula (I).

Processes for Preparation of Compounds of the Present Invention, e.g. Compounds of Formula (I)

Processes for preparation of compounds, e.g. a compound of formula (I) (which optionally can be an agrochemically acceptable salt thereof), are now described, and form further aspects of the present invention.

A compound of formula I, wherein G is $C_1$-$C_8$alkyl, $C_2$-$C_8$fluoroalkyl, phenyl$C_1$-$C_8$alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano or nitro), heteroaryl$C_1$-$C_8$alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), $C_2$-$C_7$alkenyl-$CH_2$—, $C_2$-$C_7$alkenyl-CH(Me)-, $C_2$-$C_7$alkenyl-$CMe_2$-, $C_2$-$C_4$fluoroalkenyl-$CH_2$—, $C_2$-$C_7$alkynyl-$CH_2$—, —C($X^a$)—$R^a$, —C($X^b$)—$X^c$—$R^b$, —C($X^d$)—N($R^c$)—$R^d$, —$SO_2$—$R^g$, —P($X^e$)($R^f$)—$R^g$ or —$CH_2$—$X^f$—$R^h$, may be prepared by treating a compound of formula (A), which is a compound of formula I wherein G is H, with a reagent G-Z, wherein G-Z is an alkylating agent such as an alkyl halide (the definition of alkyl halides includes simple $C_1$-$C_8$ alkyl halides such as methyl iodide and ethyl iodide, substituted alkyl halides such as chloromethyl alkyl ethers, Cl—$CH_2$—$X^f$—$R^h$, wherein $X^f$ is oxygen, and chloromethyl alkyl sulfides Cl—$CH_2$—$X^f$—$R^h$, wherein $X^f$ is sulfur), a $C_1$-$C_8$alkyl sulfonate, or a di($C_1$-$C_8$alkyl) sulfate, or with a $C_3$-$C_8$alkenyl halide, or with a $C_3$-$C_8$alkynyl halide, or with an acylating agent such as a carboxylic acid, HO—C($X^a$)$R^a$, wherein $X^a$ is oxygen, an acid chloride, Cl—C($X^a$)$R^a$, wherein $X^a$ is oxygen, or acid anhydride, [$R^a$C($X^a$)]$_2$O, wherein $X^a$ is oxygen, or an isocyanate, $R^c$N=C=O, or a carbamoyl chloride, Cl—C($X^d$)—N($R^c$)—$R^d$ (wherein $X^d$ is oxygen and with the proviso that neither $R^c$ or $R^d$ is hydrogen), or a thiocarbamoyl chloride Cl—($X^d$)—N($R^c$)—$R^d$ (wherein $X^d$ is sulfur and with the proviso that neither $R^c$ or $R^d$ is hydrogen) or a chloroformate, Cl—C($X^b$)—$X^c$—$R^b$, (wherein $X^b$ and $X^c$ are oxygen), or a chlorothioformate Cl—C($X^b$)—$X^c$—$R^b$ (wherein $X^b$ is oxygen and $X^c$ is sulfur), or a chlorodithioformate Cl—C($X^b$)—$X^c$—$R^b$, (wherein $X^b$ and $X^c$ are sulfur), or an isothiocyanate, $R^c$N=C=S, or by sequential treatment with carbon disulfide and an alkylating agent, or with a phosphorylating agent such as a phosphoryl chloride, Cl—P($X^e$)($R^f$)—$R^g$ or with a sulfonylating agent such as a sulfonyl chloride Cl—$SO_2$—$R^e$, preferably in the presence of at least one equivalent of base. Where substituents $R^3$ and $R^4$ are not equal to substituents $R^5$ and $R^6$, these reactions may produce, in addition to a compound of formula I, a second compound of formula (IA). This invention covers both a compound of formula I and a compound of formula (IA), together with mixtures of these compounds in any ratio.

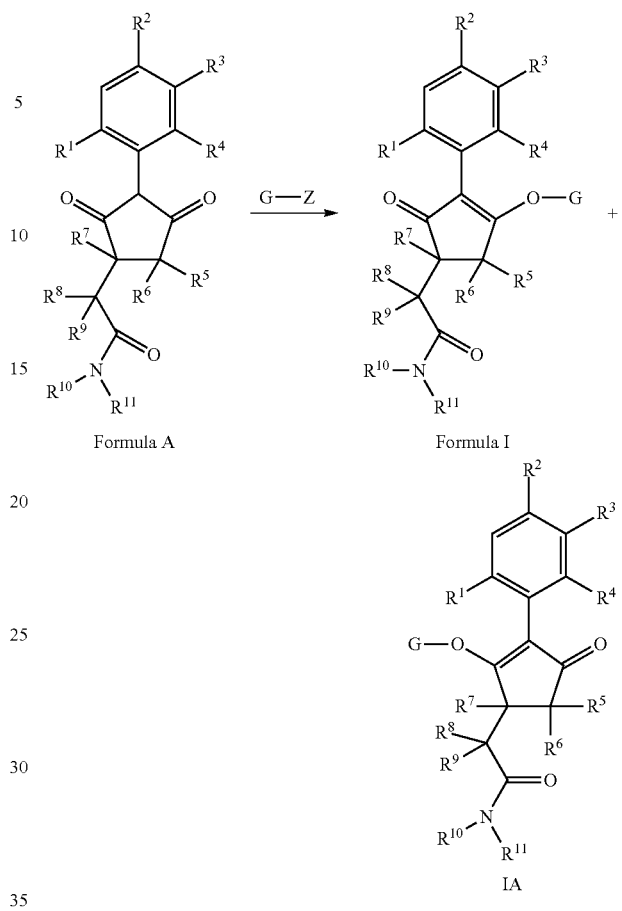

The O-alkylation of cyclic 1,3-diones is known; suitable methods are described, for example, by T. Wheeler, U.S. Pat. No. 4,436,666. Alternative procedures have been reported by M. Pizzorno and S. Albonico, *Chem. Ind. (London)*, (1972), 425-426; H. Born et al., *J. Chem. Soc.*, (1953), 1779-1782; M. G. Constantino et al., *Synth. Commun.*, (1992), 22 (19), 2859-2864; Y. Tian et al., *Synth. Commun.*, (1997), 27 (9), 1577-1582; S. Chandra Roy et al., *Chem. Letters*, (2006), 35 (1), 16-17; P. K. Zubaidha et al., *Tetrahedron Lett.*, (2004), 45, 7187-7188.

The O-acylation of cyclic 1,3-diones may be effected by procedures similar to those described, for example, by R. Haines, U.S. Pat. No. 4,175,135, and by T. Wheeler, U.S. Pat. No. 4,422,870, U.S. Pat. No. 4,659,372 and U.S. Pat. No. 4,436,666. Typically diones of formula (A) may be treated with an acylating agent preferably in the presence of at least one equivalent of a suitable base, and optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide; a suitable metal hydride is sodium hydride; and suitable organic bases include trialkylamines, such as trimethylamine and triethylamine, pyridines or other amine bases such as 1,4-diazobicyclo[2.2.2]-octane and 1,8-diazabicyclo[5.4.0] undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a known coupling agent such as 2-chloro-1-methylpyridinium iodide, N,N'-dicyclohexylcarbodiimide, 1-(3-dimethylaminopropyl)-3-ethylcarbodiimide and N,N'-carbodiimidazole, and optionally in the presence of a base such as triethylamine or pyridine in a suitable solvent such as tetrahydrofuran, dichloromethane or acetonitrile. Suitable procedures are described, for example, by W. Zhang and G. Pugh, *Tetrahedron Lett.*, (1999), 40 (43), 7595-7598; T. Isobe and T. Ishikawa, *J. Org. Chem.*, (1999), 64 (19), 6984-6988 and K. Nicolaou, T. Montagnon, G. Vassilikogiannakis, C. Mathison, *J. Am. Chem. Soc.*, (2005), 127(24), 8872-8888.

Phosphorylation of cyclic 1,3-diones may be effected using a phosphoryl halide or thiophosphoryl halide and a base by procedures analogous to those described by L. Hodakowski, U.S. Pat. No. 4,409,153.

Sulfonylation of a compound of formula (A) may be achieved using an alkyl or aryl sulfonyl halide, preferably in the presence of at least one equivalent of base, for example by the procedure of C. Kowalski and K. Fields, *J. Org. Chem.*, (1981), 46, 197-201

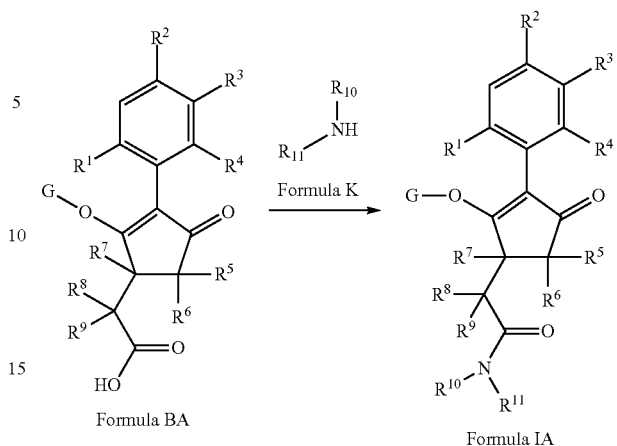

In an identical fashion, a compound of formula IA may be prepared from a compound of formula BA.

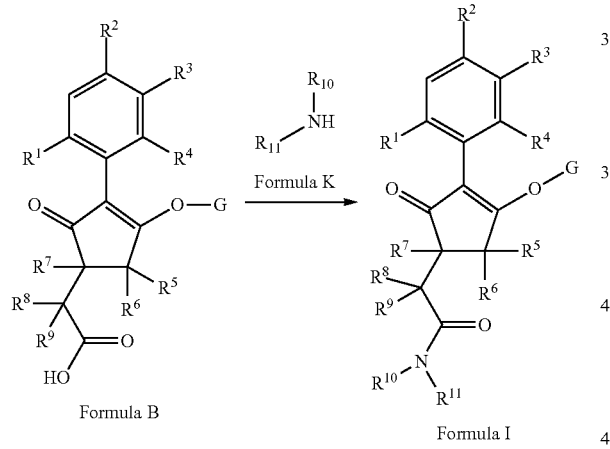

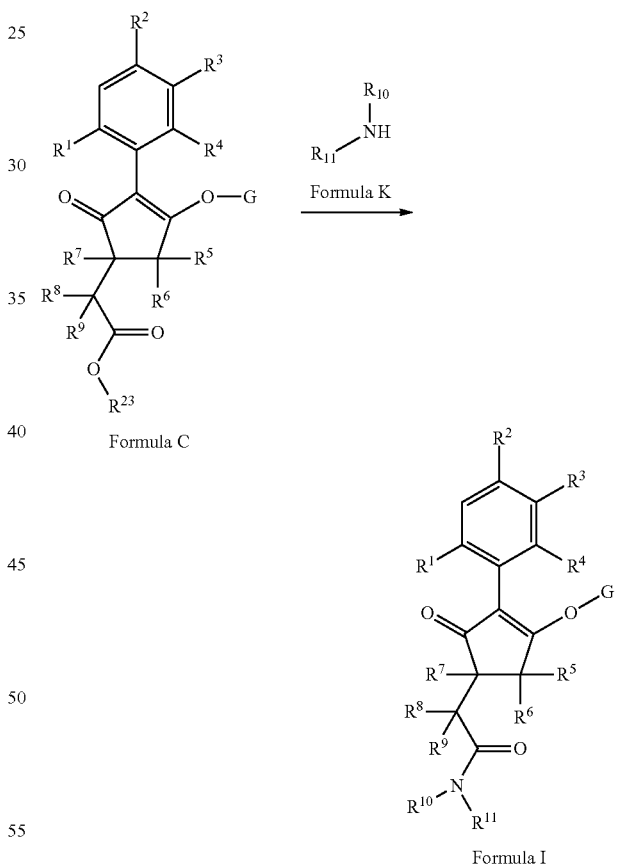

A compound of formula I may be prepared from a compound of formula B via an amide bond forming reaction with a compound of formula K optionally in the presence of a suitable solvent and/or in the presence of a suitable coupling reagent and/or in the presence of a suitable base or via transformation to an activated intermediate. Suitable solvents include N,N-dimethylformamide or dichloromethane, suitable coupling reagents include a carbodiimide (e.g. dicyclohexylcarbodiimide) or a phosphonic anhydride (e.g. 2,4,6-tripropyl-1,3,5,2,4,6-trioxatriphosphorinane-2,4,6-trioxide) or a (benzotriazol-1-yloxy)trialkylaminophosphonium salt (e.g. benzotriazol-1-yloxy(tripyrrolidin-1-yl)phosphonium hexafluorophosphate) and suitable bases include N,N-diisopropylethylamine or triethylamine. Suitable activated intermediates include acid chlorides, mixed anhydrides or activated esters (e.g. pentafluorophenyl ester).

Compounds of formula K are well known in the literature, are available from commercial sources or can be prepared via methods well known in the literature.

In an alternative approach, a compound of formula I may be prepared from a compound of formula C (where $R^{23}$ is typically, but not limited to $C_1$-$C_6$ alkyl) via a direct amide formation optionally in the presence of a suitable solvent and/or in the presence of a suitable catalyst. Suitable catalysts may include 1,5,7-triazabicyclo[4.4.0]dec-5-ene (see for example R. M. Waymouth et al J. Org. Chem (2009) 9490) or $Zr(Ot\text{-}Bu)_4$ (see for example J. A. Porco Jr et al J. Am. Chem. Soc (2005) 10039). Suitable solvents may include THF or toluene.

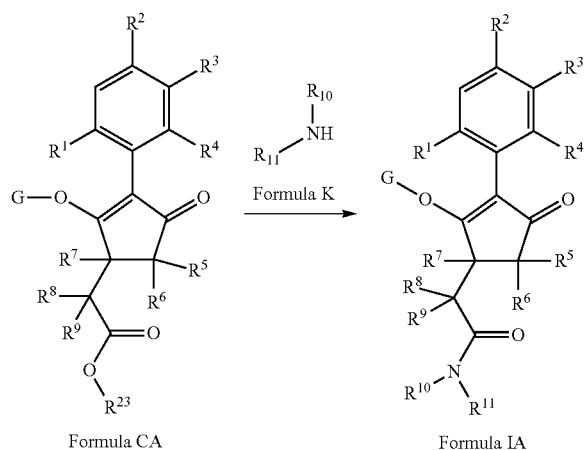

Formula CA → Formula IA

In an identical fashion, a compound of formula IA may be prepared from a compound of formula CA.

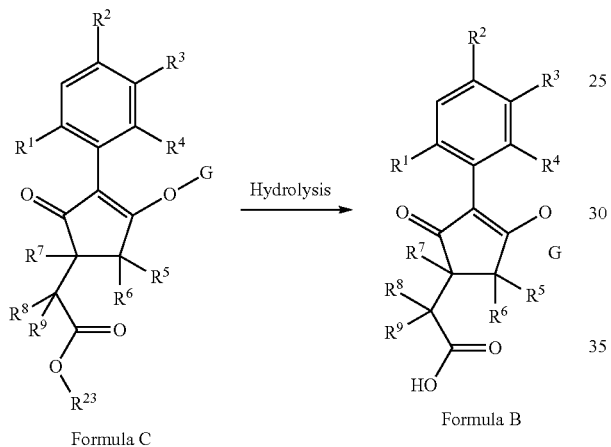

Formula C → Formula B (Hydrolysis)

A compound of formula B may be prepared from a compound of formula C (where $R^{23}$ is typically, but not limited to $C_1$-$C_6$ alkyl) via an ester hydrolysis reaction optionally in the presence of a suitable solvent and/or using a suitable reagent. Suitable solvents include tetrahydrofuran or water and suitable reagents include alkali metal hydroxides such as lithium, sodium or potassium hydroxide or other hydroxide sources such as tetrabutyl ammonium hydroxide (see for example H. Yamamoto et al Synlett (1998) 882).

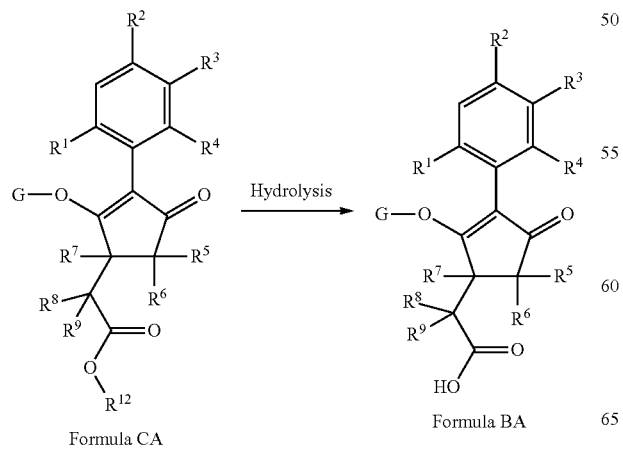

Formula CA → Formula BA (Hydrolysis)

In an identical fashion, a compound of formula BA may be prepared from a compound of formula CA.

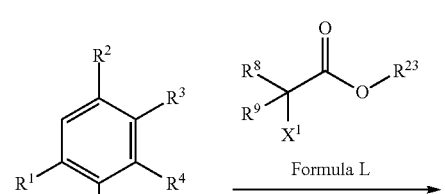

Formula D → (Formula L, Alkylation)

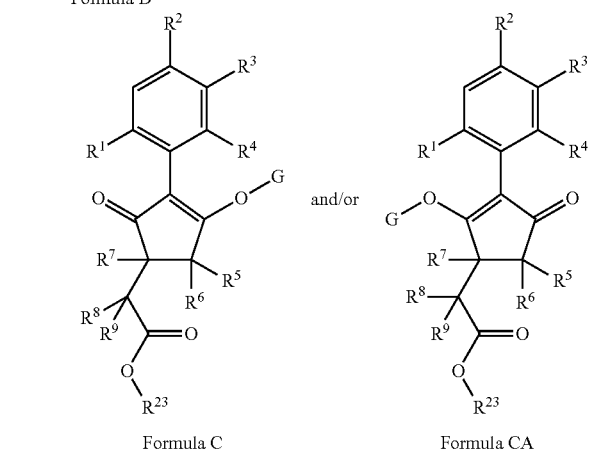

Formula C and/or Formula CA

A compound of formula C and/or of formula CA may be prepared from a compound of formula D via an alkylation reaction with a compound of formula L (where $X^1$ is a suitable leaving group such as, but not limited to I, Br or OTf), optionally in the presence of a suitable solvent and/or using a suitable base. Suitable solvents include tetrahydrofuran and suitable bases include lithium, sodium or potassium hexamethyldisilazide or lithium diisopropylamide (see for example WO2010069834).

Compounds of formula L are well known in the literature, are available from commercial sources or can be prepared via methods well known in the literature.

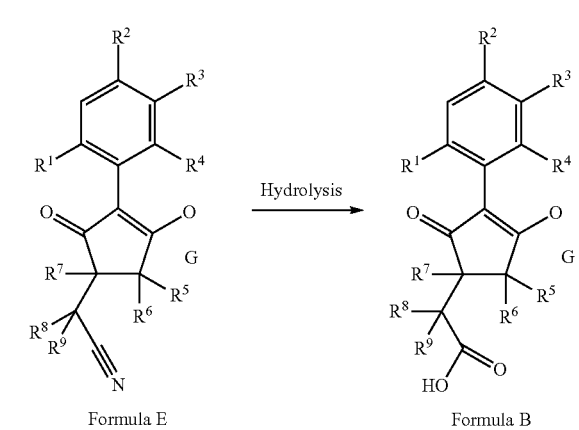

Formula E → Formula B (Hydrolysis)

In an alternative approach, a compound of formula B may be prepared from a compound of formula E via a hydrolysis reaction, optionally in the presence of a suitable reagent and/or in a suitable solvent. Suitable reagents may include phthalic acid (see for example F. Chemat et al; J. Chem. Soc (1994), 2597), sodium hydroxide or hydrogen chloride. Suitable solvents include water, ethanol or 1,4-dioxane.

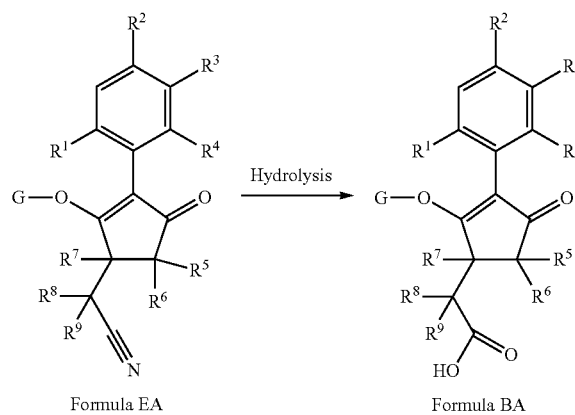

Formula EA → Hydrolysis → Formula BA

In an identical fashion, a compound of formula BA may be prepared from a compound of formula EA.

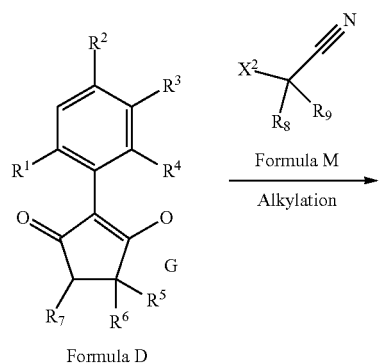

Formula D + Formula M → Alkylation

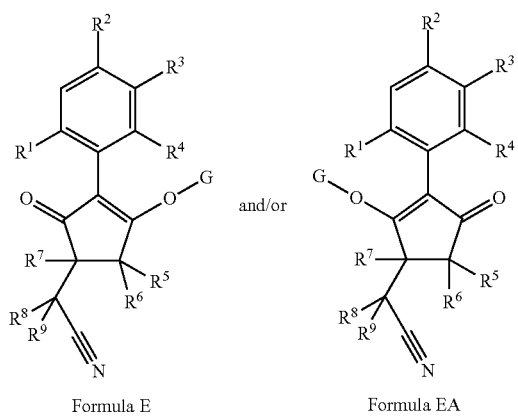

Formula E and/or Formula EA

A compound of formula E and/or a compound of formula EA may be prepared from a compound of formula D via an alkylation reaction with a compound of formula M (where $X^2$ is a suitable leaving group such as but not limited to I, Br or OTf), optionally in the presence of a suitable solvent and/or using a suitable base. Suitable solvents include tetrahydrofuran and suitable bases may include lithium, sodium or potassium hexamethyldisilazide (see for example Merck Sharp and Dohme Corp; WO2012/139495), lithium diisopropyl amide (see for example R. D. Dillard et al; J. Med. Chem (1991), 2768) or sodium hydride (see for example A. S. Demir et al; Tetrahedron (2005), 10482).

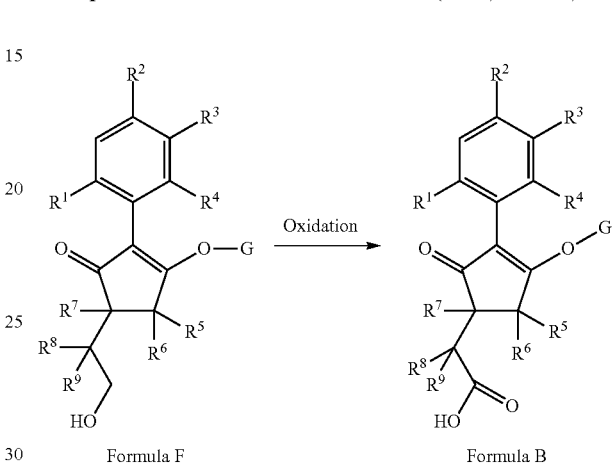

Formula F → Oxidation → Formula B

In a yet further alternative approach, a compound of formula B may be prepared from a compound of formula F via an oxidation reaction, optionally in the presence of a suitable solvent and/or in the presence of a suitable oxidising agent. Suitable solvents include acetone, t-butanol, water or carbon tetrachloride. Suitable oxidising agents may include but are not limited to Jones' reagent (see for example S. Poulain et al; Tetrahedron (1999), 3595), potassium permanganate (see for example M. Kordes et al; EJOC (2000), 3235) or ruthenium trichloride/sodium periodate (see for example Merrell Pharmaceuticals Inc; U.S. Pat. No. 6,340, 761).

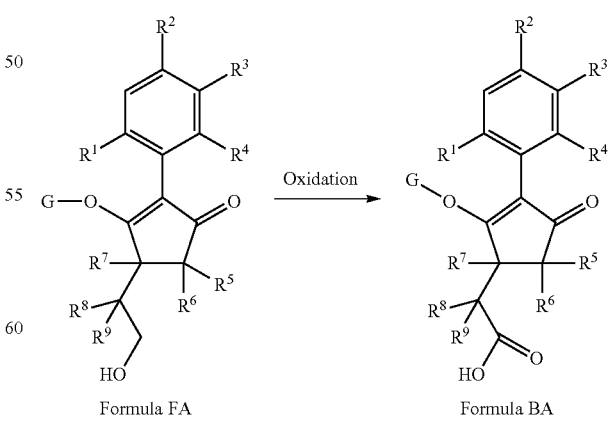

Formula FA → Oxidation → Formula BA

In an identical fashion, a compound of formula BA may be prepared from a compound of formula FA.

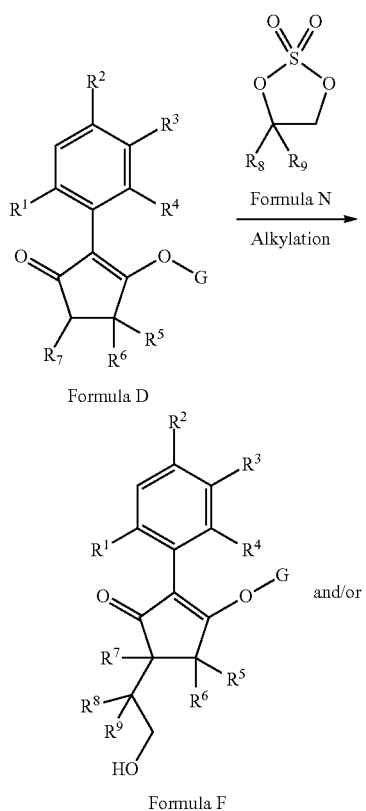

Formula D

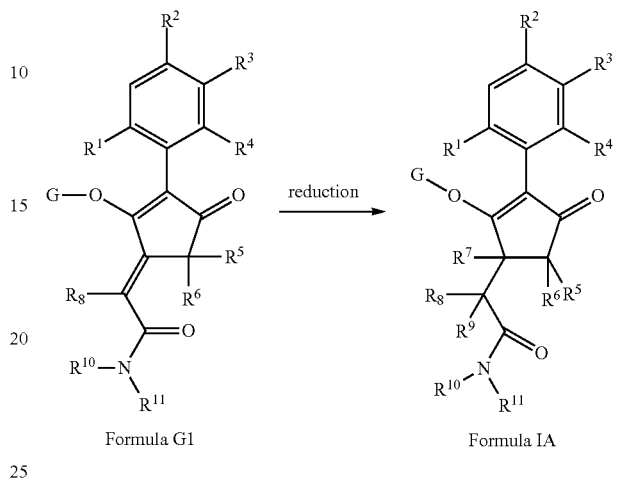

Formula G1 → Formula IA

In an identical fashion, a compound of formula 1A may be prepared from a compound of formula G1.

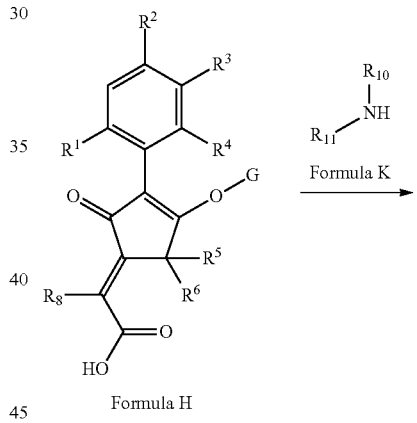

Formula H

Formula F and/or Formula FA

A compound of formula F and/or a compound of formula FA may be prepared from a compound of formula D via alkylation with a compound of formula N (see for example T. Schlaeger et al; Synthesis (2008), 1793) optionally in the presence of a suitable base and/or in the presence of a suitable solvent. Suitable bases may include lithium, sodium or potassium hexamethyldisilazide or lithium diisopropyl amide. Suitable solvents may include tetrahydrofuran.

Compounds of formula N are well known in the literature, are available from commercial sources or can be prepared via methods well known in the literature.

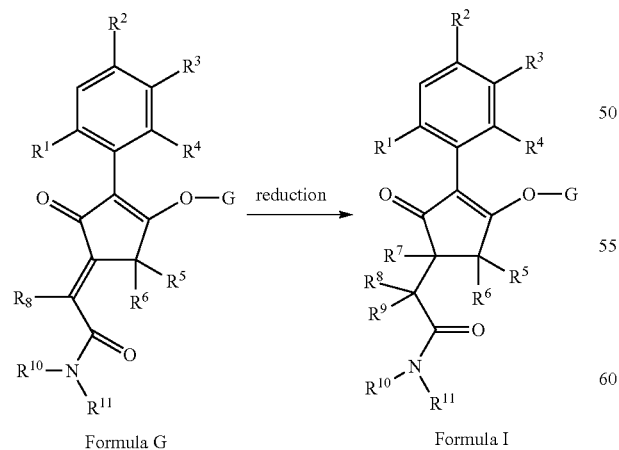

Formula G → Formula I

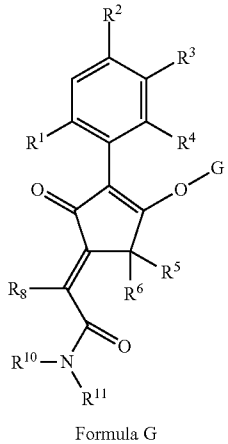

Formula G

A compound of Formula I may be prepared from a compound of formula G via a reduction using a suitable reducing agent, optionally in the presence of a suitable catalyst and/or in the presence of a suitable solvent. Suitable reducing agents may include hydrogen gas or zinc dust/acetic acid. Suitable catalysts may include, but not limited to, palladium on carbon. Suitable solvents may include ethanol, methanol or ethyl acetate.

In an alternative approach, a compound of formula G may be prepared from a compound of formula H via an amide bond forming reaction with a compound of formula K optionally in the presence of a suitable solvent and/or in the presence of a suitable coupling reagent and/or in the presence of a suitable base or via transformation to an activated intermediate. Suitable solvents include N,N-dimethylformamide or dichloromethane, suitable coupling reagents include a carbodiimide (e.g. dicyclohexylcarbodiimide) or a phosphonic anhydride (e.g. 2,4,6-tripropyl-1,3,5,2,4,6-trioxatriphosphorinane-2,4,6-trioxide) or a (benzotriazol-1-yloxy)trialkylaminophosphonium salt (e.g. benzotriazol-1-yloxy(tripyrrolidin-1-yl)phosphonium hexafluorophosphate) and suitable bases include N,N-diisopropylethylamine or triethylamine. Suitable activated intermediates include acid chlorides, mixed anhydrides or activated esters (e.g. pentafluorophenyl ester).

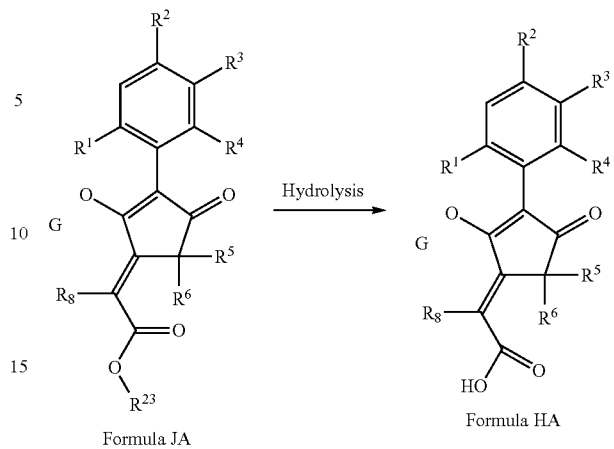

Formula JA → Formula HA

In an identical fashion, a compound of formula HA may be prepared from a compound of formula JA

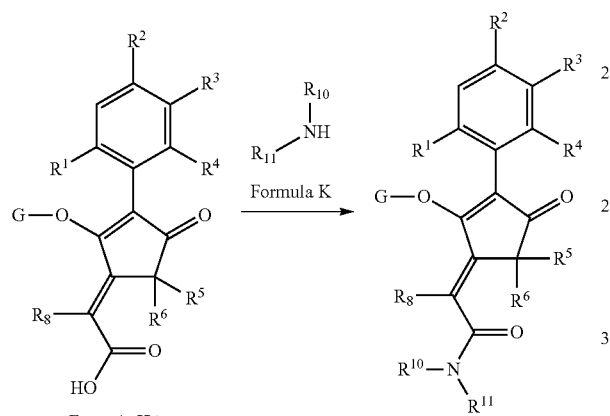

Formula HA → Formula GA

In an identical fashion, a compound of formula GA may be prepared from a compound of formula HA.

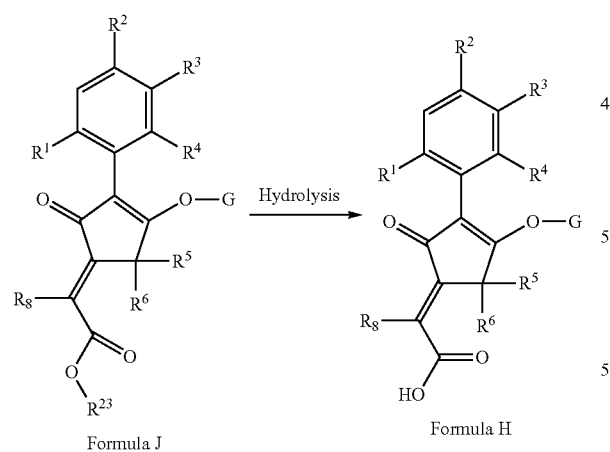

Formula J → Formula H

A compound of formula H may be prepared from a compound of formula J via a hydrolysis reaction optionally in the presence of a suitable reagent and/or in the presence of a suitable solvent. Suitable reagents may include lithium, sodium or potassium hydroxide or trifluoroacetic acid. Suitable solvents may include tetrahydrofuran, water or dichloromethane.

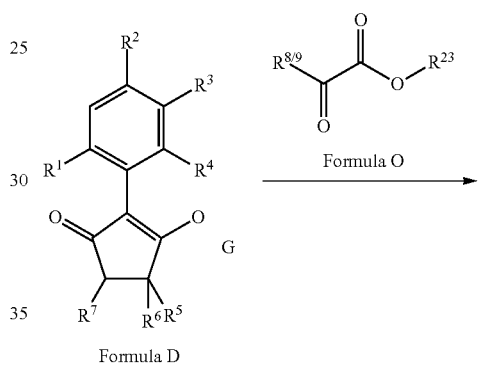

Formula D

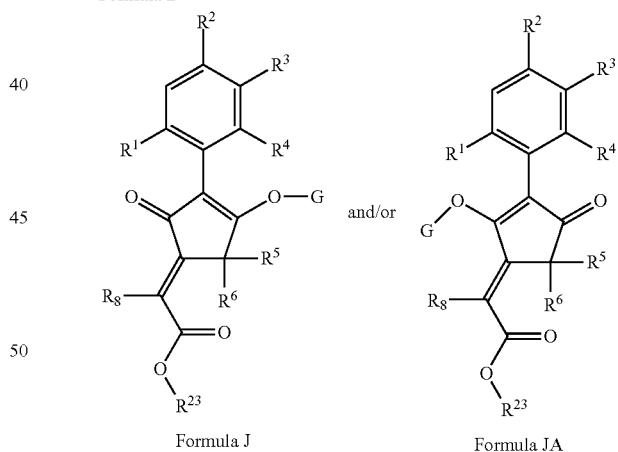

Formula J and/or Formula JA

A compound of formula J and/or and compound of formula JA may be prepared from a compound of Formula D (where R7=H) via reaction with a compound of formula O via a condensation reaction, optionally in the presence of a suitable base and an elimination reaction optionally in the presence of a suitable reagent. Suitable bases for the condensation may include lithium diisopropylamide (see for example S. Chasset et al WO12140243) and suitable reagents for the elimination may include methane sulfonyl chloride, optionally in the presence of a suitable base such as triethylamine (see for example B. M. Trost et al JACS (2005) 14785).

Compounds of formula O are well known in the literature, are available from commercial sources or can be prepared via methods well known in the literature.

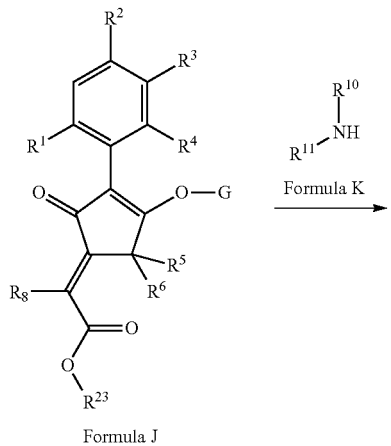

Formula J

In an alternative approach, a compound of formula G may be prepared from a compound of formula J (where $R^{23}$ is typically, but not limited to $C_1$-$C_6$ alkyl) via a direct amide forming reaction with a compound of formula K optionally in the presence of a suitable solvent and/or in the presence of a suitable catalyst. Suitable catalysts may include 1,5,7-triazabicyclo[4.4.0]dec-5-ene (see for example R. M. Waymouth et al J. Org. Chem (2009) 9490) or Zr(Ot-Bu)$_4$ (see for example J. A. Porco Jr et al J. Am. Chem. Soc (2005) 10039). Suitable solvents may include THF or toluene.

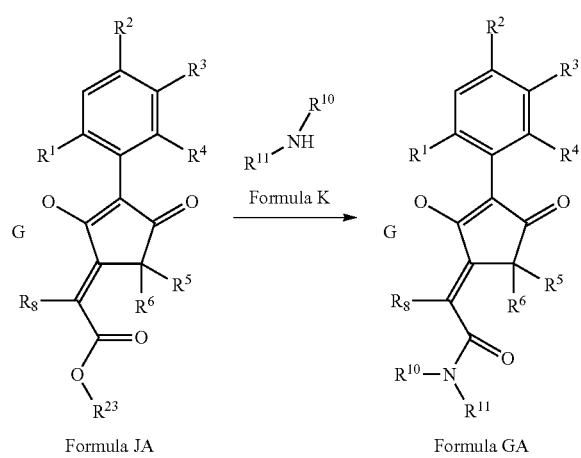

Formula JA      Formula GA

In an identical fashion, a compound of formula GA may be prepared from a compound of formula JA.

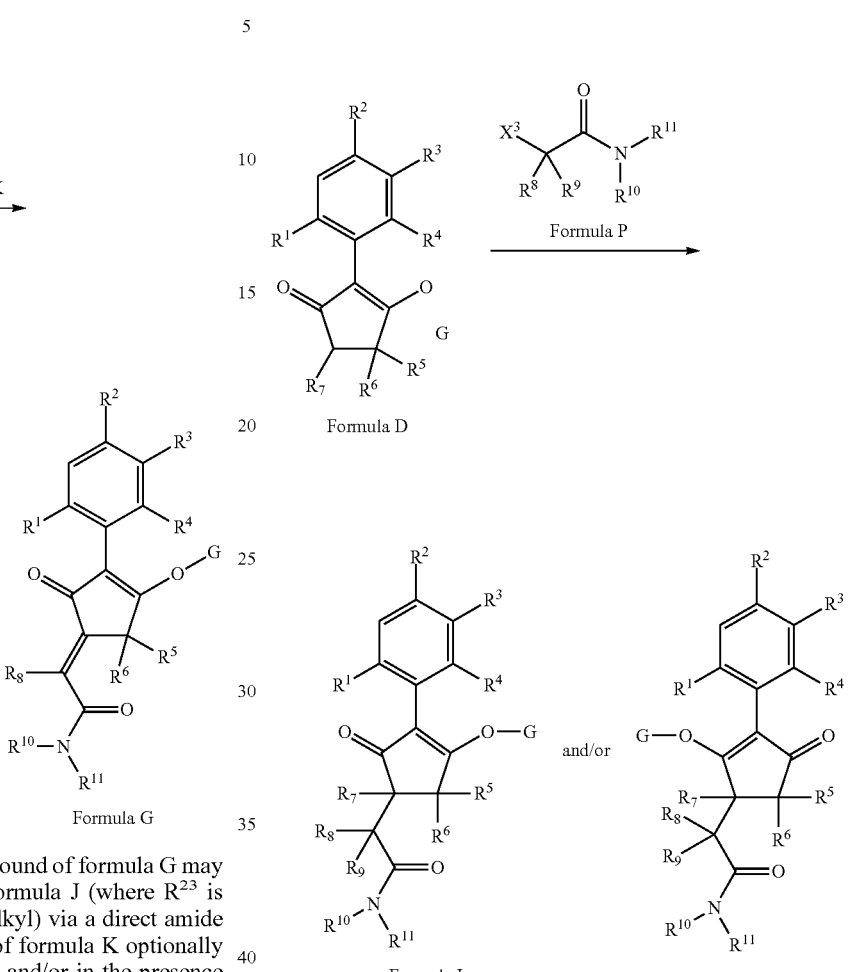

In yet another alternative approach, a compound of formula I and/or a compound of formula IA may be prepared from a compound of formula D via alkylation with a compound of formula P (where $X^3$ is a suitable leaving group such as, but not limited to I, Br or OTf) optionally in the presence of a suitable base and/or in the presence of a suitable solvent. Suitable bases may include lithium, sodium or potassium hexamethyldisilazide or lithium diisopropyl amide. Suitable solvents may include tetrahydrofuran.

Compounds of formula P are well known in the literature, are available from commercial sources or can be prepared via methods well known in the literature.

In one embodiment, compounds within Formula D are made using the processes described in WO 2013/079708 and WO 2010/089210. The reaction scheme for these processes is shown below (and is illustrated for compounds of Formula D in which $R^2$ is Br, $R^1$ and $R^4$ are Me; $R^3$, $R^5$, $R^6$ and $R^7$ are H; and G is Me):

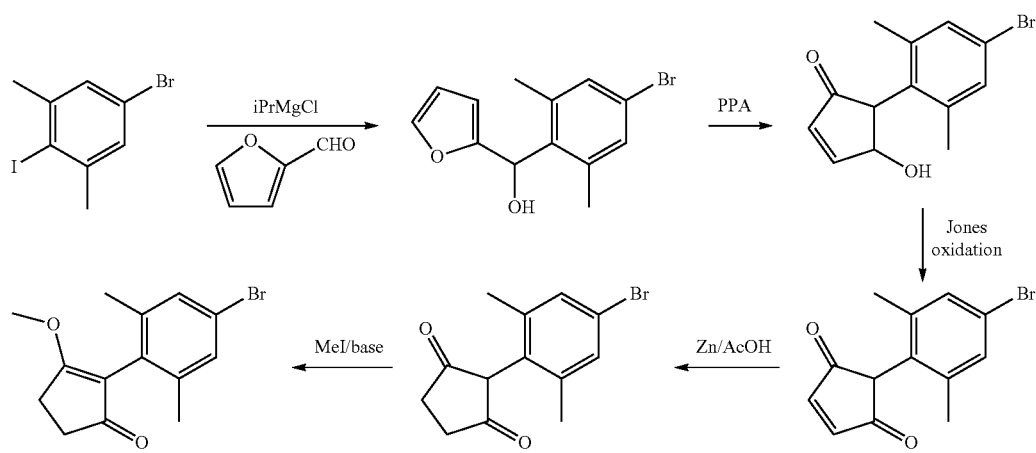

In an alternative embodiment, compounds within Formula D are made via the following coupling process scheme, as disclosed in Example 1 step 1 on pages 54-55 of WO 2010/000773 A1 and/or as disclosed in WO 2010/069834 A1 and/or WO 2011/073060 A2. The coupling process scheme below is illustrated for compounds of Formula D in which $R^1$, $R^2$ and $R^4$ are Me; $R^3$, $R^5$, $R^6$ and $R^7$ are H; and G is Me:

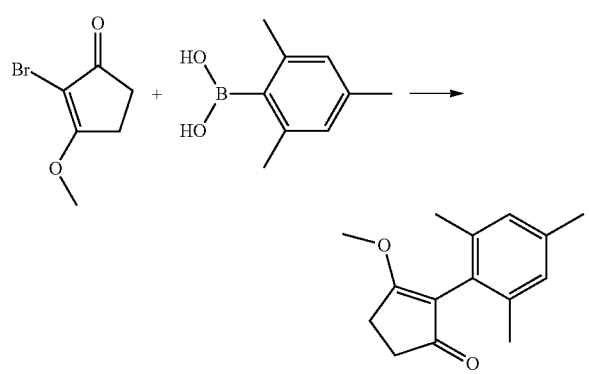

Typical reagents for the above-shown coupling process (in WO 2010/000773 A1) are potassium phosphate, Pd(OAc)$_2$, and S-Phos (which is 2-(dicyclohexylphosphino)-2',6'-dimethoxybiphenyl). The 2,4,6-trimethyl-phenyl boronic acid shown above is commercially available.

Herbicidal Compositions

In another aspect, the present invention provides a herbicidal composition, e.g. for use in a method of controlling weeds (preferably monocotyledonous such as grassy monocotyledonous weeds) in crops of useful plants, which composition comprises a compound of formula (I) as defined herein (e.g. a herbicidally effective amount thereof), and a substantially-inert agrochemically acceptable substance (e.g. an agrochemically acceptable carrier, diluent and/or solvent, an agrochemically acceptable adjuvant, an an agrochemically acceptable emulsifier/surfactant/surface-active substance, and/or another agrochemically acceptable additive).

In a further aspect, the present invention provides a herbicidal composition, e.g. for use in a method of controlling weeds (preferably monocotyledonous such as grassy monocotyledonous weeds) in crops of useful plants, comprising a compound of formula (I) as defined herein (e.g. a herbicidally effective amount thereof), and an agrochemically acceptable carrier, diluent and/or solvent.

In all aspects of the invention, the compound of the formula (I) is optionally present (e.g. where chemically possible) as an agrochemically acceptable salt (e.g. agrochemically acceptable metal, sulfonium or ammonium salt) thereof.

In one particular embodiment, the herbicidal composition also comprises one or more further herbicides, e.g. as mixture partner(s) for the compound of formula (I), and/or a safener. See the combinations and mixtures section herein for more details of examples of these.

The compounds of formula (I) according to the invention can be used as crop protection agents in unmodified form, as obtained by synthesis, but, for use as herbicides, they are generally formulated into herbicidal compositions (formulations), e.g. in a variety of ways, containing one or more substantially-inert agrochemically acceptable substances (e.g. an agrochemically acceptable carrier, diluent and/or solvent, an agrochemically acceptable adjuvant, an agrochemically acceptable emulsifier/surfactant/surface-active substance, and/or another agrochemically acceptable additive).

The formulations (herbicidal compositions) can be in various physical forms, for example in the form of dusting powders, gels, wettable powders, coated or impregnated granules for manual or mechanical distribution on target sites, water-dispersible granules, water-soluble granules, emulsifiable granules, water-dispersible tablets, effervescent compressed tablets, water-soluble tapes, emulsifiable concentrates, microemulsifiable concentrates, oil-in-water (EW) or water-in-oil (WO) emulsions, other multiphase systems such as oil/water/oil and water/oil/water products, oil flowables, aqueous dispersions, oily dispersions, suspoemulsions, capsule suspensions, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. The active ingredient may be incorporated into microfibers or micro-rods formed of polymers or polymerizable monomers and having diameter of about 0.1 to about 50 microns and aspect ratio of between about 10 and about 1000.

Such formulations can either be used directly or are diluted prior to use. They can then be applied through suitable ground or aerial application spray equipment or other ground application equipment such as central pivot irrigation systems or drip/trickle irrigation means. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be contained in fine microcapsules consisting of a core and a polymeric shell. Microcapsules usually have a diameter of from 0.1 to 500 microns. They contain active ingredients in an amount of about from 25 to 95% by weight of the capsule weight. The active ingredients can be present in the form of liquid technical material, in the form of a suitable solution, in the form of fine particles in solid or liquid dispersion or as a monolithic solid. The encapsulating membranes comprise, for example, natural and synthetic gums, cellulose, styrene-butadiene copolymers or other similar suitable membrane forming material, polyacrylonitrile, polyacrylate, polyester, polyamides, polyureas, polyurethane, aminoplast resins or chemically modified starch or other polymers that are known to the person skilled in the art in this connection.

Alternatively it is possible for fine so called "microcapsules" to be formed wherein the active ingredient is present in the form of finely divided particles in a solid matrix of a base substance, but in that case the microcapsule is not encapsulated with a diffusion limiting membrane as outlined in the preceding paragraph.

The active ingredients may be adsorbed on a porous carrier. This may enable the active ingredients to be released into their surroundings in controlled amounts (e.g. slow release). Other forms of controlled release formulations are granules or powders in which the active ingredient is dispersed or dissolved in a solid matrix consisting of a polymer, a wax or a suitable solid substance of lower molecular weight. Suitable polymers are polyvinyl acetates, polystyrenes, polyolefins, polyvinyl alcohols, polyvinyl pyrrolidones, alkylated polyvinyl pyrrolidones, copolymers of polyvinyl pyrrolidones and maleic anhydride and esters and half-esters thereof, chemically modified cellulose esters like carboxymethyl cellulose, methyl cellulose, hydroxyethyl cellulose, examples of suitable waxes are polyethylene wax, oxidized polyethylene wax, ester waxes like montan waxes, waxes of natural origin like carnauba wax, candelilla wax, bees wax etc. Other suitable matrix materials for slow release formulations are starch, stearin, lignin.

The formulation ingredients (e.g. inert ingredients) suitable for the preparation of the compositions according to the invention are generally known per se.

As a liquid carrier and/or solvent (e.g. organic solvent), e.g. for use in the herbicidal composition(s) according to the invention, there may be used: water, an aromatic solvent such as toluene, m-xylene, o-xylene, p-xylene or a mixture thereof, cumene, an aromatic hydrocarbon blend with a boiling range between 140 and 320° C. (e.g. known under various trademarks such as Solvesso®, Shellsol A®, Caromax®, Hydrosol®), a paraffinic or isoparaffinic carrier such as paraffin oil, mineral oil, a de-aromatized hydrocarbon solvent with a boiling range between 50 and 320° C. (e.g. known for instance under the trademark Exxsol®), a non-dearomatized hydrocarbon solvent with a boiling range between 100 and 320° C. (e.g. known under the tradename Varsol®), an isoparaffinic solvent with a boiling range between 100 and 320° C. (e.g. known under tradenames like Isopar® or Shellsol T®), a hydrocarbon such as cyclohexane, tetrahydronaphthalene (tetralin), decahydronaphthalene, alpha-pinene, d-limonene, hexadecane, isooctane; an ester solvent such as ethyl acetate, n- or iso-butyl acetate, amyl acetate, i-bornyl acetate, 2-ethylhexyl acetate, a $C_6$-$C_{18}$ alkyl ester of acetic acid (e.g. known under the tradename Exxate®), lactic acid ethylester, lactic acid propylester, lactic acid butylester, benzyl benzoate, benzyl lactate, dipropyleneglycol dibenzoate, or a dialkyl ester of succinic, maleic or fumaric acid; a polar solvent such as N-methyl pyrrolidone, N-ethyl pyrrolidone, $C_3$-$C_{18}$-alkyl pyrrolidones, gamma-butyrolactone, dimethylsulfoxide, N,N-dimethylformamide, N,N-dimethylacetamide, N,N-dimethyllactamide, a $C_4$-$C_{18}$ fatty acid dimethylamide, benzoic acid dimethylamide, acetonitrile, acetone, methyl ethyl ketone, methyl-isobutyl ketone, isoamyl ketone, 2-heptanone, cyclohexanone, isophorone, methyl isobutenyl ketone (mesityl oxide), acetophenone, ethylene carbonate, propylene carbonate, or butylene carbonate;

an alcoholic solvent or diluent such as methanol, ethanol, propanol, n- or iso-butanol, n- or iso-pentanol, 2-ethyl hexanol, n-octanol, tetrahydrofurfuryl alcohol, 2-methyl-2,4-pentanediol, 4-hydroxy-4-methyl-2-pentanone, cyclohexanol, benzyl alcohol, ethylene glycol, ethylene glycol butyl ether, ethylene glycol methyl ether, diethylene glycol, diethylene glycol butyl ether, diethylene glycol monoethyl ether, diethylene glycol monomethyl ether, propylene glycol, dipropylene glycol, dipropylene glycol monomethyl ether, or another similar glycol monoether solvent based on a ethylene glycol, propylene glycol or butylene glycol feedstock, triethylene glycol, polyethylene glycol (e.g. PEG 400), a polypropylenglycol with a molecular mass of 400-4000, or glycerol;

glycerol acetate, glycerol diacetate, glycerol triacetate, 1,4-dioxane, diethylene glycol abietate, chlorobenzene, chlorotoluene; a fatty acid ester such as methyl octanoate, isopropyl myristate, methyl laurate, methyl oleate, a mixture of $C_8$-$C_{10}$ fatty acid methyl esters, rapeseed oil methyl ester, rapeseed oil ethyl ester, soybean oil methyl ester, soybean oil ethyl ester; a vegetable oil (e.g. rapeseed oil or soybean oil); a fatty acid such as oleic acid, linoleic acid, or linolenic acid; or an ester of phosphoric or phosphonic acid such as triethyl phosphate, a $C_3$-$C_{18}$-tris-alkyl phosphate, an alkylaryl phosphate, or bis-octyl-octyl phosphonate.

Water is generally the liquid carrier of choice for the dilution of the concentrates.

Suitable solid carriers are, for example, talc, titanium dioxide, pyrophyllite clay, silica (fumed or precipated silica and optionally functionalised or treated, for instance silanised), attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in the EPA CFR 180.1001. (c) & (d). Powdered or granulated fertilisers can also be used as solid carriers.

A large number of surface-active substances can advantageously be used both in solid and in liquid formulations (herbicidal compositions), especially in those formulations (herbicidal compositions) which can be diluted with a carrier prior to use. Surface-active substances may be anionic, cationic, amphoteric, non-ionic or polymeric and they may be used as emulsifying, wetting, dispersing or suspending agents or for other purposes. Typical surface-active substances include, for example, salts of alkyl sulfates, such as diethanolammonium lauryl sulfate; Sodium lauryl sulfate, salts of alkylarylsulfonates, such as calcium or sodium dodecylbenzenesulfonate; alkylphenol-alkylene oxide addition products, such as nonylphenol ethoxylates; alcohol-alkylene oxide addition products, such as tridecyl alcohol ethoxylate; soaps, such as sodium stearate; salts of alkyl-naphthalenesulfonates, such as sodium dibutylnaphthalene-sulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further formulation ingredients (e.g. inert ingredients) which can typically be used in formulations (herbicidal compositions) include crystallisation inhibitors, viscosity-modifying substances, suspending agents, dyes, anti-oxidants, foaming agents, light absorbers, mixing aids, antifoams, complexing agents, neutralising or pH-modifying substances and/or buffers, corrosion-inhibitors, fragrances, wetting agents, absorption improvers, micronutrients, plasticisers, glidants, lubricants, dispersants, thickeners, antifreezes, microbiocides, compatibility agents and/or solubilisers; and/or also liquid and/or solid fertilisers.

The herbicidal compositions (formulations) may also comprise additional active substances, for example further herbicides, herbicide safeners, plant growth regulators, fungicides or insecticides.

The herbicidal compositions according to the invention can additionally include an additive (commonly referred to as an adjuvant), comprising a mineral oil, an oil of vegetable or animal origin, alkyl (e.g. $C_1$-$C_6$alkyl) esters of such oils or mixtures of such oils and oil derivatives/oil esters. The amount of oil additive (oil adjuvant) used in the composition according to the invention is generally from 0.01 to 10%, based on the spray mixture. For example, the oil additive (oil adjuvant) can be added to the spray tank in the desired concentration after the spray mixture has been prepared. Preferred oil additives (oil adjuvants) comprise mineral oils or an oil of vegetable origin, for example rapeseed oil, olive oil or sunflower oil, emulsifiable vegetable oil, such as AMIGO® (Loveland Products Inc.), $C_1$-$C_6$alkyl esters of oils of vegetable origin, for example the methyl esters, or an oil of animal origin, such as fish oil or beef tallow. A preferred oil additive (oil adjuvant) contains methylated rapeseed oil (rapeseed oil methyl ester). Another preferred oil additive (oil adjuvant) contains, for example, as active components essentially 80% by weight alkyl esters of fish oils and 15% by weight methylated rapeseed oil (rapeseed oil methyl ester), and also 5% by weight of customary emulsifiers and pH modifiers. Especially preferred oil additives (oil adjuvants) comprise $C_1$-$C_6$alkyl ester(s) of $C_8$-$C_{22}$ fatty acid(s), especially the methyl ester(s) of $C_8$-$C_{22}$ (especially $C_{12}$-$C_{18}$) fatty acid(s); preferably the methyl ester of lauric acid, of palmitic acid, or of oleic acid. Those esters are known as methyl laurate (CAS-111-82-0), methyl palmitate (CAS-112-39-0) and methyl oleate (CAS-112-62-9) respectively. A preferred fatty acid methyl ester derivative is AGNIQUE ME 18 RD-F® (e.g. available from Cognis). Those and other oil derivatives are also known from the Compendium of Herbicide Adjuvants, 5th Edition, Southern Illinois University, 2000.

The application and action of the above-mentioned oil additives (oil adjuvants) can be further improved by combining them with surface-active substances, such as non-ionic, anionic, cationic or amphoteric surfactants. Examples of suitable anionic, non-ionic, cationic or amphoteric surfactants, e.g. for this purpose, are listed on pages 7 and 8 of WO97/34485. Preferred surface-active substances are anionic surfactants of the dodecylbenzylsulfonate type, especially the calcium salts thereof, and also non-ionic surfactants of the fatty alcohol ethoxylate type. As non-ionic surfactants, special preference is given to ethoxylated $C_{12}$-$C_{22}$ fatty alcohols preferably having a degree of ethoxylation of from 5 to 40. Examples of commercially available surfactants are the Genapol types (Clariant). Also preferred are silicone surfactants, especially polyalkyl-oxide-modified heptamethyltrisiloxanes, which are commercially available e.g. as SILWET L-77®, and also perfluorinated surfactants. The concentration of surface-active substances in relation to the total oil additive (oil adjuvant) is generally from 1 to 50% by weight of the oil additive (oil adjuvant). Examples of oil additives (oil adjuvants) that consist of mixtures of oils and/or mineral oils and/or derivatives thereof with surfactants are TURBOCHARGE®, ADIGOR® (both (Syngenta Crop Protection AG), ACTIPRON® (BP Oil UK Limited), AGRI-DEX® (Helena Chemical Company).

The above-mentioned surface-active substances may also be used in the formulations alone, that is to say without oil additives (oil adjuvants).

Furthermore, the addition of an organic solvent to the oil additive (oil adjuvant)/surfactant mixture can contribute to a further enhancement of action. Suitable solvents are, for example, heavy aromatic hydrocarbon solvents such as SOLVESSO® or AROMATIC® solvents (Exxon Corporation). The concentration of such solvents can e.g. be from 10 to 80% by weight of the oil additive (oil adjuvant). Such oil additives (oil adjuvants), which may be in admixture with solvents, are described, for example, in U.S. Pat. No. 4,834, 908. A commercially available oil additive disclosed therein is known by the name MERGE® (BASF). Further such oil additives (oil adjuvants) that are preferred according to the invention are SCORE® and ADIGOR® (both Syngenta Crop Protection AG).

In addition to the oil additives (oil adjuvants) listed above, in order to enhance the activity of the compositions according to the invention it is also possible for formulations of alkylpyrrolidones, (e.g. AGRIMAX® from ISP) to be added to the spray mixture. Formulations of synthetic latices, such as, for example, polyacrylamide, polyvinyl compounds or poly-1-p-menthene (e.g. BOND®, COURIER® or EMERALD®) can also be used.

A particularly preferred oil adjuvant (oil additive), e.g. for use in the herbicidal compositions of the invention, is an emulsifiable concentrate which consists of:

(i) ethoxylated alcohols, which preferably includes ethoxylated $C_{12}$-$C_{22}$ fatty alcohols (preferably having a degree of ethoxylation of from 5 to 40); and (ii) a mixture of heavy aromatic hydrocarbons, which preferably includes (or more preferably includes 50% or more by weight of the heavy aromatic hydrocarbons of) a mixture of naphthalenes each of which is substituted by one or more alkyls wherein the alkyl(s) in total have 1-4 carbon atoms per naphthalene molecule (e.g. Solvesso 200 ND™); and (iii) methylated rapeseed oil (rapeseed oil methyl ester) (e.g. Agnique ME 18 RD-F™), as an adjuvant; preferably present at about 47% w/w and/or about 45% w/v of the oil adjuvant/oil additive/emulsifiable concentrate. One example of such a emulsifiable concentrate oil adjuvant (oil additive) is ADIGOR™, currently available in many countries from Syngenta.

When the above emulsifiable concentrate oil adjuvant is used, it is preferably added to the herbicidal composition after dilution (e.g. with water and/or in a spray tank), typically before application to weeds and/or to crops of useful plants and/or to the locus thereof. In one particular embodiment, the herbicidal composition, e.g. after dilution (e.g. with water and/or in a spray tank), contains the above emulsifiable concentrate oil adjuvant, and additionally ammonium sulphate and/or isopropyl alcohol.

Such adjuvant oils as described in the preceding paragraphs may be employed as a or the carrier liquid in which an active compound is dissolved, emulsified or dispersed as appropriate to the physical form of the active compound.

In an alternative particular embodiment, the herbicidal composition of the invention comprises an agrochemically acceptable adjuvant comprising 1,2-cyclohexane dicarboxylic acid di-isononyl ester (e.g. CAS Registry no. 166412-78-8), e.g. as available from BASF as Hexamoll™ DINCH™. "Isononyl" in this context is thought to mean one or more, preferably a mixture of two or more, branched isomers of $C_9H_{19}$. In one particular embodiment, the herbicidal composition, e.g. after dilution (e.g. with water and/or in a spray tank), contains 1,2-cyclohexane dicarboxylic acid di-isononyl ester, and additionally ammonium sulphate and/or isopropyl alcohol.

In an alternative particular embodiment, the herbicidal composition of the invention comprises an agrochemically acceptable adjuvant comprising an organic phosphate and/or organic phosphonate adjuvant. Preferably, the phosphate adjuvant is a tris-[$C_4$-$C_{12}$alkyl or 2-($C_2$-$C_6$alkoxy)ethyl-] ester of phosphoric acid, or more preferably is tris-(2-ethylhexyl) phosphate, tris-n-octyl phosphate and/or tris-[2-(n-butoxy)ethyl] phosphate, or most preferably is tris-(2-ethylhexyl) phosphate. Preferably, the phosphonate adjuvant is a bis-($C_3$-$C_{12}$alkyl) ester of a $C_3$-$C_{12}$alkyl-phosphonic acid, or more preferably is bis-(2-ethylhexyl) (2-ethylhexyl) phosphonate, bis-(2-ethylhexyl) (n-octyl)phosphonate and/or di-n-butyl (n-butyl)phosphonate.

The formulations (herbicidal compositions) generally contain from 0.1 to 99% by weight, especially from 0.1 to 95% by weight, of a compound of formula I and from 1 to 99.9% by weight of a substantially-inert agrochemically acceptable substance, which preferably includes a formulation adjuvant and/or from 0 to 30% or from 0 to 25% (in particular from 0.5 to 30% or from 0.5 to 25%) by weight of a surface-active substance. Whereas herbicidal compositions (especially commercial products) will preferably be formulated as concentrates, the end user will normally employ dilute formulations (herbicidal compositions), e.g. formulations (herbicidal compositions) diluted with water, in particular when applying the herbicidal composition to weeds and/or to crops of useful plants and/or to the locus thereof.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied (preferably post-emergence) at a rate of from 1 to 2000 g/ha, preferably from 1 to 1000 g/ha and most preferably at from 1 to 500 g/ha or from 5 to 500 g/ha.

Preferred formulations/compositions have especially the following representative compositions:
(%=percent by weight of the composition):

| Emulsifiable concentrates: | |
| --- | --- |
| active ingredient: | 0.3 to 95%, preferably 0.5 to 60% such as 1 to 40% |
| surface-active agents: | 1 to 30%, preferably 3 to 20% such as 5 to 15% |
| solvents as liquid carrier: | 1 to 80%, preferably 1 to 60% such as 1 to 40% |
| Dusts: | |
| active ingredient: | 0.1 to 10%, preferably 0.1 to 5% |
| solid carriers: | 99.9 to 90%, preferably 99.9 to 99% |
| Suspension concentrates: | |
| active ingredient: | 1 to 75%, preferably 3 to 50% or 10 to 50% |
| water: | 98 to 24%, preferably 95 to 30% or 88 to 30% |
| surface-active agents: | 1 to 40%, preferably 2 to 30% |
| Wettable powders: | |
| active ingredient: | 0.5 to 90%, preferably 1 to 80% |
| surface-active agents: | 0.5 to 20%, preferably 1 to 15% |
| solid carriers: | 5 to 95%, preferably 15 to 90% |
| Granules: | |
| active ingredient: | 0.1 to 30%, preferably 0.1 to 15% |
| solid carriers: | 99.5 to 70%, preferably 97 to 85% |
| Water-dispersible granules: | |
| active ingredient: | 1 to 90%, preferably 10 to 80% |
| surface-active agents: | 0.5 to 80%, preferably 5 to 30% |
| solid carriers: | 90 to 10%, preferably 70 to 30% |

The following Examples further illustrate, but do not limit, the invention.

| F1. Emulsifiable concentrates | | | | |
| --- | --- | --- | --- | --- |
| | a) | b) | c) | d) |
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP (N-methyl-2-pyrrolidone) | — | 10% | — | 20% |
| aromatic hydrocarbon mixture $C_9$-$C_{12}$ | 85% | 68% | 65% | 16% |

Emulsions of any desired concentration can be prepared from such concentrates by dilution with water.

| F2. Solutions | | | | |
| --- | --- | --- | --- | --- |
| | a) | b) | c) | d) |
| active ingredient | 5% | 10% | 50% | 90% |
| 1-methoxy-3-(3-methoxy-propoxy)-propane | 40% | 50% | — | — |

F2. Solutions

|  | a) | b) | c) | d) |
|---|---|---|---|---|
| polyethylene glycol MW 400 | 20% | 10% | — | — |
| NMP (N-methyl-2-pyrrolidone) | — | — | 50% | 10% |
| aromatic hydrocarbon mixture $C_9$-$C_{12}$ | 35% | 30% | — | — |

The solutions are suitable for application undiluted or after dilution with water.

F3. Wettable powders

|  | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalenesulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

F4. Coated granules

|  | a) | b) | c) |
|---|---|---|---|
| active ingredient | 0.1% | 5% | 15% |
| highly dispersed silica | 0.9% | 2% | 2% |
| inorganic carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated off in vacuo.

F5. Coated granules

|  | a) | b) | c) |
|---|---|---|---|
| active ingredient | 0.1% | 5% | 15% |
| polyethylene glycol MW 200 | 1.0% | 2% | 3% |
| highly dispersed silica | 0.9% | 1% | 2% |
| inorganic carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

F6. Extruded granules

|  | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

F7. Water-dispersible granules

|  | a) | b) | c) | d) |
|---|---|---|---|---|
| active ingredient | 5% | 10% | 40% | 90% |
| sodium lignosulfonate | 20% | 20% | 15% | 7% |
| dibutyl naphthalene sulfonate | 5% | 5% | 4% | 2% |
| Gum arabic | 2% | 1% | 1% | 1% |
| Diatomaceous earth | 20% | 30% | 5% | — |
| Sodium sulfate | — | 4% | 5% | — |
| kaolin | 48% | 30% | 30% | — |

The active ingredient is mixed and ground with the adjuvants and the mixture is moistened with water. The resulting mixture is extruded and then dried in a stream of air.

F8. Dusts

|  | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

F9. Suspension concentrates

|  | a) | b) | c) | d) |
|---|---|---|---|---|
| active ingredient | 3% | 10% | 25% | 50% |
| propylene glycol | 5% | 5% | 5% | 5% |
| nonylphenol polyglycol ether (15 mol of ethylene oxide) | — | 1% | 2% | — |
| sodium lignosulfonate | 3% | 3% | 7% | 6% |
| heteropolysacharide (Xanthan) | 0.2% | 0.2% | 0.2% | 0.2% |
| 1,2-benzisothiazolin-3-one | 0.1% | 0.1% | 0.1% | 0.1% |
| silicone oil emulsion | 0.7% | 0.7% | 0.7% | 0.7% |
| water | 88% | 80% | 60% | 38% |

The finely ground active ingredient is intimately mixed with the adjuvants, yielding a suspension concentrate from which suspensions of any desired concentration can be prepared by dilution with water.

Herbicidal Uses—Crops of Useful Plants, Weeds, Application Rates.

In a further aspect, the present invention provides a method of controlling weeds (e.g. monocotyledonous weeds such as grassy monocotyledonous weeds) in crops of useful plants, which comprises applying a compound of the formula (I), or a herbicidal composition comprising such a compound, to the weeds and/or to the plants and/or to the locus thereof.

In a further aspect, the present invention provides a herbicidal composition, in particular for use in a method of controlling weeds (preferably monocotyledonous weeds, more preferably grassy monocotyledonous weeds) in crops of useful plants, comprising a compound of formula (I) as defined herein (e.g. a herbicidally effective amount thereof), and an agrochemically acceptable carrier, diluent and/or solvent.

In all aspects of the invention, the compound of the formula (I) is optionally present (e.g. where chemically possible) as an agrochemically acceptable salt (e.g. agrochemically acceptable metal, sulfonium or ammonium salt) thereof.

In one particular embodiment, the herbicidal composition also comprises one or more further herbicides, e.g. as mixture partner(s) for the compound of formula (I), and/or a safener. See the combinations and mixtures section herein for more details of examples of these.

In all aspects of the invention (e.g. the methods of use of the invention), crops of useful plants, e.g. on or in which or at the locus of which the compounds or compositions according to the invention can be used, comprise (e.g. are), in particular, cereals (preferably non-oat cereals, in particular wheat, barley, rye and/or triticale), rice, corn (maize), sugarcane, leguminous crops [preferably soybean, peanut, and/or pulse crops; more preferably soybean; wherein typically the pulse crops comprise dry beans (e.g. kidney or haricot or pinto bean which is *Phaseolus vulgaris*, or mung bean which is *Vigna radiata*), chickpea, blackeye bean (i.e. black-eyed pea, *Vigna unguiculata*), lentil, dry broad beans, and/or dry peas such as garden peas], cotton, rape (in particular oilseed rape or canola), sunflower, linseed, sugarbeet, fodder beet, potato, vegetables (preferably dicotyledonous vegetables), flax, tobacco, plantation crops (such as conifer trees, olives and/or olive trees, oil palms, coffee, or vines), and/or fruit crops (in particular dicotyledonous and/or broadleaved fruit, and/or in particular pome fruit, stone fruit, bush fruit, citrus fruit, pineapple, banana, and/or strawberry).

Preferably, in all aspects of the invention, the crops of useful plants, e.g. on or in which or at the locus of which the compounds or compositions according to the invention can be used, comprise (e.g. are) cereals (preferably non-oat cereals, more particularly wheat, barley, rye and/or triticale), rice, corn (maize), sugarcane, leguminous crops (preferably soybean, peanut, and/or pulse crops, more preferably soybean), cotton, rape (in particular oilseed rape or canola), sunflower, linseed, sugarbeet, fodder beet, potato, and/or vegetables (preferably dicotyledonous vegetables).

Most preferably, in all aspects of the invention, the crops of useful plants, e.g. on or in which or at the locus of which the compounds or compositions according to the invention can be used, comprise (e.g. are) non-oat cereals, more particularly wheat, barley, rye and/or triticale.

The term "crops" is to be understood as also including crops that have been rendered tolerant to herbicides or classes of herbicides (for example ALS, GS, EPSPS, PPO and/or HPPD inhibitors, and/or 2,4-D or dicamba) as a result of conventional methods of breeding or genetic engineering. An example of a crop that has been rendered tolerant e.g. to imidazolinones (which are ALS inhibitors), such as imazamox, by conventional methods of breeding is Clearfield® summer rape (canola) and/or Clearfield® wheat and/or Clearfield® rice (all from BASF). Examples of crops that have been rendered tolerant to herbicides by genetic engineering methods include e.g. glyphosate- or glufosinate-resistant/tolerant maize or soybean varieties, in particular those commercially available under the trade name RoundupReady® or RoundupReady® 2 (both from Monsanto, both glyphosate-tolerant) or LibertyLink® (from Bayer, glufosinate-tolerant). Glufosinate-tolerant rice (LibertyLink®) also has been published.

Other crops of useful plants include 2,4-D-tolerant soybean, e.g. soybean genetically-modified to be tolerant to the herbicide 2,4-D, or dicamba-tolerant soybean, e.g. soybean genetically-modified to be tolerant to the herbicide dicamba. Such 2,4-D-tolerant or dicamba-tolerant soybean crops can also, in particular, be tolerant to glyphosate or glufosinate. For example, crops of useful plants include soybeans containing a dicamba-tolerance trait combined (stacked) with a glyphosate-tolerance trait, such that these soybeans have tolerance to the herbicides glyphosate and dicamba (for example Genuity® Roundup Ready® 2 Xtend soybeans, currently under development by Monsanto).

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

In all aspects of the invention, the weeds, e.g. to be controlled and/or growth-inhibited, may be either monocotyledonous (e.g. grassy) and/or dicotyledonous weeds. Preferably the weeds, e.g. to be controlled and/or growth-inhibited, comprise or are monocotyledonous weeds, more preferably grassy monocotyledonous weeds.

In all aspects of the invention, typically, the monocotyledonous (preferably grassy monocotyledonous) weeds, e.g. to be controlled and/or growth-inhibited, comprise (e.g. are) weeds from the genus *Agrostis, Alopecurus, Apera, Avena, Brachiaria, Bromus, Cenchrus, Cyperus* (a genus of sedges), *Digitaria, Echinochloa, Eleusine, Eriochloa, Fimbristylis* (a genus of sedges), *Juncus* (a genus of rushes), *Leptochloa, Lolium, Monochoria, Ottochloa, Panicum, Pennisetum, Phalaris, Poa, Rottboellia, Sagittaria, Scirpus* (a genus of sedges), *Setaria* and/or *Sorghum*; in particular: *Alopecurus myosuroides* (ALOMY, English name "blackgrass"), *Apera spica-venti, Avena fatua* (AVEFA, English name "wild oats"), *Avena ludoviciana, Avena sterilis, Avena sativa* (English name "oats" (volunteer)), *Brachiaria decumbens, Brachiaria plantaginea, Bromus tectorum, Digitaria horizontalis, Digitaria insularis, Digitaria sanguinalis* (DIGSA), *Echinochloa crus-galli* (English name "common barnyard grass", ECHCG), *Echinochloa oryzoides, Echinochloa colona* or *colonum, Eleusine indica, Eriochloa villosa* (English name "woolly cupgrass"), *Leptochloa chinensis, Leptochloa panicoides, Lolium perenne* (LOLPE, English name "perennial ryegrass"), *Lolium multiflorum* (LOLMU, English name "Italian ryegrass"), *Lolium persicum* (English name "Persian darnel"), *Lolium rigidum, Panicum miliaceum* (English name "wild proso millet"), *Phalaris minor, Phalaris paradoxa, Poa annua* (POAAN, English name "annual bluegrass"), *Scirpus maritimus, Scirpus juncoides*,

*Setaria viridis* (SETVI, English name "green foxtail"), *Setaria faberi* (SETFA, English name "giant foxtail"), *Setaria glauca*, *Setaria lutescens* (English name "yellow foxtail"), *Sorghum bicolor*, and/or *Sorghum halepense* (English name "Johnson grass").

In one preferred embodiment of all aspects of the invention, the monocotyledonous weeds, e.g. to be controlled and/or growth-inhibited, are grassy monocotyledonous weeds; in which case they typically comprise (e.g. are) weeds from the genus *Agrostis, Alopecurus, Apera, Avena, Brachiaria, Bromus, Cenchrus, Digitaria, Echinochloa, Eleusine, Eriochloa, Leptochloa, Lolium, Ottochloa, Panicum, Pennisetum, Phalaris, Poa, Rottboellia, Setaria* and/or *Sorghum*.

In one particular embodiment of all aspects of the invention, the grassy monocotyledonous weeds, e.g. to be controlled and/or growth-inhibited, are "warm-season" grassy weeds; in which case they typically comprise (e.g. are) weeds from the genus *Brachiaria, Cenchrus, Digitaria, Echinochloa, Eleusine, Eriochloa, Leptochloa, Ottochloa, Panicum, Pennisetum, Phalaris, Rottboellia, Setaria* and/or *Sorghum*.

In another particular embodiment of all aspects of the invention, the grassy monocotyledonous weeds, e.g. to be controlled and/or growth-inhibited, are "cool-season" grassy weeds; in which case they typically comprise (e.g. are) weeds from the genus *Agrostis, Alopecurus, Apera, Avena, Bromus, Lolium* and/or *Poa*.

In non-oat cereal crops such as wheat and/or barley, control and/or growth inhibition of weeds from the genus *Alopecurus, Apera, Avena*, especially *Avena fatua, Bromus, Lolium, Phalaris*, and/or *Setaria* is preferred; in particular *Alopecurus, Avena* (especially *Avena fatua*), *Lolium* and/or *Setaria* (especially *Setaria viridis, Setaria lutescens, Setaria faberi* and/or *Setaria glauca*).

In all aspects of the invention, in a particular embodiment, the weeds, e.g. to be controlled and/or growth-inhibited e.g. by applying a compound of formula (I), may be grassy monocotyledonous weeds (e.g. *Agrostis, Alopecurus, Apera, Avena, Brachiaria, Bromus, Cenchrus, Digitaria, Echinochloa, Eleusine, Eriochloa, Leptochloa, Lolium, Ottochloa, Panicum, Pennisetum, Phalaris, Poa, Rottboellia, Setaria* and/or *Sorghum* weeds), which are resistant to one or more ACCase inhibitor herbicides (ACCase=acetyl-coenzyme A carboxylase) selected from the group consisting of pinoxaden, clodinafop-propargyl, fenoxaprop-P-ethyl, diclofop-methyl, fluazifop-P-butyl, haloxyfop-P-methyl, quizalofop-P-ethyl, propaquizafop, cyhalofop-butyl, clethodim, sethoxydim, cycloxydim, tralkoxydim and butroxydim;

and/or which are resistant to glyphosate;

and/or which are resistant to one or more ALS inhibitor herbicides (ALS=acetolactate synthase), such as one or more sulfonyl urea herbicides (e.g. iodosulfuron-methyl, mesosulfuron-methyl, tribenuron-methyl, triasulfuron, prosulfuron, sulfosulfuron, pyrazosulfuron-ethyl, bensulfuron-methyl, nicosulfuron, flazasulfuron, iofensulfuron, metsulfuron-methyl, or any other sulfonyl urea herbicide disclosed in The Pesticide Manual, 15th edition (2009) or 16th edition (2012), ed. C. D. S. Tomlin, British Crop Protection Council) and/or one or more triazolopyrimidine herbicides (e.g. florasulam, pyroxsulam or penoxsulam) and/or one or more pyrimidinyl-(thio or oxy)-benzoate herbicides (e.g. bispyribac-sodium or pyriftalid) and/or one or more sulfonylamino-carbonyl-triazolinone herbicides (e.g. thiencarbazone-methyl, propoxycarbazone-sodium or flucarbazone-sodium) and/or one or more imidazolinone herbicides (e.g. imazamox).

Such resistant (in particular ACCase-inhibitor-resistant, glyphosate-resistant, and/or ALS-inhibitor-resistant) grassy weeds can more particularly comprise *Alopecurus myosuroides, Apera spica-venti, Avena fatua, Avena sterilis, Brachiaria decumbens, Brachiaria plantaginea, Digitaria horizontalis, Digitaria insularis, Digitaria sanguinalis, Echinochloa colona, Echinochloa crus-galli, Eleusine indica, Lolium multiflorum, Lolium rigidum, Lolium perenne, Phalaris minor, Phalaris paradoxa, Setaria viridis, Setaria faberi, Setaria glauca*, and/or *Sorghum halepense*; or can more particularly comprise *Alopecurus myosuroides, Apera spica-venti, Avena fatua, Avena sterilis, Digitaria sanguinalis, Echinochloa colona, Echinochloa crus-galli, Lolium multiflorum, Lolium rigidum, Lolium perenne, Phalaris minor, Phalaris paradoxa, Setaria viridis, Setaria faberi* and/or *Sorghum halepense*.

In an even more particular embodiment of the invention, the compound of formula (I) can be applied to grassy monocotyledonous weeds (e.g. selected from one of the above-mentioned list(s) of grassy weeds):

(a1) which are resistant to one or more ACCase inhibitor herbicides (e.g. selected from the above-mentioned list of ACCase inhibitor herbicides) at least partly by means of mutation (e.g. substitution) of one or more amino acids on the ACCase target site in the weed (e.g. see S. B. Powles and Qin Yu, "Evolution in Action: Plants Resistant to Herbicides", *Annu. Rev. Plant Biol.*, 2010, 61, pp. 317-347, e.g. see pages 325-327 therein in particular Table 3, incorporated herein by reference, for examples of such resistant weeds and/or amino acid substitutions); and/or (a2) which are resistant to glyphosate at least partly by means of mutation (e.g. substitution) of one or more amino acids on the EPSPS target site in the weed targeted by glyphosate (e.g. see above-mentioned S. B. Powles and Qin Yu article, pp. 327-329); and/or (a3) which are resistant to one or more ALS inhibitor herbicides (e.g. selected from the above-mentioned list of ALS inhibitor herbicides) at least partly by mutation (e.g. substitution) of one or more amino acids on the ALS target site in the weed (e.g. see S. B. Powles and Qin Yu, "Evolution in Action: Plants Resistant to Herbicides", *Annu. Rev. Plant Biol.*, 2010, 61, pp. 317-347, e.g. see pages 322-324 therein in particular Table 2, incorporated herein by reference, for examples of such resistant weeds and/or amino acid substitutions); and/or (b) which are resistant to: one or more ACCase inhibitor herbicides (e.g. selected from the above-mentioned list), and/or glyphosate, and/or one or more ALS inhibitor herbicides (e.g. selected from the above-mentioned list); at least partly by metabolic-type herbicidal resistance e.g. at least partly by cytochrome P450-mediated herbicide metabolism (e.g. see S. B. Powles and Qin Yu, "Evolution in Action: Plants Resistant to Herbicides", *Annu. Rev. Plant Biol.*, 2010, 61, pp. 317-347, e.g. see Table 4 on page 328 therein, incorporated herein by reference, for examples of such resistant weeds).

Typically, dicotyledonous weeds, e.g. to be controlled, comprise (e.g. are) *Abutilon, Amaranthus, Chenopodium, Chrysanthemum, Galium, Ipomoea, Kochia, Nasturtium, Polygonum, Sida, Sinapsis, Solanum, Stellaria, Viola, Veronica* and/or *Xanthium*.

Areas under cultivation, and/or the locus (e.g. of weeds and/or of crops of useful plants), are to be understood as including land where the crop plants are already growing as well as land intended for the cultivation of those crop plants.

In all aspects of the invention, the rate of application (typically to the weeds and/or to the crops of useful plants and/or to the locus thereof) of the compound of formula (I) (which optionally may be an agrochemically acceptable salt thereof) is generally from 1 to 2000 g of the compound of formula (I) per hectare (ha) (measured as the free compound, i.e. excluding the weight of any associated salt counterion(s)), in particular from 5 to 500 g/ha, preferably from 10 to 400 g/ha, of the compound of formula (I) (measured as the salt-free compound, i.e. excluding the weight of any associated salt counterion(s)).

In all aspects of the invention, the compound of formula (I) can be applied (typically to the weeds and/or to the crops of useful plants and/or to the locus thereof) pre- and/or post-emergence, but preferably is applied post-emergence.

Combinations and Mixtures

In a further aspect, the present invention provides a herbicidal composition, e.g. for use in a method of controlling weeds (in particular monocotyledonous such as grassy monocotyledonous weeds) in crops of useful plants, comprising a compound of formula (I) as defined herein (e.g. a herbicidally effective amount thereof), and an agrochemically acceptable carrier, diluent and/or solvent, and also comprising one or more further herbicides, and/or a safener.

In all aspects of the invention, the compound of the formula (I) is optionally present (e.g. where chemically possible) as an agrochemically acceptable salt (e.g. agrochemically acceptable metal, sulfonium or ammonium salt) thereof.

Examples of these mixtures/compositions, comprising one or more further herbicides and/or a safener, follow.

The compounds of formula (I) according to the invention can be used in combination with one or more further herbicides, e.g. as mixture partner(s) for the compound of formula (I). Preferably, in these mixtures (in particular in the specific mixtures disclosed hereinbelow), the compound of the formula (I) is one of the specific compounds disclosed herein e.g. hereinbelow (in particular, any of compounds A1 to A29, or A30 to A41, or A42 or A45, or any of the compounds disclosed in any of Tables 1 to 60), present either as a free compound and/or as an agrochemically acceptable salt thereof.

In particular, the following mixtures of the compound of formula (I) with one or more further herbicides are particularly disclosed:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+bromoxynil heptanoate, compound of formula I+bromoxynil octanoate, compound of formula I+bromoxynil heptanoate+bromoxynil octanoate, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chloransulam, compound of formula I+chloransulam-methyl, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+2,4-D-dimethylammonium, compound of formula I+2,4-D-2-ethylhexyl, compound of formula I+a choline salt of 2,4-D (see e.g. Examples 2 and 3 of WO2010/123871A1), compound of formula I+2,4-D+glyphosate, compound of formula I+2,4-D-dimethylammonium+glyphosate, compound of formula I+2,4-D-2-ethylhexyl+glyphosate, compound of formula I+a choline salt of 2,4-D+glyphosate (see e.g. Examples 2 and 3 of WO2010/123871A1), compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dicamba-dimethylammonium, compound of formula I+dicamba-potassium, compound of formula I+dicamba-sodium, compound of formula I+dicamba-diglycolamine, compound of formula I+a N,N-bis[aminopropyl]methylamine salt of dicamba (see e.g. US2012/0184434A1), compound of formula I+dicamba+glyphosate, compound of formula I+dicamba-dimethylammonium+glyphosate, compound of formula I+dicamba-potassium+glyphosate, compound of formula I+dicamba-sodium+glyphosate, compound of formula I+dicamba-diglycolamine+glyphosate, compound of formula I+a N,N-bis-[aminopropyl]methylamine salt of dicamba+glyphosate (see e.g. US2012/0184434A1), compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula (I)+fenoxaprop, compound of formula (I)+fenoxaprop-ethyl, compound of formula I+fenoxaprop-P, compound of formula I+fenoxaprop-P-ethyl, compound of formula I+fenoxasulfone (CAS Reg. No. 639826-16-7), compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+flurochloridone, compound of formula I+fluroxypyr, compound of formula I+fluroxypyr-meptyl, compound of formula I+fluroxypyr-butometyl, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glufosinate-P, compound of formula I+glyphosate, compound of formula I+glyphosate-diammonium, compound of formula I+glyphosate-isopropylammonium, compound of formula I+glyphosate-potassium, compound of formula I+halosulfuron, compound of formula I+halosulfuron-methyl, compound of formula I+haloxyfop, compound of formula I+haloxyfop-P, compound of formula (I)+haloxyfop-methyl, compound of formula (I)+haloxyfop-P-methyl, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+ipfencarbazone (CAS Reg. No. 212201-70-2), compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+metazosulfuron (NC-620, CAS Reg. No. 868680-84-6), compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyrisulfuron (TH-547, CAS Reg. No. 570415-88-2), compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-ethyl, compound of formula I+quizalofop-P, compound of formula I+quizalofop-P-ethyl, compound of formula I+quizalofop-P-tefuryl, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS Reg. No. 353292-31-6), compound of formula I+4-[(4,5-dihydro-3-methoxy-4-methyl-5-oxo)-1H-1,2,4-triazol-1-ylcarbonylsulfamoyl]-5-methylthiophene-3-carboxylic acid (BAY636), compound of formula I+BAY747 (CAS Reg. No. 335104-84-2), compound of formula I+topramezone (CAS Reg. No. 210631-68-8), compound of formula I+4-hydroxy-3-[[2-[(2-methoxyethoxy)-methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula I+4-hydroxy-3-[[2-(3-methoxypropyl)-6-(difluoromethyl)-3-pyridinyl]carbonyl]-bicyclo[3.2.1]oct-3-en-2-one, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9, and which is also compound A-13 disclosed in pages 4, 5, 7 and 11 of WO 2011/073616 A2, these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9, and which is also compound A-12 disclosed in page 10 of WO 2011/073616 A2, these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1, and which is also compound A-4 disclosed on page 7 of WO 2011/073615 A2, these parts of these publications being incorporated herein by reference), compound of formula (I)+4-(2',4'-dichloro-4-ethylbiphenyl-3-yl)-2,2,6,6-tetramethyl-2H-pyran-3,5(4H,6H)-dione (which is compound A-45 disclosed on page 93 of WO 2008/071405 A1, and which is also the compound of Example P10 disclosed on pages 41 and 45 of WO 2010/136431 A9, and which is also compound A-7 disclosed on page 7 of WO 2011/073615 A2, these parts of these publications being incorporated herein by reference), compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1, and which is also compound A-9 disclosed on page 8 of WO 2011/073615 A2, these parts of these publications being incorporated herein by reference), compound of formula (I)+one of the specific herbicidal compounds disclosed in WO 2010/059676 (e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (e.g. as defined in one of the examples therein and/or e.g. can be plus cloquintocet-mexyl or another safener) these parts of which are incorporated herein by reference, and compound of formula (I)+one of the specific herbicidal compounds disclosed in WO 2010/059671 (e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+aminocyclopyrachlor (which is 6-amino-5-chloro-2-cyclopropylpyrimidine-4-carboxylic acid, CAS Reg. No. 858956-08-8), compound of formula I+aminocyclopyrachlor-methyl (which is methyl 6-amino-5-chloro-2-cyclopropylpyrimidine-4-carboxylate, CAS Reg. No. 858954-83-3), compound of formula I+aminocyclopyrachlor-potassium (which is potassium 6-amino-5-chloro-2-cyclopropylpyrimidine-4-carboxylate, CAS Reg. No. 858956-35-1), compound of formula I+saflufenacil (which is N'-{2-chloro-4-fluoro-5-[1,2,3,6-tetrahydro-3-methyl-2,6-dioxo-4-(trifluoromethyl)pyrimidin-1-yl]benzoyl}-N-isopropyl-N-methylsulfamide, CAS Reg. No. 372137-35-4), compound of formula I+iofensulfuron (which is 1-(2-iodophenylsulfonyl)-3-(4-methoxy-6-methyl-1,3,5-triazin-2-yl) urea, CAS Reg. No. 1144097-22-2), compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2), compound of formula I+clacyfos (which is dimethyl [(1RS)-1-(2,4-dichlorophenoxyacetoxy)ethyl]phosphonate, also named Ivxiancaolin or lüxiancaolin, CAS Reg. No. 215655-76-8), compound of formula I+cyclopyrimorate (which is 6-chloro-3-(2-cyclopropyl-6-methylphenoxy)pyridazin-4-yl morpholine-4-carboxylate, CAS Reg. No. 499231-24-2), or compound of formula I+triafamone (which is N-[2-[(4,6-dimethoxy-1,3,5-triazin-2-yl)carbonyl]-6-fluorophenyl]-N-methyl-1,1-difluoromethanesulfonamide, CAS Reg. No. 874195-61-6).

The mixture partners for the compound of formula (I) are optionally in the form of an ester (in particular an agrochemically acceptable ester) or a salt (in particular an agrochemically acceptable salt) thereof (e.g. where chemically possible). The above-mentioned mixture partners for the compound of formula (I), are generally mentioned e.g. in The Pesticide Manual, 15th Edition (2009) or 16th edition (2012), ed. C. D. S. Tomlin, British Crop Production Council.

In the present patent specification, "CAS Reg. No." or "CAS RN" means the Chemical Abstracts Service Registry Number of the stated compound.

For applications in cereals, the following mixtures are preferred: compound of formula I+aclonifen, compound of formula I+amidosulfuron, compound of formula I+aminopyralid, compound of formula I+beflubutamid, compound of formula I+benfluralin, compound of formula I+bifenox, compound of formula I+bromoxynil, compound of formula I+bromoxynil heptanoate, compound of formula I+bromoxynil octanoate, compound of formula I+bromoxynil heptanoate+bromoxynil octanoate, compound of formula I+butafenacil, compound of formula I+carbetamide, compound of formula I+carfentrazone, compound of formula I+carfentrazone-ethyl, compound of formula I+chlorotoluron, compound of formula I+chlorpropham, compound of formula I+chlorsulfuron, compound of formula I+cinidon-ethyl, compound of formula I+clodinafop, compound of formula I+clodinafop-propargyl, compound of formula I+clopyralid, compound of formula I+2,4-D, compound of formula I+2,4-D-dimethylammonium, compound of formula I+2,4-D-2-ethylhexyl, compound of formula I+a choline salt of 2,4-D (see e.g. Examples 2 and 3 of WO2010/123871A1), compound of formula I+dicamba, compound of formula I+dicamba-dimethylammonium, compound of formula I+dicamba-potassium, compound of formula I+dicamba-sodium, compound of formula I+dicamba-diglycolamine, compound of formula I+a N,N-bis-[aminopropyl] methylamine salt of dicamba (see e.g. US2012/0184434A1), compound of formula I+dichlobenil, compound of formula I+dichlorprop, compound of formula I+diclofop, compound of formula I+diclofop-methyl, compound of formula I+difenzoquat, compound of formula I+difenzoquat metilsulfate, compound of formula I+diflufenican, compound of formula I+diquat, compound of formula I+diquat dibromide, compound of formula (I)+fenoxaprop, compound of formula (I)+fenoxaprop-ethyl, compound of formula I+fenoxaprop-P, compound of formula I+fenoxaprop-P-ethyl, compound of formula I+flamprop-M, compound of formula I+florasulam, compound of formula I+fluazifop-P-butyl, compound of formula I+flucarbazone, compound of formula I+flucarbazone-sodium, compound of formula I+flufenacet, compound of formula I+flupyrsulfuron, compound of formula I+flupyrsulfuron-methyl-sodium, compound of formula I+flurochloridone, compound of formula I+fluroxypyr, compound of formula I+fluroxypyr-meptyl, compound of formula I+fluroxypyr-butometyl, compound of formula I+flurtamone, compound of formula I+imazamethabenz-methyl, compound of formula I+imazamox, compound of formula I+iodosulfuron, compound of formula I+iodosulfuron-methyl-sodium, compound of formula I+ioxynil, compound of formula I+isoproturon, compound of formula I+linuron, compound of formula I+MCPA, compound of formula I+mecoprop, compound of formula I+mecoprop-P, compound of formula I+mesosulfuron, compound of formula I+mesosulfuron-methyl, compound of formula I+mesotrione, compound of formula I+metribuzin, compound of formula I+metsulfuron, compound of formula I+metsulfuron-methyl, compound of formula I+pendimethalin, compound of formula I+picolinafen, compound of formula I+pinoxaden, compound of formula I+prodiamine, compound of formula I+propanil, compound of formula I+propoxycarbazone, compound of formula I+propoxycarbazone-sodium, compound of formula I+prosulfocarb, compound of formula I+pyrasulfotole, compound of formula I+pyridate, compound of formula I+pyroxasulfone (KIH-485), compound of formula I+pyroxsulam compound of formula I+sulfosulfuron, compound of formula I+tembotrione, compound of formula I+terbutryn, compound of formula I+thifensulfuron, compound of formula I+thiencarbazone, compound of formula I+thifensulfuron-methyl, compound of formula I+topramezone, compound of formula I+tralkoxydim, compound of formula I+tri-allate, compound of formula I+triasulfuron, compound of formula I+tribenuron, compound of formula I+tribenuron-methyl, compound of formula I+trifluralin, compound of formula I+trinexapac-ethyl and compound of formula I+tritosulfuron, compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula (I)+one of the specific herbicidal compounds disclosed in WO 2010/059676 (e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (e.g. as defined in one of the examples therein and/or e.g. can be plus cloquintocet-mexyl or another safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), or compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2);

wherein the mixture partners for the compound of formula (I) may optionally be in the form of an ester (in particular an agrochemically acceptable ester) or a salt (in particular an agrochemically acceptable salt) thereof (e.g. where chemically possible).

For applications in cereals, more preferred is a mixture comprising: a compound of formula (I)+amidosulfuron, compound of formula (I)+aminopyralid, compound of formula (I)+beflubutamid, compound of formula (I)+bromoxynil, compound of formula (I)+bromoxynil heptanoate, compound of formula (I)+bromoxynil octanoate, compound of formula (I)+bromoxynil heptanoate+bromoxynil octanoate, compound of formula (I)+carfentrazone, compound of formula (I)+carfentrazone-ethyl, compound of formula (I)+chlorotoluron, compound of formula (I)+chlorsulfuron, compound of formula (I)+clodinafop, compound of formula (I)+clodinafop-propargyl, compound of formula (I)+clopyralid, compound of formula (I)+2,4-D, compound of formula (I)+2,4-D-dimethylammonium, compound of formula (I)+2,4-D-2-ethylhexyl, compound of formula (I)+a choline salt of 2,4-D (see e.g. Examples 2 and 3 of WO2010/123871A1), compound of formula (I)+dicamba, compound of formula (I)+dicamba-dimethylammonium, compound of formula (I)+dicamba-potassium, compound of formula (I)+dicamba-sodium, compound of formula (I)+dicamba-diglycolamine, compound of formula (I)+a N,N-bis-[aminopropyl]methylamine salt of dicamba (see e.g. US2012/0184434A1), compound of formula (I)+difenzoquat, compound of formula (I)+difenzoquat metilsulfate, compound of formula (I)+diflufenican, compound of formula (I)+fenoxaprop-P, compound of formula (I)+fenoxaprop-P-ethyl, compound of formula (I)+florasulam, compound of formula (I)+flucarbazone, compound of formula (I)+flucarbazone-sodium, compound of formula (I)+flufenacet, compound of formula (I)+flupyrsulfuron, compound of formula (I)+flupyrsulfuron-methyl-sodium, compound of formula (I)+fluroxypyr, compound of formula I+fluroxypyr-meptyl, compound of formula I+fluroxypyr-butometyl, compound of formula (I)+flurtamone, compound of formula (I)+iodosulfuron, compound of formula (I)+iodosulfuron-methyl-sodium, compound of formula (I)+MCPA, compound of formula (I)+mesosulfuron, compound of formula (I)+mesosulfuron-methyl, compound of formula (I)+metsulfuron, compound of formula (I)+metsulfuron-methyl, compound of formula (I)+pendimethalin, compound of formula (I)+picolinafen, compound of formula (I)+pinoxaden, compound of formula (I)+prosulfocarb, compound of formula (I)+pyrasulfotole, compound of formula (I)+pyroxasulfone (KIH-485), compound of formula (I)+pyroxsulam, compound of formula (I)+sulfosulfuron, compound of formula (I)+thifensulfuron, compound of formula (I)+thifensulfuron-methyl, compound of formula I+topramezone, compound of formula (I)+tralkoxydim, compound of formula (I)+triasulfuron, compound of formula (I)+tribenuron, compound of formula (I)+tribenuron-methyl, compound of formula (I)+trifluralin, compound of formula (I)+trinexapac-ethyl, compound of formula (I)+tritosulfuron, compound of formula I+4-hydroxy-3-[[2-[(2-methoxyethoxy)-methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula (I)+one of the specific herbicidal compounds disclosed in WO 2010/059676 (e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (e.g. as defined in one of the examples therein and/or e.g. can be plus cloquintocet-mexyl or another safener) these parts of which are incorporated herein by reference, compound of formula I+halauxifen (which is 4-amino-3-chloro-6-(4-chloro-2-fluoro-3-methoxyphenyl) pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl) pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl) urea, CAS Reg. No. 1144097-22-2), or compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2);

wherein the mixture partners for the compound of formula (I) may optionally be in the form of an ester (in particular an agrochemically acceptable ester) or a salt (in particular an agrochemically acceptable salt) thereof (e.g. where chemically possible).

For applications in rice, the following mixtures are preferred: compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+butachlor, compound of formula (I)+cafenstrole, compound of formula (I)+cinosulfuron, compound of formula (I)+clomazone, compound of formula (I)+clomeprop, compound of formula (I)+cyclosulfamuron, compound of formula (I)+cyhalofop, compound of formula (I)+cyhalofop-butyl, compound of formula (I)+2,4-D, compound of formula (I)+2,4-D-dimethylammonium, compound of formula (I)+2,4-D-2-ethylhexyl, compound of formula (I)+a choline salt of 2,4-D (see e.g. Examples 2 and 3 of WO2010/123871A1), compound of formula (I)+daimuron, compound of formula (I)+dicamba, compound of formula (I)+dicamba-dimethylammonium, compound of formula (I)+dicamba-potassium, compound of formula (I)+dicamba-sodium, compound of formula (I)+dicamba-diglycolamine, compound of formula (I)+a N,N-bis-[aminopropyl]methylamine salt of dicamba (see e.g. US2012/0184434A1), compound of formula (I)+diquat, compound of formula (I)+diquat dibromide, compound of formula (I)+esprocarb, compound of formula (I)+ethoxysulfuron, compound of formula (I)+fenoxaprop, compound of formula (I)+fenoxaprop-ethyl, compound of formula (I)+fenoxaprop-P, compound of formula (I)+fenoxaprop-P-ethyl, compound of formula I+fenoxasulfone (CAS Reg. No. 639826-16-7), compound of formula (I)+fentrazamide, compound of formula (I)+florasulam, compound of formula (I)+glufosinate-ammonium, compound of formula (I)+glyphosate, compound of formula (I)+glyphosate-diammonium, compound of formula (I)+glyphosate-isopropylammonium, compound of formula (I)+glyphosate-potassium, compound of formula (I)+halosulfuron, compound of formula (I)+halosulfuron-methyl, compound of formula (I)+imazosulfuron, compound of formula I+ipfencarbazone (CAS Reg. No. 212201-70-2), compound of formula (I)+MCPA, compound of formula (I)+mefenacet, compound of formula (I)+mesotrione, compound of formula (I)+metamifop, compound of formula I+metazosulfuron (NC-620, CAS Reg. No. 868680-84-6), compound of formula (I)+metsulfuron, compound of formula (I)+metsulfuron-methyl, compound of formula (I)+n-methyl glyphosate, compound of formula (I)+orthosulfamuron, compound of formula (I)+oryzalin, compound of formula (I)+oxadiargyl, compound of formula (I)+oxadiazon, compound of formula (I)+paraquat dichloride, compound of formula (I)+pendimethalin, compound of formula (I)+penoxsulam, compound of formula (I)+pretilachlor, compound of formula (I)+profoxydim, compound of formula (I)+propanil, compound of formula I+propyrisulfuron (TH-547, CAS Reg. No. 570415-88-2), compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron and compound of formula (I)+trinexapac-ethyl, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9, and which is also compound A-13 disclosed in pages 4, 5, 7 and 11 of WO 2011/073616 A2, these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9, and which is also compound A-12 disclosed in page 10 of WO 2011/073616 A2, these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1, and which is also compound A-4 disclosed on page 7 of WO 2011/073615 A2, these parts of these publications being incorporated herein by reference), compound of formula (I)+4-(2',4'-dichloro-4-ethylbiphenyl-3-yl)-2,2,6,6-tetramethyl-2H-pyran-3,5(4H,6H)-dione (which is compound A-45 disclosed on page 93 of WO 2008/071405 A1, and which is also the compound of Example P10 disclosed on pages 41 and 45 of WO 2010/136431 A9, and which is also compound A-7 disclosed on page 7 of WO 2011/073615 A2, these parts of these publications being incorporated herein by reference), compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1, and which is also compound A-9 disclosed on page 8 of WO 2011/073615 A2, these parts of these publications being incorporated herein by reference), compound of formula (I)+one of the specific herbicidal compounds disclosed in WO 2010/059671 (e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2), or compound of formula I+triafamone (which is N-[2-[(4,6-dimethoxy-1,3,5-triazin-2-yl)carbonyl]-6-fluorophenyl]-N-methyl-1,1-difluoromethanesulfonamide, CAS Reg. No. 874195-61-6);

wherein the mixture partners for the compound of formula (I) may optionally be in the form of an ester (in particular an agrochemically acceptable ester) or a salt (in particular an agrochemically acceptable salt) thereof (e.g. where chemically possible).

For applications in rice, more preferred is a mixture comprising: a compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+clomazone, compound of formula (I)+clomeprop, compound of formula (I)+cyhalofop, compound of formula (I)+cyhalofop-butyl, compound of formula (I)+2,4-D, compound of formula (I)+2,4-D-dimethylammonium, compound of formula (I)+2,4-D-2-ethylhexyl, compound of formula (I)+a choline salt of 2,4-D (see e.g. Examples 2 and 3 of WO2010/123871A1), compound of formula (I)+daimuron, compound of formula (I)+dicamba, compound of formula (I)+dicamba-dimethylammonium, compound of formula (I)+dicamba-potassium, compound of formula (I)+dicamba-sodium, compound of formula (I)+dicamba-diglycolamine, compound of formula (I)+a N,N-bis-[aminopropyl]methylamine salt of dicamba (see e.g. US2012/0184434A1), compound of formula (I)+esprocarb, compound of formula (I)+ethoxysulfuron, compound of formula (I)+fenoxaprop-P, compound of formula (I)+fenoxaprop-P-ethyl, compound of formula I+fenoxasulfone (CAS Reg. No. 639826-16-7), compound of formula (I)+fentrazamide, compound of formula (I)+florasulam, compound of formula (I)+halosulfuron, compound of formula (I)+halosulfuron-methyl, compound of formula (I)+imazosulfuron, compound of formula I+ipfencarbazone (CAS Reg. No. 212201-70-2), compound of formula (I)+MCPA, compound of formula (I)+mefenacet, compound of formula (I)+mesotrione, compound of formula I+metazosulfuron (NC-620, CAS Reg. No. 868680-84-6), compound of formula (I)+metsulfuron, compound of formula (I)+metsulfuron-methyl, compound of formula (I)+orthosulfamuron, compound of formula (I)+oxadiargyl, compound of formula (I)+oxadiazon, compound of formula (I)+pendimethalin, compound of formula (I)+penoxsulam, compound of formula (I)+pretilachlor, compound of formula I+propyrisulfuron (TH-547, CAS Reg. No. 570415-88-2), compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron and compound of formula (I)+trinexapac-ethyl, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9, and which is also compound A-13 disclosed in pages 4, 5, 7 and 11 of WO 2011/073616 A2, these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9, and which is also compound A-12 disclosed in page 10 of WO 2011/073616 A2, these parts of these publications being incorporated herein by reference), compound of formula (I)+4-(4'-chloro- 4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1, and which is also compound A-4 disclosed on page 7 of WO 2011/073615 A2, these parts of these publications being incorporated herein by reference), compound of formula (I)+4-(2',4'-dichloro-4-ethylbiphenyl-3-yl)-2,2,6,6-tetramethyl-2H-pyran-3,5(4H,6H)-dione (which is compound A-45 disclosed on page 93 of WO 2008/071405 A1, and which is also the compound of Example P10 disclosed on pages 41 and 45 of WO 2010/136431 A9, and which is also compound A-7 disclosed on page 7 of WO 2011/073615 A2, these parts of these publications being incorporated herein by reference), compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1, and which is also compound A-9 disclosed on page 8 of WO 2011/073615 A2, these parts of these publications being incorporated herein by reference), compound of formula (I)+one of the specific herbicidal compounds disclosed in WO 2010/059671 (e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2), or compound of formula I+triafamone (which is N-[2-[(4,6-dimethoxy-1,3,5-triazin-2-yl)carbonyl]-6-fluorophenyl]-N-methyl-1,1-difluoromethanesulfonamide, CAS Reg. No. 874195-61-6);

wherein the mixture partners for the compound of formula (I) may optionally be in the form of an ester (in particular an agrochemically acceptable ester) or a salt (in particular an agrochemically acceptable salt) thereof (e.g. where chemically possible).

For applications in soybean, the following mixtures are preferred:

compound of formula (I)+acifluorfen, compound of formula (I)+acifluorfen-sodium, compound of formula (I)+ametryn, compound of formula (I)+atrazine, compound of formula (I)+bentazone, compound of formula (I)+bicyclopyrone, compound of formula (I)+bromoxynil, compound of formula (I)+bromoxynil heptanoate, compound of formula (I)+bromoxynil octanoate, compound of formula (I)+bromoxynil heptanoate+bromoxynil octanoate, compound of formula (I)+carfentrazone, compound of formula (I)+carfentrazone-ethyl, compound of formula (I)+chloransulam, compound of formula (I)+chloransulam-methyl, compound of formula (I)+chlorimuron, compound of formula (I)+chlorimuron-ethyl, compound of formula (I)+clethodim, compound of formula (I)+clomazone, compound of formula (I)+cyanazine, compound of formula (I)+2,4-D (especially for applications to 2,4-D-tolerant soybean, e.g. genetically-modified), compound of formula (I)+2,4-D-dimethylammonium (especially for applications to 2,4-D-tolerant soybean, e.g. genetically-modified), compound of formula (I)+2,4-D-2-ethylhexyl (especially for applications to 2,4-D-tolerant soybean, e.g. genetically-modified), compound of formula (I)+a choline salt of 2,4-D (see e.g. Examples 2 and 3 of WO2010/123871A1) (especially for applications to 2,4-D-tolerant soybean, e.g. genetically-modified), compound of formula (I)+2,4-D+glyphosate (especially for applications to 2,4-D-tolerant and/or glyphosate-tolerant soybean, e.g. genetically-modified), compound of formula (I)+2,4-D-dimethylammonium+glyphosate (especially for applications to 2,4-D-tolerant and/or glyphosate-tolerant soybean, e.g. genetically-modified), compound of formula (I)+2,4-D-2-ethylhexyl+glyphosate (especially for applications to 2,4-D-tolerant and/or glyphosate-tolerant soybean, e.g. genetically-modified), compound of formula (I)+a choline salt of 2,4-D+glyphosate (see e.g. Examples 2 and 3 of WO2010/123871A1) (especially for applications to 2,4-D-tolerant and/or glyphosate-tolerant soybean, e.g. genetically-modified), compound of formula (I)+dicamba (especially for applications to dicamba-tolerant soybean, e.g. genetically-modified), compound of formula (I)+dicamba-dimethylammonium (especially for applications to dicamba-tolerant soybean, e.g. genetically-modified), compound of formula (I)+dicamba-potassium (especially for applications to dicamba-tolerant soybean, e.g. genetically-modified), compound of formula (I)+dicamba-sodium (especially for applications to dicamba-tolerant soybean, e.g. genetically-modified), compound of formula (I)+dicamba-diglycolamine (especially for applications to dicamba-tolerant soybean, e.g. genetically-modified), compound of formula (I)+a N,N-bis-[aminopropyl]methylamine salt of dicamba (see e.g. US2012/0184434A1) (especially for applications to dicamba-tolerant soybean, e.g. genetically-modified), compound of formula (I)+dicamba+glyphosate (especially for applications to dicamba-tolerant and/or glyphosate-tolerant soybean, e.g. genetically-modified), compound of formula (I)+dicamba-dimethylammonium+glyphosate (especially for applications to dicamba-tolerant and/or glyphosate-tolerant soybean, e.g. genetically-modified), compound of formula (I)+dicamba-potassium+glyphosate (especially for applications to dicamba-tolerant and/or glyphosate-tolerant soybean, e.g. genetically-modified), compound of formula (I)+dicamba-sodium+glyphosate (especially for applications to dicamba-tolerant and/or glyphosate-tolerant soybean, e.g. genetically-modified), compound of formula (I)+dicamba-diglycolamine+glyphosate (especially for applications to dicamba-tolerant and/or glyphosate-tolerant soybean, e.g. genetically-modified), compound of formula (I)+a N,N-bis-[aminopropyl]methylamine salt of dicamba+glyphosate (see e.g. US2012/0184434A1) (especially for applications to dicamba-tolerant and/or glyphosate-tolerant soybean, e.g. genetically-modified), compound of formula (I)+diclosulam, compound of formula (I)+dimethenamid, compound of formula (I)+dimethenamid-P, compound of formula (I)+diquat, compound of formula (I)+diquat dibromide, compound of formula (I)+diuron, compound of formula (I)+fenoxaprop, compound of formula (I)+fenoxaprop-ethyl, compound of formula (I)+fenoxaprop-P, compound of formula (I)+fenoxaprop-P-ethyl, compound of formula (I)+fluazifop, compound of formula (I)+fluazifop-butyl, compound of formula (I)+fluazifop-P, compound of formula (I)+fluazifop-P-butyl, compound of formula (I)+flufenacet, compound of formula (I)+flumetsulam, compound of formula (I)+flumioxazin, compound of formula (I)+fluthiacet, compound of formula (I)+fluthiacet-methyl, compound of formula (I)+fomesafen, compound of formula (I)+glufosinate (especially for applications to glufosinate-tolerant soybean, e.g. genetically-modified), compound of formula (I)+glufosinate-ammonium (especially for applications to glufosinate-tolerant soybean, e.g. genetically-modified), compound of formula (I)+glyphosate (especially for applications to glyphosate-tolerant soybean, e.g. genetically-modified), compound of formula (I)+glyphosate-diammonium (especially for applications to glyphosate-tolerant soybean, e.g. genetically-modified), compound of formula (I)+glyphosate-isopropylammonium (especially for applications to glyphosate-tolerant soybean, e.g. genetically-modified), compound of formula (I)+glyphosate-potassium (especially for applications to glyphosate-tolerant soybean, e.g. genetically-modified), compound of formula (I)+imazethapyr, compound of formula (I)+lactofen, compound of formula (I)+mesotrione, compound of formula (I)+metolachlor, compound of formula (I)+S-metolachlor, compound of formula (I)+metribuzin, compound of formula (I)+oxyfluorfen, compound of formula (I)+paraquat, compound of formula (I)+paraquat dichloride, compound of formula (I)+pendimethalin, compound of formula (I)+pyroxasulfone, compound of formula I+quizalofop, compound of formula I+quizalofop-ethyl, compound of formula I+quizalofop-P, compound of formula I+quizalofop-P-ethyl, compound of formula I+quizalofop-P-tefuryl, compound of formula (I)+saflufenacil, compound of formula (I)+sethoxydim, compound of formula (I)+sulfentrazone, compound of formula (I)+thifensulfuron, compound of formula (I)+thifensulfuron-methyl, compound of formula (I)+tribenuron, compound of formula (I)+tribenuron-methyl, compound of formula (I)+trifluralin, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9, and which is also compound A-13 disclosed in pages 4, 5, 7 and 11 of WO 2011/073616 A2, these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9, and which is also compound A-12 disclosed in page 10 of WO 2011/073616 A2, these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1, and which is also compound A-4 disclosed on page 7 of WO 2011/073615 A2, these parts of these publications being incorporated herein by reference), compound of formula (I)+4-(2',4'-dichloro-4-ethylbiphenyl-3-yl)-2,2,6,6-tetramethyl-2H-pyran-3,5(4H,6H)-dione (which is compound A-45 disclosed on page 93 of WO 2008/071405 A1, and which is also the compound of Example P10 disclosed on pages 41 and 45 of WO 2010/136431 A9 (, and which is also compound A-7 disclosed on page 7 of WO 2011/073615 A2, these parts of these publications being incorporated herein by reference), or compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1, and which is also compound A-9 disclosed on page 8 of WO 2011/073615 A2 these parts of these publications being incorporated herein by reference);

wherein the mixture partners for the compound of formula (I) may optionally be in the form of an ester (in particular an agrochemically acceptable ester) or a salt (in particular an agrochemically acceptable salt) thereof (e.g. where chemically possible).

The following mixtures with safeners, especially, come into consideration:

compound of formula I+cloquintocet-mexyl, compound of formula I+cloquintocet acid or an agrochemically acceptable salt thereof, compound of formula I+fenchlorazole-ethyl, compound of formula I+fenchlorazole acid or an agrochemically acceptable salt thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula (I)+N-(2-methoxybenzoyl)-4-[(methylaminocarbonyl)amino]benzenesulfonamide, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+CL 304,415, compound of formula I+dicyclonon, compound of formula I+fluxofenim, compound of formula I+DKA-24, compound of formula I+R-29148 and compound of formula I+PPG-1292.

The above-mentioned safeners and herbicides are described, for example, in the Pesticide Manual, 14th Edition, British Crop Production Council, 2006; or The Pesticide Manual 15$^{th}$ edition (2009) or 16th edition (2012), ed. C. D. S. Tomlin, British Crop Production Council. R-29148 is described, for example by P. B. Goldsbrough et al., *Plant Physiology*, (2002), Vol. 130 pp. 1497-1505 and references therein. PPG-1292 is known from WO 2009/211761. N-(2-methoxybenzoyl)-4-[(methylaminocarbonyl)amino]benzenesulfonamide is known from e.g. EP365484.

Even more preferably, the safener comprises (e.g. is) cloquintocet-mexyl, cloquintocet acid or an agrochemically acceptable salt thereof, mefenpyr-diethyl and/or isoxadifen-ethyl; in particular for use on non-oat cereals such as wheat, barley, rye and/or triticale. Cloquintocet-mexyl is particularly valuable and is the most preferred safener, especially for use on non-oat cereals such as wheat, barley, rye and/or triticale.

In the above-mentioned compositions or mixtures comprising a compound of formula (I) (in particular, one of the specific compounds disclosed herein, present either as a free compound and/or as an agrochemically acceptable salt thereof) with a safener, the weight ratio of the compound of formula (I) to the safener can vary over a large range and is, typically, from 200:1 to 1:200, especially from 50:1 to 1:50, more especially from 20:1 to 1:20, even more especially from 20:1 to 1:10. Preferably, the safener comprises (e.g. is) cloquintocet-mexyl, cloquintocet acid or an agrochemically acceptable salt thereof, mefenpyr-diethyl and/or isoxadifen-ethyl, and the weight ratio of the compound of formula (I) to the safener is from 20:1 to 1:10, more preferably from 15:1 to 1:2 (this can be, for example, for use on non-oat cereals). Typically, these weight ratios are measured as the free compound(s), i.e. excluding the weight of any associated salt counterion(s).

Application rates of herbicide (e.g. compound of formula (I)) and/or safener: The rate of application of safener relative to the compound of formula (I) is largely dependent upon the mode of application. In the case of field and/or soil and/or plant treatment (e.g. in a field or glasshouse): for example from 0.5 to 1000 g of safener per ha, or preferably from 1 to 250 g or from 2 to 200 g of safener per ha, are applied; and/or generally from 1 to 2000 g of compound of formula (I) per ha, or preferably from 5 to 500 g or from 10 to 400 g of compound of formula (I) per ha, are applied.

ha=hectare. Typically, these application rates are measured as the free compound, i.e. excluding the weight of any associated salt counterion(s). In field and/or plant treatment, the application of the compound of formula (I) is preferably post-emergence.

The compounds and/or herbicidal compositions according to the invention are suitable for all methods of application customary in agriculture, such as, for example, pre-emergence application, post-emergence application and seed dressing. Post-emergence application is preferred. Depending upon the intended use, the safeners can be used for pretreating the seed material of the crop plant (dressing the seed or seedlings) or introduced into the soil before or after sowing, followed by the application of the (unsafened) compound of the formula (I), optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field and/or soil and/or plant treatment (e.g. in a field or glasshouse), generally from 0.001 to 5.0 kg of safener/ha, preferably from 0.001 to 0.5 kg of safener/ha, are applied. Ha=hectare. In the case of seed dressing, generally from 0.001 to 10 g of safener/kg of seed, preferably from 0.05 to 2 g of safener/kg of seed, are applied. When the safener is applied in liquid form, with seed soaking, shortly before sowing, it is advantageous to use safener solutions which contain the active ingredient in a concentration of from 1 to 10 000 ppm, preferably from 100 to 1000 ppm.

In the invention, in the case of field and/or soil and/or plant treatment (e.g. post-emergence application), generally from 1 to 2000 g of herbicide (in particular compound of formula (I))/ha, but preferably from 5 to 1000 g of herbicide (in particular compound of formula (I))/ha, more preferably from 10 to 400 g of herbicide (in particular compound of formula (I))/ha, is applied. If a safener is used, in the case of field and/or soil and/or plant treatment (e.g. post-emergence application), generally from 0.5 to 1000 g of safener/ha, preferably from 2 to 500 g of safener/ha, more preferably from 5 to 200 g of safener/ha, is applied.

In one particular embodiment, the herbicidal composition or mixture comprising the compound of formula (I) and one or more further herbicides (e.g. as mentioned hereinabove) can be applied together with one of the safeners mentioned herein, e.g. hereinabove.

The following Examples illustrate the invention further but do not limit the invention.

PREPARATION EXAMPLES

Those skilled in the art will appreciate that certain compounds described below are β-ketoenols (beta-ketoenols), and as such may exist as a single tautomer or as a mixture of keto-enol and diketone tautomers, as described, for example by J. March, Advanced Organic Chemistry, third edition, John Wiley and Sons. The compounds shown below, and in Table T1 herein, are generally drawn as an arbitrary single enol tautomer, but it should be inferred that this description covers both the diketone form and any possible enols which could arise through tautomerism. Where more than one tautomer is observed in proton NMR ($^1$H NMR), the data shown are for the mixture of tautomers. Furthermore, some of the compounds shown below have the possibility of being present in at least two enantiomeric forms; unless drawn as single enantiomers, these compounds will usually be present as a mixture of enantiomers. Additionally, some of the compounds can exist as diastereoisomers, and it should be inferred that these can be present as a mixture of diastereoisomers or as any possible single diastereoisomer. Within the detailed experimental section the diketone tautomer is chosen for naming purposes, even if the predominant tautomer is the enol form.

Typical Abbreviations

DCM—dichloromethane
DMF—N,N-dimethylformamide
LDA—lithium diisopropylamide
Tf—trifluoromethanesulfonate
THF—tetrahydrofuran
RT—room temperature (typically ca. 15-30° C. such as ca. 18-25° C.)
NMR—nuclear magnetic resonance Example 1: Synthesis of 2-[2,4-dioxo-3-(2,4,6-trimethylphenyl)cyclopentyl]-N-phenethyl-acetamide (Compound A1)

Step 1: Synthesis of ethyl 2-(trifluoromethylsulfonyloxy)acetate

To a stirred solution of ethyl glycolate (7.1 g, 0.068 mol) in DCM (200 mL) at 0° C. was added pyridine (11.0 mL, 0.136 mol) followed by dropwise addition of trifluoromethane sulfonic anhydride (14.3 mL, 0.085 mol). The reaction was stirred at 0° C. for 3 hours then allowed to warm to room temperature. The reaction was quenched by addition of water (100 mL) and 2M HCl (50 mL). The phases were separated and the aqueous phase extracted with further DCM (2×50 mL). The combined organic extracts were washed with 2M HCl (50 mL), water (50 mL), saturated aqueous NaHCO$_3$ solution (50 mL) and water (50 mL) then dried over MgSO$_4$ and evaporated to dryness under reduced pressure to give the desired product (8.2 g) as a colourless oil which was used without further purification.

$^1$H NMR (400 MHz, CDCl$_3$) δ ppm 4.90 (s, 2H), 4.30 (q, 2H), 1.30 (t, 3H).

Step 2: Synthesis of ethyl 2-[4-methoxy-2-oxo-3-(2,4,6-trimethylphenyl)cyclopent-3-en-1-yl]acetate To a stirred solution of 3-methoxy-2-(2,4,6-trimethylphenyl)cyclopent-2-en-1-one (3.97 g, 0.0173 mol) in THF (170 mL) at −78° C. under an N$_2$ atmosphere was added dropwise a solution of LDA (10.0 mL of a 1.8M solution in THF/heptane/ethylbenzene). The reaction was stirred at −78° C. for 1.5 hours then a solution of ethyl 2-(trifluoromethylsulfonyloxy)acetate (4.5 g, 0.019 mol) in THF (25 mL) was added portionwise over 5 minutes. The reaction was stirred at −78° C. for 30 minutes then allowed to warm to room temperature. The reaction was quenched with water (100 mL) and brine (50 mL) then was extracted with EtOAc (3×75 mL). The combined organic extracts were washed with brine (50 mL), dried over MgSO$_4$ and evaporated to dryness under reduced pressure to give a yellow oil (5.92 g). The crude product was purified by flash chromatography on silica using a gradient of 100% isohexane to 100% EtOAc as eluent to give the desired product (3.83 g, 73%) as a colourless oil.

$^1$H NMR (400 MHz, CDCl$_3$) δ ppm 6.85 (s, 2H), 4.15 (q, 2H), 3.75 (s, 3H), 3.05 (dd, 1H), 3.05-2.95 (m, 2H), 2.60 (dd, 1H), 2.50 (dd, 1H), 2.25 (s, 3H), 2.10 (2×s, 2×3H), 1.25 (t, 3H).

Step 3: Synthesis of 2-[4-methoxy-2-oxo-3-(2,4,6-trimethylphenyl)cyclopent-3-en-1-yl]acetic acid To a stirred solution of ethyl 2-[4-methoxy-2-oxo-3-(2,4,6-trimethylphenyl)cyclopent-3-en-1-yl]acetate (1.08 g, 0.0034 mol) in THF (40 mL) and water (40 mL) was added NaOH (0.273 g, 0.0068 mol). The reaction was stirred at room temperature for 3 hours then diluted with water (40 mL). The reaction pH was adjusted to 3-4 with 2M HCl then extracted with EtOAc (3×50 mL). The combined organic extracts were dried over MgSO$_4$ and evaporated to dryness under reduced pressure to give the desired product (0.748 g) as a white solid which was used without further purification.

$^1$H NMR (400 MHz, CDCl$_3$) δ ppm 6.85 (s, 2H), 3.75 (s, 3H), 3.10 (dd, 1H), 3.00-2.90 (m, 2H), 2.60-2.55 (m, 2H), 2.30 (s, 3H), 2.10 (2×s, 2×3H).

Step 4: Synthesis of 2-[4-methoxy-2-oxo-3-(2,4,6-trimethylphenyl)cyclopent-3-en-1-yl]-N-phenethyl-acetamide To a stirred solution of 2-[4-methoxy-2-oxo-3-(2,4,6-trimethylphenyl)cyclopent-3-en-1-yl]acetic acid (0.35 g, 0.0012 mol) in DCM (25 mL) was added oxalyl chloride (0.213 mL, 0.0024 mol) followed by 2 drops of NMP (effervescence ensued). The reaction was stirred at room temperature for 3 hours then evaporated to dryness under reduced pressure. The residue was dissolved in DCM (25 mL) and Et$_3$N (0.75 mL, 0.005 mol) added followed by dropwise addition of phenethylamine (0.525 mL, 0.0042 mol). The reaction was stirred at room temperature for 73 hours then diluted with water (25 mL). The phases were separated and the aqueous phase extracted with DCM (2×25 mL). The combined organic extracts were dried over MgSO$_4$ and evaporated to dryness under reduced pressure to give a brown oil (0.411 g). The crude product was purified by flash chromatography on silica using a gradient of 100% isohexane to 100% EtOAc as eluent to give the desired product (0.081 g)

$^1$H NMR (400 MHz, CDCl$_3$) δ ppm 7.30-7.15 (m, 5H), 6.85 (s, 2H), 6.35 (br, 1H), 3.80 (s, 3H), 3.55-3.45 (m, 1H), 3.40-3.35 (m, 1H), 3.05 (dd, 1H), 2.95-2.90 (m, 1H), 2.80-2.70 (m, 4H), 2.35 (dd, 1H), 2.25 (s, 3H), 2.10 (s, 3H), 2.05 (s, 3H).

Step 5: Synthesis of 2-[2,4-dioxo-3-(2,4,6-trimethylphenyl)cyclopentyl]-N-phenethyl-acetamide A solution of 2-[4-methoxy-2-oxo-3-(2,4,6-trimethylphenyl)cyclopent-3-en-1-yl]-N-phenethyl-acetamide (0.064 g, 0.00016 mol) in acetone (2 mL) and 2M HCl (2 mL) was added to a microwave vial, capped and heated at 50° C. for 10 minutes under microwave irradiation followed by further heating at 100° C. for 5 minutes under microwave irradiation. The reaction was diluted with water (20 mL) and extracted with EtOAc (3×10 mL). The combined organic extracts were washed with brine (10 mL), dried over MgSO$_4$ and evaporated to dryness under reduced pressure. The crude product was purified by flash chromatography on silica using a gradient of 100% isohexane to 100% EtOAc as eluent to give the desired product as an off-white solid (0.034 g).

$^1$H NMR (400 MHz, CDCl$_3$) δ ppm 7.35-7.30 (m, 2H), 7.25 (m, 1H), 7.20 (d, 2H), 6.85 (s, 6H), 6.05 (br, 1H), 3.60 (m, 2H), 3.25 (m, 1H), 2.90-2.80 (m, 3H), 2.65 (d, 2H), 2.25 (s, 3H), 2.20 (dd, 1H), 2.10 (2×s, 2×3H).

Example 2: Synthesis of N-tert-butyl-2-[2,4-dioxo-3-(2,4,6-trimethylphenyl)cyclopentyl]-acetamide (Compound A2)

Step 1: Synthesis of N-tert-butyl-2-[4-methoxy-2-oxo-3-(2,4,6-trimethylphenyl)cyclopent-3-en-1-yl]acetamide To a solution of 2-[4-methoxy-2-oxo-3-(2,4,6-trimethylphenyl)cyclopent-3-en-1-yl]acetic acid (0.15 g, 0.00052 mol) in DMF (5 mL) were added t-butylamine (0.047 g, 0.00062 mol), 1-propane phosphonic anhydride (50 mass % solution in EtOAc) (0.50 g, 0.00078 mol) and 4-dimethylaminopyridine (0.064 g, 0.00052 mol). The reaction was stirred at room temperature for 24 hours then diluted with Et$_2$O and washed with brine (×3). The organic phase was dried over MgSO$_4$ and evaporated to dryness under reduced pressure to give an orange gum (161 mg). The crude product was purified by flash chromatography on silica using a gradient of 5% EtOAc in isohexane to 100% EtOAc as eluent to give the desired product (0.087 g, 47%).

$^1$H NMR (400 MHz, CDCl$_3$) δ 6.86 (s, 2H), 6.03 (br, 1H), 3.77 (s, 3H), 3.10 (dd, 1H), 2.99-2.91 (m, 1H), 2.78 (dd, 1H), 2.71 (dd, 1H), 2.33-2.29 (m, 1H), 2.26 (s, 3H), 2.20-2.04 (m, 6H), 1.33 (s, 9H).

Step 2: Synthesis of N-tert-butyl-2-[2,4-dioxo-3-(2,4,6-trimethylphenyl)cyclopentyl]acetamide A suspension of N-tert-butyl-2-[4-methoxy-2-oxo-3-(2,4,6-trimethylphenyl)cyclopent-3-en-1-yl]acetamide (0.087 g, 0.00025 mol) in morpholine (1 mL) was heated at 100° C. for six hours. The reaction was evaporated to dryness under reduced pressure and the residue partitioned between 2M HCl and DCM. The aqueous phase was extracted with DCM (×2) and the combined organic extracts washed with water and brine, dried over MgSO$_4$ and evaporated to dryness under reduced pressure to give a pale yellow gum. The crude product was purified by flash chromatography on silica using a gradient of 5% EtOAc in isohexane to 100% EtOAc to give the desired product (0.019 g, 23%) as a white powder.

$^1$H NMR (400 MHz, CDCl$_3$) δ ppm 6.87 (s, 2H), 5.83 (s, 1H), 3.32-3.23 (m, 1H), 2.93-2.83 (m, 1H), 2.72-2.58 (m, 2H), 2.25 (s, 3H), 2.24-2.14 (m, 1H), 2.11 (s, 6H), 1.38 (s, 9H).

Example 3: Synthesis of 2-[3-(2,6-dimethyl-4-prop-1-ynyl-phenyl)-2,4-dioxo-cyclopentyl]-N-isopropyl-acetamide (Compound A8)

Step 1: Synthesis of ethyl 2-[3-(2,6-dimethyl-4-prop-1-ynyl-phenyl)-4-methoxy-2-oxo-cyclopent-3-en-1-yl]acetate A microwave vial was charged with ethyl 2-[3-(4-bromo-2,6-dimethyl-phenyl)-4-methoxy-2-oxo-cyclopent-3-en-1-yl]acetate (0.20 g, 0.0005 mol), cesium fluoride (0.159 g, 0.00105 mmol), Cu(I)I (0.02 g, 0.000105 mmol), PdCl2

(dppf) (0.058 g, 0.00008 mol) and DMF (2 mL). The vial was capped, evacuated and purged with nitrogen. Tributyl (prop-1-ynyl)stannane (0.52 g, 0.0016 mol) was then added and the reaction mixture heated at 120° C. under microwave irradiation for 1 hour. The reaction mixture was diluted with water and extracted with ethyl acetate (×3). The combined organic extracts were washed with water and brine, dried over MgSO$_4$ and evaporated to dryness under reduced pressure to give a brown gum. The crude product was purified by flash chromatography on silica using a gradient of 5% EtOAc in isohexane to 100% EtOAc to give the desired product (0.168 g, 94%) as an orange gum.

1H NMR δ ppm 7.08 (s, 2H), 4.16 (q, 2H), 3.72 (s, 3H), 3.11-3.02 (m, 1H), 3.01-2.93 (m, 2H), 2.63-2.55 (m, 1H), 2.54-2.43 (m, 1H), 2.09 (d, 6H), 2.02 (s, 3H), 1.26 (t, 3H).

Step 2: Synthesis of 2-[3-(2,6-dimethyl-4-prop-1-ynyl-phenyl)-4-methoxy-2-oxo-cyclopent-3-en-1-yl]acetic acid To a solution of ethyl 2-[3-(2,6-dimethyl-4-prop-1-ynyl-phenyl)-4-methoxy-2-oxo-cyclopent-3-en-1-yl]acetate (0.168 g, 0.00049 mol) in THF (1.7 mL) was added a solution of lithium hydroxide monohydrate (0.041 g, 0.00099 mol) in water (1.7 mL). The reaction mixture was allowed to stir at room temperature overnight then diluted with water and the pH adjusted to ~4 with 2M HCl. The reaction was then extracted with ethyl acetate (×3) and the combined organic extracts washed with water, then brine, dried over MgSO$_4$ and evaporated to dryness under reduced pressure to give the desired product (0.153 g, 99%) as a brown gum which was used without further purification.

$^1$H NMR (CDCl$_3$) δ ppm 7.08 (s, 2H), 3.74 (s, 3H), 3.15-2.83 (m, 3H), 2.70-2.52 (m, 2H), 2.11 (s, 3H), 2.07 (s, 3H), 2.03 (s, 3H).

Step 3: Synthesis of 2-[3-(2,6-dimethyl-4-prop-1-ynyl-phenyl)-2,4-dioxo-cyclopentyl]-N-isopropyl-acetamide To a solution of 2-[3-(2,6-dimethyl-4-prop-1-ynyl-phenyl)-4-methoxy-2-oxo-cyclopent-3-en-1-yl]acetic acid (0.153 g, 0.0004898 mol) in DMF (2 mL) was added 1-propanephosponic anhydride (50 mass % solution in EtOAc) (0.44 mL, 0.001469 mmol), isopropylamine (0.083 mL, 0.00098 mol) and 4-dimethylaminopyridine (0.06 g, 0.00049 mol). The reaction was stirred at room temperature overnight and then evaporated to dryness under reduced pressure to give a brown solid.

The crude intermediate enol ether was dissolved in morpholine (2 mL) and heated at 100° C. for 3 hrs and then evaporated to dryness under reduced pressure to give an orange syrup. The crude product was diluted with 2M HCl and extracted with EtOAc (×3). The combined organic extracts were washed with water, then brine, dried over MgSO$_4$ and evaporated to dryness under reduced pressure to give a pale yellow gum (0.25 g). The crude product was purified by flash chromatography on silica using a gradient of 5% EtOAc in isohexane to 100% EtOAc as eluent to give an off-white powder (88 mg) which was triturated with Et$_2$O to give the desired product (0.04 g, 24%) as a white powder.

$^1$H NMR (d4-MeOH) δ ppm 7.03 (s, 2H), 3.98 (m, 1H), 3.19-3.10 (m, 1H), 2.87 (dd, 1H), 2.71 (dd, 1H), 2.47-2.34 (m, 2H), 2.06 (s, 6H), 1.99 (s, 3H), 1.14 (dd, 6H)

Example 4: Synthesis of 2-[3-(4-ethynyl-2,6-dimethyl-phenyl)-2,4-dioxo-cyclopentyl]-N-sec-butyl-acetamide (Compound A9)

Step 1: Synthesis of ethyl 2-[3-[2,6-dimethyl-4-(2-trimethylsilylethynyl)phenyl]-4-methoxy-2-oxo-cyclopent-3-en-1-yl]acetate A solution of ethyl 2-[3-(4-bromo-2,6-dimethyl-phenyl)-4-methoxy-2-oxo-cyclopent-3-en-1-yl]acetate (2.0 g, 0.0052 mol) in degassed toluene (40 mL) was divided equally into four microwave vials. To each vial was added palladium(0) tetrakis(triphenylphosphine) (0.045 g, 0.00004 mol per vial/0.182 g, 0.0001574 mol in total). The vials were capped then evacuated and purged with nitrogen. To each vial was added tributyl(trimethylsilylethynyl)tin (0.635 g, 0.0016 mol per vial/2.54 g, 0.0065 mol in total) was added to each vial and they were each heated at 130° C. under microwave irradiation for 30 mins. The reactions were combined, poured into water and extracted with ethyl acetate (×3). The combined organic extracts were washed with brine, dried over MgSO$_4$ and evaporated to dryness under reduced pressure to give a brown oil (6.0 g). The crude product was purified by flash chromatography on silica using a gradient of 5-100% ethyl acetate in isohexane as eluent to give the desired product (1.99 g, 95%) as a yellow oil.

$^1$H NMR (400 MHz, CDCl$_3$) δ ppm 7.17 (s, 2H), 4.16 (q, 2H), 3.71 (s, 3H), 3.11-3.02 (m, 1H), 3.02-2.92 (m, 2H), 2.63-2.55 (m, 1H), 2.56-2.47 (m, 1H), 2.10 (s, 6H), 1.28 (t, 3H), 0.22 (s, 9H).

Step 2: Synthesis of 2-[3-(4-ethynyl-2,6-dimethyl-phenyl)-4-methoxy-2-oxo-cyclopent-3-en-1-yl]acetic acid To a stirred solution of ethyl 2-[3-[2,6-dimethyl-4-(2-trimethylsilylethynyl)phenyl]-4-methoxy-2-oxo-cyclopent-3-en-1-yl]acetate (0.50 g, 0.001254 mol) in THF (5 mL) was added a solution of lithium hydroxide monohydrate (0.105 g, 0.0025 mol) in water (5 mL). The reaction was stirred at room temperature overnight then diluted with water and then the pH adjusted to ~4 with 2M HCl. The reaction mixture was then extracted with ethyl acetate (×3). The combined organic extracts were, washed with water, then brine, dried over MgSO4 and evaporated to dryness under reduced pressure to give the desired product (0.391 g, quant) which was used without further purification.

$^1$H NMR (400 MHz, CDCl3) δ ppm 7.18 (s, 2H), 3.76 (s, 1H), 3.44 (s, 3H), 3.14-2.82 (m, 3H), 2.70-2.40 (m, 2H), 2.12 (s, 6H).

Step 3: Synthesis of 2-[3-(4-ethynyl-2,6-dimethyl-phenyl)-2,4-dioxo-cyclopentyl]-N-sec-butyl-acetamide To a solution of 2-[3-(4-ethynyl-2,6-dimethyl-phenyl)-4-methoxy-2-oxo-cyclopent-3-en-1-yl]acetic acid (0.391 g, 0.0013 mol) in DMF (2 mL) was added 1-propanephosponic anhydride (50 mass % solution in EtOAc) (1.17 mL, 0.0039 mmol), sec-butylamine (0.192 g, 0.00262 mol) and 4-dimethylaminopyridine (0.160 g, 0.00131 mol). The reaction was stirred at room temperature overnight then evaporated to dryness under reduced pressure. To the residue was added morpholine (2 mL) and the reaction heated to 100° C. for 3 hours. The reaction was evaporated to dryness under reduced pressure to give a brown syrup. To this residue was added 2M HCl then extracted with DCM (×3). The combined organic extracts were washed with water, then brine, dried over MgSO$_4$ and evaporated to dryness under reduced pressure to give a brown gum (0.506 g). The crude product was purified by flash chromatography on silica using a 5% EtOAc in isohexane to 100% EtOAc gradient as eluent followed by mass-directed HPLC to give the desired product (0.108 g, 24%) as an off white solid.

$^1$H NMR (400 MHz, d$_4$-MeOH) δ ppm 7.14 (s, 2H), 3.81 (q, 1H), 3.38 (s, 1H), 3.21-3.11 (m, 1H), 2.93-2.85 (m, 1H), 2.78-2.69 (m, 1H), 2.50-2.38 (m, 2H), 2.09 (s, 6H), 1.56-1.42 (m, 2H), 1.22 (d, 3H), 0.96-0.87 (m, 3H).

Example 5: Synthesis of 2-[3-[4-(4-fluorophenyl)-2,6-dimethyl-phenyl]-2,4-dioxo-cyclopentyl]-N-isopropyl-acetamide (Compound A34)

Step 1: Synthesis of ethyl 2-[3-[4-(4-fluorophenyl)-2,6-dimethyl-phenyl]-4-methoxy-2-oxo-cyclopent-3-en-1-yl]acetate A microwave vial was charged with ethyl 2-[3-(4-bromo-2,6-dimethyl-phenyl)-4-methoxy-2-oxo-cyclopent-3-en-1-yl]acetate (0.50 g, 0.0013 mol), cesium fluoride (0.598 g, 0.00393 mol), PdCl$_2$(dppf) (0.096 g, 0.00013 mol), 4-fluorophenyl boronic acid (0.257 g, 0.00184 mol) and degassed 1,2-dimethoxyethane (4 mL). The vial was capped, evacuated and purged with nitrogen and then the reaction heated at 160° C. under microwave irradiation for 40 minutes. The reaction mixture was evaporated to dryness under reduced pressure and the crude product purified by flash chromatography on silica using a gradient of 5% EtOAc in isohexane to 100% EtOAc as eluent to give the desired product (0.38 g, 73%) as a pale orange solid.

1H NMR (400 MHz, CDCl$_3$) δ ppm 7.55-7.48 (m, 2H), 7.22 (s, 2H), 7.12-7.05 (m, 2H), 4.18 (q, 2H), 3.80 (s, 3H), 3.17-3.06 (m, 1H), 3.06-2.95 (m, 2H), 2.64 (dd, 1H), 2.58-2.48 (m, 1H), 2.19 (s, 6H), 1.29 (t, 3H).

Step 2: Synthesis of 2-[3-[4-(4-fluorophenyl)-2,6-dimethyl-phenyl]-4-methoxy-2-oxo-cyclopent-3-en-1-yl]acetic acid To a stirred solution of ethyl 2-[3-[4-(4-fluorophenyl)-2,6-dimethyl-phenyl]-4-methoxy-2-oxo-cyclopent-3-en-1-yl]acetate (0.35 g, 0.00088 mol) in THF (3.5 mL) was added a solution of lithium hydroxide (0.085 g, 0.0035 mol). The reaction was stirred at room temperature for 2 hrs then poured into water, acidified with 2M HCl and extracted with DCM (×3). The combined organic extracts were washed with water, then brine, dried over MgSO$_4$ and evaporated to dryness under reduced pressure to give the desired product (0.378 g, quant) as a pale yellow solid.

$^1$H NMR (400 MHz, CDCl$_3$) δ ppm 7.55-7.47 (m, 2H), 7.22 (s, 2H), 7.09 (t, 2H), 3.81 (s, 3H), 3.19-3.10 (m, 1H), 3.10-2.94 (m, 2H), 2.71-2.60 (m, 2H), 2.19 (d, 6H).

Step 3: Synthesis of 2-[3-[4-(4-fluorophenyl)-2,6-dimethyl-phenyl]-2,4-dioxo-cyclopentyl]-N-isopropyl-acetamide To a solution of 2-[3-[4-(4-fluorophenyl)-2,6-dimethyl-phenyl]-4-methoxy-2-oxo-cyclopent-3-en-1-yl]acetic acid (0.189 g, 0.000513 mol) in DMF (2 mL) was added 1-propanephosponic anhydride (50 mass % solution in EtOAc) (0.46 mL, 0.00154 mmol), isopropylamine (0.087 mL, 0.00103 mol) and 4-dimethylaminopyridine (0.063 g, 0.000513 mol). The reaction was stirred at room temperature overnight then evaporated to dryness under reduced pressure. To the residue was added morpholine (2 mL) and the reaction heated to 100° C. for 4 hours. The reaction was evaporated to dryness under reduced pressure to give a brown syrup. To this residue was added 2M HCl then extracted with EtOAc (×3). The combined organic extracts were washed with water, then brine, dried over MgSO$_4$ and evaporated to dryness under reduced pressure. The crude product was purified by mass-directed HPLC to give the desired product (0.077 g, 38%) as an off white solid.

$^1$H NMR (400 MHz, d4-MeOH) δ ppm 7.62-7.57 (m, 2H), 7.27 (s, 2H), 7.13 (t, 2H), 3.99 (m, 1H), 3.22-3.12 (m, 1H), 2.94-2.85 (m, 1H), 2.77-2.70 (m, 1H), 2.49-2.38 (m, 2H), 2.17 (s, 6H), 1.19-1.12 (m, 6H).

Example 6: Synthesis of N-tert-butyl-2-[3-[4-(5-chloro-3-fluoro-2-pyridyl)-2,6-dimethyl-phenyl]-2,4-dioxo-cyclopentyl]acetamide (Compound A39)

Step 1: Synthesis of ethyl 2-[3-[2,6-dimethyl-4-(4,4,5,5-tetramethyl-1,3,2-dioxaborolan-2-yl)phenyl]-4-methoxy-2-oxo-cyclopent-3-en-1-yl]acetate Two microwave vials were charged with equal portions of ethyl 2-[3-(4-bromo-2,6-dimethyl-phenyl)-4-methoxy-2-oxo-cyclopent-3-en-1-yl]acetate (1.20 g, 0.0031 mol), bis(pinacolato)diboron (1.20 g, 0.0047 mol), tris(dibenzylideneacetone)dipalladium(0) (0.12 g, 0.00013 mol), 2-dicyclohexylphosphino-2',6'-dimethoxybiphenyl (0.21 g, 0.0005 mol), potassium acetate (0.46 g, 0.0047 mol) and 1,4-dioxane (24 mL). The vials were capped, evacuated and purged with nitrogen and heated at 150° C. under microwave irradiation for 15 minutes. The reactions were combined, evaporated to dryness under reduced pressure and the residue purified by flash chromatography on silica using a gradient of 5% EtOAc in isohexane to 100% EtOAc as eluent to give the desired product as (1.40 g,) an orange oil.

$^1$H NMR (400 MHz CDCl$_3$) δ ppm 7.49 (s, 2H), 4.17 (q, 2H), 3.69 (s, 3H), 3.12-3.02 (m, 1H), 3.02-2.92 (m, 2H), 2.62-2.54 (m, 1H), 2.54-2.44 (m, 1H), 2.13 (d, 6H), 1.33 (s, 12H), 1.25 (t, 3H).

Step 2: Synthesis of ethyl 2-[3-[4-(5-chloro-3-fluoro-2-pyridyl)-2,6-dimethyl-phenyl]-4-methoxy-2-oxo-cyclopent-3-en-1-yl]acetate A microwave vial was charged with ethyl 2-[3-[2,6-dimethyl-4-(4,4,5,5-tetramethyl-1,3,2-dioxaborolan-2-yl)phenyl]-4-methoxy-2-oxo-cyclopent-3-en-1-yl]acetate (0.20 g, 0.00047 mol), 2-bromo-5-chloro-3-fluoro-pyridine (0.147 g, 0.0007 mol) and PdCl$_2$(dppf) (0.068 g, 0.000093 mmol), 1,2-dimethoxyethane (degassed) (3.2 mL) and a solution of tripotassium phosphate (0.397 g, 0.00187 mol) in water (0.8 mL). The vial was capped then evacuated and purged with nitrogen and the reaction heated at 130° C. under microwave irradiation for 30 minutes. The reaction mixture was diluted with water and EtOAc and then filtered through celite. The phases of the filtrate were separated and the aqueous extracted with EtOAc (×2). The combined organic extracts were washed with brine, dried over MgSO$_4$ and evaporated to dryness under reduced pressure to give a brown gum. The crude product was purified by flash chromatography on silica using a gradient of 5% EtOAc in isohexane to 100% EtOAc to give the desired product (0.131 g) as a brown gum (131 mg), ¹H NMR (400 MHz, CDCl3) δ ppm 8.47 (s, 1H), 7.62 (s, 2H), 7.51 (d, 1H), 4.18 (q, 2H), 3.76 (s, 3H), 3.14-2.94 (m, 3H), 2.68-2.45 (m, 2H), 2.22 (s, 6H), 1.28 (t, 3H).

Step 3: Synthesis of 2-[3-[4-(5-chloro-3-fluoro-2-pyridyl)-2,6-dimethyl-phenyl]-4-methoxy-2-oxo-cyclopent-3-en-1-yl]acetic acid To a stirred solution of ethyl 2-[3-[4-(5-chloro-3-fluoro-2-pyridyl)-2,6-dimethyl-phenyl]-4-methoxy-2-oxo-cyclopent-3-en-1-yl]acetate (0.131 g, 0.00033 mol) in THF (1.3 mL) and water (2.6 mL) was added lithium hydroxide (0.029 g, 0.0012 mol). The reaction was stirred at room temperature overnight then diluted with water and the pH adjusted to 5 with 2M HCl. The reaction was extracted with ethyl acetate (×3) and the combined organic extracts dried over MgSO₄ and evaporated to dryness under reduced pressure to give the desired product (0.081 g) as a brown gum which was used without further purification.
¹H NMR (400 MHz, d4-MeOH) δ ppm 8.39 (s, 1H), 7.53 (d, 1H), 7.47 (s, 2H), 3.69 (s, 3H), 3.16-3.04 (m, 1H), 2.93-2.79 (m, 1H), 2.79-2.66 (m, 2H), 2.38-2.25 (m, 1H), 2.16 (s, 3H), 2.09 (s, 3H).

Step 4: Synthesis of N-tert-butyl-2-[3-[4-(5-chloro-3-fluoro-2-pyridyl)-2,6-dimethyl-phenyl]-2,4-dioxo-cyclopentyl]acetamide To a solution of 2-[3-[4-(5-chloro-3-fluoro-2-pyridyl)-2,6-dimethyl-phenyl]-4-methoxy-2-oxo-cyclopent-3-en-1-yl]acetic acid (0.189 g, 0.000513 mol) in DMF (2 mL) was added 1-propanephosponic anhydride (50 mass % solution in EtOAc) (0.38 mL, 0.00064 mmol), t-butylamine (0.045 mL, 0.00042 mol) and 4-dimethylaminopyridine (0.027 g, 0.00021 mol). The reaction was stirred at room temperature overnight then evaporated to dryness under reduced pressure. The residue was diluted with water and the pH was adjusted to 5 with saturated aqueous sodium hydrogen carbonate solution then extracted with EtOAc (×3). The combined organic extracts were washed with brine, dried over MgSO₄ and evaporated to dryness under reduced pressure to give a brown gum. The crude product was purified by flash chromatography on silica using a gradient of 5% EtOAc in isohexane to 100% EtOAc as eluent to give the desired product (0.030 g, 32%) as a brown gum.
¹H NMR (400 MHz d4-MeOH) δ ppm 8.46 (s, 1H), 7.85 (br.s, 1H), 7.81 (d, 1H), 7.59 (s, 2H), 3.21-3.12 (m, 1H), 2.99-2.83 (m, 1H), 2.74-2.68 (m, 1H), 2.50-2.39 (m, 2H), 2.19 (s, 6H), 1.34 (s, 9H).

Example 7: Synthesis of N-tert-butyl-2-[3-[4-(4-chloropyrazol-1-yl)-2,6-dimethyl-phenyl]-2,4-dioxo-cyclopentyl]acetamide (Compound A67)

Step 1: Synthesis of ethyl 2-[3-[4-(4-chloropyrazol-1-yl)-2,6-dimethyl-phenyl]-2,4-dioxo-cyclopentyl]acetate To a solution of ethyl 2-[3-(4-bromo-2,6-dimethyl-phenyl)-4-methoxy-2-oxo-cyclopent-3-en-1-yl]acetate (6.6 g, 0.017 mol) in DMF (130 mL) was added 4-chloropyrazole (3.5 g, 0.035 mol), CuI (6.6 g, 0.035 mol), dimethyl glycine (7.1 g, 0.069 mol) and potassium carbonate (6.9 g, 0.069 mol). The reaction was evacuated and purged with nitrogen three times then heated at 140° C. overnight. The reaction was allowed to cool to room temperature then diluted with water and the pH was adjusted to 4 with 2M HCl. The reaction mixture was extracted with Et₂OAc (×3). The combined organic extracts were washed with brine, dried over MgSO₄ and evaporated to dryness under reduced pressure to give a brown oil. The residue was dissolved in acetone (260 mL) and potassium carbonate (17.9 g, 0.129 mol) and methyl iodide (26.8 mL, 0.431 mol) were added. The reaction was stirred at room temperature for two hours then evaporated to dryness under reduced pressure. The residue was diluted with water and extracted with EtOAc (×3). The combined organic extracts were dried over MgSO₄ and evaporated to dryness under reduced pressure to give a brown solid. The crude product was purified by flash chromatography on silica using a gradient of 5% EtOAc in isohexane to 100% EtOAc as eluent to give the desired product (3.12 g, 46%) as a pale orange solid.
¹H NMR (400 MHz, d4-MeOH) δ ppm 8.34 (s, 1H), 7.68 (s, 1H), 7.46 (s, 2H), 4.18 (q, 2H), 3.13-3.03 (m, 1H), 3.03-2.95 (m, 1H), 2.92-2.81 (m, 1H), 2.69-2.53 (m, 2H), 2.20 (s, 6H), 1.28 (t, 3H)

Step 2: Synthesis of 2-[3-[4-(4-chloropyrazol-1-yl)-2,6-dimethyl-phenyl]-2,4-dioxo-cyclopentyl]acetic acid To a stirred solution of 2-[3-[4-(4-chloropyrazol-1-yl)-2,6-dimethyl-phenyl]-2,4-dioxo-cyclopentyl]acetate (3.12 g, 0.00802 mol) in THF (31 mL) and water (31 mL) was added lithium hydroxide monohydrate (0.673 g, 0.016 mmol) and the reaction stirred at room temperature overnight. The reaction mixture pH was adjusted to ~5 with 2M HCl then extracted with EtOAc (×3). The combined organic extracts were washed with water then brine, dried over MgSO₄ and evaporated to dryness under reduced pressure to give the desired product (3.1 g, quant) as a pale yellow crushed foam which was used without further purification.
¹H NMR (400 MHz, d4-MeOH) δ ppm 8.31 (s, 1H), 7.64 (s, 1H), 7.42 (s, 2H), 3.10-3.02 (m, 1H), 3.02-2.92 (m, 1H), 2.89-2.80 (m, 1H), 2.63-2.50 (m, 2H), 2.18 (s, 6H).

Step 3: Synthesis of N-tert-butyl-2-[3-[4-(4-chloropyrazol-1-yl)-2,6-dimethyl-phenyl]-2,4-dioxo-cyclopentyl]acetamide To a solution of 2-[3-[4-(4-chloropyrazol-1-yl)-2,6-dimethyl-phenyl]-2,4-dioxo-cyclopentyl]acetic acid (0.17 g, 0.00047 mol) in DMF (2 mL) was added 1-propanephosponic anhydride (50 mass % solution in EtOAc) (0.42 mL, 0.00141 mol), t-butylamine (0.10 mL, 0.00094 mol) and 4-dimethylaminopyridine (0.058 g, 0.000471 mol) and the reaction stirred at room temperature overnight. The reaction mixture was diluted with water and the pH adjusted to 5 with 2M HCl. It was then extracted with Et₂O (×3). The combined organic extracts were washed with brine, dried over MgSO₄ and evaporated to dryness under reduced pressure to give a yellow gum. The crude product was purified by flash chromatography on silica using a gradient of 50% EtOAc in isohexane to 100% EtOAc as eluent to give the desired product (0.098 g, 50%) as a white crushed foam.
¹H NMR (400 MHz, d4-MeOH) δ 8.33 (s, 1H), 7.67 (s, 1H), 7.44 (s, 2H), 3.23-3.12 (m, 1H), 2.98-2.85 (m, 1H), 2.76-2.65 (m, 1H), 2.52-2.38 (m, 2H), 2.20 (s, 6H), 1.38 (s, 9H).

Example 8: Synthesis of 2-[2,4-dioxo-3-(2,4,6-trimethylphenyl)cyclopentyl]-N-[[3-(trifluoromethyl)phenyl]methyl]acetamide (Compound A93)

Step 1: Synthesis of ethyl 2-[2-methoxy-4-oxo-3-(2,4,6-trimethylphenyl)cyclopent-2-en-1-yl]acetate To a stirred solution of 3-methoxy-2-(2,4,6-trimethylphenyl)cyclopent-2-en-1-one (8.31 g, 0.0361 mol) in THF (70 mL) at −78° C. under a nitrogen atmosphere was added dropwise lithium bis(trimethylsilyl)amide (1M in THF) (39.7 mL, 0.0397 mol) was added dropwise maintaining temperature at <−60° C. Once addition was complete the reaction mixture was warmed to 0° C. (ice bath) and allowed to stir at this temperature for 1.5 hrs. The reaction was then cooled to −78° C. and a solution of ethyl 2-(trifluoromethylsulfonyloxy)acetate (9.54 g, 0.0404 mmol) in THF (15 ml) was added dropwise maintaining temperature at <−60° C. Once addition was complete the reaction mixture was allowed to warm to 0° C. and stir at this temperature for 2 hrs. The reaction mixture was quenched with water. The organic solvent was removed under reduced pressure and the residue was extracted with ethyl acetate (×3). The combined organic extracts were washed with brine, dried over $MgSO_4$ and evaporated to dryness under reduced pressure to give an orange oil (14.5 g). The crude product was purified by flash chromatography on silica using a gradient of 5% EtOAc in isohexane to 100% EtOAc as eluent to give the desired product (11.8 g, quant) as an orange oil.

$^1$H NMR (400 MHz, CDCl3) δ ppm 6.84 (2H, s), 4.18 (2H, q), 3.52 (3H, s), 3.37-3.29 (1H, m), 2.91-2.80 (2H, m), 2.49-2.41 (1H, m), 2.33 (1H, d), 2.00 (6H, s), 1.28 (3H, t).

Step 2: Synthesis of 2-[2-methoxy-4-oxo-3-(2,4,6-trimethylphenyl)cyclopent-2-en-1-yl]acetic acid To a solution of ethyl 2-[2-methoxy-4-oxo-3-(2,4,6-trimethylphenyl)cyclopent-2-en-1-yl]acetate (1.0 g, 0.0032 mol) in EtOH (7.5 mL) was added a suspension of tetrabutylammonium hydroxide (2.46 g, 0.0095 mol) in water (2.5 mL). This reaction was stirred at room temperature for 2.5 hrs then diluted with water, acidified with 2M HCl and extracted with EtOAc (×3). The combined organic extracts were washed with water, then brine, dried over $MgSO_4$ and evaporated to dryness under reduced pressure to give the desired product as an orange solid (804 mg) which was used without further purification.

$^1$H NMR (400 MHz, d4MeOH) δ ppm 6.88 (2H, s), 3.54 (3H, s), 3.39-3.27 (1H, m), 2.88-2.77 (2H, m), 2.58-2.50 (1H, m), 2.39 (1H, dd), 2.15 (3H, s), 2.09 (6H, s).

Step 3: Synthesis of (2,3,4,5,6-pentafluorophenyl) 2-[2-methoxy-4-oxo-3-(2,4,6-trimethylphenyl)cyclopent-2-en-1-yl]acetate To a stirred solution of 2-[2-methoxy-4-oxo-3-(2,4,6-trimethylphenyl)cyclopent-2-en-1-yl]acetic acid (8.94 g, 0.031 mol) in DCM (110 mL) was added 2,3,4,5,6-pentafluorophenol (7.13 g, 0.039 mmol) followed by 1-Ethyl-3-(3-dimethylaminopropyl)carbodiimide hydrochloride (7.43 g, 0.039 mmol). This reaction mixture was stirred at room temperature for 72 hours then the solvent removed under reduced pressure. The residue was diluted with water and extracted with EtOAc (×3). The combined organic extracts were washed with saturated aqueous $NaHCO_3$, then water and brine, dried over $MgSO_4$ and evaporated to dryness under reduced pressure to give a dark orange oil (35 g). The crude product was purified by flash chromatography on silica using a gradient of 5% EtOAc in isohexane to 100% EtOAc as eluent to give the desired product (12.39 g) as an orange oil.

$^1$H NMR (400 MHz, CDCl3) δ ppm 6.84 (2H, s), 3.55 (3H, s), 3.52-3.43 (1H, m), 3.18 (1H, dd), 2.99-2.84 (2H, m), 2.42 (1H, dd), 2.25 (3H, s), 2.11 (6H, s).

Step 4: Synthesis of 2-[2-methoxy-4-oxo-3-(2,4,6-trimethylphenyl)cyclopent-2-en-1-yl]-N-[[3-(trifluoromethyl)phenyl]methyl]acetamide To a stirred solution of (2,3,4,5,6-pentafluorophenyl) 2-[2-methoxy-4-oxo-3-(2,4,6-trimethylphenyl)cyclopent-2-en-1-yl]acetate (1.00 g, 0.0022 mol) in DCM (10 mL) was added the [3-(trifluoromethyl)phenyl]methanamine (0.463 g, 0.002.64 mmol) followed by the N,N-diethylethanamine (0.767 mL, 0.0055 mol). The reaction was stirred overnight at room temperature then evaporated to dryness under reduced pressure. The crude product was purified by flash chromatography on silica using a gradient of 100% isohexane to 100% EtOAc to give the desired product (0.680 g).

$^1$H NMR (400 MHz, CDCl3) δ ppm 7.60-7.45 (m, 4H), 6.85 (s, 2H), 5.95 (br, 1H), 4.55 (dd, 1H), 4.45 (dd, 1H), 3.50 (s, 3H), 3.50-3.40 (m, 1H), 2.90-2.80 (m, 2H), 2.35-2.25 (m, 2H), 2.25 (s, 3H), 2.05 (2×s, 2×3H).

Step 5: Synthesis of 2-[2,4-dioxo-3-(2,4,6-trimethylphenyl)cyclopentyl]-N-[[3-(trifluoromethyl)phenyl]methyl]acetamide To a stirred solution of 2-[4-methoxy-2-oxo-3-(2,4,6-trimethylphenyl)cyclopent-3-en-1-yl]-N-[[3-(trifluoromethyl)phenyl]methyl]acetamide (0.680 g, 0.00153 mol,) in acetone (15 mL) was added 2M HCl (10 mL). The reaction was heated at 70° C. for 1 hour then organic solvent was removed under reduced pressure. The aqueous residue was extracted with DCM and the organic extract evaporated to dryness under reduced pressure. The crude product was purified by flash chromatography on silica using a gradient of 100% isohexane to 100% EtOAc as eluent to give the desired product (0.363 g) as a white solid.

$^1$H NMR (400 MHz, d4-MeOH) δ ppm 8.70 (br, 1H), 7.55-7.45 (m, 4H), 6.85 (s, 2H), 4.45 (s, 2H), 3.20-3.10 (m, 1H), 2.90-2.75 (m, 2H), 2.50-2.35 (m, 2H), 2.25 (s, 3H), 2.05 (2×s, 2×3H).

Example 9: Synthesis of [4-[2-(tert-butylamino)-2-oxo-ethyl]-2-[4-(5-chloropyrimidin-2-yl)-2,6-dimethyl-phenyl]-3-oxo-cyclopenten-1-yl] 4-methoxybenzoate (compound P1)

Step 1: Synthesis of [4-[2-(tert-butylamino)-2-oxo-ethyl]-2-[4-(5-chloropyrimidin-2-yl)-2,6-dimethyl-phenyl]-3-oxo-cyclopenten-1-yl] 4-methoxybenzoate To a stirred solution of N-tert-butyl-2-[3-[4-(5-chloropyrimidin-2-yl)-2,6-dimethyl-phenyl]-2,4-dioxo-cyclopentyl]acetamide (0.15 g, 0.3505 mmol) in DCM was added triethylamine (0.054 ml, 0.351 mmol) and 4-methoxybenzoyl chloride (0.066 g, 0.386 mmol). The reaction was stirred at room temperature for 2 hours then evaporated to dryness under reduced pressure. The crude material was purified by flash chromatography on silica using a gradient of 5% EtOAc/isohexane to 100% EtOAc as eluent to give the desired product (0.163 g, 83%) as a white solid.

$^1$H NMR (400 MHz, CDCl$_3$) 8.70 (s, 2H), 8.09 (s, 2H), 7.83 (d, 2H), 6.86 (d, 2H), 5.91 (s, 1H), 3.80 (s, 3H), 3.53 (dd, 1H), 3.28-3.14 (m, 2H), 2.79 (dd, 1H), 2.48-2.39 (m, 1H), 2.27 (d, 6H), 1.33 (s, 9H)

Example 10: Synthesis of tert-butyl-2-[3-[4-(3,5-difluoro-2-pyridyl)-2-ethynyl-6-methyl-phenyl]-2,4-dioxo-cyclopentyl]acetamide (compound B381)

Step 1: Synthesis of 2,4-dibromo-6-methyl-phenyl)-(2-furyl)methanol

To a solution of 1,5-dibromo-2-iodo-3-methyl-benzene (5.00 g, 13.30 mmol) in dry tetrahydrofuran (27 mL) under $N_2$ at −78° C. was added dropwise a solution of isopropylmagnesium chloride lithium chloride complex (1.12 mol/L in THF 15.57 mmol) over a period of 90 mins, maintaining the temperature below −78° C. The reaction was stirred for 30 min and a solution of furan-2-carbaldehyde (15.30 mmol) in tetrahydrofuran (6 mL) was then added dropwise over 15 mins. The mixture was stirred cold for a further 30 mins, allowed to warm to room temperature and stirred for 1 hour. The mixture was added into saturated $NH_4Cl$(aq) and this mixture was extracted with ethyl acetate. The combined ethyl acetate layers were dried (MgSO4) and concentrated under reduced pressure. The residue was purified by flash chromatography on silica using a gradient of 100% isohexane to 20% EtOAc/isohexane as eluent to give (2,4-dibromo-6-methyl-phenyl)-(2-furyl)methanol (2.838 g, 62% yield).

1H NMR (400 MHz, CDCl$_3$) 7.64-7.54 (m, 1H), 7.43-7.38 (m, 1H), 7.31 (d, 1H), 6.46 (d, 1H), 6.35-6.31 (m, 1H), 6.09-6.03 (m, 1H), 2.78 (d, 1H), 2.43-2.38 (m, 3H)

Step 2: Synthesis of 2-(2,4-dibromo-6-methyl-phenyl)-3-methoxy-cyclopent-2-en-1-one (2,4-dibromo-6-methyl-phenyl)-(2-furyl)methanol (2.830 g, 6.543 mmol) was dissolved in N,N-dimethylacetamide (28 mL, 300 mmol). 4-methylbenzenesulfonic acid hydrate (3.952 mmol) was added and the mixture was heated under reflux for 4 h, then cooled to 0° C. After the addition of potassium carbonate (19.63 mmol) and methyl iodide (3.0 equiv., 19.63 mmol), the mixture was allowed to warm to room temperature and stirred overnight. The mixture was poured into 2M HCl(aq) (200 mL), then partitioned with ethyl acetate (100 mL). The phases were separated and the aqueous layer was extracted with ethyl acetate (100 mL). The combined organic layers were washed sequentially with 2M HCl(aq) (2×100 mL) and brine (100 mL). The organic layer was dried (MgSO4) and concentrated under reduced pressure. The residue was purified by flash chromatography on silica using a gradient of 10% EtOAc/isohexane to 100% EtOAc as eluent to give 2-(2,4-dibromo-6-methyl-phenyl)-3-methoxy-cyclopent-2-en-1-one (1.462 g, 62% yield).

1H NMR (400 MHz, CDCl$_3$) 7.61 (d, 1H), 7.37-7.28 (m, 1H), 3.82-3.71 (m, 3H), 2.88-2.76 (m, 2H), 2.69-2.57 (m, 2H), 2.18 (s, 3H)

Step 3: Synthesis of 2-[2-bromo-4-(3,5-difluoro-2-pyridyl)-6-methyl-phenyl]-3-methoxy-cyclopent-2-en-1-one To a solution of 2-(2,4-dibromo-6-methyl-phenyl)-3-methoxy-cyclopent-2-en-1-one (0.150 g, 0.417 mmol) in N,N-dimethylformamide (5 L/mol) was added tributyl-(3,5-difluoro-2-pyridyl)stannane (0.625 mmol) followed by cesium fluoride (0.833 mmol) and cuprous hydroiodide (0.0417 mmol). After degassing with nitrogen, the Palladium (dppf) dichloride (0.0208 mmol) was added and the mixture heated in the microwave for 30 mins at 130° C. The reaction was diluted with EtOAc, filtered and concentrated in vacuo. The resulting residue was purified by flash chromatography on silica using a gradient of 5% EtOAc/isohexane to 100% EtOAc/isohexane as eluent to give 2-[2-bromo-4-(3,5-difluoro-2-pyridyl)-6-methyl-phenyl]-3-methoxy-cyclopent-2-en-1-one (0.066 g, 40% yield)

1H NMR (400 MHz, CDCl$_3$) 8.46-8.39 (m, 1H), 7.75 (s, 1H), 7.35-7.30 (m, 1H), 3.82-3.78 (m, 3H), 2.85-2.76 (m, 2H), 2.69-2.58 (m, 2H), 2.32-2.25 (m, 3H)

Step 4: Synthesis of 2-[3-[2-bromo-4-(3,5-difluoro-2-pyridyl)-6-methyl-phenyl]-2-methoxy-4-oxo-cyclopent-2-en-1-yl]acetonitrile 2-[2-bromo-4-(3,5-difluoro-2-pyridyl)-6-methyl-phenyl]-3-methoxy-cyclopent-2-en-1-one (0.400 g, 1.01 mmol) was dissolved in tetrahydrofuran (30 mL/g) and cooled to −70° C. Lithium bis(trimethylsilyl)amide (1M in THF, 1.12 mmol) was added dropwise, and stirred for 1 hour. 2-Bromoacetonitrile (1.14 mmol) was then added dropwise and after stirring for 30 mins, the reaction mixture was allowed to warm to 0° C. and was stirred for a further 1 hr. The reaction mixture was quenched with 0.5M $NH_4Cl$ and extracted with ethyl acetate. The organic layer was combined, washed with brine, dried (MgSO4) and concentrated. The resulting residue was purified by flash chromatography on silica using a gradient of 5% EtOAc/isohexane to 100% EtOAc as eluent to give 2-[3-[2-bromo-4-(3,5-difluoro-2-pyridyl)-6-methyl-phenyl]-4-methoxy-2-oxo-cyclopent-3-en-1-yl]acetonitrile (0.104 g, 24% yield) and 2-[3-[2-bromo-4-(3,5-difluoro-2-pyridyl)-6-methyl-phenyl]-2-methoxy-4-oxo-cyclopent-2-en-1-yl]acetonitrile (0.230 g, 52% yield).

2-[3-[2-bromo-4-(3,5-difluoro-2-pyridyl)-6-methyl-phenyl]-4-methoxy-2-oxo-cyclopent-3-en-1-yl]acetonitrile: 1H NMR (400 MHz, CDCl$_3$) 8.48-8.41 (m, 1H), 8.04 (s, 1H), 7.84-7.74 (m, 1H), 7.37-7.26 (m, 1H), 3.74-3.66 (m, 3H), 3.00-2.76 (m, 2H), 2.55-2.48 (m, 2H), 2.43-2.37 (m, 3H), 2.32-2.20 (m, 1H). 2-[3-[2-bromo-4-(3,5-difluoro-2-pyridyl)-6-methyl-phenyl]-2-methoxy-4-oxo-cyclopent-2-en-1-yl]acetonitrile: 1H NMR (400 MHz, CDCl$_3$) 8.48-8.41 (m, 1H), 8.04 (s, 1H), 7.84-7.74 (m, 1H), 7.37-7.26 (m, 1H), 3.74-3.66 (m, 3H), 3.00-2.76 (m, 2H), 2.55-2.48 (m, 2H), 2.43-2.37 (m, 3H), 2.32-2.20 (m, 1H)

Step 5: Synthesis of 2-[3-[2-bromo-4-(3,5-difluoro-2-pyridyl)-6-methyl-phenyl]-2-methoxy-4-oxo-cyclopent-2-en-1-yl]-N-tert-butyl-acetamide The 2-[3-[2-bromo-4-(3,5-difluoro-2-pyridyl)-6-methyl-phenyl]-2-methoxy-4-oxo-cyclopent-2-en-1-yl]acetonitrile (0.500 g, 1.15 mmol) was suspended in tert-butyl acetate (5.00 mL, 37.1 mmol) and sulfuric acid (0.3 mL, 6 mmol) was added. The reaction mixture was heated at 45° C. for 5 h 30 mins, allowed to cool to room temperature then diluted with saturated sodium bicarbonate solution and extracted with EtOAc. The organic layer was dried and concentrated in vacuo and purified by flash chromatography on silica using a 5% MeOH/DCM eluant to give 2-[3-[2-bromo-4-(3,5-difluoro-2-pyridyl)-6-methyl-phenyl]-2-methoxy-4-oxo-cyclopent-2-en-1-yl]-N-tert-butyl-acetamide (0.558 g, 95% yield)

1H NMR (400 MHz, CDCl$_3$) 8.46-8.40 (m, 1H), 8.06-8.00 (m, 1H), 7.76 (s, 1H), 7.37-7.27 (m, 1H), 3.66-3.61 (m, 3H), 3.51-3.41 (m, 1H), 2.92-2.76 (m, 2H), 2.33-2.26 (m, 4H), 2.22-2.14 (m, 1H), 1.40-1.35 (m, 9H).

Step 6: Synthesis of N-tert-butyl-2-[3-[4-(3,5-difluoro-2-pyridyl)-2-methyl-6-(2-trimethylsilylethynyl)phenyl]-2-methoxy-4-oxo-cyclopent-2-en-1-yl]acetamide 2-[3-[2-bromo-4-(3,5-difluoro-2-pyridyl)-6-methyl-phenyl]-2-methoxy-4-oxo-cyclopent-2-en-1-yl]-N-tert-butylacetamide (0.294 g, 0.579 mmol), trimethyl(2-tributylstannylethynyl)silane (0.869 mmol) and [1,1'-bis(diphenylphosphino)ferrocene] dichloropalladium(II) (0.0290 mmol) was dissolved in toluene (17 mL/mmol). The reaction was stirred at 160° C. for 2 hours under air. Upon cooling, the reaction was filtered and concentrated in vacuo and purified by flash chromatography on silica using a 5% MeOH/DCM eluant to give N-tert-butyl-2-[3-[4-(3,5-difluoro-2-pyridyl)-2-methyl-6-(2-trimethylsilylethynyl)phenyl]-2-methoxy-4-oxo-cyclopent-2-en-1-yl]acetamide (0.272 g, 89% yield).

1H NMR (400 MHz, CDCl$_3$) 8.46-8.36 (m, 1H), 7.95-7.88 (m, 1H), 7.80-7.68 (m, 1H), 7.34-7.28 (m, 1H), 3.69-3.59 (m, 3H), 3.53-3.31 (m, 1H), 2.94-2.73 (m, 2H), 2.41-2.31 (m, 1H), 2.29-2.24 (m, 3H), 2.23-2.08 (m, 1H), 1.58-1.51 (m, 9H), 0.24-0.18 (m, 9H)

Step 7: Synthesis of N-tert-butyl-2-[3-[4-(3,5-difluoro-2-pyridyl)-2-ethynyl-6-methyl-phenyl]-2,4-dioxo-cyclopentyl]acetamide The N-tert-butyl-2-[3-[4-(3,5-difluoro-2-pyridyl)-2-methyl-6-(2-trimethylsilylethynyl)phenyl]-2-methoxy-4-oxo-cyclopent-2-en-1-yl]acetamide (0.270 g, 0.515 mmol) was suspended in acetone (5 mL/mmol) and hydrochloric acid (2M solution, 5.15 mmol) was added. The reaction mixture was heated at 60° C. for 10.5 h. The reaction mixture was concentrated in vacuo and the resulting aqueous layer was extracted with EtOAc. The organic layer was dried and concentrated in vacuo and purified by flash chromatography on silica using a 5% MeOH/DCM eluant to give N-tert-butyl-2-[3-[4-(3,5-difluoro-2-pyridyl)-2-methyl-6-(2-trimethylsilylethynyl)phenyl]-2,4-dioxo-cyclopentyl]acetamide (0.113 g, 43% yield) and N-tert-butyl-2-[3-[4-(3,5-difluoro-2-pyridyl)-2-ethynyl-6-methyl-phenyl]-2,4-dioxo-cyclopentyl]acetamide (0.043 g, 19% yield).

N-tert-butyl-2-[3-[4-(3,5-difluoro-2-pyridyl)-2-methyl-6-(2-trimethylsilylethynyl)phenyl]-2,4-dioxo-cyclopentyl]acetamide: 1H NMR (400 MHz, CD$_3$OD) 8.31-8.23 (m, 1H), 7.61 (d, 1H), 7.56 (s, 1H), 7.49-7.41 (m, 1H), 3.04-2.86 (m, 1H), 2.79-2.62 (m, 1H), 2.56-2.41 (m, 1H), 2.35-2.17 (m, 2H), 2.07-1.96 (m, 3H), 1.16 (d, 9H), 0.03-0.05 (m, 9H)

N-tert-butyl-2-[3-[4-(3,5-difluoro-2-pyridyl)-2-ethynyl-6-methyl-phenyl]-2,4-dioxo-cyclopentyl]acetamide: 1H NMR (400 MHz, CD$_3$OD) δ=8.51 (dd, 1H), 8.13-8.01 (m, 1H), 7.95 (s, 1H), 7.75-7.68 (m, 1H), 3.24-3.07 (m, 1H), 2.99-2.79 (m, 1H), 2.75-2.65 (m, 1H), 2.54 (d, 1H), 2.44 (br. s., 2H), 2.31 (s, 3H), 1.41-1.35 (m, 9H)

Example 11: Synthesis of tert-butyl-2-[3-[4-(3,5-difluoro-2-pyridyl)-2-ethynyl-6-methyl-phenyl]-2,4-dioxo-cyclopentyl]acetamide (compound B382)

Step 1: Synthesis of N-tert-butyl-2-[3-[4-(3,5-difluoro-2-pyridyl)-2-methyl-6-vinyl-phenyl]-2,4-dioxo-cyclopentyl]acetamide 2-[3-[2-bromo-4-(3,5-difluoro-2-pyridyl)-6-methyl-phenyl]-2-methoxy-4-oxo-cyclopent-2-en-1-yl]-N-tert-butyl-acetamide (0.294 g, 0.579 mmol), tributyl(vinyl)stannane (0.869 mmol) and [1,1'-bis(diphenylphosphino)ferrocene]dichloropalladium(II) (0.0290 mmol) was dissolved in toluene (17 mL/mmol) and stirred at 160° C. for 2 hours under air. The reaction was cooled to room temperature, filtered and the solvent removed in vacuo. The resulting residue was purified by flash chromatography on silica using a 10% MeOH/DCM eluant to give N-tert-butyl-2-[3-[4-(3,5-difluoro-2-pyridyl)-2-methyl-6-vinyl-phenyl]-2-methoxy-4-oxo-cyclopent-2-en-1-yl]acetamide (0.201 g, 76% yield).

1H NMR (400 MHz, CDCl$_3$) 8.44 (d, 1H), 7.97 (s, 1H), 7.70 (br. s., 1H), 7.34-7.28 (m, 1H), 6.66 (dt, 1H), 5.81-5.71 (m, 1H), 5.31-5.26 (m, 1H), 3.56-3.50 (m, 3H), 3.43 (br. s., 1H), 2.95-2.81 (m, 1H), 2.77-2.65 (m, 1H), 2.46-2.38 (m, 2H), 2.29-2.22 (m, 3H), 1.37 (d, 9H).

Step 2: Synthesis of N-tert-butyl-2-[3-[4-(3,5-difluoro-2-pyridyl)-2-methyl-6-vinyl-phenyl]-2,4-dioxo-cyclopentyl]acetamide The N-tert-butyl-2-[3-[4-(3,5-difluoro-2-pyridyl)-2-methyl-phenyl]-2-methoxy-4-oxo-cyclopent-2-en-1-yl]acetamide (0.200 g, 0.467 mmol) was suspended in acetone (5.89 mL/mmol) and hydrochloric acid (2M solution) (5.89 mL/mmol, 5.50 mmol) was added. The reaction mixture was heated at 60° C. for 10.5 hour. The reaction mixture was concentrated in vacuo to remove the acetone and the resulting aqueous layer was extracted with EtOAc. The organic layers were dried (MgSO$_4$) and concentrated in vacuo, and the resulting residue was purified by flash chromatography on silica using a 10% MeOH/DCM eluant to give N-tert-butyl-2-[3-[4-(3,5-difluoro-2-pyridyl)-2-methyl-6-vinyl-phenyl]-2,4-dioxo-cyclopentyl]acetamide (0.090 g, 44% yield).

1H NMR (400 MHz, CD$_3$OD) δ=8.50-8.45 (m, 1H), 7.97 (s, 1H), 7.74-7.64 (m, 2H), 6.70 (ddd, 1H), 5.73 (dd, 1H), 5.28-5.17 (m, 1H), 3.26-3.13 (m, 1H), 2.99-2.86 (m, 1H), 2.79-2.68 (m, 1H), 2.52-2.41 (m, 2H), 2.25-2.19 (m, 3H), 1.40-1.33 (m, 9H)

Example 12: Synthesis of 2-[3-[4-(4-chloropyrazol-1-yl)-2,6-dimethyl-phenyl]-2,4-dioxo-cyclopentyl]-N-propyl-acetamide (compound B314)

Step 1: Synthesis of 6-[4-(4-chloropyrazol-1-yl)-2,6-dimethyl-phenyl]-3a,4-dihydro-3H-cyclopenta[b]furan-2,5-dione The 2-[3-[4-(4-chloropyrazol-1-yl)-2,6-dimethyl-phenyl]-2,4-dioxo-cyclopentyl]acetic acid (1.66 mmol, 0.600 g) was dissolved in dichloromethane (15.0 mL) and 3-(ethyliminomethyleneamino)-N,N-dimethyl-propan-1-amine hydrochloride (2.08 mmol, 0.399 g) was added. After 3 h, a further portion of 3-(ethyliminomethyleneamino)-N,N-dimethyl-propan-1-amine hydrochloride (0.249 mmol, 0.0478 g) was added and stirring continued for a further 1 hour. The crude reaction mixture was directly used in the next step without further processing.

Step 2: Synthesis of 2-[3-[4-(4-chloropyrazol-1-yl)-2,6-dimethyl-phenyl]-2,4-dioxo-cyclopentyl]-N-propyl-acetamide A DCM solution of 6-[4-(4-chloropyrazol-1-yl)-2,6-dimethyl-phenyl]-3a,4-dihydro-3H-cyclopenta[b]furan-2,5-dione (0.415 mmol, 0.142 g) was added to propan-1-amine hydrochloride (0.498 mmol, 0.0476 g) and N,N-diethylethanamine (0.830 mmol, 0.0840 g, 0.116 mL) and stirred at room temperature overnight. The reaction mixture was washed with 2M HCl then purified by flash chromatography on silica using a 0% to 50% MeCN/DCM as eluant to give 2-[3-[4-(4-chloropyrazol-1-yl)-2,6-dimethyl-phenyl]-2,4-dioxo-cyclopentyl]-N-propyl-acetamide (82 mg).

1H NMR (400 MHz, CDCl$_3$) 14.16-13.45 (m, 1H), 7.87 (s, 1H), 7.59 (s, 1H), 7.31 (s, 2H), 7.15-7.01 (m, 1H), 3.36-3.03 (m, 3H), 2.85 (dd, 1H), 2.61 (d, 2H), 2.18 (d, 7H), 1.57-1.32 (m, 2H), 0.87 (t, 3H)

Example 13—Chiral HPLC or SFC Separation of Enantiomers

In one optional embodiment of the invention, any specific compound of the invention is separated into the two corresponding enantiomerically pure (or substantially enantiomerically pure) compounds using a chiral HPLC or SFC column. In one optional example, the chiral HPLC uses the following method and the following conditions.

Chiral HPLC column: a (s,s) WhelkO1-5 micron-21 mm×250 mm HPLC column, manufactured by Regis Technologies, Inc. In this column, the chiral stationary phase is (S,S) 1-(3-5-dinitrobenzamido)-1,2,3,4-tetrahydrophenanthrene.

The solvent system to be used as an eluent for the column varies depending on the racemic compound to be separated into enantiomers, but one example of a solvent system is:

a 30:70 (by volume) mixture of Solvent A and Solvent B, in which:

Solvent A is isohexane containing 0.1% v/v of trifluoroacetic acid (TFA), and

Solvent B is ethanol.

Other conditions (these are sample conditions only and may vary widely):

Flow rate through column: about 21 ml/minute. Run time: about 20 minutes.

Loading (compound loaded onto column): about 50 mg/ml of compound in ethanol.

Volume of sample (compound) injected per run=about 1800 microliters.

Number of injections of compound=about 5.

Abbreviation

HPLC=high performance (or high pressure) liquid chromatography.

SFC=Supercritical fluid chromatography

General Note on Chiral HPLC or SFC Separation of Enantiomers:

The above procedure using chiral HPLC is used to separate the enantiomers of other compounds of formula (I) of the present the invention. Alternative chiral columns which might be useful to achieve this are as follows:

(s,s) WhelkO1-5 micron-21 mm×250 mm HPLC column, manufactured by Regis Technologies, Inc [in this column, the chiral stationary phase is (S,S) 1-(3-5-dinitrobenzamido)-1,2,3,4-tetrahydrophenanthrene];

Kromasil® AmyCoat™ [whose chiral stationary phase is tris-(3,5-dimethylphenyl)carbamoyl amylose];

Kromasil® CelluCoat™ [whose chiral stationary phase is tris-(3,5-dimethylphenyl)carbamoyl cellulose];

Chiralpak® IA [whose chiral stationary phase is a (3,5-dimethylphenyl)carbamate derivative of amylose];

Chiralpak® IB [whose chiral stationary phase is tris-(3,5-dimethylphenyl)carbamate derivative of cellulose];

Chiralpak® IC [whose chiral stationary phase is cellulose tris(3,5-dichlorophenyl) carbamate];

Lux® Amylose-2 [whose chiral stationary phase is amylose tris(5-chloro-2-methylphenylcarbamate)]; or Lux® Cellulose-2 [whose chiral stationary phase is Cellulose tris(3-chloro-4-methylphenylcarbamate)].

Lux® Cellulose-4 [whose chiral stationary phase is Cellulose tris(4-chloro-3-methylphenylcarbamate)]

Example 14—Chiral HPLC Separation of Enantiomers of Compound B75

Compound B75 (racemic), was separated into individual enantiomer compounds using a chiral HPLC column, by the following method and under the following conditions.

The chiral HPLC column used was a (s,s) WhelkO1-5 micron-20 mm×250 mm HPLC column, manufactured by Regis Technologies Inc. In this column, the chiral stationary phase is (S,S) 1-(3-5-dinitrobenzamido)-1,2,3,4-tetrahydrophenanthrene.

The solvent system used as an eluent for the column was a 63:37 (by volume) mixture of Solvent A and Solvent B, in which:

Solvent A is isohexane containing 1.0% v/v of ethanol and 0.2% v/v of glacial acetic acid, and Solvent B is ethanol. Other conditions were as follows:

Flow rate through column: 24 ml/minute.

Loading (compound loaded onto column): 53 mg/ml in isopropanol.

Volume of sample (compound) injected per run=0.30 to 0.35 ml

Number of injections of compound=60

Length of run=20 minutes

Chiral HPLC on a total of 150 mg of compound B75 (racemic) under the above conditions gave 41 mg of 100% enantiomeric excess (e.e.) at retention time 14.77 and 37 mg of 93% e.e at retention time 16.48.

General Note on NMR and HPLC:

NMR spectra were run in the deuterated solvent specified and on an instrument operating at the indicated frequency.

HPLC retention times were acquired on Waters Aquity UPLC-MS using a Sample Organizer with Sample Manager FTN, H-class QSM, Column Manager, 2×Column Manager Aux, photodiode array, ELSD and SQD 2 equipped with a Waters HSS T3 C18 column (column length 30 mm, internal diameter of column 2.1 mm, particle size 1.8 micron). The analysis was conducted using a two minute run time, according to the following gradient table:

| Time (mins) | Solvent A (%) | Solvent B (%) | Flow (ml/mn) |
|---|---|---|---|
| 0 | 95 | 5 | 0.7 |
| 1.75 | 0 | 100 | 0.7 |
| 1.76 | 0 | 100 | 0.7 |
| 2 | 0 | 5 | 0.7 |
| 2.01 | 95 | 5 | 0.7 |
| 2.11 | 95 | 5 | 0.7 |

Solvent A: $H_2O$ with 0.05% TFA
Solvent B: $CH_3CN$ with 0.05% TFA

Additional compounds in Tables T1 an T2 below illustrate the present invention, and are particular embodiments of the compounds of formula (I) according to the present invention.

For the most part, these compounds can generally be prepared by methods similar to those shown in the Examples and/or in the process section hereinabove using appropriate starting materials.

TABLE T1

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (400 MHz, CDCl$_3$) unless stated |
|---|---|---|
| A1 | 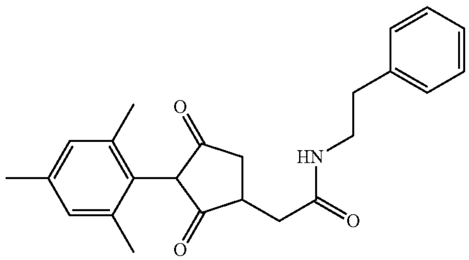 [SMILES: Cc1cc(C)c(C2C(=O)CC(CC(=O)NCCc3ccccc3)C2=O)c(C)c1] | 7.35-7.30 (m, 2H), 7.25 (m, 1H), 7.20 (d, 2H), 6.85 (s, 6H), 6.05 (br, 1H), 3.60 (m, 2H), 3.25 (m, 1H), 2.90-2.80 (m, 3H), 2.65 (d, 2H), 2.25 (s, 3H), 2.20 (dd, 1H), 2.10 (2 × s, 2 × 3H). |
| A2 | 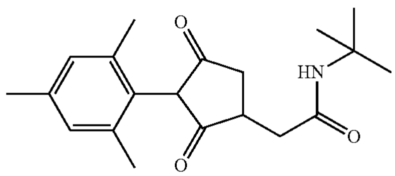 [SMILES: Cc1cc(C)c(C2C(=O)CC(CC(=O)NC(C)(C)C)C2=O)c(C)c1] | 6.87 (s, 2H), 5.83 (s, 1H), 3.32-3.23 (m, 1H), 2.93-2.83 (m, 1H), 2.72-2.58 (m, 2H), 2.25 (s, 3H), 2.24-2.14 (m, 1H), 2.11 (s, 6H), 1.38 (s, 9H). |
| A3 | 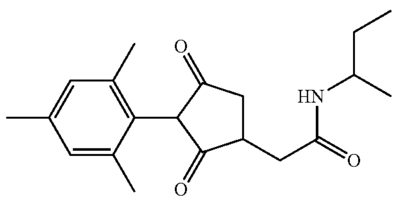 [SMILES: CCC(C)NC(=O)CC1CC(=O)C(c2c(C)cc(C)cc2C)C1=O] | 6.86 (s, 2H), 5.92 (br. s, 1H), 3.99-3.87 (m, 1H), 3.32-3.21 (m, 1H), 2.94-2.84 (m, 1H), 2.69 (d, 2H), 2.25 (s, 3H), 2.24-2.15 (m, 1H), 2.11 (s, 6H), 1.55-1.44 (m, 2H), 1.20-1.12 (m, 3H), 0.98-0.88 (m, 3H) |
| A4 | 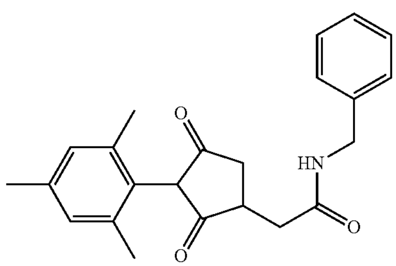 [SMILES: Cc1cc(C)c(C2C(=O)CC(CC(=O)NCc3ccccc3)C2=O)c(C)c1] | 7.39-7.29 (m, 3H), 7.29-7.23 (m, 2H), 6.86 (s, 2H), 6.70 (br. m, 1H), 4.49-4.36 (m, 2H), 3.30-3.21 (m, 1H), 2.89-2.81 (m, 1H), 2.74-2.62 (m, 2H), 2.24 (s, 3H), 2.22-2.12 (m, 1H), 2.09 (s, 6H) |
| A5 | 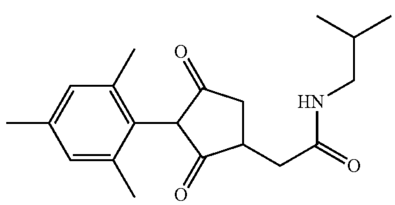 [SMILES: Cc1cc(C)c(C2C(=O)CC(CC(=O)NCC(C)C)C2=O)c(C)c1] | 7.60 (s, 1H), 6.85 (s, 2H), 3.28-3.15 (m, 1H), 3.13-3.02 (m, 2H), 2.94-2.72 (m, 2H), 2.72-2.61 (m, 2H), 2.25 (s, 3H), 2.10 (s, 6H), 1.87-1.74 (m, 1H), 0.92 (d, 6H) |
| A6 | 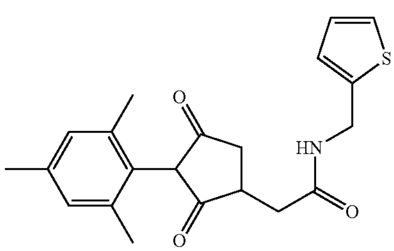 [SMILES: Cc1cc(C)c(C2C(=O)CC(CC(=O)NCc3cccs3)C2=O)c(C)c1] | 7.26 (m, 1H), 6.97 (m, 2H), 6.87 (d, 2H), 6.67 (br.s, 1H), 4.68-4.53 (m, 2H), 3.31-3.22 (m, 1H), 2.92-2.82 (m, 1H), 2.73-2.62 (m, 2H), 2.25 (s, 3H), 2.23-2.14 (m, 1H), 2.10 (d, 6H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (400 MHz, CDCl$_3$) unless stated |
|---|---|---|
| A7 | 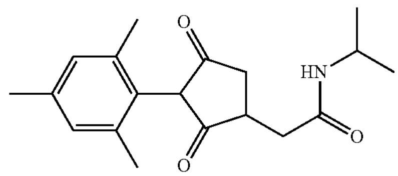 [SMILES: Cc1cc(C)c(C2C(=O)CC(CC(=O)NC(C)C)C2=O)c(C)c1] | 6.84 (s, 2H), 4.02-3.93 (m, 1H), 3.18-3.08 (m, 1H), 2.91-2.82 (m, 1H), 2.74-2.68 (m, 1H), 2.44-2.33 (m, 2H), 2.23 (s, 3H), 2.04 (s, 6H), 1.15 (d, 6H) |
| A8 | 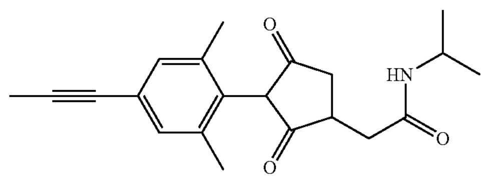 [SMILES: CC#Cc1cc(C)c(C2C(=O)CC(CC(=O)NC(C)C)C2=O)c(C)c1] | (d$_4$-MeOH) 7.03 (s, 2H), 3.98 (m, 1H), 3.19-3.10 (m, 1H), 2.87 (dd, 1H), 2.71 (dd, 1H), 2.47-2.34 (m, 2H), 2.06 (s, 6H), 1.99 (s, 3H), 1.14 (dd, 6H) |
| A9 | 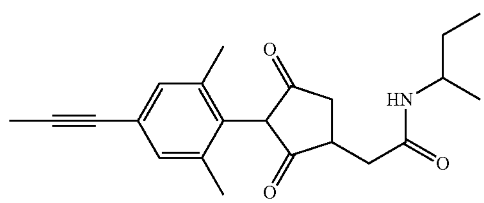 [SMILES: CC#Cc1cc(C)c(C2C(=O)CC(CC(=O)NC(C)CC)C2=O)c(C)c1] | (d4-MeOH) 7.14 (s, 2H), 3.81 (q, 1H), 3.38 (s, 1H), 3.21-3.11 (m, 1H), 2.93-2.85 (m, 1H), 2.78-2.69 (m, 1H), 2.50-2.38 (m, 2H), 2.09 (s, 6H), 1.56-1.42 (m, 2H), 1.22 (d, 3H), 0.96-0.87 (m, 3H) |
| A10 | 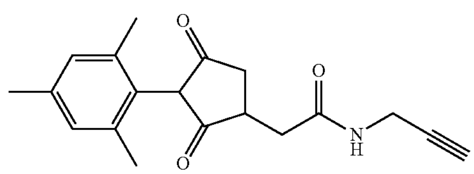 [SMILES: C#CCNC(=O)CC1CC(=O)C(c2c(C)cc(C)cc2C)C1=O] | 12.40 (1H, br), 6.95 (t, 1H), 6.85 (2 × s, 2H), 4.10-3.95 (m, 2H), 3.30-3.20 (m, 1H), 2.90 (dd, 1H), 2.80-2.60 (m, 2H), 2.30 (s, 1H), 2.25 (s, 3H), 2.20 (d, 1H), 2.10 (s, 6H) |
| A11 | 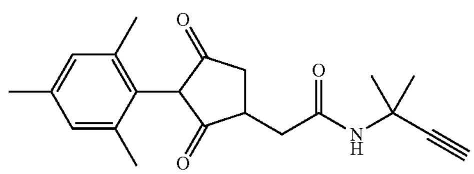 [SMILES: C#CC(C)(C)NC(=O)CC1CC(=O)C(c2c(C)cc(C)cc2C)C1=O] | (d4-MeOH) (resticted rotation) 6.85 (s, 2H), 3.12 (br, 1H), 2.95-2.85 (m, 1H), 2.80-2.70 (m, 1H), 2.50-2.30 (m, 2H), 2.25 (s, 3H), 2.12 (s, 1H), 2.05 (s, 6H), 1.60 (s, 3.9H), 1.35 (s, 2.1H) |
| A12 | 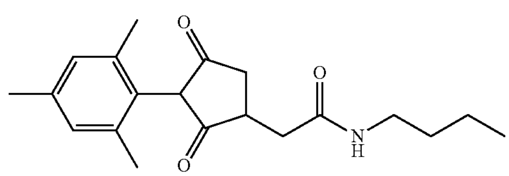 [SMILES: CCCCNC(=O)CC1CC(=O)C(c2c(C)cc(C)cc2C)C1=O] | 13.10 (br, 1H), 6.85 (2 × s, 2H), 6.50 (t, 1H), 3.30-3.15 (3H, m), 2.90 (d, 1H), 2.70-2.60 (m, 2H), 2.25 (s, 3H), 2.20 (d, 1H), 2.10 (s, 6H), 1.50-1.40 (m, 2H), 1.35-1.30 (m, 2H), 0.90 (t, 3H) |
| A13 | 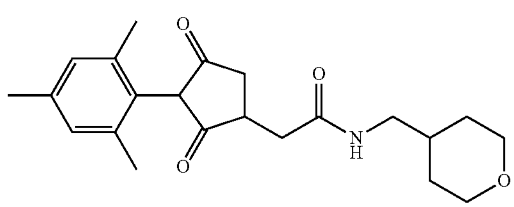 [SMILES: Cc1cc(C)c(C2C(=O)CC(CC(=O)NCC3CCOCC3)C2=O)c(C)c1] | 13.10 (br, 1H), 7.05 (t, 1H), 6.87 (2 × s, 2H), 4.00-3.90 (m, 2H), 3.35 (t, 2H), 3.30-3.20 (m, 1H), 3.15-3.00 (m, 2H), 2.90 (dd, 1H), 2.75 (d, 1H), 2.65-2.60 (m, 1H), 2.30 (s, 3H), 2.20 (dd, 1H), 2.10 (s, 6H), 1.75-1.65 (m, 1H), 1.55 (d, 2H), 1.30-1.20 (m, 2H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (400 MHz, CDCl$_3$) unless stated |
|---|---|---|
| A14 | 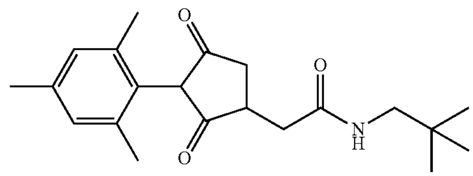 [SMILES: Cc1cc(C)c(C2C(=O)CC(CC(=O)NCC(C)(C)C)C2=O)c(C)c1] | (d4-MeOH) 6.85 (2H, s), 3.20-3.10 (1H, m), 3.05 (2H, s), 2.90 (1H, dd), 2.80 (1H, dd), 2.50-2.40 (2H, m), 2.25 (3H, s), 2.05 (6H, s), 0.90 (9H, s) |
| A15 | 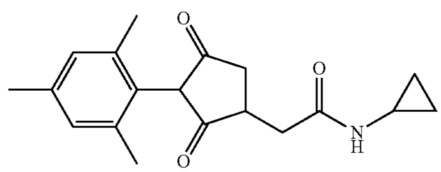 [SMILES: Cc1cc(C)c(C2C(=O)CC(CC(=O)NC3CC3)C2=O)c(C)c1] | 6.87 (s, 2H), 3.25-3.15 (m, 1H), 2.92-2.78 (m, 2H), 2.80-2.70 (m, 1H), 2.70-2.58 (m, 1H), 2.25 (s, 3H), 2.15 (d, 1H), 2.12 (s, 6H), 0.85-0.75 (m, 2H), 0.60-0.50 (m, 2H) |
| A16 | 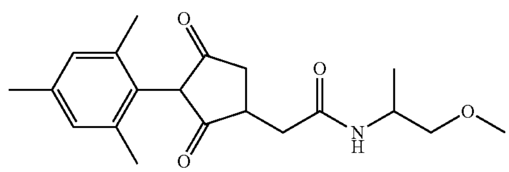 | (d4-MeOH) 6.90 (2H, s), 4.14-4.10 (1H, m), 3.90-3.80 (5H, m), 3.20-3.10 (1H, m), 2.90 (1H, dd), 2.75 (1H, dd), 2.50-2.40 (2H, m), 2.18 (3H, s), 2.10 (6H, s), 1.18 (3H, d) |
| A17 | 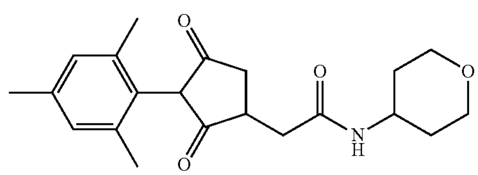 [SMILES: Cc1cc(C)c(C2C(=O)CC(CC(=O)NC3CCOCC3)C2=O)c(C)c1] | 6.88 (s, 1H), 6.87 (s, 1H), 6.72 (br, 1H), 4.05-3.90 (m, 3H), 3.50-3.42 (m, 2H), 3.25 (br, 1H), 2.89 (dd, 1H), 2.25 (s, 3H), 2.17 (d, 1H), 2.11 (s, 3H), 2.10 (s, 3H), 2.06-1.97 (m, 2H), 1.90-1.80 (m, 2H), 1.55-1.40 (m, 2H) |
| A18 | 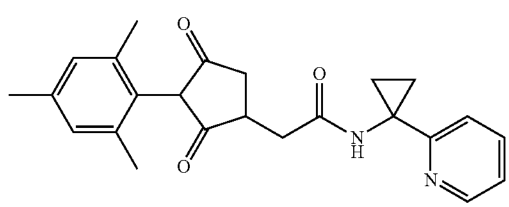 [SMILES: Cc1cc(C)c(C2C(=O)CC(CC(=O)NC3(c4ccccn4)CC3)C2=O)c(C)c1] | 9.88 (s, 1H), 8.60 (d, 1H), 8.20 (t, 1H), 7.68-7.60 (m, 2H), 6.85 (s, 2H), 3.25-3.15 (m, 1H), 2.92-2.78 (m, 2H), 2.70-2.58 (m, 1H), 2.26 (d, 1H), 2.23 (s, 3H), 2.05 (s, 6H), 1.60-1.50 (m, 4H) |
| A19 | 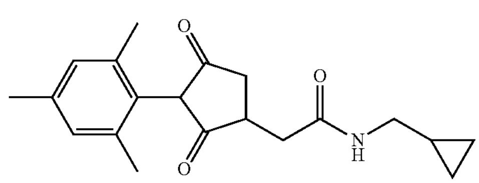 [SMILES: Cc1cc(C)c(C2C(=O)CC(CC(=O)NCC3CC3)C2=O)c(C)c1] | (d4MeOH) 6.87 (s, 2H), 3.20-3.10 (m, 1H), 3.08 (d, 2H), 2.90-2.82 (m, 1H), 2.78-2.72 (m, 1H), 2.50-2.38 (m, 2H), 2.23 (s, 3H), 2.05 (s, 6H), 1.02-0.90 (m, 1H), 0.55-0.45 (m, 2H), 0.24-0.18 (m, 2H) |
| A20 | 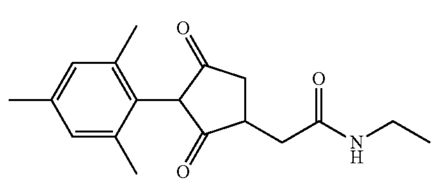 [SMILES: CCNC(=O)CC1CC(=O)C(c2c(C)cc(C)cc2C)C1=O] | (d4MeOH) 6.86 (s, 2H), 3.22 (q, 2H), 3.18-2.18 (m, 1H), 2.92-2.82 (m, 1H), 2.76-2.70 (m, 1H), 2.50-2.38 (m, 2H), 2.24 (s, 3H), 2.00 (s, 6H), 1.12 (t, 3H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (400 MHz, CDCl$_3$) unless stated |
|---|---|---|
| A21 | 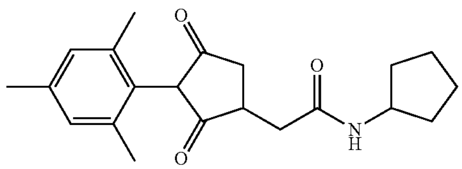 [SMILES: Cc1cc(C)c(C2C(=O)CC(CC(=O)NC3CCCC3)C2=O)c(C)c1] | (d4MeOH) 6.86 (s, 2H), 4.18-4.08 (m, 1H), 3.20-3.10 (m, 1H), 2.90-2.80 (m, 1H), 2.74-2.64 (m, 1H), 2.45-2.35 (m, 2H), 2.23 (s, 3H), 2.05 (s, 6H), 2.00-1.88 (m, 2H), 1.75-1.65 (m, 2H), 1.65-1.55 (m, 2H), 1.52-1.40 (m, 2H) |
| A22 | 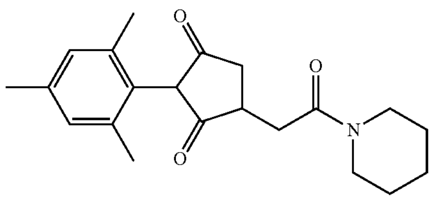 [SMILES: Cc1cc(C)c(C2C(=O)CC(CC(=O)N3CCCCC3)C2=O)c(C)c1] | (d4MeOH) 6.85 (s, 2H), 3.65-3.45 (m, 4H), 3.20-3.10 (m, 1H), 2.94-2.82 (m, 2H), 2.80-2.70 (m, 1H), 2.43 (d, 1H), 2.25 (s, 3H), 2.05 (s, 6H), 1.70-1.50 (m, 6H) |
| A23 | 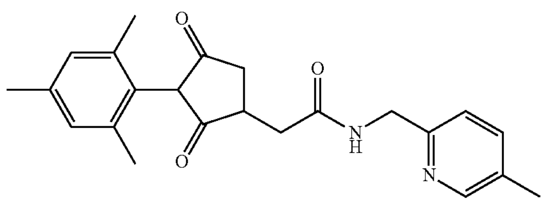 | 9.80 (s, 1H), 8.45 (s, 1H), 8.10 (dd, 1H), 7.80 (d, 1H), 6.87 (s, 2H), 4.70 (s, 2H), 3.22-3.13 (m, 1H), 2.93-2.82 (m, 2H), 2.70-2.62 (1H, m), 2.52 (3H, s), 2.26 (d, 1H), 2.23 (3H, s), 2.06 (d, 6H) |
| A24 | 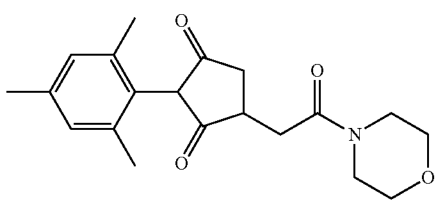 [SMILES: Cc1cc(C)c(C2C(=O)CC(CC(=O)N3CCOCC3)C2=O)c(C)c1] | 12.1 (s, 1H), 6.86 (d, 2H), 3.82-2.58 (m, 8H), 3.47-3.35 (m, 1H), 3.11 (d, 1H), 2.98-2.88 (m, 1H), 2.64-2.50 (m, 1H), 2.30-2.20 (m, 1H), 2.25 (s, 3H), 2.10 (d, 6H) |
| A25 | 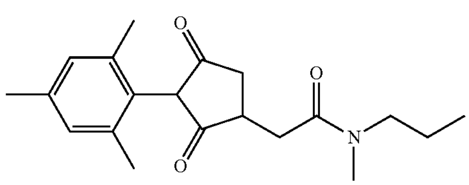 [SMILES: CCCN(C)C(=O)CC1CC(=O)C(c2c(C)cc(C)cc2C)C1=O] | (restricted rotation) 12.70 (1H, 2 × s), 6.85 (2H, 2 × s), 3.60-3.25 (3H, m), 3.10 (1H, d), 3.05 (3H, 2 × s), 2.65-2.50 (1H, s), 2.30-2.20 (4H, m), 2.10 (6H, 2 × s), 1.70-1.55 (2H, m), 1.00-0.90 (3H, 2 × t) |
| A26 | 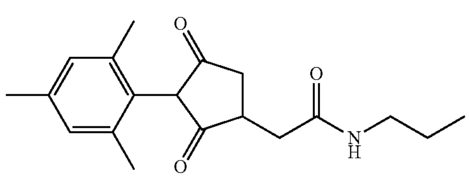 [SMILES: CCCNC(=O)CC1CC(=O)C(c2c(C)cc(C)cc2C)C1=O] | 12.8 (s, 1H), 6.86 (s, 2H), 6.35 (br, 1H), 3.30-3.18 (m, 3H), 2.92-2.84 (m, 1H), 2.72-2.65 (m, 2H), 2.30 (s, 3H), 2.20 (d, 1H), 2.12 (s, 6H), 1.55 (q, 2H), 0.95 (t, 3H) |
| A27 | 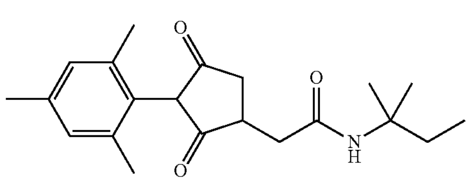 [SMILES: CCC(C)(C)NC(=O)CC1CC(=O)C(c2c(C)cc(C)cc2C)C1=O] | 12.8 (s, 1H), 6.87 (s, 2H), 5.73 (s, 1H), 3.30-3.20 (m, 1H), 2.90-2.80 (m, 1H), 2.75-2.65 (m, 2H), 2.27 (s, 3H), 2.20 (d, 1H), 2.12 (s, 6H), 1.75 (q, 2H), 1.32 (s, 6H), 0.86 (t, 3H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (400 MHz, CDCl$_3$) unless stated |
|---|---|---|
| A28 | 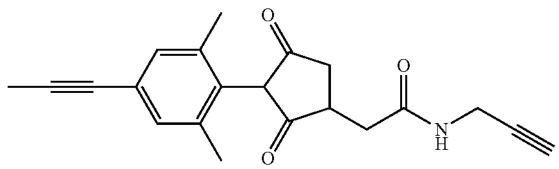 [SMILES: C#CCNC(=O)CC1CC(=O)C(c2c(C)cc(C#CC)cc2C)C1=O] | (d4-MeOH) 7.05 (2H, s), 3.98 (2H, s), 3.15-3.10 (1H, m), 2.90 (1H, dd), 2.75 (1H, dd), 2.60 (1H, s), 2.50-2.40 (2H, m), 2.10 (6H, s), 2.00 (3H, s) |
| A29 | 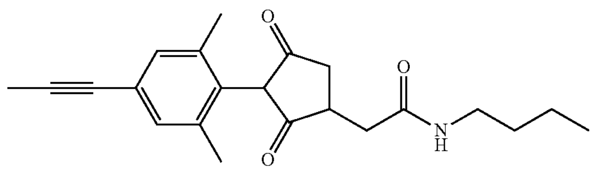 | 13.1 (1H, s), 7.09 (2H, s), 6.49-6.42 (1H, br), 3.30-3.20 (3H, m), 2.93-2.83 (1H, m), 2.70-2.60 (2H, m), 2.20 (1H, d), 2.12 (6H, s), 2.01 (3H, s), 1.52-1.42 (2H, m), 1.40-1.29 (2H, m), 0.92 (3H, t) |
| A30 | 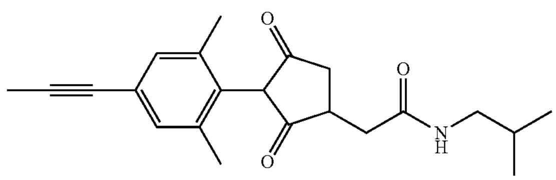 [SMILES: CC#Cc1cc(C)c(C2C(=O)CC(CC(=O)NCC(C)C)C2=O)c(C)c1] | 13.1 (1H, s), 7.08 (2H, s), 6.58 (br, 1H), 3.30-3.20 (1H, m), 3.15-3.05 (2H, m), 2.93-2.83 (1H, m), 2.75-2.60 (2H, m), 2.18 (1H, d), 2.10 (6H, s), 2.02 (3H, s), 1.83-1.70 (1H, m), 0.92 (6H, d) |
| A31 | 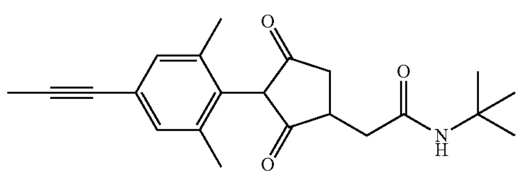 [SMILES: CC#Cc1cc(C)c(C2C(=O)CC(CC(=O)NC(C)(C)C)C2=O)c(C)c1] | 13.1 (1H, s), 7.08 (2H, s), 5.95 (1H, br), 3.30-3.21 (1H, m), 2.92-2.82 (1H, m), 2.67-.60 (2H, m), 2.17 (1H, d), 2.10 (6H, s), 2.02 (3H, s), 1.36 (9H, s) |
| A32 | 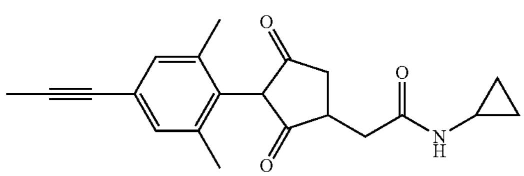 [SMILES: CC#Cc1cc(C)c(C2C(=O)CC(CC(=O)NC3CC3)C2=O)c(C)c1] | 13.20 (1H, br), 7.10 (2H, 2 × s), 6.90 (1H, br), 3.30-3.20 (1H, br), 2.85 (1H, dd), 2.80-2.70 (1H, m), 2.20-2.10 (8H, m), 2.05 (3H, s), 0.85-0.75 (2H, m), 0.55-0.50 (2H, m) |
| A33 | 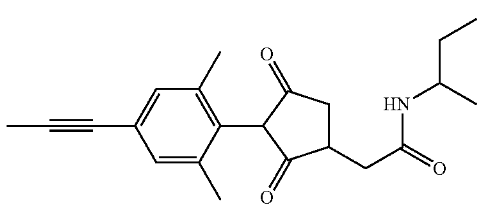 [SMILES: CC#Cc1cc(C)c(C2C(=O)CC(CC(=O)NC(C)CC)C2=O)c(C)c1] | (d4-MeOH) 7.06 (s, 2H), 3.84 (m, 1H), 3.22-3.13 (m, 1H), 2.92 (dd, 1H), 2.76 (dd, 1H), 2.52-2.42 (m, 2H), 2.09 (s, 6H), 2.02 (s, 3H), 1.52 (m, 2H), 1.16 (d, 3H), 0.99-0.91 (m, 3H) |
| A34 | 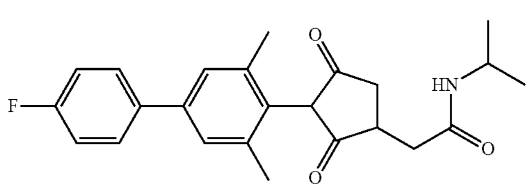 [SMILES: Cc1cc(-c2ccc(F)cc2)cc(C)c1C1C(=O)CC(CC(=O)NC(C)C)C1=O] | (d4-MeOH) 7.62-7.57 (m, 2H), 7.27 (s, 2H), 7.13 (t, 2H), 3.99 (m, 1H), 3.22-3.12 (m, 1H), 2.94-2.85 (m, 1H), 2.77-2.70 (m, 1H), 2.49-2.38 (m, 2H), 2.17 (s, 6H), 1.19-1.12 (m, 6H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (400 MHz, CDCl$_3$) unless stated |
|---|---|---|
| A35 | 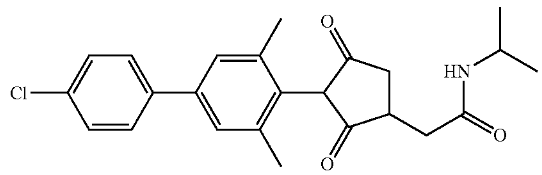 [SMILES: Cc1cc(-c2ccc(Cl)cc2)cc(C)c1C1C(=O)CC(CC(=O)NC(C)C)C1=O] | (d4-MeOH) 7.58 (d, 2H), 7.40 (d, 2H), 7.29 (s, 2H), 3.99 (m, 1H), 3.22-3.11 (m, 1H), 2.95-2.85 (m, 1H), 2.78-2.69 (m, 1H), 2.50-2.38 (m, 2H), 2.18 (s, 6H), 1.99-1.02 (m, 6H) |
| A36 | 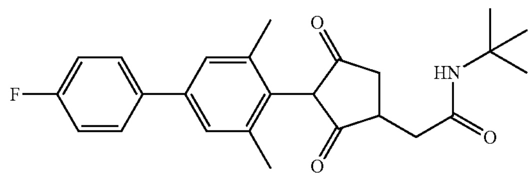 [SMILES: Cc1cc(-c2ccc(F)cc2)cc(C)c1C1C(=O)CC(CC(=O)NC(C)(C)C)C1=O] | (d4-MeOH) 7.62-7.56 (m, 2H), 7.26 (s, 2H), 7.12 (t, 2H), 3.22-3.12 (m, 1H), 2.94-2.85 (m, 1H), 2.74-2.66 (m, 1H), 2.51-2.35 (m, 2H), 2.17 (s, 6H), 1.35 (s, 9H) |
| A37 | 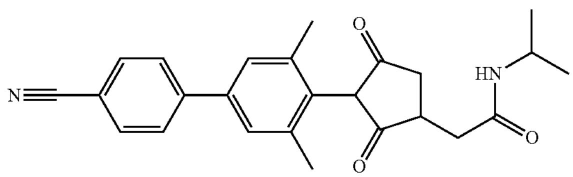 [SMILES: Cc1cc(-c2ccc(C#N)cc2)cc(C)c1C1C(=O)CC(CC(=O)NC(C)C)C1=O] | (d4-MeOH) 7.85-7.77 (m, 4H), 7.39 (s, 2H), 4.02 (m, 1H), 3.28-3.16 (m, 1H), 3.00-2.91 (m, 1H), 2.80-2.72 (m, 1H), 2.54-2.42 (m, 2H), 2.22 (s, 6H), 1.22-1.16 (m, 6H) |
| A38 | 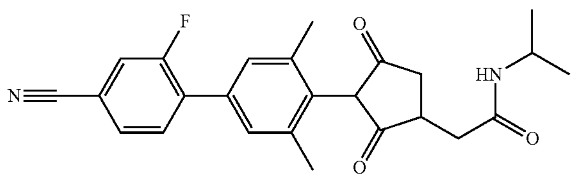 [SMILES: Cc1cc(-c2ccc(C#N)cc2F)cc(C)c1C1C(=O)CC(CC(=O)NC(C)C)C1=O] | (d4-MeOH) 7.69-7.59 (m, 3H), 7.26 (s, 2H), 3.99 (m, 1H), 3.23-3.12 (m, 1H), 2.96-2.87 (m, 1H), 2.78-2.70 (m, 1H), 2.51-2.37 (m, 2H), 2.19 (s, 6H), 1.20-1.12 (m, 6H) |
| A39 | 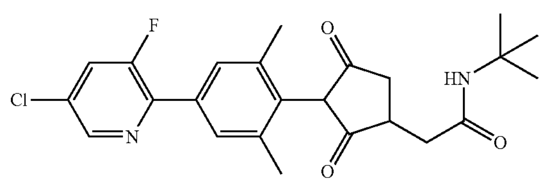 [SMILES: Cc1cc(-c2ncc(Cl)cc2F)cc(C)c1C1C(=O)CC(CC(=O)NC(C)(C)C)C1=O] | (d4-MeOH) 8.50 (s, 1H), 7.85 (d, 1H), 7.61 (s, 2H), 3.24-3.13 (m, 1H), 2.98-2.88 (m, 1H), 2.77-2.68 (m, 1H), 2.53-2.39 (m, 2H), 2.21 (s, 6H), 1.38 (s, 9H) |
| A40 | 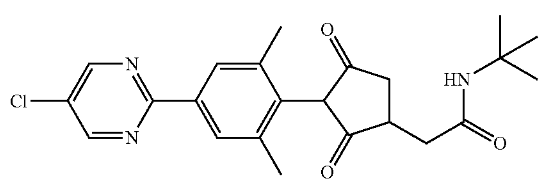 [SMILES: Cc1cc(-c2ncc(Cl)cn2)cc(C)c1C1C(=O)CC(CC(=O)NC(C)(C)C)C1=O] | (d4-MeOH) 8.81 (s, 2H), 8.09 (s, 2H), 3.23-3.11 (m, 1H), 2.97-2.86 (m, 1H), 2.75-2.65 (m, 1H), 2.54-2.33 (m, 2H), 2.21 (s, 6H), 1.35 (s, 9H) |
| A41 | 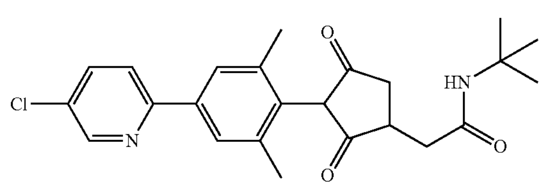 [SMILES: Cc1cc(-c2ccc(Cl)cn2)cc(C)c1C1C(=O)CC(CC(=O)NC(C)(C)C)C1=O] | (d4-MeOH) 8.58 (1H, s), 7.92-7.85 (2H, m), 7.68 (2H, s), 3.25-3.12 (1H, br), 2.98-2.88 (1H, m), 2.77-2.68 (1H, m), 2.52-2.39 (2H, br.m), 2.22 (6H, s), 1.38 (9H, s) |
| A42 | 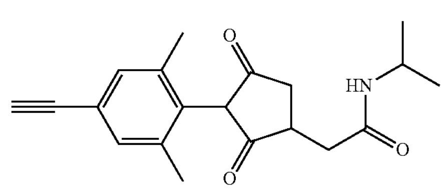 [SMILES: C#Cc1cc(C)c(C2C(=O)CC(CC(=O)NC(C)C)C2=O)c(C)c1] | (d4-MeOH) 7.18 (s, 2H), 4.06-3.94 (m, 1H), 3.40 (s, 1H), 3.22-3.12 (m, 1H), 2.98-2.85 (m, 1H), 2.78-2.69 (m, 1H), 2.50-2.38 (m, 2H), 2.11 (s, 6H), 1.17 (d, 6H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (400 MHz, CDCl$_3$) unless stated |
|---|---|---|
| A43 | 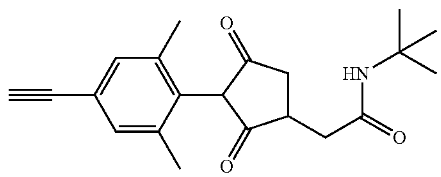 [SMILES: C#Cc1cc(C)c(C2C(=O)CC(CC(=O)NC(C)(C)C)C2=O)c(C)c1] | (d4-MeOH) 7.16 (s, 2H), 3.41 (s, 1H), 3.22-3.12 (m, 1H), 2.95-2.85 (m, 1H), 2.74-2.65 (m, 1H), 2.51-2.38 (m, 2H), 2.11 (s, 6H), 1.37 (s, 9H) |
| A44 | 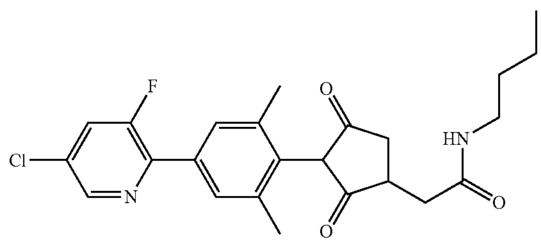 [SMILES: CCCCNC(=O)CC1CC(=O)C(c2c(C)cc(-c3ncc(Cl)cc3F)cc2C)C1=O] | (d4-MeOH) 8.50 (s, 1H), 7.85 (d, 1H), 7.61 (s, 2H), 3.28-3.16 (m, 1H), 3.23 (t, 2H), 3.00-2.90 (m, 1H), 2.83-2.74 (m, 1H), 2.55-2.43 (m, 2H), 2.21 (s, 6H), 1.59-1.48 (m, 2H), 1.47-1.34 (m, 2H), 0.98 (t, 3H) |
| A45 | 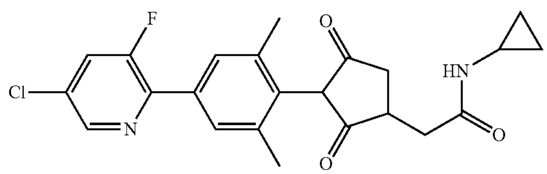 [SMILES: Cc1cc(-c2ncc(Cl)cc2F)cc(C)c1C1C(=O)CC(CC(=O)NC2CC2)C1=O] | (d4-MeOH) 8.50 (s, 1H), 7.85 (d, 1H), 7.62 (s, 2H), 3.23-3.13 (m, 1H), 3.00-2.90 (m, 1H), 2.79-2.66 (m, 2H), 2.54-2.35 (m, 2H), 2.22 (s, 6H), 0.79-0.71 (m, 2H), 0.56-0.49 (m, 2H) |
| A46 | 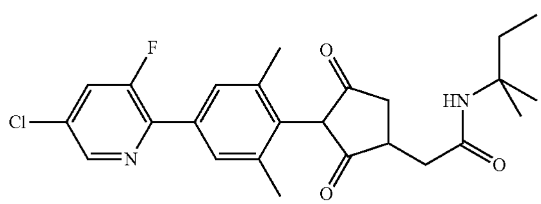 [SMILES: CCC(C)(C)NC(=O)CC1CC(=O)C(c2c(C)cc(-c3ncc(Cl)cc3F)cc2C)C1=O] | (d4-MeOH) 8.49 (s, 1H), 7.82 (d, 1H), 7.61 (s, 2H), 3.23-3.13 (m, 1H), 2.98-2.89 (m, 1H), 2.79-2.69 (m, 1H), 2.53-2.40 (m, 2H), 2.21 (s, 6H), 1.78 (q, 2H), 1.32 (s, 6H), 0.89 (t, 3H) |
| A47 | 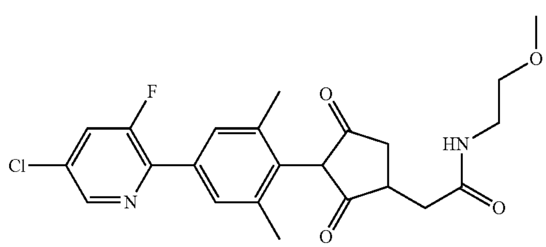 [SMILES: COCCNC(=O)CC1CC(=O)C(c2c(C)cc(-c3ncc(Cl)cc3F)cc2C)C1=O] | (d4-MeOH) 8.51 (s, 1H), 7.85 (d, 1H), 7.62 (s, 2H), 3.50 (t, 2H), 3.42 (t, 2H), 3.38 (s, 3H), 3.24-3.13 (m, 1H), 2.98-2.88 (m, 1H), 2.85-2.77 (m, 1H), 2.57-2.44 (m, 2H), 2.22 (s, 6H) |
| A48 | 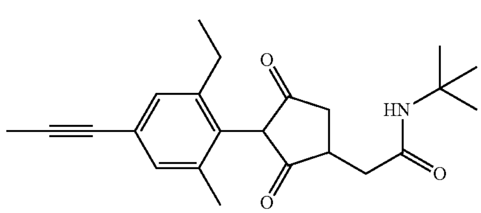 [SMILES: CC#Cc1cc(C)c(C2C(=O)CC(CC(=O)NC(C)(C)C)C2=O)c(CC)c1] | (d4-MeOH) 7.04 (s, 2H), 3.20-3.08 (m, 1H), 2.92-2.82 (m, 1H), 2.72-2.65 (m, 1H), 2.45-2.32 (m, 4H), 2.04 (s, 3H), 2.00 (s, 3H), 1.34 (s, 9H), 1.05 (t, 3H) |

TABLE T1-continued

It should be noted that certain compounds of the invention may exist as a mixture of isomers, including sometimes atropisomers, e.g. as noted above, under the conditions used to obtain the ¹H NMR data. Where this has occurred, the characterising data are reported for all isomers present at ambient temperature in the specified solvent. Unless otherwise stated, proton (¹H) NMR spectra disclosed herein were recorded at ambient temperature.

| Compound Number | Structure | ¹H NMR (400 MHz, CDCl₃) unless stated |
|---|---|---|
| A49 | 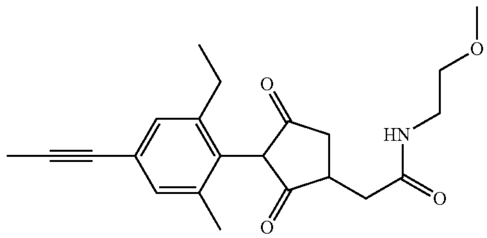 [SMILES: CC#Cc1cc(C)c(C2C(=O)CC(CC(=O)NCCOC)C2=O)c(CC)c1] | (d4-MeOH) 7.05 (s, 2H), 3.49-3.42 (m, 2H), 3.42-3.35 (m, 2H), 3.34 (s, 3H), 3.19-3.09 (m, 1H), 2.93-2.83 (m, 1H), 2.79-2.70 (m, 1H), 2.50-2.32 (m, 4H), 2.04 (s, 3H), 2.00 (s, 3H), 1.05 (t, 3H) |
| A50 | 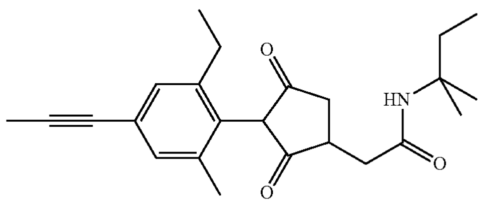 [SMILES: CC#Cc1cc(C)c(C2C(=O)CC(CC(=O)NC(C)(C)CC)C2=O)c(CC)c1] | (d4-MeOH) 7.05 (s, 2H), 3.20-3.06 (m, 1H), 2.93-2.81 (m, 1H), 2.74-2.66 (m, 1H), 2.49-2.33 (m, 4H), 2.04 (s, 3H), 2.00 (s, 3H), 1.80-1.70 (m, 2H), 1.29 (s, 6H), 1.05 (t, 3H), 0.87 (t, 3H) |
| A51 | 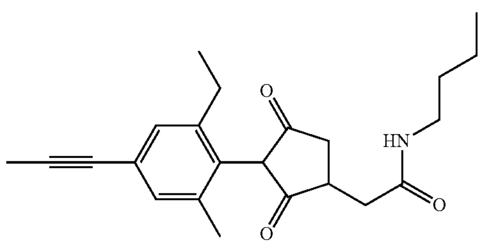 [SMILES: CC#Cc1cc(C)c(C2C(=O)CC(CC(=O)NCCCC)C2=O)c(CC)c1] | (d4-MeOH) 7.06 (s, 2H), 3.20 (t, 2H), 3.18-3.10 (m, 1H), 2.93-2.84 (m, 1H), 2.78-2.69 (m, 1H), 2.48-2.32 (m, 4H), 2.04 (s, 3H), 2.00 (s, 3H), 1.54-1.45 (m, 2H), 1.42-1.32 (m, 2H), 1.05 (t, 3H), 0.94 (t, 3H) |
| A52 | 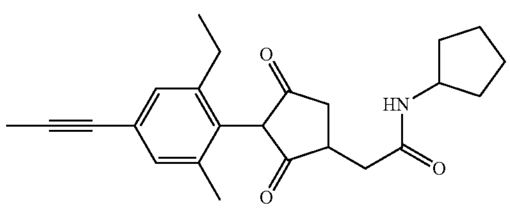 [SMILES: CC#Cc1cc(C)c(C2C(=O)CC(CC(=O)NC3CCCC3)C2=O)c(CC)c1] | (d4-MeOH) 7.06 (s, 2H), 4.17-4.07 (m, 1H), 3.20-3.08 (m, 1H), 2.92-2.81 (m, 1H), 2.74-2.67 (m, 1H), 2.49-2.33 (m, 4H), 2.03 (s, 3H), 2.00 (s, 3H), 2.00-1.87 (m, 2H), 1.78-1.65 (m, 2H), 1.65-1.53 (m, 2H), 1.53-1.41 (m, 2H), 1.05 (t, 3H) |
| A53 | 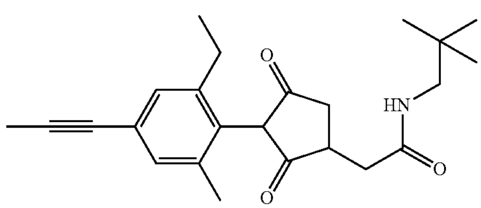 [SMILES: CC#Cc1cc(C)c(C2C(=O)CC(CC(=O)NCC(C)(C)C)C2=O)c(CC)c1] | (d4-MeOH) 7.05 (s, 2H), 3.20-3.10 (m, 1H), 3.03 (s, 2H), 2.94-2.84 (m, 1H), 2.83-2.73 (m, 1H), 2.53-2.43 (m, 2H), 2.43-2.33 (q, 2H), 2.04 (s, 3H), 2.00 (s, 3H), 1.05 (t, 3H), 0.92 (s, 9H) |
| A54 | 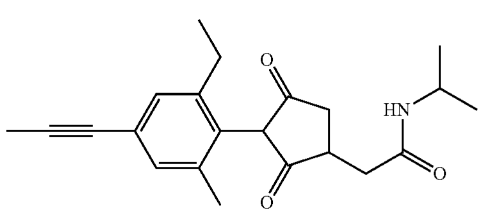 [SMILES: CC#Cc1cc(C)c(C2C(=O)CC(CC(=O)NC(C)C)C2=O)c(CC)c1] | (d4-MeOH) 7.05 (s, 2H), 4.03-3.93 (m, 1H), 3.20-3.08 (m, 1H), 2.93-2.81 (m, 1H), 2.74-2.66 (m, 1H), 2.50-2.32 (m, 4H), 2.04 (s, 3H), 2.00 (s, 3H), 1.19-1.10 (m, 6H), 1.04 (t, 3H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (400 MHz, CDCl$_3$) unless stated |
|---|---|---|
| A55 | 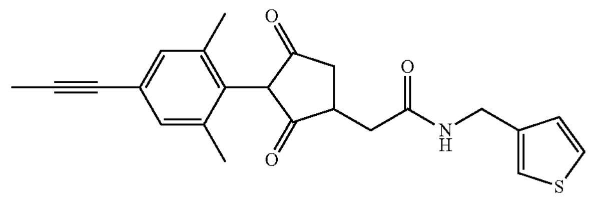 [SMILES: CC#Cc1cc(C)c(C2C(=O)CC(CC(=O)NCc3ccsc3)C2=O)c(C)c1] | 12.85 (1H, br), 7.36-7.34 (1H, m), 7.20 (1H, s), 7.10 (2H, 2 × s), 7.05 (1H, d), 6.55 (1H, br), 4.55-4.40 (1H, m), 3.35-3.25 (1H, m), 2.90 (1H, dd), 2.75-2.70 (1H, m), 2.20 (1H, dd), 2.15-2.10 (7H, m), 2.05 (3H, s) |
| A56 | 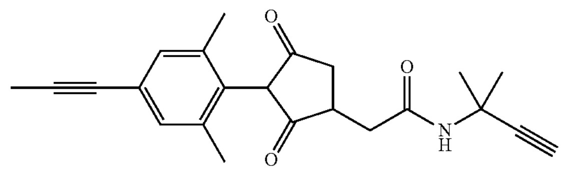 [SMILES: C#CC(C)(C)NC(=O)CC1CC(=O)C(c2c(C)cc(C#CC)cc2C)C1=O] | (d6-DMSO) Diagnostic peaks 7.03 (s, 2H), 2.95-2.85 (m, 1H), 2.80-2.70 (m, 1H), 2.70-2.55 (m, 1H), 2.40-2.30 (m, 1H), 2.30-2.15 (m, 1H), 2.05-1.97 (m, 12H) |
| A57 | 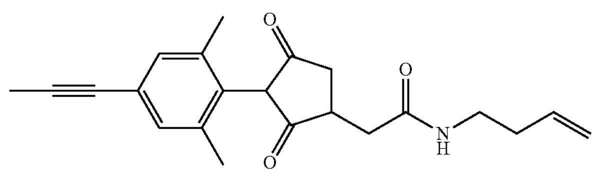 [SMILES: C=CCCNC(=O)CC1CC(=O)C(c2c(C)cc(C#CC)cc2C)C1=O] | 12.90 (1H, br), 7.10 (2H, 2 × s), 6.00-5.95 (1H, br), 5.80-5.70 (1H, m), 5.20 (1H, s), 5.15 (1H, d), 3.45-3.40 (2H, m), 3.30-3.25 (1H, m), 2.90 (1H, dd), 2.70 (1H, d), 2.35-2.30 (2H, m), 2.25 (1H, dd), 2.15-2.10 (7H, m), 2.05 (3H, s) |
| A58 | 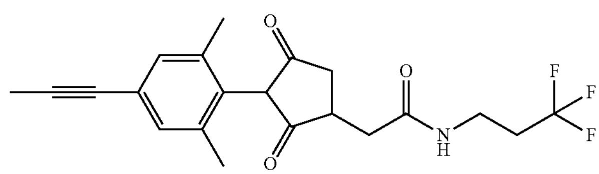 [SMILES: CC#Cc1cc(C)c(C2C(=O)CC(CC(=O)NCCC(F)(F)F)C2=O)c(C)c1] | 12.60 (1H, br), 7.10 (2H, 2 × s), 6.75 (1H, br), 3.55-3.45 (2H, m), 3.35 (1H, br), 2.90 (1H, dd), 2.75-2.65 (1H, m), 2.45-2.30 (2H, m), 2.20 (1H, dd), 2.15-2.10 (7H, m), 2.02 (3H, s) |
| A59 | 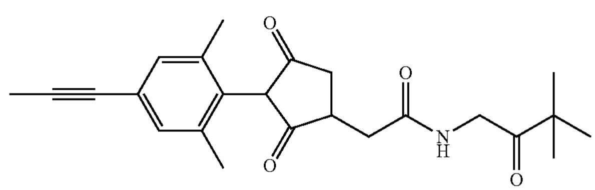 [SMILES: CC#Cc1cc(C)c(C2C(=O)CC(CC(=O)NCC(=O)C(C)(C)C)C2=O)c(C)c1] | 12.55 (1H, br), 7.10 (2H, 2 × s), 6.85 (1H, br), 4.30 (2H, br), 3.30 (1H, br), 2.95-2.80 (1H, m), 2.75 (1H, dd), 2.25 (1H, dd), 2.15-2.10 (7H, m), 2.05 (3H, s), 1.20 (9H, s) |
| A60 | 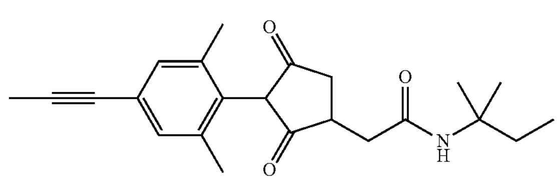 [SMILES: CC#Cc1cc(C)c(C2C(=O)CC(CC(=O)NC(C)(C)CC)C2=O)c(C)c1] | 13.10 (1H, br), 7.10 (2H, 2 × s), 5.65 (1H, br), 3.30-3.20 (1H, m), 2.90 (1H, dd), 2.70-2.65 (1H, m), 2.20 (1H, dd), 2.15-2.10 (7H, m), 2.05 (3H, s), 1.75 (2H, q), 1.35 (6H, s), 0.85 (3H, t) |
| A61 | 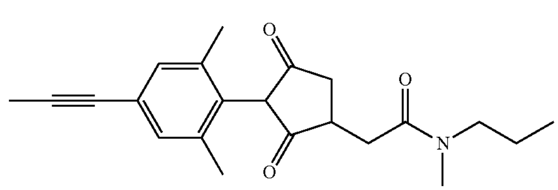 [SMILES: CC#Cc1cc(C)c(C2C(=O)CC(CC(=O)N(C)CCC)C2=O)c(C)c1] | Restricted rotation 12.60 (1H, br), 7.05 (2H, 2 × s), 3.50-3.25 (2H, m), 3.10 (1H, d), 3.05 (3H, s), 2.90 (1H, dd), 2.60-2.50 (1H, m), 2.35 (1H, d), 2.10-2.05 (7H, m), 2.00 (3H, s), 1.70-1.50 (2H, m), 0.90 (3H, t) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (400 MHz, CDCl$_3$) unless stated |
|---|---|---|
| A62 | 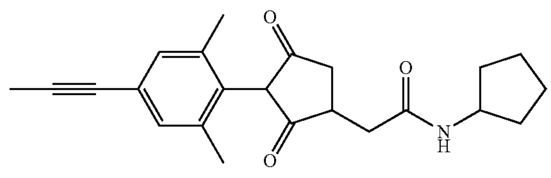 [SMILES: CC#Cc1cc(C)c(C2C(=O)CC(CC(=O)NC3CCCC3)C2=O)c(C)c1] | 13.15 (1H, br), 7.08 (2H, 2 × s), 6.20 (1H, br), 4.25-4.15 (1H, m), 3.25 (1H, br), 2.88 (1H, dd), 2.70-2.65 (1H, m), 2.18 (1H, dd), 2.15-2.05 (7H, m), 2.05 (3H, s), 1.80-1.30 (8H, m) |
| A63 | 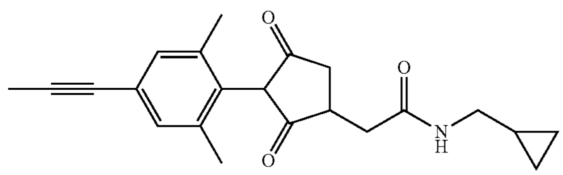 [SMILES: CC#Cc1cc(C)c(C2C(=O)CC(CC(=O)NCC3CC3)C2=O)c(C)c1] | 7.08 (s, 2H), 3.86 (br, 1H), 3.40-3.35 (m, 1H), 3.10 (d, 2H), 2.95-2.82 (m, 1H), 2.72-2.60 (m, 2H), 2.14-2.05 (m, 7H), 2.02 (s, 3H), 1.03-0.94 (m, 1H), 0.58-0.50 (m, 2H), 0.25-0.20 (m, 2H) |
| A64 | 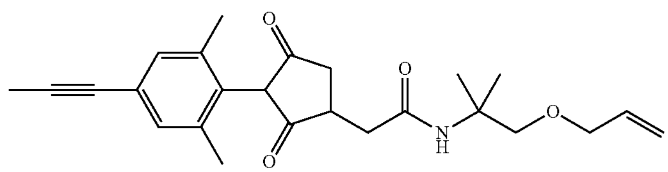 [SMILES: C=CCOCC(C)(C)NC(=O)CC1CC(=O)C(c2c(C)cc(C#CC)cc2C)C1=O] | 13.10 (1H, br), 7.10 (2H, 2 × s), 6.22 (1H, br), 5.95-5.80 (1H, m), 5.35-5.20 (2H, m), 4.02 (2H, d), 3.38 (2H, s), 3.25 (1H, br), 2.90 (1H, dd), 2.70 (1H, d), 2.20 (1H, dd), 2.15-2.10 (7H, m), 2.05 (3H, s), 1.40 (6H, 2 × s) |
| A65 | 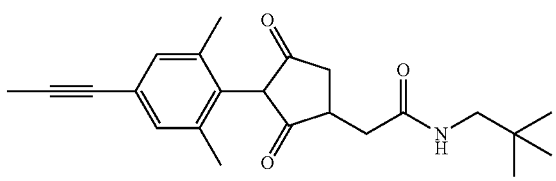 [SMILES: CC#Cc1cc(C)c(C2C(=O)CC(CC(=O)NCC(C)(C)C)C2=O)c(C)c1] | 13.15 (1H, br), 7.10 (2H, 2 × s), 6.40 (1H, br), 3.30-3.20 (1H, m), 3.10-3.00 (2H, m), 2.90 (1H, dd), 2.70-2.65 (1H, m), 2.20 (1H, dd), 2.15-2.10 (7H, m), 2.05 (3H, s), 0.90 (9H, s) |
| A66 | 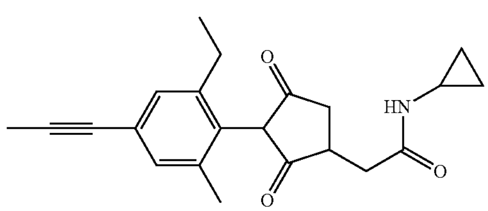 [SMILES: CC#Cc1cc(C)c(C2C(=O)CC(CC(=O)NC3CC3)C2=O)c(CC)c1] | (d4-MeOH) 7.08 (s, 2H), 3.20-3.10 (m, 1H), 2.95-2.85 (m, 1H), 2.76-2.68 (m, 2H), 2.50-2.32 (m, 4H), 2.07 (s, 3H), 2.02 (s, 3H), 1.06 (t, 3H), 0.79-0.72 (m, 2H), 0.55-0.48 (m, 2H) |
| A67 | 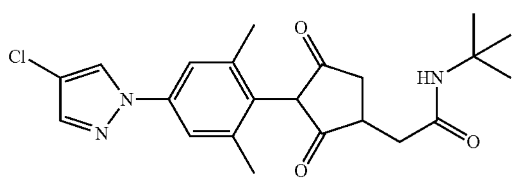 [SMILES: Cc1cc(-n2cc(Cl)cn2)cc(C)c1C1C(=O)CC(CC(=O)NC(C)(C)C)C1=O] | (d4-MeOH) 8.33 (s, 1H), 7.67 (s, 1H), 7.44 (s, 2H), 3.23-3.12 (m, 1H), 2.98-2.85 (m, 1H), 2.76-2.65 (m, 1H), 2.52-2.38 (m, 2H), 2.20 (s, 6H), 1.38 (s, 9H) |
| A68 | 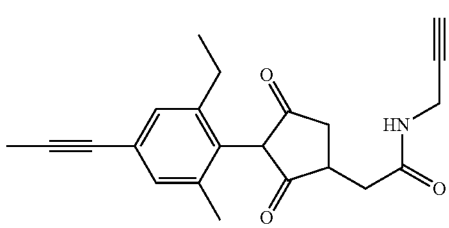 [SMILES: C#CCNC(=O)CC1CC(=O)C(c2c(C)cc(C#CC)cc2CC)C1=O] | (d4-MeOH) 7.08 (s, 2H), 4.00 (s, 2H), 3.20-3.10 (m, 1H), 2.97-2.86 (m, 1H), 2.83-2.73 (m, 1H), 2.61 (s, 1H), 2.51-2.35 (m, 4H), 2.07 (s, 3H), 2.01 (s, 3H), 1.08 (t, 3H) |

TABLE T1-continued

It should be noted that certain compounds of the invention may exist as a mixture of isomers, including sometimes atropisomers, e.g. as noted above, under the conditions used to obtain the ¹H NMR data. Where this has occurred, the characterising data are reported for all isomers present at ambient temperature in the specified solvent. Unless otherwise stated, proton (¹H) NMR spectra disclosed herein were recorded at ambient temperature.

| Compound Number | Structure | ¹H NMR (400 MHz, CDCl₃) unless stated |
|---|---|---|
| A69 | 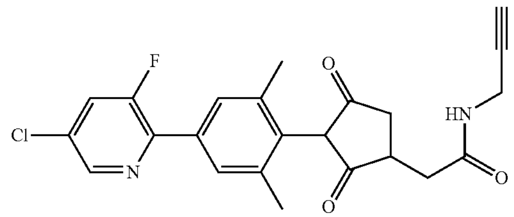 [SMILES: C#CCNC(=O)CC1CC(=O)C(c2c(C)cc(-c3ncc(Cl)cc3F)cc2C)C1=O] | (d4-MeOH) 8.47 (s, 1H), 7.82 (d, 1H), 7.59 (s, 2H), 3.99 (s, 2H), 3.21-3.11 (m, 1H), 2.99-2.88 (m, 1H), 2.82-2.73 (m, 1H), 2.61 (s, 1H), 2.54-2.41 (m, 2H), 2.18 (s, 6H) |
| A70 | 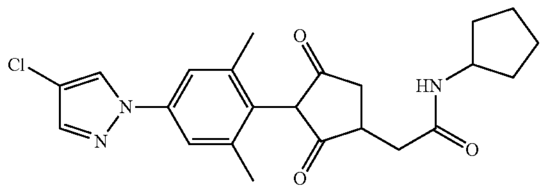 [SMILES: Cc1cc(-n2cc(Cl)cn2)cc(C)c1C1C(=O)CC(CC(=O)NC2CCCC2)C1=O] | (d4-MeOH) 8.21 (s, 1H), 7.53 (s, 1H), 7.32 (s, 2H), 4.08-3.99 (m, 1H), 3.11-3.02 (m, 1H), 2.84-2.74 (m, 1H), 2.68-2.59 (m, 1H), 2.41-2.28 (m, 2H), 2.08 (s, 6H), 1.90-1.75 (m, 2H), 1.71-1.57 (m, 2H), 1.57-1.43 (m, 2h), 1.43-1.30 (m, 2H) |
| A71 | 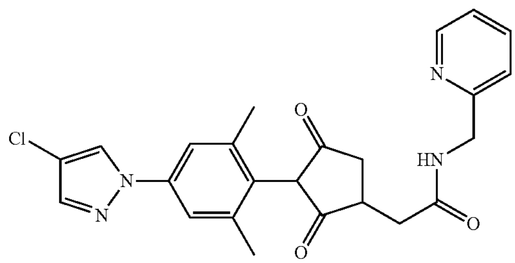 [SMILES: Cc1cc(-n2cc(Cl)cn2)cc(C)c1C1C(=O)CC(CC(=O)NCc2ccccn2)C1=O] | (d4-MeOH) 8.50 (d, 1H), 8.32 (s, 1H), 7.84 (t, 1H), 7.66 (s, 1H), 7.49-7.41 (m, 1H), 7.43 (s, 2H), 7.38-7.31 (m, 1H), 4.55 (s, 2H), 3.28-3.18 (m, 1H), 3.02-2.82 (m, 2H), 2.65-2.51 (m, 2H), 2.19 (d, 6H) |
| A72 | 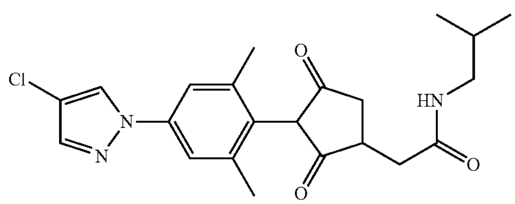 [SMILES: Cc1cc(-n2cc(Cl)cn2)cc(C)c1C1C(=O)CC(CC(=O)NCC(C)C)C1=O] | (d4-MeOH) 8.34 (s, 1H), 7.68 (s, 1H), 7.44 (s, 2H), 3.25-3.12 (m, 1H), 3.05 (d, 2H), 2.99-2.88 (m, 1H), 2.84-2.74 (m, 1H), 2.54-2.43 (m, 2H), 2.20 (s, 6H), 1.88-1.74 (m, 1H), 0.94 (d, 6H) |
| A73 | 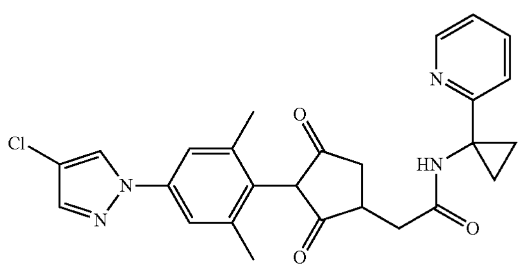 [SMILES: Cc1cc(-n2cc(Cl)cn2)cc(C)c1C1C(=O)CC(CC(=O)NC2(c3ccccn3)CC2)C1=O] | (d4-MeOH) 8.41 (d, 1H), 8.32 (s, 1H), 7.73 (t, 1H), 7.66 (s, 1H), 7.49 (d, 1H), 7.43 (s, 2H), 7.22-7.13 (m, 1H), 3.27-3.18 (m, 1H), 3.03-2.53 (m, 1H), 2.90-2.81 (m, 1H), 2.63-2.52 (m, 2H), 2.19 (d, 6H), 1.64-1.56 (m, 2H), 1.34-1.26 (m, 2H) |
| A74 | 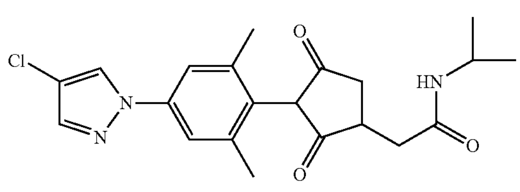 [SMILES: Cc1cc(-n2cc(Cl)cn2)cc(C)c1C1C(=O)CC(CC(=O)NC(C)C)C1=O] | (d4-MeOH) 8.33 (1H, s), 7.68 (1H, s), 7.45 (2H, s), 4.08-3.94 (1H, m), 3.25-3.12 (1H, br), 2.99-2.88 (1H, m), 2.80-2.70 (1H, m), 2.54-2.49 (2H, br.m), 2.20 (6H, s), 1.18 (6H, d) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (400 MHz, CDCl$_3$) unless stated |
|---|---|---|
| A75 | 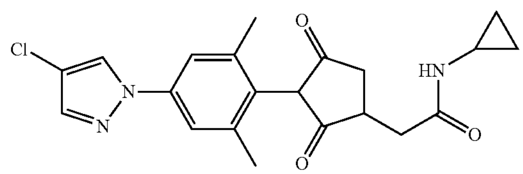 [SMILES: Cc1cc(-n2cc(Cl)cn2)cc(C)c1C1C(=O)CC(CC(=O)NC2CC2)C1=O] | (d4-MeOH) 8.33 (1H, s), 7.68 (1H, s), 7.45 (2H, s), 3.23-3.12 (1H, br), 2.99-2.89 (1H, m), 2.79-2.69 (1H, m), 2.54-2.49 (2H, br.m), 2.20 (6H, s), 0.79-0.72 (m, 2H), 0.57-0.48 (m, 2H) |
| A76 | 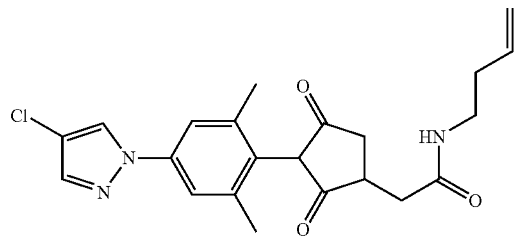 [SMILES: C=CCCNC(=O)CC1CC(=O)C(c2c(C)cc(-n3cc(Cl)cn3)cc2C)C1=O] | (d4-MeOH) 8.33 (1H, s), 7.66 (1H, s), 7.44 (2H, s), 5.89-5.77 (1H, m), 5.15-5.03 (2H, m), 3.35-3.26 (2H, m), 3.22-3.12 (1H, br), 2.99-2.88 (1H, m), 2.81-2.71 (1H, m), 2.53-2.41 (2H, br.m), 2.35-2.24 (2H, m), 2.19 (6H, s) |
| A77 | 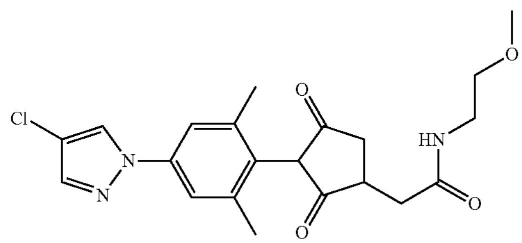 [SMILES: COCCNC(=O)CC1CC(=O)C(c2c(C)cc(-n3cc(Cl)cn3)cc2C)C1=O] | (d4-MeOH) 8.33 (1H, s), 7.67 (1H, s), 7.44 (2H, s), 3.53-3.46 (2H, m), 3.46-3.38 (2H, m), 3.37 (3H, s), 3.25-3.12 (1H, br), 2.98-2.88 (1H, m), 2.82-2.73 (1H, m), 2.56-2.44 (2H, br.m), 2.20 (6H, s) |
| A78 | 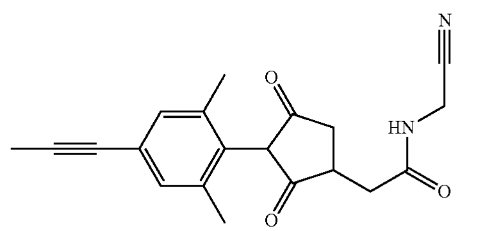 [SMILES: CC#Cc1cc(C)c(C2C(=O)CC(CC(=O)NCC#N)C2=O)c(C)c1] | (d4-MeOH) 7.05 (2H, s), 4.18 (2H, s), 3.18-3.08 (1H, br), 2.99-2.90 (1H, m), 2.86-2.78 (1H, m), 2.54-2.42 (2H, m), 2.08 (6H, s), 2.01 (3H, s) |
| A79 | 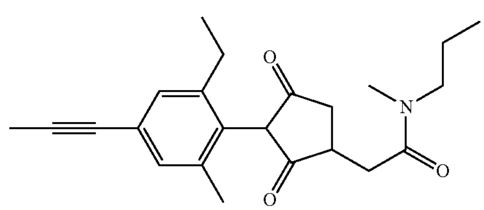 [SMILES: CC#Cc1cc(C)c(C2C(=O)CC(CC(=O)N(C)CCC)C2=O)c(CC)c1] | (d4-MeOH) 7.05 (s, 2H), 3.41-3.32 (m, 2H), 3.23-3.12 (m, 1H), 3.06, 2.96 (s, 3H), 2.97-2.72 (m, 2H), 2.50-2.34 (m, 4H), 2.06 (s, 3H), 2.00 (s, 3H), 1.70-1.52 (m, 2H), 1.06 (t, 3H), 0.98-0.86 (m, 3H) |
| A80 | 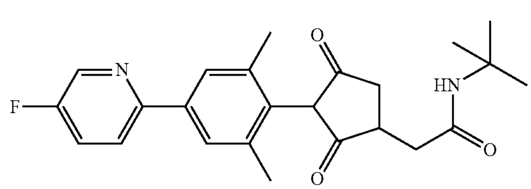 [SMILES: Cc1cc(-c2ccc(F)cn2)cc(C)c1C1C(=O)CC(CC(=O)NC(C)(C)C)C1=O] | (d4-MeOH) 8.36 (1H, s), 7.78-7.72 (1H, m), 7.56-7.49 (1H, m), 7.51 (2H, s), 3.12-3.02 (1H, m), 2.84-2.75 (1H, m), 2.63-2.54 (1H, m), 2.38-2.36 (2H, m), 2.09 (6H, s), 1.24 (9H, s) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (400 MHz, CDCl$_3$) unless stated |
|---|---|---|
| A81 | 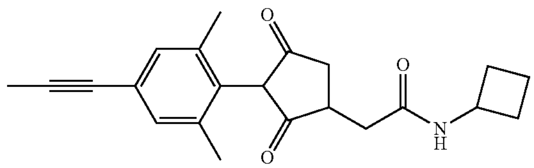 [SMILES: CC#Cc1cc(C)c(C2C(=O)CC(CC(=O)NC3CCC3)C2=O)c(C)c1] | 12.90 (1H, s), 7.10 (2H, 2 × s), 6.05 (1H, br), 4.45-4.35 (1H, m), 3.30-3.25 (1H, m), 2.90 (1H, dd), 2.75-2.70 (1H, m), 2.45-2.35 (2H, m), 2.20 (1H, dd), 2.15-2.10 (7H, m), 2.05 (3H, s), 2.00-1.85 (2H, m), 1.85-1.75 (2H, m) |
| A82 | 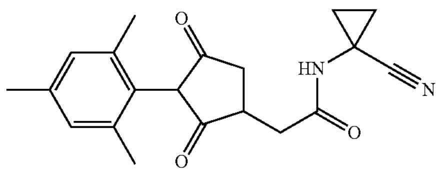 [SMILES: Cc1cc(C)c(C2C(=O)CC(CC(=O)NC3(C#N)CC3)C2=O)c(C)c1] | (d4-MeOH) 6.89 (2H, s), 3.16-3.07 (1H, m), 2.99-2.89 (1H, m), 2.78-2.68 (1H, m), 2.52-2.43 (1H, m), 2.41-2.32 (1H, m), 2.27 (3H, s), 2.07 (6H, s), 1.52-1.45 (2H, m), 1.28-1.18 (2H, m) |
| A83 | 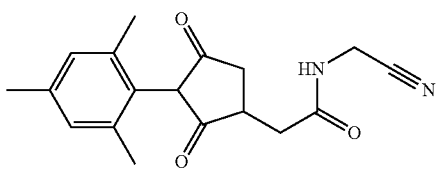 [SMILES: Cc1cc(C)c(C2C(=O)CC(CC(=O)NCC#N)C2=O)c(C)c1] | (d4-MeOH) 6.88 (2H, s), 4.18 (2H, s), 3.18-3.08 (1H, m), 2.99-2.49 (1H, m), 2.87-2.78 (1H, m), 2.53-2.40 (2H, m), 2.26 (3H, s), 2.07 (6H, s) |
| A84 | 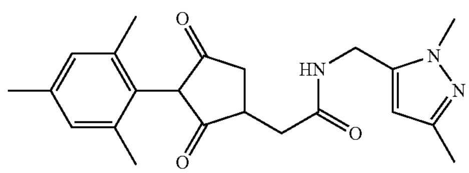 [SMILES: Cc1cc(C)c(C2C(=O)CC(CC(=O)NCc3cc(C)nn3C)C2=O)c(C)c1] | (d4-MeoH) 6.87 (2H, s), 6.02 (1H, s), 4.39 (2H, s), 3.75 (2H, s), 3.19-3.10 (1H, m), 2.95-2.85 (1H, m), 2.83-2.73 (1H, m), 2.50-2.40 (2H, m), 2.27 (3H, s), 2.18 (3H, s), 2.06 (6H, d) |
| A85 | 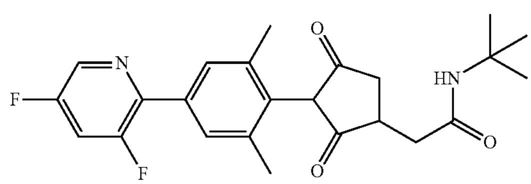 [SMILES: Cc1cc(-c2ncc(F)cc2F)cc(C)c1C1C(=O)CC(CC(=O)NC(C)(C)C)C1=O] | (d4-MeOH) 8.45 (1H, s), 7.67 (1H, t), 7.56 (2H, s), 3.24 (1H, br), 2.98-2.88 (1H, m), 2.78-2.69 (1H, m), 2.53-2.48 (2H, br. m), 2.21 (6H, s), 1.38 (9H, s) |
| A86 | 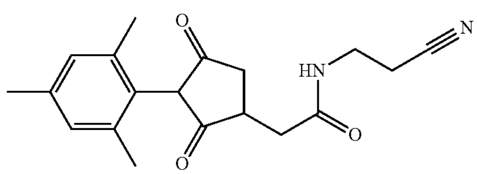 [SMILES: Cc1cc(C)c(C2C(=O)CC(CC(=O)NCCC#N)C2=O)c(C)c1] | (d4-MeOH) 6.89 (2H, s), 3.94 (t, 2H), 3.19-3.11 (1H, m), 2.97-2.87 (1H, m), 2.83-2.75 (1H, m), 2.67 (2H, t), 2.51-2.39 (2H, m), 2.27 (3H, s), 2.08 (6H, s) |
| A87 | 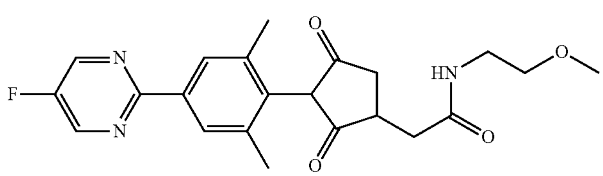 [SMILES: COCCNC(=O)CC1CC(=O)C(c2c(C)cc(-c3ncc(F)cn3)cc2C)C1=O] | (d4-MeOH) 8.62 (2H, s), 7.95 (2H, s), 3.39-3.32 (2H, m), 3.32-3.26 (2H, m), 3.25 (3H, s), 3.12-3.03 (m, 1H), 2.87-2.78 (m, 1H), 2.72-2.62 (1H, m), 2.44-2.32 (2H, m), 2.11 (6H, s) |
| A88 | 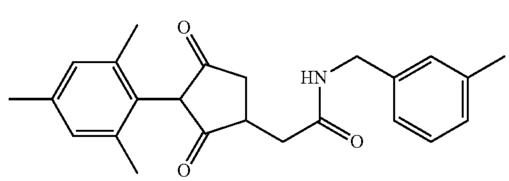 | (d4-MeOH) 7.20 (1H, t), 7.15-7.05 (3H, m), 6.85 (2H, s), 4.35 (2H, s), 3.15-3.10 (1H, m), 2.90 (1H, dd), 2.80 (1H, dd), 2.50-2.40 (2H, m), 2.35 (3H, s), 2.25 (3H, s), 2.10 (6H, s) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (400 MHz, CDCl$_3$) unless stated |
|---|---|---|
| A89 | 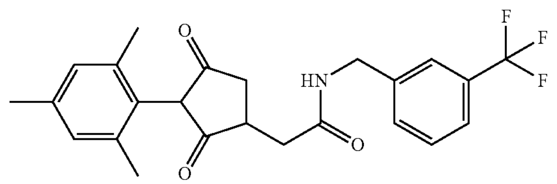 [SMILES: Cc1cc(C)c(C2C(=O)CC(CC(=O)NCc3cccc(C(F)(F)F)c3)C2=O)c(C)c1] | (d4-MeOH) 7.60-7.45 (4H, m), 6.85 (2H, s), 4.45 (2H, s), 3.20-3.10 (1H, m), 2.90-2.80 (2H, m), 2.50-2.40 (2H, m), 2.25 (3H, s), 2.05 (6H, 2 × s) |
| A90 | 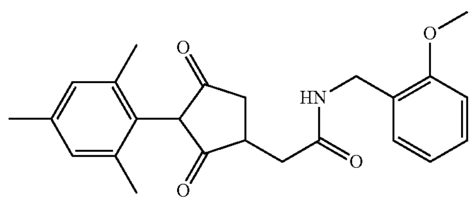 | (d4-MeOH) 7.25-7.15 (2H, m), 6.95-6.85 (2H, m), 6.85 (2H, s), 4.35 (2H, s), 3.80 (3H, s), 3.15-3.05 (1H, m), 2.85 (1H, dd), 2.75 (1H, dd), 2.50-2.35 (2H, m), 2.25 (3H, s), 2.05 (6H, s) |
| A91 | 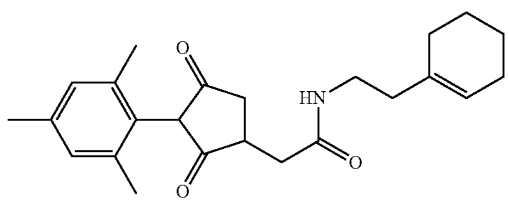 [SMILES: Cc1cc(C)c(C2C(=O)CC(CC(=O)NCCC3=CCCCC3)C2=O)c(C)c1] | (d4-MeOH) 6.85 (2H, s), 5.50-5.45 (1H, m), 3.30-3.25 (2H, m), 3.15-3.10 (1H, m), 2.85 (1H, dd), 2.75 (1H, dd), 2.45-2.35 (2H, m), 2.25 (3H, s), 2.15 (2H, t), 2.05 (6H, s), 2.00-1.90 (4H, m), 1.70-1.55 (4H, m) |
| A92 | 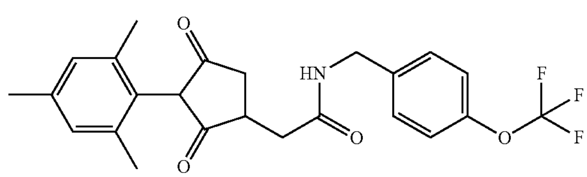 [SMILES: Cc1cc(C)c(C2C(=O)CC(CC(=O)NCc3ccc(OC(F)(F)F)cc3)C2=O)c(C)c1] | (d4-MeoH) 7.50 (2H, d), 7.25 (2H, d), 6.85 (2H, s), 4.40 (2H, s), 3.20-3.15 (1H, m), 2.90 (1H, dd), 2.80 (1H, dd), 2.55-2.45 (2H, m), 2.30 (3H, s), 2.05 (6H, 2 × s) |
| A93 | 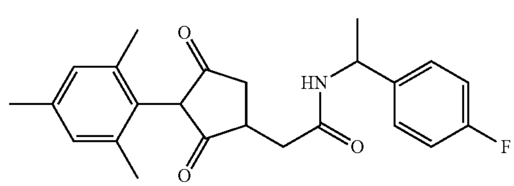 [SMILES: Cc1cc(C)c(C2C(=O)CC(CC(=O)NC(C)c3ccc(F)cc3)C2=O)c(C)c1] | (d4-MeOH) 7.35 (2H, t), 7.05 (2H, t), 6.85 (2H, s), 5.05-4.95 (1H, m), 3.15-3.05 (1H, m), 2.85 (1H, dd), 2.75 (1H, dd), 2.50-2.40 (2H, m), 2.25 (3H, s), 2.05 (6H, s), 1.40 (3H, s) |
| A94 | 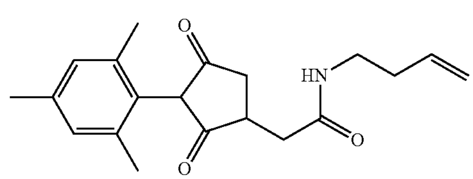 [SMILES: C=CCCNC(=O)CC1CC(=O)C(c2c(C)cc(C)cc2C)C1=O] | (d4-MeoH) 6.85 (2H, s), 5.85-5.70 (1H, m), 5.12-5.00 (2H, m), 3.25 (2H, t), 3.15-3.10 (1H, m), 2.85 (1H, dd), 2.70 (1H, dd), 2.45-2.35 (2H, m), 2.25-2.20 (5H, m), 2.05 (6H, s) |
| A95 | 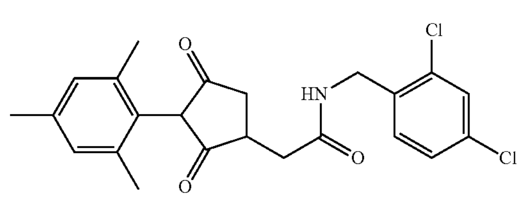 [SMILES: Cc1cc(C)c(C2C(=O)CC(CC(=O)NCc3ccc(Cl)cc3Cl)C2=O)c(C)c1] | (d4-MeOH) 7.45 (1H, s), 7.40 (1H, d), 7.30 (1H, d), 6.85 (1H, s), 4.45 (2H, s), 3.20-3.10 (1H, m), 2.90 (1H, dd), 2.85 (1H, dd), 2.55-2.45 (2H, m), 2.25 (3H, s), 2.07 (3H, s), 2.05 (3H, s) |

TABLE T1-continued

It should be noted that certain compounds of the invention may exist as a mixture of isomers, including sometimes atropisomers, e.g. as noted above, under the conditions used to obtain the ¹H NMR data. Where this has occurred, the characterising data are reported for all isomers present at ambient temperature in the specified solvent. Unless otherwise stated, proton (¹H) NMR spectra disclosed herein were recorded at ambient temperature.

| Compound Number | Structure | ¹H NMR (400 MHz, CDCl₃) unless stated |
|---|---|---|
| A96 | 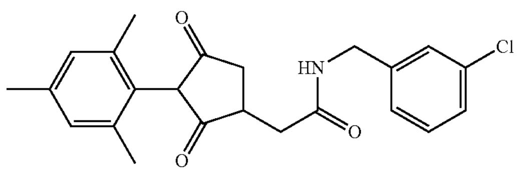 [SMILES: Cc1cc(C)c(C2C(=O)CC(CC(=O)NCc3cccc(Cl)c3)C2=O)c(C)c1] | (d4-MeoH), 7.30-7.15 (4H, m), 6.85 (2H, s), 4.30 (2H, s), 3.15-3.10 (1H, m), 2.85 (1H, dd), 2.75 (1H, dd), 2.45-2.40 (2H, m), 2.25 (3H, s), 2.05 (6H, s) |
| A97 | 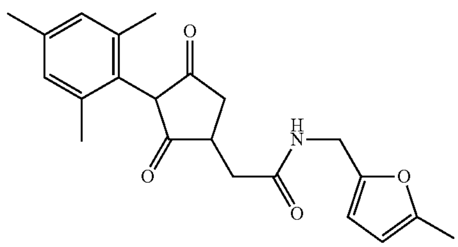 | (d4-MeOH) 6.85 (2H, s), 6.10 (1H, d), 5.90 (1H, d), 4.30 (2H, s), 3.15-3.10 (1H, m), 2.85 (1H, dd), 2.75 (1H, dd), 2.45-2.40 (2H, m), 2.22 (3H, s), 2.21 (3H, s), 2.05 (6H, s) |
| A98 | 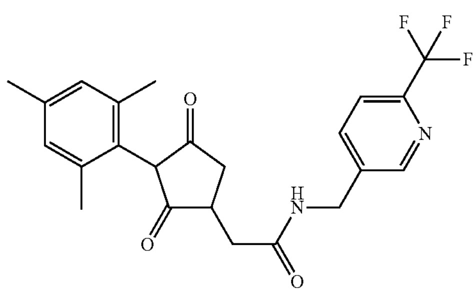 [SMILES: Cc1cc(C)c(C2C(=O)CC(CC(=O)NCc3ccc(C(F)(F)F)nc3)C2=O)c(C)c1] | (d4-MeOH) 8.65 (1H, s), 7.95 (1H, d), 7.75 (1H, d), 6.85 (2H, s), 4.47 (2H, s), 3.20-3.15 (1H, m), 2.90 (1H, dd), 2.80 (1H, dd), 2.55-2.45 (2H, m), 2.25 9(3H, s), 2.04 (3H, s), 2.02 (3H, s) |
| A99 | 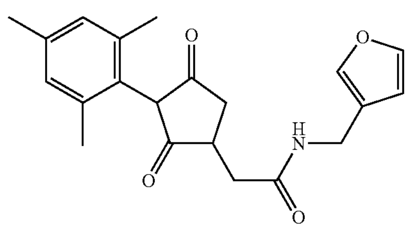 [SMILES: Cc1cc(C)c(C2C(=O)CC(CC(=O)NCc3ccoc3)C2=O)c(C)c1] | (d4-MeOH) 7.45 (2H, d), 6.85 (2H, s), 6.40 (1H, s), 4.20 (2H, s), 3.20-3.10 (1H, m), 2.85 (1H, dd), 2.75 (1H, dd), 2.45-2.35 (2H, m), 2.20 (3H, s), 2.05 (6H, s) |
| A100 | 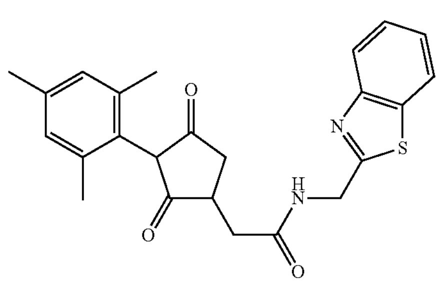 [SMILES: Cc1cc(C)c(C2C(=O)CC(CC(=O)NCc3nc4ccccc4s3)C2=O)c(C)c1] | (d4-MeOH) 7.90 (2H, t), 7.45 (1H, t), 7.35 (1H, t), 6.82 (2H, s), 4.75 (2H, s), 3.20-3.10 (1H, m), 2.95-2.85 (2H, m), 2.60-2.45 (2H, m), 2.22 (3H, s), 2.05 (6H, s) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (400 MHz, CDCl$_3$) unless stated |
|---|---|---|
| A101 | 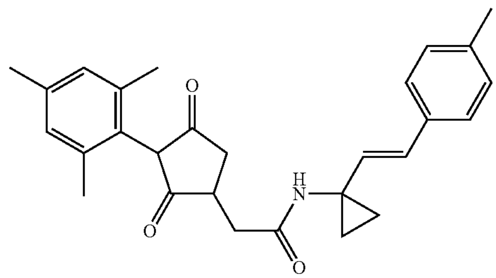 | (d4-MeOH) 7.22 (2H, d), 7.05 (2H, d), 6.85 (2H, 2 × s), 6.35 (1H, d), 5.82 (1H, d), 3.25-3.15 (1H, m), 2.95 (1H, dd), 2.80 (1H, dd), 2.55-2.40 (2H, m), 2.30 (3H, s), 2.25 (3H, s), 2.05 (6H, s), 1.15-1.05 (4H, m) |
| A102 | 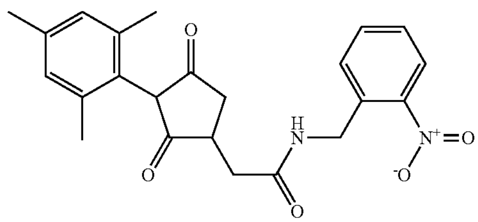 | (d4-MeoH) 8.02 (1H, d), 7.65 (1H, t), 7.60 (1H, d), 7.50 (1H, t), 6.85 (2H, s), 4.65 (2H, s), 3.20-3.10 (1H, m), 2.90 (1H, dd), 2.55-2.40 (2H, m), 2.25 (3H, s), 2.03 (3H, s), 2.02 (3H, s) |
| A103 | 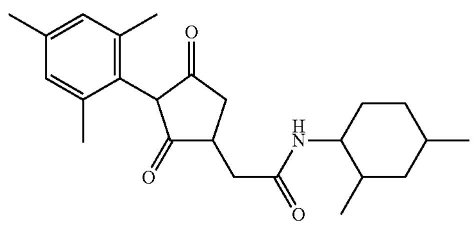 | (d4-MeOH) (diagnostic peaks) 6.85 (s, 2H), 3.15 (br, 1H), 2.92-2.83 (m, 1H), 2.80-2.70 (m, 1H), 2.48-2.35 (m, 2H), 2.25 (s, 3H), 2.05 (s, 6H), 1.95-0.85 (m, 14H) |
| A104 | 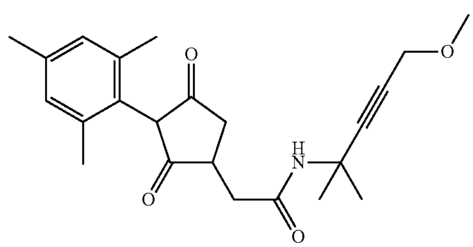 | (d4-MeOH) 6.85 (2H, s), 4.10 (2H, s), 3.35 (3H, s), 3.15-3.10 (1H, m), 2.90 (1H, dd), 2.75 (1H, dd), 2.45-2.35 (2H, m), 2.25 (3H, s), 2.05 (6H, s), 1.60 (6H, s) |
| A105 | 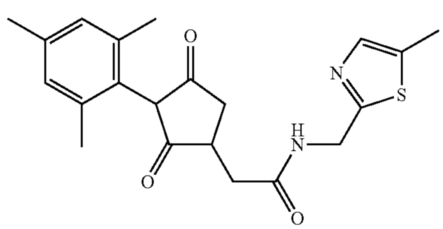 | (d4-MeOH) 7.35 (1H, s), 6.85 (2H, s), 4.60 (2H, s), 3.20-3.10 (1H, m), 2.95 (1H, dd), 2.85 (1H, dd), 2.50-2.45 (2H, m), 2.45 (3H, s), 2.15 (3H, s), 2.05 (6H, s) |
| A106 | 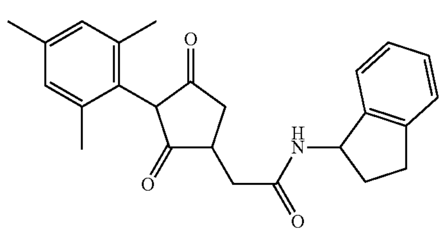 [SMILES: Cc1cc(C)c(C2C(=O)CC(CC(=O)NC3CCc4ccccc43)C2=O)c(C)c1] | (d4-MeOH) 7.30-7.15 (4H, m), 6.85 (2H, m), 5.37 (1H, t), 3.20-3.10 (1H, m), 3.00-2.70 (4H, m), 2.50-2.40 (3H, m), 2.25 (3H, s), 2.05 (6H, s), 1.90-1.80 (1H, m) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (400 MHz, CDCl$_3$) unless stated |
|---|---|---|
| A107 | 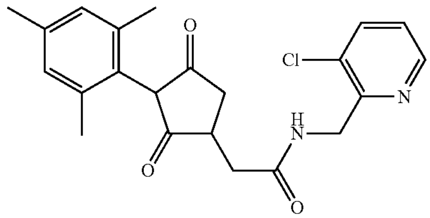 [SMILES: Cc1cc(C)c(C2C(=O)CC(CC(=O)NCc3ncccc3Cl)C2=O)c(C)c1] | (d4-MeoH) 8.45 (1H, d), 7.75 (1H, d), 7.35 (1H, dd), 6.85 (2H, s), 4.62 (2H, s), 3.20-3.10 (1H, m), 2.95-2.80 (2H, m), 2.60-2.45 (2H, m), 2.25 (3H, s), 2.03 (3H, s), 2.02 (3H, s) |
| A108 | 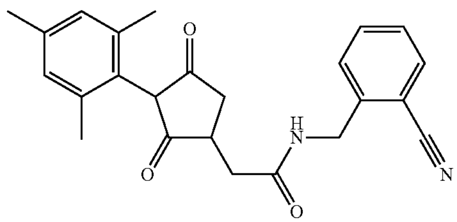 [SMILES: Cc1cc(C)c(C2C(=O)CC(CC(=O)NCc3ccccc3C#N)C2=O)c(C)c1] | (d4-MeOH) 7.72 (d, 1H), 7.65 (dd, 1H), 7.51 (d, 1H), 7.45 (dd, 1H), 6.83 (s, 2H), 4.60 (s, 2H), 3.16 (br, 1H), 2.98-2.70 (m, 2H), 2.52-2.45 (m, 2H), 2.25 (s, 3H), 2.04 (s, 3H), 2.02 (s, 3H) |
| A109 | 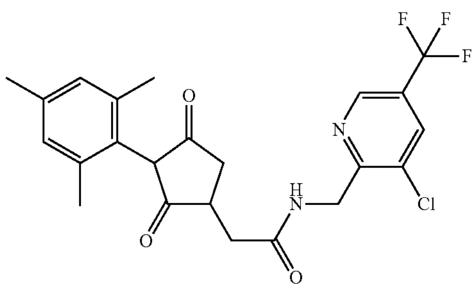 [SMILES: Cc1cc(C)c(C2C(=O)CC(CC(=O)NCc3ncc(C(F)(F)F)cc3Cl)C2=O)c(C)c1] | (d4-MeOH) 8.78 (1H, s), 8.20 (1H, s), 6.85 (2H, s), 4.65 (2H, dd), 3.20-3.10 (1H, m), 2.95-2.85 (2H, m), 2.65-2.50 (2H, m), 2.25 (3H, s), 2.04 (3H, s), 2.02 (3H, s) |
| A110 | 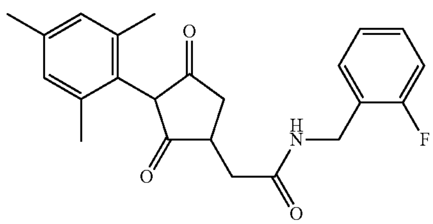 [SMILES: Cc1cc(C)c(C2C(=O)CC(CC(=O)NCc3ccccc3F)C2=O)c(C)c1] | (d4-MeOH) 7.35 (1H, t), 7.27 (1H, dd), 7.15-7.05 (2H, m), 6.85 (2H, s), 4.40 (2H, s), 3.15-3.10 (1H, m), 2.85 (1H, dd), 2.80 (1H, dd), 2.50-2.40 (2H, m), 2.25 (3H, s), 2.05 (6H, s) |
| A111 | 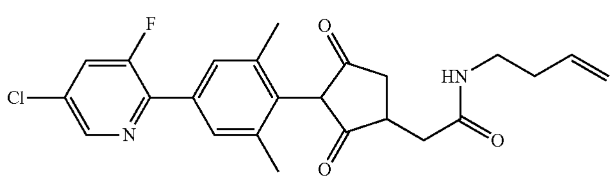 [SMILES: C=CCCNC(=O)CC1CC(=O)C(c2c(C)cc(-c3ncc(Cl)cc3F)cc2C)C1=O] | 13.25 (1H, br), 8.45 (1H, s), 7.62 (2H, s), 7.50 (1H, d), 6.65 (1H, br), 5.80-5.70 (1H, m), 5.15-5.10 (2H, m), 3.40-3.20 (3H, m), 2.90 (1H, dd), 2.75-2.65 (2H, m), 2.30-2.20 (9H, m) |
| A112 | 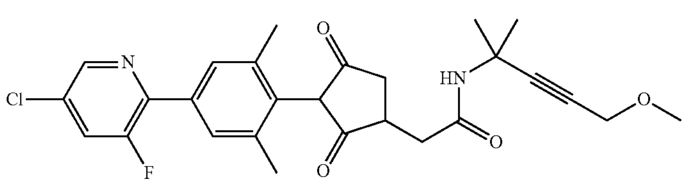 [SMILES: COCC#CC(C)(C)NC(=O)CC1CC(=O)C(c2c(C)cc(-c3ncc(Cl)cc3F)cc2C)C1=O] | 12.90 (1H, br), 8.45 (1H, s), 7.65 (2H, s), 7.50 (1H, d), 6.95 (1H, br), 4.10 (2H, s), 3.35 (3H, s), 3.35-3.25 (1H, m), 2.90 (1H, dd), 2.75-2.60 (2H, m), 2.30-2.20 (7H, m), 1.65 (6H, s) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (400 MHz, CDCl$_3$) unless stated |
|---|---|---|
| A113 | 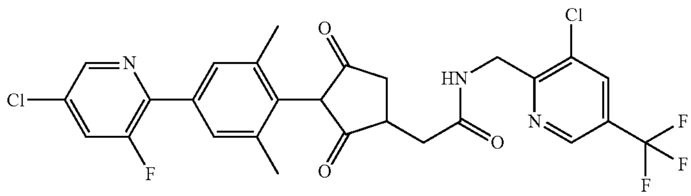 [SMILES: Cc1cc(-c2ncc(Cl)cc2F)cc(C)c1C1C(=O)CC(CC(=O)NCc2ncc(C(F)(F)F)cc2Cl)C1=O] | 12.70 (1H, br), 8.72 (1H, s), 8.45 (1H, s), 8.00 (1H, s), 7.70-7.60 (3H, m), 7.50 (1H, d), 4.80-4.75 (2H, m), 3.45-3.30 (1H, m), 3.05-2.50 (3H, m), 2.35 (1H, d), 2.23 (3H, s), 2.22 (3H, s) |
| A114 | 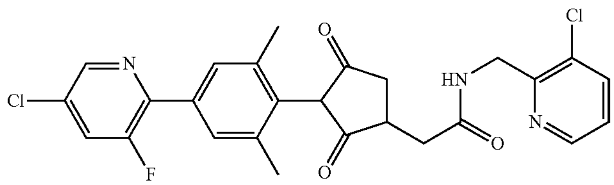 [SMILES: Cc1cc(-c2ncc(Cl)cc2F)cc(C)c1C1C(=O)CC(CC(=O)NCc2ncccc2Cl)C1=O] | 8.45 (3H, s), 7.90 (1H, br), 7.78 (1H, d), 7.65 (2H, s), 7.50 (1H, d), 7.35-7.30 (1H, m), 4.75-4.70 (2H, m), 3.40-3.35 (1H, m), 3.05-2.70 (3H, m), 2.35 (1H, dd), 2.23 (3H, s), 2.22 (3H, s) |
| A115 | 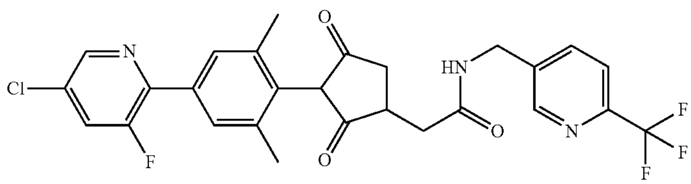 [SMILES: Cc1cc(-c2ncc(Cl)cc2F)cc(C)c1C1C(=O)CC(CC(=O)NCc2ccc(C(F)(F)F)nc2)C1=O] | 13.00 (1H, br), 8.60 (1H, s), 8.45 (1H, s), 8.25 (1H, br), 7.75 (1H, br), 7.65-7.55 (3H, m), 7.50 (1H, d), 4.45-4.20 (2H, m), 3.25 (1H, br), 2.95-2.60 (3H, m), 2.25-2.15 (7H, m) |
| A116 | 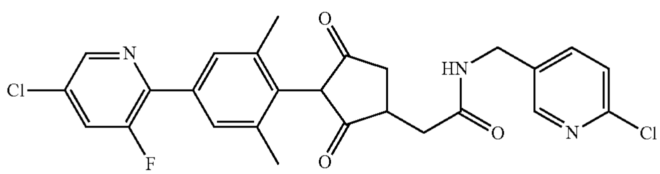 [SMILES: Cc1cc(-c2ncc(Cl)cc2F)cc(C)c1C1C(=O)CC(CC(=O)NCc2ccc(Cl)nc2)C1=O] | 8.45 (1H, s), 8.25 (1H, s), 8.15 (1H, br), 7.60 (2H, s), 7.5-7.45 (2H, m), 7.25 (1H, d), 4.30-4.20 (2H, m), 3.25-3.20 (1H, m), 2.90 (1H, dd), 2.70-2.60 (2H, m), 2.25 (1H, d), 2.20 (3H, s), 2.15 (3H, s) |
| A117 | 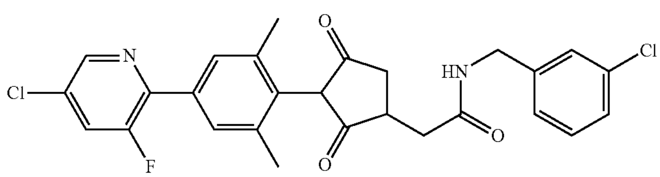 [SMILES: Cc1cc(-c2ncc(Cl)cc2F)cc(C)c1C1C(=O)CC(CC(=O)NCc2cccc(Cl)c2)C1=O] | 12.90 (1H, br), 8.45 (1H, s), 7.62 (2H, s), 7.50 (1H, d), 7.30 (2H, d), 7.15 (1H, br), 6.90 (1H, br), 4.50-4.30 (2H, m), 3.40-3.30 (1H, m), 2.95 (1H, dd), 2.80-2.70 (2H, m), 2.30-2.20 (7H, m) |
| A118 | 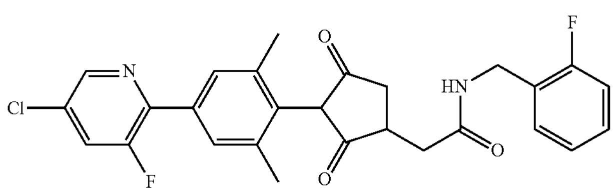 [SMILES: Cc1cc(-c2ncc(Cl)cc2F)cc(C)c1C1C(=O)CC(CC(=O)NCc2ccccc2F)C1=O] | 13.00 (1H, br), 8.45 (1H, s), 7.60 (2H, s), 7.50 (1H, d), 7.35-7.30 (2H, m), 7.15-7.00 (2H, m), 4.55-4.40 (2H, m), 3.30-3.20 (1H, m), 2.90 (1H, dd), 2.75-2.65 (2H, m), 2.25-2.15 (7H, m) |
| A119 | 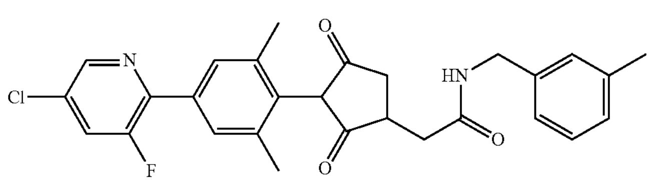 [SMILES: Cc1cccc(CNC(=O)CC2CC(=O)C(c3c(C)cc(-c4ncc(Cl)cc4F)cc3C)C2=O)c1] | 8.45 (1H, s), 7.62 (2H, s), 7.50 (2H, d), 7.40 (1H, br), 7.25 (1H, t), 7.10-7.00 (2H, m), 4.35 (2H, d), 3.30-3.20 (1H, m), 2.85 (1H, dd), 2.75-2.65 (2H, m), 2.35 (3H, s), 2.25-2.15 (7H, m) |

TABLE T1-continued

It should be noted that certain compounds of the invention may exist as a mixture of isomers, including sometimes atropisomers, e.g. as noted above, under the conditions used to obtain the ¹H NMR data. Where this has occurred, the characterising data are reported for all isomers present at ambient temperature in the specified solvent. Unless otherwise stated, proton (¹H) NMR spectra disclosed herein were recorded at ambient temperature.

| Compound Number | Structure | ¹H NMR (400 MHz, CDCl$_3$) unless stated |
|---|---|---|
| A120 | 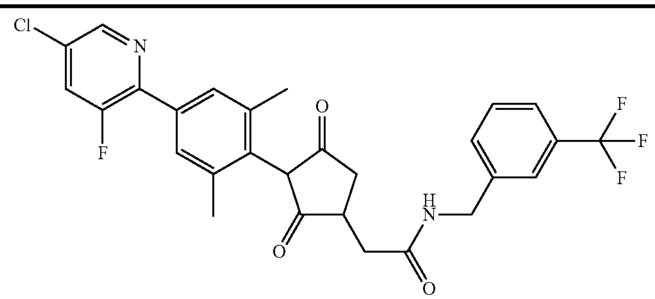 | 13.30 (1H, br), 8.45 (1H, s), 7.90 (1H, br), 7.60 (2H, s), 7.60-7.40 (5H, m), 4.45-4.30 (2H, m), 3.25 (1H, br), 2.90 (1H, dd), 2.75-2.60 (2H, m), 2.25-2.10 (7H, m) |
| A121 | 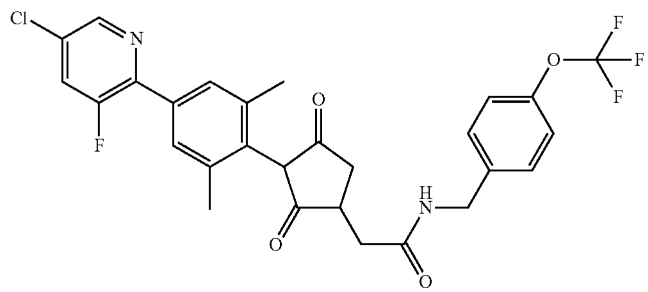 [SMILES: Cc1cc(-c2ncc(Cl)cc2F)cc(C)c1C1C(=O)CC(CC(=O)NCc2ccc(OC(F)(F)F)cc2)C1=O] | 12.60 (1H, br), 8.45 (1H, s), 7.65 (2H, s), 7.50 (1H, d), 7.35 (2H, d), 7.20 (2H, d), 6.45 (1H, br), 4.55-4.45 (2H, m), 3.35 (1H, br), 2.95 (1H, dd), 2.85-2.75 (2H, m), 2.30-2.20 (7H, m) |
| A122 | 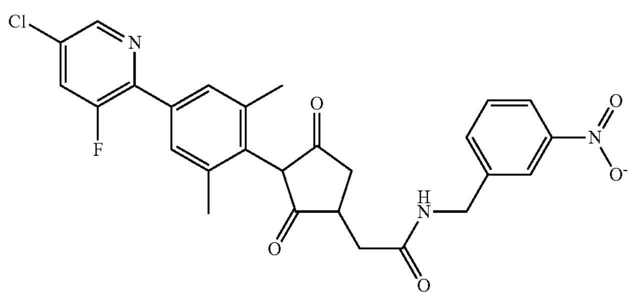 | 13.30 (1H, br), 8.40 (1H, s), 8.35 (1H, br), 8.15-8.05 (2H, m), 7.60-7.45 (5H, m), 4.40-4.30 (2H, m), 3.25 (1H, br), 2.90 (1H, dd), 2.85-2.65 (2H, m), 2.20-2.15 (7H, m) |
| A123 | 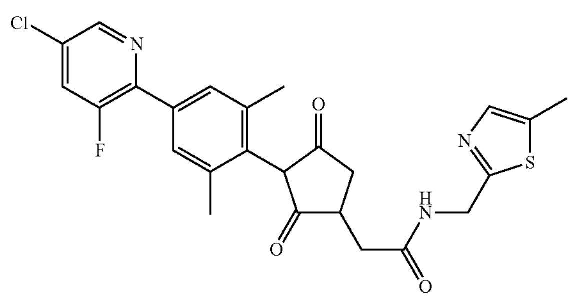 [SMILES: Cc1cnc(CNC(=O)CC2CC(=O)C(c3c(C)cc(-c4ncc(Cl)cc4F)cc3C)C2=O)s1] | (d4-MeOH) 8.50 (s, 1H), 7.85 (d, 1H), 7.60 (s, 2H), 7.37 (s, 1H), 4.61 (s, 2H), 3.20 (br, 1H), 3.00-2.90 (m, 1H), 2.87 (dd, 1H), 2.55-2.50 (m, 2H), 2.45 (s, 3H), 2.20 (s, 6H) |
| A124 | 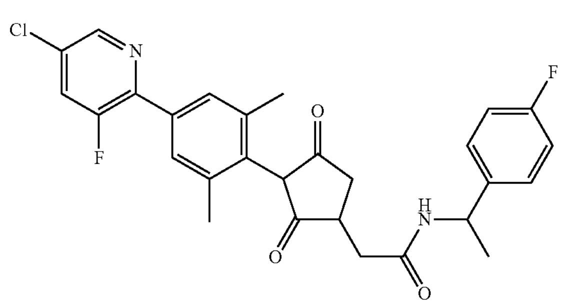 [SMILES: Cc1cc(-c2ncc(Cl)cc2F)cc(C)c1C1C(=O)CC(CC(=O)NC(C)c2ccc(F)cc2)C1=O] | Restricted rotation 13.25 (1H, br), 8.45 (1H, s), 7.65-7.60 (3H, m), 7.50 (1H, d), 7.30-7.20 (2H, m), 7.05-6.95 (2H, m), 5.10-5.00 (1H, m), 3.25 (1H, br), 2.95-2.65 (3H, m), 2.25-2.15 (7H, m), 1.50-1.40 (3H, m) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (400 MHz, CDCl$_3$) unless stated |
|---|---|---|
| A125 | 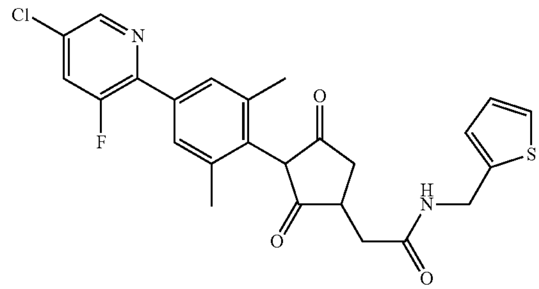 [SMILES: Cc1cc(-c2ncc(Cl)cc2F)cc(C)c1C1C(=O)CC(CC(=O)NCc2cccs2)C1=O] | 13.10 (1H, br), 8.45 (1H, s), 7.65 (2H, s), 7.50 (1H, d), 7.40 (1H, br), 7.25-7.20 (1H, m), 7.00-6.90 (2H, m), 4.65-4.50 (2H, m), 3.30 (1H, br), 2.90 (1H, dd), 2.75-2.65 (2H, m), 2.25-2.15 (7H, m) |
| A126 | 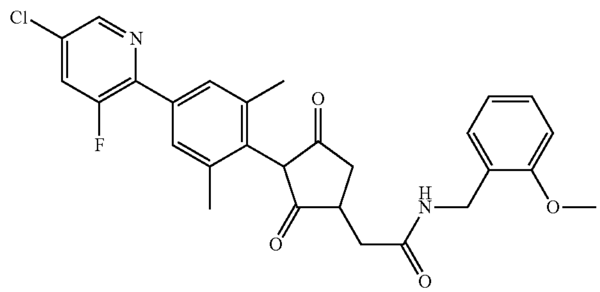 [SMILES: COc1ccccc1CNC(=O)CC1CC(=O)C(c2c(C)cc(-c3ncc(Cl)cc3F)cc2C)C1=O] | 13.20 (1H, br), 8.45 (1H, s), 7.65 (2H, s), 7.50 (1H, d), 7.35-7.25 (2H, m), 7.00-6.90 (2H, m), 6.75 (1H, br), 4.50 (2H, d), 3.90 (3H, s), 3.30 (1H, br), 2.90 (1H, dd), 2.75-2.70 (2H, m), 2.25-2.15 (7H, m) |
| A127 | 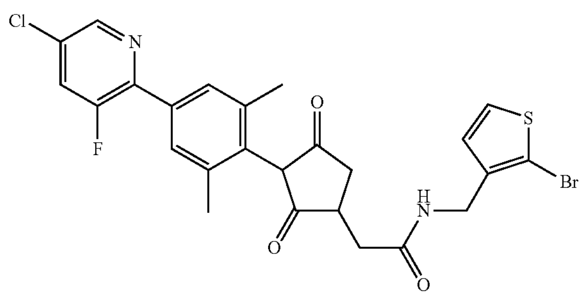 [SMILES: Cc1cc(-c2ncc(Cl)cc2F)cc(C)c1C1C(=O)CC(CC(=O)NCc2ccsc2Br)C1=O] | 13.00 (1H, br), 8.45 (1H, s), 7.62 (2H, s), 7.25 (1H, s), 6.95 (1H, br), 6.92 (1H, d), 4.45-4.35 (2H, m), 3.30 (1H, br), 2.90 (1H, dd), 2.65-2.60 (2H, m), 2.25-2.15 (7H, m) |
| A128 | 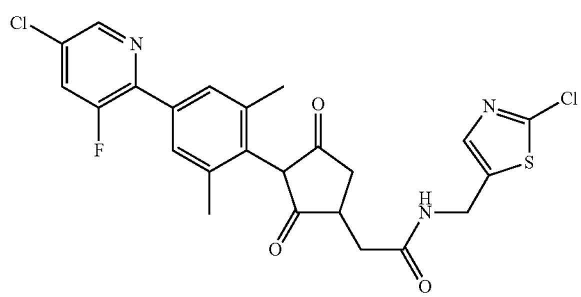 [SMILES: Cc1cc(-c2ncc(Cl)cc2F)cc(C)c1C1C(=O)CC(CC(=O)NCc2cnc(Cl)s2)C1=O] | 8.45 (1H, s), 7.95 (1H, t), 7.60 (2H, 2 × s), 7.55 (1H, d), 7.35 (1H, s), 4.40-4.30 (2H, m), 3.25 (1H, br), 2.90 (1H, dd), 2.70-2.60 (2H, m), 2.25-2.20 (1H, m), 2.20 (3H, s), 2.15 (3H, s) |
| A129 | 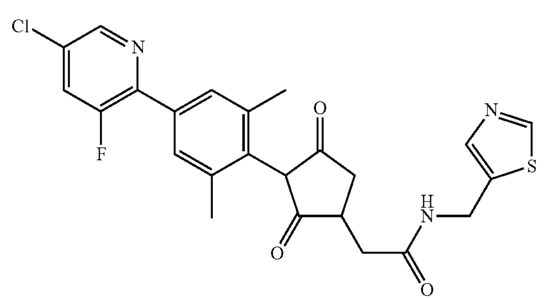 [SMILES: Cc1cc(-c2ncc(Cl)cc2F)cc(C)c1C1C(=O)CC(CC(=O)NCc2cncs2)C1=O] | |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (400 MHz, CDCl$_3$) unless stated |
|---|---|---|
| A130 | 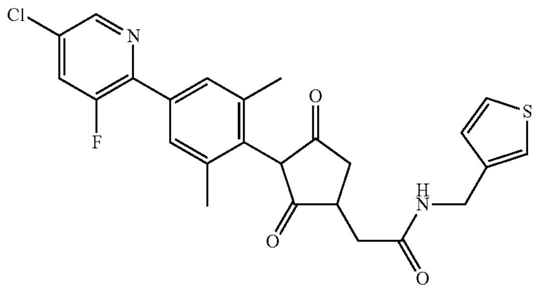 [SMILES: Cc1cc(-c2ncc(Cl)cc2F)cc(C)c1C1C(=O)CC(CC(=O)NCc2ccsc2)C1=O] | 13.30 (1H, br), 8.40 (1H, s), 7.60 (2H, s), 7.55 (1H, br), 7.50 (1H, d), 7.30 (1H, br), 7.15 (1H, s), 7.00 (1H, d), 4.45-4.35 (2H, m), 3.25 (1H, br), 2.90 (1H, dd), 2.80-2.65 (2H, m), 2.25-2.10 (7H, m) |
| A131 | 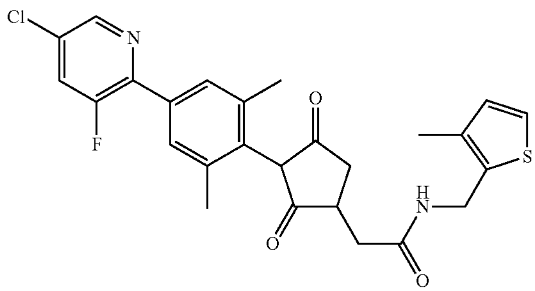 [SMILES: Cc1ccsc1CNC(=O)CC1CC(=O)C(c2c(C)cc(-c3ncc(Cl)cc3F)cc2C)C1=O] | 13.00 (1H, br), 8.45 (1H, s), 7.65 (2H, s), 7.50 (1H, d), 7.15 (1H, br), 7.15 (1H, d), 6.70 (1H, d), 4.60-4.50 (2H, m), 3.30 (1H, br), 2.90 (1H, dd), 2.75-2.65 (2H, m), 22.5-2.15 (10H, m) |
| A132 | 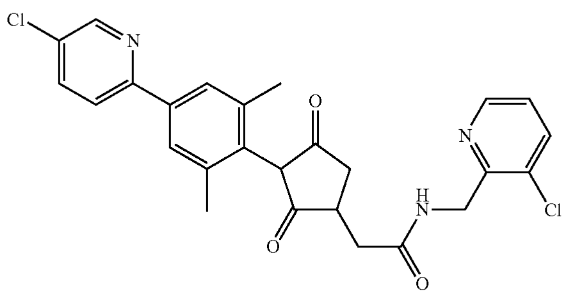 [SMILES: Cc1cc(-c2ccc(Cl)cn2)cc(C)c1C1C(=O)CC(CC(=O)NCc2ncccc2Cl)C1=O] | (d4-MeOH) 8.54 (s, 1H), 8.50 (d, 1H), 7.98-7.90 (m, 2H, 7.87 (d, 1H), 7.62 (s, 2H), 7.41-7.35 (m, 1H), 4.68 (s, 2H), 3.27-3.18 (m, 1H), 3.00-2.82 (m, 2H), 2.68-2.52 (m, 2H), 2.19 (d, 6H) |
| A133 | 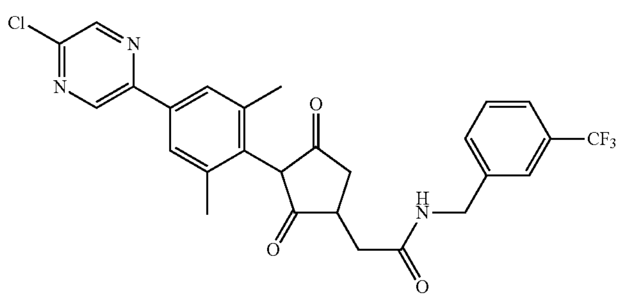 [SMILES: Cc1cc(-c2cnc(Cl)cn2)cc(C)c1C1C(=O)CC(CC(=O)NCc2cccc(C(F)(F)F)c2)C1=O] | (d4-MeOH) 8.95 (s, 2H), 7.64-7.50 (m, 4H), 7.39 (s, 2H), 4.48 (s, 2H), 3.26-3.14 (m, 1H), 2.94 (dd, 1H), 2.84 (dd, 1H), 2.59-2.47 (m, 2H), 2.20 (d, 6H) |
| A134 | 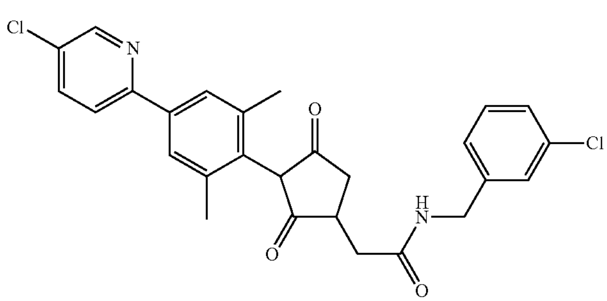 [SMILES: Cc1cc(-c2ccc(Cl)cn2)cc(C)c1C1C(=O)CC(CC(=O)NCc2cccc(Cl)c2)C1=O] | (d4-MeOH) 8.59 (s, 1H), 7.92-7.82 (m, 2H), 7.66 (s, 2H), 7.37-7.21 (m, 4H), 4.39 (s, 2H), 3.24-3.14 (m, 1H), 2.94 (dd, 1H), 2.83 (dd, 1H), 2.59-2.47 (m, 2H), 2.19 (d, 6H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (400 MHz, CDCl$_3$) unless stated |
|---|---|---|
| A135 | 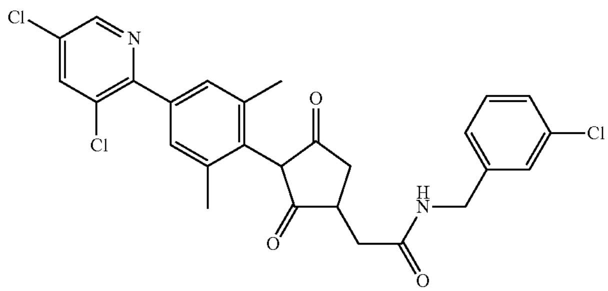 [SMILES: Cc1cc(-c2ncc(Cl)cc2Cl)cc(C)c1C1C(=O)CC(CC(=O)NCc2cccc(Cl)c2)C1=O] | (d4-MeOH) 8.53 (s, 1H), 8.07 (s, 1H), 7.37-7.20 (m, 6H), 4.36 (s, 2H), 3.24-3.14 (m, 1H), 2.94 (dd, 1H), 2.83 (dd, 1H), 2.56-2.44 (m, 2H), 2.18 (d, 6H) |
| A136 | 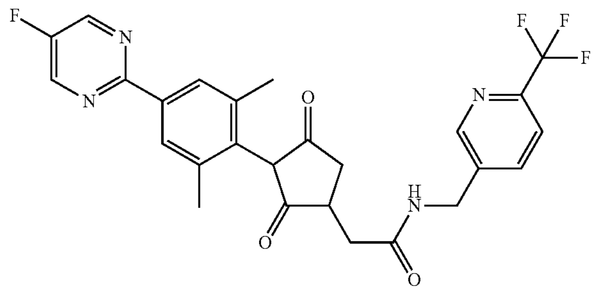 [SMILES: Cc1cc(-c2ncc(F)cn2)cc(C)c1C1C(=O)CC(CC(=O)NCc2ccc(C(F)(F)F)nc2)C1=O] | (d4-MeOH) 8.75 (s, 2H), 8.67 (s, 1H), 8.08 (s, 2H), 7.99 (d, 1H), 7.78 (d, 1H), 4.52 (s, 2H), 3.25-3.16 (m, 1H), 2.98 (dd, 1H), 2.85 (dd, 1H), 2.61-2.50 (m, 2H), 2.20 (d, 6H) |
| A137 | 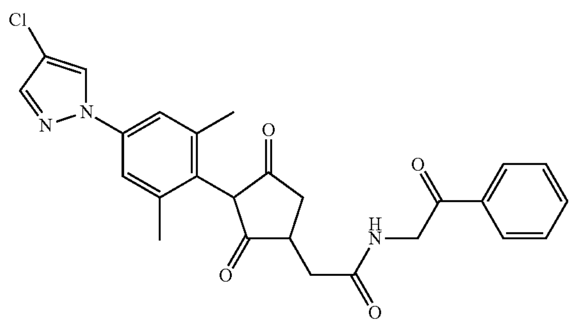 [SMILES: Cc1cc(-n2cc(Cl)cn2)cc(C)c1C1C(=O)CC(CC(=O)NCC(=O)c2ccccc2)C1=O] | 8.00-7.84 (m, 2H), 7.82-7.73 (m, 1H), 7.67-7.58 (m, 2H), 7.54-7.40 (m, 3H), 7.27 (d, 2H), 4.76-4.56 (m, 2H), 3.32 (br, 1H), 3.03-2.87 (m, 2H), 2.84-2.70 (m, 1H), 2.29 (d, 1H), 2.18 (d, 6H) |
| A138 | 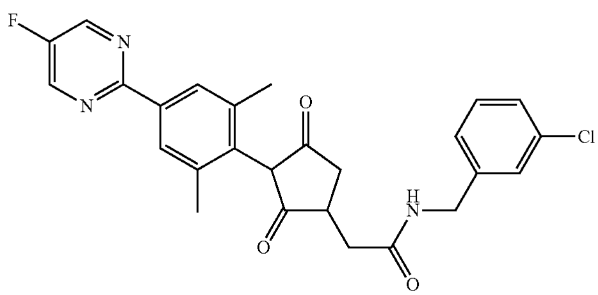 [SMILES: Cc1cc(-c2ncc(F)cn2)cc(C)c1C1C(=O)CC(CC(=O)NCc2cccc(Cl)c2)C1=O] | (d4-MeOH) 8.72 (s, 2H), 8.04 (s, 2H), 7.33-7.19 (m, 4H), 4.37 (s, 2H), 3.25-3.13 (m, 1H), 2.93 (dd, 1H), 2.82 (dd, 1H), 2.57-2.43 (m, 2H), 2.19 (s, 6H) |
| A139 | 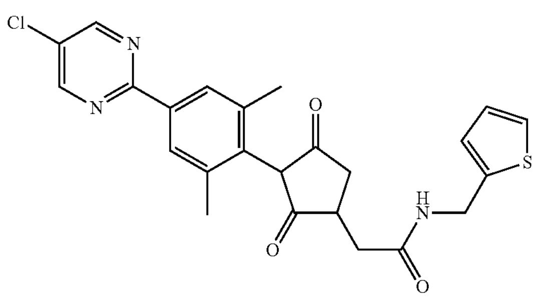 [SMILES: Cc1cc(-c2ncc(Cl)cn2)cc(C)c1C1C(=O)CC(CC(=O)NCc2cccs2)C1=O] | (d4-MeOH) 8.90 (s, 2H), 7.34 (s, 2H), 7.28 (d, 1H), 6.99 (s, 1H), 6.95-6.91 (m, 1H), 4.54 (s, 2H), 3.22-3.13 (m, 1H), 2.92 (dd, 1H), 2.79 (dd, 1H), 2.53-2.42 (m, 2H), 2.18 (s, 6H) |

TABLE T1-continued

It should be noted that certain compounds of the invention may exist as a mixture of isomers, including sometimes atropisomers, e.g. as noted above, under the conditions used to obtain the ¹H NMR data. Where this has occurred, the characterising data are reported for all isomers present at ambient temperature in the specified solvent. Unless otherwise stated, proton (¹H) NMR spectra disclosed herein were recorded at ambient temperature.

| Compound Number | Structure | ¹H NMR (400 MHz, CDCl₃) unless stated |
|---|---|---|
| A140* | 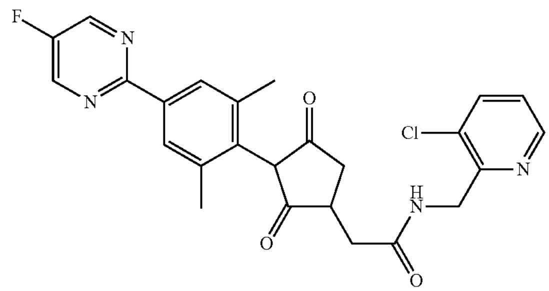 [SMILES: Cc1cc(-c2ncc(F)cn2)cc(C)c1C1C(=O)CC(CC(=O)NCc2ncccc2Cl)C1=O] | (d4-MeOH) 8.72 (s, 2H), 8.51-8.44 (m, 1H), 8.02 (s, 2H), 7.96 (d, 1H), 7.44-7.38 (m, 1H), 4.64 (s, 2H), 3.28-3.18 (m, 1H), 3.02-2.92 (m, 1H), 2.91-2.81 (m, 1H), 2.69-2.52 (m, 2H), 2.19 (d, 6H) |
| A141 | 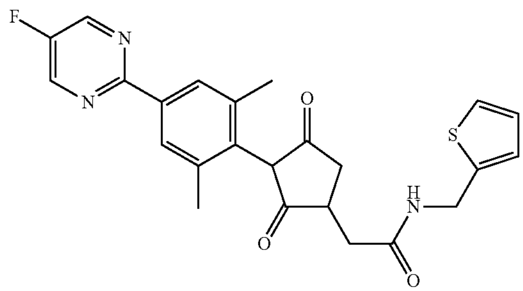 [SMILES: Cc1cc(-c2ncc(F)cn2)cc(C)c1C1C(=O)CC(CC(=O)NCc2cccs2)C1=O] | (d4-MeOH) 8.71 (s, 2H), 8.04 (s, 2H), 7.28 (d, 1H), 6.99 (s, 1H), 6.96-6.91 (m, 1H), 4.55 (s, 2H), 3.22-3.12 (m, 1H), 2.92 (dd, 1H), 2.79 (dd, 1H), 2.52-2.41 (m, 2H), 2.18 (s, 6H) |
| A142 | 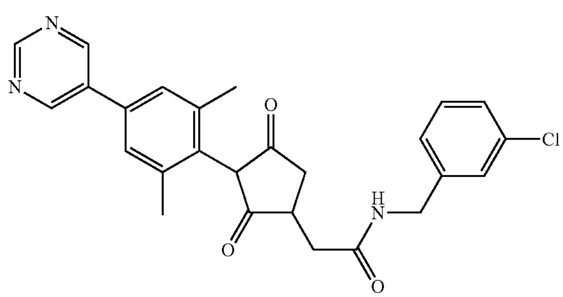 [SMILES: Cc1cc(-c2cncnc2)cc(C)c1C1C(=O)CC(CC(=O)NCc2cccc(Cl)c2)C1=O] | (d-4 MeOH) 9.11 (s, 1H) 9.04 (s, 2H), 7.39 (s, 2H), 7.35-7.21 (m, 4H), 4.39 (s, 2H), 3.24-3.16 (m, 1H), 2.95 (dd, 1H), 2.83 (dd, 1H), 2.59-2.47 (m, 2H), 2.20 (s, 6H) |
| A143* | 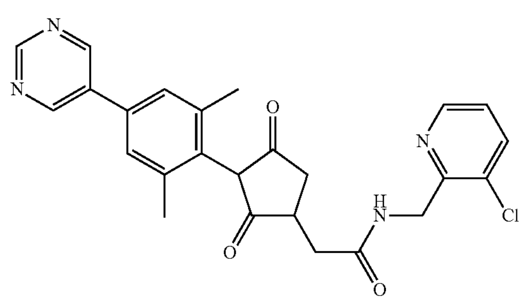 [SMILES: Cc1cc(-c2cncnc2)cc(C)c1C1C(=O)CC(CC(=O)NCc2ncccc2Cl)C1=O] | (d4-MeOH) 9.10 (s, 1H), 9.02 (s, 2H), 8.49 (d, 1H), 7.93 (d, 1H), 7.42-7.35 (m, 3H), 4.68 (s, 2H), 3.28-3.19 (m, 1H), 2.98 (dd, 1H), 2.88 (dd, 1H), 2.69-2.53 (m, 2H), 2.20 (d, 6H) |
| A144 | 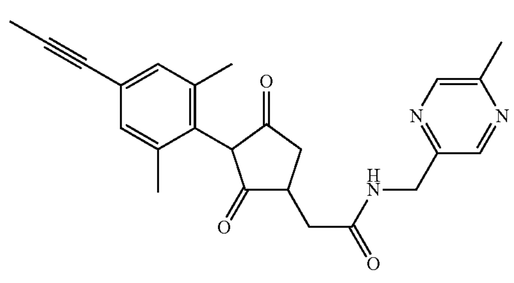 [SMILES: CC#Cc1cc(C)c(C2C(=O)CC(CC(=O)NCc3cnc(C)cn3)C2=O)c(C)c1] | (d4-MeoH) 8.36 (s, 2H), 6.92 (s, 2H), 4.40 (s, 2H), 3.11-3.00 (m, 1H), 2.84-2.69 (m, 2H), 2.47-2.34 (m, 2H), 2.42 (s, 3H), 1.94 (d, 6H), 1.89 (s, 3H) |

TABLE T1-continued

It should be noted that certain compounds of the invention may exist as a mixture of isomers, including sometimes atropisomers, e.g. as noted above, under the conditions used to obtain the ¹H NMR data. Where this has occurred, the characterising data are reported for all isomers present at ambient temperature in the specified solvent. Unless otherwise stated, proton (¹H) NMR spectra disclosed herein were recorded at ambient temperature.

| Compound Number | Structure | ¹H NMR (400 MHz, CDCl₃) unless stated |
|---|---|---|
| A145 | 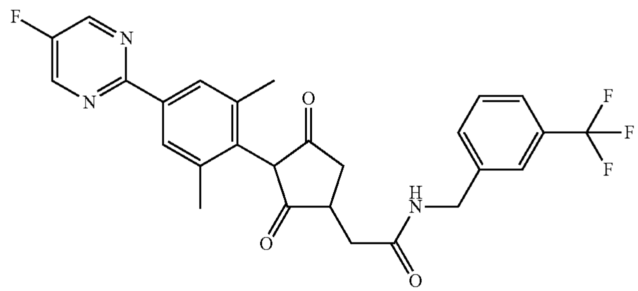 [SMILES: Cc1cc(-c2ncc(F)cn2)cc(C)c1C1C(=O)CC(CC(=O)NCc2cccc(C(F)(F)F)c2)C1=O] | (d4-MeOH) 8.73 (s, 2H), 8.06 (s, 2H), 7.64-7.49 (m, 4H), 4.46 (s, 2H), 3.26-3.14 (m, 1H), 2.94 (dd, 1H), 2.84 (dd, 1H), 2.57-2.43 (m, 2H), 2.19 (d, 6H) |
| A146 | 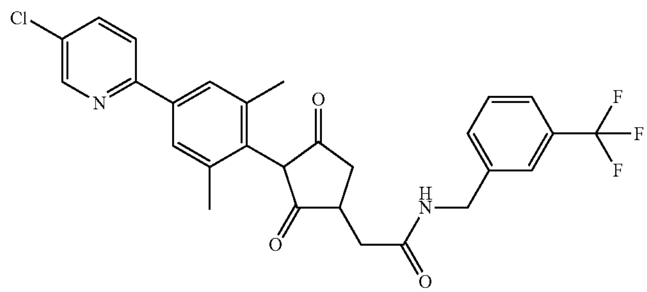 [SMILES: Cc1cc(-c2ccc(Cl)cn2)cc(C)c1C1C(=O)CC(CC(=O)NCc2cccc(C(F)(F)F)c2)C1=O] | (d4-MeOH) 8.56 (s, 1H), 7.90-7.81 (m, 2H), 7.65 (s, 2H), 7.62 (s, 1H), 7.60-7.49 (m, 3H), 4.46 (s, 2H), 3.24-3.14 (m, 1H), 2.94 (dd, 1H), 2.84 (dd, 1H), 2.59-2.45 (m, 2H), 2.19 (d, 6H) |
| A147 | 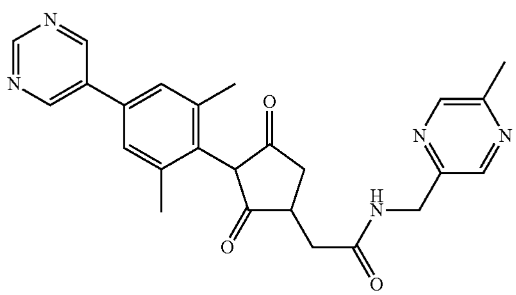 [SMILES: Cc1cnc(CNC(=O)CC2CC(=O)C(c3c(C)cc(-c4cncnc4)cc3C)C2=O)cn1] | (d4-MeOH) 9.11 (s, 1H), 8.75 (s, 2H), 8.50 (s, 1H), 8.40 (s, 1H), 7.69-7.58 (m, 1H), 7.18 (d, 2H), 4.65-4.52 (m, 2H), 3.47-3.26 (m, 1H), 2.99 (dd, 1H), 2.89-2.76 (m, 2H), 2.58 (s, 3H), 2.47-2.34 (m, 1H), 2.20 (d, 6H) |
| A148 | 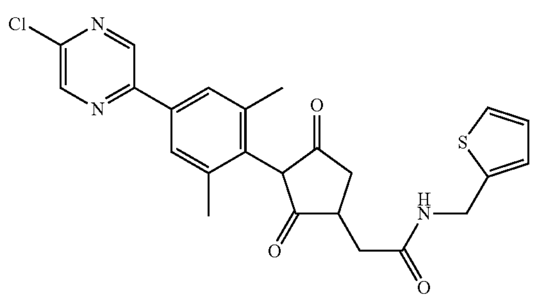 [SMILES: Cc1cc(-c2cnc(Cl)cn2)cc(C)c1C1C(=O)CC(CC(=O)NCc2cccs2)C1=O] | (d4-MeOH) 8.87 (s, 1H), 8.63 (s, 1H), 7.73 (s, 2H), 7.28 (d, 1H), 6.99 (s, 1H), 6.96-6.91 (m, 1H), 4.56 (s, H), 3.33-3.13 (m, 1H), 2.93 (dd, 1H), 2.79 (dd, 1H), 2.54-2.42 (m, 2H), 2.19 (s, 6H) |
| A149 | 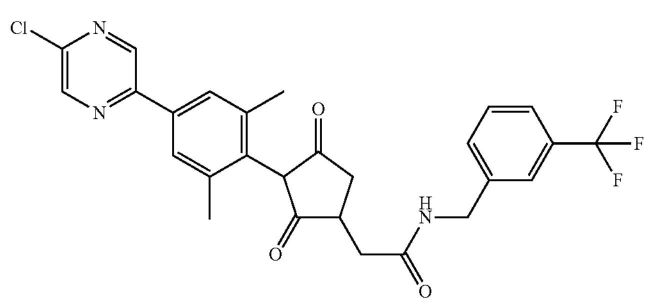 [SMILES: Cc1cc(-c2cnc(Cl)cn2)cc(C)c1C1C(=O)CC(CC(=O)NCc2cccc(C(F)(F)F)c2)C1=O] | (d4-MeOH) 8.90 (s, 1H), 8.66 (s, 1H), 7.76 (s, 2H), 7.63-7.50 (m, 4H), 4.48 (s, 2H), 3.27-3.14 (m, 1H), 4.95 (dd, 1H), 2.84 (dd, 1H), 2.59-2.45 (m, 2H), 2.19 (d, 6H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (400 MHz, CDCl$_3$) unless stated |
|---|---|---|
| A150 | 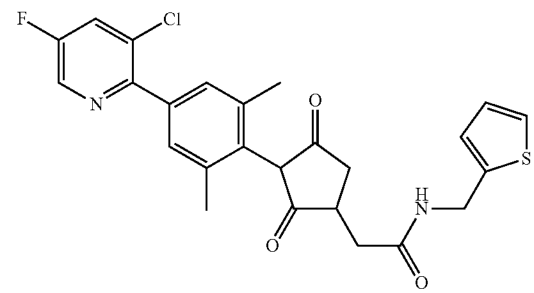 [SMILES: Cc1cc(-c2ncc(F)cc2Cl)cc(C)c1C1C(=O)CC(CC(=O)NCc2cccs2)C1=O] | (d4-MeOH) 8.48 (s, 1H), 7.89 (dd, 1H), 7.31 (s, 2H), 7.28 (d, 1H), 7.01-6.98 (m, 1H), 6.95-6.91 (m, 1H), 4.56 (s, 2H), 3.22-3.14 (m, 1H), 2.92 (dd, 1H), 2.79 (dd, 1H), 2.52-2.41 (m, 2H), 2.18 (d, 6H) |
| A151 | 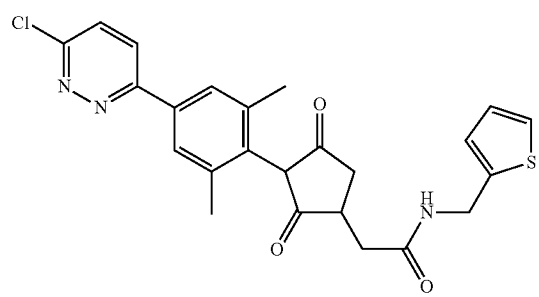 [SMILES: Cc1cc(-c2ccc(Cl)nn2)cc(C)c1C1C(=O)CC(CC(=O)NCc2cccs2)C1=O] | (d4-MeOH) 8.16 (d, 1H), 7.81 (d, 1H), 7.77 (s, 2H), 7.29 (d, 1H), 7.00 (s, 1H), 6.97-6.91 (m, 1H), 4.58 (s, 2H), 3.25-3.12 (m, 1H), 2.94 (dd, 1H), 2.81 (dd, 1H), 2.56-2.41 (m, 2H), 2.22 (s, 6H) |
| A152 | 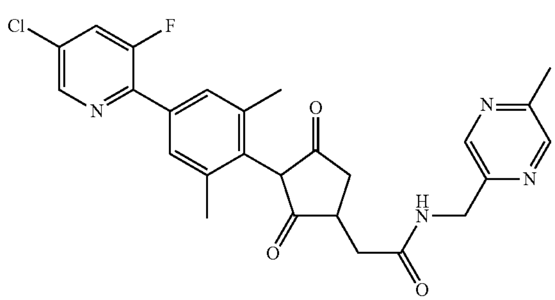 [SMILES: Cc1cnc(CNC(=O)CC2CC(=O)C(c3c(C)cc(-c4ncc(Cl)cc4F)cc3C)C2=O)cn1] | (d4-MeOH) 8.50-8.44 (m, 3H), 7.82 (d, 1H), 7.59 (s, 2H), 4.52 (s, 2H), 3.24-3.14 (m, 1H), 2.94 (dd, 1H), 2.86 (dd, 1H), 2.60-2.49 (m, 2H), 2.52 (s, 3H), 2.18 (d, 6H) |
| A153 | 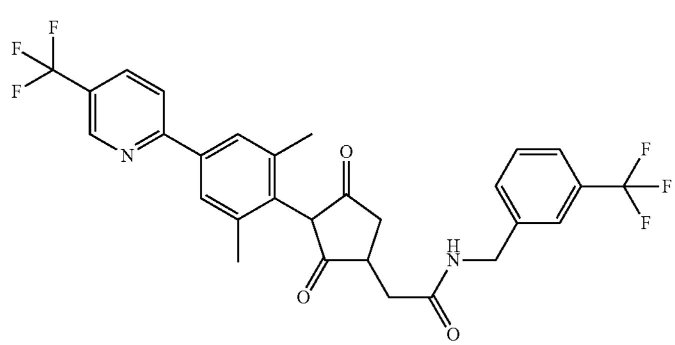 [SMILES: Cc1cc(-c2ccc(C(F)(F)F)cn2)cc(C)c1C1C(=O)CC(CC(=O)NCc2cccc(C(F)(F)F)c2)C1=O] | (d4-MeOH) 8.89 (s, 1H), 8.12 (d, 1H), 8.03 (d, 1H), 7.78 (s, 2H), 7.64-7.49 (m, 4H), 4.47 (s, 2H), 3.25-3.14 (m, 1H), 2.95 (dd, 1H), 2.84 (dd, 1H), 2.59-2.47 (m, 2H), 2.21 (d, 6H) |

TABLE T1-continued

It should be noted that certain compounds of the invention may exist as a mixture of isomers, including sometimes atropisomers, e.g. as noted above, under the conditions used to obtain the ¹H NMR data. Where this has occurred, the characterising data are reported for all isomers present at ambient temperature in the specified solvent. Unless otherwise stated, proton (¹H) NMR spectra disclosed herein were recorded at ambient temperature.

| Compound Number | Structure | ¹H NMR (400 MHz, CDCl$_3$) unless stated |
|---|---|---|
| A154 | 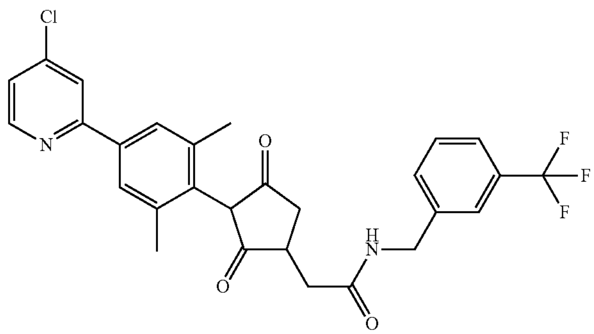 [SMILES: Cc1cc(-c2cc(Cl)ccn2)cc(C)c1C1C(=O)CC(CC(=O)NCc2cccc(C(F)(F)F)c2)C1=O] | (d4-MeOH) 8.56 (s, 1H), 8.04 (s, 1H), 7.66-7.60 (m, 3H), 7.60-7.48 (m, 4H), 4.46 (s, 2H), 3.25-3.14 (m, 1H), 2.95 (dd, 1H), 2.83 (dd, 1H), 2.60-2.48 (m, 2H), 2.21 (d, 6H) |
| A155* | 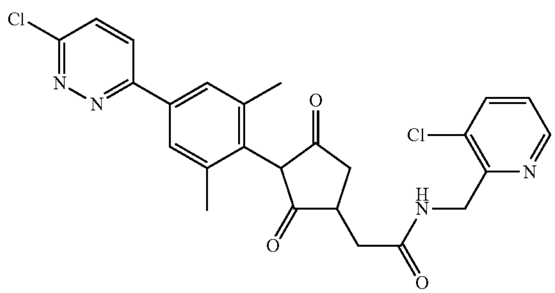 [SMILES: Cc1cc(-c2ccc(Cl)nn2)cc(C)c1C1C(=O)CC(CC(=O)NCc2ncccc2Cl)C1=O] | (d4-MeOH) 8.49 (d, 1H), 8.14 (d, 1H), 7.94 (d, 1H), 7.82 (d, 1H), 7.74 (s, 2H), 7.43-7.38 (m, 1H), 4.67 (s, 2H), 3.28-3.18 (m, 1H), 2.98 (dd, 1H), 2.88 (dd, 1H), 2.69-2.53 (m, 2H), 2.21 (d, 6H) |
| A156 | 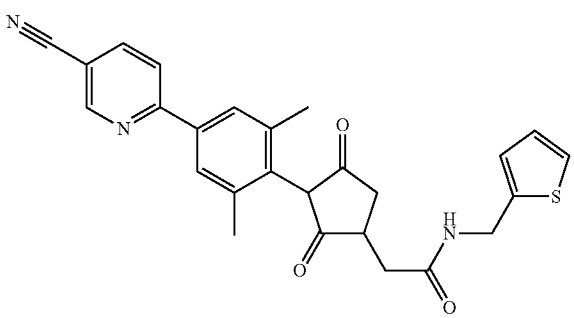 [SMILES: Cc1cc(-c2ccc(C#N)cn2)cc(C)c1C1C(=O)CC(CC(=O)NCc2cccs2)C1=O] | (d4-MeOH) 8.90 (s, 1H), 8.13 (d, 1H), 8.01 (d, 1H), 7.78 (s, 2H), 7.28 (d, 1H), 6.99 (s, 1H), 6.96-6.92 (m, 1H), 4.57 (s, 2H), 3.22-3.13 (m, 1H), 2.92 (dd, 1H), 2.80 (dd, 1H), 2.53-2.42 (m, 2H), 2.19 (s, 6H) |
| A157 | 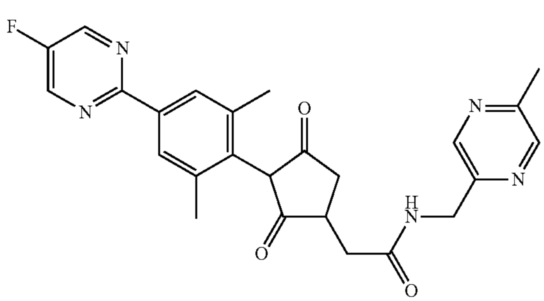 [SMILES: Cc1cnc(CNC(=O)CC2CC(=O)C(c3c(C)cc(-c4ncc(F)cn4)cc3C)C2=O)cn1] | (d4-MeOH) 8.73 (s, 2H), 8.47 (d, 2H), 8.04 (s, 2H), 4.52 (s, 2H), 3.22-3.14 (m, 1H), 2.93 (dd, 1H), 2.86 (dd, 1H), 2.59-2.48 (m, 2H), 2.53 (s, 3H), 2.18 (d, 6H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (400 MHz, CDCl$_3$) unless stated |
|---|---|---|
| A158 | 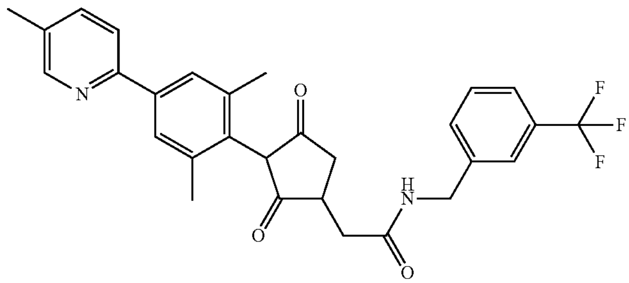 [SMILES: Cc1ccc(-c2cc(C)c(C3C(=O)CC(CC(=O)NCc4cccc(C(F)(F)F)c4)C3=O)c(C)c2)nc1] | (d4-MeOH) 8.41 (s, 1H), 7.75 (s, 2H), 7.64-7.50 (m, 6H), 4.47 (s, 2H), 3.22-3.12 (m, 1H), 2.96-2.82 (m, 2H), 2.53-2.42 (m, 2H), 2.39 (s, 3H), 2.19 (d, 6H) |
| A159 | 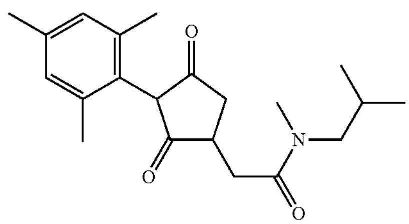 [SMILES: Cc1cc(C)c(C2C(=O)CC(CC(=O)N(C)CC(C)C)C2=O)c(C)c1] | Restricted rotation 6.86 (2H, 2 × s), 3.45-3.05 (4H, m), 3.03 and 2.99 (3H, 2 × s), 2.95-2.85 (1H, m), 2.62-2.50 (1H, m), 2.30-2.25 (1H, m), 2.24 (3H, s), 2.15-2.05 (6H, m), 0.96 (3H, t), 0.90 (3H, dd) |
| A160 | 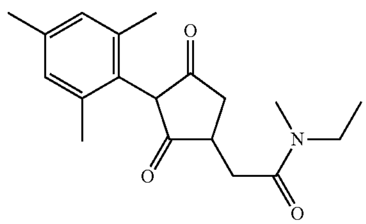 [SMILES: CCN(C)C(=O)CC1CC(=O)C(c2c(C)cc(C)cc2C)C1=O] | Restricted rotation 6.75 (2H, 2 × s), 3.55-3.30 (3H, m), 3.15-2.92 (2H, m), 3.04 and 3.00 (3H, 2 × s), 2.65-2.50 (1H, m), 2.35 (1H, d), 2.16 (3H, s), 2.08 (3H, s), 2.07 (3H, s), 1.25 and 1.15 (3H, 2 × t) |
| A161 | 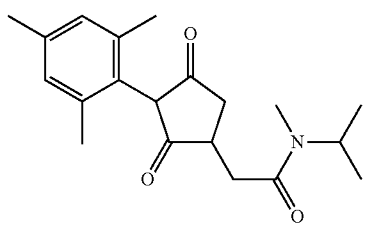 [SMILES: Cc1cc(C)c(C2C(=O)CC(CC(=O)N(C)C(C)C)C2=O)c(C)c1] | Restricted rotation 6.84 and 6.82 (2H, 2 × s), 4.95-4.80 (0.6H, m), 4.12-4.02 (0.4H, m), 3.40 (1H, br), 3.20-3.02 (1H, m), 2.97-2.90 (1H, m), 2.88 and 2.87 (3H, 2 × s), 2.60-2.45 (1H, m), 2.27 (1H, d), 2.22 (3H, s), 2.11 (3H, s), 2.10 (3H, s), 1.25 (2.4H, t), 1.14 (3.6H, t) |
| A162 | 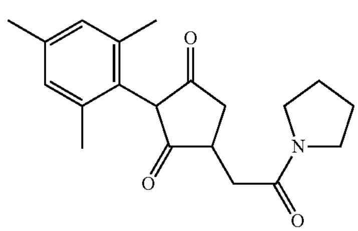 [SMILES: Cc1cc(C)c(C2C(=O)CC(CC(=O)N3CCCC3)C2=O)c(C)c1] | 6.79 (s, 2H), 3.61-3.45 (m, 2H), 3.45-3.40 (m, 1H), 3.05-2.95 (m, 2H), 2.70-2.60 (m, 1H), 2.35 (d, 1H), 2.19 (s, 3H), 2.12-1.95 (m, 12H) |
| A163 | 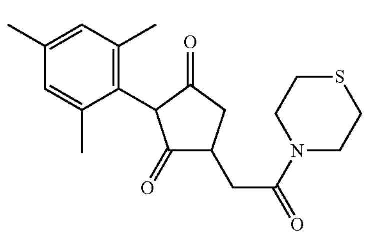 [SMILES: Cc1cc(C)c(C2C(=O)CC(CC(=O)N3CCSCC3)C2=O)c(C)c1] | 6.84 (2H, 2 × s), 4.03-3.83 (2H, m), 3.77-3.64 (2H, m), 3.37 (1H, br), 3.07 (1H, d), 2.90 (1H, dd), 2.70-2.50 (5H, m), 2.30-2.20 (1H, m), 2.23 (3H, s), 2.10 (3H, s), 2.08 (3H, s) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (400 MHz, CDCl$_3$) unless stated |
|---|---|---|
| A164 | 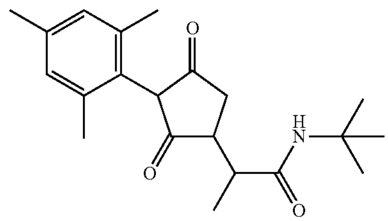 [SMILES: Cc1cc(C)c(C2C(=O)CC(C(C)C(=O)NC(C)(C)C)C2=O)c(C)c1] | (d4-MeOH) 8.30-8.10 (m, 1H), 6.88 (2 × s, 2H), 3.15-2.59 (m, 3H), 2.27 (s, 4H), 2.19-2.03 (m, 6H), 1.44-1.30 (m, 9H), 1.26-0.95 (m, 3H |
| A165 | 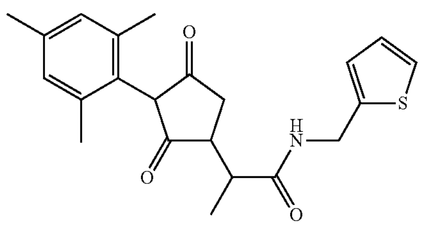 [SMILES: Cc1cc(C)c(C2C(=O)CC(C(C)C(=O)NCc3cccs3)C2=O)c(C)c1] | (d4-MeOH) 8.68-8.48 (m, 1H), 7.39-7.20 (m, 1H), 7.07-6.83 (m, 4H), 4.71-4.41 (m, 2H), 3.42-2.62 (m, 3H), 2.52-2.35 (m, 1H), 2.27 (s, 3H), 2.14-2.02 (m, 6H), 1.32-1.00 (m, 3H) |
| A166 | 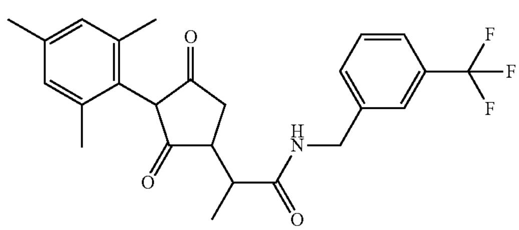 [SMILES: Cc1cc(C)c(C2C(=O)CC(C(C)C(=O)NCc3cccc(C(F)(F)F)c3)C2=O)c(C)c1] | (d4-MeOH) 7.75-7.41 (m, 4H), 6.88 (d, 2H), 4.60-4.28 (m, 2H), 3.41-2.38 (m, 4H), 2.26 (s, 3H), 2.07 (d, 6H), 1.33-1.04 (m, 3H) |
| A167 | 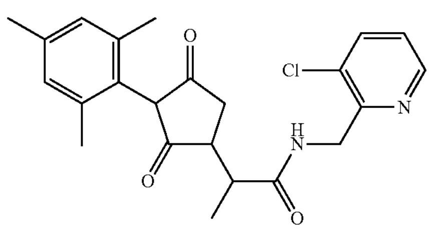 [SMILES: Cc1cc(C)c(C2C(=O)CC(C(C)C(=O)NCc3ncccc3Cl)C2=O)c(C)c1] | (d4-MeOH) 8.46 (d, 1H), 8.05-7.88 (m, 1H), 7.75 (d, 1H), 7.26 (br. s., 1H), 6.88 (s, 2H), 4.73-4.48 (m, 2H), 3.47-2.29 (m, 4H), 2.29-1.94 (m, 9H), 1.34-1.02 (m, 3H) |
| A168 | 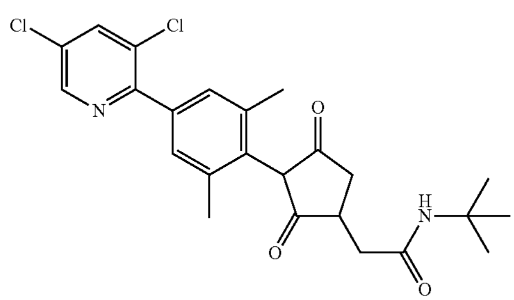 [SMILES: Cc1cc(-c2ncc(Cl)cc2Cl)cc(C)c1C1C(=O)CC(CC(=O)NC(C)(C)C)C1=O] | (d4-MeOH) 8.53 (s, 1H), 8.08 (s, 1H), 7.87 (br.s, 1H), 7.34 (s, 2H), 3.22-3.12 (m, 1H), 2.91 (dd, 1H), 2.70 (dd, 1H), 2.51-2.37 (m, 2H), 2.18 (s, 6H), 1.35 (s, 9H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (400 MHz, CDCl$_3$) unless stated |
|---|---|---|
| A169 | 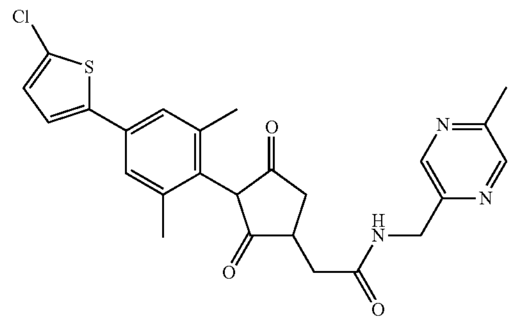 [SMILES: Cc1cnc(CNC(=O)CC2CC(=O)C(c3c(C)cc(-c4ccc(Cl)s4)cc3C)C2=O)cn1] | (d6- DMSO) 2.35 (br.s, 1H), 8.31 (br.s, 1H), 7.98 (br.s, 1H), 7.90 (br.s, 1H), 7.32 (d, 1H), 7.18-7.10 (br.s, 2H), 7.13 (d, 1H), 4.01 (br.s, 2H), 3.25-3.14 (br.m, 1H), 3.04-2.94 (br.m, 1H), 2.67-2.54 (br.m, 1H), 2.43 (s, 3H), 2.08-2.00 (m, 2H), 1.88 (br.d, 6H) |
| A170 | 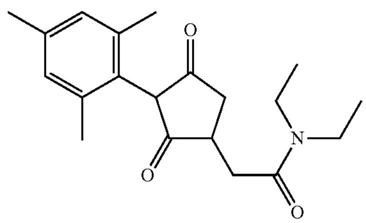 [SMILES: CCN(CC)C(=O)CC1CC(=O)C(c2c(C)cc(C)cc2C)C1=O] | 6.83 (2H, 2 × s), 3.49-3.40 (2H, m), 3.39-3.30 (3H, m), 3.05 (1H, d), 2.90 (1H, dd), 2.52 (1H, dd), 2.30 (1H, dd), 2.22 (3H, s), 2.11 (3H, s), 2.09 (3H, s), 1.24 (3H, t), 1.16 (3H, t) |
| A171 | 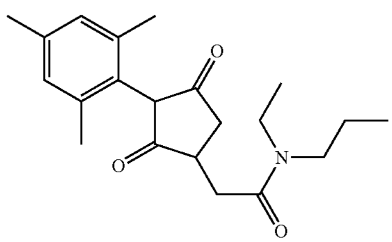 [SMILES: CCCN(CC)C(=O)CC1CC(=O)C(c2c(C)cc(C)cc2C)C1=O] | Restricted rotation 6.87 and 6.86 (2H, 2 × s), 3.43 (1H, q), 3.36-3.32 (3H, m), 3.24 (1H, t), 3.15 91H, br d), 2.88 (1H, dd), 2.56 (1H, br), 2.27 (1H, d), 2.25 (3H, s), 2.12 (3H, s), 2.10 (3H, s), 1.67-1.56 (2H, m), 1.23 and 1.16 (3H, 2 × 5), 0.96 and 0.91 (3H, 2 × t) |
| A172 | 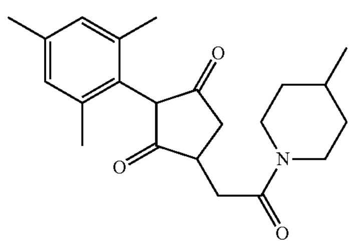 | Restricted rotation 6.87 and 6.85 (2H, 2 × s), 4.65-4.50 (1H, m), 3.75 (1H, d), 3.37 (1H, br), 3.20-3.05 (2H, m), 2.95-2.85 (1H, m), 2.70-2.50 (2H, m), 2.30-2.20 (1H, m), 2.25 (3H, s), 2.15-2.08 (6H, m), 1.80-1.55 (3H, m), 1.20-1.10 (2H, m), 0.98 (3H, dd) |
| A173 | 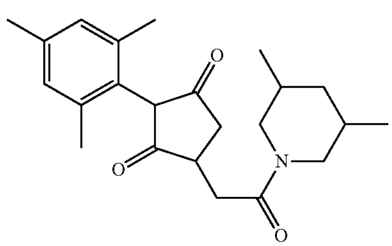 | Restricted rotation 6.88 and 6.86 (2 × s, 2H), 4.70-4.53 (m, 1H), 3.81-3.67 (m, 1H), 3.50-3.32 (m, 1H), 3.21-3.03 (m, 1H), 2.96-2.83 (m, 1H), 2.69-2.46 (m, 2H), 2.34-2.20 (m, 4H, 2.17-2.04 (m, 7H), 1.96-1.79 (m, 1H), 1.75-1.59 (m, 2H), 1.00-0.90 (m, 6H), 0.88-0.75 (m, 1H) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (400 MHz, CDCl$_3$) unless stated |
|---|---|---|
| A174 | 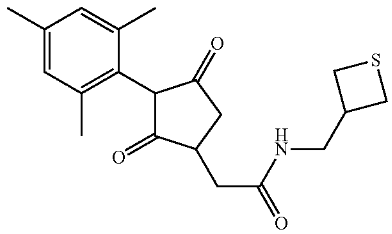 [SMILES: Cc1cc(C)c(C2C(=O)CC(CC(=O)NCC3CSC3)C2=O)c(C)c1] | 14.10-13.35 (m, 1H), 8.02 (br. s., 1H), 6.89 (d, 2H), 3.44-2.97 (m, 6H), 2.97-2.54 (m, 4H), 2.54-2.31 (m, 1H), 2.31-1.86 (m, 10H) |
| A175 | 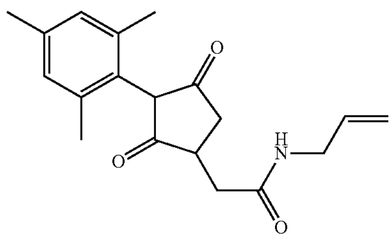 [SMILES: C=CCNC(=O)CC1CC(=O)C(c2c(C)cc(C)cc2C)C1=O] | 13.50 (1H, br), 7.42 (1H, br), 6.86 (2H, s), 5.79-5.60 (1H, m), 5.18-5.03 (2H, m), 3.72-3.60 (2H, m), 3.08 (1H, br), 2.81 (1H, dd), 2.62 (1H, d), 2.54-2.36 (1H, m), 2.23 (3H, s), 2.20-2.10 (1H, m), 2.10 (6H, s) |
| A176 | 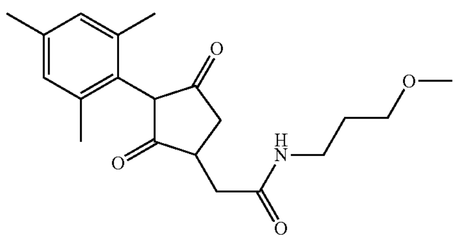 | 13.60 (1H, br), 7.45 (1H, br), 6.87 (2H, s), 3.42 (2H, t), 3.35 (3H, s), 3.30-3.20 (2H, m), 3.15 (1H, br), 2.75 (1H,dd), 2.62-2.45 (2H, m), 2.25 (3H, s), 2.15 (1H, d), 2.10 (6H, s), 1.75-1.65 (2H, m) |
| A177 | 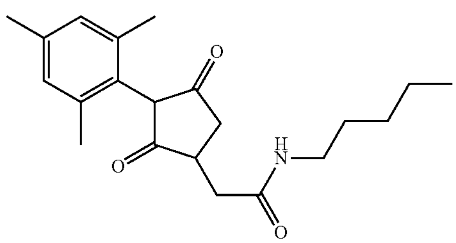 [SMILES: CCCCCNC(=O)CC1CC(=O)C(c2c(C)cc(C)cc2C)C1=O] | 7.60 (1H, br), 6.86 (2H, s), 3.15 (1H, br), 3.05-2.90 (1H, m), 2.90-2.75 (2H, m), 2.65 (1H, d), 2.50-2.40 (1H, m), 2.25 (3H, s), 2.12 (1H, d), 2.09 (6H, s), 1.50-1.25 (2H, m), 1.12-1.00 (1H, m), 0.90-0.80 (6H, m) |
| A178 | 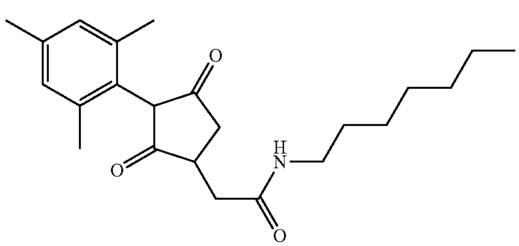 [SMILES: CCCCCCCNC(=O)CC1CC(=O)C(c2c(C)cc(C)cc2C)C1=O] | 7.35 (1H, br), 6.85 (2H, s), 3.20-3.10 (1H, m), 3.10-3.00 (2H, m), 2.82 (1H, dd), 2.62 (1H, d), 2.50-2.10 (1H, m), 2.25 (3H, s), 2.12 (1H, d), 2.10 (6H, s), 1.40-1.20 (10H, m), 0.88 (3H, t) |
| A179 | 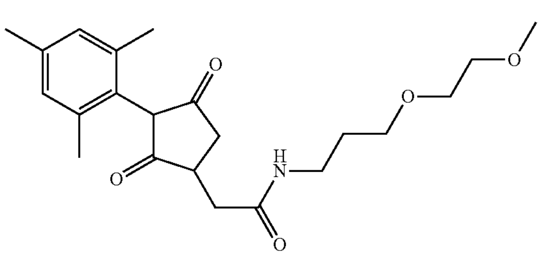 | 13.60 (1H, br), 7.72 (1H, br), 6.87 (2H, s), 3.60-3.50 (6H, m), 3.39 (3H, s), 3.38-3.29 (2H, m), 3.18 (1H, m), 2.75 (1H, dd), 2.68-2.47 (2H, m), 2.25 (3H, s), 2.18 (1H, d), 2.10 (6H, s), 1.79-1.70 (2H, m) |

TABLE T1-continued

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (400 MHz, CDCl$_3$) unless stated |
|---|---|---|
| A180 | 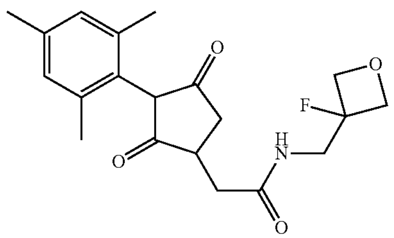 [SMILES: Cc1cc(C)c(C2C(=O)CC(CC(=O)NCC3(F)COC3)C2=O)c(C)c1] | 13.25 (1H, br), 8.08 (1H, br), 6.87 (2H, s), 4.69 (2H, dd), 4.51-4.41 (2H, m), 3.18 (1H, br), 2.87 (1H, dd), 2.70 (1H, d), 2.52-2.45 (1H, m), 2.28 (3H, s), 2.16 (1H, d), 2.10 (6H, s) |
| A181 | 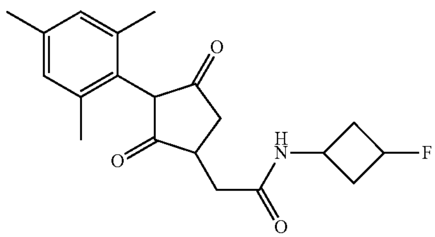 [SMILES: Cc1cc(C)c(C2C(=O)CC(CC(=O)NC3CC(F)C3)C2=O)c(C)c1] | (~1:1 mixture of cis/trans) 8.20 (1H, br), 6.87 (2H, s), 5.20-5.00 (0.5H, m), 4.90-4.65 (0.5H, m), 4.48-4.35 (m, 0.5H), 3.90-3.80 (0.5H, m), 3.10 (1H, br), 2.95-2.75 (2H, m), 2.65-2.40 (3H, m), 2.30-2.10 (5H, m), 2.10-2.05 (7H, m) |
| A182 | 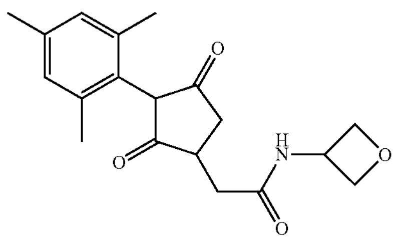 [SMILES: Cc1cc(C)c(C2C(=O)CC(CC(=O)NC3COC3)C2=O)c(C)c1] | 8.50 (1H, br), 6.85 (2H, s), 4.85-4.70 (3H, m), 4.45-4.35 (2H m), 3.15-3.05 (1H, m), 2.81 (1H, dd), 2.57 (1H, d), 2.45-2.40 (1H, m), 2.25 (3H, s), 2.20 (1H, d), 2.10 (6H, s) |
| A183 | 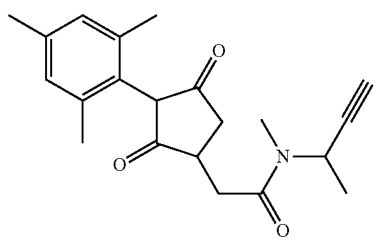 [SMILES: C#CC(C)N(C)C(=O)CC1CC(=O)C(c2c(C)cc(C)cc2C)C1=O] | Restricted rotation and mix of diastereoisomers 6.86 (2H, s), 5.66-5.50 (1H, m), 3.32 (1H, br), 3.16-2.77 (5H, m), 2.72-2.49 (1H, m), 2.36 (1H, s), 2.30-2.18 (4H, m), 2.15-2.03 (6H, m), 1.55-1.33 (3H, m) |
| A184 | 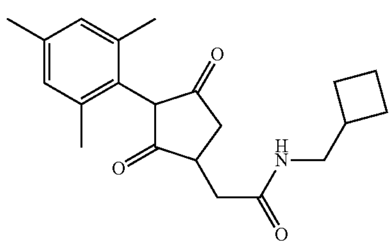 | 7.34 (1H, br), 6.87 (2H, s), 3.20-3.00 (3H, m), 2.72 (1H, dd), 2.65 (1H, d), 2.50-2.40 (1H, m), 2.35-2.25 (1H, m), 2.25 (3H, s), 2.12 (1H, d), 2.10 (6H, s), 2.00-1.90 (2H, m), 1.85-1.75 (2H, m), 1.67-1.52 (2H, m) |
| A185 | 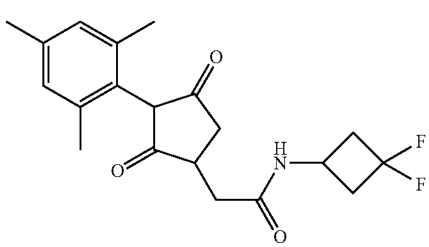 [SMILES: Cc1cc(C)c(C2C(=O)CC(CC(=O)NC3CC(F)(F)C3)C2=O)c(C)c1] | (d4-MeOH) 6.85 (2H, s), 4.15-4.10 (1H, m), 2.95-2.85 (3H, m), 2.75-2.65 (2H, m), 2.60-2.45 (2H, m), 2.30-2.25 (2H, m), 2.25 (3H, s), 2.10 (3H, s), 2.05 (3H, s) |

TABLE T1-continued

It should be noted that certain compounds of the invention may exist as a mixture of isomers, including sometimes atropisomers, e.g. as noted above, under the conditions used to obtain the ¹H NMR data. Where this has occurred, the characterising data are reported for all isomers present at ambient temperature in the specified solvent. Unless otherwise stated, proton (¹H) NMR spectra disclosed herein were recorded at ambient temperature.

| Compound Number | Structure | ¹H NMR (400 MHz, CDCl₃) unless stated |
|---|---|---|
| A186 | 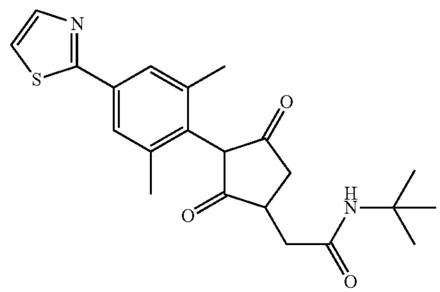 [SMILES: Cc1cc(-c2nccs2)cc(C)c1C1C(=O)CC(CC(=O)NC(C)(C)C)C1=O] | (d4-MeOH) 7.82 (d, 1H), 7.62 (s, 2H), 7.54 (d, 1H), 3.21-3.13 (m, 1H), 2.41 (dd, 1H), 2.70 (dd, 1H), 2.50-2.39 (m, 2H), 2.19 (s, 6H), 1.35 (s, 9H) |
| A187 | 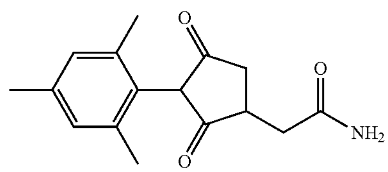 [SMILES: Cc1cc(C)c(C2C(=O)CC(CC(N)=O)C2=O)c(C)c1] | (d4-MeOH) 6.87 (s, 2H), 4.60 (br, 2H), 3.20-3.12 (m, 1H), 2.92 (dd, 1H), 2.73 (dd, 1H), 2.54 (dd, 1H), 2.41 (d, 1H), 2.25 (s, 3H), 2.10 (s, 6H) |

TABLE T2

| Compound Number | Structure | Physical Data LCMS or ¹H NMR (400 MHz, CDCl₃) unless stated. |
|---|---|---|
| B1 | 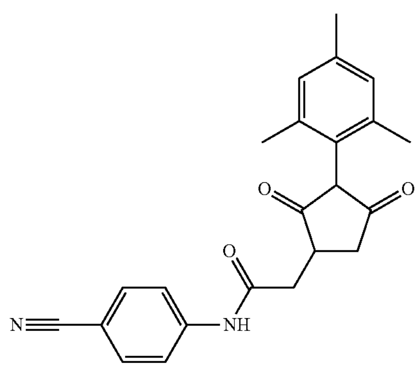 [SMILES: Cc1cc(C)c(C2C(=O)CC(CC(=O)Nc3ccc(C#N)cc3)C2=O)c(C)c1] | 1H NMR (400 MHz, d6-DMSO) 10.4 (s, 1H), 7.72 (s, 4H), 6.74 (s, 2H), 3.00-2.70 (m, 3H), 2.48-2.35 (m, 2H), 2.14 (s, 3H), 1.92 (d, 6H) |
| B2 | 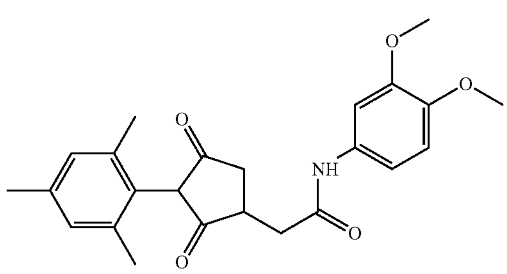 | 1H NMR (CDCl3 + 2 drops of d6-DMSO) 9.65 (br, 1H), 7.30 (s, 1H), 6.99 (d, 1H), 6.87 (d, 2H), 6.81 (d, 1H), 3.86 (2 × s, 6H), 3.40-3.22 (m, 1H), 3.06-2.75 (m, 2H), 2.26 (s, 3H), 2.20-2.02 (m, 8H) |

TABLE T2-continued

| Compound Number | Structure | Physical Data LCMS or $^1$H NMR (400 MHz, CDCl$_3$) unless stated. |
|---|---|---|
| B3 | 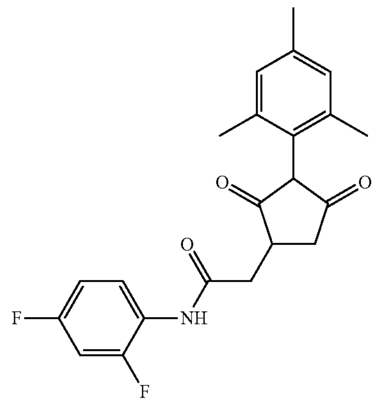 [SMILES: Cc1cc(C)c(C2C(=O)CC(CC(=O)Nc3ccc(F)cc3F)C2=O)c(C)c1] | 8.66 (br.s, 1H), 7.95-7.85 (m, 1H), 6.91-6.81 (m, 1H), 6.81 (s, 2H), 3.31-3.22 (m, 1H), 2.97-2.82 (m, 2H), 2.82-2.72 (m, 1H), 2.32-2.23 (m, 1H), 2.20 (s, 3H), 2.06 (s, 6H) |
| B4 | 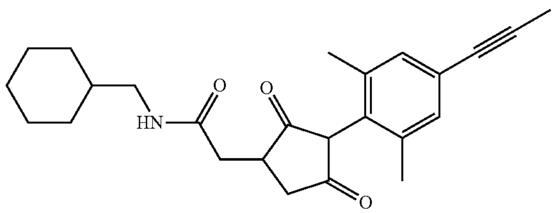 [SMILES: CC#Cc1cc(C)c(C2C(=O)CC(CC(=O)NCC3CCCCC3)C2=O)c(C)c1] | 1.83 mins m/z 394.28 [M + H]+ |
| B5 | 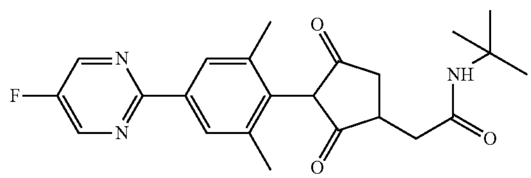 [SMILES: Cc1cc(-c2ncc(F)cn2)cc(C)c1C1C(=O)CC(CC(=O)NC(C)(C)C)C1=O] | 1H NMR (400 MHz, CD3OD) 8.75 (s, 2H), 8.07 (s, 2H), 3.24-3.11 (m, 1H), 3.01-2.84 (m, 1H), 2.79-2.62 (m, 1H), 2.54-2.33 (m, 2H), 2.20 (s, 6H), 1.36 (s, 9H) |
| B6 | 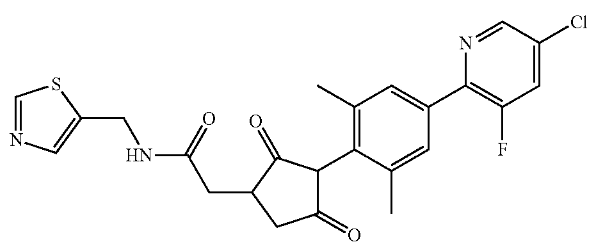 [SMILES: Cc1cc(-c2ncc(Cl)cc2F)cc(C)c1C1C(=O)CC(CC(=O)NCc2cncs2)C1=O] | 1.20 mins, m/z = 484.14 (M + H)+ |
| B7 | 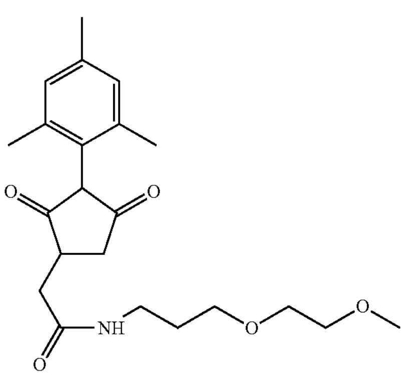 | 7.84-7.60 (m, 1H), 6.86 (s, 2H), 3.66-3.49 (m, 6H), 3.43-3.08 (m, 6H), 2.83 (s, 1H), 2.70-2.44 (m, 2H), 2.32-2.02 (m, 10H), 1.75 (t, 2H) |
| B8 | 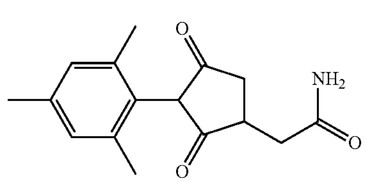 [SMILES: Cc1cc(C)c(C2C(=O)CC(CC(N)=O)C2=O)c(C)c1] | 1H NMR (400 MHz, CD3OD) 6.88 (s, 2H), 4.57 (br.s., 2H), 3.25-3.08 (m, 1H), 2.92 (dd, 1H), 2.74 (d, 1H), 2.63-2.35 (m, 2H), 2.26 (s, 3H), 2.09 (d, 6H) |

TABLE T2-continued

| Compound Number | Structure | Physical Data LCMS or ¹H NMR (400 MHz, CDCl₃) unless stated. |
|---|---|---|
| B9 | 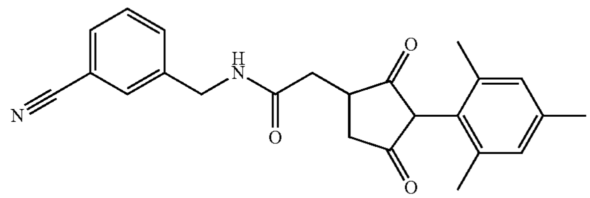 [SMILES: Cc1cc(C)c(C2C(=O)CC(CC(=O)NCc3cccc(C#N)c3)C2=O)c(C)c1] | 1.22 mins, m/z = 389.24 (M + H)+ |
| B10 | 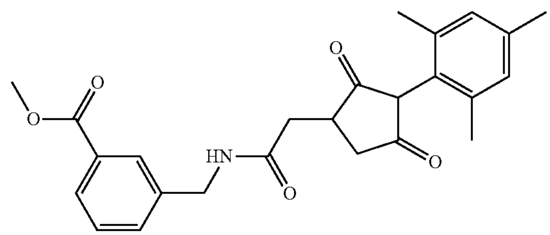 | 1.27 mins, m/z = 422.26 (M + H)+ |
| B11 | 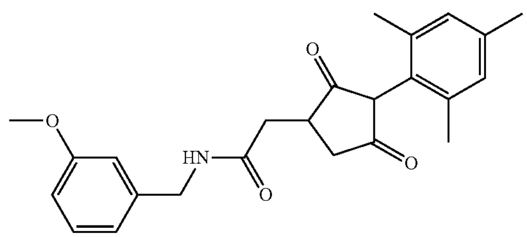 | 1.29 mins, m/z = 394.26 (M + H)+ |
| B12 | 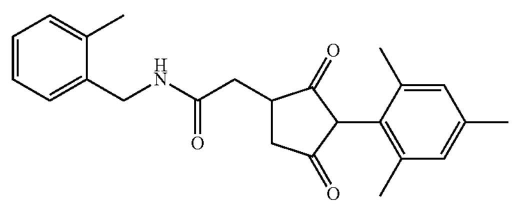 [SMILES: Cc1cc(C)c(C2C(=O)CC(CC(=O)NCc3ccccc3C)C2=O)c(C)c1] | 1.36 mins, m/z = 378.26 (M + H)+ |
| B13 | 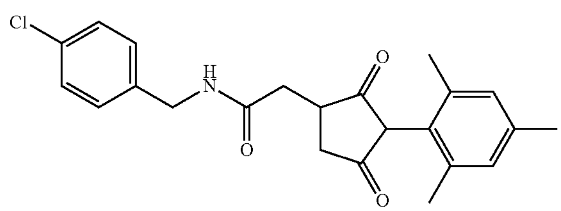 [SMILES: Cc1cc(C)c(C2C(=O)CC(CC(=O)NCc3ccc(Cl)cc3)C2=O)c(C)c1] | 1.38 mins, m/z = 398.21 (M + H)+ |
| B14 | 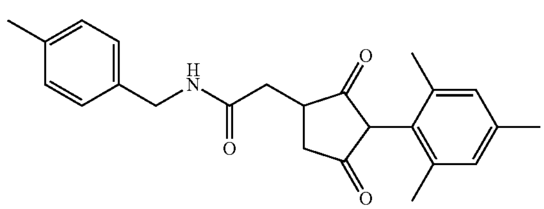 | 1.37 mins, m/z = 378.25 (M + H)+ |
| B15 | 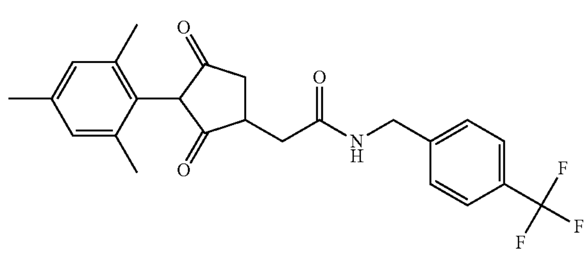 [SMILES: Cc1cc(C)c(C2C(=O)CC(CC(=O)NCc3ccc(C(F)(F)F)cc3)C2=O)c(C)c1] | 1.41 mins, m/z = 432.24 (M + H)+ |

TABLE T2-continued

| Compound Number | Structure | Physical Data LCMS or ¹H NMR (400 MHz, CDCl₃) unless stated. |
|---|---|---|
| B16 | 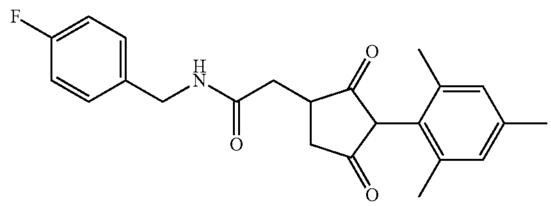 [SMILES: Cc1cc(C)c(C2C(=O)CC(CC(=O)NCc3ccc(F)cc3)C2=O)c(C)c1] | 1.30 mins, m/z = 382.21 (M + H)+ |
| B17 | 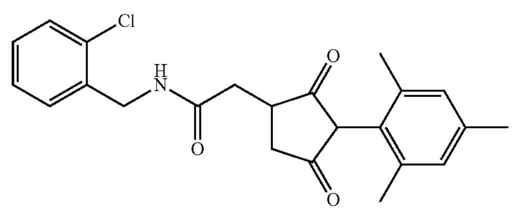 | 1.36 mins, m/z = 398.21 (M + H)+ |
| B18 | 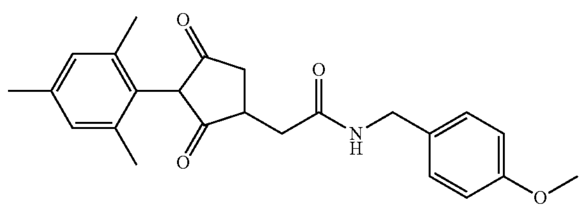 | 1.29 mins, m/z = 394.26 (M + H)+ |
| B19 | 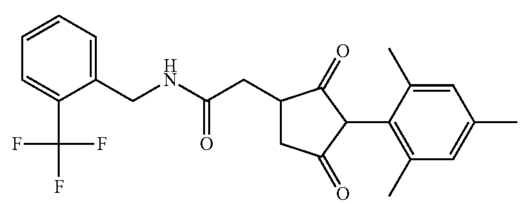 [SMILES: Cc1cc(C)c(C2C(=O)CC(CC(=O)NCc3ccccc3C(F)(F)F)C2=O)c(C)c1] | 1.41 mins, m/z = 432.23 (M + H)+ |
| B20 | 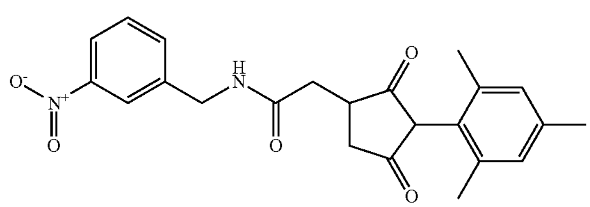 [SMILES: Cc1cc(C)c(C2C(=O)CC(CC(=O)NCc3cccc([N+](=O)[O-])c3)C2=O)c(C)c1] | 1.27 mins, m/z = 409.25 (M + H)+ |
| B21 | 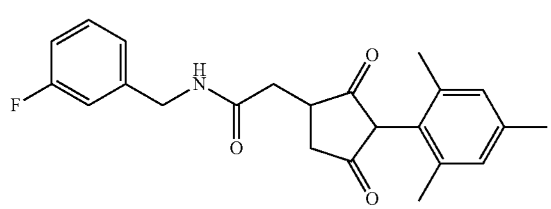 [SMILES: Cc1cc(C)c(C2C(=O)CC(CC(=O)NCc3cccc(F)c3)C2=O)c(C)c1] | 1.30 mins, m/z = 382.21 (M + H)+ |
| B22 | 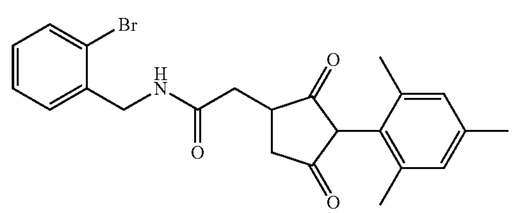 [SMILES: Cc1cc(C)c(C2C(=O)CC(CC(=O)NCc3ccccc3Br)C2=O)c(C)c1] | 1.38 mins, m/z = 442.1 (M + H)+ |

TABLE T2-continued

| Compound Number | Structure | Physical Data LCMS or ¹H NMR (400 MHz, CDCl₃) unless stated. |
|---|---|---|
| B23 | 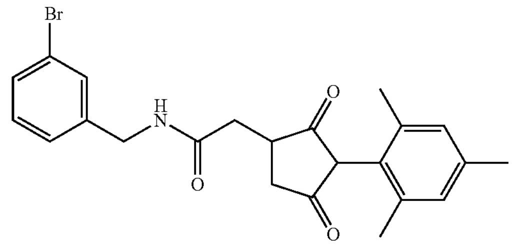 [SMILES: Cc1cc(C)c(C2C(=O)CC(CC(=O)NCc3cccc(Br)c3)C2=O)c(C)c1] | 1.40 mins, m/z = 442.1 (M + H)+ |
| B24 | 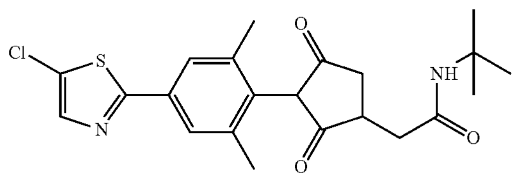 [SMILES: Cc1cc(-c2ncc(Cl)s2)cc(C)c1C1C(=O)CC(CC(=O)NC(C)(C)C)C1=O] | 7.60 (s, 1H), 7.52 (s, 2H), 6.42 (s, 1H), 3.28-3.19 (m, 1H), 2.84 (dd, 1H), 2.65-2.59 (m, 2H), 2.19 (d, 6H), 2.19-2.12 (m, 1H), 1.33 (s, 9H) |
| B25 | 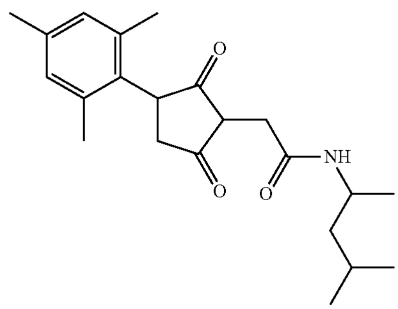 [SMILES: Cc1cc(C)c(C2CC(=O)C(CC(=O)NC(C)CC(C)C)C2=O)c(C)c1] | 6.87 (s, 2H), 6.76 (d, 1H), 4.09-3.94 (m, 1H), 3.30-3.12 (m, 1H), 2.93-2.79 (m, 1H), 2.73-2.48 (m, 2H), 2.25 (s, 3H), 2.10 (s, 6H), 1.65-1.48 (m, 1H), 1.37-1.14 (m, 3H), 1.11-1.02 (m, 3H), 0.94-0.81 (m, 6H) |
| B26 | 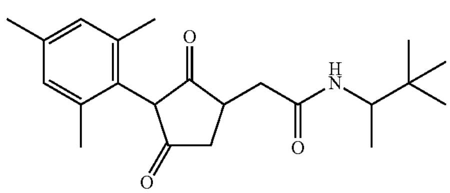 [SMILES: Cc1cc(C)c(C2C(=O)CC(CC(=O)NC(C)C(C)(C)C)C2=O)c(C)c1] | 6.78 (s, 2H), 6.66-6.53 (m, 1H), 3.93-3.80 (m, 1H), 3.30-3.16 (m, 1H), 2.96-2.81 (m, 1H), 2.75-2.55 (m, 2H), 2.25-2.18 (m, 4H), 2.07 (s, 6H), 1.09-0.98 (m, 3H), 0.90-0.85 (m, 9H) |
| B27 | 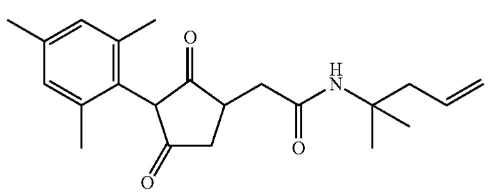 [SMILES: C=CCC(C)(C)NC(=O)CC1CC(=O)C(c2c(C)cc(C)cc2C)C1=O] | 6.78 (s, 2H), 6.27 (s, 1H), 5.81-5.62 (m, 1H), 5.18-5.04 (m, 2H), 3.72-3.54 (m, 1H), 3.24-3.20 (m, 1H), 2.92-2.85 (m, 1H), 2.63-2.58 (m, 1H), 2.44-2.40 (m, 2H), 2.23-2.18 (m, 4H), 2.08 (s, 3H), 2.07 (s, 3H), 1.32 (s, 6H) |
| B28 | 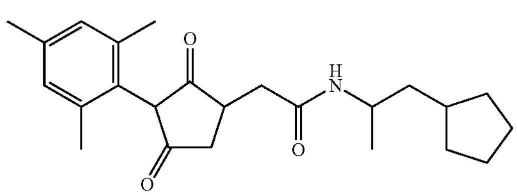 [SMILES: Cc1cc(C)c(C2C(=O)CC(CC(=O)NC(C)CC3CCCC3)C2=O)c(C)c1] | 6.79 (s, 2H), 6.62 (d, 1H), 4.07-3.90 (m, 1H) 3.75-3.54 (m, 1H), 3.27-3.20 (m, 1H), 2.95-2.82 (m, 1H), 2.67-2.50 (m, 2H), 2.25-2.20 (m, 4H), 2.08 (s, 6H), 1.88-1.66 (m, 3H), 1.64-1.32 (m, 5H), 1 16-0.99 (m, 5H) |
| B29 | 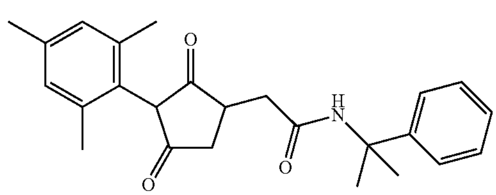 [SMILES: Cc1cc(C)c(C2C(=O)CC(CC(=O)NC(C)(C)c3ccccc3)C2=O)c(C)c1] | 7.37-7.19 (m, 5H), 7.08 (s, 1H), 6.79 (s, 2H), 3.70-3.55 (m, 1H), 3.23-3.12 (m, 1H), 2.88-2.82 (m, 1H), 2.72-2.67 (m, 1H), 2.59-2.52 (m, 1H), 2.19 (s, 3H), 2.07 (s, 3H), 2.04 (s, 3H), 1.65 (s, 3H), 1.63 (s, 3H) |

TABLE T2-continued

| Compound Number | Structure | Physical Data LCMS or ¹H NMR (400 MHz, CDCl₃) unless stated. |
|---|---|---|
| B30 | 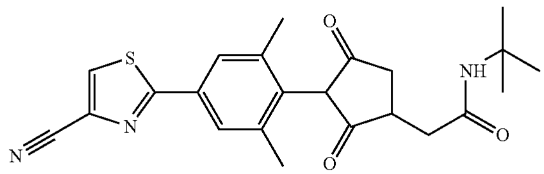 [SMILES: Cc1cc(-c2nc(C#N)cs2)cc(C)c1C1C(=O)CC(CC(=O)NC(C)(C)C)C1=O] | 1H NMR (400 MHz, CD3OD) 8.44 (s, 1H), 7.69 (s, 2H), 3.22-3.13 (m, 1H), 2.92 (dd, 1H), 2.70 (dd, 1H), 2.52-2.39 (m, 2H), 2.20 (s, 6H), 1.36 (s, 9H) |
| B31 | 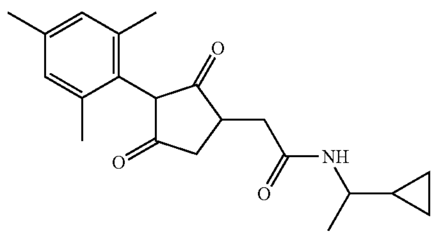 [SMILES: Cc1cc(C)c(C2C(=O)CC(CC(=O)NC(C)C3CC3)C2=O)c(C)c1] | 6.81 (s, 2H), 6.49-6.38 (m, 1H), 3.44-3.25 (m, 2H), 2.97-2.81 (m, 1H), 2.73-2.61 (m, 2H), 2.25-2.21 (m, 4H), 2.09 (s, 6H), 1.23-1.19 (m, 3H), 0.77-0.73 (m, 1H), 0.59-0.39 (m, 2H), 0.38-0.16 (m, 2H) |
| B32 | 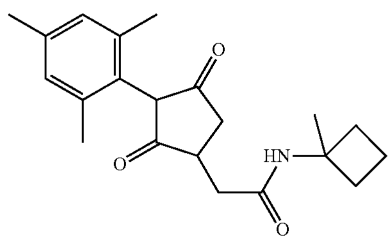 [SMILES: Cc1cc(C)c(C2C(=O)CC(CC(=O)NC3(C)CCC3)C2=O)c(C)c1] | 6.88 (s, 2H), 3.20-3.10 (m, 1H), 2.93-2.86 (m, 1H), 2.74-2.68 (m, 1H), 2.45-2.32 (m, 4H), 2.27 (s, 3H), 2.08 (s, 6H), 2.08-2.00 (m, 2H), 1.95-1.85 (m, 2H), 1.47 (s, 3H) |
| B33 | 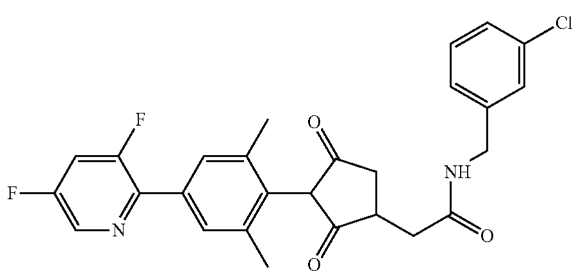 [SMILES: Cc1cc(-c2ncc(F)cc2F)cc(C)c1C1C(=O)CC(CC(=O)NCc2cccc(Cl)c2)C1=O] | 1H NMR (400 MHz, CD3OD) 8.42 (s, 1H), 7.68-7.60 (m, 1H), 7.53 (s, 2H), 7.34-7.20 (m, 4H), 4.38 (s, 2H), 3.23-3.14 (m, 1H), 2.93 (dd, 1H), 2.83 (dd, 1H), 2.56-2.46 (m, 2H), 2.19 (d, 6H) |
| B34 | 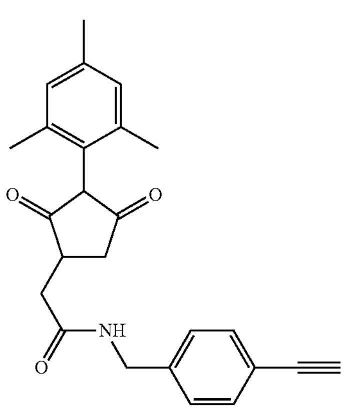 [SMILES: C#Cc1ccc(CNC(=O)CC2CC(=O)C(c3c(C)cc(C)cc3C)C2=O)cc1] | 7.42 (d, 2H), 7.27 (d, 2H), 6.84 (s, 2H), 4.37 (s, 2H), 3.44 (s, 1H), 3.19-3.10 (m, 1H), 2.88 (dd, 1H), 2.79 (dd, 1H), 2.50-2.39 (m, 2H), 2.23 (s, 3H), 2.03 (d, 6H) |

TABLE T2-continued

| Compound Number | Structure | Physical Data LCMS or ¹H NMR (400 MHz, CDCl₃) unless stated. |
|---|---|---|
| B35 | 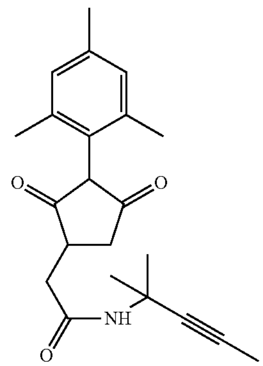 [SMILES: CC#CC(C)(C)NC(=O)CC1CC(=O)C(c2c(C)cc(C)cc2C)C1=O] | 13.16-12.86 (m, 1H), 6.86 (d, 3H), 3.32-3.12 (m, 1H), 2.90-2.70 (m, 1H), 2.69-2.42 (m, 2H), 2.25 (s, 3H), 2.10 (s, 7H), 1.80 (s, 3H), 1.53 (d, 6H) |
| B36 | 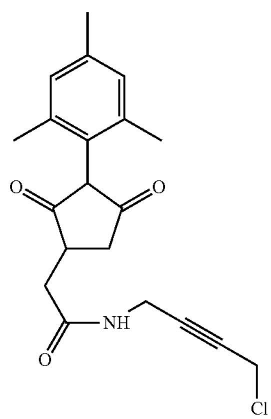 [SMILES: Cc1cc(C)c(C2C(=O)CC(CC(=O)NCC#CCCl)C2=O)c(C)c1] | 8.00-7.63 (m, 1H), 6.88 (d, 2H), 4.11 (t, 2H), 3.83 (d, 2H), 3.29-3.07 (m, 1H), 2.85 (dd, 1H), 2.60 (br.s., 2H), 2.31-2.03 (m, 10H) |
| B37 | 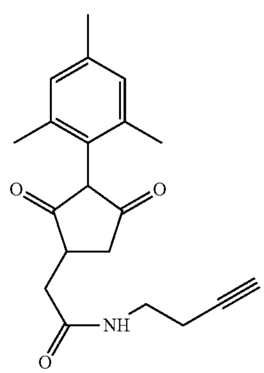 [SMILES: C#CCCNC(=O)CC1CC(=O)C(c2c(C)cc(C)cc2C)C1=O] | 7.71-7.43 (m, 1H), 6.88 (d, 2H), 3.29-3.06 (m, 3H), 2.83 (dd, 1H), 2.73-2.39 (m, 2H), 2.34-1.94 (m, 13H) |
| B38 | 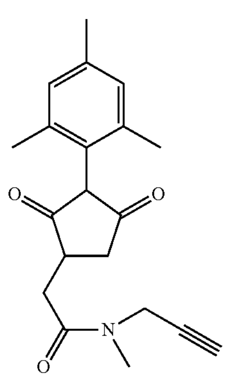 [SMILES: C#CCN(C)C(=O)CC1CC(=O)C(c2c(C)cc(C)cc2C)C1=O] | 6.86 (d, 2H), 4 40-3.95 (m, 2H), 3.42-3.26 (m, 1H), 3.18-2.95 (m, 4H), 2.88 (dd, 1H), 2.77-2.53 (m, 1H), 2.44-2.19 (m, 5H), 2.10 (d, 6H) |

TABLE T2-continued

| Compound Number | Structure | Physical Data LCMS or $^1$H NMR (400 MHz, CDCl$_3$) unless stated. |
|---|---|---|
| B39 | 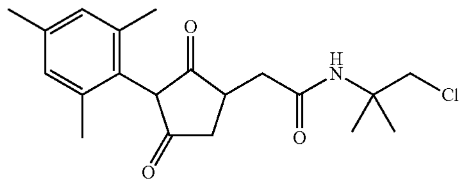 [SMILES: Cc1cc(C)c(C2C(=O)CC(CC(=O)NC(C)(C)CCl)C2=O)c(C)c1] | 1HNMR (400 MHz, CD3OD) 6.86 (s, 2H), 4.00-3.80 (m, 2H), 3.16-3.04 (m, 1H), 2.87 (dd, 1H), 2.74 (dd, 1H), 2.49-2.32 (m, 2H), 2.25 (s, 3H), 2.06 (s, 6H), 1.39 (d, 6H) |
| B40 | 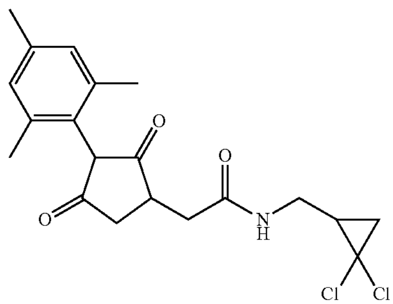 [SMILES: Cc1cc(C)c(C2C(=O)CC(CC(=O)NCC3CC3(Cl)Cl)C2=O)c(C)c1] | 1H NMR (400 MHz, CD3OD) 6.91-6.80 (m, 2H), 3.56-3.39 (m, 1H), 3.28-3.11 (m, 2H), 2.95-2.76 (m, 2H), 2.50-2.41 (m, 2H), 2.28-2.21 (m, 3H), 2.11-2.01 (m, 6H), 1.99-1.86 (m, 1H), 1.66 (dd, 1H), 1.31 (t, 1H) |
| B41 | 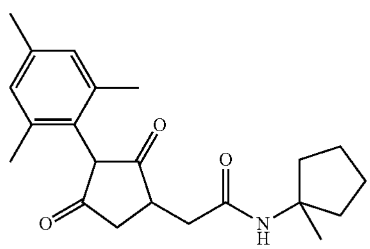 [SMILES: Cc1cc(C)c(C2C(=O)CC(CC(=O)NC3(C)CCCC3)C2=O)c(C)c1] | 1H NMR (400 MHz, CD3OD) 6.86 (s, 2H), 3.13 (dq, 1H), 2.86 (dd, 1H), 2.72-2.64 (m, 1H), 2.45-2.33 (m, 2H), 2.25 (s, 3H), 2.07-1.98 (m, 8H), 1.79-1.57 (m, 6H), 1.44-1.36 (m, 3H) |
| B42 | 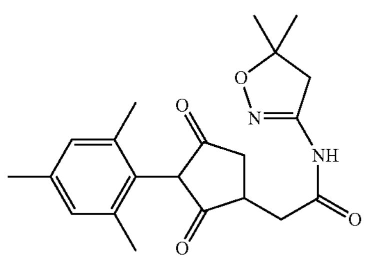 [SMILES: Cc1cc(C)c(C2C(=O)CC(CC(=O)NC3=NOC(C)(C)C3)C2=O)c(C)c1] | 10.63-10.36 (m, 1H), 6.85 (d, 2H), 3.24 (d, 3H), 2.66 (br.s., 3H), 2.24 (s, 4H), 2.06 (d, 6H), 1.40 (d, 6H) |
| B43 | 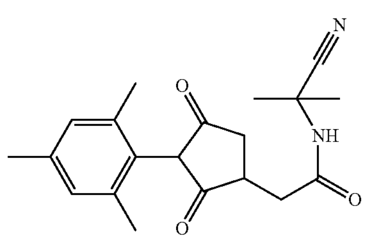 [SMILES: Cc1cc(C)c(C2C(=O)CC(CC(=O)NC(C)(C)C#N)C2=O)c(C)c1] | 8.16 (s, 1H), 6.87 (d, 2H), 3.30-3.11 (m, 1H), 2.95-2.44 (m, 3H), 2.26 (s, 4H), 2.07 (s, 6H), 1.49 (d, 6H) |
| B44 | 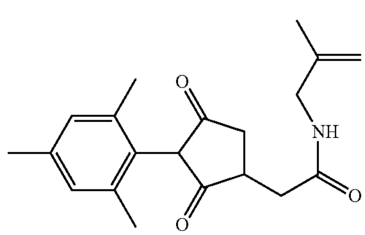 [SMILES: C=C(C)CNC(=O)CC1CC(=O)C(c2c(C)cc(C)cc2C)C1=O] | 13.94-13.14 (m, 1H), 7.72-7.37 (m, 1H), 6.86 (s, 2H), 4.91-4.58 (m, 2H), 3.69-3.37 (m, 2H), 3.26-3.03 (m, 1H), 2.81 (dd, 3H), 2.31-2.00 (m, 10H), 1.67 (s, 3H) |

TABLE T2-continued
| Compound Number | Structure | Physical Data LCMS or ¹H NMR (400 MHz, CDCl₃) unless stated. |
|---|---|---|
| B45 | 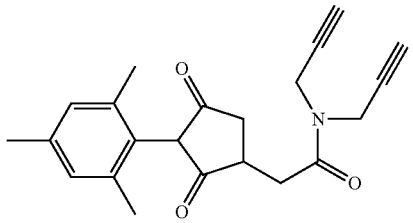 [SMILES: C#CCN(CC#C)C(=O)CC1CC(=O)C(c2c(C)cc(C)cc2C)C1=O] | 6.86 (d, 2H), 4 44-4.14 (m, 4H), 3.45-2.95 (m, 2H), 2.89 (dd, 1H), 2.81-2.64 (m, 1H), 2.40 (s, 1H), 2.34-2.19 (m, 5H), 2.09 (d, 6H) |
| B46 | 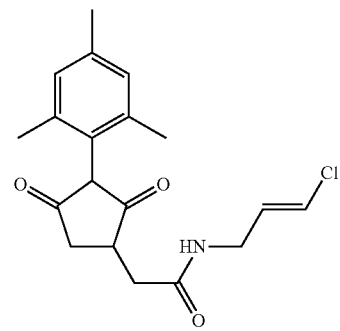 [SMILES: Cc1cc(C)c(C2C(=O)CC(CC(=O)NC/C=C/Cl)C2=O)c(C)c1] | 13.68-13.20 (m, 1H), 7.98-7.53 (m, 1H), 6.88 (d, 2H), 6.05 (d, 1H), 5.82-5.57 (m, 1H), 3.93-3.36 (m, 2H), 3.23-3.01 (m, 1H), 2.92-2.72 (m, 1H), 2.70-2.35 (m, 2H), 2.34-2.02 (m, 10H) |
| B47 | 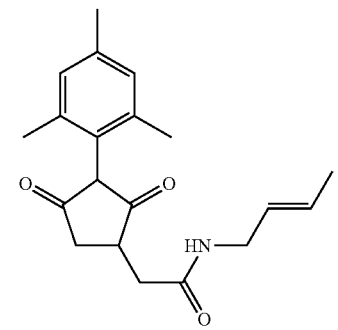 [SMILES: C/C=C/CNC(=O)CC1CC(=O)C(c2c(C)cc(C)cc2C)C1=O] | 13.69-13.30 (m, 1H), 7.22-7.00 (m, 1H), 6.86 (s, 2H), 5.68-5.19 (m, 2H), 3.66 (d, 2H), 3.32-3.02 (m, 1H), 2.79 (d, 1H), 2.67-2.38 (m, 2H), 2.33-1.95 (m, 10H), 1.75-1.55 (m, 3H) |
| B48 | 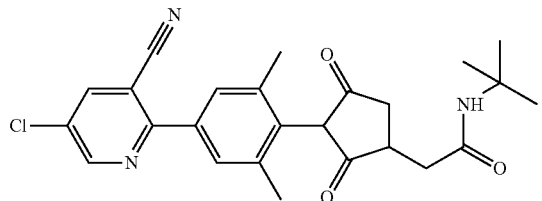 | 1H NMR (400 MHz, CD3OD) 8.83 (s, 1H), 8.37 (s, 1H), 7.59 (s, 2H), 3.22-3.13 (m, 1H), 2.91 (dd, 1H), 2.72 (dd, 1H), 2.50-2.39 (m, 2H), 2.22 (s, 6H), 1.36 (s, 9H) |
| B49 | 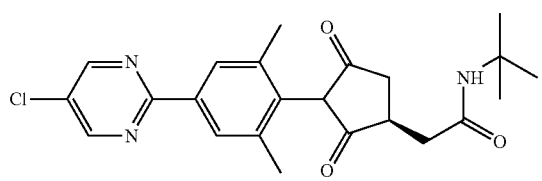 [SMILES: Cc1cc(-c2ncc(Cl)cn2)cc(C)c1C1C(=O)C[C@@H](CC(=O)NC(C)(C)C)C1=O] | 1HNMR (400 MHz, CD3OD) 8.78 (s, 2H), 8.06 (s, 2H), 7.87 (br, 1H), 3.22-3.13 (m, 1H), 2.92 (dd, 1H), 2.70 (dd, 1H), 2.50-2.38 (m, 2H), 2.20 (s, 6H), 1.34 (s, 9H) |
| B50 | 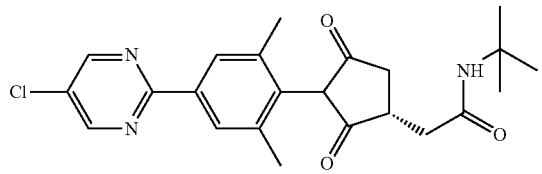 [SMILES: Cc1cc(-c2ncc(Cl)cn2)cc(C)c1C1C(=O)C[C@H](CC(=O)NC(C)(C)C)C1=O] | 1HNMR (400 MHz, CD3OD) 8.75 (s, 2H), 8.04 (s, 2H), 7.88 (br, 1H), 3.22-3.13 (m, 1H), 2.91 (dd, 1H), 2.69 (dd, 1H), 2.51-2.38 (m, 2H), 2.20 (s, 6H), 1.34 (s, 9H) |

TABLE T2-continued

| Compound Number | Structure | Physical Data LCMS or ¹H NMR (400 MHz, CDCl₃) unless stated. |
|---|---|---|
| B51 | 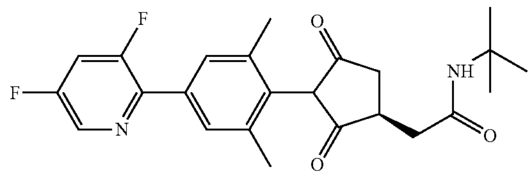 [SMILES: Cc1cc(-c2ncc(F)cc2F)cc(C)c1C1C(=O)C[C@@H](CC(=O)NC(C)(C)C)C1=O] | 1HNMR (400 MHz, d4MeOH, 14ba357) 8.41 (s, 1H), 7.88 (br, 1H), 7.62 (t, 1H), 7.53 (s, 2H), 3.22-3.13 (m, 1H), 2.91 (dd, 1H), 2.70 (dd, 1H), 2.50-2.38 (m, 2H), 2.19 (s, 6H), 1.34 (s, 9H) |
| B52 | 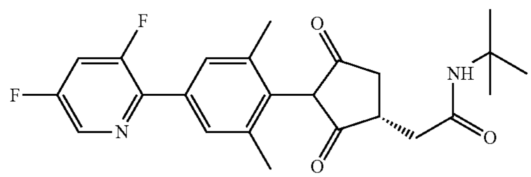 [SMILES: Cc1cc(-c2ncc(F)cc2F)cc(C)c1C1C(=O)C[C@H](CC(=O)NC(C)(C)C)C1=O] | 1HNMR (400 MHz, CD3OD) 8.41 (s, 1H), 7.78 (br, 1H), 7.52 (t, 1H), 7.42 (s, 2H), 3.11-3.02 (m, 1H), 2.80 (dd, 1H), 2.59 (dd, 1H), 2.39-2.28 (m, 2H), 2.08 (s, 6H), 1.24 (s, 9H) |
| B53 | 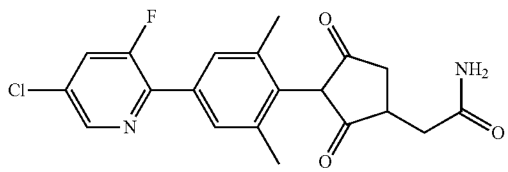 [SMILES: Cc1cc(-c2ncc(Cl)cc2F)cc(C)c1C1C(=O)CC(CC(N)=O)C1=O] | 8.48 (s, 1H), 7.81 (d, 1H), 7.58 (s, 2H), 3.21-3.12 (m, 1H), 2.93 (dd, 1H), 2.79 (dd, 1H), 2.56-2.43 (m, 2H), 2.19 (s, 6H) |
| B54 | 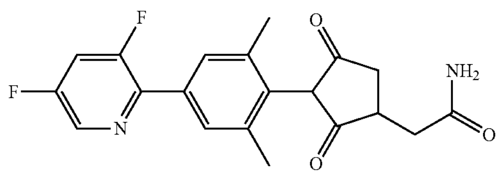 [SMILES: Cc1cc(-c2ncc(F)cc2F)cc(C)c1C1C(=O)CC(CC(N)=O)C1=O] | 1H NMR (400 MHz, CD3OD) 8.44 (d, 1H), 7.65 (ddd, 8.4, 1H), 7.55 (s, 2H), 3.24-3.12 (m, 1H), 2.95 (dd, 1H), 2.80 (m, 1H), 2.51 (t, 2H), 2.23-2.13 (m, 6H) |
| B55 | 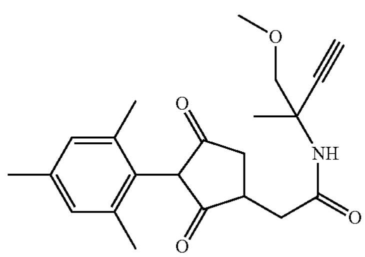 [SMILES: C#CC(C)(COC)NC(=O)CC1CC(=O)C(c2c(C)cc(C)cc2C)C1=O] | 7.20-7.03 (m, 1H), 6.86 (d, 2H), 3.64-3.30 (m, 5H), 3.27-3.14 (m, 1H), 2.93-2.74 (m, 1H), 2.74-2.47 (m, 2H), 2.40 (d, 1H), 2.32-1.89 (m, 10H), 1.58 (s, 3H) |
| B56 | 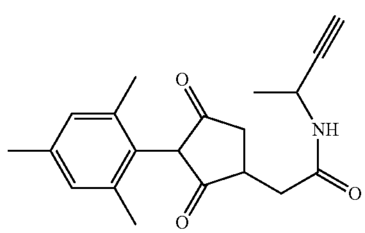 [SMILES: C#CC(C)NC(=O)CC1CC(=O)C(c2c(C)cc(C)cc2C)C1=O] | 7.76-7.47 (m, 1H), 6.87 (s, 2H), 4.82-4.48 (m, 1H), 3.23-3.03 (m, 1H), 2.89-2.70 (m, 1H), 2.65-2.34 (m, 2H), 2.31-2.03 (m, 11H), 1.37 (d, 3H) |
| B57 | 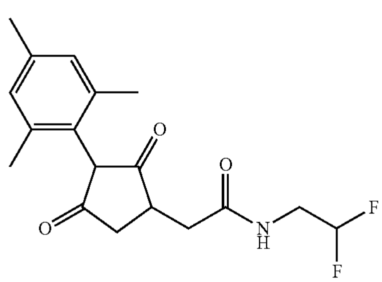 [SMILES: Cc1cc(C)c(C2C(=O)CC(CC(=O)NCC(F)F)C2=O)c(C)c1] | 1H NMR (400 MHz, CD3OD) 6.85 (s, 2H), 6.09-5.71 (m, 1H), 3.64-3.50 (m, 2H), 3.15-3.04 (m, 1H), 2.93-2.76 (m, 2H), 2.46-2.36 (m, 2H), 2.24 (s, 3H), 2.08-2.01 (m, 6H) |

TABLE T2-continued

| Compound Number | Structure | Physical Data LCMS or ¹H NMR (400 MHz, CDCl₃) unless stated. |
|---|---|---|
| B58 | 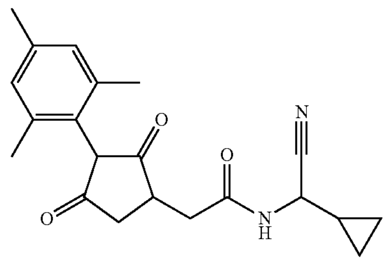 [SMILES: Cc1cc(C)c(C2C(=O)CC(CC(=O)NC(C#N)C3CC3)C2=O)c(C)c1] | 1H NMR (400 MHz, CD3OD) 6.89-6.81 (m, 2H), 4.44 (dd, 1H), 3.12 (br.s., 1H), 2.99-2.75 (m, 2H), 2.54-2.36 (m, 2H), 2.28-2.21 (m, 3H), 2.06 (d, 6H), 1.36-1.28 (m, 1H), 0.78-0.62 (m, 2H), 0.57-0.43 (m, 2H) |
| B59 | 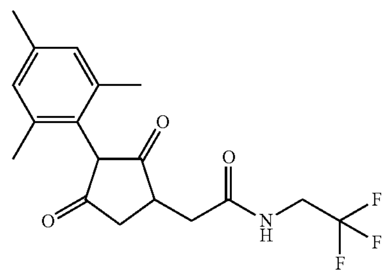 [SMILES: Cc1cc(C)c(C2C(=O)CC(CC(=O)NCC(F)(F)F)C2=O)c(C)c1] | 1H NMR (400 MHz, CD3OD) 6.86 (s, 2H), 3.97-3.84 (m, 2H), 3.17-3.04 (m, 1H), 2.94-2.79 (m, 2H), 2.49-2.36 (m, 2H), 2.26-2.19 (m, 3H), 2.05 (s, 6H) |
| B60 | 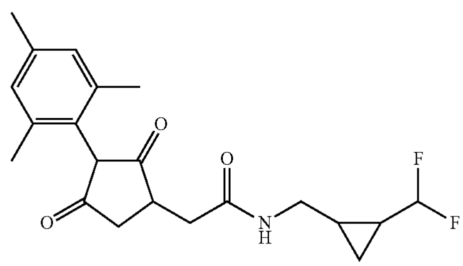 [SMILES: Cc1cc(C)c(C2C(=O)CC(CC(=O)NCC3CC3C(F)F)C2=O)c(C)c1] | 1H NMR (400 MHz, CD3OD) 6.86 (s, 2H), 5.84-5.53 (m, 1H), 3.40 (d, 2H), 3.13 (dd, 1H), 2.95-2.72 (m, 2H), 2.49-2.36 (m, 2H), 2.27-2.19 (m, 3H), 2.09-2.01 (m, 6H), 0.83-0.66 (m, 4H) |
| B61 | 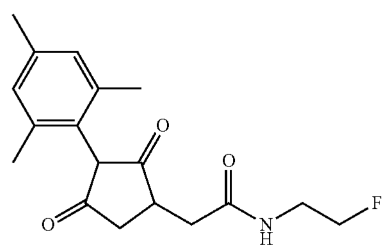 [SMILES: Cc1cc(C)c(C2C(=O)CC(CC(=O)NCCF)C2=O)c(C)c1] | 1H NMR (400 MHz, CD3OD) 6.89-6.80 (m, 2H), 4.56-4.35 (m, 2H), 3.58-3.41 (m, 2H), 3.19-3.07 (m, 1H), 2.94-2.71 (m, 2H), 2.49-2.40 (m, 2H), 2.24 (s, 3H), 2.09-2.03 (m, 6H) |
| B62 | 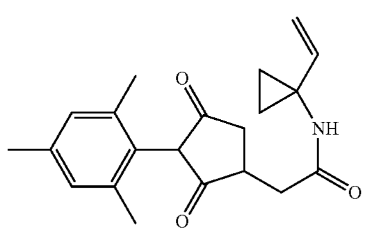 [SMILES: C=CC1(NC(=O)CC2CC(=O)C(c3c(C)cc(C)cc3C)C2=O)CC1] | 7.88-7.67 (m, 1H), 6.87 (d, 2H), 5.44-4.89 (m, 3H), 3.26-3.04 (m, 1H), 2.87 (d, 1H), 2.74-2.48 (m, 2H), 2.25 (s, 4H), 2.15-2.02 (m, 6H), 1.21-0.79 (m, 4H) |
| B63 | 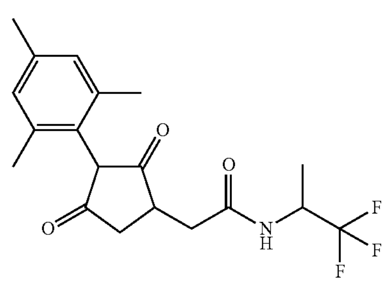 [SMILES: Cc1cc(C)c(C2C(=O)CC(CC(=O)NC(C)C(F)(F)F)C2=O)c(C)c1] | 1H NMR (400 MHz, CD3OD) 6.92-6.76 (m, 2H), 4.65 (dtd, 1H), 3.13 (d, 1H), 2.94-2.76 (m, 2H), 2.51-2.33 (m, 2H), 2.25 (s, 3H), 2.05 (s, 6H), 1.36-1.28 (m, 3H) |

TABLE T2-continued

| Compound Number | Structure | Physical Data LCMS or $^1$H NMR (400 MHz, CDCl$_3$) unless stated. |
|---|---|---|
| B64 | 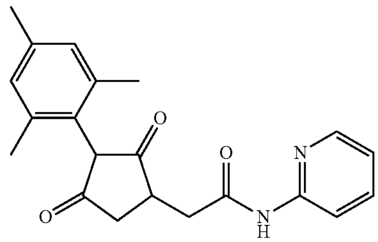 [SMILES: Cc1cc(C)c(C2C(=O)CC(CC(=O)Nc3ccccn3)C2=O)c(C)c1] | 1H NMR (400 MHz, CD3OD) 8.31-8.23 (m, 1H), 8.09 (d, 1H), 7.77 (ddd, 1H), 7.16-7.02 (m, 1H), 6.91-6.80 (m, 2H), 3.20 (dtd, 1H), 3.05-2.88 (m, 2H), 2.67 (dd, 1H), 2.56 (dd, 1H), 2.28-2.19 (m, 3H), 2.07 (d, 6H) |
| B65 | 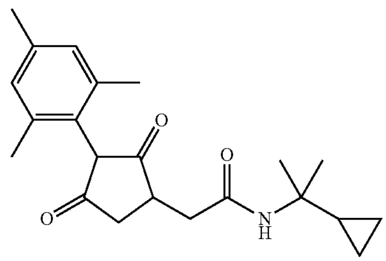 [SMILES: Cc1cc(C)c(C2C(=O)CC(CC(=O)NC(C)(C)C3CC3)C2=O)c(C)c1] | 1H NMR (400 MHz, CD3OD) 6.85 (s, 2H), 3.13 (d, 1H), 2.86 (dd, 1H), 2.70 (dd, 1H), 2.48-2.31 (m, 2H), 2.24 (s, 3H), 2.06 (s, 6H), 1.36-1.28 (m, 1H), 1.25 (d, 6H), 0.46-0.30 (m, 4H) |
| B66 | 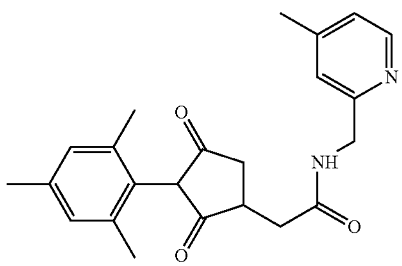 [SMILES: Cc1ccnc(CNC(=O)CC2CC(=O)C(c3c(C)cc(C)cc3C)C2=O)c1] | 1H NMR (400 MHz, CD3OD) 8.30 (d, 1H), 7.27 (s, 1H), 7.17 (d, 1H), 6.84 (s, 2H), 4 48 (s, 2H), 3.19-3.10 (m, 1H), 2.93-2.80 (m, 2H), 2.57-2.42 (m, 2H), 2.36 (s, 3H), 2.23 (s, 3H), 2.03 (d, 6H) |
| B67 | 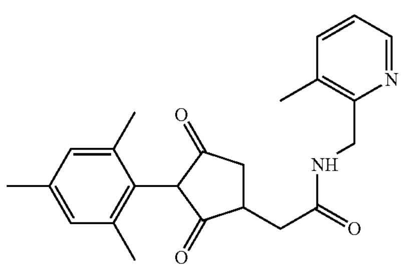 [SMILES: Cc1cc(C)c(C2C(=O)CC(CC(=O)NCc3ncccc3C)C2=O)c(C)c1] | 1H NMR (400 MHz, CD3OD) 8.32 (d, 1H), 7.67 (d, 1H), 7.30-7.23 (m, 1H), 6.82 (s, 2H), 4.53 (s, 2H), 3.20-3.11 (m, 1H), 2.91-2.76 (m, 2H), 2.57-2.49 (m, 1H), 2.49-2.40 (m, 1H), 2.35 (s, 3H), 2.12 (s, 3H), 2.03 (d, 6H) |
| B68 | 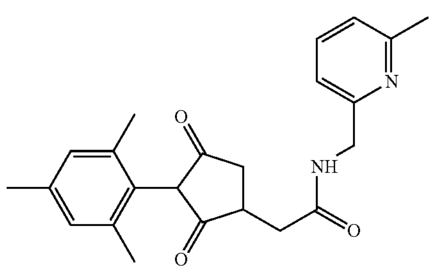 | 1H NMR (400 MHz, CD3OD) 7.69 (t, 1H), 7.24-7.14 (m, 2H), 6.83 (s, 2H), 4 47 (s, 2H), 3.19-3.10 (m, 1H), 2.92-2.78 (m, 2H), 2.55-2.42 (m, 2H), 2.52 (s, 3H), 2.23 (s, 3H), 2.04 (d, 6H) |

TABLE T2-continued

| Compound Number | Structure | Physical Data LCMS or ¹H NMR (400 MHz, CDCl₃) unless stated. |
|---|---|---|
| B69 | 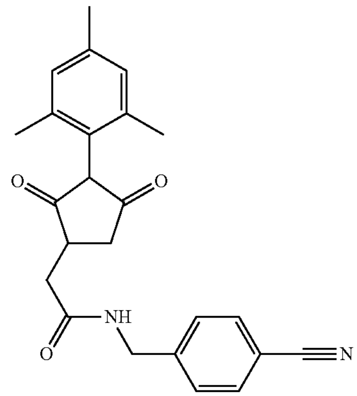 [SMILES: Cc1cc(C)c(C2C(=O)CC(CC(=O)NCc3ccc(C#N)cc3)C2=O)c(C)c1] | 1H NMR (400 MHz, CD3OD) 7.64 (d, 2H), 7 44 (d, 2H), 6.84 (s, 2H), 4.42 (s, 2H), 3.18-3.10 (m, 1H), 2.89 (dd, 1H), 2.80 (dd, 1H), 2.52-2.41 (m, 2H), 2.23 (s, 3H), 2.03 (d, 6H) |
| B70 | 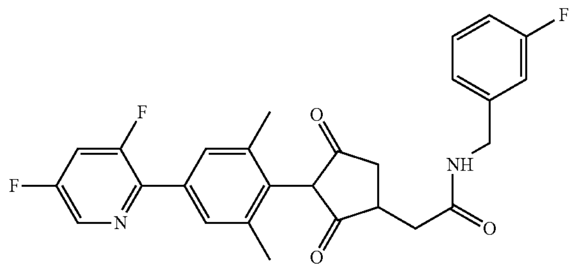 [SMILES: Cc1cc(-c2ncc(F)cc2F)cc(C)c1C1C(=O)CC(CC(=O)NCc2cccc(F)c2)C1=O] | 1H NMR (400 MHz, CD3OD) 8.41 (s, 1H), 7.67-7.59 (m, 1H), 7.52 (s, 2H), 7.36-7.28 (m, 1H), 7.11 (d, 1H), 7.03 (d, 1H), 7.11-6.93 (m, 1H), 4.39 (s, 2H), 3.23-3.14 (m, 1H), 2.93 (dd, 1H), 2.83 (dd, 1H), 2.57-2.46 (m, 2H), 2.18 (s, 6H) |
| B71 | 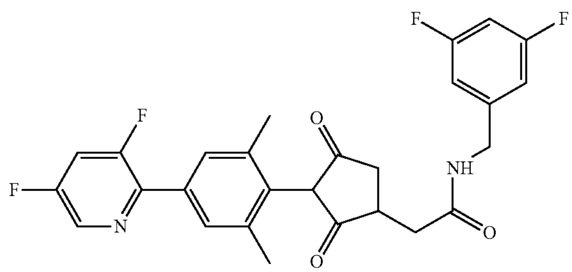 [SMILES: Cc1cc(-c2ncc(F)cc2F)cc(C)c1C1C(=O)CC(CC(=O)NCc2cc(F)cc(F)c2)C1=O] | 1H NMR (400 MHz, CD3OD) 8.42 (s, 1H), 7.67-7.59 (m, 1H), 7.52 (s, 2H), 6.95-6.88 (m, 2H), 6.87-6.78 (m, 1H), 4.38 (s, 2H), 3.22-3.14 (m, 1H), 2.94 (dd, 1H), 2.85 (dd, 1H), 2.57-2.48 (m, 2H), 2.18 (s, 6H) |
| B72 | 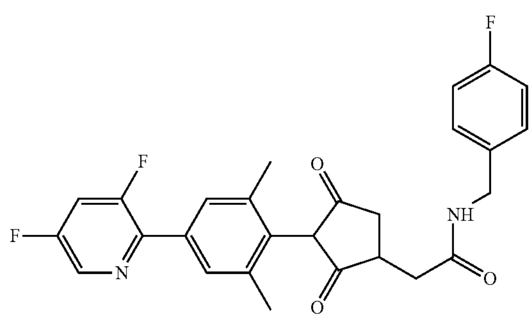 [SMILES: Cc1cc(-c2ncc(F)cc2F)cc(C)c1C1C(=O)CC(CC(=O)NCc2ccc(F)cc2)C1=O] | 1H NMR (400 MHz, CD3OD) 8.42 (s, 1H), 7.68-7.59 (m, 1H), 7.53 (s, 2H), 7.36-7.28 (m, 2H), 7.08-7.00 (m, 2H), 4.37 (s, 2H), 3.23-3.14 (m, 1H), 2.92 (dd, 1H), 2.81 (dd, 1H), 2.56-2.44 (m, 2H), 2.19 (s, 6H) |
| B73 | 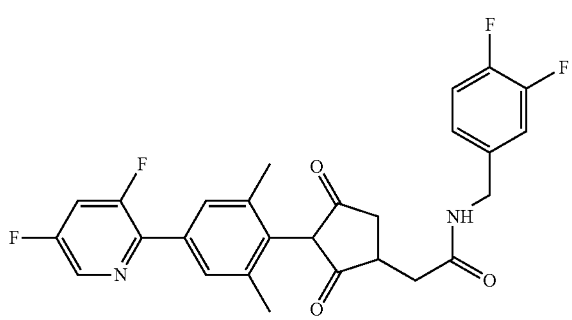 [SMILES: Cc1cc(-c2ncc(F)cc2F)cc(C)c1C1C(=O)CC(CC(=O)NCc2ccc(F)c(F)c2)C1=O] | 1H NMR (400 MHz, CD3OD) 8.42 (s, 1H), 7.69-7.62 (m, 1H), 7 54 (s, 2H), 7.27-7.15 (m, 2H), 7.15-7.08 (m, 1H), 4.36 (s, 2H), 3.23-3.14 (m, 1H), 2.93 (dd, 1H), 2.82 (dd, 1H), 2.54-2.44 (m, 2H), 2.19 (s, 6H) |

TABLE T2-continued

| Compound Number | Structure | Physical Data LCMS or ¹H NMR (400 MHz, CDCl₃) unless stated. |
|---|---|---|
| B74 | 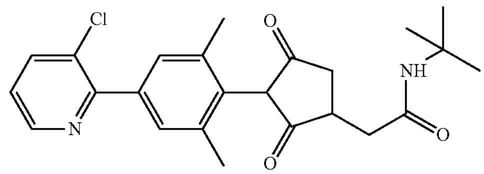 [SMILES: Cc1cc(-c2ncccc2Cl)cc(C)c1C1C(=O)CC(CC(=O)NC(C)(C)C)C1=O] | 8.51 (d, 1H), 7.97 (d, 1H), 7.89-7.83 (m, 1H), 7.31 (s, 2H), 3.22-3.13 (m, 1H), 2.91 (dd, 1H), 2.71 (dd, 1H), 2.49-2.39 (m, 2H), 2.19 (s, 6H), 1.34 (s, 9H) |
| B75 | 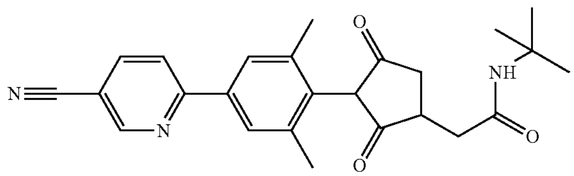 [SMILES: Cc1cc(-c2ccc(C#N)cn2)cc(C)c1C1C(=O)CC(CC(=O)NC(C)(C)C)C1=O] | 1H NMR (400 MHz, CD3OD) 8.99-8.79 (m, 1H), 8.18-8.01 (m, 1H), 7.99-7.86 (m, 1H), 7.74 (s, 2H), 7.64-7.51 (m, 1H), 3.30-3.13 (m, 1H), 3.04-2.86 (m, 1H), 2.78-2.51 (m, 2H), 2.48-2.33 (m, 1H), 2.25 (d, 6H), 1.38 (s, 9H) |
| B76 | 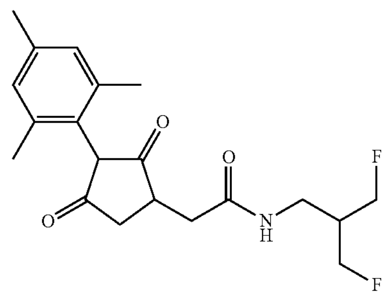 [SMILES: Cc1cc(C)c(C2C(=O)CC(CC(=O)NCC(CF)CF)C2=O)c(C)c1] | 1H NMR (400 MHz, CD3OD) 6.91-6.79 (m, 2H), 4.60-4.39 (m, 4H), 3.36-3.32 (m, 2H), 3.14 (d, 1H), 2.93-2.71 (m, 2H), 2.49-2.39 (m, 2H), 2.36-2.27 (m, 1H), 2.27-2.21 (m, 3H), 2.10-2.00 (m, 6H) |
| B77 | 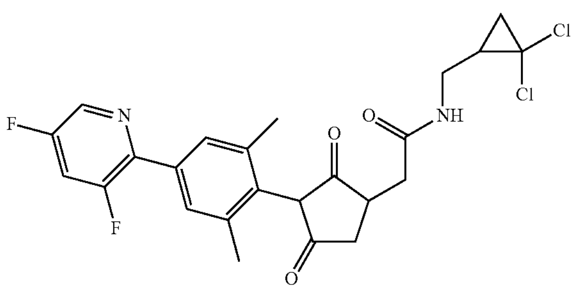 [SMILES: Cc1cc(-c2ncc(F)cc2F)cc(C)c1C1C(=O)CC(CC(=O)NCC2CC2(Cl)Cl)C1=O] | 1H NMR (400 MHz, CD3OD) 8.44 (d, 1H), 7.65 (ddd, 1H), 7.55 (s, 2H), 3.56-3.43 (m, 1H), 3.28-3.21 (m, 1H), 3.24-3.11 (m, 1H), 2.99-2.90 (m, 1H), 2.85-2.75 (m, 1H), 2.57-2.45 (m, 2H), 2.22-2.14 (m, 6H), 2.00-1.87 (m, 1H), 1.68 (dd, 1H), 1.35-1.26 (m, 1H) |
| B78 | 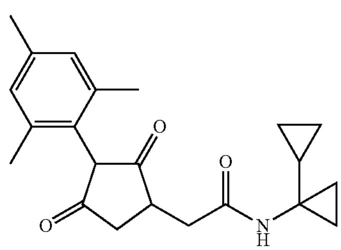 [SMILES: Cc1cc(C)c(C2C(=O)CC(CC(=O)NC3(C4CC4)CC3)C2=O)c(C)c1] | 1HNMR (400 MHz, CD3OD) 6.88-6.79 (m, 2H), 3.12 (dd, 1H), 2.87 (dd, 1H), 2.74-2.62 (m, 1H), 2.45-2.29 (m, 2H), 2.27-2.19 (m, 3H), 2.09-1.97 (m, 6H), 1.42-1.28 (m, 1H), 0.72-0.57 (m, 4H), 0.44-0.35 (m, 2H), 0.23-0.12 (m, 2H) |
| B79 | 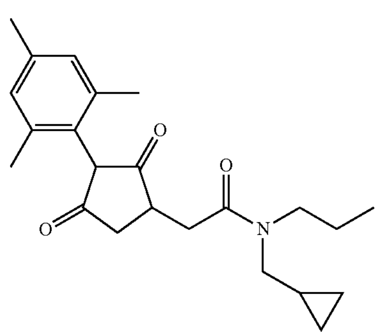 [SMILES: CCCN(CC1CC1)C(=O)CC1CC(=O)C(c2c(C)cc(C)cc2C)C1=O] | 1H NMR (400 MHz, CD3OD) 6.86 (s, 2H), 3.48-3.36 (m, 2H), 3.37-3.27 (m, 1H), 3.25-3.10 (m, 1H), 2.98-2.86 (m, 2H), 2.80 (br.s., 1H), 2.42 (d, 1H), 2.27-2.20 (m, 3H), 2.10-2.01 (m, 6H), 1.74-1.57 (m, 2H), 1.12-0.99 (m, 1H), 0.93 (td, 3H), 0.53-0.45 (m, 1H), 0.63-0.44 (m, 2H), 0.34-0.23 (m, 2H) |

TABLE T2-continued

| Compound Number | Structure | Physical Data LCMS or ¹H NMR (400 MHz, CDCl₃) unless stated. |
|---|---|---|
| B80 | 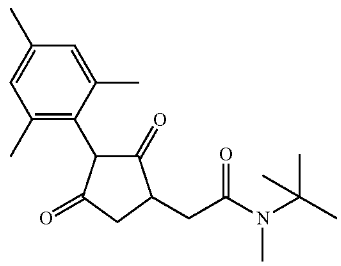 [SMILES: Cc1cc(C)c(C2C(=O)CC(CC(=O)N(C)C(C)(C)C)C2=O)c(C)c1] | 1H NMR (400 MHz, CD3OD) 6.90-6.80 (m, 2H), 3.16 (br.s., 1H), 3.01-2.99 (m, 3H), 2.97-2.83 (m, 1H), 2.41-2.21 (m, 5H), 2.13-2.08 (m, 1H), 2.09-1.98 (m, 6H), 1.46-1.43 (m, 9H) |
| B81 | 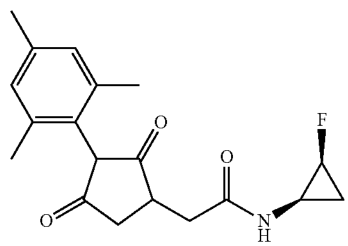 [SMILES: Cc1cc(C)c(C2C(=O)CC(CC(=O)N[C@@H]3C[C@@H]3F)C2=O)c(C)c1] | 1H NMR (400 MHz, CD3OD) 6.86 (s, 2H), 4.74-4.50 (m, 1H), 3.21-3.05 (m, 1H), 2.94-2.68 (m, 3H), 2.51-2.35 (m, 2H), 2.25 (s, 3H), 2.05 (s, 6H), 1.18-1.04 (m, 1H), 0.99-0.84 (m, 1H) |
| B82 | 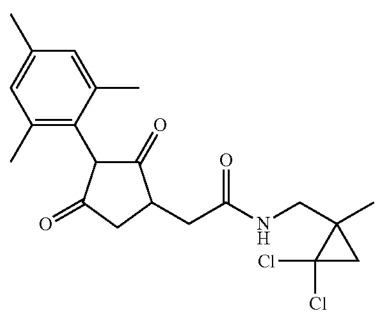 [SMILES: Cc1cc(C)c(C2C(=O)CC(CC(=O)NCC3(C)CC3(Cl)Cl)C2=O)c(C)c1] | 1H NMR (400 MHz, CD3OD) 6.90-6.78 (m, 2H), 3.74-3.64 (m, 1H), 3.26 (s, 1H), 3.15 (d, 1H), 2.93-2.75 (m, 2H), 2.57-2.37 (m, 2H), 2.26-2.18 (m, 3H), 2.10-2.01 (m, 6H), 1.54-1.47 (m, 1H), 1.41-1.36 (m, 3H), 1.34-1.25 (m, 1H) |
| B83 | 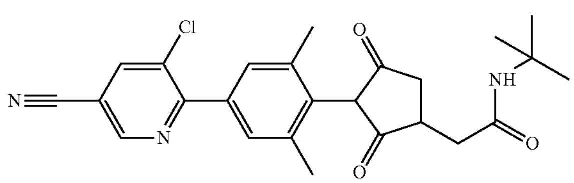 [SMILES: Cc1cc(-c2ncc(C#N)cc2Cl)cc(C)c1C1C(=O)CC(CC(=O)NC(C)(C)C)C1=O] | 1H NMR (400 MHz, CD3OD) 8.84 (s, 1H), 8.36 (s, 1H), 7.42 (s, 2H), 3.22-3.14 (m, 1H), 2.92 (dd, 1H), 2.70 (dd, 1H), 2.51-2.39 (m, 2H), 2.19 (s, 6H), 1.34 (s, 9H) |
| B84 | 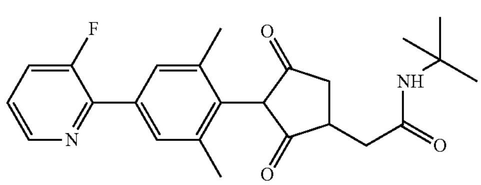 | 1H NMR (400 MHz, CD3OD) 8.47 (d, 1H), 7.78 (t, 1H), 7.52 (s, 2H), 7.51-7.44 (m, 1H), 3.22-3.14 (m, 1H), 2.91 (dd, 1H), 2.71 (dd, 1H), 2.52-2.39 (m, 2H), 2.19 (s, 6H), 1.34 (s, 9H) |
| B85 | 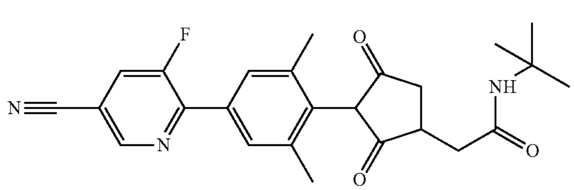 [SMILES: Cc1cc(-c2ncc(C#N)cc2F)cc(C)c1C1C(=O)CC(CC(=O)NC(C)(C)C)C1=O] | 8.77 (s, 1H), 8.14 (dd, 1H), 7.53 (s, 2H), 3.23-3.14 (m, 1H), 2.92 (dd, 1H), 2.71 (dd, 1H), 2.51-2.39 (m, 2H), 2.21 (s, 6H), 1.35 (s, 9H) |

TABLE T2-continued

| Compound Number | Structure | Physical Data LCMS or ¹H NMR (400 MHz, CDCl$_3$) unless stated. |
|---|---|---|
| B86 | 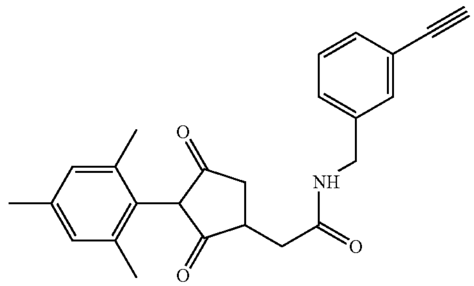 [SMILES: C#Cc1cccc(CNC(=O)CC2CC(=O)C(c3c(C)cc(C)cc3C)C2=O)c1] | 7.42-7.26 (m, 4H), 6.84 (s, 2H), 4.33 (s, 2H), 3.48 (s, 1H), 3.19-3.09 (m, 1H), 2.88 (dd, 1H), 2.79 (dd, 1H), 2.50-2.38 (m, 2H), 2.23 (s, 3H), 2.04 (s, 6H) |
| B87 | 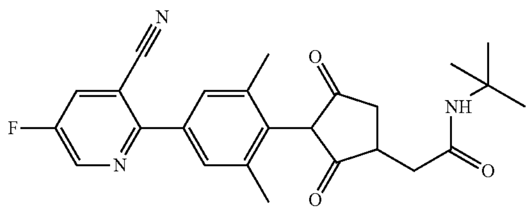 [SMILES: Cc1cc(-c2ncc(F)cc2C#N)cc(C)c1C1C(=O)CC(CC(=O)NC(C)(C)C)C1=O] | 8.78 (s, 1H), 8.15 (dd, 1H), 7.54 (s, 2H), 3.23-3.14 (m, 1H), 2.92 (dd, 1H), 2.71 (dd, 1H), 2.51-2.40 (m, 2H), 2.21 (s, 6H), 1.35 (s, 9H) |
| B88 | 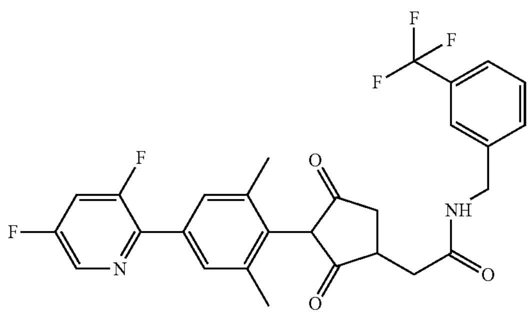 [SMILES: Cc1cc(-c2ncc(F)cc2F)cc(C)c1C1C(=O)CC(CC(=O)NCc2cccc(C(F)(F)F)c2)C1=O] | 1H NMR (400 MHz, CD3OD) 8.43 (s, 1H), 7.69-7.49 (m, 7H), 4.48 (s, 2H), 3.25-3.17 (m, 1H), 2.95 (dd, 1H), 2.87 (dd, 1H), 2.59-2.49 (m, 2H), 2.20 (d, 6H) |
| B89 | 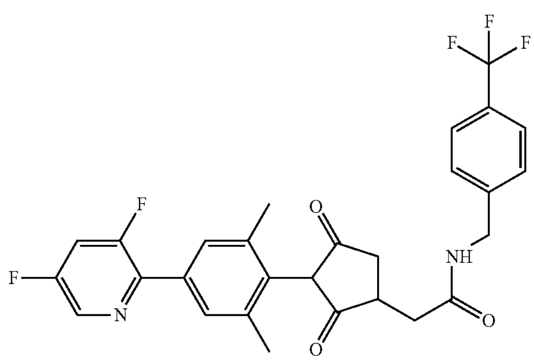 [SMILES: Cc1cc(-c2ncc(F)cc2F)cc(C)c1C1C(=O)CC(CC(=O)NCc2ccc(C(F)(F)F)cc2)C1=O] | 1H NMR (400 MHz, CD3OD) 8.45 (s, 1H), 7.71-7.60 (m, 3H), 7.57 (s, 2H), 7.51 (d, 2H), 4.49 (s, 2H), 3.27-3.18 (m, 1H), 2.97 (dd, 1H), 2.87 (dd, 1H), 2.60-2.51 (m, 2H), 2.20 (d, 6H) |
| B90 | 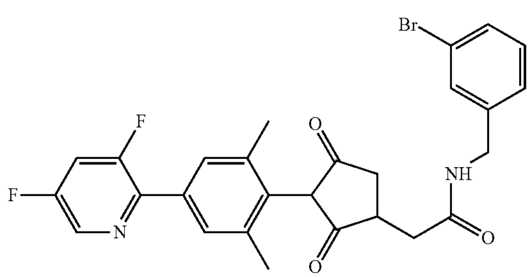 [SMILES: Cc1cc(-c2ncc(F)cc2F)cc(C)c1C1C(=O)CC(CC(=O)NCc2cccc(Br)c2)C1=O] | 1H NMR (400 MHz, CD3OD) 8.44 (s, 1H), 7.70-7.62 (m, 1H), 7.56 (s, 2H), 7.50 (s, 1H), 7.42 (d, 1H), 7.33-7.22 (m, 2H), 4.39 (s, 2H), 3.25-3.17 (m, 1H), 2.96 (dd, 1H), 2.85 (dd, 1H), 2.58-2.48 (m, 2H), 2.20 (s, 6H) |

TABLE T2-continued

| Compound Number | Structure | Physical Data LCMS or ¹H NMR (400 MHz, CDCl₃) unless stated. |
|---|---|---|
| B91 | 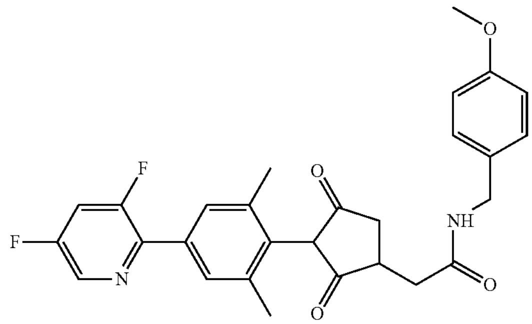 [SMILES: COc1ccc(CNC(=O)CC2CC(=O)C(c3c(C)cc(-c4ncc(F)cc4F)cc3C)C2=O)cc1] | 1H NMR (400 MHz, CD3OD) 8.42 (s, 1H), 7.66-7.58 (m, 1H), 7.53 (s, 2H), 7.21 (d, 2H), 6.86 (d, 2H), 4.32 (s, 2H), 3.73 (s, 3H), 3.23-3.14 (m, 1H), 2.91 (dd, 1H), 2.79 (dd, 1H), 2.53-2.43 (m, 2H), 2.18 (d, 6H) |
| B92 | 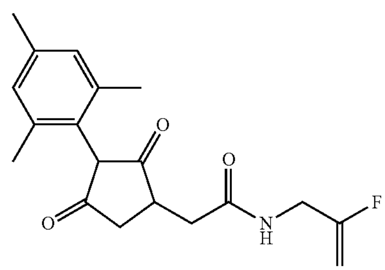 [SMILES: C=C(F)CNC(=O)CC1CC(=O)C(c2c(C)cc(C)cc2C)C1=O] | 1H NMR (400 MHz, CD3OD) 6.89-6.79 (m, 2H), 4.71-4.46 (m, 2H), 3.94 (d, 2H), 3.19-3.05 (m, 1H), 2.94-2.75 (m, 2H), 2.50-2.38 (m, 2H), 2.28-2.21 (m, 3H), 2.05 (s, 6H) |
| B93 | 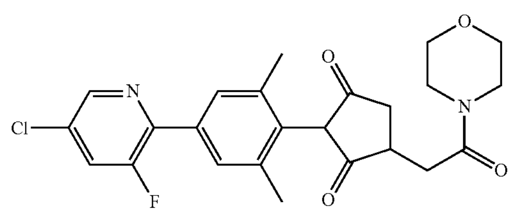 [SMILES: Cc1cc(-c2ncc(Cl)cc2F)cc(C)c1C1C(=O)CC(CC(=O)N2CCOCC2)C1=O] | 1NMR (400 MHz, CD3OD) 8.49 (dd, 1H), 7.88-7.78 (m, 1H), 7.60 (s, 2H), 3.75-3.51 (m, 8H), 3.25-3.11 (m, 1H), 3.07-2.86 (m, 2H), 2.83-2.44 (m, 2H), 2.21 (d, 6H) |
| B94 | 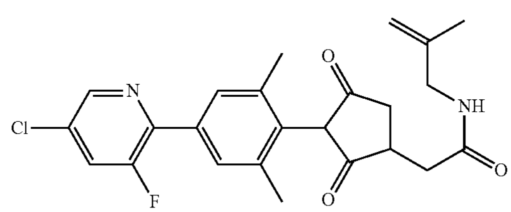 [SMILES: C=C(C)CNC(=O)CC1CC(=O)C(c2c(C)cc(-c3ncc(Cl)cc3F)cc2C)C1=O] | 1H NMR (400 MHz, CD3OD) 8.49 (dd, 1H), 7.89-7.78 (m, 1H), 7.60 (s, 2H), 4.87-4.81 (m, 2H), 3.78 (s, 2H), 3.24-3.13 (m, 1H), 3.00-2.78 (m, 2H), 2.56-2.40 (m, 2H), 2.20 (s, 6H), 1.78-1.71 (m, 3H) |
| B95 | 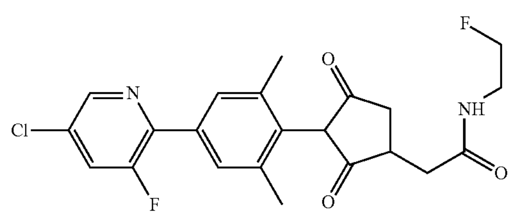 [SMILES: Cc1cc(-c2ncc(Cl)cc2F)cc(C)c1C1C(=O)CC(CC(=O)NCCF)C1=O] | 1H NMR (400 MHz, CD3OD) 8.49 (dd, 1H), 7.90-7.77 (m, 1H), 7.60 (s, 2H), 4.57-4.37 (m, 2H), 3.57-3.43 (m, 2H), 3.24-3.12 (m, 1H), 2.94 (dd, 1H), 2.81 (dd, 1H), 2.53-2.42 (m, 2H), 2.23-2.14 (m, 6H) |
| B96 | 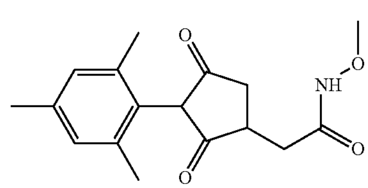 | 1H NMR (400 MHz, CD3OD) 6.86 (s, 2H), 3.72-3.66 (m, 3H), 3.17-3.05 (m, 1H), 2.89 (dd, 1H), 2.68-2.44? (m, 2H), 2.29-2.19 (m, 4H), 2.09-1.98 (m, 6H) |

TABLE T2-continued

| Compound Number | Structure | Physical Data LCMS or ¹H NMR (400 MHz, CDCl₃) unless stated. |
|---|---|---|
| B97 | 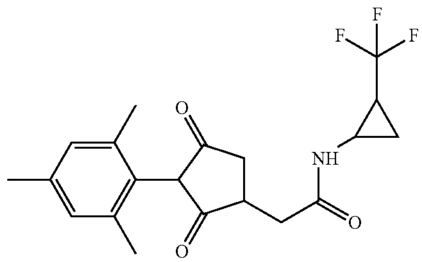 [SMILES: Cc1cc(C)c(C2C(=O)CC(CC(=O)NC3CC3C(F)(F)F)C2=O)c(C)c1] | 1H NMR (500 MHz, CD3OD) 6.91-6.78 (m, 2H), 3.26-3.23 (m, 1H), 2.93-2.81 (m, 1H), 2.76-2.67 (m, 1H), 2.82-2.65 (m, 1H), 2.46-2.30 (m, 2H), 2.28-2.21 (m, 3H), 2.07-2.00 (m, 6H), 1.34-1.20 (m, 2H), 1.14-0.99 (m, 1H) |
| B98 | 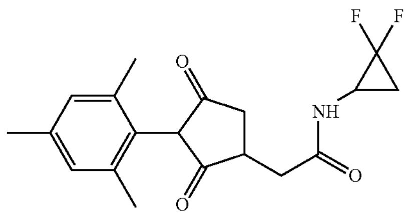 [SMILES: Cc1cc(C)c(C2C(=O)CC(CC(=O)NC3CC3(F)F)C2=O)c(C)c1] | 1H NMR (500 MHz, CD3OD) 6.91-6.82 (m, 2H), 3.34-3.22 (m, 1H), 3.18-3.00 (m, 1H), 2.95-2.86 (m, 1H), 2.78 (ddd, 1H), 2.50-2.34 (m, 2H), 2.28-2.20 (m, 3H), 2.09-1.97 (m, 6H), 1.85-1.73 (m, 1H), 1.48-1.33 (m, 1H) |
| B99 | 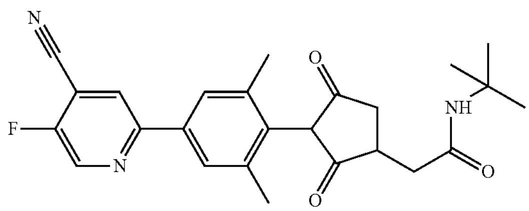 [SMILES: Cc1cc(-c2cc(C#N)c(F)cn2)cc(C)c1C1C(=O)CC(CC(=O)NC(C)(C)C)C1=O] | 1H NMR (400 MHz, CD3OD) 8.78 (s, 1H), 8.26 (d, 1H), 7.73 (s, 2H), 3.22-3.14 (m, 1H), 2.92 (dd, 1H), 2.70 (dd, 1H), 2.51-2.39 (m, 2H), 2.20 (s, 6H), 1.36 (s, 9H) |
| B100 | 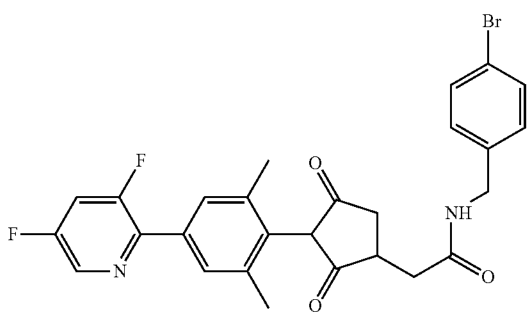 | 1H NMR (400 MHz, CD3OD) 8.41 (s, 1H), 7.67-7.58 (m, 1H), 7.53 (s, 2H), 7.44 (d, 2H), 7.21 (d, 2H), 4.33 (s, 2H), 3.22-3.14 (m, 1H), 2.92 (dd, 1H), 2.81 (dd, 1H), 2.54-2.45 (m, 2H), 2.18 (d, 6H) |
| B101 | 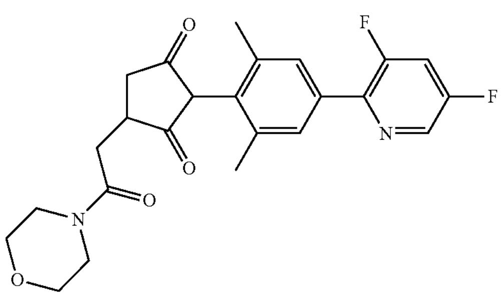 [SMILES: Cc1cc(-c2ncc(F)cc2F)cc(C)c1C1C(=O)CC(CC(=O)N2CCOCC2)C1=O] | 1H NMR (400 MHz, CD3OD) 8.48-8.35 (m, 1H), 7.65 (ddd, 1H), 7.55 (s, 2H), 3.74-3.52 (m, 8H), 3.25-3.11 (m, 1H), 3.03-2.90 (m, 2H), 2.84-2.71 (m, 1H), 2.51 (dd, 1H), 2.23-2.13 (m, 6H) |
| B102 | 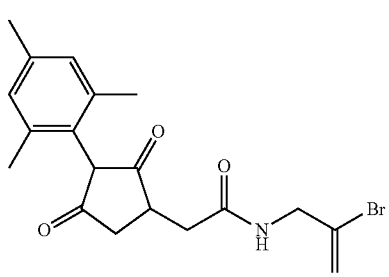 [SMILES: C=C(Br)CNC(=O)CC1CC(=O)C(c2c(C)cc(C)cc2C)C1=O] | 1H NMR (400 MHz, CD3OD) 6.93-6.76 (m, 2H), 5.88-5.78 (m, 1H), 5.59-5.44 (m, 1H), 4.10-4.01 (m, 2H), 3.20-3.08 (m, 1H), 2.98-2.76 (m, 2H), 2.55-2.37 (m, 2H), 2.27-2.21 (m, 3H), 2.09-1.97 (m, 6H) |

TABLE T2-continued

| Compound Number | Structure | Physical Data LCMS or ¹H NMR (400 MHz, CDCl₃) unless stated. |
|---|---|---|
| B103 | 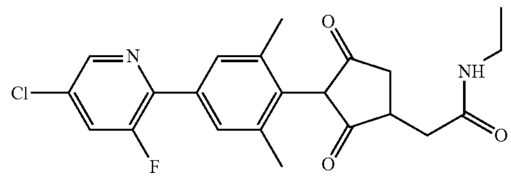 [SMILES: CCNC(=O)CC1CC(=O)C(c2c(C)cc(-c3ncc(Cl)cc3F)cc2C)C1=O] | 1H NMR (400 MHz, CD3OD) 8.49 (d, 1H), 7.88-7.79 (m, 1H), 7.60 (s, 2H), 3.28-3.13 (m, 3H), 2.93 (dd, 1H), 2.81-2.69 (m, 1H), 2.54-2.37 (m, 2H), 2.24-2.16 (m, 6H), 1.19-1.10 (m, 3H) |
| B104 | 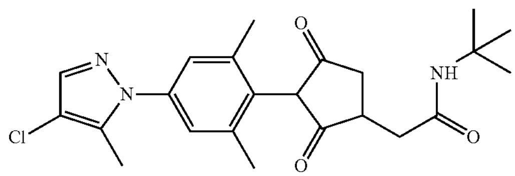 [SMILES: Cc1cc(-n2ncc(Cl)c2C)cc(C)c1C1C(=O)CC(CC(=O)NC(C)(C)C)C1=O] | 7.58 (s, 1H), 7.14 (s, 2H), 3.28-3.12 (m, 1H), 2.98-2.88 (m, 1H), 2.74-2.67 (m, 1H), 2.53-2.37 (m, 2H), 2.30 (s, 3H), 2.18 (s, 6H), 1.35 (s, 9H) |
| B105 | 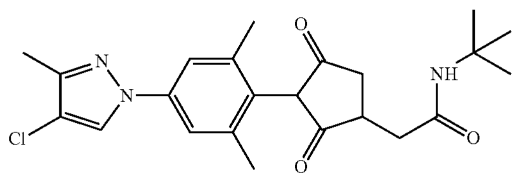 [SMILES: Cc1cc(-n2cc(Cl)c(C)n2)cc(C)c1C1C(=O)CC(CC(=O)NC(C)(C)C)C1=O] | 8.22 (s, 1H), 7.38 (s, 2H), 3.22-3.12 (m, 1H), 2.89 (dd, 1H), 2.69 (dd, 1H), 2.50-2.38 (m, 2H), 2.28 (s, 3H), 2.16 (s, 6H), 1.35 (s, 9H) |
| B106 | 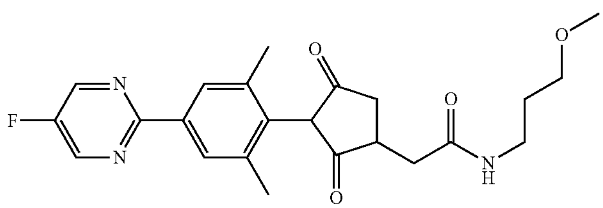 [SMILES: COCCCNC(=O)CC1CC(=O)C(c2c(C)cc(-c3ncc(F)cn3)cc2C)C1=O] | 8.62 (s, 2H), 8.13-8.00 (m, 2H), 7.46-7.32 (m, 1H), 3.46-3.35 (m, 2H), 3.31 (s, 6H), 2.95-2.75 (m, 1H), 2.69-2.54 (m, 2H), 2.23 (d, 7H), 1.78-1.60 (m, 2H) |
| B107 | 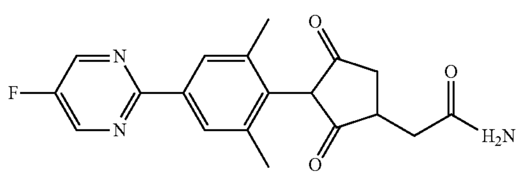 [SMILES: Cc1cc(-c2ncc(F)cn2)cc(C)c1C1C(=O)CC(CC(N)=O)C1=O] | 8.72 (s, 2H), 8.04 (s, 2H), 3.24-3.09 (m, 1H), 3.01-2.86 (m, 1H), 2.85-2.70 (m, 1H), 2.58-2.40 (m, 2H), 2.20 (s, 6H) |
| B108 | 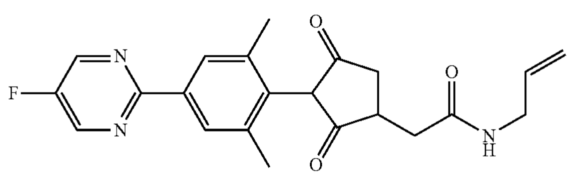 [SMILES: C=CCNC(=O)CC1CC(=O)C(c2c(C)cc(-c3ncc(F)cn3)cc2C)C1=O] | 8.62 (s, 2H), 8.05 (d, 2H), 7.48-7.30 (m, 1H), 5.81-5.58 (m, 1H), 5.20-5.01 (m, 2H), 3.83-3.59 (m, 2H), 3.28-3.07 (m, 1H), 2.95-2.77 (m, 1H), 2.72-2.44 (m, 2H), 2.20 (d, 7H) |
| B109 | 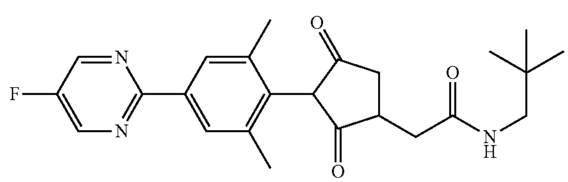 [SMILES: Cc1cc(-c2ncc(F)cn2)cc(C)c1C1C(=O)CC(CC(=O)NCC(C)(C)C)C1=O] | 8.63 (s, 2H), 8.11-8.00 (m, 2H), 7.65-7.47 (m, 1H), 3.30-3.13 (m, 1H), 3.08-2.98 (m, 2H), 2.96-2.85 (m, 1H), 2.76-2.60 (m, 2H), 2.42-2.27 (m, 1H), 2.23 (d, 6H), 0.89 (s, 9H) |
| B110 | 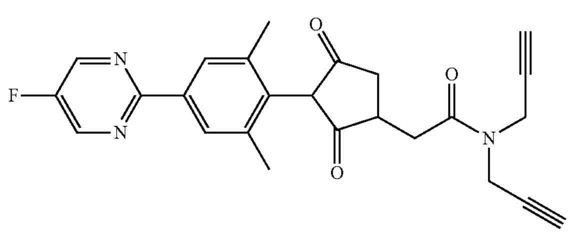 [SMILES: C#CCN(CC#C)C(=O)CC1CC(=O)C(c2c(C)cc(-c3ncc(F)cn3)cc2C)C1=O] | 8.61 (s, 2H), 8.03 (d, 2H), 4.44-4.17 (m, 4H), 3.48-3.27 (m, 1H), 2.92 (s, 3H), 2.50-2.12 (m, 9H) |

TABLE T2-continued

| Compound Number | Structure | Physical Data LCMS or $^1$H NMR (400 MHz, CDCl$_3$) unless stated. |
|---|---|---|
| B111 | 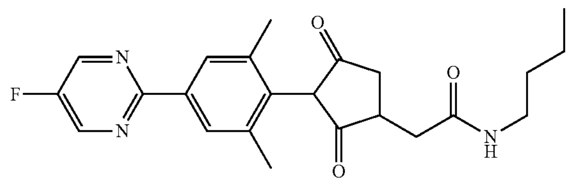 [SMILES: CCCCNC(=O)CC1CC(=O)C(c2c(C)cc(-c3ncc(F)cn3)cc2C)C1=O] | 14.14-13.60 (m, 1H), 8.62 (s, 2H), 8.07 (d, 2H), 3.08 (d, 3H), 2.95-2.78 (m, 1H), 2.72-2.44 (m, 2H), 2.22 (d, 7H), 1 46-1.14 (m, 4H), 0.85 (t, 3H) |
| B112 | 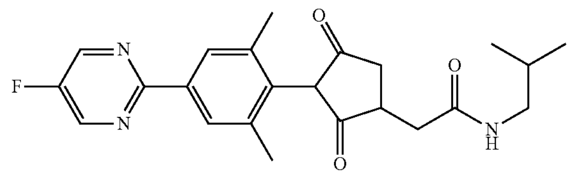 [SMILES: Cc1cc(-c2ncc(F)cn2)cc(C)c1C1C(=O)CC(CC(=O)NCC(C)C)C1=O] | 14.07-13.16 (m, 1H), 8.62 (s, 2H), 8.07 (d, 2H), 7.21-7.03 (m, 1H), 3.34-3.14 (m, 1H), 3.07-2.80 (m, 3H), 2.63 (s, 2H), 2.23 (d, 7H), 1.66 (s, 1H), 0.83 (dd, 6H) |
| B113 | 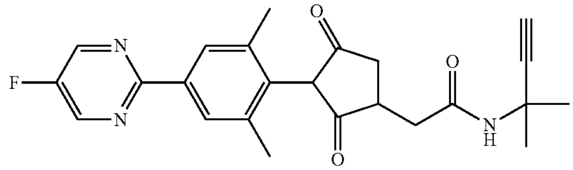 [SMILES: C#CC(C)(C)NC(=O)CC1CC(=O)C(c2c(C)cc(-c3ncc(F)cn3)cc2C)C1=O] | 1H NMR (400 MHz, CD3OD) 8.74 (s, 2H), 8.07 (s, 2H), 3.24-3.08 (m, 1H), 3.00-2.84 (m, 1H), 2.80-2.69 (m, 1H), 2.62 (s, 1H), 2.56-2.33 (m, 2H), 2.21 (s, 6H), 1.60 (s, 6H) |
| B114 | 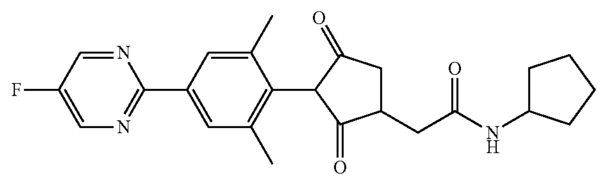 [SMILES: Cc1cc(-c2ncc(F)cn2)cc(C)c1C1C(=O)CC(CC(=O)NC2CCCC2)C1=O] | 1H NMR (400 MHz, CD3OD) 8.75 (s, 2H), 8.14-7.88 (m, 2H), 4.27-3.91 (m, 1H), 3.26-3.07 (m, 1H), 2.99-2.83 (m, 1H), 2.80-2.67 (m, 1H), 2.55-2.35 (m, 2H), 2.20 (s, 6H), 1.99-1.87 (m, 2H), 1.84-1.40 (m, 6H) |
| B115 | 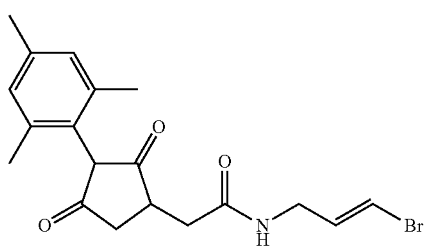 [SMILES: Cc1cc(C)c(C2C(=O)CC(CC(=O)NC/C=C/Br)C2=O)c(C)c1] | 1HNMR (400 MHz, CD3OD) 6.93-6.78 (m, 2H), 6.47-6.35 (m, 1H), 6.27-6.15 (m, 1H), 4.01-3.70 (m, 2H), 3.17-3.09 (m, 1H), 2.93-2.85 (m, 1H), 2.76 (dd, 1H), 2.51-2.37 (m, 2H), 2.27-2.20 (m, 3H), 2.10-2.01 (m, 6H) |
| B116 | 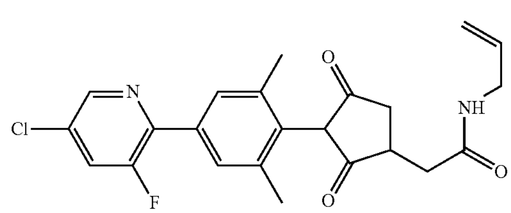 [SMILES: C=CCNC(=O)CC1CC(=O)C(c2c(C)cc(-c3ncc(Cl)cc3F)cc2C)C1=O] | 1H NMR (400 MHz, CD3OD) 8.53-8.42 (m, 1H), 7.84 (dd, 1H), 7.60? (s, 2H), 5.86 (tdd, 1H), 5.29-5.07 (m, 2H), 3.84 (d, 2H), 3.24-3.13 (m, 1H), 2.94 (dd, 1H), 2.81 (dd, 1H), 2.55-2.43 (m, 2H), 2.21-2.17 (m, 6H) |
| B117 | 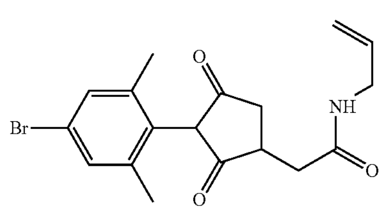 [SMILES: C=CCNC(=O)CC1CC(=O)C(c2c(C)cc(Br)cc2C)C1=O] | 1H NMR (400 MHz, Methanol) Shift = 7.25-7.08 (m, 2H), 5.85 (tdd, J = 5.4, 10.5, 17.2 Hz, 1H), 5.25-5.06 (m, 2H), 3.89-3.77 (m, 2H), 3.15 (d, J = 6.0 Hz, 1H), 2.91 (dd, J = 7.0, 17.9 Hz, 1H), 2.80-2.66 (m, 1H), 2.52-2.37 (m, 2H), 2.14-2.00 (m, 6H) |
| B118 | 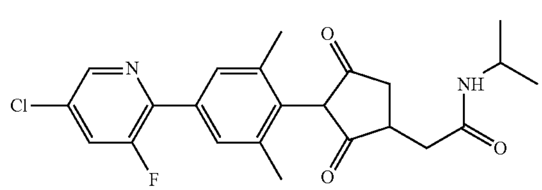 [SMILES: Cc1cc(-c2ncc(Cl)cc2F)cc(C)c1C1C(=O)CC(CC(=O)NC(C)C)C1=O] | 1H NMR (400 MHz, CD3OD) 8.55-8.40 (m, 1H), 7.84 (dd, 1H), 7.60 (s, 2H), 4.00 (quin, 1H), 3.19 (d, 1H), 2.92 (dd, 1H), 2.74 (dd, 1H), 2.52-2.39 (m, 2H), 2.24-2.17 (m, 6H), 1.18-1.13 (m, 6H) |

TABLE T2-continued

| Compound Number | Structure | Physical Data LCMS or ¹H NMR (400 MHz, CDCl₃) unless stated. |
|---|---|---|
| B119 | 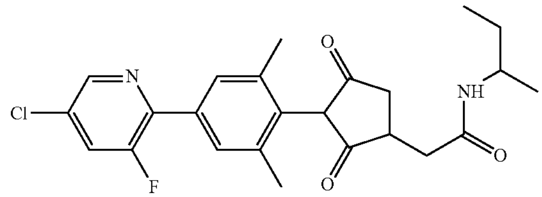 [SMILES: CCC(C)NC(=O)CC1CC(=O)C(c2c(C)cc(-c3ncc(Cl)cc3F)cc2C)C1=O] | 1H NMR (400 MHz, CD3OD) 8.55-8.45 (m, 1H), 7.84 (dd, 1H), 7.60? (s, 2H), 3.90-3.69 (m, 1H), 3.24-3.12 (m, 1H), 2.93 (dd, 1H), 2.77 (ddd, 1H), 2.53-2.33 (m, 2H), 2.23-2.17 (m, 6H), 1.56-1.40 (m, 2H), 1.14 (dd, 3H), 0.93 (dt, 3H) |
| B120 | 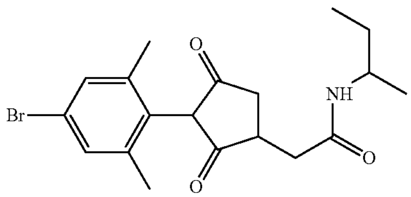 [SMILES: CCC(C)NC(=O)CC1CC(=O)C(c2c(C)cc(Br)cc2C)C1=O] | 1HNMR (400 MHz, CD3OD) 7.29-7.11 (m, 2H), 3.81 (sxt, 1H), 3.21-3.03 (m, 1H), 2.89 (ddd, 1H), 2.74 (ddd, 1H), 2.50-2.33 (m, 2H), 2.13-1.98 (m, 6H), 1.56-1.41 (m, 2H), 1.18-1.06 (m, 3H), 0.92 (dt, 3H) |
| B121 | 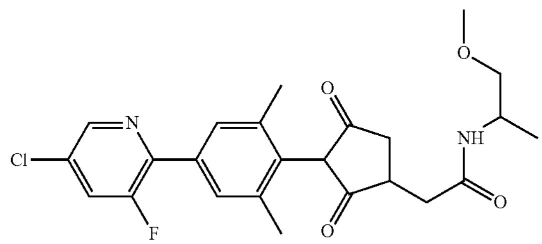 [SMILES: COCC(C)NC(=O)CC1CC(=O)C(c2c(C)cc(-c3ncc(Cl)cc3F)cc2C)C1=O] | 1H NMR (400 MHz, CD3OD) 8.52-8.40 (m, 1H), 7.84 (dd, 1H), 7.60 (s, 2H), 4.18-3.96 (m, 1H), 3.41-3.34 (m, 5H), 3.23-3.12 (m, 1H), 2.92 (dd, 1H), 2.82-2.65 (m, 1H), 2.54-2.37 (m, 2H), 2.24-2.17 (m, 6H), 1.15 (dd, 3H) |
| B122 | 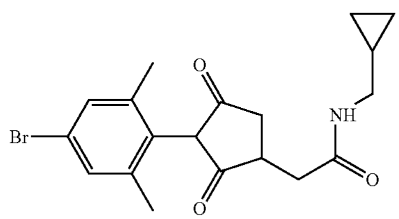 [SMILES: Cc1cc(Br)cc(C)c1C1C(=O)CC(CC(=O)NCC2CC2)C1=O] | 1HNMR (400 MHz, CD3OD) 7.25-7.13 (m, 2H), 3.26-3.12 (m, 1H), 3.07 (d, 2H), 2.90 (dd, 1H), 2.75 (dd, 1H), 2.55-2.38 (m, 2H), 2.09 (s, 6H), 1.05-0.89 (m, 1H), 0.54-0.45 (m, 2H), 0.26-0.11 (m, 2H) |
| B123 | 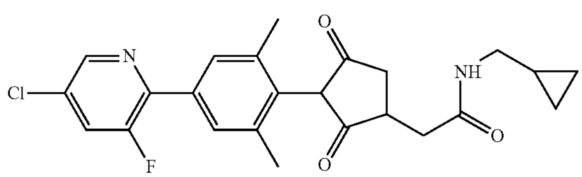 [SMILES: Cc1cc(-c2ncc(Cl)cc2F)cc(C)c1C1C(=O)CC(CC(=O)NCC2CC2)C1=O] | 1H NMR (400 MHz, CD3OD) 8.52-8.43 (m, 1H), 7.88-7.72 (m, 1H), 7.63-7.45 (m, 2H), 3.24-3.14 (m, 1H), 3.10-3.02 (m, 2H), 2.93 (dd, 1H), 2.78 (dd, 1H), 2.55-2.41 (m, 2H), 2.23-2.18 (m, 6H), 1.07-0.90 (m, 1H), 0.58-0.46 (m, 2H), 0.29-0.16 (m, 2H) |
| B124 | 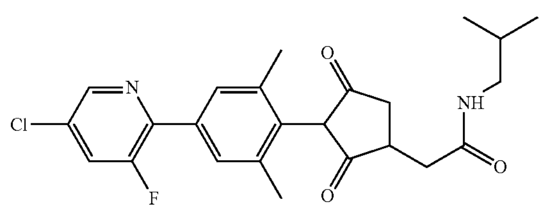 [SMILES: Cc1cc(-c2ncc(Cl)cc2F)cc(C)c1C1C(=O)CC(CC(=O)NCC(C)C)C1=O] | 1H NMR (400 MHz, CD3OD) 8.54-8.36 (m, 1H), 7.84 (dd, 1H), 7.60 (s, 2H), 3.25-3.12 (m, 1H), 3.04 (d, 2H), 2.93 (dd, 1H), 2.79 (dd, 1H), 2.55-2.41 (m, 2H), 2.20 (s, 6H), 1.80 (quind, 1H), 0.94 (d, 6H) |
| B125 | 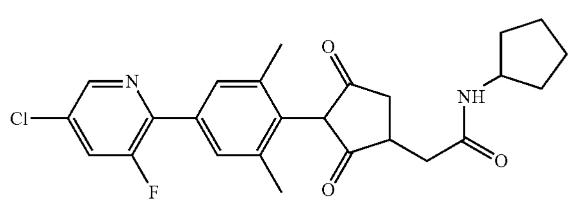 [SMILES: Cc1cc(-c2ncc(Cl)cc2F)cc(C)c1C1C(=O)CC(CC(=O)NC2CCCC2)C1=O] | 1H NMR (400 MHz, CD3OD) 8.49 (d, 1H), 7.84 (dd, 1H), 7.65-7.45 (m, 2H), 4.22-4.05 (m, 1H), 3.24-3.08 (m, 1H), 2.92 (dd, 1H), 2.74 (dd, 1H), 2.46 (d, 2H), 2.24-2.17 (m, 6H), 2.04-1 87 (m, 2H), 1 78-1.67 (m, 2H), 1.66-1.58 (m, 2H), 1.49 (td, 2H) |

TABLE T2-continued

| Compound Number | Structure | Physical Data LCMS or $^1$H NMR (400 MHz, CDCl$_3$) unless stated. |
|---|---|---|
| B126 | 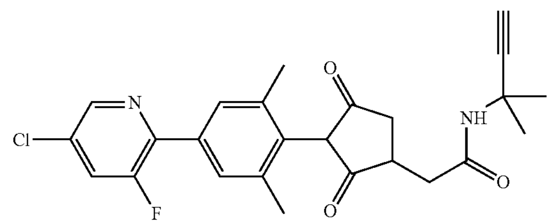 [SMILES: C#CC(C)(C)NC(=O)CC1CC(=O)C(c2c(C)cc(-c3ncc(Cl)cc3F)cc2C)C1=O] | 1H NMR (400 MHz, CD3OD) 8.49 (dd, 1H), 7 84 (dd, 1H), 7.60 (s, 2H), 3.21-3.08 (m, 1H), 2.94 (dd, 1H), 2.75 (dd, 1H), 2.65 (s, 1H), 2.52-2.38 (m, 2H), 2.21-2.17 (m, 6H), 1.62-1.52 (m, 6H) |
| B127 | 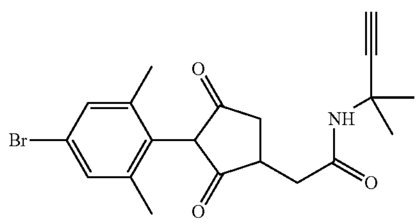 [SMILES: C#CC(C)(C)NC(=O)CC1CC(=O)C(c2c(C)cc(Br)cc2C)C1=O] | 1H NMR (400 MHz, CD3OD) 7.26-7.03 (m, 2H), 3.14 (d, 1H), 2.91 (dd, 1H), 2.72 (dd, 1H), 2.66-2.60 (m, 1H), 2.53-2.33 (m, 2H), 2.12-2.03 (m, 6H), 1.63-1.53 (m, 6H) |
| B128 | 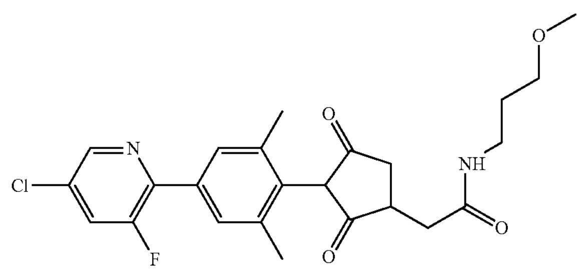 [SMILES: COCCCNC(=O)CC1CC(=O)C(c2c(C)cc(-c3ncc(Cl)cc3F)cc2C)C1=O] | 1H NMR (400 MHz, CD3OD) 8.49 (dd, 1H), 7.84 (dd, 1H), 7.60 (s, 2H), 3.44 (t, 2H), 3.33 (s, 3H), 3.29-3.26 (m, 2H), 3.24-3.10 (m, 1H), 2.93 (dd, 1H), 2.77 (dd, 1H), 2.54-2.39 (m, 2H), 2.21-2.16 (m, 6H), 1.78 (quin, 2H) |
| B129 | 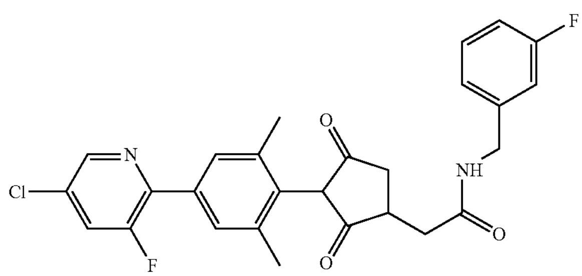 [SMILES: Cc1cc(-c2ncc(Cl)cc2F)cc(C)c1C1C(=O)CC(CC(=O)NCc2cccc(F)c2)C1=O] | 1H NMR (400 MHz, CD3OD) 8.49 (dd, 1H), 7.84 (dd, 1H), 7.65-7.54 (m, 2H), 7.34 (dt, 1H), 7.13 (d, 1H), 7.08-6.92 (m, 2H), 4.41 (s, 2H), 3.26-3.13 (m, 1H), 3.00-2.78 (m, 2H), 2.56-2.46 (m, 2H), 2.19 (d, 6H) |
| B130 | 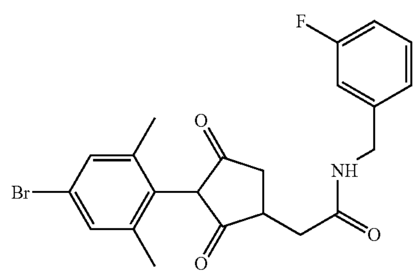 [SMILES: Cc1cc(Br)cc(C)c1C1C(=O)CC(CC(=O)NCc2cccc(F)c2)C1=O] | 1HNMR (400 MHz, CD3OD) 7.39-7.27 (m, 1H), 7.21 (s, 2H), 7.11 (d, 1H), 7.05 (dd, 1H), 6.98 (dt. 1H), 4.45-4.33 (m, 2H), 3.26-3.11 (m, 1H), 2.91 (dd, 1H), 2.81 (dd, 1H), 2.57-2.43 (m, 2H), 2.13-2.07 (m, 6H) |
| B131 | 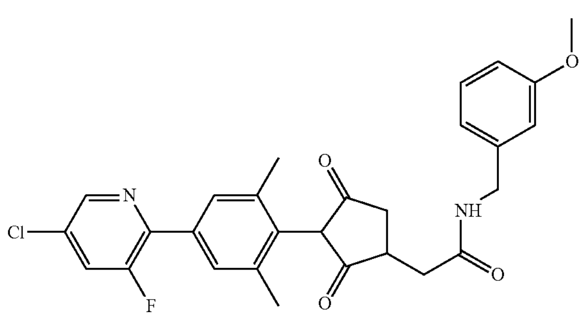 [SMILES: COc1cccc(CNC(=O)CC2CC(=O)C(c3c(C)cc(-c4ncc(Cl)cc4F)cc3C)C2=O)c1] | 1H NMR (400 MHz, CD3OD) 8.49 (dd, 1H), 7.84 (dd, 1H), 7.60 (s, 2H), 7.23 (t, 1H), 6.90-6.85 (m, 2H), 6.82 (dd, 1H), 4.41-4.33 (m, 2H), 3.80-3.75 (m, 3H), 3.26-3.10 (m, 1H), 2.94 (dd, 1H), 2.83 (dd, 1H), 2.51 (d, 2H), 2.19 (d, 6H) |

TABLE T2-continued

| Compound Number | Structure | Physical Data LCMS or $^1$H NMR (400 MHz, CDCl$_3$) unless stated. |
|---|---|---|
| B132 | 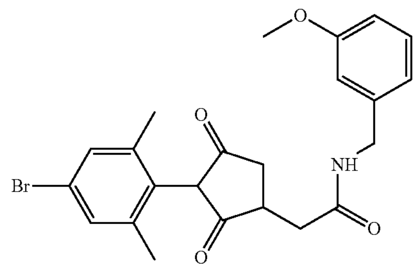 [SMILES: COc1cccc(CNC(=O)CC2CC(=O)C(c3c(C)cc(Br)cc3C)C2=O)c1] | 1HNMR (400 MHz, CD3OD) 7.25-7.17 (m, 4H), 6.91-6.85 (m, 2H), 4.41-4.29 (m, 2H), 3.80-3.73 (m, 3H), 3.17 (d, 1H), 2.91 (dd, 1H), 2.80 (dd, 1H), 2.55-2.41 (m, 2H), 2.08 (d, 6H) |
| B133 | 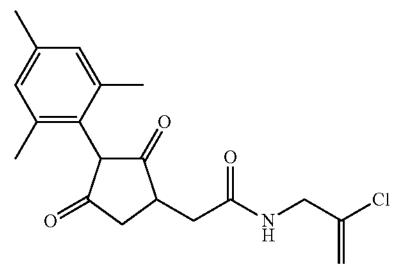 [SMILES: C=C(Cl)CNC(=O)CC1CC(=O)C(c2c(C)cc(C)cc2C)C1=O] | 1H NMR (400 MHz, CD3OD) 6.86 (s, 2H), 5.45-5.27 (m, 2H), 4.01 (s, 2H), 3.13 (br.s., 1H), 2.93-2.76 (m, 2H), 2.50-2.40 (m, 2H), 2.28-2.19 (m, 3H), 2.09-2.02 (m, 6H) |
| B134 | 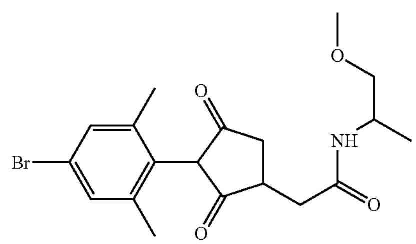 [SMILES: COCC(C)NC(=O)CC1CC(=O)C(c2c(C)cc(Br)cc2C)C1=O] | 1H NMR (400 MHz, CD3OD15bn227h1) 7.25-7.09 (m, 2H), 4.14-3.97 (m, 1H), 3.41-3.32 (m, 5H), 3.20-3.06 (m, 1H), 2.89 (dd, 1H), 2.80-2.66 (m, 1H), 2.52-2.37 (m, 2H), 2.13-2.02 (m, 6H), 1.18-1.04 (m, 3H) |
| B135 | 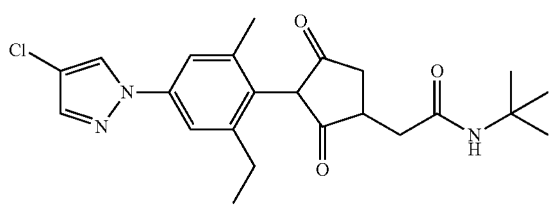 [SMILES: CCc1cc(-n2cc(Cl)cn2)cc(C)c1C1C(=O)CC(CC(=O)NC(C)(C)C)C1=O] | 13.92-13.60 (m, 1H), 7.89 (s, 1H), 7.61 (s, 1H), 7.40-7.29 (m, 2H), 6.87-6.69 (m, 1H), 3.37-3.13 (m, 1H), 2.96-2.40 (m, 5H), 2.18 (d, 4H), 1.39-1.27 (m, 9H), 1.14 (dt, 3H) |
| B136 | 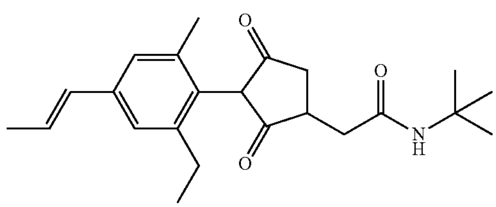 [SMILES: C/C=C/c1cc(C)c(C2C(=O)CC(CC(=O)NC(C)(C)C)C2=O)c(CC)c1] | 13.77-13.36 (m, 1H), 7.12-6.92 (m, 2H), 6.83-6.58 (m, 1H), 6.45-6.05 (m, 2H), 3.30-3.02 (m, 1H), 2.42 (d, 5H), 2.11 (s, 4H), 1.85 (dd, 3H), 1.34-1.19 (m, 9H), 1.10 (d, 3H) |
| B137 | 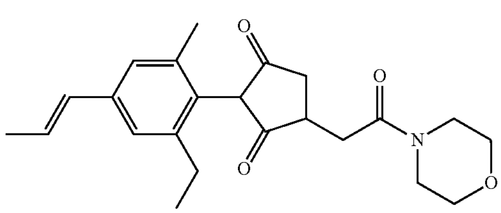 [SMILES: C/C=C/c1cc(C)c(C2C(=O)CC(CC(=O)N3CCOCC3)C2=O)c(CC)c1] | 12.50-12.02 (m, 1H), 7.03 (dd, 2H), 6.41-6.04 (m, 2H), 3.95-3.44 (m, 8H), 3.40-3.25 (m, 1H), 3.19-2.81 (m, 2H), 2.42 (d, 3H), 2.32-2.07 (m, 4H), 1 85 (dd, 3H), 1.10 (dt, 3H) |

TABLE T2-continued

| Compound Number | Structure | Physical Data LCMS or ¹H NMR (400 MHz, CDCl₃) unless stated. |
|---|---|---|
| B138 | 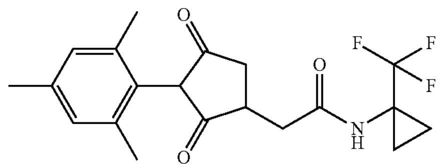 [SMILES: Cc1cc(C)c(C2C(=O)CC(CC(=O)NC3(C(F)(F)F)CC3)C2=O)c(C)c1] | 1H NMR (400 MHz, CD3OD) 8.94-8.81 (m, 1H), 6.86 (s, 2H), 3.19-3.02 (m, 1H), 2.98-2.83 (m, 1H), 2.73 (s, 1H), 2.53-2.30 (m, 2H), 2.25 (s, 3H), 2.05 (s, 6H), 1.27 (s, 2H), 1.10 (s, 2H) |
| B139 | 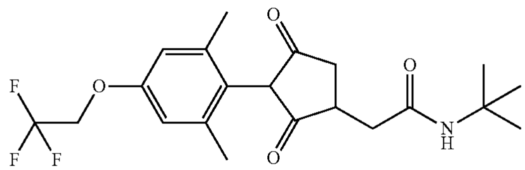 [SMILES: Cc1cc(OCC(F)(F)F)cc(C)c1C1C(=O)CC(CC(=O)NC(C)(C)C)C1=O] | 6.65 (s, 2H), 6.52-6.33 (m, 1H), 4.31 (d, 2H), 3.33-3.12 (m, 1H), 2.93-2.76 (m, 1H), 2.73-2.49 (m, 2H), 2.13 (d, 7H), 1.32 (s, 9H) |
| B140 | 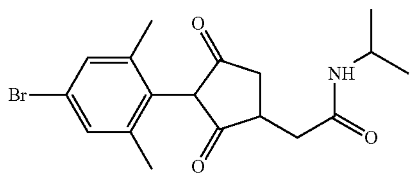 [SMILES: Cc1cc(Br)cc(C)c1C1C(=O)CC(CC(=O)NC(C)C)C1=O] | 1HNMR (400 MHz, CD3OD) 7.25-7.11 (m, 2H), 4.03-3.90 (m, 1H), 3.19-3.09 (m, 1H), 2.89 (dd, 1H), 2.73-2.65 (m, 1H), 2.49-2.36 (m, 2H), 2.09 (s, 6H), 1.19-1.11 (m, 6H) |
| B141 | 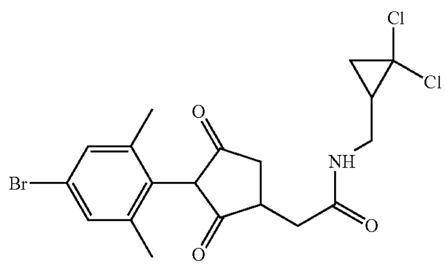 [SMILES: Cc1cc(Br)cc(C)c1C1C(=O)CC(CC(=O)NCC2CC2(Cl)Cl)C1=O] | 1H NMR (400 MHz, CD3OD) 7.24-7.14 (m, 2H), 3.51 (td, 1H), 3.29-3.21 (m, 1H), 3.15 (br.s., 1H), 2.92 (ddd, 1H), 2.78 (ddd, 1H), 2.57-2.42 (m, 2H), 2.09 (d, 6H), 2.00-1.89 (m, 1H), 1.67 (dd, 10.5 Hz, 1H), 1.38-1.21 (m, 1H) |
| B142 | 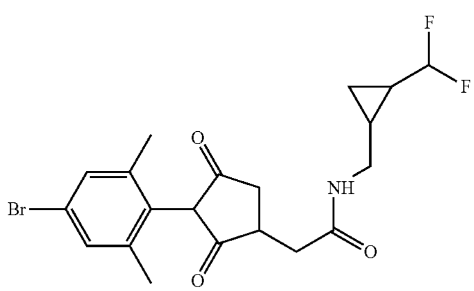 [SMILES: Cc1cc(Br)cc(C)c1C1C(=O)CC(CC(=O)NCC2CC2C(F)F)C1=O] | 1H NMR (400 MHz, CD3OD) 7.25-7.05 (m, 2H), 5.85-5.48 (m, 1H), 3.45-3.34 (m, 2H), 3.13 (d, 1H), 2.90 (dd, 1H), 2.82-2.68 (m, 1H), 2.52-2.35 (m, 2H), 2.14-2.07 (m, 6H), 0.83-0.64 (m, 4H) |
| B143 | 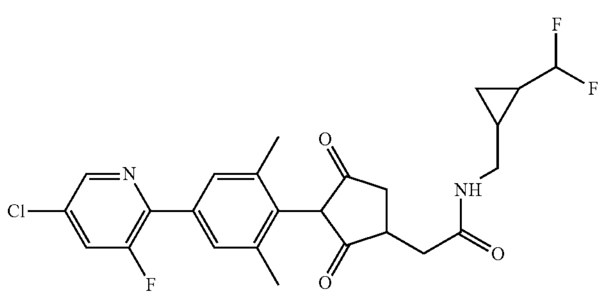 [SMILES: Cc1cc(-c2ncc(Cl)cc2F)cc(C)c1C1C(=O)CC(CC(=O)NCC2CC2C(F)F)C1=O] | 1H NMR (400 MHz, CD3OD) 8.54-8.40 (m, 1H), 7.81 (dd, 1H), 7.61-7.51 (m, 2H), 5.92-5.47 (m, 1H), 3.45-3.36 (m, 2H), 3.23-3.12 (m, 1H), 3.00-2.87 (m, 1H), 2.85-2.73 (m, 1H), 2.53-2.35 (m, 2H), 2.22-2.12 (m, 6H), 0.81-0.66 (m, 4H) |
| B144 | 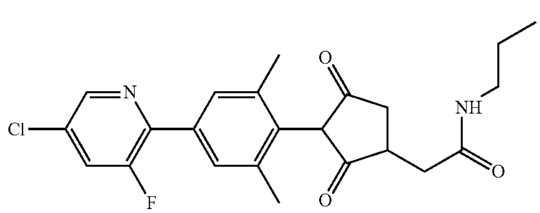 [SMILES: CCCNC(=O)CC1CC(=O)C(c2c(C)cc(-c3ncc(Cl)cc3F)cc2C)C1=O] | 1H NMR (400 MHz, CD3OD) 8.49-8.34 (m, 1H), 7.89-7.71 (m, 1H), 7.66-7.45 (m, 2H), 3.23-3.08 (m, 3H), 2.99-2.85 (m, 1H), 2.77 (dd, 1H), 2.53-2.44 (m, 2H), 2.24-2.10 (m, 6H), 1.59-1.47 (m, 2H), 1.01-0.85 (m, 3H) |

TABLE T2-continued

| Compound Number | Structure | Physical Data LCMS or ¹H NMR (400 MHz, CDCl₃) unless stated. |
|---|---|---|
| B145 | 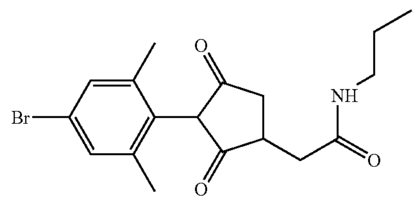 [SMILES: CCCNC(=O)CC1CC(=O)C(c2c(C)cc(Br)cc2C)C1=O] | 1HNMR (400 MHz, CD3OD) 7.2S-7.15 (m, 2H), 3.22-3.03 (m, 3H), 2.90 (dd, 1H), 2.74 (dd, 1H), 2.52-2.37 (m, 2H), 2.09 (s, 6H), 1.54 (sxt, 2H), 0.98-0.87 (m, 3H) |
| B146 | 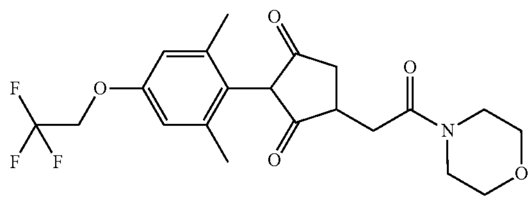 [SMILES: Cc1cc(OCC(F)(F)F)cc(C)c1C1C(=O)CC(CC(=O)N2CCOCC2)C1=O] | 6.64 (s, 2H), 4.39-4.20 (m, 2H), 3.85-3.43 (m, 8H), 3.39-3.24 (m, 1H), 2.87 (s, 2H), 2.68-2.49 (m, 1H), 2.29-2.18 (m, 1H), 2.12 (d, 6H) |
| B147 | 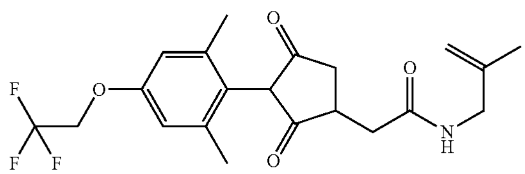 [SMILES: C=C(C)CNC(=O)CC1CC(=O)C(c2c(C)cc(OCC(F)(F)F)cc2C)C1=O] | 13.69-13.21 (m, 1H), 7.46-7.27 (m, 1H), 6.64 (s, 2H), 4.93-4.62 (m, 2H), 4.30 (d, 2H), 3.82-3.51 (m, 2H), 3.31-3.07 (m, 1H), 2.95-2.43 (m, 3H), 2.11 (s, 7H), 1.69 (s, 3H) |
| B148 | 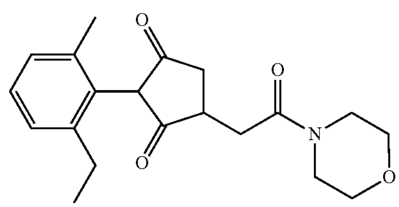 [SMILES: CCc1cccc(C)c1C1C(=O)CC(CC(=O)N2CCOCC2)C1=O] | 7.21-6.99 (m, 3H), 3.80-3.24 (m, 9H), 2.89 (dd, 2H), 2.45 (t, 3H), 2.32-2.07 (m, 4H), 1.10 (dt, 3H) |
| B149 | 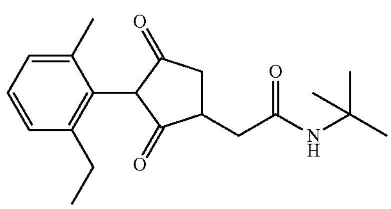 [SMILES: CCc1cccc(C)c1C1C(=O)CC(CC(=O)NC(C)(C)C)C1=O] | 7.28-6.99 (m, 4H), 3.24-3.09 (m, 1H), 2.85 (d, 1H), 2.57 (d, 2H), 2.49-2.38 (m, 2H), 2.35-2.22 (m, 1H), 2.12 (d, 3H), 1.34 (d, 9H), 1.10? (t, 3H) |
| B150 | 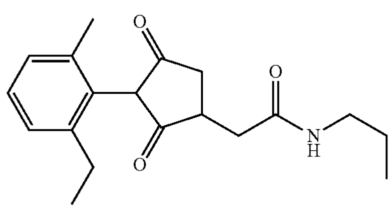 [SMILES: CCCNC(=O)CC1CC(=O)C(c2c(C)cccc2CC)C1=O] | 14.19-13.47 (m, 1H), 7.67-7.39 (m, 1H), 7.22-6.92 (m, 3H), 2.98 (s, 4H), 2.44 (dd, 4H), 2.13 (d, 4H), 1.47-1.31 (m, 2H), 1.10 (q, 3H), 0.84 (t, 3H) |
| B151 | 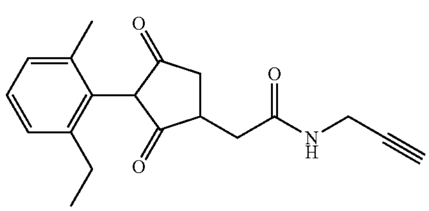 [SMILES: C#CCNC(=O)CC1CC(=O)C(c2c(C)cccc2CC)C1=O] | 13.61-13.02 (m, 1H), 8.11-7.64 (m, 1H), 7.24-6.97 (m, 3H), 3.87-3.58 (m, 2H), 3.28-3.04 (m, 1H), 2.97-2.73 (m, 1H), 2.68-2.50 (m, 1H), 2.50-2.03 (m, 8H), 1.10 (dt, 3H) |

TABLE T2-continued

| Compound Number | Structure | Physical Data LCMS or ¹H NMR (400 MHz, CDCl₃) unless stated. |
|---|---|---|
| B152 | 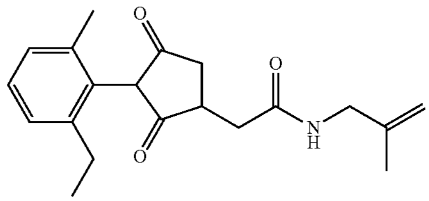 [SMILES: C=C(C)CNC(=O)CC1CC(=O)C(c2c(C)cccc2CC)C1=O] | 13.89-13.46 (m, 1H), 7.89-7.53 (m, 1H), 7.21-6.99 (m, 3H), 4.90-4.63 (m, 2H), 3.57 (d, 2H), 3.23-3.03 (m, 1H), 2.91-2.74 (m, 1H), 2.69-2.55 (m, 1H), 2.55-2.30 (m, 3H), 2.11 (d, 4H), 1.67 (s, 3H), 1.10 (td, 3H) |
| B153 | 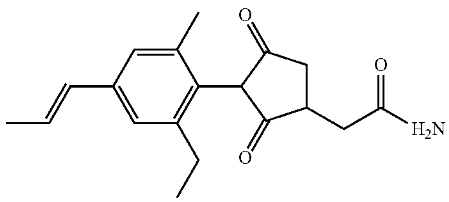 [SMILES: C/C=C/c1cc(C)c(C2C(=O)CC(CC(N)=O)C2=O)c(CC)c1] | 7.05 (s, 2H), 6.33 (d, 2H), 3.23-3.05 (m, 1H), 2.74 (d, 2H), 2.54-2.33 (m, 4H), 2.07 (s, 3H), 1.92-1.76 (m, 3H), 1.07 (t, 3H) |
| B154 | 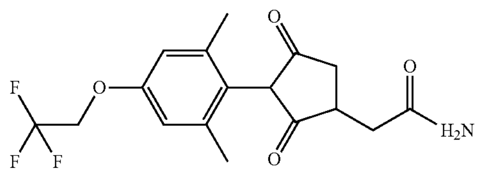 [SMILES: Cc1cc(OCC(F)(F)F)cc(C)c1C1C(=O)CC(CC(N)=O)C1=O] | 1H NMR (400 MHz, CD3OD) 6.71 (s, 2H), 4.46 (d, 2H), 3.21-2.36 (m, 5H), 2.09 (s, 6H) |
| B155 | 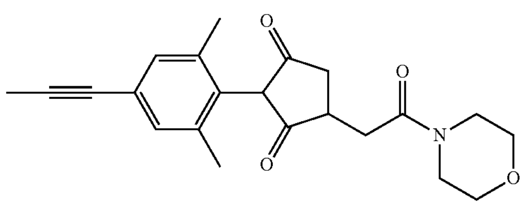 [SMILES: CC#Cc1cc(C)c(C2C(=O)CC(CC(=O)N3CCOCC3)C2=O)c(C)c1] | 7.07 (d, 2H), 3.81-3.20 (m, 9H), 2.86 (dd, 2H), 2.71-2.43 (m, 1H), 2.31-1.98 (m, 10H) |
| B156 | 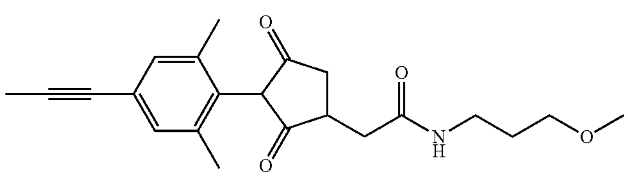 [SMILES: CC#Cc1cc(C)c(C2C(=O)CC(CC(=O)NCCCOC)C2=O)c(C)c1] | 7.52-7.31 (m, 1H), 7.08 (s, 2H), 3.42 (t, 2H), 3.36-3.11 (m, 6H), 2.90-2.76 (m, 1H), 2.62-2.44 (m, 2H), 2.23-1.95 (m, 10H), 1.71 (s, 2H) |
| B157 | 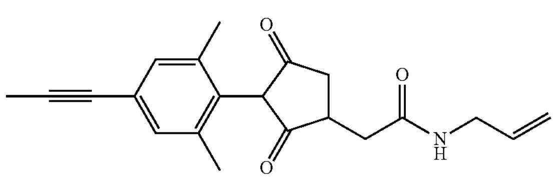 [SMILES: C=CCNC(=O)CC1CC(=O)C(c2c(C)cc(C#CC)cc2C)C1=O] | 7.48-7.30 (m, 1H), 7.08 (s, 2H), 5.80-5.51 (m, 1H), 5.20-5.04 (m, 2H), 3.71 (s, 2H), 3.24-3.04 (m, 1H), 2.91-2.74 (m, 1H), 2.67-2.38 (m, 2H), 2.22-1.95 (m, 10H) |
| B158 | 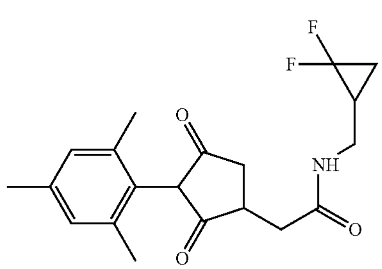 [SMILES: Cc1cc(C)c(C2C(=O)CC(CC(=O)NCC3CC3(F)F)C2=O)c(C)c1] | 1H NMR (400 MHz, CD3OD) 6.86 (s, 2H), 3.45-3.37 (m, 1H), 3.23 (dd, 1H), 3.13 (d, 1H), 2.88 (dd, 1H), 2.77 (dd, 1H), 2.50-2.35 (m, 2H), 2.28-2.20 (m, 3H), 2.06 (s, 6H), 1.96-1.83 (m, 1H), 1.49 (ddt, 1H), 1.23-1.10 (m, 1H) |

TABLE T2-continued

| Compound Number | Structure | Physical Data LCMS or ¹H NMR (400 MHz, CDCl₃) unless stated. |
|---|---|---|
| B159 | 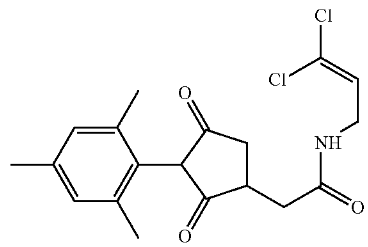 [SMILES: Cc1cc(C)c(C2C(=O)CC(CC(=O)NCC=C(Cl)Cl)C2=O)c(C)c1] | 1H NMR (400 MHz, CD3OD) 6.86 (s, 2H), 6.04 (t, 1H), 3.93 (d, 2H), 3.13 (br.s., 1H), 2.93-2.87 (m, 1H), 2.81-2.68 (m, 1H), 2.48-2.34 (m, 2H), 2.27-2.20 (m, 3H), 2.08-2.00 (m, 6H) |
| B160 | 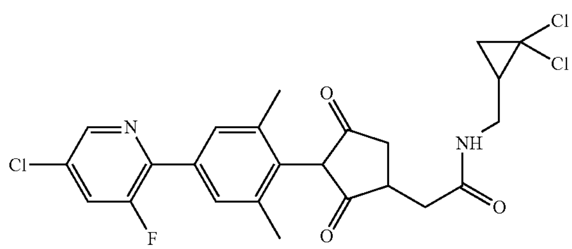 [SMILES: Cc1cc(-c2ncc(Cl)cc2F)cc(C)c1C1C(=O)CC(CC(=O)NCC2CC2(Cl)Cl)C1=O] | 1H NMR (400 MHz, CD3OD) 8.48 (s, 1H), 7.83 (dd, 1H), 7.60 (s, 2H), 3.51 (td, 1H), 3.31-3.24 (m, 1H), 3.19 (d, 1H), 2.95 (dd, 1H), 2.81 (ddd, 1H), 2.58-2.37 (m, 2H), 2.25-2.14 (m, 6H), 2.02-1.90 (m, 1H), 1.72-1.60 (m, 1H), 1.36-1.18 (m, 1H) |
| B161 | 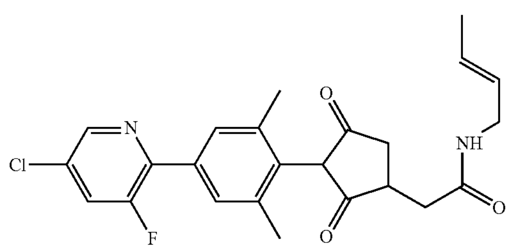 [SMILES: C/C=C/CNC(=O)CC1CC(=O)C(c2c(C)cc(-c3ncc(Cl)cc3F)cc2C)C1=O] | 1H NMR (400 MHz, CD3OD) 8.56-8.37 (m, 1H), 7.84 (dd, 1H), 7.60 (s, 2H), 5.74-5.59 (m, 1H), 5.55-5.36 (m, 1H), 3.91-3.72 (m, 2H), 3.23-3.11 (m, 1H), 2.93 (dd, 1H), 2.77 (dd, 1H), 2.52-2.39 (m, 2H), 2.19 (s, 6H), 1.74-1.64 (m, 3H) |
| B162 | 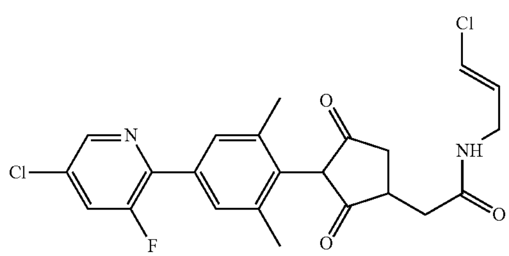 [SMILES: Cc1cc(-c2ncc(Cl)cc2F)cc(C)c1C1C(=O)CC(CC(=O)NC/C=C/Cl)C1=O] | 1H NMR (400 MHz, CD3OD) 8.49 (d, 1H), 7.84 (dd, 1H), 7.60 (s, 2H), 6.33 (d, 1H), 6.04-5.77 (m, 1H), 3.83 (d, 2H), 3.15 (d, 1H), 2.94 (dd, 1H), 2.78 (dd, 1H), 2.57-2.41 (m, 2H), 2.23-2.18 (m, 6H) |
| B163 | 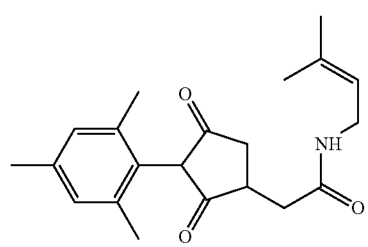 [SMILES: CC(C)=CCNC(=O)CC1CC(=O)C(c2c(C)cc(C)cc2C)C1=O] | 1H NMR (400 MHz, CD3OD) 6.90-6.71 (m, 2H), 5.27-5.14 (m, 1H), 3.79 (d, 2H), 3.23-3.03 (m, 1H), 2.87 (dd, 1H), 2.78-2.66 (m, 1H), 2.48-2.34 (m, 2H), 2.26-2.19 (m, 3H), 2.08-1.97 (m, 6H), 1.77-1.65 (m, 6H) |
| B164 | 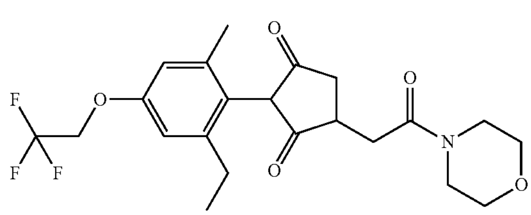 [SMILES: CCc1cc(OCC(F)(F)F)cc(C)c1C1C(=O)CC(CC(=O)N2CCOCC2)C1=O] | 12.71-12.00 (m, 1H), 6.75-6.55 (m, 2H), 4.32 (q, 2H), 3.90-3.45 (m, 8H), 3.36 (br.s., 1H), 2.90 (dd, 2H), 2.43 (quin, 3H), 2.24 (d, 1H), 2.12 (d, 3H), 1.10 (dt, 3H) |

TABLE T2-continued

| Compound Number | Structure | Physical Data LCMS or ¹H NMR (400 MHz, CDCl₃) unless stated. |
|---|---|---|
| B165 | 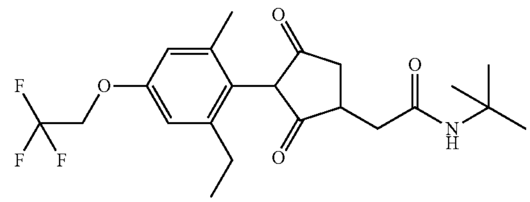 [SMILES: CCc1cc(OCC(F)(F)F)cc(C)c1C1C(=O)CC(CC(=O)NC(C)(C)C)C1=O] | 13.85-13.21 (m, 1H), 6.81-6.56 (m, 3H), 4.32 (q, 2H), 3.34-3.12 (m, 1H), 2.43 (dd, 5H), 2.11 (d, 4H), 1.37-1.25 (m, 9H), 1.10 (dt, 3H) |
| B166 | 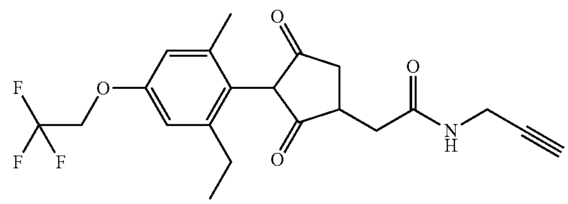 [SMILES: C#CCNC(=O)CC1CC(=O)C(c2c(C)cc(OCC(F)(F)F)cc2CC)C1=O] | 13.49-12.77 (m, 1H), 7.96-7.55 (m, 1H), 6.82-6.51 (m, 2H), 4.33 (q, 2H), 3.98-3.73 (m, 2H), 3.29-3.07 (m, 1H), 2.92-2.32 (m, 5H), 2.29-2.04 (m, 5H), 1.09 (dt, 3H) |
| B167 | 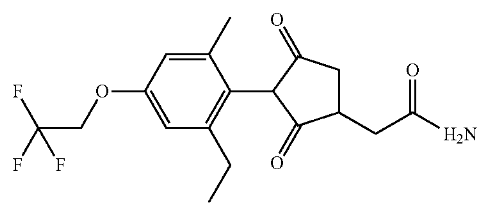 [SMILES: CCc1cc(OCC(F)(F)F)cc(C)c1C1C(=O)CC(CC(N)=O)C1=O] | 1H NMR (400 MHz, CD3OD) 6.72 (s, 2H), 4.48 (d, 2H), 3.24-3.02 (m, 1H), 2.99-2.66 (m, 2H), 2.58-2.31 (m, 4H), 2.08 (s, 3H), 1.07 (t, 3H) |
| B168 | 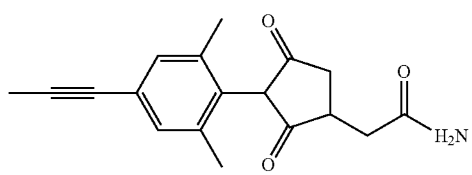 [SMILES: CC#Cc1cc(C)c(C2C(=O)CC(CC(N)=O)C2=O)c(C)c1] | 1H NMR (400 MHz, CD3OD) 7.05 (s, 2H), 3.21-3.05 (m, 1H), 2.98-2.66 (m, 2H), 2.46 (s, 2H), 2.06 (s, 6H), 2.02-1.93 (m, 3H) |
| B169 | 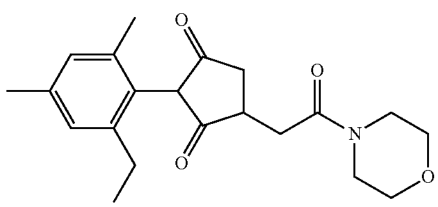 [SMILES: CCc1cc(C)cc(C)c1C1C(=O)CC(CC(=O)N2CCOCC2)C1=O] | 6.89 (t, 2H), 3.85-3.44 (m, 8H), 3.42-3.25 (m, 1H), 2.90 (dd, 2H), 2.68-2.34 (m, 3H), 2.27-2.20 (m, 4H), 2.09 (d, 3H), 1.09 (dt, 3H) |
| B170 | 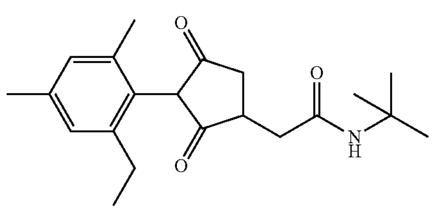 [SMILES: CCc1cc(C)cc(C)c1C1C(=O)CC(CC(=O)NC(C)(C)C)C1=O] | 6.94-6.79 (m, 2H), 6.69-6.55 (m, 1H), 3.30-3.08 (m, 1H), 2.90-2.75 (m, 1H), 2.41 (d, 4H), 2.27 (s, 3H), 2.09 (s, 4H), 1.29 (d, 9H), 1.09 (dt, 3H) |
| B171 | 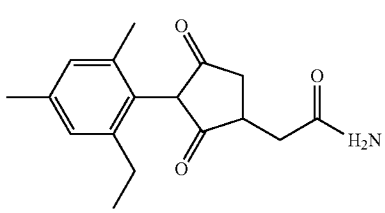 [SMILES: CCc1cc(C)cc(C)c1C1C(=O)CC(CC(N)=O)C1=O] | 1H NMR (400 MHz. CD3OD) 6.88 (br.s., 2H), 3.11 (br.s., 1H), 2.88 (dd, 1H), 2.75 (dd, 1H), 2.52-2.32 (m, 4H), 2.26 (s, 3H), 2.05 (s, 3H), 1.05 (t, 3H) |

TABLE T2-continued

| Compound Number | Structure | Physical Data LCMS or ¹H NMR (400 MHz, CDCl₃) unless stated. |
|---|---|---|
| B172 | 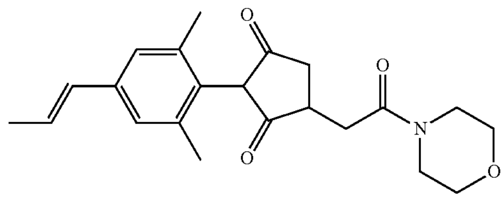 [SMILES: C/C=C/c1cc(C)c(C2C(=O)CC(CC(=O)N3CCOCC3)C2=O)c(C)c1] | 12.55-11.92 (m, 1H), 7.01 (d, 2H), 6.47-6.06 (m, 2H), 3.90-3.26 (m, 9H), 3.2-2.89 (dd, 2H), 2.66-2.45 (m, 1H), 2.38-2.03 (m, 7H), 1.85 (dd, 3H) |
| B173 | 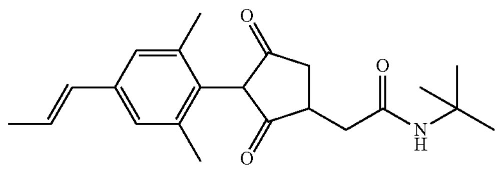 [SMILES: C/C=C/c1cc(C)c(C2C(=O)CC(CC(=O)NC(C)(C)C)C2=O)c(C)c1] | 7.09-6.93 (m, 2H), 6.74-6.53 (m, 1H), 6.40-5.96 (m, 2H), 3.32-3.05 (m, 1H), 2.93-2.71 (m, 1H), 2.69-2.40 (m, 2H), 2.12 (d, 7H), 1.84 (dd, 3H), 1.29 (s, 9H) |
| B174 | 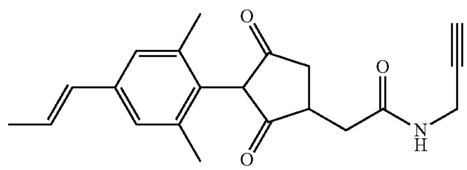 [SMILES: C#CCNC(=O)CC1CC(=O)C(c2c(C)cc(/C=C/C)cc2C)C1=O] | 7.74-7.54 (m, 1H), 7.02 (d, 2H), 6.34-6.09 (m, 2H), 3.93-3.71 (m, 2H), 3.22-3.05 (m, 1H), 2.93-2.73 (m, 1H), 2.68-2.39 (m, 2H), 2.25-2.02 (m, 8H), 1.84 (dd, 3H) |
| B175 | 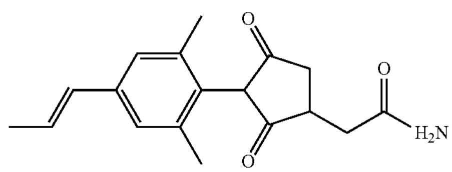 [SMILES: C/C=C/c1cc(C)c(C2C(=O)CC(CC(N)=O)C2=O)c(C)c1] | 1H NMR (400 MHz, CD3OD) 7.02 (s, 2H), 6.39-6.10 (m, 2H), 3.21-3.04 (m, 1H), 2.99-2.84 (m, 1H), 2.80-2.66 (m, 1H), 2.51-2.35 (m, 2H), 2.08 (s, 6H), 1.84 (dd, 3H) |
| B176 | 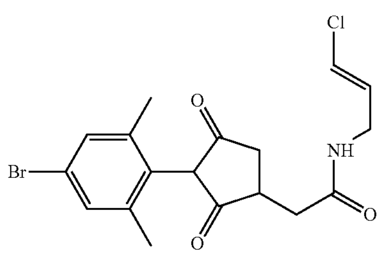 [SMILES: Cc1cc(Br)cc(C)c1C1C(=O)CC(CC(=O)NC/C=C/Cl)C1=O] | 1H NMR (400 MHz, CD3OD) 7.25-7.13 (m, 2H), 6.31 (td, 1H), 5.50-5.59 (m, 1H), 3.82 (dd, 2H), 3.14 (d, 1H), 2.91 (dd, 1H), 2.81-2.66 (m, 1H), 2.51-2.38 (m, 2H), 2.09 (s, 6H) |
| B177 | 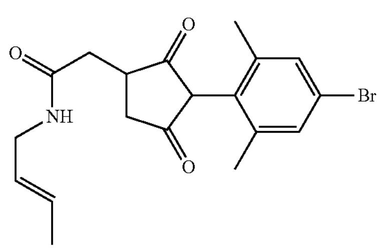 [SMILES: C/C=C/CNC(=O)CC1CC(=O)C(c2c(C)cc(Br)cc2C)C1=O] | 1H NMR (400 MHz, CD3OD) 7.26-7.12 (m, 2H), 5.73-5.59 (m, 1H), 5.54-5.39 (m, 1H), 3.91-3.70 (m, 2H), 3.22-3.09 (m, 1H), 2.95-2.80 (m, 1H), 2.74 (dd, 1H), 2.51-2.39 (m, 2H), 2.09 (s, 6H), 1.73-1.52 (m, 3H) |
| B178 | 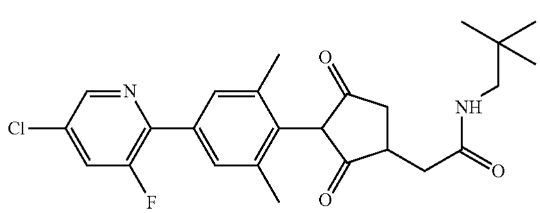 [SMILES: Cc1cc(-c2ncc(Cl)cc2F)cc(C)c1C1C(=O)CC(CC(=O)NCC(C)(C)C)C1=O] | 1H NMR (400 MHz, CD3OD) 8.52-8.39 (m, 1H), 7.84 (dd, 1H), 7.60 (s, 2H), 3.24-3.11 (m, 1H), 3.07-3.01 (m, 2H), 2.97-2.91 (m, 1H), 2.82 (dd, 1H), 2.58-2.42 (m, 2H), 2.23-2.16 (m, 6H), 0.99-0.87 (m, 9H) |

TABLE T2-continued

| Compound Number | Structure | Physical Data LCMS or ¹H NMR (400 MHz, CDCl₃) unless stated. |
|---|---|---|
| B179 | 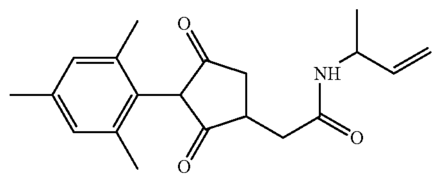 [SMILES: C=CC(C)NC(=O)CC1CC(=O)C(c2c(C)cc(C)cc2C)C1=O] | 1H NMR (400 MHz, CD3OD) 6.86 (s, 2H), 5.85 (dddd, 1H), 5.21-5.12 (m, 1H), 5.09-5.04 (m, 1H), 4.47 (t, 1H), 3.13 (d, 1H), 2.88 (dd, 1H), 2.77 (dd, 1H), 2.42 (d, 2H), 2.25 (s, 3H), 2.06 (s, 6H), 1.26-1.18 (m, 3H) |
| B180 | 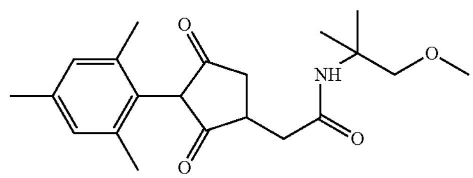 | 1H NMR (400 MHz, CD3OD) 6.91-6.76 (m, 2H), 3.53-3.44 (m, 2H), 3.35 (s, 3H), 3.20-3.03 (m, 1H), 2.86 (dd, 1H), 2.70 (dd, 1H), 2.50-2.34 (m, 2H), 2.29-2.19 (m, 3H), 2.06 (s, 6H), 1.35-1.27 (m, 6H) |
| B181 | 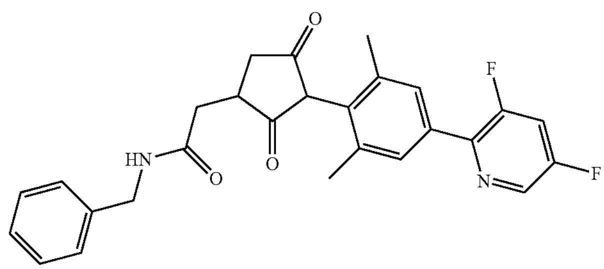 [SMILES: Cc1cc(-c2ncc(F)cc2F)cc(C)c1C1C(=O)CC(CC(=O)NCc2ccccc2)C1=O] | 1H NMR (400 MHz, CD3OD) 8.44 (d, 1H), 7.65 (ddd, 1H), 7.55 (s, 2H), 7.36-7.21 (m, 5H), 4.41 (s, 2H), 3.20 (br.s., 1H), 2.94 (dd, 1H), 2.84 (dd, 1H), 2.58-2.45 (m, 2H), 2.23-2.14 (m, 6H) |
| B182 | 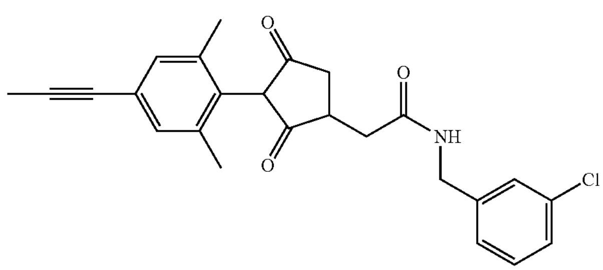 [SMILES: CC#Cc1cc(C)c(C2C(=O)CC(CC(=O)NCc3cccc(Cl)c3)C2=O)c(C)c1] | 7.91-7.57 (m, 1H), 7.29-7.20 (m, 2H), 7.16 (s, 1H), 7.10-6.95 (m, 3H), 4.28-4.03 (m, 2H), 3.27-3.09 (m, 1H), 2.91-2.72 (m, 1H), 2.69-2.42 (m, 2H), 2.27-1.91 (m, 10H) |
| B183 | 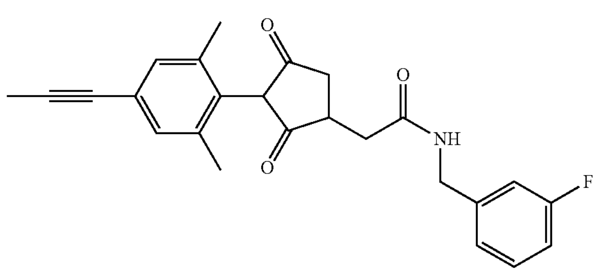 [SMILES: CC#Cc1cc(C)c(C2C(=O)CC(CC(=O)NCc3cccc(F)c3)C2=O)c(C)c1] | 13.90-13.26 (m, 1H), 8.07-7.66 (m, 1H), 7.35-7.18 (m, 1H), 7.11-6.77 (m, 5H), 4.19 (d, 2H), 3.22-3.04 (m, 1H), 2.79 (d, 1H), 2.69-2.33 (m, 2H), 2.22-1.89 (m, 9H) |
| B184 | 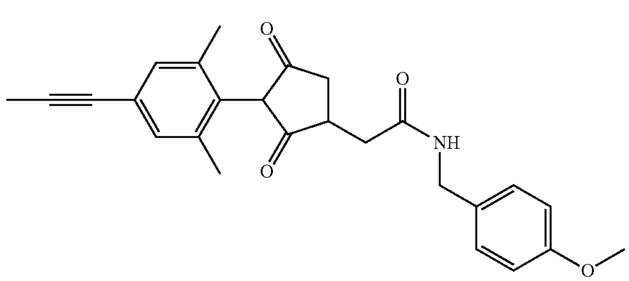 [SMILES: CC#Cc1cc(C)c(C2C(=O)CC(CC(=O)NCc3ccc(OC)cc3)C2=O)c(C)c1] | 7.78-7.51 (m, 1H), 7.19-7.01 (m, 4H), 6.83 (d, 2H), 4.20 (d, 2H), 3.77 (s, 3H), 3.24-3.05 (m, 1H), 2.74 (d, 1H), 2.47 (s, 2H), 2.14-1.93 (m, 10H) |

TABLE T2-continued

| Compound Number | Structure | Physical Data LCMS or $^1$H NMR (400 MHz, CDCl$_3$) unless stated. |
|---|---|---|
| B185 | 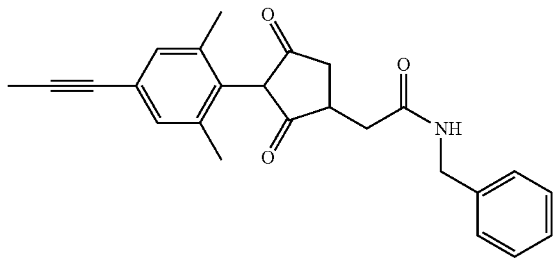 [SMILES: CC#Cc1cc(C)c(C2C(=O)CC(CC(=O)NCc3ccccc3)C2=O)c(C)c1] | 13.93-13.42 (m, 1H), 7.87-7.57 (m, 1H), 7.42-6.98 (m, 7H), 4.24 (d, 2H), 3.32-2.95 (m, 1H), 2.86-2.62 (m, 1H), 2.60-2.33 (m, 2H), 2.14-1.91 (m, 10H) |
| B186 | 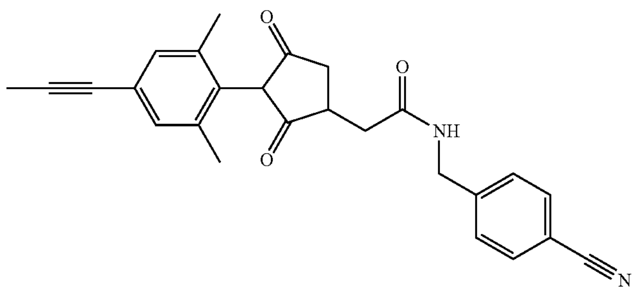 [SMILES: CC#Cc1cc(C)c(C2C(=O)CC(CC(=O)NCc3ccc(C#N)cc3)C2=O)c(C)c1] | 1H NMR (400 MHz, CD3OD) 7.67 (d, 2H), 7.46 (d, 2H), 7.04 (s, 2H), 4.44 (s, 2H), 3.23-3.09 (m, 1H), 2.99-2.72 (m, 2H), 2.59-2.41 (m, 2H), 2.13-1.94 (m, 9H) |
| B187 | 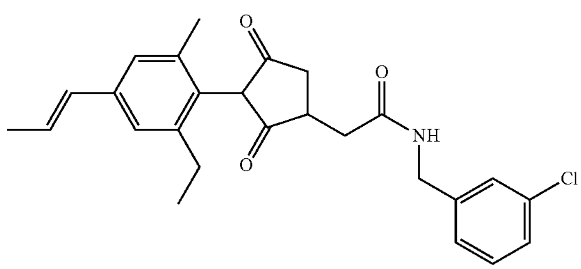 [SMILES: C/C=C/c1cc(C)c(C2C(=O)CC(CC(=O)NCc3cccc(Cl)c3)C2=O)c(CC)c1] | 13.81-12.98 (m, 1H), 7.97 (br.s., 1H), 7.41-7.08 (m, 3H), 7.06-6.89 (m, 3H), 6.43-5.96 (m, 2H), 4.19-3.86 (m, 2H), 3.30-2.96 (m, 1H), 2.88-2.61 (m, 2H), 2.36 (d, 3H), 2.21-1.92 (m, 4H), 1.85 (dd, 3H), 1.05 (td, 3H) |
| B188 | 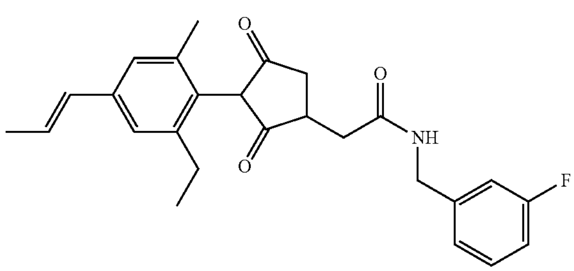 [SMILES: C/C=C/c1cc(C)c(C2C(=O)CC(CC(=O)NCc3cccc(F)c3)C2=O)c(CC)c1] | 7.79-7.56 (m, 1H), 7.33-7.19 (m, 1H), 7.08-6.79 (m, 5H), 6.39-6.07 (m, 2H), 4.28-4.01 (m, 2H), 3.33-3.11 (m, 1H), 2.94-2.65 (m, 2H), 2.55 (s, 1H), 2.45-2.27 (m, 2H), 2.05 (d, 4H), 1.85 (dd, 3H), 1.06 (td, 3H) |
| B189 | 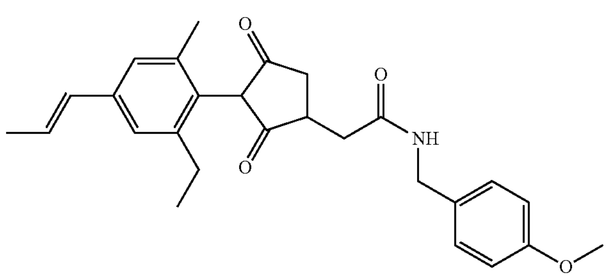 [SMILES: C/C=C/c1cc(C)c(C2C(=O)CC(CC(=O)NCc3ccc(OC)cc3)C2=O)c(CC)c1] | 7.67-7.43 (m, 1H), 7.09 (d, 2H), 7.06-6.97 (m, 2H), 6.88-6.74 (m, 2H), 6.38-6.10 (m, 2H), 4.16 (s, 2H), 3.77 (s, 3H), 3.20-3.03 (m, 1H), 2.83-2.67 (m, 1H), 2.37 (d, 4H), 2.06 (s, 4H), 1.84 (dd, 3H), 1.07 (dt, 3H) |

TABLE T2-continued

| Compound Number | Structure | Physical Data LCMS or $^1$H NMR (400 MHz, CDCl$_3$) unless stated. |
|---|---|---|
| B190 | 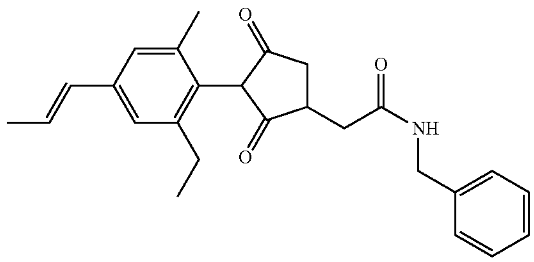 [SMILES: C/C=C/c1cc(C)c(C2C(=O)CC(CC(=O)NCc3ccccc3)C2=O)c(CC)c1] | 13.80-13.02 (m, 1H), 7.92-7.58 (m, 1H), 7.40-7.08 (m, 5H), 7 00 (d, 2H), 6.42-5.89 (m, 2H), 4.19 (s, 2H), 3.28-2.99 (m, 1H), 2.84-2.26 (m, 5H), 2.16-1.75 (m, 7H), 1.06 (dt, 3H) |
| B191 | 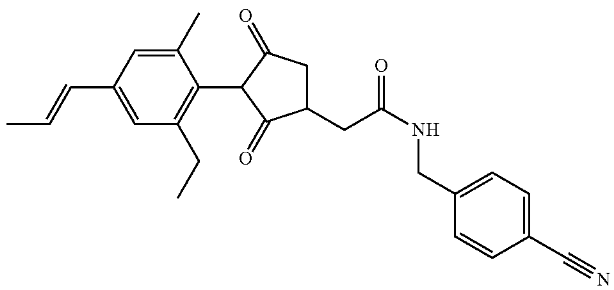 [SMILES: C/C=C/c1cc(C)c(C2C(=O)CC(CC(=O)NCc3ccc(C#N)cc3)C2=O)c(CC)c1] | 13.76-12.91 (m, 1H), 8.60-8.25 (m, 1H), 7.53 (d, 2H), 7.16 (d, 2H), 7.03-6.87 (m, 2H), 6.39-6.07 (m, 2H), 4.19-3.81 (m, 2H), 3.31-3.11 (m, 1H), 2.96-2.76 (m, 2H), 2.63-2.45 (m, 1H), 2.45-2.11 (m, 3H), 2.02 (d, 3H), 1.86 (dd, 3H), 1.03 (td, 3H) |
| B192 | 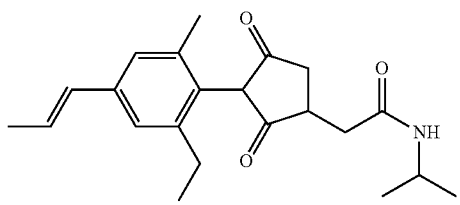 [SMILES: C/C=C/c1cc(C)c(C2C(=O)CC(CC(=O)NC(C)C)C2=O)c(CC)c1] | 14.12-13.30 (m, 1H), 7.20-6.94 (m, 3H), 6.47-5.98 (m, 2H), 4.13-3.82 (m, 1H), 3.16 (br.s., 1H), 2.81 (dd, 1H), 2.67-2.34 (m, 4H), 2.23-2.01 (m, 4H), 1.85 (dd, 3H), 1.20-0.97 (m, 9H) |
| B193 | 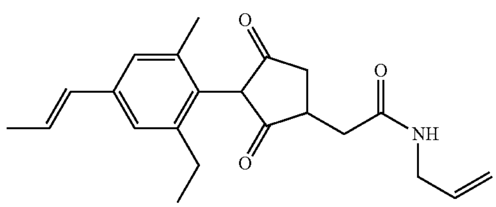 [SMILES: C=CCNC(=O)CC1CC(=O)C(c2c(C)cc(/C=C/C)cc2CC)C1=O] | 13.83-12.88 (m, 1H), 7.63-7.34 (m, 1H), 7.11-6.90 (m, 2H), 6.47-6.05 (m, 2H), 5.79-5.55 (m, 1H), 5.19-4.97 (m, 2H), 3.65 (br.s., 2H), 3.28-3.03 (m, 1H), 2.93-2.72 (m, 1H), 2.40 (d, 4H), 2.09 (s, 4H), 1.85 (dd, 3H), 1.08 (dt, 3H) |
| B194 | 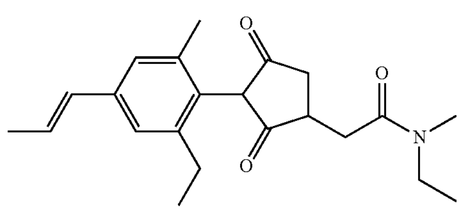 [SMILES: C/C=C/c1cc(C)c(C2C(=O)CC(CC(=O)N(C)CC)C2=O)c(CC)c1] | 12.84 (br.s., 1H), 7.09-6.93 (m, 2H), 6.46-6.05 (m, 2H), 3.63-3.20 (m, 3H), 3.16-2.66 (m, 5H), 2.61-1.96 (m, 7H), 1.85 (dd, 3H), 1.32-0.97 (m, 6H) |
| B195 | 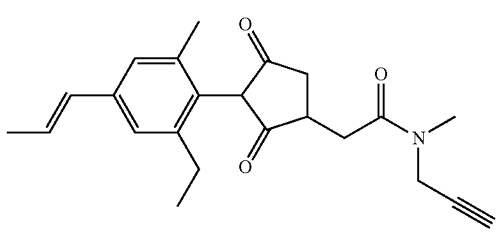 [SMILES: C#CCN(C)C(=O)CC1CC(=O)C(c2c(C)cc(/C=C/C)cc2CC)C1=O] | 12.50-11.80 (m, 1H), 7.14-6.89 (m, 2H), 6.44-6.00 (m, 2H), 4.19 (d, 2H), 3.47-2.78 (m, 5H), 2.73-1.76 (m, 12H), 1.23-0.96 (m, 3H) |

TABLE T2-continued

| Compound Number | Structure | Physical Data LCMS or ¹H NMR (400 MHz, CDCl₃) unless stated. |
|---|---|---|
| B196 | 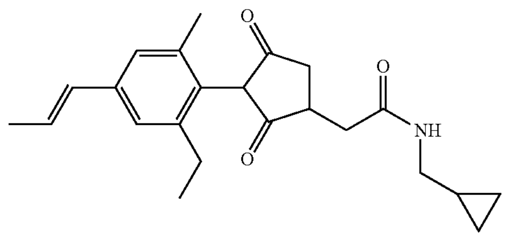 [SMILES: C/C=C/c1cc(C)c(C2C(=O)CC(CC(=O)NCC3CC3)C2=O)c(CC)c1] | 13.85-13.09 (m, 1H), 7.47-7.19 (m, 1H), 7.00-6.82 (m, 2H), 6.31-5.97 (m, 2H), 3.15-2.96 (m, 1H), 2.89-2.62 (m, 3H), 2.30 (q, 4H), 2.12-1.92 (m, 4H), 1.73 (dd, 3H), 0.97 (dt, 3H), 0.70 (br.s., 1H), 0.42-0.24 (m, 2H), 0.12-0.07 (m, 2H) |
| B197 | 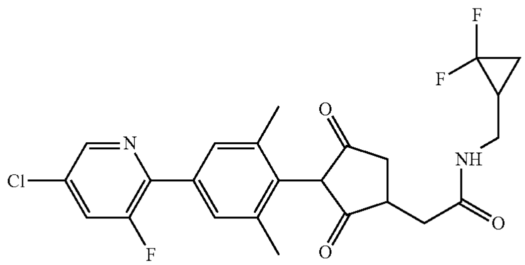 [SMILES: Cc1cc(-c2ncc(Cl)cc2F)cc(C)c1C1C(=O)CC(CC(=O)NCC2CC2(F)F)C1=O] | 1H NMR (400 MHz, CD3OD) 8.47 (dd, 1H), 7.82 (dd, 1H), 7.59 (s, 2H), 3.47-3.36 (m, 1H), 3.28-3.13 (m, 2H), 3.01-2.88 (m, 1H), 2.79 (dd, 1H), 2.51-2.42 (m, 2H), 2.19 (s, 6H), 1.94-1.84 (m, 1H), 1.58-1.43 (m, 1H), 1.27-1.10 (m, 1H) |
| B198 | 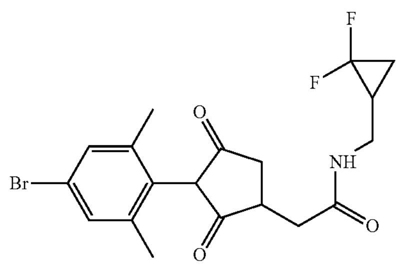 [SMILES: Cc1cc(Br)cc(C)c1C1C(=O)CC(CC(=O)NCC2CC2(F)F)C1=O] | 1H NMR (400 MHz, CD3OD) 7.28-7.13 (m, 2H), 3.45-3.35 (m, 1H), 3.25-3.12 (m, 2H), 2.97-2.88 (m, 1H), 2.76 (dd, 1H), 2.53-2.45 (m, 2H), 2.09 (s, 6H), 1.98-1.76 (m, 1H), 1.49 (ddt, 1H), 1.23-1.03 (m, 1H) |
| B199 | 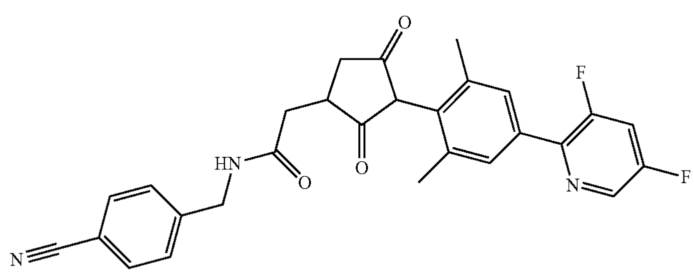 [SMILES: Cc1cc(-c2ncc(F)cc2F)cc(C)c1C1C(=O)CC(CC(=O)NCc2ccc(C#N)cc2)C1=O] | 1H NMR (400 MHz, CD3OD) 8.44 (d, 1H), 7.72-7.62 (m, 3H), 7.55 (br.s., 2H), 7.49 (d, 2H), 4.48 (s, 2H), 3.24-3.15 (m, 1H), 2.99-2.81 (m, 2H), 2.57-2.48 (m, 2H), 2.21-2.14 (m, 6H) |
| B200 | 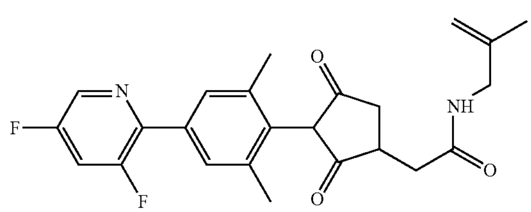 [SMILES: C=C(C)CNC(=O)CC1CC(=O)C(c2c(C)cc(-c3ncc(F)cc3F)cc2C)C1=O] | 1H NMR (400 MHz, CD3OD) 8.44 (d, 1H), 7.67-7.60 (m, 1H), 7.55 (s, 2H), 4.95-4.88 (m, 2H), 3.78 (s, 2H), 3.18 (br.s., 1H), 2.94 (dd, 1H), 2.86-2.78 (m, 1H), 2.50 (d, 2H), 2.20 (s, 6H), 1.78-1.72 (m, 3H) |
| B201 | 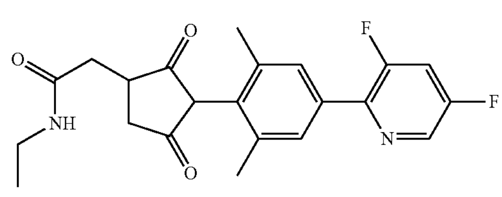 [SMILES: CCNC(=O)CC1CC(=O)C(c2c(C)cc(-c3ncc(F)cc3F)cc2C)C1=O] | 1H NMR (400 MHz, CD3OD) 8.44 (d, 1H), 7.65 (ddd, 1H), 7.55 (s, 2H), 3.28-3.22 (m, 2H), 3.20-3.10 (m, 1H), 2.92 (dd, 1H), 2.76 (dd, 1H), 2.47 (d, 2H), 2.21-2.08 (m, 6H), 1.20-1.10 (m, 3H) |

TABLE T2-continued

| Compound Number | Structure | Physical Data LCMS or ¹H NMR (400 MHz, CDCl₃) unless stated. |
|---|---|---|
| B202 | 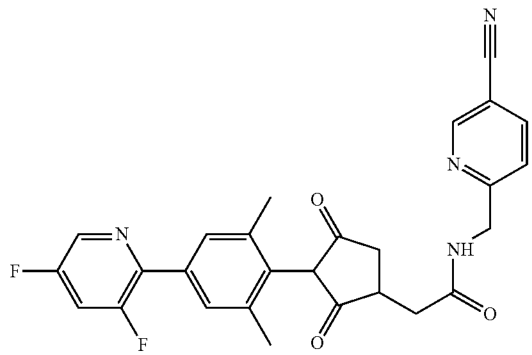 [SMILES: Cc1cc(-c2ncc(F)cc2F)cc(C)c1C1C(=O)CC(CC(=O)NCc2ccc(C#N)cn2)C1=O] | 1H NMR (400 MHz, CD3OD) 8.85 (s, 1H), 8.44 (d, 1H), 8.12 (dd, 1H), 7.69-7.61 (m, 1H), 7.60-7.52 (m, 3H), 4.59 (s, 2H), 3.18-3.08 (m, 1H), 2.95-2.84 (m, 2H), 2.61-2.45 (m, 2H), 2.19 (d, 6H) |
| B203 | 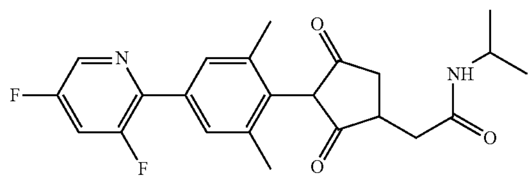 [SMILES: Cc1cc(-c2ncc(F)cc2F)cc(C)c1C1C(=O)CC(CC(=O)NC(C)C)C1=O] | 1H NMR (400 MHz, CD3OD) 8.44 (d, 1H), 7.65 (ddd, 1H), 7.55 (s, 2H), 4.05-3.92 (m, 1H), 3.26-3.11 (m, 1H), 2.91 (dd, 1H), 2.74 (dd, 1H), 2.52-2.35 (m, 2H), 2.24-2.13 (m, 6H), 1.16 (dd, 6H) |
| B204 | 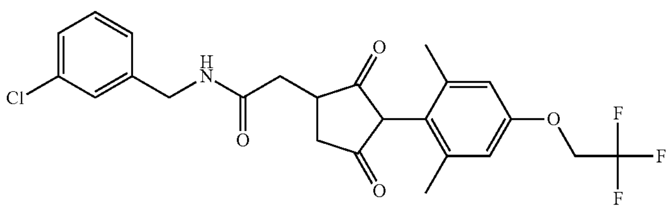 [SMILES: Cc1cc(OCC(F)(F)F)cc(C)c1C1C(=O)CC(CC(=O)NCc2cccc(Cl)c2)C1=O] | 1.43 mins, m/z = 482.14 (M + H)+ |
| B205 | 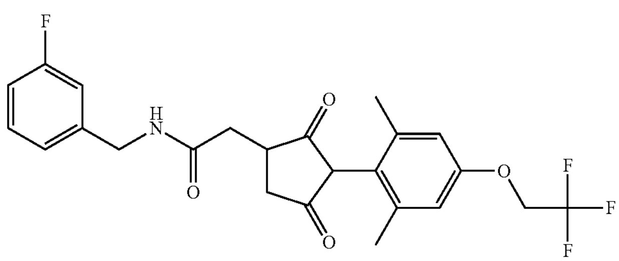 [SMILES: Cc1cc(OCC(F)(F)F)cc(C)c1C1C(=O)CC(CC(=O)NCc2cccc(F)c2)C1=O] | 1.35 mins, m/z = 466.18 (M + H)+ |
| B206 | 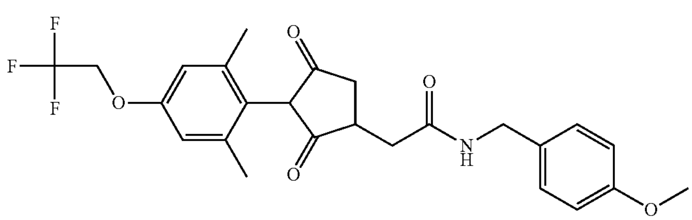 [SMILES: COc1ccc(CNC(=O)CC2CC(=O)C(c3c(C)cc(OCC(F)(F)F)cc3C)C2=O)cc1] | 1.34 mins, m/z = 478.20 (M + H)+ |
| B207 | 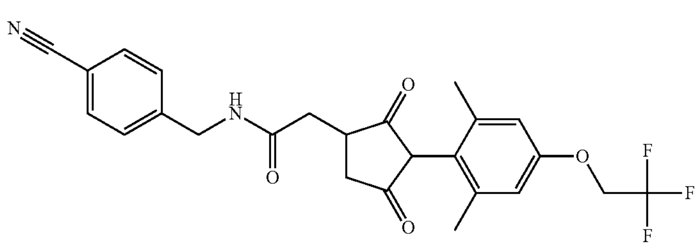 [SMILES: Cc1cc(OCC(F)(F)F)cc(C)c1C1C(=O)CC(CC(=O)NCc2ccc(C#N)cc2)C1=O] | 1.27 mins, m/z = 473.17 (M + H)+ |

TABLE T2-continued

| Compound Number | Structure | Physical Data LCMS or $^1$H NMR (400 MHz, CDCl$_3$) unless stated. |
| --- | --- | --- |
| B208 | 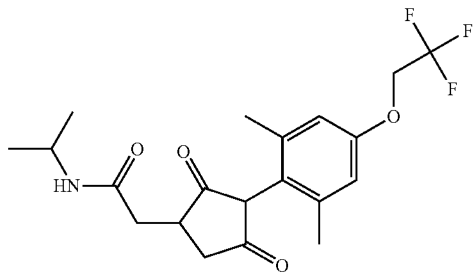 [SMILES: Cc1cc(OCC(F)(F)F)cc(C)c1C1C(=O)CC(CC(=O)NC(C)C)C1=O] | 1.26 mins, m/z = 400.18 (M + H)+ |
| B209 | 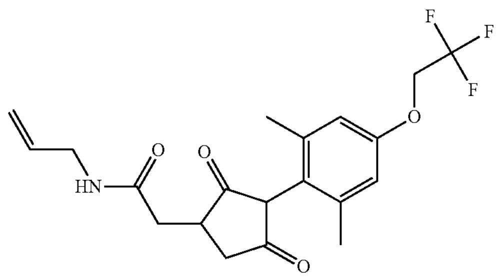 [SMILES: C=CCNC(=O)CC1CC(=O)C(c2c(C)cc(OCC(F)(F)F)cc2C)C1=O] | 1.21 mins, m/z = 398.17 (M + H)+ |
| B210 | 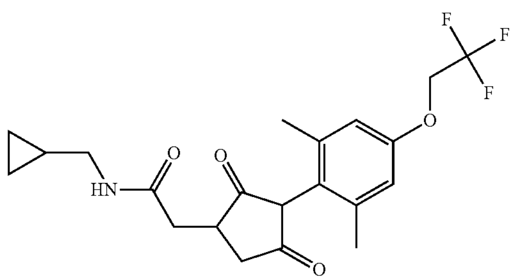 [SMILES: Cc1cc(OCC(F)(F)F)cc(C)c1C1C(=O)CC(CC(=O)NCC2CC2)C1=O] | 1.28 mins, m/z = 412.18 (M + H)+ |
| B211 | 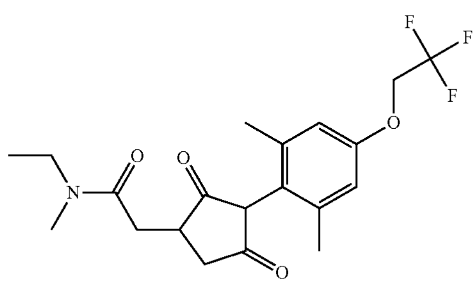 [SMILES: CCN(C)C(=O)CC1CC(=O)C(c2c(C)cc(OCC(F)(F)F)cc2C)C1=O] | 1.26 mins, m/z = 400.18 (M + H)+ |
| B212 | 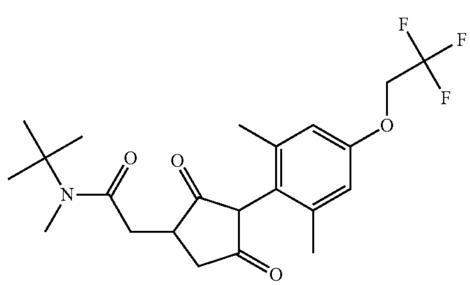 [SMILES: Cc1cc(OCC(F)(F)F)cc(C)c1C1C(=O)CC(CC(=O)N(C)C(C)(C)C)C1=O] | 1.46 mins, m/z = 428.21 (M + H)+ |

TABLE T2-continued

| Compound Number | Structure | Physical Data LCMS or ¹H NMR (400 MHz, CDCl$_3$) unless stated. |
|---|---|---|
| B213 | 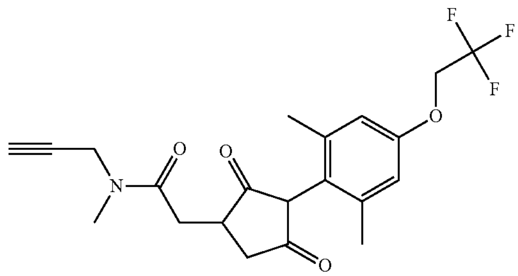 [SMILES: C#CCN(C)C(=O)CC1CC(=O)C(c2c(C)cc(OCC(F)(F)F)cc2C)C1=O] | 1.23 mins, m/z = 410.17 (M + H)+ |
| B214 | 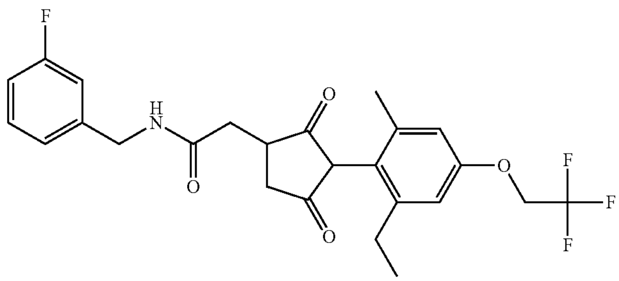 [SMILES: CCc1cc(OCC(F)(F)F)cc(C)c1C1C(=O)CC(CC(=O)NCc2cccc(F)c2)C1=O] | 1.40 mins, m/z = 480.220 (M + H)+ |
| B215 | 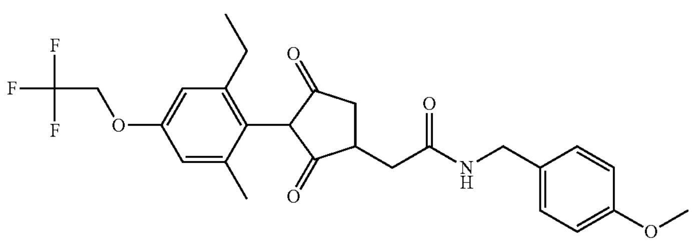 [SMILES: CCc1cc(OCC(F)(F)F)cc(C)c1C1C(=O)CC(CC(=O)NCc2ccc(OC)cc2)C1=O] | 1.38 mins, m/z = 492.21 (M + H)+ |
| B216 | 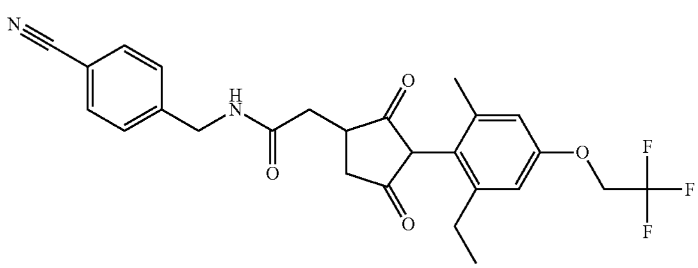 [SMILES: CCc1cc(OCC(F)(F)F)cc(C)c1C1C(=O)CC(CC(=O)NCc2ccc(C#N)cc2)C1=O] | 1.32 mins, m/z = 487.20 (M + H)+ |
| B217 | 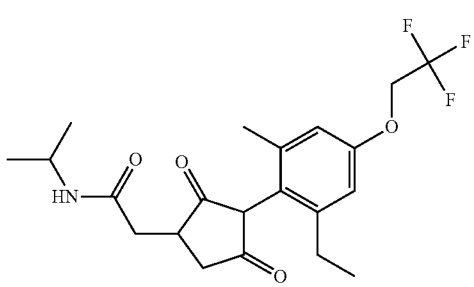 [SMILES: CCc1cc(OCC(F)(F)F)cc(C)c1C1C(=O)CC(CC(=O)NC(C)C)C1=O] | 1.31 mins, m/z = 414.20 (M + H)+ |

TABLE T2-continued
| Compound Number | Structure | Physical Data LCMS or $^1$H NMR (400 MHz, CDCl$_3$) unless stated. |
|---|---|---|
| B218 | 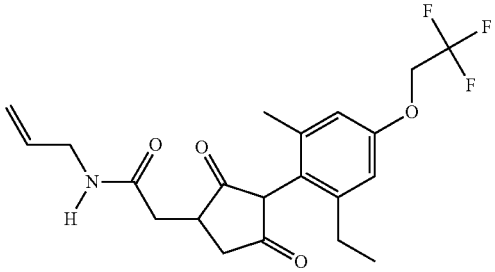 [SMILES: C=CCNC(=O)CC1CC(=O)C(c2c(C)cc(OCC(F)(F)F)cc2CC)C1=O] | 1.26 mins, m/z = 412.18 (M + H)+ |
| B219 | 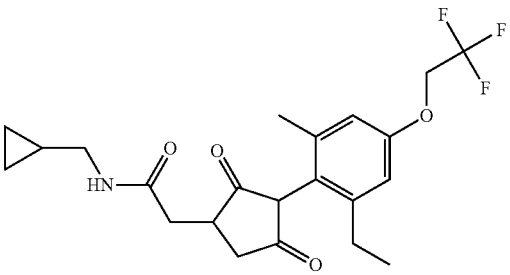 [SMILES: CCc1cc(OCC(F)(F)F)cc(C)c1C1C(=O)CC(CC(=O)NCC2CC2)C1=O] | 1.33 mins, m/z = 426.20 (M + H)+ |
| B220 | 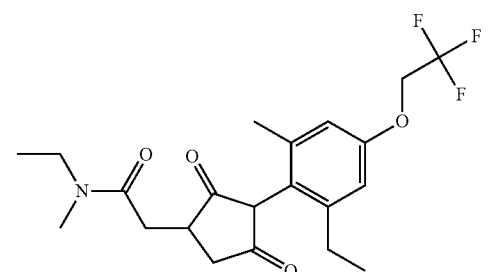 | 1.32 mins, m/z = 414.20 (M + H)+ |
| B221 | 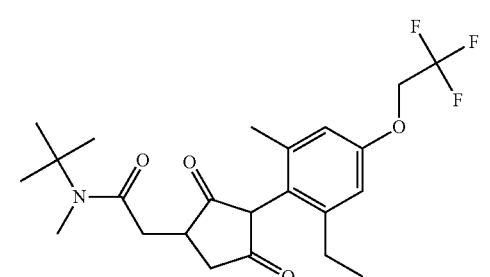 | 1.51 mins, m/z = 442.22 (M + H)+ |
| B222 | 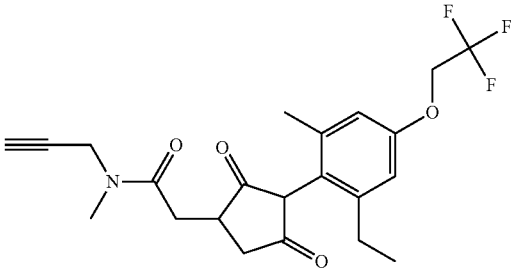 [SMILES: C#CCN(C)C(=O)CC1CC(=O)C(c2c(C)cc(OCC(F)(F)F)cc2CC)C1=O] | 1.28 mins, m/z = 424.18 (M + H)+ |

TABLE T2-continued

| Compound Number | Structure | Physical Data LCMS or ¹H NMR (400 MHz, CDCl₃) unless stated. |
|---|---|---|
| B223 | 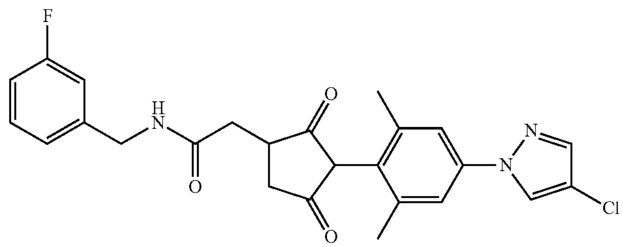 [SMILES: Cc1cc(-n2cc(Cl)cn2)cc(C)c1C1C(=O)CC(CC(=O)NCc2cccc(F)c2)C1=O] | 1.36 mins, m/z = 468.15 (M + H)+ |
| B224 | 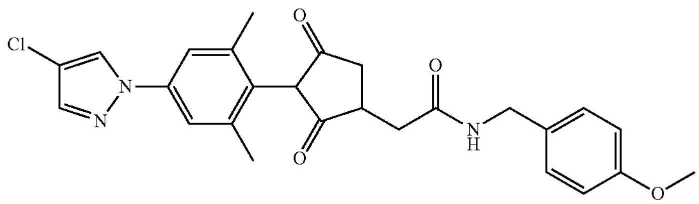 [SMILES: COc1ccc(CNC(=O)CC2CC(=O)C(c3c(C)cc(-n4cc(Cl)cn4)cc3C)C2=O)cc1] | 1.35 mins, m/z = 480.18 (M + H)+ |
| B225 | 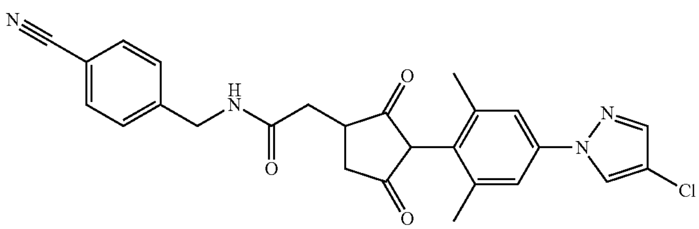 [SMILES: Cc1cc(-n2cc(Cl)cn2)cc(C)c1C1C(=O)CC(CC(=O)NCc2ccc(C#N)cc2)C1=O] | 1.27 mins, m/z = 475.17 (M + H)+ |
| B226 | 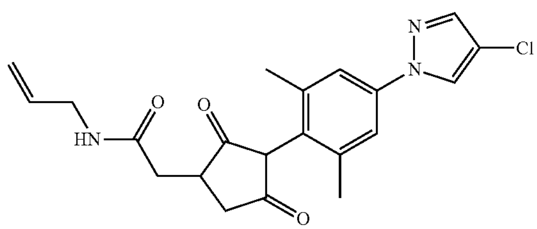 [SMILES: C=CCNC(=O)CC1CC(=O)C(c2c(C)cc(-n3cc(Cl)cn3)cc2C)C1=O] | 1.21 mins, m/z = 400.16 (M + H)+ |
| B227 | 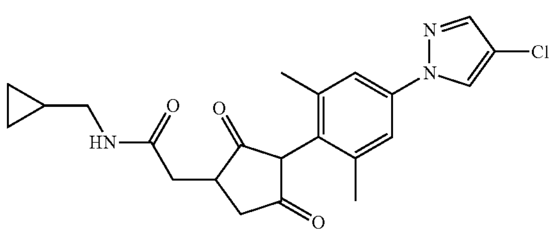 [SMILES: Cc1cc(-n2cc(Cl)cn2)cc(C)c1C1C(=O)CC(CC(=O)NCC2CC2)C1=O] | 1.28 mins, m/z = 414.17 (M + H)+ |
| B228 | 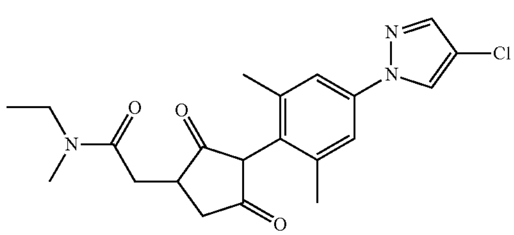 [SMILES: CCN(C)C(=O)CC1CC(=O)C(c2c(C)cc(-n3cc(Cl)cn3)cc2C)C1=O] | 1.26 mins, m/z = 402.16 (M + H)+ |

TABLE T2-continued

| Compound Number | Structure | Physical Data LCMS or ¹H NMR (400 MHz, CDCl₃) unless stated. |
|---|---|---|
| B229 | 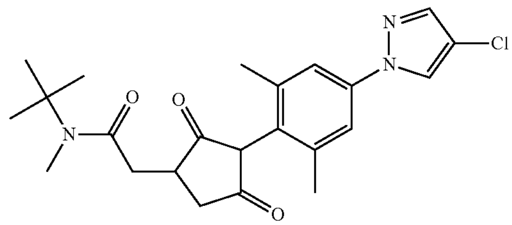 [SMILES: Cc1cc(-n2cc(Cl)cn2)cc(C)c1C1C(=O)CC(CC(=O)N(C)C(C)(C)C)C1=O] | 1.48 mins, m/z = 430.20 (M + H)+ |
| B230 | 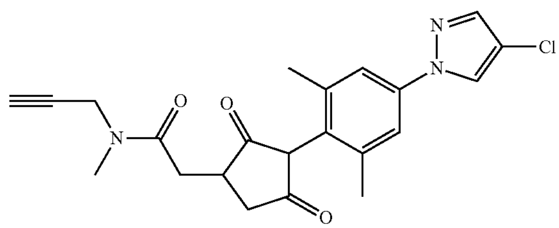 [SMILES: C#CCN(C)C(=O)CC1CC(=O)C(c2c(C)cc(-n3cc(Cl)cn3)cc2C)C1=O] | 1.23 mins, m/z = 412.14 (M + H)+ |
| B231 | 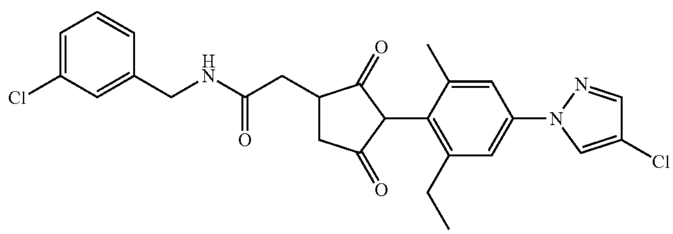 [SMILES: CCc1cc(-n2cc(Cl)cn2)cc(C)c1C1C(=O)CC(CC(=O)NCc2cccc(Cl)c2)C1=O] | 1.47 mins, m/z = 498.14 (M + H)+ |
| B232 | 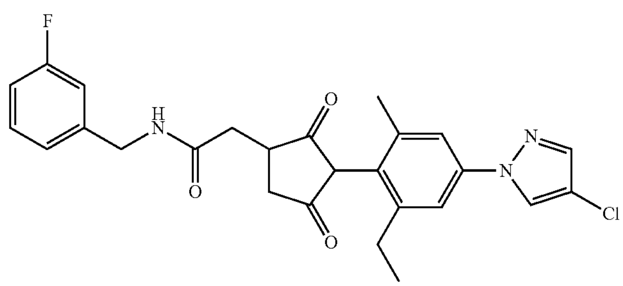 [SMILES: CCc1cc(-n2cc(Cl)cn2)cc(C)c1C1C(=O)CC(CC(=O)NCc2cccc(F)c2)C1=O] | 1.40 mins, m/z = 482.18 (M + H)+ |
| B233 | 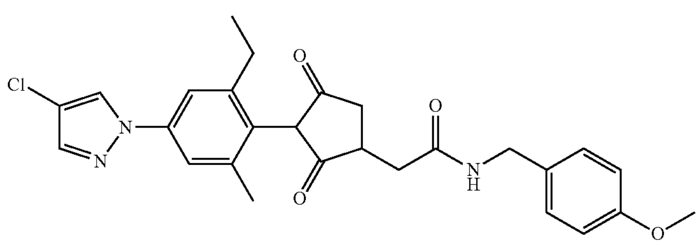 [SMILES: CCc1cc(-n2cc(Cl)cn2)cc(C)c1C1C(=O)CC(CC(=O)NCc2ccc(OC)cc2)C1=O] | 1.39 mins, m/z = 494.19 (M + H)+ |
| B234 | 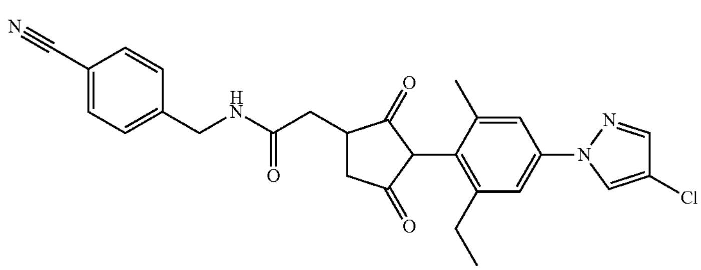 [SMILES: CCc1cc(-n2cc(Cl)cn2)cc(C)c1C1C(=O)CC(CC(=O)NCc2ccc(C#N)cc2)C1=O] | 1.32 mins, m/z = 489.18 (M + H)+ |

TABLE T2-continued

| Compound Number | Structure | Physical Data LCMS or ¹H NMR (400 MHz, CDCl₃) unless stated. |
|---|---|---|
| B235 | 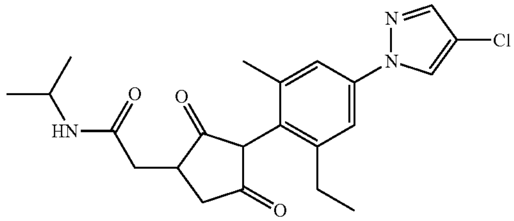 [SMILES: CCc1cc(-n2cc(Cl)cn2)cc(C)c1C1C(=O)CC(CC(=O)NC(C)C)C1=O] | 1.32 mins, m/z = 416.17 (M + H)+ |
| B236 | 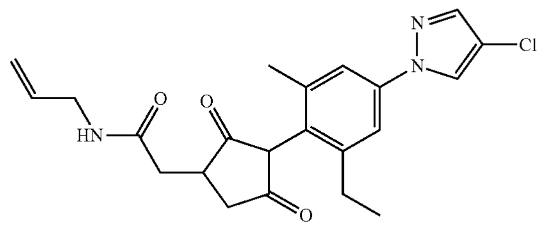 [SMILES: C=CCNC(=O)CC1CC(=O)C(c2c(C)cc(-n3cc(Cl)cn3)cc2CC)C1=O] | 1.26 mins, m/z = 414.16 (M + H)+ |
| B237 | 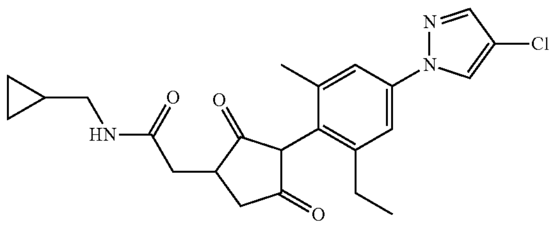 [SMILES: CCc1cc(-n2cc(Cl)cn2)cc(C)c1C1C(=O)CC(CC(=O)NCC2CC2)C1=O] | 1.34 mins, m/z = 428.18 (M + H)+ |
| B238 | 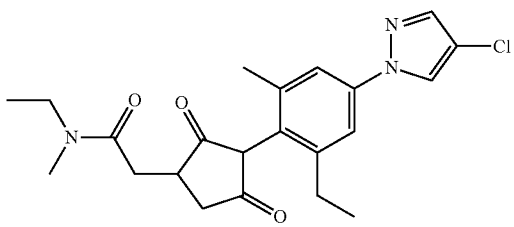 [SMILES: CCc1cc(-n2cc(Cl)cn2)cc(C)c1C1C(=O)CC(CC(=O)N(C)CC)C1=O] | 1.32 mins, m/z = 416.19 (M + H)+ |
| B239 | 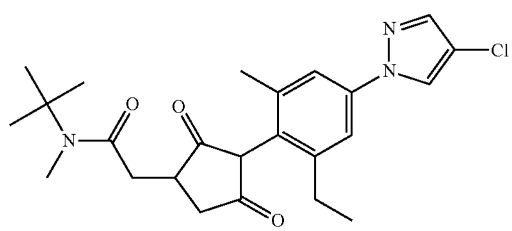 [SMILES: CCc1cc(-n2cc(Cl)cn2)cc(C)c1C1C(=O)CC(CC(=O)N(C)C(C)(C)C)C1=O] | 1.52 mins, m/z = 444.21 (M + H)+ |
| B240 | 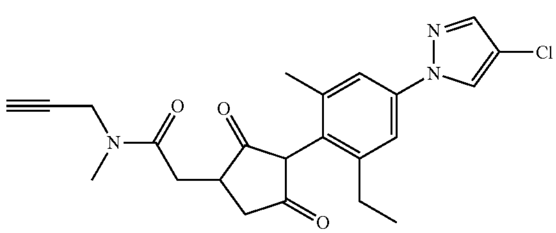 [SMILES: C#CCN(C)C(=O)CC1CC(=O)C(c2c(C)cc(-n3cc(Cl)cn3)cc2CC)C1=O] | 1.28 mins, m/z = 426.17 (M + H)+ |

TABLE T2-continued

| Compound Number | Structure | Physical Data LCMS or $^1$H NMR (400 MHz, CDCl$_3$) unless stated. |
|---|---|---|
| B241 | 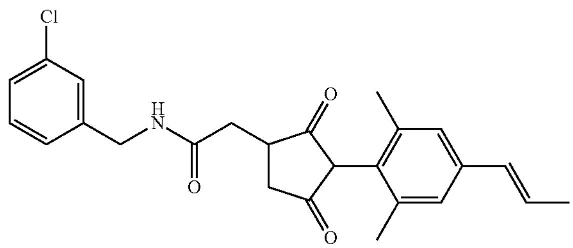 [SMILES: C/C=C/c1cc(C)c(C2C(=O)CC(CC(=O)NCc3cccc(Cl)c3)C2=O)c(C)c1] | 1.47 mins, m/z = 424.19 (M + H)+ |
| B242 | 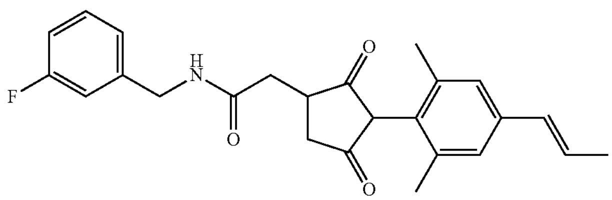 [SMILES: C/C=C/c1cc(C)c(C2C(=O)CC(CC(=O)NCc3cccc(F)c3)C2=O)c(C)c1] | 1.41 mins, m/z = 408.21 (M + H)+ |
| B243 | 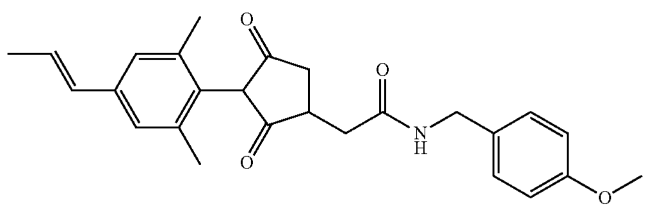 [SMILES: C/C=C/c1cc(C)c(C2C(=O)CC(CC(=O)NCc3ccc(OC)cc3)C2=O)c(C)c1] | 1.39 mins, m/z = 420.24 (M + H)+ |
| B244 | 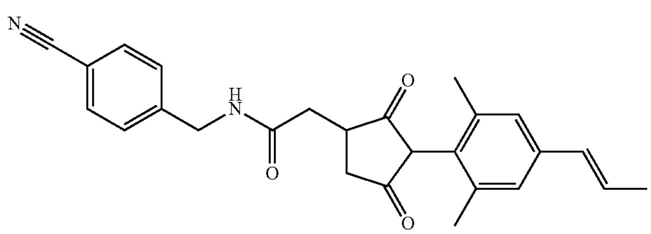 [SMILES: C/C=C/c1cc(C)c(C2C(=O)CC(CC(=O)NCc3ccc(C#N)cc3)C2=O)c(C)c1] | 1.32 mins, m/z = 415.21 (M + H)+ |
| B245 | 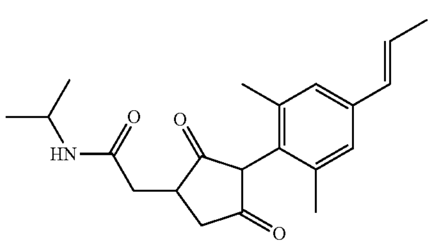 [SMILES: C/C=C/c1cc(C)c(C2C(=O)CC(CC(=O)NC(C)C)C2=O)c(C)c1] | 1.31 mins, m/z = 342.22 (M + H)+ |
| B246 | 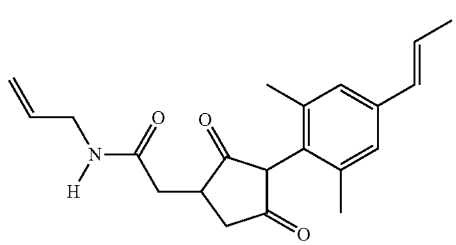 [SMILES: C=CCNC(=O)CC1CC(=O)C(c2c(C)cc(/C=C/C)cc2C)C1=O] | 1.26 mins, m/z = 340.22 (M + H)+ |

TABLE T2-continued

| Compound Number | Structure | Physical Data LCMS or ¹H NMR (400 MHz, CDCl₃) unless stated. |
|---|---|---|
| B247 | 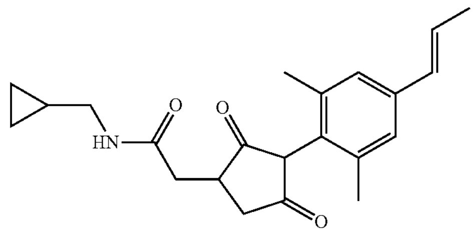 [SMILES: C/C=C/c1cc(C)c(C2C(=O)CC(CC(=O)NCC3CC3)C2=O)c(C)c1] | 1.33 mins, m/z = 354.21 (M + H)+ |
| B248 | 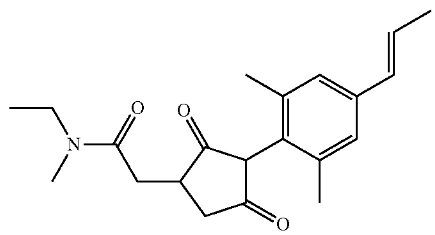 [SMILES: C/C=C/c1cc(C)c(C2C(=O)CC(CC(=O)N(C)CC)C2=O)c(C)c1] | 1.32 mins, m/z = 342.23 (M + H)+ |
| B249 | 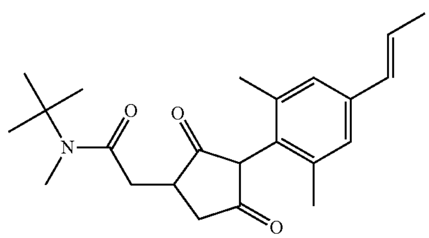 [SMILES: C/C=C/c1cc(C)c(C2C(=O)CC(CC(=O)N(C)C(C)(C)C)C2=O)c(C)c1] | 1.53 mins, m/z = 370.24 (M + H)+ |
| B250 | 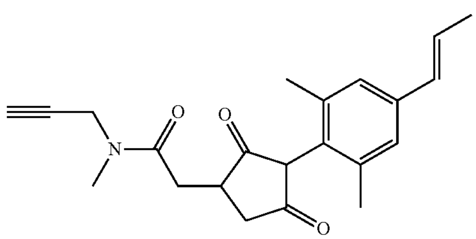 [SMILES: C#CCN(C)C(=O)CC1CC(=O)C(c2c(C)cc(/C=C/C)cc2C)C1=O] | 1.28 mins, m/z = 352.20 (M + H)+ |
| B251 | 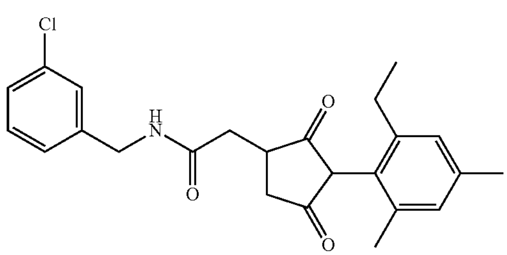 [SMILES: CCc1cc(C)cc(C)c1C1C(=O)CC(CC(=O)NCc2cccc(Cl)c2)C1=O] | 1.43 mins, m/z = 412.18 (M + H)+ |
| B252 | 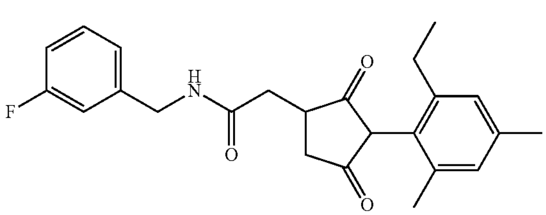 [SMILES: CCc1cc(C)cc(C)c1C1C(=O)CC(CC(=O)NCc2cccc(F)c2)C1=O] | 1.35 mins, m/z = 396.20 (M + H)+ |

TABLE T2-continued

| Compound Number | Structure | Physical Data LCMS or $^1$H NMR (400 MHz, CDCl$_3$) unless stated. |
|---|---|---|
| B253 | 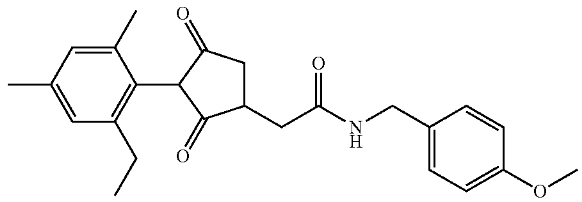 | 1.35 mins, m/z = 408.23 (M + H)+ |
| B254 | 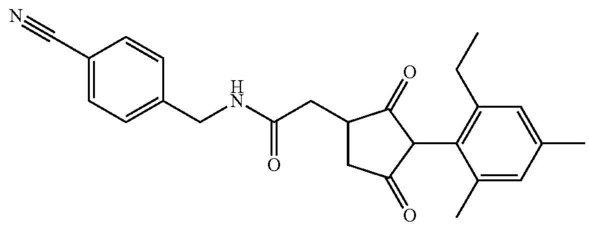 [SMILES: CCc1cc(C)cc(C)c1C1C(=O)CC(CC(=O)NCc2ccc(C#N)cc2)C1=O] | 1.27 mins, m/z = 403.21 (M + H)+ |
| B255 | 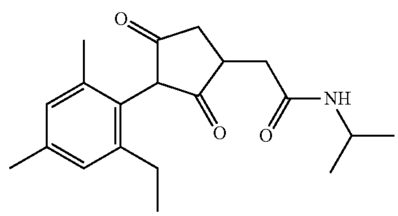 [SMILES: CCc1cc(C)cc(C)c1C1C(=O)CC(CC(=O)NC(C)C)C1=O] | 1.25 mins, m/z = 330.23 (M + H)+ |
| B256 | 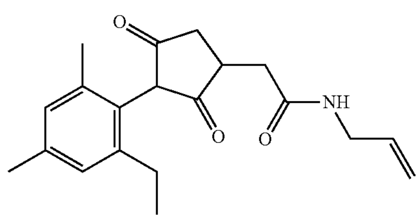 [SMILES: C=CCNC(=O)CC1CC(=O)C(c2c(C)cc(C)cc2CC)C1=O] | 1.19 mins, m/z = 328.21 (M + H)+ |
| B257 | 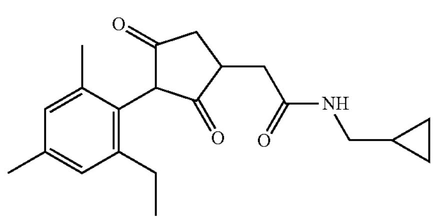 [SMILES: CCc1cc(C)cc(C)c1C1C(=O)CC(CC(=O)NCC2CC2)C1=O] | 1.27 mins, m/z = 342.23 (M + H)+ |
| B258 | 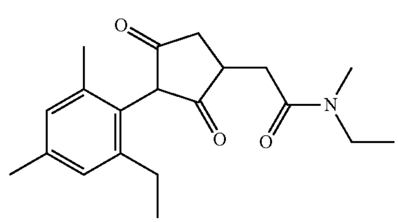 [SMILES: CCc1cc(C)cc(C)c1C1C(=O)CC(CC(=O)N(C)CC)C1=O] | 1.25 mins, m/z = 330.23 (M + H)+ |
| B259 | 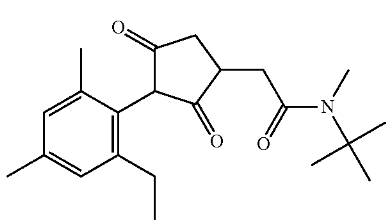 [SMILES: CCc1cc(C)cc(C)c1C1C(=O)CC(CC(=O)N(C)C(C)(C)C)C1=O] | 1.48 mins, m/z = 358.23 (M + H)+ |

TABLE T2-continued

| Compound Number | Structure | Physical Data LCMS or ¹H NMR (400 MHz, CDCl₃) unless stated. |
|---|---|---|
| B260 | 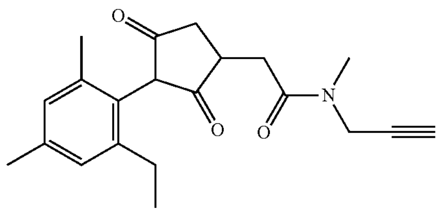 [SMILES: C#CCN(C)C(=O)CC1CC(=O)C(c2c(C)cc(C)cc2CC)C1=O] | 1.21 mins, m/z = 340.21 (M + H)+ |
| B261 | 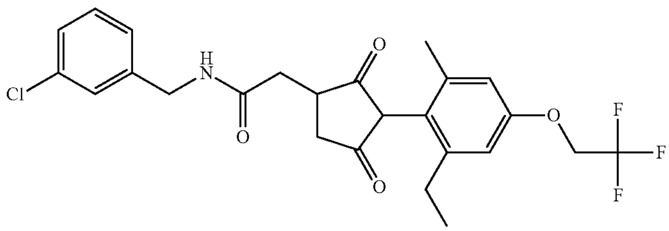 [SMILES: CCc1cc(OCC(F)(F)F)cc(C)c1C1C(=O)CC(CC(=O)NCc2cccc(Cl)c2)C1=O] | 1.46 mins, m/z = 496.16 (M + H)+ |
| B262 | 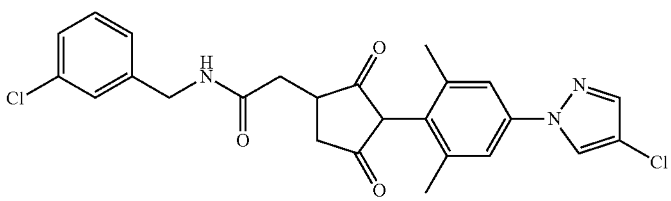 [SMILES: Cc1cc(-n2cc(Cl)cn2)cc(C)c1C1C(=O)CC(CC(=O)NCc2cccc(Cl)c2)C1=O] | 484.13 mins, m/z = 1.38 (M + H)+ |
| B263 | 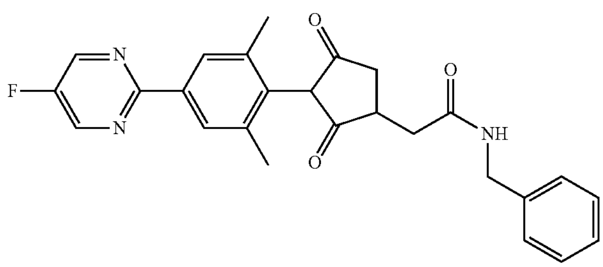 [SMILES: Cc1cc(-c2ncc(F)cn2)cc(C)c1C1C(=O)CC(CC(=O)NCc2ccccc2)C1=O] | 13.76-13.08 (m, 1H), 8.60 (s, 2H), 8.04 (s, 2H), 7 47-7.11 (m, 6H), 4.32 (d, 2H), 3.38-3.09 (m, 1H), 2.95-2.73 (m, 1H), 2.62 (br.s., 2H), 2.19 (d, 7H) |
| B264 | 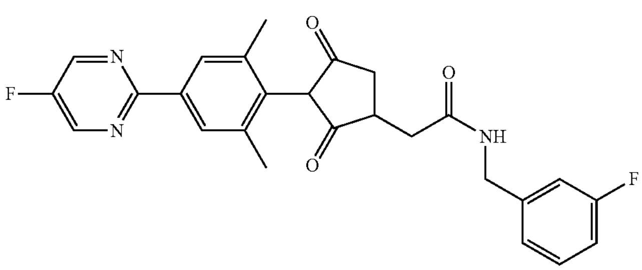 [SMILES: Cc1cc(-c2ncc(F)cn2)cc(C)c1C1C(=O)CC(CC(=O)NCc2cccc(F)c2)C1=O] | 8.60 (s, 2H), 8.02 (s, 2H), 7.73-7.54 (m, 1H), 7.33-7.18 (m, 1H), 7.02-6.79 (m, 3H), 4.23 (dd, 2H), 3.31-3.11 (m, 1H), 2.85 (dd, 1H), 2.77-2.49 (m, 2H), 2.28-2.09 (m, 7H) |
| B265 | 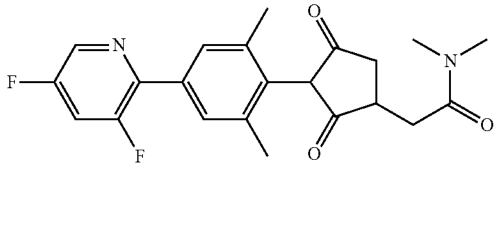 [SMILES: Cc1cc(-c2ncc(F)cc2F)cc(C)c1C1C(=O)CC(CC(=O)N(C)C)C1=O] | 1H NMR (400 MHz, CD3OD) 8.44 (d, 1H), 7.72-7.63 (m, 1H), 7.58-7.52 (m, 2H), 3.26-3.13 (m, 1H), 3.12-3.07 (m, 3H), 2.99 (s, 4H), 2.97-2.86 (m, 2H), 2.48 (d, 1H), 2.25-2.16 (m, 6H) |

TABLE T2-continued

| Compound Number | Structure | Physical Data LCMS or ¹H NMR (400 MHz, CDCl₃) unless stated. |
|---|---|---|
| B266 | 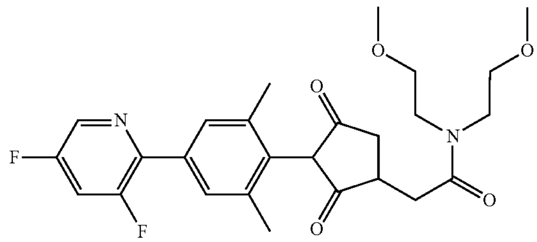 [SMILES: COCCN(CCOC)C(=O)CC1CC(=O)C(c2c(C)cc(-c3ncc(F)cc3F)cc2C)C1=O] | 1H NMR (400 MHz, CD3OD) 8.44 (d, 1H), 7.65 (ddd, 1H), 7.59-7.49 (m, 2H), 3.65-3.52 (m, 8H), 3.38-3.34 (m, 6H), 3.25-3.12 (m, 1H), 2.99-2.84 (m, 3H), 2.51-2.34 (m, 1H), 2.20 (d, 6H) |
| B267 | 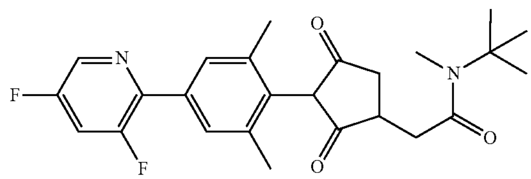 [SMILES: Cc1cc(-c2ncc(F)cc2F)cc(C)c1C1C(=O)CC(CC(=O)N(C)C(C)(C)C)C1=O] | 1H NMR (400 MHz, CD3OD) 8.44 (d, 1H), 7.69-7.60 (m, 1H), 7.58-7.52 (m, 2H), 3.48-3.36 (m, 1H), 3.25-3.12 (m, 1H), 3.02-2.96 (m, 3H), 2.99-2.82 (m, 2H), 2.48-2.31 (m, 1H), 2.24-2.14 (m, 6H), 1.49-1.43 (m, 9H) |
| B268 | 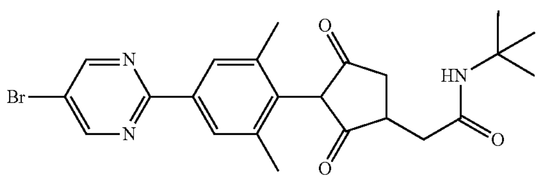 [SMILES: Cc1cc(-c2ncc(Br)cn2)cc(C)c1C1C(=O)CC(CC(=O)NC(C)(C)C)C1=O] | 1H NMR (400 MHz, CD3OD) 8.96-8.81 (m, 2H), 8.10 (s, 2H), 3.20-3.09 (m, 1H), 2.90 (dd, 1H), 2.71 (dd, 1H), 2.49-2.34 (m, 2H), 2.21 (s, 6H), 1.36 (s, 9H) |
| B269 | 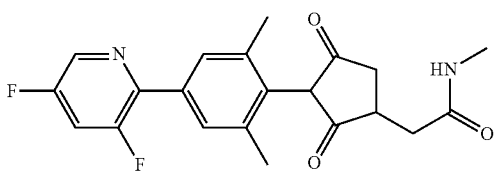 [SMILES: CNC(=O)CC1CC(=O)C(c2c(C)cc(-c3ncc(F)cc3F)cc2C)C1=O] | 1H NMR (400 MHz, CD3OD) 8.44 (d, 1H), 7.65 (ddd, 1H), 7.55 (s, 2H), 3.22-3.11 (m, 1H), 2.92 (dd, 1H), 2.80-2.71 (m, 4H), 2.47 (d, 2H), 2.19 (s, 6H) |
| B270 | 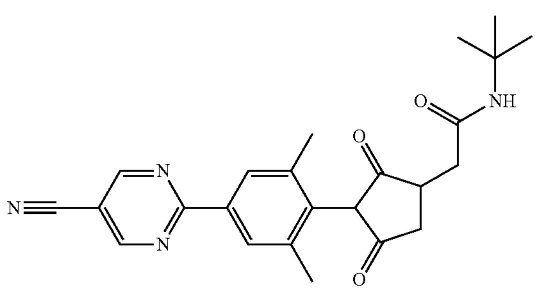 [SMILES: Cc1cc(-c2ncc(C#N)cn2)cc(C)c1C1C(=O)CC(CC(=O)NC(C)(C)C)C1=O] | 1H NMR (400 MHz, CD3OD) 9.11-9.03 (m, 2H), 8.15 (s, 2H), 3.25-3.14 (m, 1H), 2.99-2.85 (m, 1H), 2.78-2.64 (m, 1H), 2.54-2.38 (m, 2H), 2.26-2.18 (m, 6H), 1.38-1.31 (m, 9H) |
| B271 | 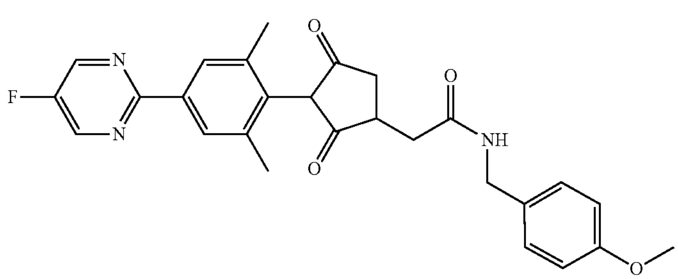 [SMILES: COc1ccc(CNC(=O)CC2CC(=O)C(c3c(C)cc(-c4ncc(F)cn4)cc3C)C2=O)cc1] | 8.60 (s, 2H), 8.14-7.95 (m, 2H), 7.23-7.08 (m, 3H), 6.92-6.71 (m, 2H), 4.37-4.20 (m, 2H), 3.78 (s, 3H), 3.35-3.09 (m, 1H), 2.93-2.75 (m, 1H), 2.72-2.50 (m, 2H), 2.20 (d, 7H) |

TABLE T2-continued

| Compound Number | Structure | Physical Data LCMS or ¹H NMR (400 MHz, CDCl₃) unless stated. |
| --- | --- | --- |
| B272 | 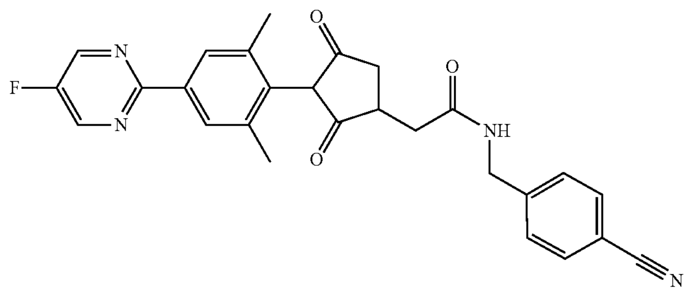 [SMILES: Cc1cc(-c2ncc(F)cn2)cc(C)c1C1C(=O)CC(CC(=O)NCc2ccc(C#N)cc2)C1=O] | 8.62 (s, 2H), 8.39-8.17 (m, 1H), 7.99 (s, 2H), 7.50 (d, 2H), 7.24-7.08 (m, 2H), 4.30-3.98 (m, 2H), 3.30-3.12 (m, 1H), 2.95-2.70 (m, 2H), 2.67-2.51 (m, 1H), 2.15 (s, 7H), |
| B273 | 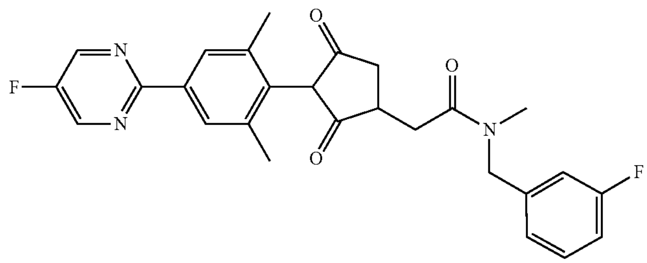 [SMILES: Cc1cc(-c2ncc(F)cn2)cc(C)c1C1C(=O)CC(CC(=O)N(C)Cc2cccc(F)c2)C1=O] | 12.87-12.10 (m, 1H), 8.62 (s, 2H), 8.07 (d, 2H), 7.44-6.77 (m, 4H), 4.56 (s, 2H), 3.57-3.35 (m, 1H), 3.28-2.79 (m, 5H), 2.77-2.54 (m, 1H), 2.41-2.14 (m, 7H) |
| B274 | 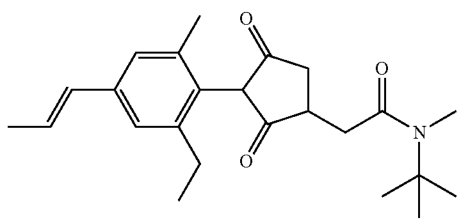 [SMILES: C/C=C/c1cc(C)c(C2C(=O)CC(CC(=O)N(C)C(C)(C)C)C2=O)c(CC)c1] | 12.75-12.43 (m, 1H), 7.10-6.93 (m, 2H), 6.43-5.99 (m, 2H), 3.51-3.30 (m, 1H), 2.99 (d, 5H), 2.69-2.20 (m, 4H), 2.12 (d, 3H), 1.85 (dd, 3H), 1.45 (s, 9H), 1.11 (t, 3H) |
| B275 | 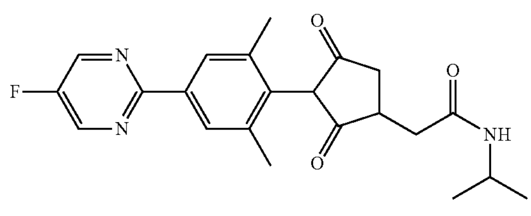 [SMILES: Cc1cc(-c2ncc(F)cn2)cc(C)c1C1C(=O)CC(CC(=O)NC(C)C)C1=O] | 13.60-12.87 (m, 1H), 8.63 (s, 2H), 8.07 (d, 2H), 6.35-5.93 (m, 1H), 4.30-3.94 (m, 1H), 3.45-3.11 (m, 1H), 2.90 (s, 1H), 2.67 (d, 2H), 2.25 (d, 7H), 1.18 (dd, 6H) |
| B276 | 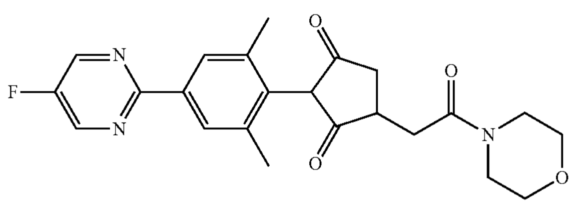 [SMILES: Cc1cc(-c2ncc(F)cn2)cc(C)c1C1C(=O)CC(CC(=O)N2CCOCC2)C1=O] | 12.74-11.76 (m, 1H), 8.63 (s, 2H), 8.07 (d, 2H), 3.99-3.27 (m, 9H), 2.94 (m, 2H), 2.70-2.49 (m, 1H), 2.25 (d, 6H) |
| B277 | 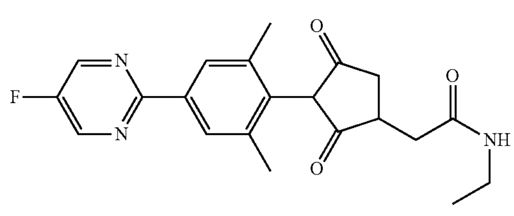 [SMILES: CCNC(=O)CC1CC(=O)C(c2c(C)cc(-c3ncc(F)cn3)cc2C)C1=O] | 13.63-13.02 (m, 1H), 8.63 (s, 2H), 8.07 (br.s., 2H), 6.75-6.45 (m, 1H), 3.26 (d, 3H), 2.98-2.79 (m, 1H), 2.66 (br.s., 2H), 2.24 (d, 7H), 1.12 (t, 3H) |

TABLE T2-continued

| Compound Number | Structure | Physical Data LCMS or ¹H NMR (400 MHz, CDCl₃) unless stated. |
|---|---|---|
| B278 | 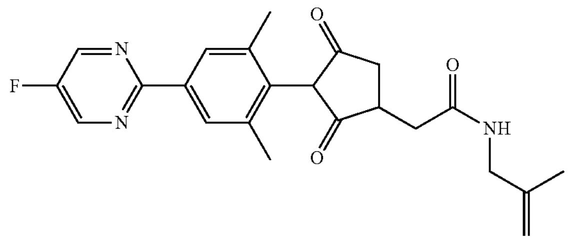 [SMILES: C=C(C)CNC(=O)CC1CC(=O)C(c2c(C)cc(-c3ncc(F)cn3)cc2C)C1=O] | 13.53-13.03 (m, 1H), 8.62 (s, 2H), 8.06 (br.s., 2H), 7.07-6.78 (m, 1H), 4.95-4.65 (m, 2H), 3.88-3.53 (m, 2H), 3.41-3.14 (m, 1H), 3.03-2.51 (m, 3H), 2.22 (d, 7H), 1.69 (s, 3H) |
| B279 | 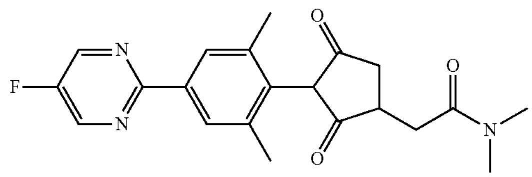 [SMILES: Cc1cc(-c2ncc(F)cn2)cc(C)c1C1C(=O)CC(CC(=O)N(C)C)C1=O] | 13.05-12.46 (m, 1H), 8.63 (s, 2H), 8.06 (d, 2H), 3.52-3.26 (m, 1H), 3.05 (d, 8H), 2.68-2.51 (m, 1H), 2.25 (d, 7H) |
| B280 | 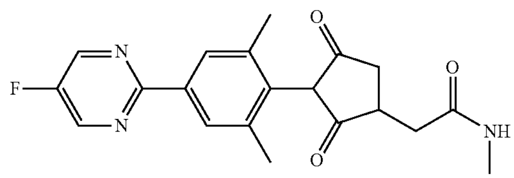 [SMILES: CNC(=O)CC1CC(=O)C(c2c(C)cc(-c3ncc(F)cn3)cc2C)C1=O] | 8.63 (s, 2H), 8.05 (d, 2H), 7.19-7.03 (m, 1H), 3.35-3.10 (m, 1H), 3.02-2.81 (m, 1H), 2.75-2.46 (m, 5H), 2.22 (d, 7H) |
| B281 | 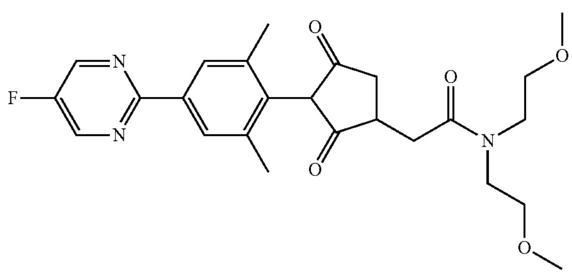 [SMILES: COCCN(CCOC)C(=O)CC1CC(=O)C(c2c(C)cc(-c3ncc(F)cn3)cc2C)C1=O] | 13.03-12.28 (m, 1H), 8.62 (s, 2H), 8.20-7.84 (m, 2H), 3.77-3.45 (m, 8H), 3.33 (d, 8H), 3.00-2.83 (m, 1H), 2.76-2.51 (m, 1H), 2.26 (d, 7H) |
| B282 | 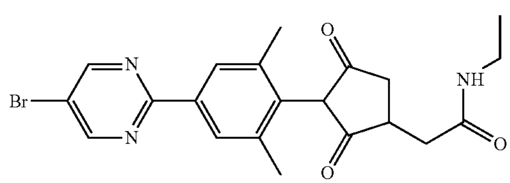 | 1H NMR (400 MHz, Methanol) Shift = 8.90 (s, 2H), 8.18-8.02 (m, 2H), 3.27-3.22 (m, 2H), 3.18 (br. s., 1H), 2.92 (dd, J = 7.1, 18.0 Hz, 1H), 2.76 (dd, J = 6.5, 15.1 Hz, 1H), 2.47 (d, J = 16.0 Hz, 2H), 2.20 (s, 6H), 1.14 (t, J = 7.3 Hz, 3H) |
| B283 | 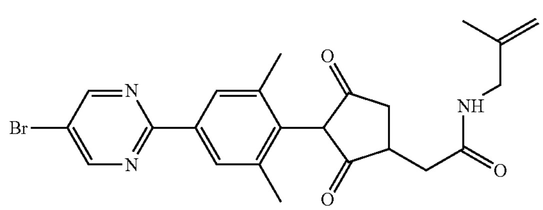 [SMILES: C=C(C)CNC(=O)CC1CC(=O)C(c2c(C)cc(-c3ncc(Br)cn3)cc2C)C1=O] | 1H NMR (400 MHz, CD3OD) 8.90 (s, 2H), 8.10 (s, 2H), 4.86-4.77 (m, 2H), 3.78 (s, 2H), 3.23-3.13 (m, 1H), 2.94 (dd, 1H), 2.83 (dd, 1H), 2.50 (d, 2H), 2.20 (s, 6H), 1.75 (s, 3H) |
| B284 | 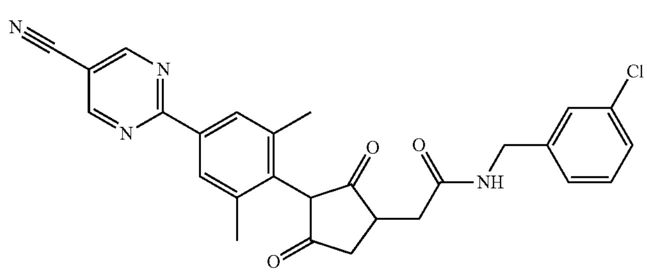 [SMILES: Cc1cc(-c2ncc(C#N)cn2)cc(C)c1C1C(=O)CC(CC(=O)NCc2cccc(Cl)c2)C1=O] | 1H NMR (400 MHz, CD3OD) 9.14 (s, 2H), 8.21 (s, 2H), 7.36-7.21 (m, 4H), 4.39 (s, 2H), 3.26-3.15 (m, 1H), 2.99-2.78 (m, 2H), 2.59-2.45 (m, 2H), 2.26-2.17 (m, 6H) |

TABLE T2-continued

| Compound Number | Structure | Physical Data LCMS or ¹H NMR (400 MHz, CDCl₃) unless stated. |
|---|---|---|
| B285 | 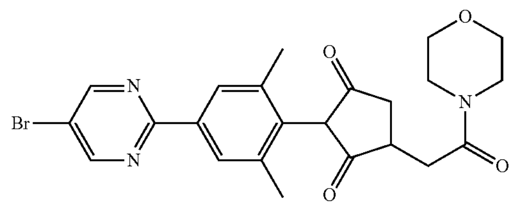 [SMILES: Cc1cc(-c2ncc(Br)cn2)cc(C)c1C1C(=O)CC(CC(=O)N2CCOCC2)C1=O] | 1H NMR (400 MHz, CD3OD) 8.97-8.80 (m, 2H), 8.17-7.85 (m, 2H), 3.78-3.49 (m, 8H), 3.24-3.12 (m, 1H), 3.05-2.89 (m, 2H), 2.82-2.72 (m, 1H), 2.61-2.31 (m, 1H), 2.26-2.16 (m, 6H) |
| B286 | 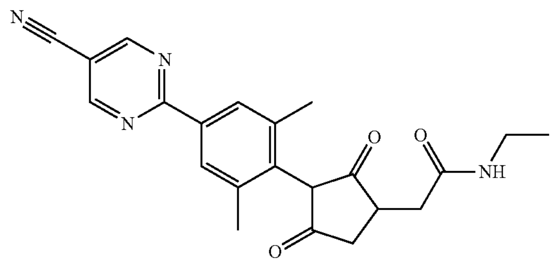 [SMILES: CCNC(=O)CC1CC(=O)C(c2c(C)cc(-c3ncc(C#N)cn3)cc2C)C1=O] | 1H NMR (400 MHz, CD3OD) 9.14 (s, 2H), 8.21 (br.s., 2H), 3.24 (d, 3H), 2.99-2.88 (m, 1H), 2.80-2.68 (m, 1H), 2.51-2.37 (m, 2H), 2.22 (s, 6H), 1.15(1, 3H) |
| B287 | 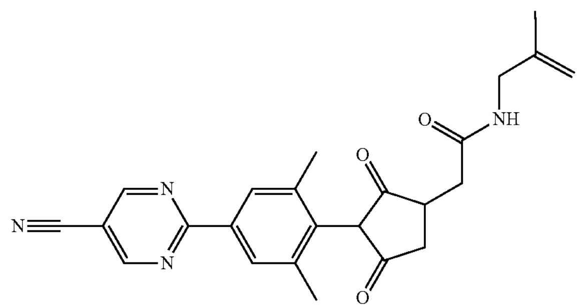 [SMILES: C=C(C)CNC(=O)CC1CC(=O)C(c2c(C)cc(-c3ncc(C#N)cn3)cc2C)C1=O] | 1H NMR (400 MHz, CD3OD) 9.14 (s, 2H), 8.21 (s, 2H), 4.85 (br.s., 2H), 3.84-3.70 (m, 2H), 3.20 (br.s., 1H), 3.01-2.92 (m, 1H), 2.87-2.76 (m, 1H), 2.51 (d, 2H), 2.24-2.14 (m, 6H), 1.80-1.66 (m, 3H) |
| B288 | 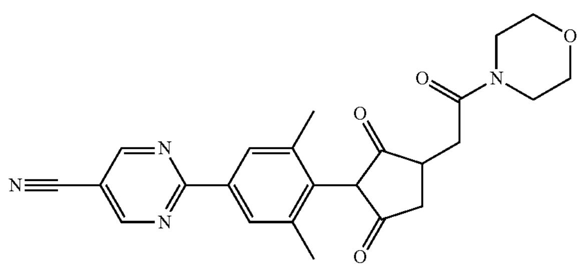 [SMILES: Cc1cc(-c2ncc(C#N)cn2)cc(C)c1C1C(=O)CC(CC(=O)N2CCOCC2)C1=O] | 1H NMR (400 MHz, CD3OD) 9.18-9.05 (m, 2H), 8.20 (s, 2H), 3.72-3.50 (m, 6H), 3.20 (d, 1H), 3.05-2.74 (m, 5H), 2.59-2.41 (m, 1H), 2.27-2.17 (m, 6H) |
| B289 | 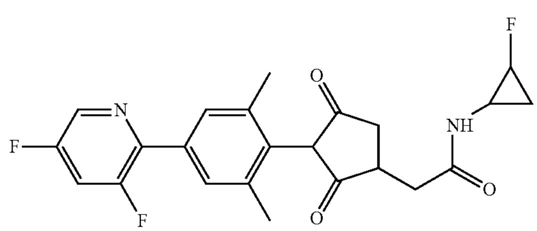 [SMILES: Cc1cc(-c2ncc(F)cc2F)cc(C)c1C1C(=O)CC(CC(=O)NC2CC2F)C1=O] | 1H NMR (400 MHz, CD3OD) 8.44 (d, 1H), 7.65 (ddd, 1H), 7.55 (s, 2H), 4.77-4.50 (m, 1H), 3.22-3.07 (m, 1H), 2.98-2.70 (m, 3H), 2.56-2.38 (m, 2H), 2.20 (s, 6H), 1.16-1.05 (m, 1H), 1.00-0.86 (m, 1H) |
| B290 | 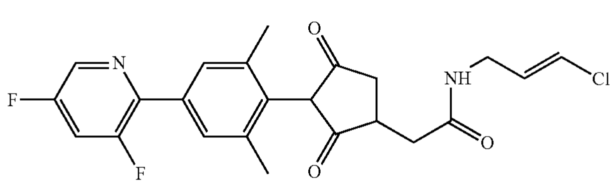 [SMILES: Cc1cc(-c2ncc(F)cc2F)cc(C)c1C1C(=O)CC(CC(=O)NC/C=C/Cl)C1=O] | 1H NMR (400 MHz, CD3OD) 8.44 (d, 1H), 7.65 (ddd, 1H), 7.55 (s, 2H), 6.33 (td, 1H), 6.01-5.89 (m, 1H), 3.87-3.75 (m, 2H), 3.23-3.08 (m, 1H), 3.00-2.88 (m, 1H), 2.84-2.66 (m, 1H), 2.56-2.37 (m, 2H), 2.23-2.17 (m, 6H) |

TABLE T2-continued

| Compound Number | Structure | Physical Data LCMS or ¹H NMR (400 MHz, CDCl₃) unless stated. |
|---|---|---|
| B291 | 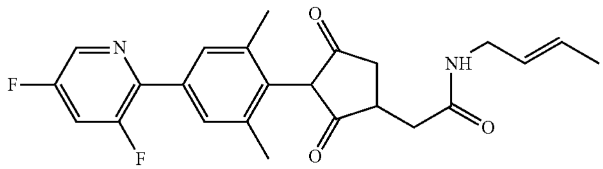 [SMILES: C/C=C/CNC(=O)CC1CC(=O)C(c2c(C)cc(-c3ncc(F)cc3F)cc2C)C1=O] | 1H NMR (400 MHz, CD3OD) 12.43-12.31 (m, 1H), 11.64-11.55 (m, 1H), 11.54-11.47 (m, 2H), 9.71-9.54 (m, 1H), 9.50-9.37 (m, 1H), 7.87-7.67 (m, 2H), 7.20-7.06 (m, 1H), 6.94-6.66 (m, 2H), 6.50-6.36 (m, 2H), 6.17-6.09 (m, 6H), 5.69-5.56 (m, 3H) |
| B292 | 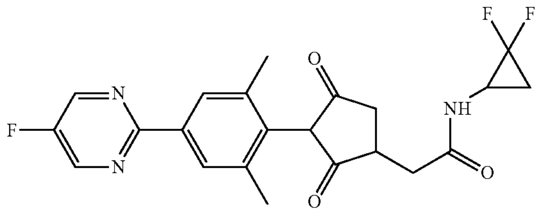 [SMILES: Cc1cc(-c2ncc(F)cn2)cc(C)c1C1C(=O)CC(CC(=O)NC2CC2(F)F)C1=O] | 1H NMR (400 MHz, Methanol) Shift = 8.75 (s, 2H), 8.16-7.98 (m, 2H), 3.38-3.32 (m, 1H), 3.23-3.07 (m, 1H), 2.95 (ddd, J = 3.9, 7.1, 17.9 Hz, 1H), 2.82 (dd, J = 5.0, 15.3 Hz, 1H), 2.56-2.39 (m, 2H), 2.20 (s, 6H), 1.88-1.73 (m, 1H), 1.51-1.37 (m, 1H) |
| B293 | 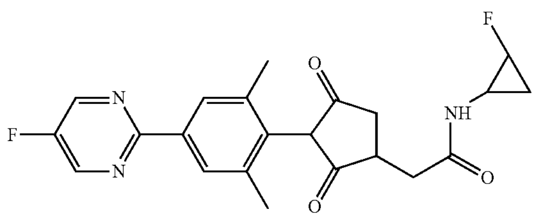 [SMILES: Cc1cc(-c2ncc(F)cn2)cc(C)c1C1C(=O)CC(CC(=O)NC2CC2F)C1=O] | 1H NMR (400 MHz, CD3OD) 8.80-8.62 (m, 2H), 8.08 (s, 2H), 4.79-4.51 (m, 1H), 3.24-3.08 (m, 1H), 2.98-2.72 (m, 3H), 2.58-2.40 (m, 2H), 2.24-2.10 (m, 6H), 1.18-1.06 (m, 1H), 1.01-0.82 (m, 1H) |
| B294 | 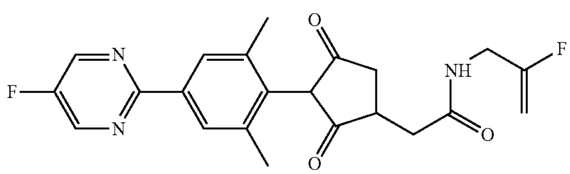 [SMILES: C=C(F)CNC(=O)CC1CC(=O)C(c2c(C)cc(-c3ncc(F)cn3)cc2C)C1=O] | 1H NMR (400 MHz, CD3OD) 8.75 (s, 2H), 8.08 (s, 2H), 4.69-4.46 (m, 2H), 3.95 (d, 2H), 3.23-3.11 (m, 1H), 2.95 (dd, 1H), 2.84-2.72 (m, 1H), 2.58-2.42 (m, 2H), 2.23-2.15 (m, 6H) |
| B295 | 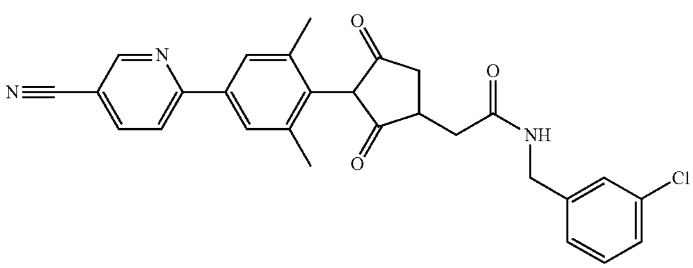 [SMILES: Cc1cc(-c2ccc(C#N)cn2)cc(C)c1C1C(=O)CC(CC(=O)NCc2cccc(Cl)c2)C1=O] | 8.86 (d, 1H), 7.94 (dd, 1H), 7.77 (d, 1H), 7.67 (s, 3H), 7.26-7.02 (m, 4H), 4.28 (dd, 2H), 3.36-3.14 (m, 1H), 2.95-2.54 (m, 3H), 2.18 (d, 7H) |
| B296 | 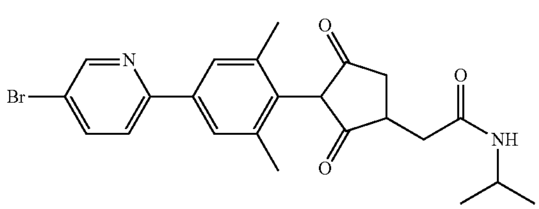 [SMILES: Cc1cc(-c2ccc(Br)cn2)cc(C)c1C1C(=O)CC(CC(=O)NC(C)C)C1=O] | 8.75-8.58 (m, 1H), 7.99-7.80 (m, 1H), 7.61 (s, 3H), 4.14-3.93 (m, 1H), 3.28-3.10 (m, 1H), 2.93 (br.s., 4H), 2.76-2.28 (m, 3H), 2.22 (d, 6H), 1.25-1.11 (m, 6H) |
| B297 | 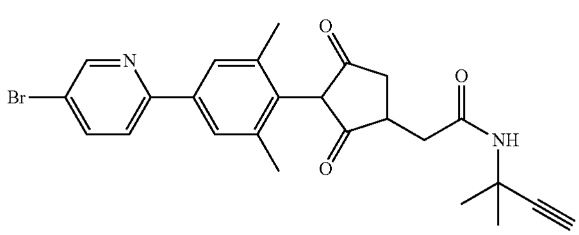 [SMILES: C#CC(C)(C)NC(=O)CC1CC(=O)C(c2c(C)cc(-c3ccc(Br)cn3)cc2C)C1=O] | 12.54-12.26 (m, 1H), 8.78-8.56 (m, 1H), 7.91-7.77 (m, 1H), 7 64 (s, 3H), 6.27-5.90 (m, 1H), 3.49-3.24 (m, 1H), 3.06-2.85 (m, 1H), 2.79-2.61 (m, 2H), 2.42 (s, 1H), 2.24 (d, 7H), 1.69 (d, 6H) |

TABLE T2-continued

| Compound Number | Structure | Physical Data LCMS or $^1$H NMR (400 MHz, CDCl$_3$) unless stated. |
|---|---|---|
| B298 | 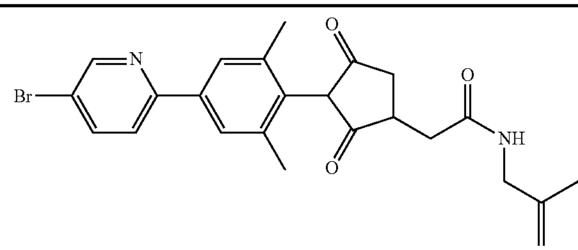 | 8.79-8.58 (m, 1H), 7.89-7.78 (m, 1H), 7.64 (s, 3H), 6.19-5.90 (m, 1H), 5.00-4.77 (m, 2H), 4.00-3.70 (m, 2H), 3.41-3.25 (m, 1H), 3.03-2.84 (m, 1H), 2.83-2.70 (m, 2H), 2.24 (d, 7H), 1.77 (s, 3H) |
| B299 | 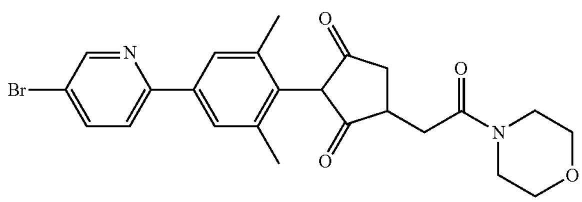 [SMILES: Cc1cc(-c2ccc(Br)cn2)cc(C)c1C1C(=O)CC(CC(=O)N2CCOCC2)C1=O] | 12.45-12.14 (m, 1H), 8.78-8.54 (m, 1H), 7.91-7.76 (m, 1H), 7.70-7.53 (m, 3H), 3.89-3.34 (m, 8H), 3.21-3.05 (m, 1H), 3.02-2.81 (m, 1H), 2.69-2.49 (m, 1H), 2.24 (d, 7H) |
| B300 | 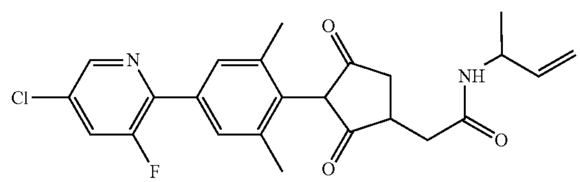 [SMILES: C=CC(C)NC(=O)CC1CC(=O)C(c2c(C)cc(-c3ncc(Cl)cc3F)cc2C)C1=O] | 1H NMR (400 MHz, CD3OD) 8.49 (dd, 1H), 7.84 (dd, 1H), 7.64-7.45 (m, 2H), 5.89-5.76 (m, 1H), 5.23-5.15 (m, 1H), 5.07 (qd, 1H), 4.49 (quin, 1H), 3.24-3.11 (m, 1H), 2.94 (dd, 1H), 2.79 (dd, 1H), 2.57-2.42 (m, 2H), 2.23-2.12 (m, 6H), 1.31-1.16 (m, 3H) |
| B301 | 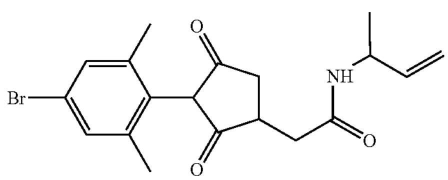 [SMILES: C=CC(C)NC(=O)CC1CC(=O)C(c2c(C)cc(Br)cc2C)C1=O] | 1HNMR (400 MHz, CD3OD) 7.25-7.04 (m, 2H), 5.94-5.68 (m, 1H), 5.23-5.12 (m, 1H), 5.07 (qd, 1H), 4.53-4.39 (m, 1H), 3.20-3.08 (m, 1H), 2.90 (dd, 1H), 2.76 (ddd, 1H), 2.56-2.34 (m, 2H), 2.14-2.01 (m, 6H), 1.28-1.03 (m, 3H) |
| B302 | 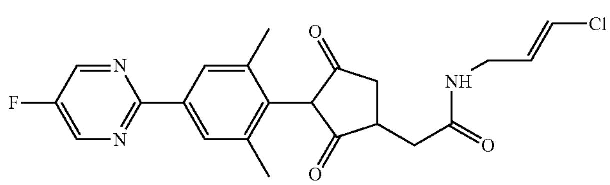 [SMILES: Cc1cc(-c2ncc(F)cn2)cc(C)c1C1C(=O)CC(CC(=O)NC/C=C/Cl)C1=O] | 1H NMR (400 MHz, CD3OD) 8.82-8.68 (m, 2H), 8.14-7.99 (m, 2H), 6.32 (td, 1H), 6.01-5.86 (m, 1H), 3.83 (dd, 2H), 3.24-3.10 (m, 1H), 2.94 (dd, 1H), 2.78 (dd, 1H), 2.56-2.38 (m, 2H), 2.24-2.16 (m, 6H) |
| B303 | 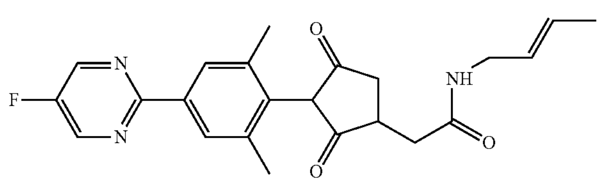 [SMILES: C/C=C/CNC(=O)CC1CC(=O)C(c2c(C)cc(-c3ncc(F)cn3)cc2C)C1=O] | 1H NMR (400 MHz, Methanol) Shift = 8.77-8.70 (m, 2H), 8.07 (s, 2H), 5.73-5.61 (m, 1H), 5.53-5.41 (m, 1H), 3.76 (d, J = 5.9 Hz, 2H), 3.22 - 3.09 (m, 1H), 2.91 (dd, J = 7.2, 18.0 Hz, 1H), 2.78 (dd, J = 6.2, 14.9 Hz, 1H), 2.53-2.38 (m, 2H), 2.20 (s, 6H), 1.71-1.61 (m, 3H) |
| B304 | 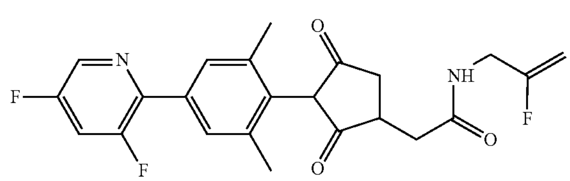 [SMILES: C=C(F)CNC(=O)CC1CC(=O)C(c2c(C)cc(-c3ncc(F)cc3F)cc2C)C1=O] | 1H NMR (400 MHz, CD3OD) 8.48-8.34 (m, 1H), 7.69-7.60 (m, 1H), 7.55 (s, 2H), 4.70-4.46 (m, 2H), 4.00-3.89 (m, 2H), 3.22-3.09 (m, 1H), 2.94 (dd, 1H), 2.86-2.75 (m, 1H), 2.56-2.41 (m, 2H), 2.22-2.16 (m, 6H) |
| B305 | 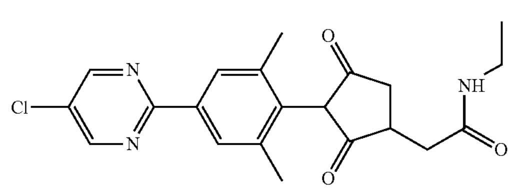 [SMILES: CCNC(=O)CC1CC(=O)C(c2c(C)cc(-c3ncc(Cl)cn3)cc2C)C1=O] | 14.28-13.63 (m, 1H), 8.70 (s, 2H), 8.08 (d, 2H), 7.46-7.30 (m, 1H), 3.14 (dd, 3H), 2.94-2.78 (m, 1H), 2.69-2.40 (m, 2H), 2.22 (d, 7H), 1.03 (t, 3H) |

TABLE T2-continued

| Compound Number | Structure | Physical Data LCMS or ¹H NMR (400 MHz, CDCl₃) unless stated. |
|---|---|---|
| B306 | 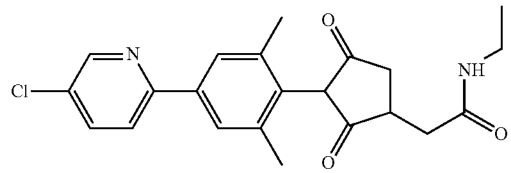 | 14.19-13.13 (m, 1H), 8.57 (d, 1H), 7.85-7.51 (m, 4H), 7.41-7.26 (m, 1H), 3.18 (quin, 3H), 2.83 (dd, 1H), 2.53 (d, 2H), 2.32-2.06 (m, 7H), 1.06 (t, 3H) |
| B307 | 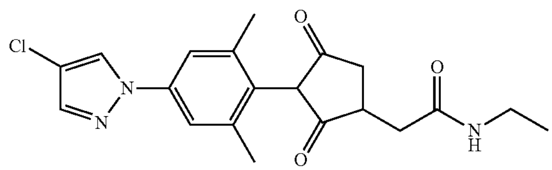 [SMILES: CCNC(=O)CC1CC(=O)C(c2c(C)cc(-n3cc(Cl)cn3)cc2C)C1=O] | 13.90 (br.s., 1H), 7.88 (s, 1H), 7.59 (s, 1H), 7.38-7.18 (m, 2H), 3.32-3.09 (m, 3H), 2.96-2.74 (m, 1H), 2.69-2.45 (m, 2H), 2.18 (d, 7H), 1.07 (t, 3H) |
| B308 | 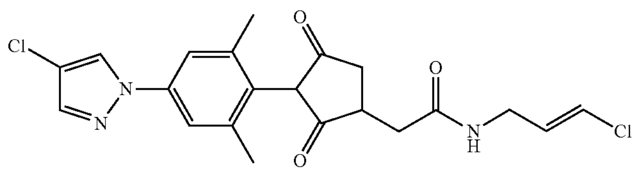 [SMILES: Cc1cc(-n2cc(Cl)cn2)cc(C)c1C1C(=O)CC(CC(=O)NC/C=C/Cl)C1=O] | 13.73-12.98 (m, 1H), 7.87 (s, 1H), 7.59 (s, 2H), 7.36-7.26 (m, 2H), 6.12 (d, 1H), 5.88-5.61 (m, 1H), 3.96 (s, 1H), 3.72 (br.s., 1H), 3.34-3.07 (m, 1H), 2.81 (s, 1H), 2.57 (br.s., 2H), 2.16 (d, 7H) |
| B309 | 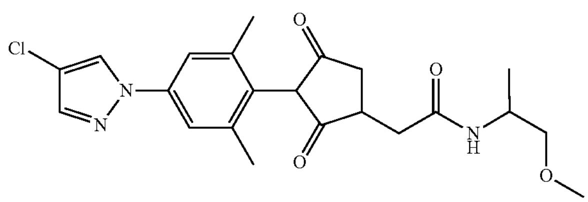 [SMILES: COCC(C)NC(=O)CC1CC(=O)C(c2c(C)cc(-n3cc(Cl)cn3)cc2C)C1=O] | 13.49 (br.s., 1H), 7.87 (s, 1H), 7.60 (s, 1H), 7.43-7.22 (m, 2H), 7.06-6.74 (m, 1H), 4.34-3.98 (m, 1H), 3.52-3.13 (m, 6H), 2.68 (br.s., 3H), 2.20 (d, 7H), 1.34-1.08 (m, 3H) |
| B310 | 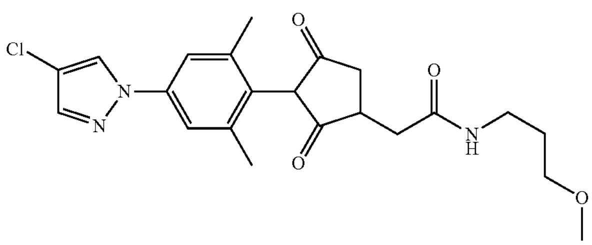 [SMILES: COCCCNC(=O)CC1CC(=O)C(c2c(C)cc(-n3cc(Cl)cn3)cc2C)C1=O] | 13.93-12.81 (m, 1H), 7.88 (s, 1H), 7.60 (s, 1H), 7.38-7.25 (m, 2H), 7.15-6.98 (m, 1H), 4.28-3.98 (m, 1H), 3.46-3.12 (m, 6H), 3.02-2.78 (m, 1H), 2.76-2.52 (m, 2H), 2.18 (d, 7H), 1 16 (dd, 3H) |
| B311 | 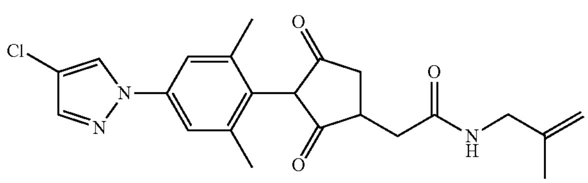 [SMILES: C=C(C)CNC(=O)CC1CC(=O)C(c2c(C)cc(-n3cc(Cl)cn3)cc2C)C1=O] | 7.86 (s, 1H), 7.59 (s, 1H), 7.35-7.17 (m, 3H), 4.90-4.72 (m, 2H), 3.73 (d, 2H), 3.33-3.14 (m, 1H), 2.85 (dd, 1H), 2.65 (d, 2H), 2.28-2.08 (m, 7H), 1.74-1.64 (m, 3H) |
| B312 | 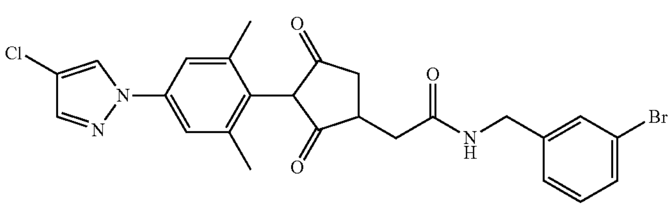 [SMILES: Cc1cc(-n2cc(Cl)cn2)cc(C)c1C1C(=O)CC(CC(=O)NCc2cccc(Br)c2)C1=O] | 13.82-13.18 (m, 1H), 7.82 (s, 2H), 7.56 (s, 1H), 7.44-7.02 (m, 6H), 4.24 (t, 2H), 3.33-3.09 (m, 1H), 2.92-2.45 (m, 3H), 2.13 (d, 7H) |
| B313 | 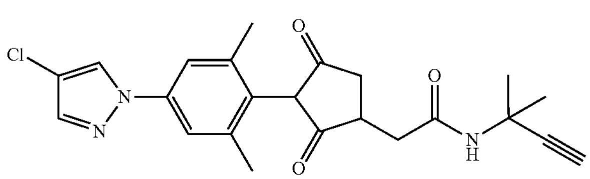 [SMILES: C#CC(C)(C)NC(=O)CC1CC(=O)C(c2c(C)cc(-n3cc(Cl)cn3)cc2C)C1=O] | 7.87 (s, 1H), 7.59 (s, 1H), 7.42 (s, 1H), 7.34-7.24 (m, 2H), 3.34-3.11 (m, 1H), 2.82 (dd, 1H), 2.58 (d, 2H), 2.36 (s, 1H), 2.26-2.06 (m, 7H), 1.66-1.48 (m, 6H) |

TABLE T2-continued

| Compound Number | Structure | Physical Data LCMS or $^1$H NMR (400 MHz, CDCl$_3$) unless stated. |
|---|---|---|
| B314 | 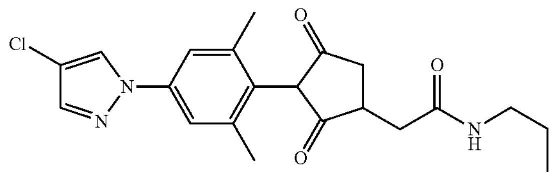 [SMILES: CCCNC(=O)CC1CC(=O)C(c2c(C)cc(-n3cc(Cl)cn3)cc2C)C1=O] | 14.16-13.45 (m, 1H), 7.87 (s, 1H), 7.59 (s, 1H), 7.31 (s, 2H), 7.15-7.01 (m, 1H), 3.36-3.03 (m, 3H), 2.85 (dd, 1H), 2.61 (d, 2H), 2.18 (d, 7H), 1.57-1.32 (m, 2H), 0.87 (t, 3H) |
| B315 | 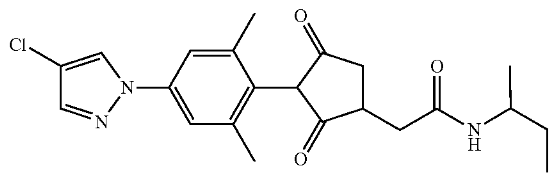 | 14.33-13.55 (m, 1H), 7.87 (s, 1H), 7.59 (s, 1H), 7.37-7.24 (m, 2H), 7.08 (br.s., 1H), 3.84 (s, 1H), 3.35-3.10 (m, 1H), 3.02-2.75 (m, 1H), 2.70-2.49 (m, 2H), 2.18 (d, 7H), 1.51-1.31 (m, 2H), 1.08 (dd, 3H), 0.85 (td, 3H) |
| B316 | 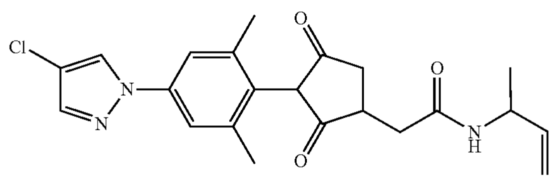 [SMILES: C=CC(C)NC(=O)CC1CC(=O)C(c2c(C)cc(-n3cc(Cl)cn3)cc2C)C1=O] | 7.87 (s, 1H), 7.58 (s, 2H), 7.33-7.23 (m, 2H), 5.87-5.64 (m, 1H), 5.23-5.00 (m, 2H), 4.59-4.36 (m, 1H), 3.32-3.10 (m, 1H), 2.94-2.77 (m, 1H), 2.75-2.47 (m, 2H), 2.16 (d, 7H), 1.20 (dd, 3H) |
| B317 | 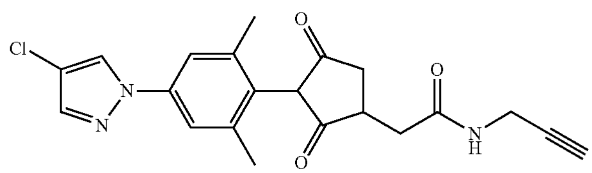 [SMILES: C#CCNC(=O)CC1CC(=O)C(c2c(C)cc(-n3cc(Cl)cn3)cc2C)C1=O] | 13.36-12.89 (m, 1H), 7.86 (s, 1H), 7.60 (s, 2H), 7.28 (d, 2H), 3.94 (br.s., 2H), 3.38-3.11 (m, 1H), 2.94-2.76 (m, 1H), 2.74-2.44 (m, 2H), 2.33-2.03 (m, 8H) |
| B318 | 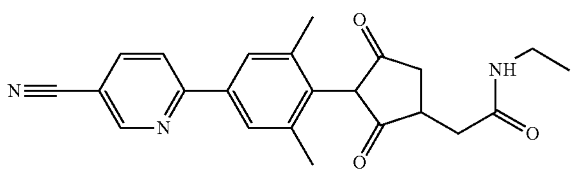 [SMILES: CCNC(=O)CC1CC(=O)C(c2c(C)cc(-c3ccc(C#N)cn3)cc2C)C1=O] | 1H NMR (400 MHz, CD3OD) 8.95-8.84 (m, 1H), 8.19-8.07 (m, 1H), 8.00 (s, 1H), 7.76 (s, 2H), 3.23 (s, 3H), 3.04-2.83 (m, 1H), 2.82-2.69 (m, 1H), 2.56-2.41 (m, 2H), 2.21 (s, 6H), 1 14 (t, 3H) |
| B319 | 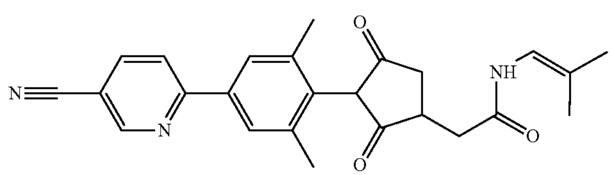 [SMILES: CC(C)=CNC(=O)CC1CC(=O)C(c2c(C)cc(-c3ccc(C#N)cn3)cc2C)C1=O] | 8.90 (dd, 1H), 7.99 (dd, 1H), 7.84 (dd, 1H), 7.71 (s, 2H), 4.94-4.77 (m, 2H), 3.81 (s, 2H), 3.34-3.17 (m, 1H), 3.04-2.86 (m, 2H), 2.78-2.65 (m, 2H), 2.47-2.30 (m, 1H), 2.24 (d, 6H), 1.75 (s, 3H) |
| B320 | 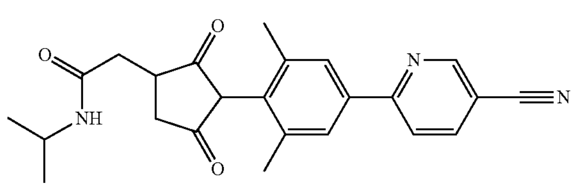 [SMILES: Cc1cc(-c2ccc(C#N)cn2)cc(C)c1C1C(=O)CC(CC(=O)NC(C)C)C1=O] | 8.90 (dd, 1H), 8.06-7.95 (m, 1H), 7.85 (d, 1H), 7.71 (s, 2H), 4.12-3.93 (m, 1H), 3.32-3.13 (m, 1H), 3.03-2.79 (m, 1H), 2.73-2.57 (m, 2H), 2.45-2.30 (m, 1H), 2.24 (d, 6H), 1.17 (t, 6H) |
| B321 | 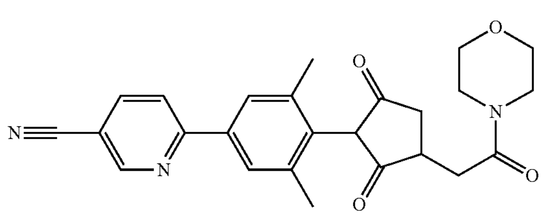 [SMILES: Cc1cc(-c2ccc(C#N)cn2)cc(C)c1C1C(=O)CC(CC(=O)N2CCOCC2)C1=O] | 1H NMR (400 MHz, CD3OD) 8.91 (d, 1H), 8.20-8.06 (m, 1H), 7.97 (s, 1H), 7.75 (s, 2H), 3.72 (d, 8H), 3.29-3.16 (m, 1H), 3.11-2.86 (m, 2H), 2.84-2.59 (m, 1H), 2.57-2.43 (m, 1H), 2.25 (s, 6H) |

TABLE T2-continued

| Compound Number | Structure | Physical Data LCMS or $^1$H NMR (400 MHz, CDCl$_3$) unless stated. |
|---|---|---|
| B322 | 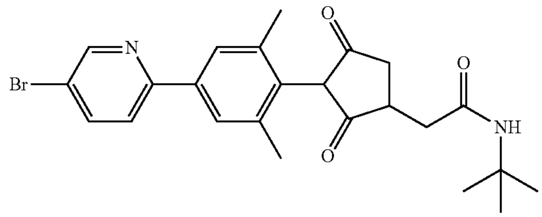 [SMILES: Cc1cc(-c2ccc(Br)cn2)cc(C)c1C1C(=O)CC(CC(=O)NC(C)(C)C)C1=O] | 13.20-12.79 (m, 1H), 8.83-8.56 (m, 1H), 7.91-7.72 (m, 1H), 7.64 (s, 3H), 5.97-5.48 (m, 1H), 3.39-3.24 (m, 1H), 3.08-2.82 (m, 1H), 2.79-2.57 (m, 2H), 2.24 (d, 7H), 1.40 (s, 9H) |
| B323 | 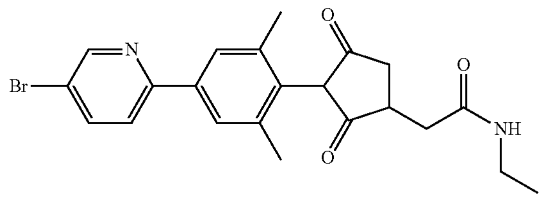 [SMILES: CCNC(=O)CC1CC(=O)C(c2c(C)cc(-c3ccc(Br)cn3)cc2C)C1=O] | 13.14-12.73 (m, 1H), 8.83-8.57 (m, 1H), 7.92-7.75 (m, 1H), 7.64 (s, 3H), 6.15-5.79 (m, 1H), 3.57-3.20 (m, 5H), 3.00-2.84 (m, 1H), 2.24 (d, 7H), 1.35-1.06 (m, 3H) |
| B324 | 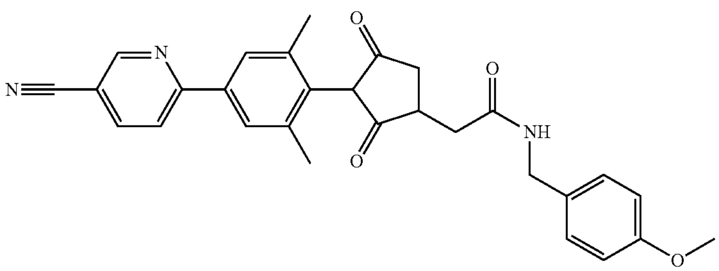 [SMILES: COc1ccc(CNC(=O)CC2CC(=O)C(c3c(C)cc(-c4ccc(C#N)cn4)cc3C)C2=O)cc1] | 8.82 (dd, 1H), 7.98-7.87 (m, 1H), 7.83-7.71 (m, 1H), 7.67 (s, 2H), 7.48-7.33 (m, 1H), 7.15 (d, 2H), 6.83 (d, 2H), 4.37-4.19 (m, 2H), 3.77 (s, 3H), 3.29-3.09 (m, 1H), 2.89-2.72 (m, 1H), 2.70-2.48 (m, 2H), 2.19 (d, 7H) |
| B325 | 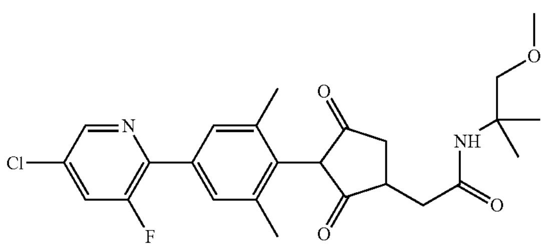 [SMILES: COCC(C)(C)NC(=O)CC1CC(=O)C(c2c(C)cc(-c3ncc(Cl)cc3F)cc2C)C1=O] | 1H NMR (400 MHz, CD3OD) 8.49 (dd, 1H), 7.84 (dd, 1H), 7.60 (s, 2H), 3.53-3.43 (m, 2H), 3.36 (s, 3H), 3.21-3.09 (m, 1H), 2.90 (dd, 1H), 2.73 (dd, 1H), 2.45 (d, 2H), 2.23-2.13 (m, 6H), 1.32 (d, 6H) |
| B326 | 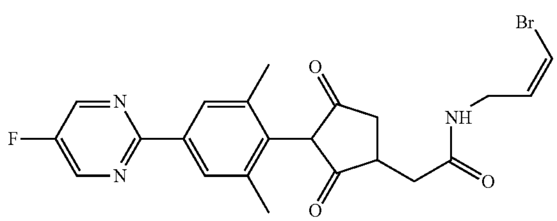 [SMILES: Cc1cc(-c2ncc(F)cn2)cc(C)c1C1C(=O)CC(CC(=O)NC/C=C\Br)C1=O] | 1HNMR (400 MHz, CD3OD) 8.75 (s, 2H), 8.80-8.71 (m, 2H), 8.80-8.71 (m, 2H), 8.08 (s, 2H), 6.43 (td, 1H), 6.27-6.17 (m, 1H), 3.98 (dd, 2H), 3.22-3.12 (m, 1H), 2.94 (dd, 1H), 2.79 (dd, 1H), 2.54-2.41 (m, 2H), 2.20 (s, 6H) |
| B327 | 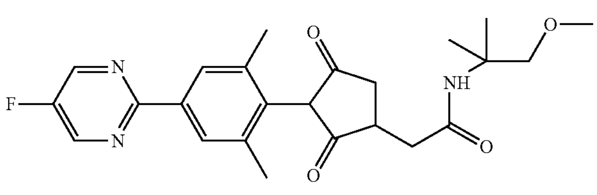 [SMILES: COCC(C)(C)NC(=O)CC1CC(=O)C(c2c(C)cc(-c3ncc(F)cn3)cc2C)C1=O] | 1H NMR (400 MHz, Methanol) Shift = 8.75 (s, 2H), 8.08 (s, 2H), 3.63-3.54 (m, 1H), 3.52-3.42 (m, 3H), 3.35-3.33 (m, 1H), 3.27-3.11 (m, 2H), 2.90 (dd, J = 7.0, 17.9 Hz, 1H), 2.73 (dd, J = 6.5, 15.0 Hz, 1H), 2.53-2.35 (m, 2H), 2.21 (s, 6H), 1.32 (d, J = 1.3 Hz, 6H) |
| B328 | 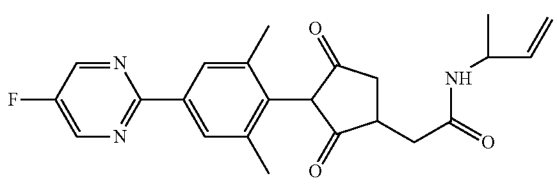 [SMILES: C=CC(C)NC(=O)CC1CC(=O)C(c2c(C)cc(-c3ncc(F)cn3)cc2C)C1=O] | 1H NMR (400 MHz, CD3OD) 8.75 (s, 2H), 8.13-7.94 (m, 2H), 5.86 (dddd, 1H), 5.24-5.13 (m, 1H), 5.07 (dd, 1H), 4.56-4.41 (m, 1H), 3.17 (br.s., 1H), 2.93 (dd, 1H), 2.79 (dd, 1H), 2.48 (d, 2H), 2.21 (s, 6H), 1.27-1.19 (m, 3H) |

TABLE T2-continued

| Compound Number | Structure | Physical Data LCMS or $^1$H NMR (400 MHz, CDCl$_3$) unless stated. |
|---|---|---|
| B329 | 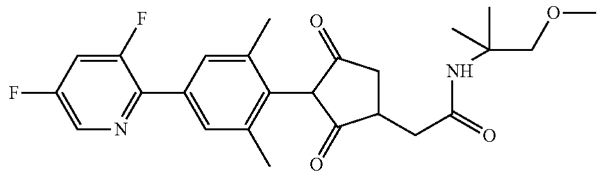 [SMILES: COCC(C)(C)NC(=O)CC1CC(=O)C(c2c(C)cc(-c3ncc(F)cc3F)cc2C)C1=O] | 1H NMR (400 MHz, CD3OD) 8.44 (d, 1H), 7.67-7.60 (m, 1H), 7.55 (s, 2H), 3.51-3.44 (m, 2H), 3.37 (s, 3H), 3.21-3.06 (m, 1H), 2.90 (dd, 1H), 2.73 (dd, 1H), 2.44 (d, 2H), 2.20 (s, 6H), 1.32 (d, 6H) |
| B330 | 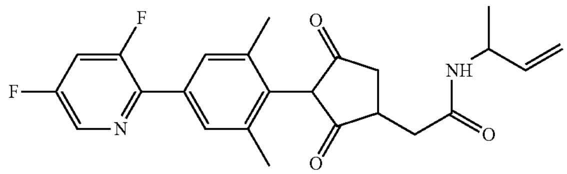 [SMILES: C=CC(C)NC(=O)CC1CC(=O)C(c2c(C)cc(-c3ncc(F)cc3F)cc2C)C1=O] | 1H NMR (400 MHz, CD3OD) 8.44 (d, 1H), 7.65 (ddd, 1H), 7.55 (s, 2H), 5.86 (dddd, 1H), 5.17 (qd, 1H), 5.07 (qd, 1H), 4.49 (t, 1H), 3.25-3.13 (m, 1H), 2.93 (dd, 1H), 2.79 (dd, 1H), 2.57-2.39 (m, 2H), 2.20 (s, 6H), 1.30-1.22 (m, 3H) |
| B331 | 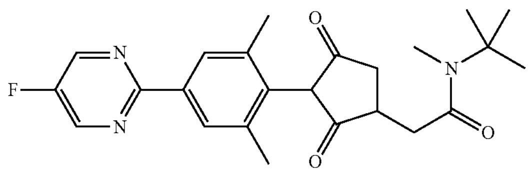 [SMILES: Cc1cc(-c2ncc(F)cn2)cc(C)c1C1C(=O)CC(CC(=O)N(C)C(C)(C)C)C1=O] | 1H NMR (400 MHz, CD3OD) 8.75 (s, 2H), 8.08 (s, 2H), 3.26-3.13 (m, 1H), 3.01 (s, 3H), 2.99-2.87 (m, 2H), 2.82 (d, 1H), 2.42 (d, 1H), 2.25-2.09 (m, 6H), 1.50-1.39 (m, 9H) |
| B332 | 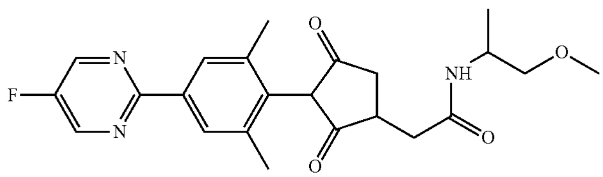 [SMILES: COCC(C)NC(=O)CC1CC(=O)C(c2c(C)cc(-c3ncc(F)cn3)cc2C)C1=O] | 1H NMR (400 MHz, CD3OD) 8.75 (s, 2H), 8.08 (s, 2H), 4.20-4.04 (m, 1H), 3.40-3.32 (m, 5H), 3.27-3.10 (m, 1H), 2.92 (dd, 1H), 2.77 (dd, 1H), 2.53-2.36 (m, 2H), 2.25-2.08 (m, 6H), 1.15 (dd, 3H) |
| B333 | 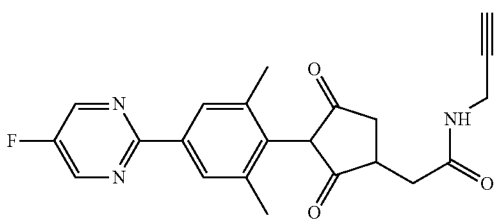 [SMILES: C#CCNC(=O)CC1CC(=O)C(c2c(C)cc(-c3ncc(F)cn3)cc2C)C1=O] | 1H NMR (400 MHz, CD3OD) 8.79-8.68 (m, 2H), 8.11-8.01 (m, 2H), 4.03-3.95 (m, 2H), 3.23-3.09 (m, 1H), 2.94 (dd, 1H), 2.79 (dd, 1H), 2.63-2.59 (m, 1H), 2.58-2.39 (m, 2H), 2.22-2.18 (m, 6H) |
| B334 | 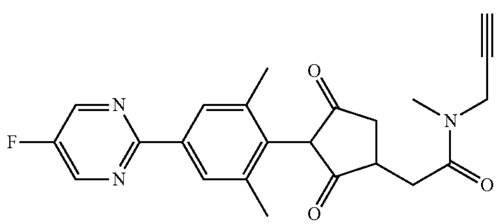 [SMILES: C#CCN(C)C(=O)CC1CC(=O)C(c2c(C)cc(-c3ncc(F)cn3)cc2C)C1=O] | 1H NMR (400 MHz, Methanol) Shift = 8.75 (s, 2H), 8.08 (s, 2H), 4.27-4.20 (m, 2H), 3.23-3.09 (m, 3H), 3.06-2.93 (m, 3H), 2.83 (s, 1H), 2.66 (t, J = 2.5 Hz, 1H), 2.50 (d, J = 16.1 Hz, 1H), 2.21 (d, J = 4.3 Hz, 6H) |
| B335 | 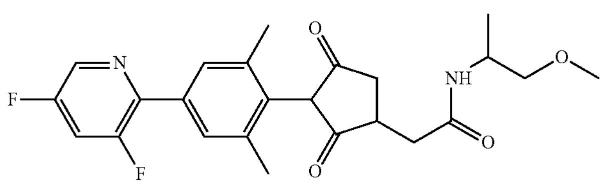 [SMILES: COCC(C)NC(=O)CC1CC(=O)C(c2c(C)cc(-c3ncc(F)cc3F)cc2C)C1=O] | 1H NMR (400 MHz, CD3OD) 8.44 (d, 1H), 7.65 (ddd, 1H), 7.55 (s, 2H), 4.18-4.04 (m, 1H), 3.39-3.33 (m, 5H), 3.24-3.12 (m, 1H), 2.92 (dd, 1H), 2.82-2.71 (m, 1H), 2.46 (d, 2H), 2.20 (s, 6H), 1.17-1.10 (m, 3H) |
| B336 | 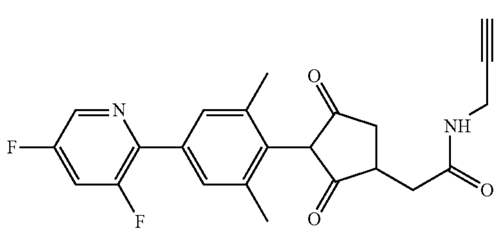 [SMILES: C#CCNC(=O)CC1CC(=O)C(c2c(C)cc(-c3ncc(F)cc3F)cc2C)C1=O] | 1H NMR (400 MHz, CD3OD) 8.44 (d, 1H), 7.65 (ddd, 1H), 7.55 (s, 2H), 3.99 (d, 2H), 3.22-3.08 (m, 1H), 2.93 (dd, 1H), 2.86-2.72 (m, 1H), 2.61 (t, 1H), 2.54-2.38 (m, 2H), 2.24-2.17 (m, 6H) |

TABLE T2-continued

| Compound Number | Structure | Physical Data LCMS or ¹H NMR (400 MHz, CDCl₃) unless stated. |
|---|---|---|
| B337 | 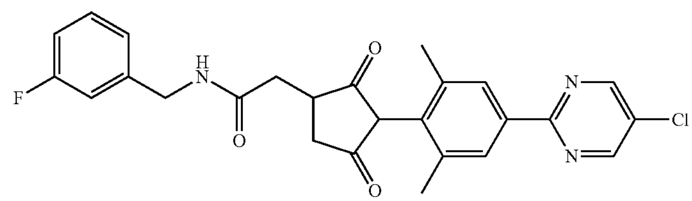 [SMILES: Cc1cc(-c2ncc(Cl)cn2)cc(C)c1C1C(=O)CC(CC(=O)NCc2cccc(F)c2)C1=O] | 1.38 mins, m/z = 480.22 (M + H)+ |
| B338 | 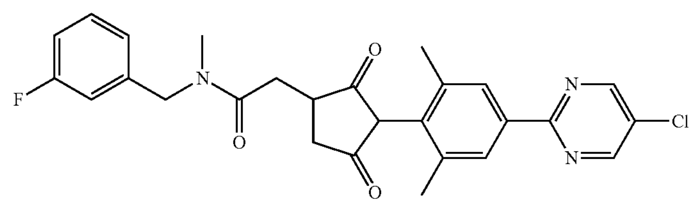 [SMILES: Cc1cc(-c2ncc(Cl)cn2)cc(C)c1C1C(=O)CC(CC(=O)N(C)Cc2cccc(F)c2)C1=O] | 1.45 mins, m/z = 494.24 (M + H)+ |
| B339 | 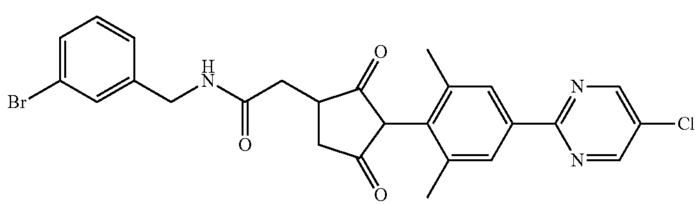 | 1.47 mins, m/z = 542.13 (M + H)+ |
| B340 | 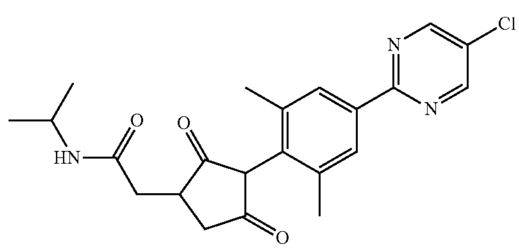 [SMILES: Cc1cc(-c2ncc(Cl)cn2)cc(C)c1C1C(=O)CC(CC(=O)NC(C)C)C1=O] | 1.27 mins, m/z = 414.23 (M + H)+ |
| B341 | 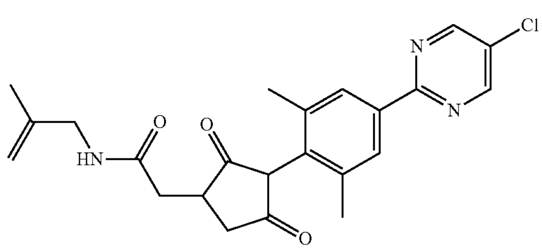 [SMILES: C=C(C)CNC(=O)CC1CC(=O)C(c2c(C)cc(-c3ncc(Cl)cn3)cc2C)C1=O] | 1.29 mins, m/z = 426.21 (M + H)+ |
| B342 | 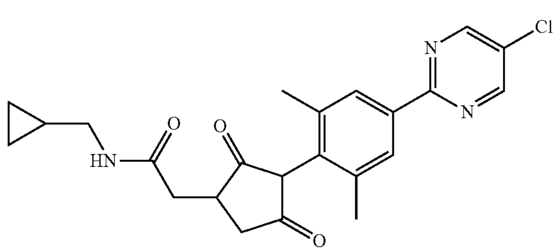 [SMILES: Cc1cc(-c2ncc(Cl)cn2)cc(C)c1C1C(=O)CC(CC(=O)NCC2CC2)C1=O] | 1.29 mins, m/z = 426.22 (M + H)+ |

TABLE T2-continued

| Compound Number | Structure | Physical Data LCMS or ¹H NMR (400 MHz, CDCl₃) unless stated. |
|---|---|---|
| B343 | 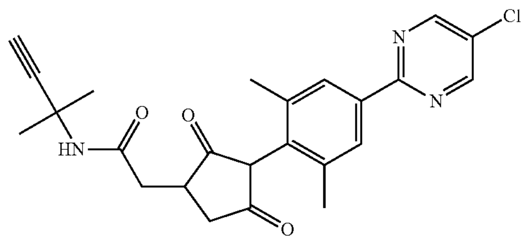 [SMILES: C#CC(C)(C)NC(=O)CC1CC(=O)C(c2c(C)cc(-c3ncc(Cl)cn3)cc2C)C1=O] | 1.28 mins, m/z = 438.22 (M + H)+ |
| B344 | 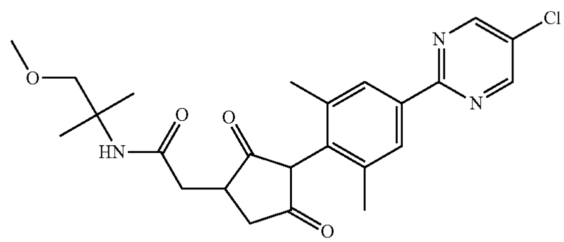 [SMILES: COCC(C)(C)NC(=O)CC1CC(=O)C(c2c(C)cc(-c3ncc(Cl)cn3)cc2C)C1=O] | 1.35 mins, m/z = 458.26 (M + H)+ |
| B345 | 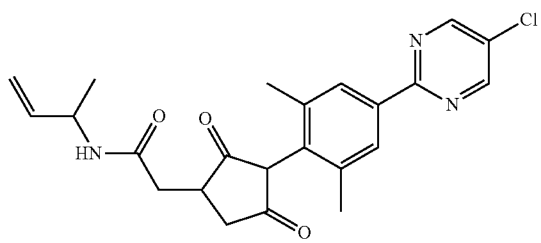 [SMILES: C=CC(C)NC(=O)CC1CC(=O)C(c2c(C)cc(-c3ncc(Cl)cn3)cc2C)C1=O] | 1.29 mins, m/z = 426.21 (M + H)+ |
| B346 | 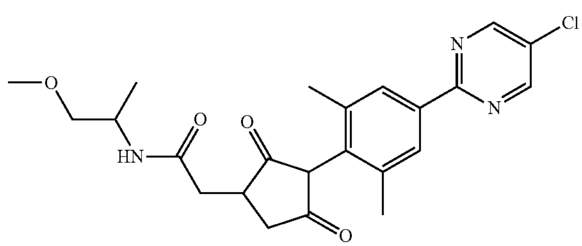 [SMILES: COCC(C)NC(=O)CC1CC(=O)C(c2c(C)cc(-c3ncc(Cl)cn3)cc2C)C1=O] | 1.21 mins, m/z = 444.23 (M + H)+ |
| B347 | 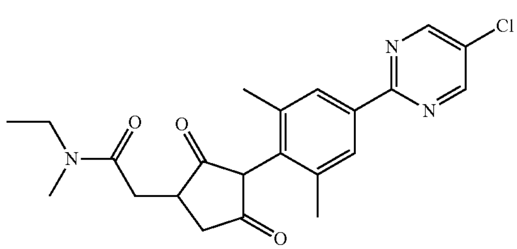 [SMILES: CCN(C)C(=O)CC1CC(=O)C(c2c(C)cc(-c3ncc(Cl)cn3)cc2C)C1=O] | 1.28 mins, m/z = 414.23 (M + H)+ |
| B348 | 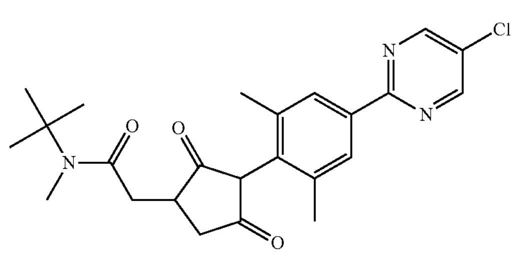 [SMILES: Cc1cc(-c2ncc(Cl)cn2)cc(C)c1C1C(=O)CC(CC(=O)N(C)C(C)(C)C)C1=O] | 1.51 mins, m/z = 442.25 (M + H)+ |

TABLE T2-continued

| Compound Number | Structure | Physical Data LCMS or ¹H NMR (400 MHz, CDCl₃) unless stated. |
|---|---|---|
| B349 | 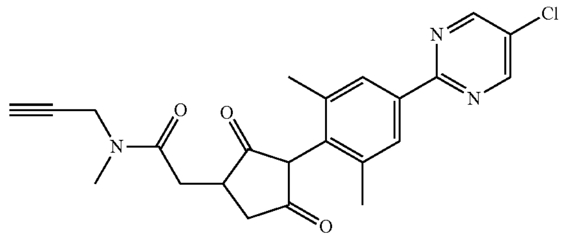 [SMILES: C#CCN(C)C(=O)CC1CC(=O)C(c2c(C)cc(-c3ncc(Cl)cn3)cc2C)C1=O] | 1.24 mins, m/z = 424.20 (M + H)+ |
| B350 | 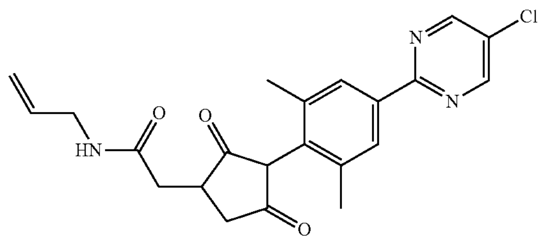 [SMILES: C=CCNC(=O)CC1CC(=O)C(c2c(C)cc(-c3ncc(Cl)cn3)cc2C)C1=O] | 1.21 mins, m/z = 412.21 (M + H)+ |
| B351 | 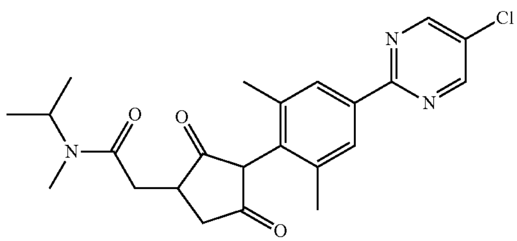 [SMILES: Cc1cc(-c2ncc(Cl)cn2)cc(C)c1C1C(=O)CC(CC(=O)N(C)C(C)C)C1=O] | 1.36 mins, m/z = 428.23 (M + H)+ |
| B352 | 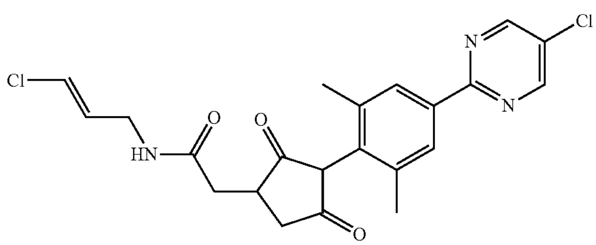 [SMILES: Cc1cc(-c2ncc(Cl)cn2)cc(C)c1C1C(=O)CC(CC(=O)NC/C=C/Cl)C1=O] | 1.29 mins, m/z = 446.17 (M + H)+ |
| B353 | 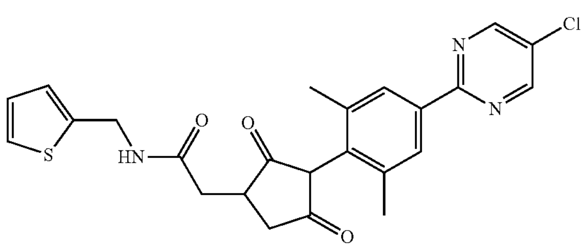 [SMILES: Cc1cc(-c2ncc(Cl)cn2)cc(C)c1C1C(=O)CC(CC(=O)NCc2cccs2)C1=O] | 1.32 mins, m/z = 468.20 (M + H)+ |
| B354 | 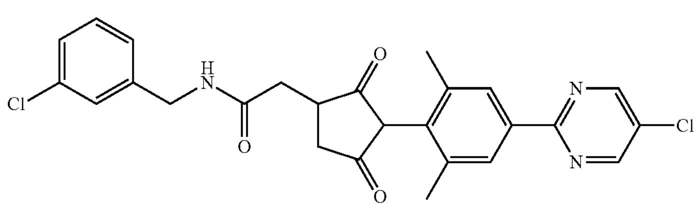 | 1.44 mins, m/z = 496.20 (M + H)+ |

TABLE T2-continued

| Compound Number | Structure | Physical Data LCMS or ¹H NMR (400 MHz, CDCl₃) unless stated. |
|---|---|---|
| B355 | 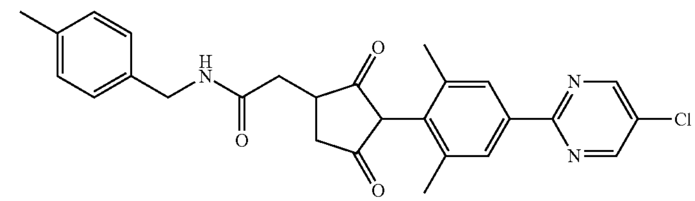 [SMILES: Cc1ccc(CNC(=O)CC2CC(=O)C(c3c(C)cc(-c4ncc(Cl)cn4)cc3C)C2=O)cc1] | 1.45 mins, m/z = 476.25 (M + H)+ |
| B356 | 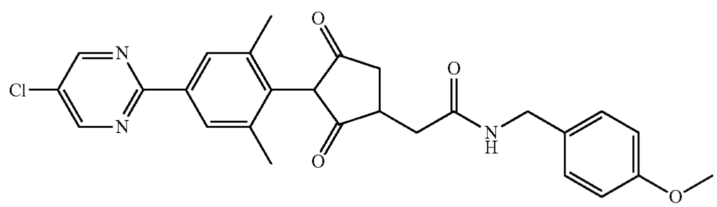 [SMILES: COc1ccc(CNC(=O)CC2CC(=O)C(c3c(C)cc(-c4ncc(Cl)cn4)cc3C)C2=O)cc1] | 1.36 mins, m/z = 492.25 (M + H)+ |
| B357* | 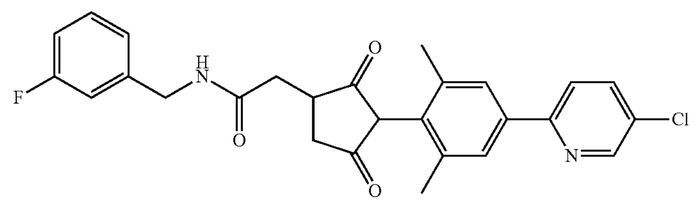 [SMILES: Cc1cc(-c2ccc(Cl)cn2)cc(C)c1C1C(=O)CC(CC(=O)NCc2cccc(F)c2)C1=O] | 1.36 mins, m/z = 479.24 (M + H)+ |
| B358* | 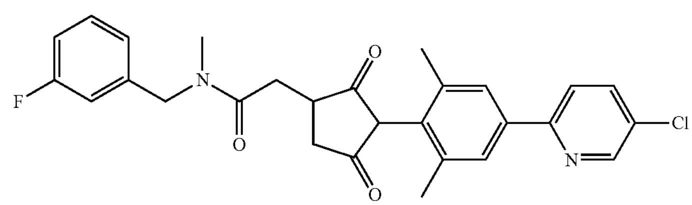 | 1.43 mins, m/z = 493.24 (M + H)+ |
| B359* | 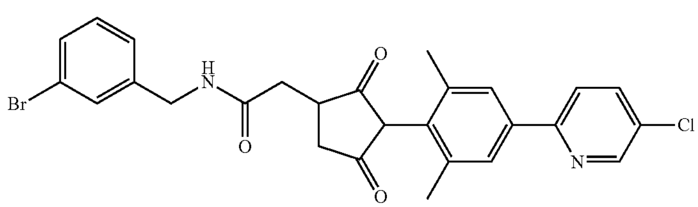 [SMILES: Cc1cc(-c2ccc(Cl)cn2)cc(C)c1C1C(=O)CC(CC(=O)NCc2cccc(Br)c2)C1=O] | 1.45 mins, m/z = 541.13 (M + H)+ |
| B360* | 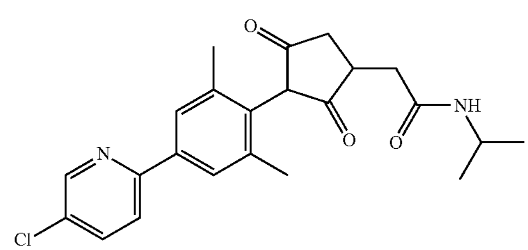 [SMILES: Cc1cc(-c2ccc(Cl)cn2)cc(C)c1C1C(=O)CC(CC(=O)NC(C)C)C1=O] | 1.26 mins, m/z = 413.24 (M + H)+ |
| B361* | 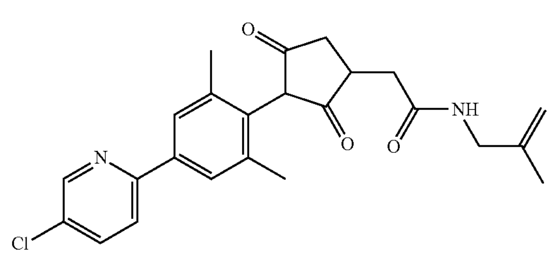 [SMILES: C=C(C)CNC(=O)CC1CC(=O)C(c2c(C)cc(-c3ccc(Cl)cn3)cc2C)C1=O] | 1.27 mins, m/z = 425.24 (M + H)+ |

TABLE T2-continued
| Compound Number | Structure | Physical Data LCMS or $^1$H NMR (400 MHz, CDCl$_3$) unless stated. |
|---|---|---|
| B362* | 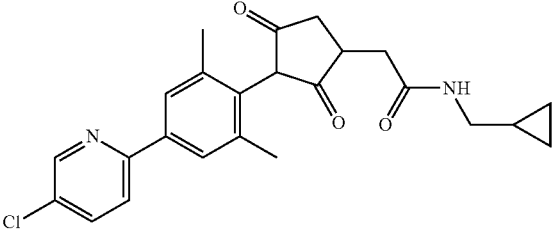 [SMILES: Cc1cc(-c2ccc(Cl)cn2)cc(C)c1C1C(=O)CC(CC(=O)NCC2CC2)C1=O] | 1.28 mins, m/z = 425.23 (M + H)+ |
| B363* | 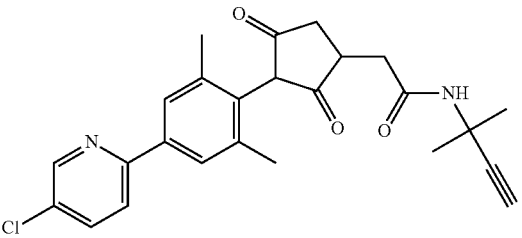 [SMILES: C#CC(C)(C)NC(=O)CC1CC(=O)C(c2c(C)cc(-c3ccc(Cl)cn3)cc2C)C1=O] | 1.27 mins, m/z = 437.23 (M + H)+ |
| B364* | 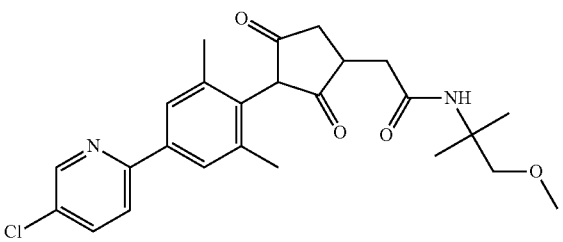 [SMILES: COCC(C)(C)NC(=O)CC1CC(=O)C(c2c(C)cc(-c3ccc(Cl)cn3)cc2C)C1=O] | 1.33 mins, m/z = 457.27 (M + H)+ |
| B365* | 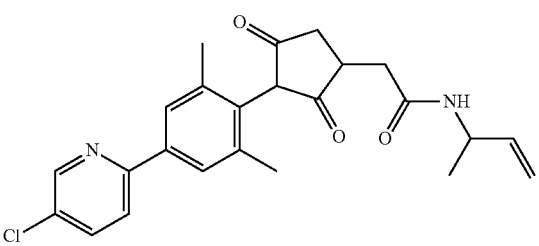 [SMILES: C=CC(C)NC(=O)CC1CC(=O)C(c2c(C)cc(-c3ccc(Cl)cn3)cc2C)C1=O] | 1.28 mins, m/z = 425.23 (M + H)+ |
| B366* | 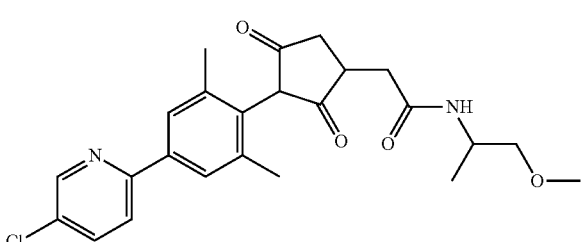 | 1.18 mins, m/z = 443.24 (M + H)+ |
| B367* | 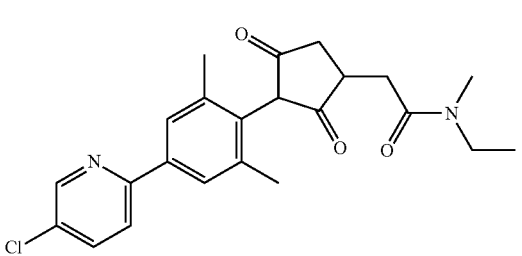 [SMILES: CCN(C)C(=O)CC1CC(=O)C(c2c(C)cc(-c3ccc(Cl)cn3)cc2C)C1=O] | 1.26 mins, m/z = 413.23 (M + H)+ |

TABLE T2-continued
| Compound Number | Structure | Physical Data LCMS or ¹H NMR (400 MHz, CDCl₃) unless stated. |
|---|---|---|
| B368* | 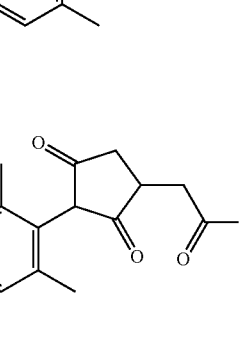 | 1.48 mins, m/z = 441.26 (M + H)+ |
| B369* | 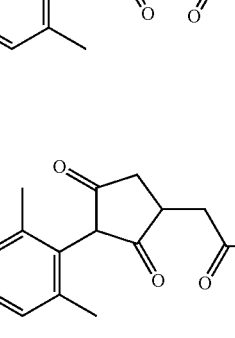 | 1.22 mins, m/z = 423.23 (M + H)+ |
| B370* | 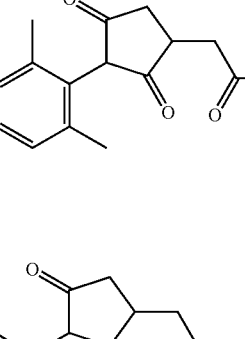 | 1.20 mins, m/z = 411.22 (M + H)+ |
| B371* | 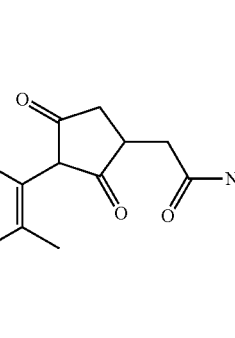 | 1.34 mins, m/z = 427.24 (M + H)+ |
| B372* | 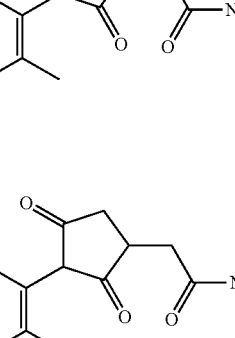 | 1.27 mins, m/z = 445.17 (M + H)+ |
| B373* | 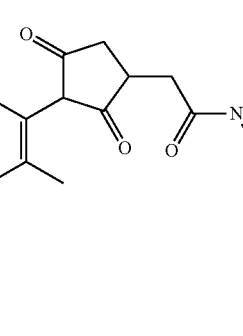 | 1.31 mins, m/z = 467.19 (M + H)+ |

TABLE T2-continued
| Compound Number | Structure | Physical Data LCMS or ¹H NMR (400 MHz, CDCl₃) unless stated. |
|---|---|---|
| B374* | 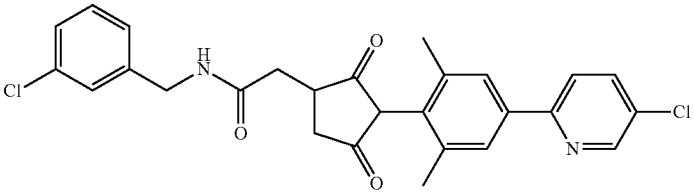 [SMILES: Cc1cc(-c2ccc(Cl)cn2)cc(C)c1C1C(=O)CC(CC(=O)NCc2cccc(Cl)c2)C1=O] | 1.44 mins, m/z = 495.20 (M + H)+ |
| B375* | 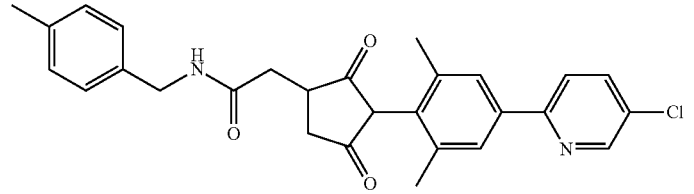 [SMILES: Cc1ccc(CNC(=O)CC2CC(=O)C(c3c(C)cc(-c4ccc(Cl)cn4)cc3C)C2=O)cc1] | 1.43 mins, m/z = 475.25 (M + H)+ |
| B376 | 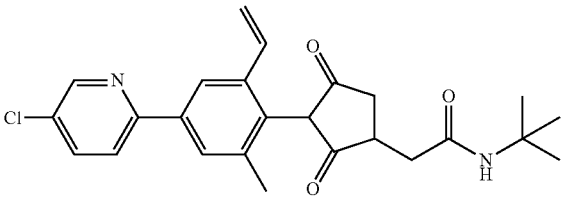 [SMILES: C=Cc1cc(-c2ccc(Cl)cn2)cc(C)c1C1C(=O)CC(CC(=O)NC(C)(C)C)C1=O] | 1HNMR (400 MHz, CD3OD) 9.05-8.99 (m, 1H), 8.71-8.63 (m, 1H), 8.44-8.36 (m, 1H), 8.08-7.99 (m, 1H), 7.77-7.71 (m, 1H), 6.78-6.61 (m, 1H), 5.88 (d, 1H), 5.33 (dd, 1H), 3.27-3.17 (m, 1H), 3.02-2.89 (m, 1H), 2.79-2.67 (m, 1H), 2.64-2.47 (m, 2H), 2.28 (d, 3H), 1.40-1.33 (m, 9H) |
| B377 | 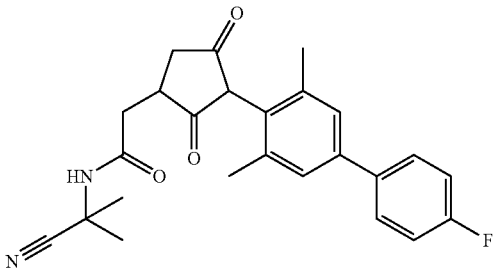 [SMILES: Cc1cc(-c2ccc(F)cc2)cc(C)c1C1C(=O)CC(CC(=O)NC(C)(C)C#N)C1=O] | 12.71 (br. s., 1H), 7.94 (br. s., 1H), 7.51 (dd, J = 8.5, 5.4 Hz, 2H), 7.24 (s, 2H), 7.03-7.17 (m, 2H), 3.34 (br. s., 1H), 2.96 (d, J = 11.1 Hz, 2H), 2.52-2.76 (m, 1H), 2.34 (br. s., 1H), 2.18 (s, 6H), 1.53 (d, J = 7.1 Hz, 6H). |
| B378 | 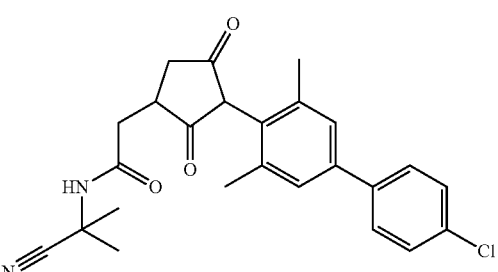 | 8.33 (s, 1H), 7.48 (d, J = 8.3 Hz, 2H), 7.36 (d, J = 8.3 Hz, 2H), 7.23 (br. s., 2H), 3.20 (br. s., 1H), 2.89-3.08 (m, 1H), 2.69 (br. s., 2H), 2.35 (br. s., 1H), 2.19 (d, J = 4.6 Hz, 6H), 1.65 (s, 6H). |
| B379 | 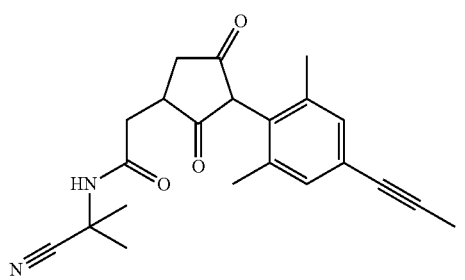 [SMILES: CC#Cc1cc(C)c(C2C(=O)CC(CC(=O)NC(C)(C)C#N)C2=O)c(C)c1] | 12.25-13.40 (br.s., 1H), 8.05 (br. s., 1H), 6.95-7.19 (m, 2H), 3.29 (br. s., 1H), 2.88 (d, J = 11.0 Hz, 2H), 2.59 (br. s., 1H), 2.12-2.25 (m, 1H), 1.96-2.12 (m, 9H), 1.51 (d, J = 9.9 Hz, 6H). |

TABLE T2-continued

| Compound Number | Structure | Physical Data LCMS or ¹H NMR (400 MHz, CDCl₃) unless stated. |
|---|---|---|
| B380* | 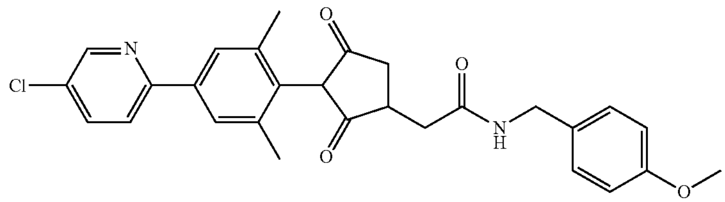 [SMILES: COc1ccc(CNC(=O)CC2CC(=O)C(c3c(C)cc(-c4ccc(Cl)cn4)cc3C)C2=O)cc1] | 1.35 mins, m/z = 491.25 (M + H)+ |
| B381* | 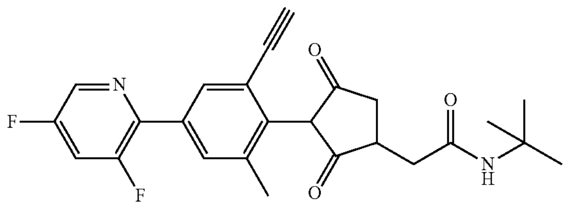 [SMILES: C#Cc1cc(-c2ncc(F)cc2F)cc(C)c1C1C(=O)CC(CC(=O)NC(C)(C)C)C1=O] | 1HNMR (400 MHz, CD3OD) 8.52-8.46 (m, 1H), 7.88 (s, 1H), 7.80 (s, 1H), 7.74-7.66 (m, 1H), 3.15 (d, 1H), 2.92 (ddd, 1H), 2.74 (ddd, 1H), 2.60-2.50 (m, 1H), 2.53-2.34 (m, 2H), 2.26 (d, 3H), 1.42-1.34 (m, 9H) |
| B382 | 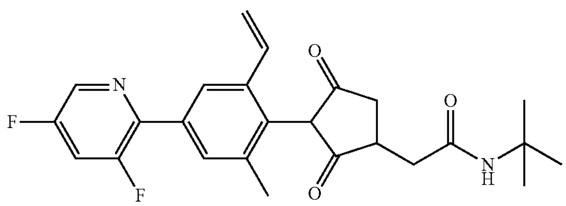 [SMILES: C=Cc1cc(-c2ncc(F)cc2F)cc(C)c1C1C(=O)CC(CC(=O)NC(C)(C)C)C1=O] | 1HNMR (400 MHz, CD3OD) 8.50-8.45 (m, 1H), 7.97 (s, 1H), 7.74-7.64 (m, 2H), 6.70 (ddd, 1H), 5.73 (dd, 1H), 5.28-5.17 (m, 1H), 3.26-3.13 (m, 1H), 2.99-2.86 (m, 1H), 2.79-2.68 (m, 1H), 2.52-2.41 (m, 2H), 2.25-2.19 (m, 3H), 1.40-1.33 (m, 9H) |
| B383* | 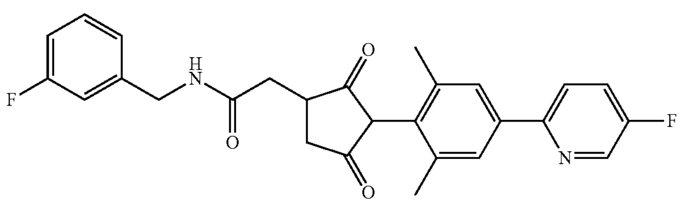 [SMILES: Cc1cc(-c2ccc(F)cn2)cc(C)c1C1C(=O)CC(CC(=O)NCc2cccc(F)c2)C1=O] | 1.27 mins, m/z = 463.24 (M + H)+ |
| B384* | 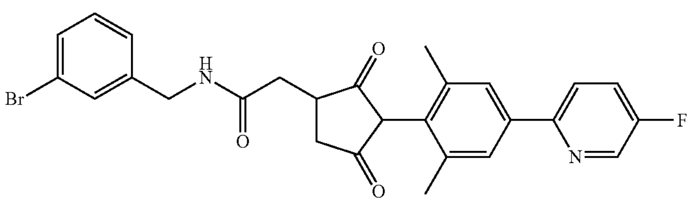 [SMILES: Cc1cc(-c2ccc(F)cn2)cc(C)c1C1C(=O)CC(CC(=O)NCc2cccc(Br)c2)C1=O] | 1.34 mins, m/z = 523.14/525.12 (M + H)+ |
| B385* | 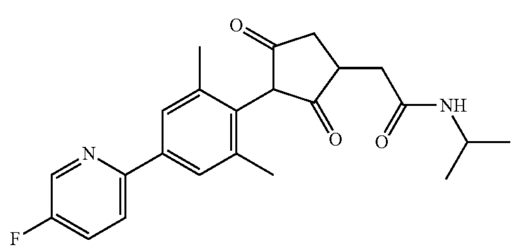 [SMILES: Cc1cc(-c2ccc(F)cn2)cc(C)c1C1C(=O)CC(CC(=O)NC(C)C)C1=O] | 1.13 mins, m/z = 397.24 (M + H)+ |
| B386* | 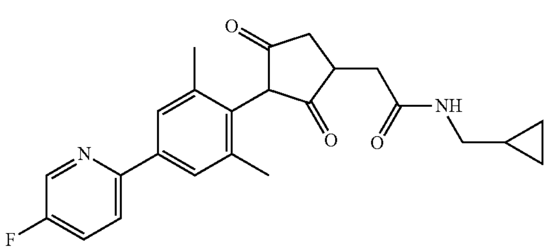 [SMILES: Cc1cc(-c2ccc(F)cn2)cc(C)c1C1C(=O)CC(CC(=O)NCC2CC2)C1=O] | 1.16 mins, m/z = 409.23 (M + H)+ |

TABLE T2-continued

| Compound Number | Structure | Physical Data LCMS or $^1$H NMR (400 MHz, CDCl$_3$) unless stated. |
|---|---|---|
| B387* | 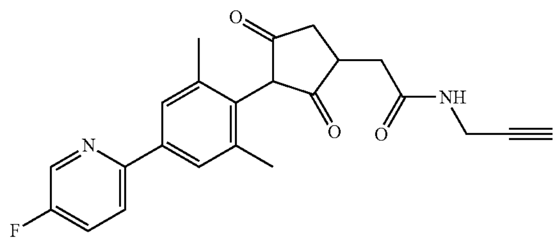 [SMILES: C#CCNC(=O)CC1CC(=O)C(c2c(C)cc(-c3ccc(F)cn3)cc2C)C1=O] | 1.01 mins, m/z = 393.21 (M + H)+ |
| B388* | 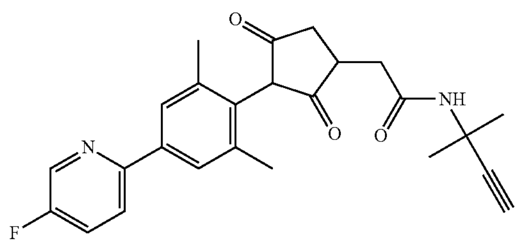 [SMILES: C#CC(C)(C)NC(=O)CC1CC(=O)C(c2c(C)cc(-c3ccc(F)cn3)cc2C)C1=O] | 1.15 mins, m/z = 421.23 (M + H)+ |
| B389* | 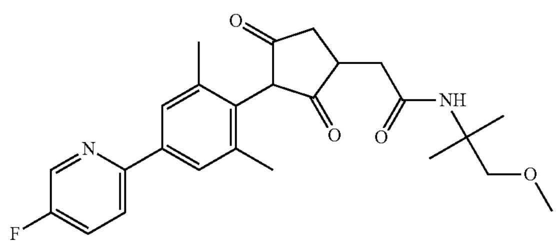 [SMILES: COCC(C)(C)NC(=O)CC1CC(=O)C(c2c(C)cc(-c3ccc(F)cn3)cc2C)C1=O] | 1.21 mins, m/z = 441.25 (M + H)+ |
| B390* | 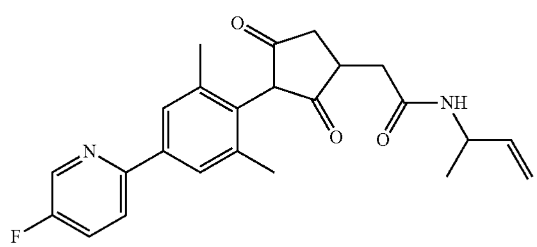 [SMILES: C=CC(C)NC(=O)CC1CC(=O)C(c2c(C)cc(-c3ccc(F)cn3)cc2C)C1=O] | 1.16 mins, m/z = 409.24 (M + H)+ |
| B391* | 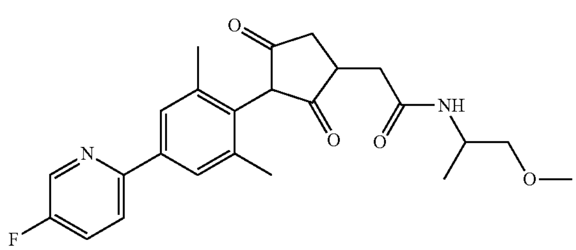 [SMILES: COCC(C)NC(=O)CC1CC(=O)C(c2c(C)cc(-c3ccc(F)cn3)cc2C)C1=O] | 1.06 mins, m/z = 427.26 (M + H)+ |
| B392* | 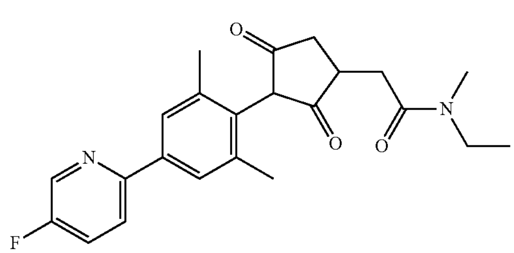 [SMILES: CCN(C)C(=O)CC1CC(=O)C(c2c(C)cc(-c3ccc(F)cn3)cc2C)C1=O] | 1.13 mins, m/z = 397.24 (M + H)+ |

TABLE T2-continued
| Compound Number | Structure | Physical Data LCMS or ¹H NMR (400 MHz, CDCl₃) unless stated. |
|---|---|---|
| B393* | 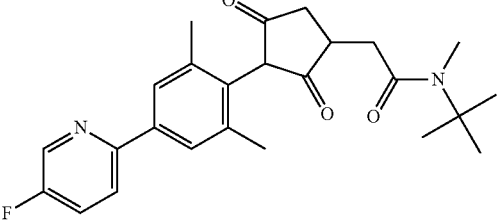 | 1.36 mins, m/z = 425.28 (M + H)+ |
| B394* | 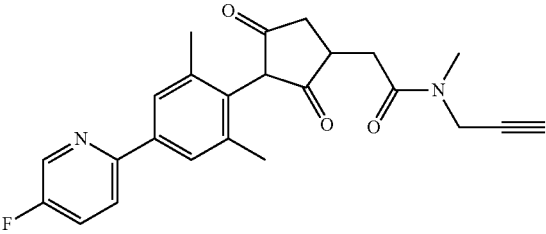 [SMILES: C#CCN(C)C(=O)CC1CC(=O)C(c2c(C)cc(-c3ccc(F)cn3)cc2C)C1=O] | 1.10 mins, m/z = 407.21 (M + H)+ |
| B395* | 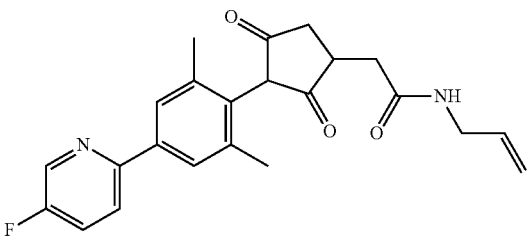 [SMILES: C=CCNC(=O)CC1CC(=O)C(c2c(C)cc(-c3ccc(F)cn3)cc2C)C1=O] | 1.07 mins, m/z = 395.23 (M + H)+ |
| B396* | 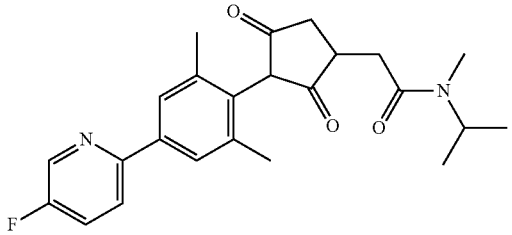 [SMILES: Cc1cc(-c2ccc(F)cn2)cc(C)c1C1C(=O)CC(CC(=O)N(C)C(C)C)C1=O] | 1.21 mins, m/z = 411.26 (M + H)+ |
| B397* | 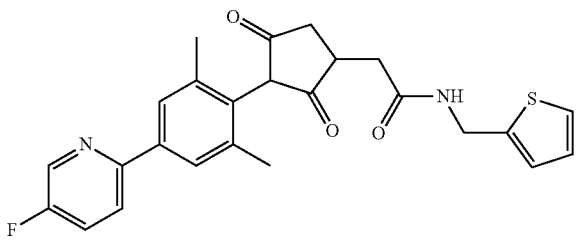 [SMILES: Cc1cc(-c2ccc(F)cn2)cc(C)c1C1C(=O)CC(CC(=O)NCc2cccs2)C1=O] | 1.19 mins, m/z = 451.19 (M + H)+ |
| B398* | 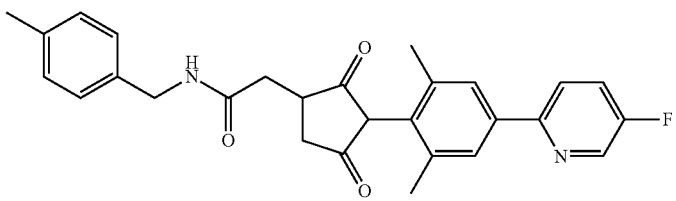 [SMILES: Cc1ccc(CNC(=O)CC2CC(=O)C(c3c(C)cc(-c4ccc(F)cn4)cc3C)C2=O)cc1] | 1.31 mins, m/z = 459.27 (M + H)+ |

TABLE T2-continued

| Compound Number | Structure | Physical Data LCMS or ¹H NMR (400 MHz, CDCl₃) unless stated. |
|---|---|---|
| B399* | 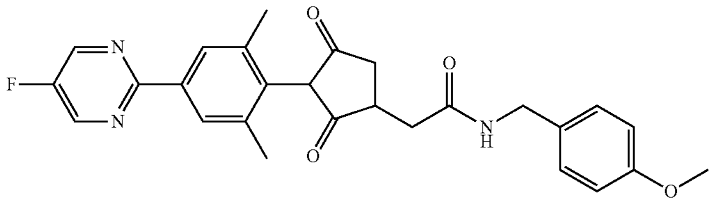 [SMILES: COc1ccc(CNC(=O)CC2CC(=O)C(c3c(C)cc(-c4ncc(F)cn4)cc3C)C2=O)cc1] | 1.23 mins, m/z = 475.25 (M + H)+ |
| B400* | 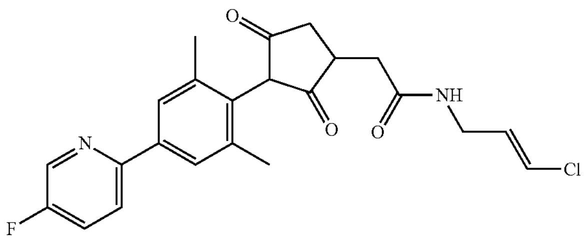 [SMILES: Cc1cc(-c2ccc(F)cn2)cc(C)c1C1C(=O)CC(CC(=O)NC/C=C/Cl)C1=O] | 1.16 mins, m/z = 429.18 (M + H)+ |
| B401* | 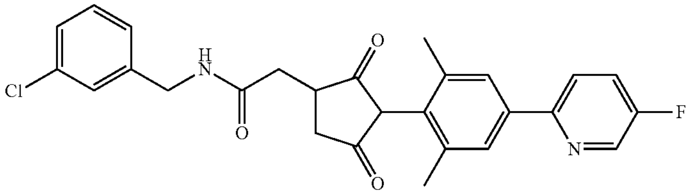 [SMILES: Cc1cc(-c2ccc(F)cn2)cc(C)c1C1C(=O)CC(CC(=O)NCc2cccc(Cl)c2)C1=O] | 1.32 mins, m/z = 479.20 (M + H)+ |
| B402 | 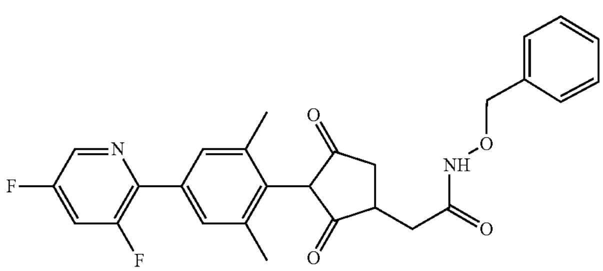 [SMILES: Cc1cc(-c2ncc(F)cc2F)cc(C)c1C1C(=O)CC(CC(=O)NOCc2ccccc2)C1=O] | 1HNMR (400 MHz, DMSO-d6) 7.76 (s, 1H), 7.04-6.94 (m, 1H), 6.82 (s, 2H), 6.74-6.57 (m, 5H), 4.13 (s, 2H), 2.33 (br.s., 1H), 2.21-2.06 (m, 1H), 1.93-1.87 (m, 1H), 1.85-1.76 (m, 1H), 1.71 (br.s., 1H), 1.53-1.45 (m, 1H), 1.44 (s, 6H) |
| B403 | 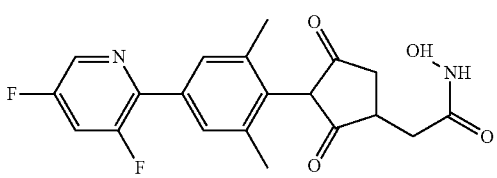 | 1HNMR (400 MHz, CD3OD) 8.43 (d, 1H), 7.65 (ddd, 1H), 7.55 (s, 2H), 3.13 (br.s., 1H), 2.89 (dd, 1H), 2.71 (dd, 1H), 2.47 (d, 1H), 2.31-2.24 (m, 1H), 2.22-2.16 (m, 6H) |
| B404 | 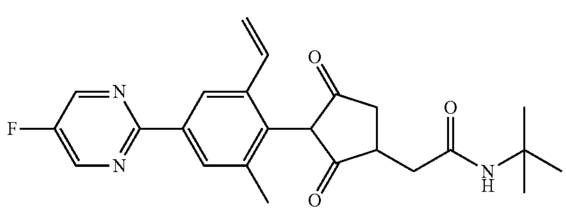 [SMILES: C=Cc1cc(-c2ncc(F)cn2)cc(C)c1C1C(=O)CC(CC(=O)NC(C)(C)C)C1=O] | 1HNMR (400 MHz, CD3OD) 8.82-8.74 (m, 2H), 8.49 (s, 1H), 8.21-8.10 (m, 1H), 6.67 (ddd, 1H), 5.83-5.70 (m, 1H), 5.27-5.12 (m, 1H), 3.24-3.13 (m, 1H), 2.93 (ddd, 1H), 2.72 (ddd, 1H), 2.51-2.38 (m, 2H), 2.25-2.17 (m, 3H), 1.40-1.31 (m, 9H) |
| B405 | 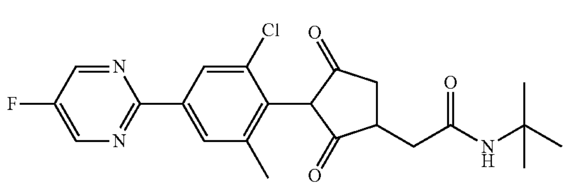 [SMILES: Cc1cc(-c2ncc(F)cn2)cc(Cl)c1C1C(=O)CC(CC(=O)NC(C)(C)C)C1=O] | 1HNMR (400 MHz, CD3OD) 8.82-8.71 (m, 2H), 8.27 (s, 1H), 8.27-8.13 (m, 1H), 3.20 (dtd, 1H), 2.93 (dd, 1H), 2.75-2.66 (m, 1H), 2.54-2.38 (m, 2H), 2.30-2.16 (m, 3H), 1.39-1.31 (m, 9H) |

*Trifluoroacetyl (TFA) salt.

| Compound Number | Structure | ¹H NMR (400 MHz, CDCl₃) unless stated |
|---|---|---|
| P1 | 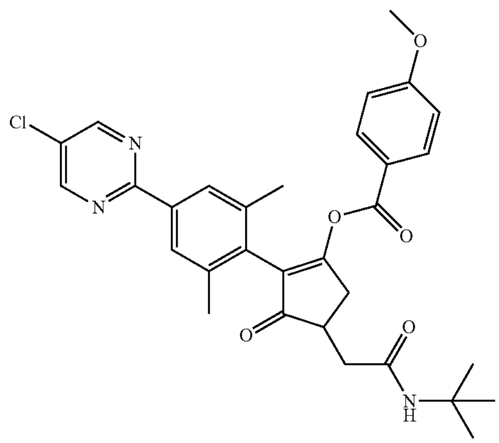 [SMILES: COc1ccc(C(=O)OC2=C(c3c(C)cc(-c4ncc(Cl)cn4)cc3C)C(=O)C(CC(=O)NC(C)(C)C)C2)cc1] | 8.70 (s, 2H), 8.09 (s, 2H), 7.83 (d, 2H), 6.86 (d, 2H), 5.91 (s, 1H), 3.80 (s, 3H), 3.53 (dd, 1H), 3.28-3.14 (m, 2H), 2.79 (dd, 1H), 2.48-2.39 (m, 1H), 2.27 (d, 6H), 1.33 (s, 9H) |
| P2 | 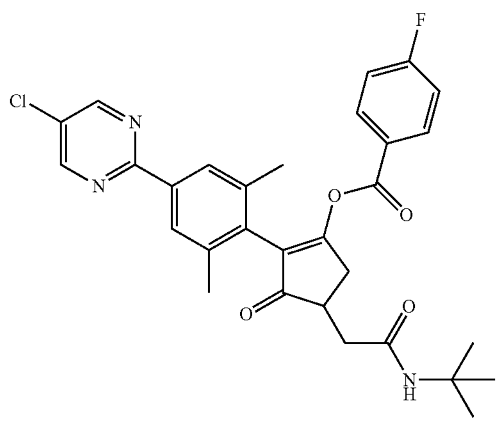 [SMILES: Cc1cc(-c2ncc(Cl)cn2)cc(C)c1C1=C(OC(=O)c2ccc(F)cc2)CC(CC(=O)NC(C)(C)C)C1=O] | (400 MHz, d4-MeOH) 8.69 (s, 2H), 8.02 (s, 2H), 7.95-7.88 (m, 2H), 7.64 (s, 1H), 7.11 (t, 2H), 3.47 (dd, 1H), 3.23-3.12 (m, 2H), 2.77 (dd, 1H), 2.56-2.48 (m, 1H), 2.26 (d, 6H), 1.36 (s, 9H) |
| P3 | 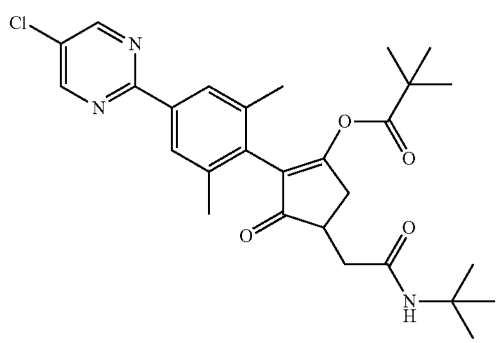 [SMILES: Cc1cc(-c2ncc(Cl)cn2)cc(C)c1C1=C(OC(=O)C(C)(C)C)CC(CC(=O)NC(C)(C)C)C1=O] | (400 MHz, d4-MeOH) 8.82 (s, 2H), 8.11 (s, 2H), 3.24 (dd, 1H), 3.17-3.09 (m, 1H), 2.92 (dd, 1H), 2.71 (dd, 1H), 2.42 (dd, 1H), 2.21 (s, 6H), 1.34 (s, 9H), 1.09 (s, 9H) |
| P4 | 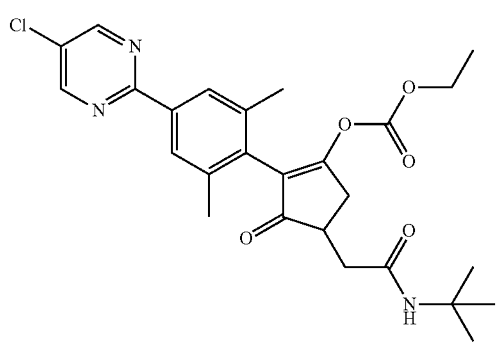 [SMILES: CCSC(=O)OC1=C(c2c(C)cc(-c3ncc(Cl)cn3)cc2C)C(=O)C(CC(=O)NC(C)(C)C)C1] | (400 MHz, d4-MeOH) 8.75 (s, 2H), 8.04 (s, 2H), 7.61 (s, 1H), 4.18 (q, 2H), 3.36 (dd, 1H), 31.5-3.08 (m, 1H), 3.03 (dd, 1H), 2.70 (dd, 1H), 2.43 (dd, 1H), 2.19 (d, 6H), 1.33 (s, 9H), 1.20 (t, 3H) |

| Compound Number | Structure | ¹H NMR (400 MHz, CDCl₃) unless stated |
|---|---|---|
| P5 | 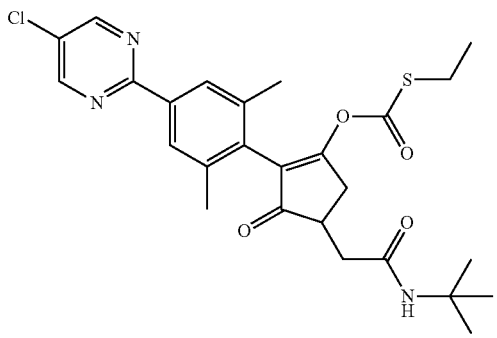 | (400 MHz, d4-MeOH) 8.74 (s, 2H), 8.04 (s, 2H), 7.59 (s, 1H), 3.33 (dd, 1H), 3.14-3.06 (m, 1H), 3.01 (dd, 1H), 2.80 (q, 2H), 2.70 (dd, 1H), 2.44 (dd, 1H), 2.19 (d, 6H), 1.33 (s, 9H), 1.27 (t, 3H) |
| P6 | 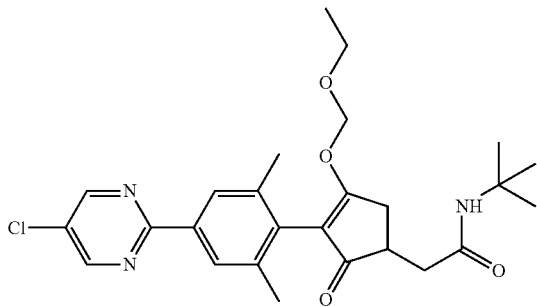 [SMILES: CCOCOC1=C(c2c(C)cc(-c3ncc(Cl)cn3)cc2C)C(=O)C(CC(=O)NC(C)(C)C)C1] | 8.72 (s, 2H), 8.09 (s, 2H), 6.12 (s, 1H), 5.13 (dd, 2H), 3.68-3.56 (m, 2H), 3.27 (dd, 1H), 3.07-3.00 (m, 1H), 2.89 (dd, 1H), 2.74 (dd, 1H), 2.36-2.28 (m, 1H), 2.21 (d, 6H), 1.32 (s, 9H), 1.18 (t, 3H) |
| P7 | 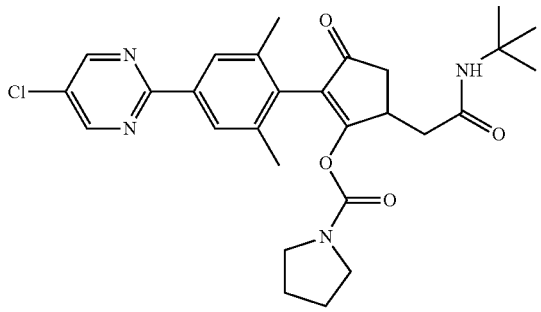 [SMILES: Cc1cc(-c2ncc(Cl)cn2)cc(C)c1C1=C(OC(=O)N2CCCC2)C(CC(=O)NC(C)(C)C)CC1=O] | 8.72 (s, 2H), 8.07 (s, 2H), 5.48 (s, 1H), 3.97-3.88 (m, 1H), 3.32-3.21 (m, 4H), 3.01 (dd, 1H), 2.71 (dd, 1H), 2.52 (d, 1H), 2.28-2.21 (m, 1H), 2.23 (d, 6H), 1.87-1.72 (m, 4H), 1.35 (s, 9H) |
| P8 | 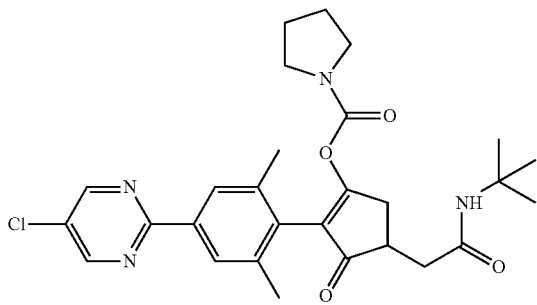 [SMILES: Cc1cc(-c2ncc(Cl)cn2)cc(C)c1C1=C(OC(=O)N2CCCC2)CC(CC(=O)NC(C)(C)C)C1=O] | 8.72 (s, 2H), 8.08 (s, 2H), 5.81 (s, 1H), 3.50 (dd, 1H), 3.40-3.32 (m, 2H), 3.23-3.07 (m, 4H), 2.74 (dd, 1H), 2.40-2.32 (m, 1H), 2.22 (d, 6H), 1.88-1.77 (m, 4H), 1.33 (s, 9H) |

-continued

| Compound Number | Structure | $^1$H NMR (400 MHz, CDCl$_3$) unless stated |
|---|---|---|
| P9 | 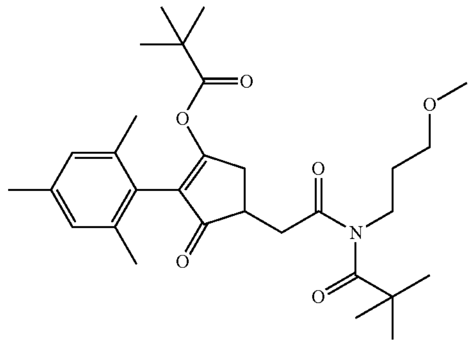 | 6.83 (s, 2H), 3.75-3.61 (m, 2H), 3.45-3.33 (m, 2H), 3.30 (s, 4H), 3.17-3.03 (m, 2H), 2.91-2.72 (m, 2H), 2.25 (s, 3H), 2.08 (d, 6H), 1.89-1.77 (m, 2H), 1.31 (s, 9H), 1.08 (s, 9H) |
| P10 | 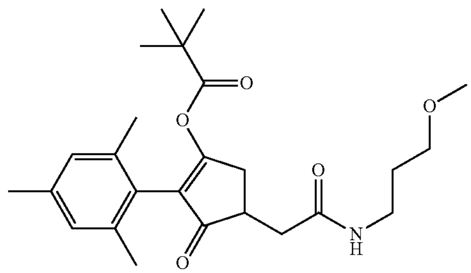 | 6.84 (s, 2H), 6.38-6.21 (m, 1H), 3.53-3.19 (m, 8H), 3.16-3.04 (m, 1H), 3.01-2.89 (m, 1H), 2.86-2.69 (m, 1H), 2.50-2.31 (m, 1H), 2.25 (s, 3H), 2.06 (d, 6H), 1.85-1.70 (m, 2H), 1.08 (s, 9H) |
| P11 | 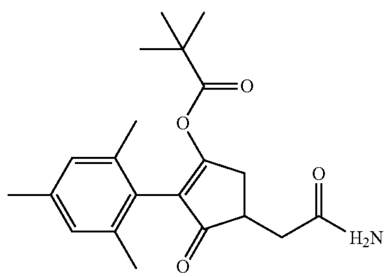 [SMILES: Cc1cc(C)c(C2=C(OC(=O)C(C)(C)C)CC(CC(N)=O)C2=O)c(C)c1] | 6.84 (s, 2H), 6.33-6.21 (m, 1H), 5.94-5.82 (m, 1H), 3.31-3.17 (m, 1H), 3.12-3.01 (m, 1H), 2.99-2.86 (m, 1H), 2.85-2.69 (m, 1H), 2.54-2.40 (m, 1H), 2.25 (s, 3H), 2.05 (d, 6H), 1.08 (s, 9H) |
| P12 | 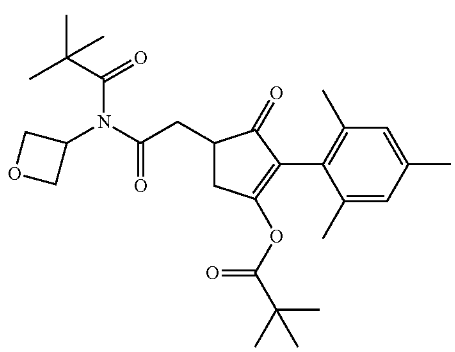 [SMILES: Cc1cc(C)c(C2=C(OC(=O)C(C)(C)C)CC(CC(=O)N(C(=O)C(C)(C)C)C3COC3)C2=O)c(C)c1] | 6.84 (s, 2H), 5.01-4.83 (m, 1H), 4.83-4.54 (m, 3H), 3.33-3.17 (m, 1H), 3.14-3.01 (m, 1H), 2.93-2.73 (m, 2H), 2.59-2.43 (m, 1H), 2.25 (s, 3H), 2.07 (d, 6H), 1.35-0.98 (m, 19H) |
| P13 | 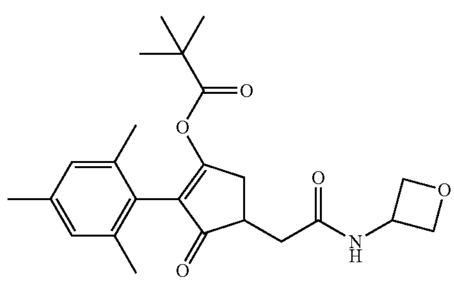 [SMILES: Cc1cc(C)c(C2=C(OC(=O)C(C)(C)C)CC(CC(=O)NC3COC3)C2=O)c(C)c1] | 7.26-7.11 (m, 1H), 6.90-6.77 (m, 2H), 5.05-4.90 (m, 1H), 4.86-4.75 (m, 2H), 4.40 (s, 2H), 3.34-3.19 (m, 1H), 3.17-3.04 (m, 1H), 2.99-2.88 (m, 1H), 2.85-2.72 (m, 1H), 2.53-2.39 (m, 1H), 2.25 (s, 3H), 2.13-1.99 (m, 6H), 1.09 (s, 9H) |

| Compound Number | Structure | ¹H NMR (400 MHz, CDCl₃) unless stated |
|---|---|---|
| P14 | 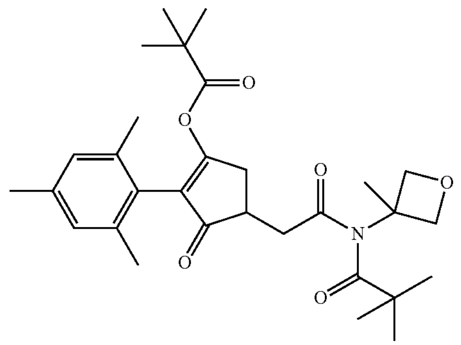 [SMILES: Cc1cc(C)c(C2=C(OC(=O)C(C)(C)C)CC(CC(=O)N(C(=O)C(C)(C)C)C3(C)COC3)C2=O)c(C)c1] | 6.84 (s, 2H), 4.75-1.7 (m, 18H), 1.35-0.98 (m, 21H) |
| P15 | 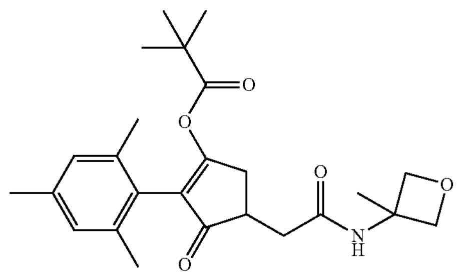 [SMILES: Cc1cc(C)c(C2=C(OC(=O)C(C)(C)C)CC(CC(=O)NC3(C)COC3)C2=O)c(C)c1] | 7.15-7.00 (s, 1H), 6.90-6.77 (m, 2H), 4.75-4.60 (m, 2H), 4.30-4.40 (m, 2H), 3.33-3.25 (m, 1H), 3.17-3.04 (m, 1H), 2.99-2.88 (m, 1H), 2.85-2.72 (m, 1H), 2.45-2.35 (m, 1H), 2.25 (s, 3H), 2.13-1.99 (m, 6H), 1.09-1.00 (m, 12H) |

BIOLOGICAL EXAMPLES

Biological Example 1

Test—Glasshouse Assay for Herbicidal Activity

Seeds of a variety of monocotyledonous and dicotyledonous test plants are sown in standard soil in pots. The plants are cultivated for one day (for pre-emergence (PRE)) or for about 12 days (for post-emergence (POST)) under controlled conditions in a glasshouse (warm climate species at 24/18° C., cool climate species at 20/16° C., both at day/night; 16 hours light; 65% humidity).

The test plants are then grown on, in a glasshouse (greenhouse) under controlled conditions (warm climate species at 24/18° C., cool climate species at 20/16° C., both at day/night; 16 hours light; 65% humidity) and are watered twice daily. 15 days after application of the test herbicide (15 DAA) (for post-emergence), and 20 days after application of the test herbicide (20 DAA) (for pre-emergence), the test plants are evaluated visually, and an assessed percentage phytotoxicity score is given for each herbicidal application on each plant species (with 100%=total damage to plant; 0%=no damage to plant).

The plant species tested are as follows: *Alopecurus myosuroides* (ALOMY), *Avena fatua* (AVEFA), *Lolium perenne* (LOLPE), *Echinochloa crus-galli* (ECHCG).

TABLE B1

| | | Pre-/Post-emergence herbicidal activity (percentage phytotoxicity) | | | | | | |
|---|---|---|---|---|---|---|---|---|
| | | LOLPE | | ALOMY | | ECHCG | | AVEFA | |
| Compound | Rate g/ha | PRE | POST | PRE | POST | PRE | POST | PRE | POST |
| A1 | 250 | 100 | 80 | 60 | 60 | 90 | 80 | 60 | 60 |
| A2 | 250 | 80 | 80 | 80 | 80 | 70 | 50 | 10 | 70 |
| A3 | 250 | 100 | 90 | 100 | 90 | 100 | 90 | 90 | 90 |
| A4 | 250 | 80 | 90 | 50 | 50 | 70 | 80 | 30 | 80 |
| A5 | 250 | 100 | 80 | 100 | 90 | 100 | 80 | 70 | 80 |
| A6 | 250 | 100 | 90 | 90 | 90 | 100 | 90 | 60 | 90 |
| A7 | 250 | 100 | 100 | 80 | 90 | 90 | 100 | 60 | 90 |
| A8 | 250 | 100 | 100 | 100 | 100 | 100 | 100 | 100 | 100 |
| A9 | 250 | 90 | 80 | 90 | 80 | 100 | 90 | 90 | 100 |
| A10 | 250 | 90 | 90 | 70 | 80 | 90 | 90 | 70 | 60 |
| A11 | 250 | 70 | 70 | 70 | 80 | 70 | 80 | 50 | 70 |
| A12 | 250 | 100 | 90 | 90 | 100 | 100 | 80 | 70 | 80 |
| A13 | 250 | 70 | 80 | 50 | 80 | 100 | 80 | 40 | 70 |
| A14 | 250 | 80 | 80 | 90 | 80 | 100 | 80 | 70 | 70 |
| A15 | 250 | 100 | 100 | 80 | 80 | 100 | 100 | 50 | 80 |
| A16 | 250 | 80 | 80 | 90 | 90 | 100 | 100 | 90 | 90 |
| A17 | 250 | 70 | 80 | 70 | 80 | 70 | 80 | 40 | 70 |
| A18 | 250 | 60 | 80 | 60 | 70 | 60 | 70 | 20 | 50 |

TABLE B1-continued

| | | \multicolumn{2}{c}{LOLPE} | \multicolumn{2}{c}{ALOMY} | \multicolumn{2}{c}{ECHCG} | \multicolumn{2}{c}{AVEFA} |
|---|---|---|---|---|---|---|---|---|
| Compound | Rate g/ha | PRE | POST | PRE | POST | PRE | POST | PRE | POST |
| A19 | 250 | 90 | 90 | 90 | 90 | 90 | 80 | 70 | 80 |
| A20 | 250 | 100 | 100 | 70 | 80 | 100 | 100 | 70 | 80 |
| A21 | 250 | 80 | 80 | 70 | 80 | 80 | 80 | 50 | 70 |
| A22 | 250 | 70 | 80 | 60 | 80 | 100 | 90 | 30 | 60 |
| A23 | 250 | 70 | 80 | 80 | 80 | 100 | 90 | 60 | 70 |
| A24 | 250 | 90 | 100 | 80 | 90 | 100 | 100 | 90 | 90 |
| A25 | 250 | 90 | 90 | 70 | 70 | 80 | 90 | 70 | 70 |
| A26 | 250 | 100 | 90 | 80 | 80 | 80 | 80 | 70 | 80 |
| A27 | 250 | 80 | 80 | 70 | 80 | 80 | 80 | 70 | 80 |
| A28 | 250 | 90 | 100 | 100 | 100 | 90 | 100 | 100 | 100 |
| A29 | 250 | 100 | 100 | 100 | 100 | 100 | 90 | 100 | 100 |
| A30 | 250 | 100 | 100 | 100 | 100 | 100 | 100 | 100 | 100 |
| A31 | 250 | 100 | 100 | 100 | 100 | 100 | 100 | 90 | 100 |
| A32 | 250 | 90 | 100 | 70 | 100 | 100 | 100 | 80 | 100 |
| A33 | 250 | 100 | 100 | 100 | 100 | 100 | 100 | 100 | 100 |
| A34 | 250 | 100 | 100 | 100 | 100 | 100 | 100 | 100 | 100 |
| A35 | 250 | 100 | 100 | 90 | 90 | 100 | 100 | 100 | 100 |
| A36 | 250 | 100 | 90 | 100 | 90 | 100 | 100 | 100 | 100 |
| A37 | 250 | 100 | 80 | 90 | 80 | 100 | 90 | 90 | 100 |
| A38 | 250 | 90 | 80 | 80 | 80 | 100 | 90 | 90 | 100 |
| A39 | 250 | 100 | 100 | 100 | 100 | 100 | 100 | 100 | 100 |
| A40 | 250 | 100 | 100 | 100 | 100 | 100 | 100 | 90 | 100 |
| A41 | 250 | 100 | 100 | 100 | 100 | 100 | 100 | 70 | 100 |
| A42 | 250 | 100 | 90 | 100 | 100 | 100 | 80 | 100 | 100 |
| A43 | 250 | 100 | 90 | 100 | 100 | 100 | 90 | 100 | 90 |
| A44 | 250 | 100 | 100 | 100 | 100 | 100 | 100 | 100 | 100 |
| A45 | 250 | 100 | 100 | 100 | 100 | 100 | 100 | 100 | 100 |
| A46 | 250 | 90 | 100 | 100 | 100 | 100 | 100 | 90 | 100 |
| A47 | 250 | 100 | 100 | 100 | 100 | 100 | 100 | 100 | 100 |
| A48 | 250 | 100 | 100 | 100 | 100 | 100 | 100 | 90 | 100 |
| A49 | 250 | 100 | 100 | 100 | 100 | 100 | 100 | 100 | 100 |
| A50 | 250 | 100 | 100 | 100 | 100 | 90 | 100 | 100 | 100 |
| A51 | 250 | 100 | 100 | 100 | 100 | 100 | 100 | 100 | 100 |
| A52 | 250 | 90 | 90 | 100 | 100 | 90 | 100 | 90 | 100 |
| A53 | 250 | 90 | 90 | 90 | 100 | 100 | 100 | 80 | 90 |
| A54 | 250 | 100 | 100 | 100 | 100 | 100 | 100 | 100 | 100 |
| A55 | 250 | 90 | 90 | 90 | 90 | 100 | 100 | 80 | 100 |
| A56 | 250 | 90 | 90 | 100 | 100 | 100 | 100 | 90 | 100 |
| A57 | 250 | 100 | 100 | 100 | 100 | 100 | 100 | 90 | 100 |
| A58 | 250 | 90 | 90 | 100 | 100 | 100 | 100 | 100 | 100 |
| A59 | 250 | 70 | 70 | 100 | 90 | 90 | 90 | 70 | 90 |
| A60 | 250 | 100 | 90 | 100 | 100 | 100 | 100 | 100 | 100 |
| A61 | 250 | 100 | 90 | 100 | 100 | 100 | 100 | 90 | 100 |
| A62 | 250 | 100 | 60 | 100 | 90 | 100 | 100 | 90 | 90 |
| A63 | 250 | 100 | 90 | 100 | 100 | 100 | 100 | 90 | 100 |
| A64 | 250 | 80 | 70 | 70 | 90 | 100 | 100 | 70 | 90 |
| A65 | 250 | 90 | 80 | 100 | 90 | 100 | 100 | 70 | 90 |
| A66 | 250 | 100 | 100 | 100 | 90 | 100 | 100 | 100 | 100 |
| A67 | 250 | 90 | 70 | 100 | 80 | 90 | 100 | 90 | 80 |
| A68 | 250 | 100 | 100 | 70 | 90 | 100 | 100 | 100 | 100 |
| A69 | 250 | 100 | 100 | 100 | 100 | 100 | 100 | 100 | 100 |
| A70 | 250 | 70 | 70 | 70 | 90 | 100 | 90 | 70 | 70 |
| A71 | 250 | 60 | 70 | 80 | 100 | 90 | 100 | 80 | 90 |
| A72 | 250 | 90 | 80 | 90 | 90 | 100 | 90 | 90 | 90 |
| A73 | 250 | 30 | 40 | 70 | 70 | 90 | 90 | 10 | 80 |
| A74 | 250 | 90 | 90 | 100 | 100 | 100 | 100 | 90 | 100 |
| A75 | 250 | 90 | 90 | 100 | 100 | 100 | 100 | 90 | 100 |
| A76 | 250 | 90 | 80 | 90 | 100 | 100 | 100 | 90 | 90 |
| A77 | 250 | 80 | 80 | 80 | 90 | 100 | 100 | 80 | 90 |
| A78 | 250 | 20 | 30 | 10 | 80 | 60 | 100 | 30 | 40 |
| A79 | 250 | 100 | 100 | 100 | 100 | 100 | 100 | 100 | 100 |
| A80 | 250 | 100 | 100 | 100 | 100 | 100 | 100 | 90 | 100 |
| A81 | 250 | 100 | 90 | 100 | 90 | 100 | 100 | 100 | 100 |
| A82 | 250 | — | 30 | — | 10 | — | 30 | — | 10 |
| A83 | 250 | — | 30 | — | 50 | — | 70 | — | 10 |
| A84 | 250 | 10 | 20 | 40 | 60 | 0 | 70 | 0 | 20 |
| A85 | 250 | 100 | 90 | 100 | 100 | 90 | 100 | 80 | 100 |
| A86 | 250 | 10 | 50 | 0 | 30 | 20 | 80 | 0 | 40 |
| A87 | 250 | 80 | 80 | 80 | 100 | 90 | 100 | 90 | 100 |
| A88 | 250 | 100 | 100 | 90 | 70 | 70 | 80 | 0 | 10 |
| A89 | 250 | 90 | 100 | 90 | 90 | 100 | 100 | 60 | 90 |
| A90 | 250 | 60 | 70 | 0 | 0 | 40 | 80 | 0 | 0 |
| A91 | 250 | 70 | 70 | 30 | 10 | 20 | 0 | 30 | 0 |
| A92 | 250 | 90 | 40 | 70 | 60 | 80 | 80 | 60 | 70 |

TABLE B1-continued

| | | \multicolumn{2}{c}{LOLPE} | \multicolumn{2}{c}{ALOMY} | \multicolumn{2}{c}{ECHCG} | \multicolumn{2}{c}{AVEFA} |
|---|---|---|---|---|---|---|---|---|---|
| Compound | Rate g/ha | PRE | POST | PRE | POST | PRE | POST | PRE | POST |
| A93 | 250 | 90 | 80 | 90 | 100 | 60 | 70 | 20 | 40 |
| A94 | 250 | 90 | 90 | 90 | 80 | 60 | 80 | 20 | 70 |
| A94 | 250 | — | 60 | — | 0 | — | 80 | — | 0 |
| A96 | 250 | 100 | 100 | 100 | 80 | 100 | 80 | 70 | 80 |
| A97 | 250 | 90 | 70 | 30 | 70 | 0 | 0 | 0 | 20 |
| A98 | 250 | 80 | 80 | 100 | 90 | 80 | 60 | 20 | 90 |
| A99 | 250 | 20 | 70 | 20 | 60 | 0 | 0 | 0 | 30 |
| A100 | 250 | 80 | 70 | 90 | 70 | 20 | 20 | 0 | 0 |
| A101 | 250 | — | 40 | — | 10 | — | 20 | — | 0 |
| A102 | 250 | 60 | 70 | 20 | 70 | 50 | 10 | 0 | 70 |
| A103 | 250 | — | 20 | — | 60 | — | 20 | — | 10 |
| A104 | 250 | 80 | 60 | 90 | 90 | 80 | 70 | 0 | 70 |
| A105 | 250 | 70 | 70 | 80 | 80 | 70 | 60 | 20 | 0 |
| A106 | 250 | 70 | 70 | 0 | 30 | 20 | 20 | 0 | 0 |
| A107 | 250 | 90 | 80 | 80 | 80 | 80 | 70 | 10 | 90 |
| A108 | 250 | 80 | 60 | 0 | 0 | 30 | 20 | 0 | 60 |
| A109 | 250 | 90 | 80 | 90 | 90 | 80 | 80 | 50 | 80 |
| A110 | 250 | 100 | 80 | 70 | 60 | 90 | 80 | 50 | 70 |
| A111 | 250 | 100 | 100 | 90 | 100 | 100 | 100 | 90 | 100 |
| A112 | 250 | 100 | 100 | 80 | 90 | 100 | 100 | 90 | 100 |
| A113 | 250 | 90 | 100 | 80 | 100 | 100 | 100 | 90 | 100 |
| A114 | 250 | 90 | 100 | 90 | 100 | 100 | 100 | 90 | 100 |
| A115 | 250 | 90 | 100 | 90 | 100 | 90 | 100 | 90 | 100 |
| A116 | 250 | 80 | 100 | 80 | 90 | 100 | 100 | 90 | 100 |
| A117 | 250 | 90 | 100 | 70 | 90 | 100 | 100 | 70 | 100 |
| A118 | 250 | 90 | 100 | 80 | 90 | 100 | 100 | 100 | 100 |
| A119 | 250 | 70 | 90 | 40 | 60 | 100 | 100 | 60 | 90 |
| A120 | 250 | 80 | 100 | 80 | 100 | 100 | 100 | 90 | 100 |
| A121 | 250 | 80 | 100 | 90 | 100 | 90 | 100 | 90 | 100 |
| A122 | 250 | 20 | 70 | 70 | 90 | 90 | 100 | 0 | 100 |
| A123 | 250 | 80 | 90 | 60 | 80 | 90 | 100 | 70 | 80 |
| A124 | 250 | 90 | 100 | 70 | 90 | 90 | 100 | 80 | 100 |
| A125 | 250 | 90 | 100 | 70 | 90 | 100 | 100 | 80 | 100 |
| A126 | 250 | 80 | 80 | 30 | 30 | 100 | 100 | 50 | 90 |
| A127 | 250 | 60 | 90 | 0 | 70 | 60 | 100 | 20 | 70 |
| A128 | 250 | 90 | 100 | 80 | 100 | 100 | 100 | 80 | 100 |
| A129 | 250 | — | 20 | — | 50 | — | 90 | — | 70 |
| A130 | 250 | 90 | 100 | 70 | 90 | 100 | 100 | 90 | 100 |
| A131 | 250 | 70 | 100 | 40 | 90 | 100 | 100 | 50 | 100 |
| A132 | 250 | 90 | 100 | 90 | 100 | 100 | 100 | 90 | 100 |
| A133 | 250 | 80 | 80 | 30 | 90 | 90 | 100 | 90 | 100 |
| A134 | 250 | 80 | 100 | 70 | 90 | 90 | 100 | 90 | 90 |
| A135 | 250 | 70 | 90 | 20 | 90 | 60 | 100 | 30 | 100 |
| A136 | 250 | 80 | 90 | 80 | 100 | 90 | 100 | 90 | 100 |
| A137 | 250 | 70 | 60 | 60 | 40 | 70 | 90 | 60 | 70 |
| A138 | 250 | 100 | 100 | 90 | 90 | 100 | 100 | 100 | 100 |
| A139 | 250 | 0 | 10 | 0 | 10 | 90 | 20 | 0 | 30 |
| A140 | 250 | 100 | 90 | 90 | 100 | 100 | 100 | 100 | 100 |
| A141 | 250 | 100 | 90 | 90 | 90 | 100 | 100 | 90 | 100 |
| A142 | 250 | 20 | 20 | 0 | — | 30 | 60 | 0 | — |
| A143 | 250 | 10 | 20 | 0 | — | 10 | 40 | 0 | — |
| A144 | 250 | 90 | 90 | 80 | 80 | 100 | 100 | 90 | 100 |
| A145 | 250 | 100 | 90 | 100 | 100 | 100 | 100 | 100 | 100 |
| A146 | 250 | 90 | 100 | 80 | 100 | 90 | 100 | 90 | 100 |
| A147 | 250 | — | 0 | — | 20 | — | 60 | — | 20 |
| A148 | 250 | 80 | 90 | 70 | 70 | 100 | 100 | 80 | 100 |
| A149 | 250 | 90 | 100 | 80 | 100 | 100 | 100 | 100 | 100 |
| A150 | 250 | 80 | 70 | 70 | 70 | 90 | 90 | 50 | 90 |
| A151 | 250 | 80 | 40 | 40 | 40 | 100 | 70 | 70 | 50 |
| A152 | 250 | 90 | 100 | 70 | 90 | 100 | 90 | 100 | 100 |
| A153 | 250 | 60 | 70 | 30 | 90 | 90 | 90 | 70 | 90 |
| A154 | 250 | 80 | 70 | 50 | 80 | 80 | 100 | 60 | 90 |
| A155 | 250 | 70 | 70 | 40 | 50 | 70 | 90 | 100 | 70 |
| A156 | 250 | 80 | 80 | 60 | 70 | 100 | 100 | 70 | 80 |
| A157 | 250 | 70 | 90 | 60 | 80 | 90 | 100 | 70 | 90 |
| A158 | 250 | 60 | 80 | 20 | 70 | 80 | 90 | 20 | 70 |
| A159 | 250 | 90 | 90 | 60 | 70 | 90 | 80 | 20 | 50 |
| A160 | 250 | 100 | 100 | 70 | 70 | 100 | 90 | 80 | 90 |
| A161 | 250 | 100 | 90 | 20 | 70 | 100 | 80 | 30 | 30 |
| A162 | 250 | 100 | 100 | 70 | 90 | 100 | 90 | 70 | 90 |
| A163 | 250 | 60 | 60 | 10 | 30 | 70 | 70 | 30 | 30 |
| A164 | 250 | 60 | 60 | 70 | 70 | 70 | 70 | 10 | 70 |
| A165 | 250 | 70 | 80 | 60 | 60 | 100 | 90 | 0 | 80 |
| A166 | 250 | 70 | 70 | 40 | 40 | 70 | 90 | 20 | 70 |

TABLE B1-continued

Pre-/Post-emergence herbicidal activity (percentage phytotoxicity)

| Compound | Rate g/ha | LOLPE PRE | LOLPE POST | ALOMY PRE | ALOMY POST | ECHCG PRE | ECHCG POST | AVEFA PRE | AVEFA POST |
|---|---|---|---|---|---|---|---|---|---|
| A167 | 250 | 80 | 60 | 20 | 20 | 80 | 80 | 10 | 70 |
| A168 | 250 | 80 | 100 | 80 | 90 | 80 | 100 | 20 | 90 |
| A171 | 250 | 70 | 80 | 60 | 70 | 80 | 70 | 20 | 70 |
| A172 | 250 | 90 | 60 | 80 | 80 | 80 | 70 | 40 | 70 |
| A173 | 250 | 80 | 60 | 50 | 20 | 10 | 30 | 10 | 30 |
| A174 | 250 | — | 0 | — | 40 | — | 10 | — | 0 |
| A175 | 250 | 100 | 90 | 80 | 80 | 90 | 90 | 70 | 90 |
| A176 | 250 | 100 | 100 | 90 | 90 | 100 | 100 | 90 | 90 |
| A177 | 250 | 100 | 80 | 100 | 80 | 90 | 90 | 60 | 80 |
| A178 | 250 | 80 | 70 | 20 | 70 | 80 | 40 | 0 | 70 |
| A179 | 250 | 90 | 80 | 100 | 100 | 80 | 100 | 90 | 100 |
| A180 | 250 | 0 | 30 | 40 | 70 | 20 | 70 | 0 | 70 |
| A181 | 250 | 100 | 100 | 90 | 90 | 90 | 80 | 90 | 90 |
| A182 | 250 | 70 | 40 | 70 | 70 | 0 | 80 | 20 | 70 |
| A183 | 250 | 90 | 70 | 50 | 70 | 80 | 80 | 0 | 70 |
| A184 | 250 | 90 | 80 | 90 | 90 | 90 | 90 | 0 | 70 |
| A185 | 250 | 70 | 70 | 80 | 80 | 70 | 70 | 60 | 80 |
| A186 | 250 | 60 | 60 | 40 | 40 | 70 | 80 | 0 | 30 |
| A187 | 250 | 100 | 90 | 80 | 80 | 90 | 100 | 90 | 100 |
| P1 | 250 | 100 | 100 | 100 | 100 | 100 | 100 | 100 | 100 |
| P2 | 250 | 100 | 100 | 90 | 100 | 100 | 100 | 90 | 100 |
| P3 | 250 | 100 | 100 | 100 | 100 | 100 | 100 | 80 | 90 |
| P4 | 250 | 100 | 100 | 90 | 90 | 100 | 100 | 90 | 100 |
| P5 | 250 | 100 | 100 | 100 | 100 | 100 | 100 | 90 | 100 |

Note:
a hyphen (—) in the table above indicates that no measurement was made.

TABLE B2

Pre-/Post-emergence herbicidal activity (percentage phytotoxicity)

| Compound | Rate g/ha | LOLPE PRE | LOLPE POST | ALOMY PRE | ALOMY POST | ECHCG PRE | ECHCG POST | AVEFA PRE | AVEFA POST |
|---|---|---|---|---|---|---|---|---|---|
| B1 | 250 | 20 | 20 | 20 | 0 | 70 | 60 | 0 | 0 |
| B2 | 250 | 80 | 30 | 40 | 40 | 80 | 10 | 60 | 30 |
| B3 | 250 | 90 | 80 | 60 | 0 | 90 | 70 | 50 | 10 |
| B5 | 250 | 100 | 90 | 100 | 100 | 100 | 100 | 90 | 100 |
| B6 | 250 | 0 | 20 | 0 | 50 | 0 | 90 | 0 | 70 |
| B7 | 250 | 90 | 80 | 100 | 100 | 80 | 100 | 90 | 100 |
| B8 | 250 | 100 | 90 | 80 | 80 | 90 | 100 | 90 | 100 |
| B9 | 250 | 90 | 70 | 70 | 70 | 100 | 70 | 70 | 70 |
| B10 | 250 | 0 | 30 | 0 | 30 | 0 | 70 | 0 | 70 |
| B11 | 250 | 90 | 80 | 70 | 70 | 90 | 70 | 70 | 70 |
| B12 | 250 | 90 | 90 | 70 | 60 | 100 | 90 | 30 | 60 |
| B13 | 250 | 90 | 90 | 50 | 50 | 90 | 80 | 40 | 70 |
| B14 | 250 | 90 | 90 | 70 | 70 | 70 | 90 | 70 | 80 |
| B15 | 250 | 100 | 90 | 80 | 70 | 90 | 90 | 80 | 90 |
| B16 | 250 | 90 | 90 | 80 | 70 | 90 | 90 | 30 | 70 |
| B17 | 250 | 90 | 70 | 20 | 40 | 90 | 70 | 0 | 50 |
| B18 | 250 | 100 | 100 | 70 | 80 | 90 | 90 | 80 | 90 |
| B19 | 250 | 80 | 70 | 10 | 50 | 90 | 70 | 20 | 50 |
| B20 | 250 | 70 | 40 | 80 | 70 | 90 | 90 | 90 | 80 |
| B21 | 250 | 100 | 90 | 80 | 80 | 100 | 90 | 50 | 90 |
| B22 | 250 | 90 | 80 | 30 | 30 | 90 | 80 | 100 | 20 |
| B23 | 250 | 100 | 90 | 70 | 60 | 90 | 90 | 60 | 70 |
| B24 | 250 | 100 | 90 | 80 | 90 | 100 | 100 | 80 | 80 |
| B25 | 250 | 90 | 80 | 90 | 80 | 90 | 90 | 70 | 80 |
| B26 | 250 | 70 | 60 | 60 | 70 | 70 | 60 | 20 | 60 |
| B27 | 250 | 60 | 70 | 30 | 70 | 60 | 40 | 20 | 70 |
| B28 | 250 | 80 | 50 | 50 | 50 | 60 | 70 | 50 | 60 |
| B29 | 250 | 80 | 70 | 30 | 70 | 80 | 70 | 10 | 60 |
| B30 | 250 | 70 | 30 | 60 | 70 | 70 | 80 | 70 | 90 |
| B31 | 250 | 90 | 80 | 100 | 80 | 90 | 80 | 70 | 80 |
| B32 | 250 | 90 | 50 | 90 | 70 | 80 | 80 | 0 | 40 |
| B33 | 250 | 100 | 90 | 100 | 90 | 100 | 100 | 100 | 100 |
| B34 | 250 | 90 | 80 | 70 | 60 | 100 | 100 | 80 | 90 |
| B35 | 250 | 80 | 70 | 90 | 80 | 80 | 70 | 0 | 70 |
| B36 | 250 | 80 | 50 | 50 | 30 | 0 | 20 | 0 | 40 |
| B37 | 250 | 100 | 80 | 70 | 70 | 90 | 90 | 90 | 100 |

TABLE B2-continued

| | | Pre-/Post-emergence herbicidal activity (percentage phytotoxicity) | | | | | | | |
|---|---|---|---|---|---|---|---|---|---|
| | Rate | LOLPE | | ALOMY | | ECHCG | | AVEFA | |
| Compound | g/ha | PRE | POST | PRE | POST | PRE | POST | PRE | POST |
| B38 | 250 | 100 | 90 | 70 | 70 | 100 | 90 | 60 | 90 |
| B39 | 250 | 60 | 60 | 30 | 80 | 0 | 50 | 30 | 70 |
| B40 | 250 | 90 | 80 | 90 | 80 | 90 | 90 | 70 | 90 |
| B41 | 250 | 70 | 60 | 70 | 80 | 60 | 60 | 30 | 70 |
| B42 | 250 | 0 | 40 | 0 | 60 | 0 | 0 | 0 | 60 |
| B43 | 250 | 60 | 80 | 70 | 80 | 40 | 60 | 30 | 80 |
| B44 | 250 | 100 | 90 | 90 | 90 | 90 | 90 | 60 | 90 |
| B45 | 250 | 80 | 80 | 70 | 80 | 60 | 80 | 10 | 80 |
| B46 | 250 | 100 | 90 | 90 | 90 | 90 | 90 | 60 | 90 |
| B47 | 250 | 100 | 90 | 90 | 90 | 90 | 90 | 60 | 80 |
| B48 | 250 | 80 | 90 | 90 | 80 | 90 | 100 | 30 | 80 |
| B49 | 250 | 100 | 100 | 100 | 100 | 100 | 100 | 90 | 100 |
| B50 | 250 | 100 | 100 | 90 | 100 | 100 | 100 | 70 | 90 |
| B51 | 250 | 100 | 100 | 90 | 100 | 100 | 100 | 80 | 100 |
| B52 | 250 | 100 | 100 | 90 | 100 | 90 | 100 | 70 | 90 |
| B53 | 250 | 90 | 100 | 90 | 90 | 90 | 100 | 100 | 100 |
| B54 | 250 | 80 | 100 | 80 | 100 | 80 | 100 | 80 | 100 |
| B55 | 250 | 70 | 70 | 80 | 80 | 50 | 60 | 30 | 60 |
| B56 | 250 | 80 | 90 | 80 | 90 | 90 | 90 | 70 | 90 |
| B57 | 250 | 80 | 80 | 70 | 70 | 90 | 80 | 20 | 80 |
| B58 | 250 | 20 | 50 | 10 | 50 | 20 | 20 | 40 | 70 |
| B59 | 250 | 90 | 80 | 70 | 70 | 90 | 80 | 30 | 70 |
| B60 | 250 | 80 | 80 | 90 | 80 | 90 | 90 | 60 | 80 |
| B61 | 250 | 90 | 90 | 70 | 80 | 90 | 90 | 70 | 90 |
| B62 | 250 | 90 | 90 | 80 | 70 | 90 | 70 | 40 | 70 |
| B63 | 250 | 80 | 70 | 80 | 70 | 80 | 70 | 50 | 70 |
| B64 | 250 | 70 | 80 | 80 | 80 | 80 | 70 | 50 | 70 |
| B65 | 250 | 80 | 70 | 80 | 70 | 90 | 70 | 60 | 50 |
| B66 | 250 | 90 | 90 | 90 | 90 | 90 | 80 | 0 | 80 |
| B67 | 250 | 90 | 70 | 90 | 90 | 90 | 80 | 10 | 80 |
| B68 | 250 | 80 | 70 | 80 | 90 | 90 | 70 | 10 | 80 |
| B69 | 250 | 90 | 80 | 50 | 40 | 90 | 80 | 80 | 100 |
| B70 | 250 | 90 | 100 | 80 | 100 | 100 | 100 | 80 | 100 |
| B71 | 250 | 90 | 100 | 90 | 100 | 100 | 100 | 90 | 100 |
| B72 | 250 | 100 | 100 | 100 | 100 | 100 | 100 | 70 | 100 |
| B73 | 250 | 90 | 100 | 90 | 100 | 100 | 100 | 90 | 100 |
| B74 | 250 | 30 | 50 | 10 | 60 | 10 | 60 | 0 | 60 |
| B75 | 250 | 90 | 100 | 100 | 100 | 100 | 100 | 90 | 100 |
| B76 | 250 | 90 | 80 | 90 | 80 | 90 | 80 | 70 | 80 |
| B77 | 250 | 100 | 100 | 90 | 100 | 100 | 100 | 90 | 100 |
| B78 | 250 | 90 | 80 | 80 | 80 | 90 | 90 | 40 | 80 |
| B79 | 250 | 80 | 80 | 60 | 60 | 80 | 60 | 0 | 10 |
| B80 | 250 | 100 | 90 | 90 | 80 | 90 | 90 | 0 | 60 |
| B81 | 250 | 90 | 90 | 70 | 80 | 90 | 80 | 0 | 90 |
| B82 | 250 | 80 | 70 | 70 | 70 | 90 | 50 | 40 | 60 |
| B83 | 250 | 80 | 80 | 80 | 70 | 90 | 90 | 30 | 80 |
| B84 | 250 | 100 | 100 | 90 | 100 | 100 | 100 | 80 | 100 |
| B85 | 250 | 70 | 80 | 70 | 70 | 20 | 100 | 10 | 50 |
| B86 | 250 | 90 | 100 | 70 | 70 | 80 | 90 | 60 | 100 |
| B87 | 250 | 70 | 80 | 40 | 70 | 20 | 80 | 10 | 30 |
| B88 | 250 | 90 | 100 | 90 | 100 | 90 | 100 | 70 | 100 |
| B89 | 250 | 90 | 100 | 90 | 100 | 100 | 100 | 60 | 100 |
| B90 | 250 | 100 | 100 | 90 | 100 | 100 | 100 | 70 | 100 |
| B91 | 250 | 90 | 100 | 80 | 100 | 80 | 100 | 70 | 100 |
| B92 | 250 | 100 | 90 | 90 | 90 | 90 | 80 | 30 | 80 |
| B93 | 250 | 90 | 100 | 80 | 100 | 100 | 100 | 70 | 100 |
| B94 | 250 | 100 | 100 | 100 | 100 | 100 | 100 | 90 | 100 |
| B95 | 250 | 100 | 100 | 100 | 100 | 100 | 100 | 100 | 100 |
| B96 | 250 | 80 | 80 | 0 | 20 | 30 | 90 | 0 | 60 |
| B97 | 250 | 80 | 70 | 80 | 70 | 90 | 80 | 0 | 50 |
| B98 | 250 | 90 | 80 | 60 | 60 | 80 | 60 | 0 | 20 |
| B99 | 250 | 80 | 80 | 70 | 70 | 70 | 80 | 30 | 20 |
| B100 | 250 | 90 | 100 | 80 | 100 | 100 | 100 | 60 | 100 |
| B101 | 250 | 100 | 100 | 90 | 90 | 100 | 100 | 70 | 90 |
| B102 | 250 | 100 | 90 | 60 | 60 | 80 | 60 | 0 | 60 |
| B103 | 250 | 100 | 100 | 100 | 100 | 100 | 100 | 90 | 100 |
| B104 | 250 | 10 | 70 | 40 | 80 | 20 | 70 | 10 | 80 |
| B105 | 250 | 70 | 60 | 70 | 70 | 100 | 100 | 20 | 60 |
| B106 | 250 | 90 | 100 | 80 | 100 | 100 | 100 | 70 | 100 |
| B107 | 250 | 20 | 80 | 60 | 80 | 60 | 80 | 10 | 90 |
| B108 | 250 | 90 | 100 | 100 | 100 | 100 | 100 | 90 | 100 |
| B109 | 63 | 60 | 70 | 70 | 20 | 80 | 90 | 100 | 80 |
| B110 | 250 | 80 | 90 | 90 | 100 | 100 | 100 | 80 | 100 |
| B111 | 250 | 100 | 100 | 70 | 100 | 100 | 100 | 90 | 100 |

TABLE B2-continued

| | | \multicolumn{2}{c}{LOLPE} | \multicolumn{2}{c}{ALOMY} | \multicolumn{2}{c}{ECHCG} | \multicolumn{2}{c}{AVEFA} |
|---|---|---|---|---|---|---|---|---|---|

| Compound | Rate g/ha | PRE | POST | PRE | POST | PRE | POST | PRE | POST |
|---|---|---|---|---|---|---|---|---|---|
| B112 | 250 | 100 | 100 | 100 | 100 | 100 | 100 | 100 | 100 |
| B113 | 250 | 90 | 100 | 90 | 100 | 100 | 100 | 90 | 100 |
| B114 | 250 | 90 | 90 | 90 | 90 | 100 | 100 | 60 | 90 |
| B115 | 250 | 100 | 100 | 80 | 80 | 100 | 90 | 50 | 80 |
| B116 | 250 | 100 | 100 | 100 | 100 | 100 | 100 | 90 | 100 |
| B117 | 250 | 70 | 70 | 70 | 80 | 70 | 70 | 20 | 70 |
| B118 | 250 | 100 | 100 | 100 | 100 | 100 | 100 | 90 | 100 |
| B119 | 250 | 100 | 100 | 100 | 100 | 100 | 100 | 90 | 100 |
| B120 | 250 | 90 | 90 | 80 | 80 | 80 | 80 | 70 | 90 |
| B121 | 250 | 100 | 100 | 100 | 100 | 100 | 100 | 90 | 100 |
| B122 | 250 | 90 | 100 | 80 | 100 | 70 | 100 | 80 | 100 |
| B123 | 250 | 100 | 100 | 100 | 100 | 100 | 100 | 90 | 100 |
| B124 | 250 | 100 | 100 | 90 | 100 | 100 | 100 | 100 | 100 |
| B125 | 250 | 100 | 100 | 80 | 90 | 100 | 100 | 40 | 100 |
| B126 | 250 | 100 | 100 | 100 | 100 | 100 | 100 | 90 | 100 |
| B127 | 250 | 70 | 90 | 90 | 90 | 70 | 100 | 80 | 100 |
| B128 | 250 | 100 | 100 | 100 | 100 | 100 | 100 | 100 | 100 |
| B129 | 250 | 90 | 100 | 90 | 100 | 70 | 100 | 50 | 100 |
| B130 | 250 | 80 | 100 | 80 | 90 | 70 | 90 | 40 | 90 |
| B131 | 250 | 80 | 90 | 80 | 90 | 90 | 100 | 30 | 100 |
| B132 | 250 | 80 | 70 | 80 | 60 | 20 | 80 | 30 | 20 |
| B133 | 250 | 100 | 90 | 80 | 50 | 80 | 50 | 0 | 60 |
| B134 | 250 | 80 | 80 | 90 | 90 | 70 | 80 | 70 | 90 |
| B135 | 250 | 100 | 100 | 100 | 100 | 100 | 100 | 90 | 100 |
| B136 | 16 | 90 | 100 | 90 | 60 | 100 | 90 | 100 | 100 |
| B137 | 250 | 50 | 100 | 20 | 100 | 60 | 90 | 50 | 100 |
| B138 | 250 | 70 | 80 | 80 | 90 | 90 | 80 | 0 | 70 |
| B139 | 250 | 90 | 80 | 60 | 90 | 100 | 100 | 50 | 90 |
| B140 | 250 | 90 | 90 | 90 | 90 | 70 | 80 | 80 | 90 |
| B141 | 250 | 80 | 80 | 90 | 80 | 70 | 80 | 60 | 90 |
| B142 | 250 | 70 | 90 | 90 | 90 | 0 | 80 | 70 | 90 |
| B143 | 250 | 100 | 100 | 90 | 100 | 100 | 100 | 90 | 100 |
| B144 | 250 | 100 | 100 | 100 | 100 | 100 | 100 | 100 | 100 |
| B145 | 250 | 90 | 90 | 70 | 80 | 80 | 80 | 60 | 90 |
| B146 | 250 | 90 | 90 | 90 | 80 | 100 | 100 | 50 | 90 |
| B147 | 250 | 90 | 60 | 90 | 80 | 100 | 90 | 50 | 90 |
| B148 | 250 | 80 | 90 | 70 | 90 | 100 | 100 | 70 | 100 |
| B149 | 250 | 90 | 80 | 90 | 90 | 100 | 90 | 80 | 90 |
| B150 | 250 | 100 | 100 | 100 | 100 | 100 | 100 | 90 | 100 |
| B151 | 250 | 90 | 90 | 100 | 100 | 100 | 100 | 90 | 100 |
| B152 | 250 | 100 | 90 | 100 | 100 | 100 | 100 | 50 | 90 |
| B153 | 250 | 80 | 100 | 90 | 100 | 90 | 100 | 70 | 100 |
| B154 | 250 | 70 | 70 | 90 | 70 | 80 | 90 | 50 | 70 |
| B155 | 250 | 100 | 100 | 90 | 100 | 100 | 100 | 100 | 100 |
| B156 | 250 | 100 | 100 | 100 | 100 | 100 | 100 | 100 | 100 |
| B157 | 250 | 100 | 100 | 100 | 100 | 100 | 100 | 90 | 100 |
| B158 | 250 | 100 | 90 | 90 | 90 | 100 | 80 | 90 | 80 |
| B159 | 250 | 90 | 90 | 80 | 70 | 90 | 80 | 0 | 90 |
| B160 | 250 | 90 | 100 | 90 | 100 | 100 | 100 | 80 | 100 |
| B161 | 250 | 100 | 100 | 90 | 100 | 90 | 100 | 80 | 100 |
| B162 | 250 | 100 | 100 | 100 | 100 | 100 | 100 | 90 | 100 |
| B163 | 250 | 100 | 80 | 90 | 80 | 90 | 90 | 50 | 80 |
| B164 | 250 | 100 | 100 | 100 | 100 | 100 | 100 | 100 | 90 |
| B165 | 250 | 100 | 100 | 100 | 100 | 100 | 100 | 100 | 100 |
| B166 | 250 | 100 | 100 | 100 | 100 | 100 | 100 | 100 | 100 |
| B167 | 250 | 100 | 90 | 100 | 100 | 100 | 100 | 90 | 100 |
| B168 | 250 | 100 | 100 | 100 | 100 | 100 | 100 | 100 | 100 |
| B169 | 250 | 100 | 100 | 100 | 100 | 100 | 100 | 100 | 100 |
| B170 | 250 | 100 | 100 | 100 | 100 | 100 | 100 | 90 | 90 |
| B171 | 250 | 100 | 90 | 100 | 100 | 100 | 100 | 100 | 100 |
| B172 | 250 | 100 | 90 | 80 | 90 | 100 | 100 | 80 | 90 |
| B173 | 250 | 90 | 80 | 90 | 90 | 90 | 90 | 60 | 80 |
| B174 | 250 | 100 | 90 | 100 | 100 | 90 | 100 | 70 | 90 |
| B175 | 250 | 100 | 80 | 100 | 90 | 100 | 90 | 90 | 100 |
| B176 | 250 | 90 | 80 | 90 | 80 | 80 | 80 | 60 | 80 |
| B177 | 250 | 90 | 80 | 90 | 80 | 90 | 90 | 30 | 80 |
| B178 | 250 | 100 | 100 | 100 | 100 | 100 | 100 | 90 | 90 |
| B179 | 250 | 100 | 90 | 90 | 90 | 100 | 100 | 70 | 80 |
| B180 | 250 | 90 | 80 | 90 | 90 | 90 | 90 | 60 | 90 |
| B181 | 250 | 100 | 100 | 70 | 100 | 100 | 100 | 70 | 100 |
| B182 | 250 | 100 | 100 | 100 | 100 | 100 | 100 | 90 | 100 |
| B183 | 250 | 100 | 90 | 100 | 100 | 100 | 100 | 90 | 100 |
| B184 | 250 | 100 | 90 | 90 | 90 | 100 | 100 | 90 | 90 |
| B185 | 250 | 70 | 100 | 80 | 100 | 100 | 100 | 60 | 100 |

TABLE B2-continued

| | | \multicolumn{2}{c}{LOLPE} | \multicolumn{2}{c}{ALOMY} | \multicolumn{2}{c}{ECHCG} | \multicolumn{2}{c}{AVEFA} |

| | Rate | LOLPE | | ALOMY | | ECHCG | | AVEFA | |
|---|---|---|---|---|---|---|---|---|---|
| Compound | g/ha | PRE | POST | PRE | POST | PRE | POST | PRE | POST |
| B186 | 250 | 90 | 90 | 90 | 90 | 100 | 100 | 100 | 90 |
| B187 | 250 | 80 | 90 | 70 | 70 | 80 | 100 | 10 | 70 |
| B188 | 250 | 80 | 90 | 60 | 80 | 80 | 100 | 40 | 100 |
| B189 | 250 | 80 | 90 | 60 | 90 | 80 | 100 | 40 | 90 |
| B190 | 250 | 70 | 80 | 60 | 70 | 80 | 100 | 40 | 90 |
| B191 | 250 | 70 | 90 | 60 | 50 | 80 | 100 | 40 | 90 |
| B192 | 250 | 100 | 100 | 100 | 100 | 100 | 100 | 90 | 100 |
| B193 | 250 | 100 | 100 | 100 | 100 | 100 | 100 | 90 | 100 |
| B194 | 250 | 100 | 100 | 100 | 100 | 90 | 100 | 80 | 100 |
| B195 | 250 | 100 | 100 | 90 | 100 | 100 | 100 | 80 | 100 |
| B196 | 250 | 100 | 100 | 100 | 100 | 100 | 100 | 80 | 100 |
| B197 | 250 | 90 | 100 | 100 | 100 | 100 | 100 | 90 | 100 |
| B198 | 250 | 70 | 100 | 90 | 100 | 80 | 100 | 60 | 100 |
| B199 | 250 | 70 | 90 | 80 | 100 | 50 | 100 | 60 | 100 |
| B200 | 250 | 100 | 100 | 100 | 100 | 100 | 100 | 90 | 100 |
| B201 | 250 | 100 | 100 | 100 | 100 | 100 | 100 | 100 | 100 |
| B202 | 250 | 60 | 70 | 80 | 90 | 70 | 90 | 70 | 80 |
| B203 | 250 | 100 | 100 | 100 | 100 | 100 | 100 | 100 | 100 |
| B204 | 250 | 90 | 90 | 90 | 100 | 90 | 100 | 80 | 100 |
| B205 | 250 | 90 | 90 | 100 | 100 | 90 | 90 | 80 | 90 |
| B206 | 250 | 80 | 90 | 80 | 90 | 90 | 90 | 70 | 90 |
| B207 | 250 | 10 | 60 | 40 | 80 | 40 | 90 | 0 | 50 |
| B208 | 250 | 80 | 90 | 90 | 90 | 100 | 100 | 80 | 90 |
| B209 | 250 | 90 | 80 | 100 | 90 | 100 | 100 | 80 | 80 |
| B210 | 250 | 100 | 90 | 100 | 100 | 100 | 100 | 80 | 90 |
| B211 | 250 | NC | 90 | 90 | 90 | 100 | 100 | 80 | 90 |
| B212 | 250 | 90 | 70 | 60 | 90 | 100 | 90 | 60 | 60 |
| B213 | 250 | 70 | 90 | 80 | 90 | 90 | 100 | 50 | 90 |
| B214 | 250 | 90 | 100 | 100 | 100 | 100 | 100 | 90 | 100 |
| B215 | 250 | 90 | 100 | 90 | 100 | 90 | 100 | 80 | 100 |
| B216 | 250 | 70 | 90 | 80 | 100 | 90 | 100 | 70 | 90 |
| B217 | 250 | 100 | 100 | 100 | 100 | 100 | 100 | 100 | 100 |
| B218 | 250 | 100 | 100 | 100 | 100 | 100 | 100 | 90 | 100 |
| B219 | 250 | 100 | 100 | 100 | 100 | 90 | 100 | 90 | 100 |
| B220 | 250 | 100 | 100 | 100 | 100 | 100 | 100 | 90 | 100 |
| B221 | 250 | 100 | 100 | 100 | 100 | 100 | 100 | 100 | 100 |
| B222 | 250 | 100 | 100 | 100 | 100 | 100 | 100 | 90 | 100 |
| B223 | 250 | 80 | 80 | 90 | 90 | 90 | 100 | 70 | 100 |
| B224 | 250 | 70 | 80 | 80 | 80 | 70 | 90 | 50 | 80 |
| B225 | 250 | 0 | 60 | 0 | 60 | 0 | 70 | 0 | 70 |
| B226 | 250 | 80 | 90 | 100 | 100 | 100 | 100 | 90 | 90 |
| B227 | 250 | 80 | 90 | 80 | 100 | 80 | 100 | 80 | 100 |
| B228 | 250 | 100 | 100 | 100 | 100 | 90 | 100 | 90 | 100 |
| B229 | 250 | 90 | 70 | 90 | 80 | 100 | 100 | 90 | 80 |
| B230 | 250 | 90 | 90 | 90 | 100 | 100 | 100 | 90 | 100 |
| B231 | 250 | 80 | 90 | 50 | 90 | 80 | 90 | 20 | 100 |
| B232 | 250 | 90 | 100 | 90 | 100 | 90 | 100 | 70 | 100 |
| B233 | 250 | 70 | 70 | 70 | 60 | 70 | 100 | 60 | 70 |
| B234 | 250 | 70 | 80 | 60 | 90 | 70 | 90 | 80 | 90 |
| B235 | 250 | 100 | 100 | 100 | 100 | 100 | 100 | 100 | 100 |
| B236 | 250 | 90 | 100 | 90 | 100 | 90 | 100 | 90 | 100 |
| B237 | 250 | 90 | 100 | 100 | 100 | 90 | 100 | 90 | 100 |
| B238 | 250 | 100 | 100 | 100 | 100 | 100 | 100 | 100 | 100 |
| B239 | 250 | 100 | 100 | 100 | 90 | 100 | 100 | 90 | 100 |
| B240 | 250 | 90 | 100 | 100 | 100 | 90 | 100 | 90 | 100 |
| B241 | 250 | 80 | 90 | 60 | 80 | 70 | 100 | 50 | 100 |
| B242 | 250 | 0 | 100 | 0 | 90 | 0 | 100 | 0 | 90 |
| B243 | 250 | 0 | 70 | 0 | 80 | 0 | 90 | 0 | 50 |
| B244 | 250 | 0 | 60 | 0 | 0 | 0 | 90 | 0 | 80 |
| B245 | 250 | 90 | 100 | 100 | 100 | 90 | 100 | 90 | 100 |
| B246 | 250 | 90 | 100 | 60 | 100 | 70 | 100 | 50 | 100 |
| B247 | 250 | 80 | 100 | 90 | 100 | 60 | 100 | 80 | 100 |
| B248 | 250 | 80 | 100 | 50 | 100 | 60 | 100 | 50 | 100 |
| B249 | 250 | 70 | 60 | 80 | 70 | 80 | 80 | 30 | 70 |
| B250 | 250 | 80 | 100 | 50 | 100 | 90 | 100 | 50 | 90 |
| B251 | 250 | 90 | 100 | 90 | 100 | 90 | 100 | 60 | 90 |
| B252 | 250 | 100 | 100 | 100 | 100 | 100 | 100 | 70 | 90 |
| B253 | 250 | 90 | 100 | 100 | 100 | 90 | 100 | 80 | 100 |
| B254 | 250 | 90 | 100 | 90 | 100 | 100 | 100 | 90 | 100 |
| B255 | 250 | 100 | 100 | 100 | 100 | 100 | 100 | 80 | 100 |
| B256 | 250 | 100 | 100 | 100 | 100 | 100 | 100 | 100 | 100 |
| B257 | 250 | 100 | 100 | 100 | 100 | 100 | 100 | 90 | 100 |
| B258 | 250 | 100 | 100 | 100 | 100 | 100 | 100 | 90 | 100 |
| B259 | 250 | 100 | 100 | 100 | 100 | 100 | 100 | 90 | 100 |

TABLE B2-continued

| | | Pre-/Post-emergence herbicidal activity (percentage phytotoxicity) | | | | | | | |
|---|---|---|---|---|---|---|---|---|---|
| | Rate | LOLPE | | ALOMY | | ECHCG | | AVEFA | |
| Compound | g/ha | PRE | POST | PRE | POST | PRE | POST | PRE | POST |
| B260 | 250 | 100 | 100 | 90 | 100 | 100 | 100 | 80 | 100 |
| B261 | 250 | 90 | 100 | 80 | 100 | 90 | 100 | 80 | 100 |
| B262 | 250 | 60 | 70 | 60 | 70 | 80 | 100 | 40 | 90 |
| B263 | 250 | 80 | 100 | 90 | 100 | 100 | 100 | 80 | 100 |
| B264 | 250 | 90 | 100 | 100 | 100 | 100 | 100 | 80 | 100 |
| B265 | 250 | 100 | 100 | 100 | 100 | 100 | 100 | 100 | 100 |
| B266 | 250 | 90 | 80 | 100 | 100 | 100 | 100 | 40 | 100 |
| B267 | 250 | 100 | 100 | 100 | 100 | 100 | 100 | 80 | 100 |
| B268 | 250 | 100 | 100 | 100 | 90 | 100 | 100 | 90 | 100 |
| B269 | 250 | 100 | 100 | 100 | 100 | 100 | 100 | 100 | 100 |
| B270 | 250 | 100 | 90 | 100 | 100 | 100 | 100 | 90 | 100 |
| B271 | 250 | 80 | 90 | 80 | 100 | 100 | 100 | 80 | 100 |
| B272 | 250 | 50 | 80 | 80 | 100 | 90 | 100 | 80 | 100 |
| B273 | 250 | 100 | 100 | 90 | 100 | 100 | 100 | 90 | 100 |
| B274 | 250 | 70 | 90 | 70 | 100 | 70 | 100 | 50 | 100 |
| B275 | 250 | 100 | 100 | 100 | 100 | 100 | 100 | 100 | 100 |
| B276 | 250 | 90 | 100 | 100 | 90 | 100 | 100 | 80 | 90 |
| B277 | 250 | 100 | 100 | 100 | 100 | 100 | 100 | 100 | 100 |
| B278 | 250 | 100 | 90 | 100 | 100 | 100 | 100 | 100 | 100 |
| B279 | 250 | 100 | 100 | 100 | 100 | 100 | 100 | 100 | 100 |
| B280 | 250 | 100 | 100 | 100 | 100 | 100 | 100 | 100 | 100 |
| B281 | 250 | 80 | 90 | 80 | 100 | 100 | 100 | 80 | 100 |
| B282 | 250 | 100 | 100 | 100 | 100 | 100 | 100 | 100 | 100 |
| B283 | 250 | 100 | 100 | 100 | 100 | 100 | 100 | 90 | 100 |
| B284 | 250 | 90 | 100 | 100 | 100 | 100 | 100 | 70 | 100 |
| B285 | 250 | 100 | 100 | 90 | 100 | 100 | 100 | 90 | 100 |
| B286 | 250 | 90 | 100 | 100 | 100 | 100 | 100 | 90 | 100 |
| B287 | 250 | 90 | 90 | 90 | 90 | 100 | 100 | 90 | 100 |
| B288 | 250 | 90 | 90 | 80 | 100 | 90 | 100 | 80 | 90 |
| B289 | 250 | 100 | 100 | 100 | 100 | 100 | 100 | 100 | 100 |
| B290 | 250 | 100 | 100 | 100 | 100 | 100 | 100 | 100 | 100 |
| B291 | 250 | 100 | 100 | 100 | 90 | 100 | 100 | 90 | 100 |
| B292 | 250 | 70 | 90 | 100 | 100 | 100 | 100 | 90 | 100 |
| B293 | 250 | 90 | 90 | 90 | 100 | 90 | 100 | 60 | 100 |
| B294 | 250 | 100 | 100 | 90 | 100 | 100 | 100 | 100 | 100 |
| B295 | 250 | 90 | 90 | 80 | 90 | 90 | 100 | 60 | 100 |
| B296 | 250 | 90 | 100 | 90 | 100 | 100 | 100 | 90 | 100 |
| B297 | 250 | 90 | 100 | 90 | 100 | 100 | 100 | 90 | 100 |
| B298 | 250 | 90 | 90 | 90 | 100 | 100 | 100 | 90 | 100 |
| B299 | 250 | 100 | 100 | 90 | 90 | 100 | 100 | 90 | 90 |
| B300 | 250 | 100 | 100 | 100 | 100 | 100 | 100 | 100 | 100 |
| B301 | 250 | 70 | 50 | 80 | 70 | 60 | 70 | 50 | 70 |
| B302 | 250 | 100 | 100 | 100 | 100 | 100 | 100 | 100 | 100 |
| B303 | 250 | 80 | 100 | 90 | 100 | 100 | 100 | 80 | 100 |
| B304 | 250 | 100 | 100 | 100 | 100 | 90 | 100 | 100 | 100 |
| B305 | 250 | 100 | 100 | 100 | 100 | 100 | 100 | 100 | 100 |
| B306 | 250 | 100 | 100 | 100 | 100 | 100 | 100 | 100 | 100 |
| B307 | 250 | 100 | 90 | 100 | 90 | 100 | 100 | 100 | 100 |
| B308 | 250 | 80 | 60 | 90 | 90 | 80 | 100 | 80 | 100 |
| B309 | 250 | 80 | 60 | 90 | 100 | 100 | 100 | 80 | 100 |
| B310 | 250 | 90 | 70 | 90 | 90 | 90 | 100 | 80 | 100 |
| B311 | 250 | 90 | 70 | 80 | 80 | 90 | 100 | 80 | 90 |
| B312 | 250 | 70 | 80 | 10 | 90 | 70 | 100 | 10 | 100 |
| B313 | 250 | 90 | 70 | 90 | 90 | 100 | 90 | 80 | 70 |
| B314 | 250 | 90 | 90 | 100 | 100 | 100 | 80 | 90 | 100 |
| B315 | 250 | 70 | 80 | 80 | 90 | 100 | 100 | 80 | 100 |
| B316 | 250 | 80 | 90 | 90 | 90 | 90 | 100 | 80 | 100 |
| B317 | 250 | 90 | 90 | 90 | 100 | 100 | 100 | 90 | 100 |
| B318 | 250 | 100 | 90 | 90 | 90 | 90 | 100 | 90 | 100 |
| B319 | 250 | 0 | 60 | 0 | 70 | 0 | 100 | 0 | 80 |
| B320 | 250 | 100 | 100 | 100 | 100 | 100 | 100 | 100 | 100 |
| B321 | 250 | 90 | 90 | 70 | 90 | 100 | 100 | 80 | 100 |
| B322 | 250 | 90 | 100 | 90 | 100 | 90 | 100 | 70 | 100 |
| B323 | 250 | 100 | 100 | 100 | 100 | 100 | 100 | 90 | 100 |
| B324 | 250 | 60 | 80 | 30 | 70 | 30 | 100 | 0 | 90 |
| B325 | 250 | 100 | 100 | 100 | 100 | 100 | 100 | 70 | 100 |
| B326 | 250 | 100 | 100 | 100 | 100 | 100 | 100 | 80 | 100 |
| B327 | 250 | 100 | 90 | 100 | 100 | 100 | 100 | 80 | 100 |
| B328 | 250 | 100 | 100 | 100 | 100 | 100 | 100 | 100 | 100 |
| B329 | 250 | 100 | 100 | 100 | 100 | 100 | 100 | 80 | 100 |
| B330 | 250 | 100 | 100 | 100 | 100 | 100 | 100 | 100 | 100 |
| B331 | 250 | 100 | 100 | 100 | 90 | 100 | 100 | 90 | 100 |
| B332 | 250 | 100 | 100 | 100 | 100 | 100 | 100 | 100 | 100 |
| B333 | 250 | 100 | 90 | 100 | 100 | 100 | 100 | 100 | 40 |

TABLE B2-continued

| | | Pre-/Post-emergence herbicidal activity (percentage phytotoxicity) | | | | | | | |
|---|---|---|---|---|---|---|---|---|---|
| | Rate | LOLPE | | ALOMY | | ECHCG | | AVEFA | |
| Compound | g/ha | PRE | POST | PRE | POST | PRE | POST | PRE | POST |
| B334 | 250 | 100 | 90 | 100 | 100 | 100 | 100 | 100 | 100 |
| B335 | 250 | 100 | 100 | 100 | 100 | 90 | 100 | 100 | 100 |
| B336 | 250 | 100 | 100 | 100 | 100 | 100 | 100 | 100 | 100 |
| B337 | 250 | 90 | 100 | 90 | 100 | 90 | 100 | 90 | 100 |
| B338 | 250 | 100 | 90 | 100 | 100 | 100 | 100 | 80 | 100 |
| B339 | 250 | 90 | 100 | 40 | 100 | 100 | 100 | 70 | 100 |
| B340 | 250 | 100 | 100 | 100 | 100 | 100 | 100 | 100 | 100 |
| B341 | 250 | 80 | 100 | 100 | 100 | 100 | 100 | 80 | 100 |
| B342 | 250 | 100 | 100 | 100 | 100 | 100 | 100 | 90 | 100 |
| B343 | 250 | 100 | 100 | 100 | 100 | 100 | 100 | 90 | 100 |
| B344 | 250 | 80 | 90 | 90 | 100 | 100 | 100 | 80 | 100 |
| B345 | 250 | 100 | 100 | 100 | 100 | 100 | 100 | 90 | 100 |
| B346 | 250 | 100 | 100 | 100 | 100 | 100 | 100 | 90 | 100 |
| B347 | 250 | 100 | 100 | 100 | 100 | 100 | 100 | 100 | 100 |
| B348 | 250 | 90 | 100 | 80 | 100 | 100 | 100 | 80 | 100 |
| B349 | 250 | 90 | 100 | 100 | 100 | 90 | 100 | 90 | 100 |
| B350 | 250 | 100 | 100 | 100 | 100 | 100 | 100 | 90 | 100 |
| B351 | 250 | 100 | 100 | 100 | 100 | 100 | 100 | 90 | 100 |
| B352 | 250 | 90 | 100 | 100 | 100 | 100 | 100 | 90 | 90 |
| B353 | 250 | 90 | 100 | 80 | 90 | 100 | 100 | 90 | 100 |
| B354 | 250 | 80 | 90 | 70 | 90 | 90 | 100 | 80 | 100 |
| B355 | 250 | 70 | 100 | 50 | 80 | 90 | 100 | 70 | 90 |
| B356 | 250 | 80 | 100 | 60 | 90 | 100 | 100 | 60 | 100 |
| B357 | 250 | 100 | 90 | 80 | 90 | 100 | 100 | 90 | 100 |
| B358 | 250 | 90 | 90 | 90 | 100 | 100 | 100 | 100 | 100 |
| B359 | 250 | 90 | 90 | 90 | 90 | 80 | 100 | 70 | 100 |
| B360 | 250 | 100 | 100 | 100 | 100 | 100 | 100 | 100 | 100 |
| B361 | 250 | 90 | 90 | 90 | 100 | 100 | 100 | 100 | 100 |
| B362 | 250 | 100 | 90 | 100 | 90 | 100 | 100 | 100 | 100 |
| B363 | 250 | 100 | 90 | 100 | 90 | 100 | 100 | 90 | 100 |
| B364 | 250 | 90 | 90 | 100 | 100 | 90 | 90 | 80 | 90 |
| B365 | 250 | 100 | 90 | 100 | 90 | 100 | 100 | 90 | 90 |
| B366 | 250 | 100 | 90 | 100 | 90 | 100 | 100 | 100 | 100 |
| B367 | 250 | 100 | 100 | 90 | 90 | 100 | 100 | 100 | 100 |
| B368 | 250 | 100 | 100 | 90 | 90 | 100 | 100 | 90 | 100 |
| B369 | 250 | 100 | 90 | 90 | 90 | 100 | 100 | 100 | 100 |
| B370 | 250 | 100 | 100 | 100 | 90 | 100 | 100 | 100 | 100 |
| B371 | 250 | 100 | 100 | 90 | 100 | 100 | 100 | 90 | 100 |
| B372 | 250 | 100 | 90 | 90 | 90 | 100 | 100 | 100 | 100 |
| B373 | 250 | 100 | 80 | 70 | 80 | 100 | 100 | 80 | 100 |
| B374 | 250 | 90 | 90 | 70 | 90 | 90 | 100 | 90 | 100 |
| B375 | 250 | 80 | 80 | 60 | 40 | 90 | 100 | 70 | 70 |
| B376 | 250 | 60 | 100 | 30 | 90 | 60 | 100 | 80 | 90 |
| B377 | 250 | 80 | 30 | 90 | 90 | 100 | 90 | 90 | 100 |
| B378 | 250 | 80 | 70 | 70 | 80 | 90 | 100 | 90 | 100 |
| B379 | 250 | 70 | 60 | 90 | 90 | 70 | 90 | 70 | 90 |
| B380 | 250 | 80 | 90 | 70 | 70 | 90 | 100 | 80 | 90 |
| B381 | 250 | 90 | 100 | 70 | 100 | 70 | 100 | 70 | 100 |
| B382 | 250 | 60 | 100 | 60 | 100 | 60 | 100 | 40 | 100 |
| B383 | 250 | 100 | 90 | 90 | 100 | 100 | 90 | 90 | 100 |
| B384 | 250 | 80 | 90 | 80 | 90 | 90 | 40 | 80 | 100 |
| B385 | 250 | 100 | 100 | 100 | 100 | 100 | 100 | 100 | 100 |
| B386 | 250 | 100 | 90 | 100 | 100 | 100 | 40 | 100 | 100 |
| B387 | 250 | 90 | 90 | 90 | 90 | 100 | 90 | 100 | 100 |
| B388 | 250 | 90 | 90 | 90 | 90 | 100 | 100 | 90 | 100 |
| B389 | 250 | 100 | 90 | 90 | 100 | 100 | 100 | 90 | 100 |
| B390 | 250 | 100 | 90 | 100 | 100 | 100 | 90 | 100 | 100 |
| B391 | 250 | 100 | 90 | 90 | 90 | 100 | 100 | 100 | 100 |
| B392 | 250 | 100 | 90 | 100 | 90 | 100 | 100 | 100 | 100 |
| B393 | 250 | 100 | 90 | 100 | 90 | 100 | 100 | 90 | 100 |
| B394 | 250 | 100 | 90 | 100 | 100 | 100 | 100 | 100 | 100 |
| B395 | 250 | 100 | 90 | 100 | 100 | 100 | 100 | 100 | 100 |
| B396 | 250 | 100 | 90 | 100 | 90 | 100 | 100 | 100 | 100 |
| B397 | 250 | 70 | 90 | 70 | 90 | 100 | 100 | 80 | 90 |
| B398 | 250 | 70 | 90 | 50 | 80 | 70 | 100 | 40 | 80 |
| B399 | 250 | 70 | 90 | 60 | 90 | 70 | 100 | 40 | 100 |
| B400 | 250 | 100 | 90 | 100 | 100 | 100 | 100 | 100 | 100 |
| B401 | 250 | 90 | 90 | 80 | 90 | 80 | 100 | 70 | 100 |
| B402 | 250 | 80 | 90 | 60 | 90 | 80 | 100 | 70 | 100 |
| B403 | 250 | 20 | 80 | 60 | 90 | 0 | 100 | 50 | 100 |
| B404 | 250 | 80 | 100 | 80 | 90 | 90 | 100 | 70 | 100 |
| B405 | 250 | 100 | 100 | 90 | 100 | 100 | 100 | 90 | 100 |
| P6 | 250 | 100 | 100 | 100 | 100 | 100 | 100 | 100 | 90 |
| P7 | 250 | 30 | 40 | 0 | 70 | 50 | 80 | 10 | 60 |

TABLE B2-continued

Pre-/Post-emergence herbicidal activity (percentage phytotoxicity)

| Compound | Rate g/ha | LOLPE PRE | LOLPE POST | ALOMY PRE | ALOMY POST | ECHCG PRE | ECHCG POST | AVEFA PRE | AVEFA POST |
|---|---|---|---|---|---|---|---|---|---|
| P8  | 250 | 50 | 70 | 30 | 70 | 70  | 90 | 10 | 80 |
| P9  | 250 | 90 | 80 | 90 | 80 | 90  | 80 | 60 | 80 |
| P10 | 250 | 90 | 90 | 90 | 90 | 90  | 90 | 60 | 90 |
| P11 | 250 | 80 | 90 | 70 | 80 | 90  | 90 | 30 | 90 |
| P12 | 250 | 60 | 80 | 20 | 80 | 70  | 60 | 0  | 60 |
| P13 | 250 | 10 | 70 | 50 | 80 | 20  | 80 | 10 | 70 |
| P14 | 250 | 70 | 80 | 70 | 80 | 70  | 70 | 10 | 80 |
| P15 | 250 | 80 | 80 | 70 | 90 | 100 | 80 | 40 | 80 |

Note:
a hyphen (—) in the table above indicates that no measurement was made.

Biological Example 2

Test—Glasshouse Assay for Crop Safety.

Seeds of the Winter Wheat variety 'Hereward' were seed treated with a wettable powder formulation of the cereal herbicide safener, cloquintocet mexyl, at a rate of 0.5 grams per kilogram of dry seed prior to the initiation of glasshouse testing. Three seeds were sown per 1.5 inch plastic pot into a sandy loam soil at a depth of 1 cm, 8 days prior to application of the test compounds and was watered and grown under controlled conditions in a glasshouse (at 24/16° C., day/night; 14 hours light; 65% humidity). The plants were sprayed Post-emergence with an aqueous spray solution derived from the formulation of the technical active ingredient in acetone/water (50:50) solution containing 0.5% Tween 20 (polyoxyethelyene sorbitan monolaurate, CAS RN 9005-64-5).

The test plants were then grown in a glasshouse under controlled conditions (at 24/16° C., day/night; 14 hours light; 65% humidity) and watered twice daily. After 13 days for pre and post-emergence, the test was evaluated (100=total damage to plant; 0=no damage to plant).

TABLE 3

Post-emergence herbicidal activity against cereal crops (wheat) +/− safener (cloquintocet-mexyl (CQC) - Results (percentage phytotoxicity) Post-emergence Crop Selectivity

| Compound | Rate (g/ha) | Wheat − CQC | +CQC |
|---|---|---|---|
| A1  | 250 | 60 | 0  |
| A2  | 250 | 10 | 10 |
| A3  | 250 | 60 | 10 |
| A4  | 250 | 60 | 10 |
| A5  | 250 | 80 | 10 |
| A6  | 250 | 70 | 10 |
| A7  | 250 | 30 | 20 |
| A12 | 250 | 70 | 0  |
| A14 | 250 | 60 | 10 |
| A15 | 250 | 20 | 20 |
| A16 | 250 | 80 | 30 |
| A18 | 250 | 70 | 20 |
| A19 | 250 | 80 | 40 |
| A20 | 250 | 40 | 20 |
| A21 | 250 | 60 | 0  |
| A22 | 250 | 60 | 50 |
| A25 | 250 | 40 | 0  |
| A26 | 250 | 70 | 40 |
| A27 | 250 | 30 | 20 |
| A39 | 250 | 80 | 50 |
| A43 | 250 | 90 | 50 |
| A59 | 250 | 80 | 50 |
| A67 | 250 | 70 | 0  |
| A70 | 250 | 70 | 20 |
| A73 | 250 | 80 | 20 |
| A80 | 250 | 70 | 20 |
| A85 | 250 | 80 | 10 |
| A138 | 250 | 70 | 40 |
| A142 | 250 | 70 | 50 |
| A145 | 250 | 60 | 30 |
| A146 | 250 | 80 | 50 |

The invention claimed is:
1. A compound of formula (I):

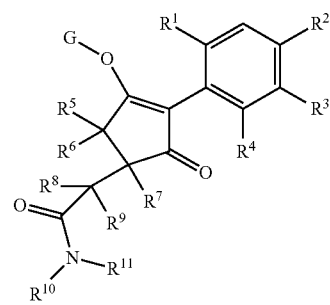

wherein:
$R^1$ is selected from the group consisting of methyl, ethyl, n-propyl, cyclopropyl, trifluoromethyl, vinyl, ethynyl, fluorine, chlorine, bromine, methoxy, difluoromethoxy and trifluoromethoxy; and
either (a): $R^2$ is $R^{2A}$ and $R^3$ is $R^{3A}$;
or (b): $R^2$ is $R^{2B}$ and $R^3$ is $R^{3B}$;
wherein:
$R^{2A}$ is selected from the group consisting of hydrogen, methyl, ethyl, n-propyl, isopropyl, cyclopropyl, $C_1$-$C_2$fluoroalkyl, vinyl, prop-1-enyl, prop-1-ynyl, —C≡C—$R^{2AA}$, halogen and ($C_1$-$C_2$fluoroalkyl)-methoxy-; wherein $R^{2AA}$ is selected from the group consisting of hydrogen, fluorine, chlorine, trifluoromethyl, ethyl and cyclopropyl;
or $R^{2A}$ is phenyl optionally substituted by 1, 2 or 3 substituents independently selected from the group consisting of halogen, $C_1$-$C_2$alkyl, $C_1$-$C_2$fluoroalkyl, methoxymethyl, vinyl, ethynyl, $C_1$-$C_3$alkoxy, $C_1$-$C_2$fluoroalkoxy, —S(O)$_p$methyl, cyano or nitro, provided that either one or none (i.e. no more than one) of these optional substituents are methoxymethyl, vinyl, ethynyl, —S(O)$_p$methyl or nitro;

or $R^{2A}$ is a monocyclic heteroaryl optionally substituted by 1, 2 or 3 substituents independently selected from the group consisting of halogen, $C_1$-$C_2$alkyl, $C_1$-$C_2$fluoroalkyl, methoxymethyl, vinyl, ethynyl, $C_1$-$C_3$alkoxy, $C_1$-$C_2$fluoroalkoxy, —S(O)$_p$methyl, cyano and nitro, provided that either one or none (i.e. no more than one) of these optional substituents are methoxymethyl, vinyl, ethynyl, —S(O)$_p$methyl or nitro;

$R^{3A}$ is selected from the group consisting of hydrogen, methyl, fluorine and chlorine;

and wherein $R^{2B}$ is hydrogen, methyl or fluorine; and either $R^{3B}$ is phenyl optionally substituted by 1, 2 or 3 substituents independently selected from the group consisting of halogen, $C_1$-$C_2$alkyl, $C_1$-$C_2$fluoroalkyl, methoxymethyl, vinyl, ethynyl, $C_1$-$C_2$alkoxy, $C_1$-$C_2$fluoroalkoxy, —S(O)$_p$methyl, cyano and nitro, provided that either one or none (i.e. no more than one) of these optional substituents are methoxymethyl, vinyl, ethynyl, —S(O)$_p$methyl or nitro; or $R^{3B}$ is a monocyclic heteroaryl optionally substituted by 1, 2 or 3 substituents independently selected from the group consisting of halogen, $C_1$-$C_2$alkyl, $C_1$-$C_2$fluoroalkyl, methoxymethyl, vinyl, ethynyl, $C_1$-$C_2$alkoxy, $C_1$-$C_2$fluoroalkoxy, —S(O)$_p$methyl, cyano and nitro, provided that either one or none (i.e. no more than one) of these optional substituents are methoxymethyl, vinyl, ethynyl, —S(O)$_p$methyl or nitro;

$R^4$ is selected from the group consisting of hydrogen, methyl, ethyl, n-propyl, cyclopropyl, trifluoromethyl, vinyl, ethynyl, fluorine, chlorine, bromine, $C_1$-$C_3$alkoxy, $C_1$-$C_2$fluoroalkoxy, $C_1$-$C_2$alkoxy-$C_1$-$C_3$alkoxy-, or $C_1$fluoroalkoxy-$C_1$-$C_3$alkoxy-;

$R^5$, $R^6$ and $R^7$ are independently selected from the group consisting of hydrogen, $C_1$-$C_6$alkyl, $C_2$-$C_3$ alkenyl, $C_2$-$C_3$alkynyl, $C_1$-$C_2$haloalkyl and $C_1$-$C_2$alkoxy$C_1$-$C_2$alkyl;

$R^8$ and $R^9$ are independently selected from the group consisting of hydrogen, fluorine and $C_1$-$C_3$alkyl;

$R^{10}$ is selected from the group consisting of hydrogen, $C_1$-$C_6$alkyl, $C_3$-$C_8$cycloalkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkylcyano, $C_1$-$C_6$alkoxy$C_1$-$C_6$-alkyl-, $C_1$-$C_6$alkoxy-$C_2$-$C_6$-alkenyl-, $C_1$-$C_6$alkoxy-$C_2$-$C_6$-alkynyl-, $C_1$-$C_6$alkenyloxy$C_1$-$C_6$-alkyl-, $C_1$-$C_6$alkoxy-$C_2$-$C_3$-alkoxy-$C_2$-$C_3$-alkyl-, $C_1$-$C_6$alkylcarbonyl- and $C_1$-$C_6$alkylcarbonyl$C_1$-$C_6$-alkyl-;

$R^{11}$ is selected from the group consisting of hydrogen, $C_1$-$C_6$alkyl, $C_3$-$C_8$cycloalkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkylcyano, $C_1$-$C_6$alkoxy$C_1$-$C_6$-alkyl-, $C_1$-$C_6$alkoxy-$C_2$-$C_6$-alkenyl-, $C_1$-$C_6$alkoxy-$C_2$-$C_6$-alkynyl-, $C_1$-$C_6$alkenyloxy$C_1$-$C_6$-alkyl-, $C_1$-$C_6$alkoxy-$C_2$-$C_3$-alkoxy-$C_2$-$C_3$-alkyl-, $C_1$-$C_6$alkylcarbonyl-, $C_1$-$C_6$alkylcarbonyl$C_1$-$C_6$-alkyl-; or $R^{11}$ is —(CR'R")$_n$—X$^1$—R$^{13}$ wherein X$^1$ is a bond, —(CH=CH)— or —(C=O)— and wherein R' and R" are independently selected from hydrogen and methyl or together from a $C_2$-$C_3$ alkylene chain); or $R^{10}$ and $R^{11}$ together form a four to six membered heterocycle, the heterocycle comprising one or more heteroatoms selected from the group consisting of oxygen, nitrogen and sulphur; the heterocycle being optionally substituted by one or more independent R$^{12}$;

$R^{12}$ is selected from the group consisting of halogen, $C_1$-$C_6$alkyl, $C_1$-$C_6$haloalkyl, $C_1$-$C_6$haloalkoxy, $C_1$-$C_6$alkoxy-, nitro, —(CO)OR$^{14}$, cyano, phenyl, pyridyl;

$R^{13}$ is a three- to ten-membered mono- or bicyclic ring system, which may be aromatic, saturated or partially saturated and can contain from 1 to 4 heteroatoms each independently selected from the group consisting of nitrogen, oxygen and sulphur the ring system being optionally substituted by one or more R$^{12}$ substituents;

$R^{14}$ is H or $C_1$-$C_6$ alkyl;

n=0, 1, 2, 3 or 4;

p=0, 1 or 2; and

G is hydrogen; an agriculturally acceptable metal, or an agriculturally acceptable sulfonium or ammonium group; or G is —C(X$^a$)—R$^a$, —C(X$^b$)—X$^c$—R$^b$, —C(X$^d$)—N(R$^c$)R$^d$, —SO$_2$—R$^e$, —P(X$^e$)(R$^f$)—R$^g$, —CH$_2$—X$^f$—R$^h$; or phenyl-CH$_2$— or phenyl-CH(C$_1$-C$_2$alkyl)- (in each of which the phenyl is optionally substituted by 1, 2 or 3 of, independently, C$_1$-C$_2$alkyl, C$_1$fluoroalkyl, C$_1$-C$_2$alkoxy, C$_1$fluoroalkoxy, fluorine, chlorine, bromine, cyano or nitro), or heteroaryl-CH$_2$— or heteroaryl-CH(C$_1$-C$_2$alkyl)- (in each of which the heteroaryl is optionally substituted by 1, 2 or 3 of, independently, C$_1$-C$_2$alkyl, C$_1$fluoroalkyl, C$_1$-C$_2$alkoxy, C$_1$fluoroalkoxy, fluorine, chlorine, bromine, cyano or nitro), or phenyl-C(O)—CH$_2$— (wherein the phenyl is optionally substituted by 1, 2 or 3 of, independently, C$_1$-C$_2$alkyl, C$_1$fluoroalkyl, C$_1$-C$_2$alkoxy, C$_1$fluoroalkoxy, fluorine, chlorine, bromine, cyano or nitro); or C$_1$-C$_6$alkoxy-C(O)—CH$_2$—, C$_1$-C$_6$alkyl-C(O)—CH$_2$—, C$_1$-C$_6$alkoxy-C(O)—CH=CH—, C$_2$-C$_7$alken-1-yl-CH$_2$—, C$_2$-C$_7$alken-1-yl-CH(C$_1$-C$_2$alkyl)-, C$_2$-C$_4$fluoroalken-1-yl-CH$_2$—, C$_2$-C$_7$alkyn-1-yl-CH$_2$—, or C$_2$-C$_7$alkyn-1-yl-CH(C$_1$-C$_2$alkyl)-;

wherein X$^a$, X$^b$, X$^c$, X$^d$, X$^e$ and X$^f$ are independently of each other oxygen or sulfur; and wherein $R^a$ is H, C$_1$-C$_2$alkyl, C$_2$-C$_{21}$alkenyl, C$_2$-C$_{18}$alkynyl, C$_1$-C$_{10}$fluoroalkyl, C$_1$-C$_{10}$cyanoalkyl, C$_1$-C$_{10}$nitroalkyl, C$_1$-C$_{10}$aminoalkyl, C$_1$-C$_5$alkylamino(C$_1$-C$_5$)alkyl, C$_2$-C$_8$dialkylamino(C$_1$-C$_5$)alkyl, C$_3$-C$_7$cycloalkyl(C$_1$-C$_5$)alkyl, C$_1$-C$_5$alkoxy(C$_1$-C$_5$)alkyl, C$_3$-C$_5$alkenyloxy(C$_1$-C$_5$)alkyl, C$_3$-C$_5$alkynyloxy(C$_1$-C$_5$)alkyl, C$_1$-C$_5$alkylthio(C$_1$-C$_5$)alkyl, C$_1$-C$_5$alkylsulfinyl(C$_1$-C$_5$)alkyl, C$_1$-C$_5$alkylsulfonyl(C$_1$-C$_5$)alkyl, C$_2$-C$_8$alkylideneaminoxy(C$_1$-C$_5$)alkyl, C$_1$-C$_5$alkylcarbonyl(C$_1$-C$_5$)alkyl, C$_1$-C$_5$alkoxycarbonyl(C$_1$-C$_5$)alkyl, aminocarbonyl(C$_1$-C$_5$)alkyl, C$_1$-C$_5$alkylaminocarbonyl(C$_1$-C$_5$)alkyl, C$_2$-C$_8$dialkylaminocarbonyl(C$_1$-C$_5$)alkyl, C$_1$-C$_5$alkylcarbonylamino(C$_1$-C$_5$)alkyl, N—(C$_1$-C$_5$)alkylcarbonyl-N—(C$_1$-C$_5$)alkylamino(C$_1$-C$_5$)alkyl, C$_3$-C$_6$trialkylsilyl(C$_1$-C$_5$)alkyl, phenyl(C$_1$-C$_5$)alkyl (wherein the phenyl is optionally substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, C$_1$-C$_3$alkylthio, C$_1$-C$_3$alkylsulfinyl, C$_1$-C$_3$alkylsulfonyl, halogen, cyano, or nitro), heteroaryl(C$_1$-C$_5$)alkyl (wherein the heteroaryl is optionally substituted by 1, 2 or 3 of, independently, C$_1$-C$_3$alkyl, C$_1$-C$_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl$C_1$-$C_5$alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkyl-thio, $C_1$-$C_3$alkylsulfinyl, $C_1$-$C_3$alkylsulfonyl, halogen, cyano, or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or by nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino or $C_3$-$C_7$cycloalkoxy;

or $R^c$ and $R^d$, together with the nitrogen to which they are bonded, to form an unsubstituted 4, 5, 6 or 7 (e.g. 5 or 6) membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_5$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_5$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$alkoxy, $C_1$-$C_{10}$fluoroalkoxy, $C_1$-$C_5$alkylamino or di($C_1$-$C_4$alkyl)amino;

$R^f$ and $R^g$ are are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$) alkyl, $C_3$-$C_5$alkenyloxy($C_1$-$C_5$)alkyl, $C_3$-$C_5$alkynyloxy ($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl ($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$fluoroalkoxy, $C_1$-$C_5$alkylamino or di($C_1$-$C_4$alkyl)amino; or benzyloxy or phenoxy, wherein the benzyl and phenyl groups are in turn optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino ($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$) alkyl, $C_3$-$C_5$alkenyloxy($C_1$-$C_5$)alkyl, $C_3$-$C_5$alkynyloxy ($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl ($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_a$alkylsulfinyl, $C_1$-$C_3$ alkylsulfonyl, halogen, cyano or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), phenoxy($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), heteroaryloxy($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; $C_1$-$C_6$alkyl-C(O)—; or phenyl-C(O)— wherein the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine, bromine, cyano or nitro;

wherein "heteroaryl" means an aromatic ring system containing at least one ring heteroatom and consisting either of a single ring or of two fused rings;

and wherein the compound of formula (I) is optionally present as an agrochemically acceptable salt thereof.

2. The compound of claim 1, wherein G is hydrogen.

3. The compound according to claim 1, wherein $R^1$ is selected from the group consisting of methyl, fluorine, chlorine, bromine, methoxy, difluoromethoxy and trifluoromethoxy.

4. The compound according to claim 1, wherein $R^2$ is $R^{2A}$ and $R^3$ is $R^{3A}$ and wherein $R^{2A}$ is selected from the group consisting of methyl, ethynyl and prop-1-ynyl and $R^{3A}$ is hydrogen or methyl.

5. The compound according to claim 1, wherein $R^2$ is $R^{2A}$ and $R^3$ is $R^{3A}$ wherein $R^{3A}$ is hydrogen or methyl, and wherein $R^{2A}$ is of sub-formula (2Aa):

(2Aa)

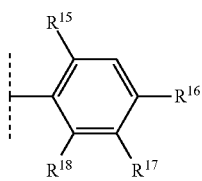

in which:

R$^{15}$ is selected from the group consisting of hydrogen, C$_1$-C$_2$alkyl, fluorine and chlorine;

R$^{16}$ is selected from the group consisting of hydrogen, halogen, C$_1$-C$_2$alkyl, C$_1$-C$_2$fluoroalkyl, C$_1$-C$_2$alkoxy, C$_1$-C$_2$fluoroalkoxy, cyano and nitro;

R$^{17}$ is selected from the group consisting of hydrogen, halogen, C$_1$-C$_2$alkyl, C$_1$-C$_2$fluoroalkyl, C$_1$-C$_2$alkoxy, C$_1$-C$_2$fluoroalkoxy, cyano and nitro; and R$^{18}$ is selected from the group consisting of hydrogen, halogen, C$_1$-C$_2$alkyl, C$_1$-C$_2$fluoroalkyl, C$_1$-C$_2$alkoxy, C$_1$-C$_2$fluoroalkoxy, cyano and nitro.

6. The compound according to claim 1, wherein: R$^{2A}$ is selected from the group consisting of (R$^{2Ab}$), (R$^{2Ac}$), (R$^{2Ad}$), (R$^{2Ae}$), (R$^{2Af}$), R$^{2Ag}$, R$^{hAh}$, R$^{2Ai}$ and R$^{2Aj}$:

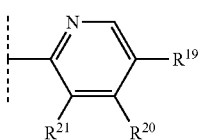 (R$^{2Ab}$)

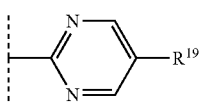 (R$^{2Ac}$)

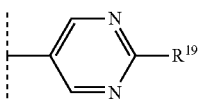 (R$^{2Ad}$)

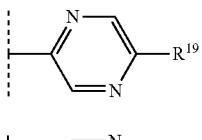 (R$^{2Ae}$)

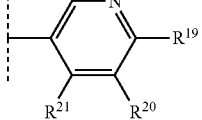 (R$^{2Af}$)

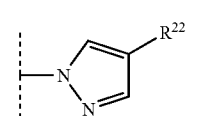 (R$^{2Ag}$)

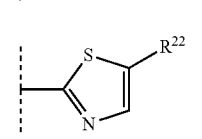 (R$^{2Ah}$)

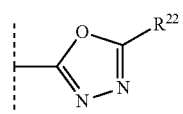 (R$^{2Ai}$)

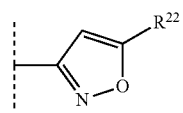 (R$^{2Aj}$)

wherein:

R$^{19}$ is selected from the group consisting of halogen, C$_1$-C$_2$alkyl, C$_1$-C$_2$fluoroalkyl, C$_1$-C$_2$alkoxy, C$_1$-C$_2$fluoroalkoxy, cyano and nitro;

R$^{20}$ is selected from the group consisting of hydrogen, halogen (in particular fluorine, chlorine or bromine, more particularly fluorine or chlorine), C$_1$-C$_2$alkyl, C$_1$-C$_2$fluoroalkyl, C$_1$-C$_2$alkoxy, C$_1$-C$_2$fluoroalkoxy, cyano and nitro; and R$^{21}$ is selected from the group consisting of hydrogen, halogen (in particular fluorine, chlorine or bromine, more particularly fluorine or chlorine), C$_1$-C$_2$alkyl, C$_1$-C$_2$fluoroalkyl, C$_1$-C$_2$alkoxy, C$_1$-C$_2$fluoroalkoxy, cyano and nitro; provided that either one or none (i.e. no more than one) of R$^{19}$, R$^{20}$ and R$^{21}$ are C$_1$-C$_2$alkyl, C$_1$-C$_2$alkoxy or nitro; and R$^{22}$ is selected from the group consisting of hydrogen, halogen, methyl, C$_1$fluoroalkyl, C$_1$fluoroalkoxy and cyano.

7. The compound according to claim 6, wherein R$^2$ is a monocyclic heteroaryl of sub-formula (2$^{Ab}$), and wherein R$^{19}$ is fluorine or chlorine, R$_{20}$ is hydrogen and R$^{21}$ is fluorine.

8. The compound according to claim 1, wherein R$^4$ is selected from the group consisting of hydrogen, methyl, fluorine, chlorine, methoxy, ethoxy, C$_1$fluoroalkyl-methoxy- and MeO—CH$_2$—CH$_2$—O—.

9. The compound according to claim 1, wherein R$^5$, R$^6$, R$^7$, R$^8$ and R$^9$ are hydrogen.

10. The compound according to claim 9, wherein R$^{10}$ is hydrogen.

11. The compound according to claim 1, wherein R$^{11}$ is selected from the group consisting of C$_1$-C$_6$alkyl, C$_2$-C$_6$alkenyl, C$_2$-C$_6$alkynyl, C$_1$-C$_6$alkoxyC$_1$-C$_6$-alkyl-, C$_1$-C$_6$alkoxy-C$_2$-C$_3$-alkoxy-C$_2$-C$_3$-alkyl- and —(CH$_2$)$_n$—X$^2$—R$^{13}$.

12. The compound according to claim 11, wherein R$^{11}$ is is —(CH$_2$)$_n$—X$^2$—R$^{13}$ and wherein R$^{13}$ is selected from the group consisting of R$^{13a}$ to R$^{13o}$

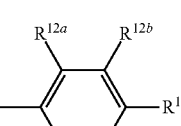 (R$^{13a}$)

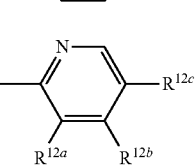 (R$^{13b}$)

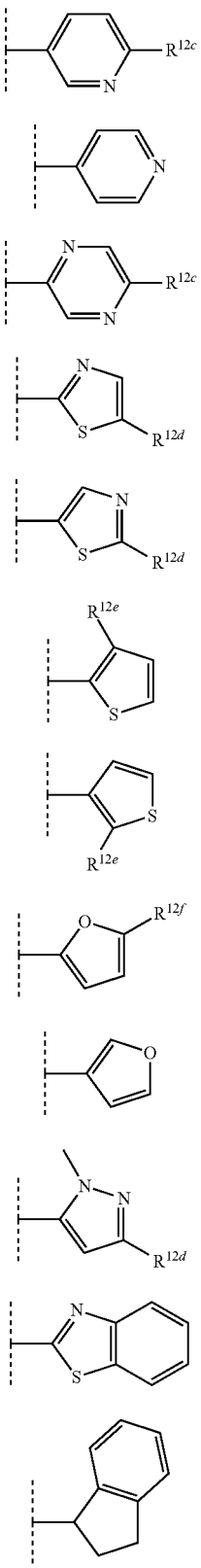

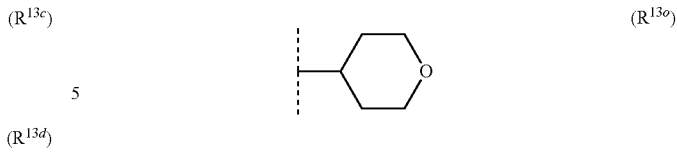

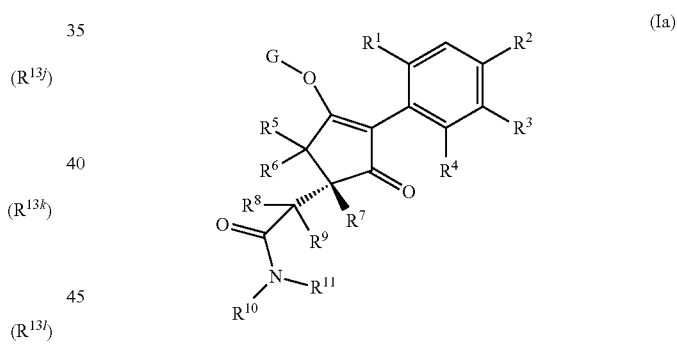

wherein $R^{12a}$ is selected from the group consisting of hydrogen, $C_1$-$C_4$alkyl, $C_1$-$C_4$haloalkyl, halogen, $C_1$-$C_4$alkoxy, cyano and nitro;

$R^{12b}$ is selected from the group consisting of hydrogen, $C_1$-$C_4$alkyl, halogen, $C_1$-$C_4$alkoxy, nitro and phenyl;

$R^{12c}$ is selected from the group consisting of hydrogen, $C_1$-$C_4$alkyl, halogen, $C_1$-$C_4$alkoxy, $C_1$-$C_4$haloalkyl and $C_1$-$C_4$haloalkoxy-;

$R^{12d}$ is hydrogen or halogen;

$R^{12e}$ is selected from the group consisting of hydrogen, halogen and $C_1$-$C_2$alkyl; and $R^{12f}$ is hydrogen or $C_1$-$C_2$alkyl.

13. The compound according to claim 1, wherein $R^{10}$ and $R^{11}$ together form a four to six membered heterocycle, the heterocycle comprising one or more heteroatoms selected from the group consisting of oxygen, nitrogen and sulphur; the heterocycle being optionally substituted by one or more independent $R^{12}$.

14. The compound of claim 1, wherein the compound of formula (I) is a compound of formula (Ia):

(Ia)

wherein $R^1$, $R^2$, $R^3$, $R^4$, $R^5$, $R^6$, $R^7$, $R^8$, $R^9$, $R^{10}$, $R^{11}$ and G are as defined therein.

15. A herbicidal composition which comprises:
(i) a compound of formula (I), as defined in claim 1,
(ii) an agrochemically acceptable carrier, diluent and/or solvent; and
(iii) optionally one or more further herbicides and/or optionally a safener.

16. A method of controlling grassy monocotyledonous weeds in crops of useful plants, comprising applying a compound of formula (I), as defined in claim 1, or a herbicidal composition comprising such a compound, to the weeds and/or to the plants and/or to the locus thereof.

* * * * *